US011542255B2

(12) United States Patent
Cooper et al.

(10) Patent No.: US 11,542,255 B2
(45) Date of Patent: *Jan. 3, 2023

(54) SULFONYLUREAS AND SULFONYLTHIOUREAS AS NLRP3 INHIBITORS

(71) Applicant: Inflazome Limited, Dublin (IE)

(72) Inventors: Matthew Cooper, Cambridge (GB); David Miller, Cambridge (GB); Angus MacLeod, Cambridge (GB); Stephen Thom, Nottingham (GB); Stephen St-Gallay, Nottingham (GB); Jonathan Shannon, Nottingham (GB); Thomas Alanine, Nottingham (GB); Stuart Onions, Nottingham (GB); Ian Strutt, Nottingham (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/638,707

(22) PCT Filed: Aug. 15, 2018

(86) PCT No.: PCT/EP2018/072123
§ 371 (c)(1),
(2) Date: Feb. 12, 2020

(87) PCT Pub. No.: WO2019/034692
PCT Pub. Date: Feb. 21, 2019

(65) Prior Publication Data
US 2021/0130329 A1 May 6, 2021

(30) Foreign Application Priority Data

| Aug. 15, 2017 | (GB) | ................................... | 1713082 |
| Nov. 9, 2017 | (GB) | ................................... | 1718563 |
| Dec. 22, 2017 | (GB) | ................................... | 1721726 |
| Dec. 22, 2017 | (GB) | ................................... | 1721732 |
| Jul. 4, 2018 | (GB) | ................................... | 1810983 |

(51) Int. Cl.
| C07D 403/12 | (2006.01) |
| C07D 231/20 | (2006.01) |
| C07D 401/12 | (2006.01) |
| C07D 405/04 | (2006.01) |
| C07D 405/12 | (2006.01) |
| C07D 413/12 | (2006.01) |
| C07D 471/04 | (2006.01) |
| C07D 487/04 | (2006.01) |

(52) U.S. Cl.
CPC ......... C07D 403/12 (2013.01); C07D 231/20 (2013.01); C07D 401/12 (2013.01); C07D 405/04 (2013.01); C07D 405/12 (2013.01); C07D 413/12 (2013.01); C07D 471/04 (2013.01); C07D 487/04 (2013.01)

(58) Field of Classification Search
CPC .. C07D 403/12; C07D 231/20; C07D 401/12; C07D 405/04; C07D 405/12; C07D 413/12; C07D 471/04; C07D 487/04
See application file for complete search history.

(56) References Cited

U.S. PATENT DOCUMENTS

| 4,723,991 | A | 2/1988 | Holyoke, Jr. et al. |
| 4,741,760 | A | 5/1988 | Meyer et al. |
| 4,795,486 | A | 1/1989 | Bohner et al. |
| 4,802,908 | A | 2/1989 | Hillemann |
| 5,169,860 | A | 12/1992 | Mohamad et al. |
| 5,219,856 | A | 6/1993 | Olson |
| 5,486,618 | A | 1/1996 | Hagen et al. |
| 10,538,487 | B2 | 1/2020 | O'Neill et al. |
| 11,130,731 | B2 | 9/2021 | O'Neill et al. |
| 11,370,776 | B2 * | 6/2022 | Cooper .................. A61P 35/00 |
| 2002/0034764 | A1 | 3/2002 | Gabel et al. |
| 2002/0077486 | A1 | 6/2002 | Scarborough et al. |
| 2006/0069093 | A1 | 3/2006 | Scarborough et al. |
| 2019/0119224 | A1 | 4/2019 | Glick et al. |
| 2019/0192478 | A1 | 6/2019 | Hacini-Rachinel |
| 2019/0337965 | A1 | 11/2019 | Stafford et al. |
| 2020/0207780 | A1 * | 7/2020 | O'Neill ..................... A61P 1/00 |
| 2020/0291003 | A1 * | 9/2020 | Cooper ................ C07D 211/96 |

(Continued)

FOREIGN PATENT DOCUMENTS

| CN | 104513239 A | 4/2015 |
| CN | 109432078 A | 3/2019 |

(Continued)

OTHER PUBLICATIONS

Guo; Nature Medicine, 2015, 21(7), 677-687. (Year: 2015).*
U.S. Appl. No. 16/638,700, Requirement for Restriction/Election dated May 3, 2021.
U.S. Appl. No. 16/638,704, Requirement for Restriction/Election dated Apr. 29, 2021.
Brown, "Bioisosteres in Medicinal Chemistry" Published by Wiley-VCH Verlag GmbH & Co. KGaA, Weinheim, Germany, (2012).
CAS 210826-40-7; STN Entry Date: Sep. 3, 1998; CN Compound Name: 2-Furansulfonamide, N-[[(1,2,3,5,6,7-hexahydro-s-indacen-4-yl)amino]carbonyl]-4-(1-hydroxy-1-methylethyl)—(CA Index Name).

(Continued)

*Primary Examiner* — Daniel R Carcanague
(74) *Attorney, Agent, or Firm* — Alston & Bird LLP

(57) ABSTRACT

The present invention relates to sulfonylureas and sulfonylthioureas comprising a 5-membered heteroaryl ring attached to the sulfonyl group, wherein the heteroaryl ring is di-substituted at the 3- and 4-positions relative to the point of attachment of the sulfonyl group, wherein at least one of the di-substituents contains a nitrogen atom. The present invention further relates to salts, solvates and prodrugs of such compounds, to pharmaceutical compositions comprising such compounds, and to the use of such compounds in the treatment and prevention of medical disorders and diseases, most especially by the inhibition of $NLRP_3$.

24 Claims, No Drawings

(56) References Cited

U.S. PATENT DOCUMENTS

| | | | |
|---|---|---|---|
| 2020/0299284 A1 | 9/2020 | O'Neill et al. | |
| 2020/0317637 A1 | 10/2020 | Cooper et al. | |
| 2020/0354341 A1 | 11/2020 | Cooper et al. | |
| 2020/0361895 A1 | 11/2020 | Cooper et al. | |
| 2021/0122716 A1 | 4/2021 | Cooper et al. | |
| 2021/0122739 A1 | 4/2021 | Cooper et al. | |
| 2021/0130359 A1 | 5/2021 | Cooper et al. | |
| 2021/0163412 A1* | 6/2021 | Shannon | A61K 31/4433 |
| 2021/0347737 A1 | 11/2021 | Cooper et al. | |

FOREIGN PATENT DOCUMENTS

| | | |
|---|---|---|
| CN | 110151749 A | 8/2019 |
| DK | 2006 00313 L | 3/2006 |
| EP | 0125864 A1 | 11/1984 |
| EP | 0176304 A1 | 4/1986 |
| EP | 0177163 A2 | 4/1986 |
| EP | 0189069 A2 | 7/1986 |
| EP | 0204513 A2 | 12/1986 |
| EP | 0224842 A2 | 6/1987 |
| EP | 0249938 A2 | 12/1987 |
| EP | 0318602 A1 | 6/1989 |
| EP | 0610653 A1 | 8/1994 |
| EP | 0795548 A1 | 9/1997 |
| EP | 0885890 A1 | 12/1998 |
| EP | 0976742 A1 | 2/2000 |
| EP | 0987552 A2 | 3/2000 |
| EP | 1236468 A1 | 9/2002 |
| EP | 1270565 A1 | 1/2003 |
| EP | 1670749 A1 | 2/2005 |
| EP | 1995240 A1 | 11/2008 |
| EP | 2543670 A1 | 1/2013 |
| EP | 2781216 A1 | 9/2014 |
| EP | 2962692 A1 | 1/2016 |
| EP | 3272739 A1 | 1/2018 |
| FR | 2068472 A1 | 8/1971 |
| GB | 797474 A | 7/1958 |
| GB | 1146979 A | 3/1969 |
| GB | 1322980 A | 7/1973 |
| JP | S6045573 A | 12/1985 |
| JP | 62-148482 A | 7/1987 |
| JP | 62-195376 A | 8/1987 |
| JP | 06199053 A | 7/1994 |
| JP | 06199054 A | 7/1994 |
| JP | 2000053649 A | 2/2000 |
| PL | 221813 B1 | 5/2016 |
| RU | 2022963 C1 | 11/1994 |
| WO | WO 91/10668 A1 | 7/1991 |
| WO | WO 92/04319 A1 | 3/1992 |
| WO | WO 93/04045 A1 | 3/1993 |
| WO | WO 93/04046 A1 | 3/1993 |
| WO | WO 97/11057 A1 | 3/1997 |
| WO | WO 98/032733 A1 | 7/1998 |
| WO | WO 2020/010118 A1 | 1/2000 |
| WO | WO 00/55126 A2 | 9/2000 |
| WO | WO 01/19390 A1 | 3/2001 |
| WO | WO 01/57037 A1 | 8/2001 |
| WO | WO 02/06246 A1 | 1/2002 |
| WO | WO 02/094176 A2 | 11/2002 |
| WO | WO 03/031194 A1 | 4/2003 |
| WO | WO 03/035076 A1 | 5/2003 |
| WO | WO 03/045400 A1 | 6/2003 |
| WO | WO 03/099805 A1 | 12/2003 |
| WO | WO 2004/039376 A1 | 5/2004 |
| WO | WO 2005/032488 A2 | 4/2005 |
| WO | WO 2005/035520 A1 | 4/2005 |
| WO | WO 2006/039212 A2 | 4/2006 |
| WO | WO 2006/085815 A1 | 8/2006 |
| WO | WO 2008/090382 A1 | 7/2008 |
| WO | WO 2009/065096 A1 | 5/2009 |
| WO | WO 2011/041694 A2 | 4/2011 |
| WO | WO 2015/069666 A1 | 5/2015 |
| WO | WO 2016/127924 A1 | 8/2016 |
| WO | WO 2016/131098 A1 | 8/2016 |
| WO | WO 2016/131098 A8 | 8/2016 |
| WO | WO 2016/138473 A1 | 9/2016 |
| WO | WO 2017/106957 A1 | 6/2017 |
| WO | WO 2017/129897 A1 | 8/2017 |
| WO | WO 2017/140778 A1 | 8/2017 |
| WO | WO 2017/184604 A1 | 10/2017 |
| WO | WO 2017/184624 A1 | 10/2017 |
| WO | WO 2017/189652 A1 | 11/2017 |
| WO | WO 2018/015445 A1 | 1/2018 |
| WO | WO 2018/136890 A1 | 7/2018 |
| WO | WO 2018/152396 A1 | 8/2018 |
| WO | WO 2018/215818 A1 | 11/2018 |
| WO | WO 2019/008025 A1 | 1/2019 |
| WO | WO 2019/008029 A1 | 1/2019 |
| WO | WO 2019/023147 A1 | 1/2019 |
| WO | WO 2019/034686 A1 | 2/2019 |
| WO | WO 2019/034688 A1 | 2/2019 |
| WO | WO 2019/034690 A1 | 2/2019 |
| WO | WO 2019/034692 A1 | 2/2019 |
| WO | WO 2019/034693 A1 | 2/2019 |
| WO | WO 2019/034696 A1 | 2/2019 |
| WO | WO 2019/034697 A1 | 2/2019 |
| WO | WO 2019/068772 A1 | 4/2019 |
| WO | WO 2019/092170 A1 | 5/2019 |
| WO | WO 2019/092171 A1 | 5/2019 |
| WO | WO 2019/092172 A1 | 5/2019 |
| WO | WO 2019/166619 A1 | 9/2019 |
| WO | WO 2019/166621 A1 | 9/2019 |
| WO | WO 2019/166623 A1 | 9/2019 |
| WO | WO 2019/166624 A1 | 9/2019 |
| WO | WO 2019/166627 A1 | 9/2019 |
| WO | WO 2019/166628 A1 | 9/2019 |
| WO | WO 2019/166629 A1 | 9/2019 |
| WO | WO 2019/166632 A1 | 9/2019 |
| WO | WO 2019/166633 A1 | 9/2019 |
| WO | WO 2019/206871 A1 | 10/2019 |
| WO | WO 2019/211463 A1 | 11/2019 |
| WO | WO 2020/010143 A1 | 1/2020 |
| WO | WO 2020/018970 A1 | 1/2020 |
| WO | WO 2020/035464 A1 | 2/2020 |
| WO | WO 2020/035465 A1 | 2/2020 |
| WO | WO 2020/035466 A1 | 2/2020 |
| WO | WO 2020/079207 A1 | 4/2020 |
| WO | WO 2020/086732 A1 | 4/2020 |
| WO | WO 2020/102096 A1 | 5/2020 |
| WO | WO 2020/104657 A1 | 5/2020 |
| WO | WO 2020/208249 A1 | 10/2020 |
| WO | WO 2021/032588 A1 | 2/2021 |
| WO | WO-2021032591 A * | 2/2021 ........... C07D 515/22 |
| WO | WO 2021/043966 A1 | 3/2021 |
| WO | WO 2021/165245 A1 | 8/2021 |

OTHER PUBLICATIONS

Coll, "In their own words . . . 2012 IEIIS Young Investigator Awardees," Endotoxin Newsletter, vol. 19, No. 1, Editor Jerold Weiss, PhD, Dept. of Internal Medicine, University of Iowa, (Oct. 2013).

Coll, et al., "Correction: The Cytokine Release inhibitory Drug CRID3 Targets ASC Oligomerisation in the NLRP3 and AIM2 Inflammasomes," PloS One, vol. 6, Issue 12, e29539, (Feb. 27, 2013).

Coll, et al., "Supporting Information: The Cytokine Release Inhibitory Drug CRID3 Targets ASC Oligomerisation in the NLRP3 and AIM2 Inflammasomes," PloS One, vol. 6, Issue 12, e29539, (Feb. 27, 2013).

Coll, et al., "The Cytokine Release Inhibitory Drug CRID3 Targets ASC Oligomerisation in the NLRP3 and AIM2 Inflammasomes," PloS One, vol. 6, Issue 12, e29539, (Dec. 2011).

Dalvie, et al., "Biotransformation Reactions of Five-Membered Aromatic Heterocyclic Rings," Chem. Res. Toxicol., vol. 15, No. 3, pp. 269-299 (2002).

Dempsey, et al., "Cytokine release inhibitor drug, CRID3, inhibits the NLRP3 inflammasome in glia," Journal of Neuroimmunology, vol. 275(1-2), p. 147, (2014).

Email from CAS Customer Center <help@cas.org>, Subject: RE: Case #66345503: question of indexing, 218-Sent: Oct. 9, 2020.

(56) References Cited

OTHER PUBLICATIONS

Febbraio, "Role of interleukins in obesity: implications for metabolic disease," Trends in Endocrinology and Metabolism, vol. 25, No. 6, pp. 312-319, (Jun. 2014).
Guo, et al., "inflammasomes: mechanism of action, role in disease, and therapeutics," Nature Medicine, vol. 21, No. 7, pp. 677-687, (Jul. 2015).
Haneklaus, et ai., "Modulatory mechanisms controlling the NLRP3 inflammasome in inflammation: recent developments," Current opinion in immunology, 25, (1), pp. 40-45, (2013).
Mullen, et al., "Pattern recognition receptors as potential therapeutic targets in inflammatory rheumatic disease," Arthritis Research & Therapy, 17:122, (2015).
St Jean, et al., "Mitigating Heterocycle Metabolism in Drug Discovery," Journal of Medicinal Chemistry, 55, pp. 6002-6020, (2012).
Stocks, et al., "On Chemistry, On Medical Chemistry," Published in Great Britain by Sci-Ink Limited, ISBN 978-0-9550072-3-1, pp. 214-215, (2007).
WIPO Application No. PCT/EP2019/055127, PCT International Preliminary Report on Patentability dated Sep. 17, 2020.
U.S. Appl. No. 16/638,648, Requirement for Restriction/Eiection dated Apr. 20, 2021.
U.S. Appl. No. 16/761,993, Requirement for Restriction/Eiection dated Apr. 9, 2021.
Alsante, et al., "Pharmaceutical Impurity Identification: A Case Study Using a Multidisciplinary Approach," Journal of Pharmaceutical Sciences, 93(9): 2296-2309, (2004).
Baldwin, et al., "Inhibiting the inflammasome: a chemical perspective," Journal of Medicinal Chemistry, 59(5): 1691-1710, (2016).
Booth, et al., "A new and efficient approach to the synthesis of 6-amidino-2-oxopurines," Journal of the Chemical Society Perkin Transactions, 1, 1(10): 1241-1251, (2001).
Braddock, et ai., "Targeting IL-1 in Inflammatory Disease: New Opportunities for Therapeutic Intervention," Nature Reviews Drug Discovery, 3(4): 330-340, (2004).
CAS 1026500-66-2; STN Entry Date: Jun. 8, 2008; CN Compound Name: 2-Thiophenesulfonamide, 5-chloro-N-[[[2-ethyl-4-[7-fluoro-6-(methylamino)-1-oxo-2(1H)-isoquinolinyl]-6-methylphenyl]amino]carbonyl]—(CA Index Name).
CAS 1026685-26-6; STN Entry Date: Jun. 9, 2008; CN Compound Name: 2-Thiophenesulfonamide, 5-chloro-N-[[[5-[6-(ethylamino)-7-fluoro-1-oxo-2(1H)-isoquinolinyl]-3-methyl-2-pyridinyl]amino]carbonyl]—(CA Index Name).
CAS 1026892-76-1 ; STN Entry Date: Jun. 10, 2008; CN Compound Name: Benzamide, 2,3,4,5,6-pentafluoro-N-[2-[4-[[[[(2,3,4-trifluorophenyl)amino]carbonyl]amino]sulfonyl]phenyl]ethyl]—(CA Index Name).
CAS 1027977-57-6; STN Entry Date: Jun. 13, 2008; CN Compound Name: 2-Thiophenesulfonamide, 5-chloro-N-[[[4-[6-(ethylamino)-7-fluoro-1-oxo-2(1H)-isoquinolinyl]-2-(2-hydroxyethoxy)-6-methylphenyl]amino]carbonyl]—(CA Index Name).
CAS 104843-72-3 STN Entry Date:1986; CN Compound Name: 1H-Pyrazole-4-carboxylic acid, 5-[[[[(4,6-dimethyl-I-oxido-2-pyrimidinyl)amino]carbonyl]amino]sulfonyl]-1-(2-pyridinyl)-, ethyl ester (CA Index Name).
CAS 123807-74-8; STN Entry Date: 1995; CN Compound Name: 2H-1,2,5-Thiadiazino[5,6-a] indole-10-sulfonamide, N-[[(3-cyano-4,6-dimethyl-2-pyridinyl)amino]carbonyl]-2-methyl-1,1-dioxide (CA Index Name).
CAS 1332606-77-5; STN Entry Date: Sep. 16, 2011; CN Compound Name: 2-(3-(3-Amino-4-(tert-butoxycarbonyl)phenylsulfonyl)ureido)-4-chlorobenzoic acid.
CAS 1347649-72-2; STN Entry Date: Dec. 2, 2001; CN Compound Name: 2-Thiophenesulfonamide, 5-chloro-N-H[4-[7-fluoro-6-(methylamino)-1-oxo-2(1H)-isoquinolinyl]-2-(methoxymethoxy)phenyl]amino]carbonyl]—(CA Index Name).
CAS 170648-58-5; STN Entry Date: 1995; CN Compound Name: Acetamide, N-[5-[[[[(2,3-dihydro-1,5-dimethyl-3-oxo-2-phenyl-1H-pyrazol-4-yl)amino]carbonyl]amino]sulfonyl]-1,3,4-thiadiazol-2-yl]—(CA Index Name).
CAS 36628-63-4; STN Entry Date: 1972; CN Compound Name: Benzamide, N-[2-[5-[[[(bicyclo[2 .2]oct-5-en-2-ylamino)carbonyl]amino]sulfonyl]-2-thienyl]ethyl]-5-chloro-2-methoxy—(CA Index Name).
CAS 438013-57-1; STN Entry Date: Jul. 10, 2002; CN Compound Name: 2-Thiophenesulfonamide, 5-methyl-N-[(1-naphthalenylamino)carbonyl]—(CA Index Name).
CAS 663215-37-0; STN Entry Date: Mar. 15, 2004; CN Compound Name: 1H-1,2,4-Triazole-1-carboxamide, N-(2-chlorophenyl)-5-[[[[(2-chlorophenyl)amino]carbonyl]amino sulfonyl]—(CA Index Name).
CAS 84884-96-2; STN Entry Date: 1983; CN Compound Name: Acetamide, N-15-[[[[(2-methy1phenyl)amino)thioxomethyl] amino]sulfonyl]-1,3,4-thiadiazol-2-yl]—(CA Index Name).
CAS 907958-32-1; STN Entry Date: Sep. 20, 2006; CN Compound Name: Acetamide, N-[5-[[[[(2,5-dioxo-4-imidazolidinyl)amino] carbonyl]amino]sulfonyl]-4-methyl-2-thiazolyl]—(CA Index Name).
CAS 959378-15-5; STN Entry Date: Dec. 21, 2007; CN Compound Name: Benzo[b]thiophene-3-carboxylic acid,4,5,6,7-tetrahydro-6,6-dimethyl-2-[[[[(2-methyl-1H-imidazol-1-yl)sulfonyl]amino]carbonyl]amino]-, ethyl ester (CA Index Name).
CAS 959664-76-7; STN Entry Date: Dec. 28, 2007; CN Compound Name: Benzo[b]thiophene-3-carboxylic acid, 4,5,6,7-tetrahydro-6,6-dimethyl-2-[[[[(5-methyl-1H-pyrazol-1-yl)sulfonyl]amino]carbonyl]amino]-, ethyl ester (CA Index Name).
CAS RN 1026469-15-7; STN Entry Date: Jun. 8, 2008; CN Compound Name: 2-Thiophenesulfonamide, 5-chloro-N-[[[2-(cyclopropyloxy)-4-[7-fluoro-6-(methylamino)-1-oxo-2(1H)-isoquinolinyl]phenyl]amino]carbonyl]—(CA Index Name).
CAS RN 84884-72-0; STN Entry Date: 1983; CN Compound Name: Acetamide, N-[5-[[[[(2-chlorophenyl)amino]carbonyl] amino]sulfonyl]-1,3,4-thiadiazol-2-yl]—(CA Index Name).
CAS RN 84884-75-3; STN Entry Date:1983; CN Compound Name: Acetamide, N-(5-[[[[(2-bromophenyl)amino]carbonyl]amino]sulfonyl]-1,3,4-thiadiazol-2-yl]—(CA Index Name).
CAS RN 84884-76-4; STN Entry Date: 1983; CN Compound Name: Acetamide, N-[5-[[[[(2-methylphenyl)amino]carbonyl] amino]sulfonyl]-1,3,4-thiadiazol-2-yl]—(CA Index Name).
CAS RN 84884-82-2; STN Entry Date: 1983; CN Compound Name: Acetamide, N-[5-[[[1-naphthalenylamino)carbonyl] amino]sulfonyl]-1,3,4-thiadiazol-2-yl]—(CA Index Name).
Coll, et al., "A small-molecule inhibitor of the NLRP3 inflammasome for the treatment of inflammatory diseases," Nature Medicine, 21(3): 248-255, (2015).
Cubrilovic, et al., "Determination of Protein-Ligand Binding Constants of a Cooperatively Regulated Tetrameric Enzyme Using Electrospray Mass Spectrometry," ACS Chemical Biology, 9(1): 218-226, (2014).
Dias, et al., "Synthesis of new imidazo[4,5-d][1,3]diazepine derivatives from 5-amino-4-(cyanoformimidoyl)imidazoles," Journal of Heterocyclic Chemistry, 33(3): 855-862, (1996).
El-Telbany, et al., "Synthesis of Thiophenesulphonylureas and Thioureas Structurally Related to Certain Oral Hypoglycemic drugs. Part I," Egypt Journal of Pharmaceutical Science, 16(4): 397-401, (1975).
Fleming, et al., "Novel axially chiral bis-arylthiourea-based organocatalysts for asymmetric Friedel-Crafts type reactions," Tetrahedron Letters, 47(39): 7037-7042, (2006).
Groß, et al. "K+ Eflux-Independent NLRP3 Inflammasome Activation by Small Molecules Targeting Mitochondria," Immunity, 45(4):761-773, (2016).
Hebeisen, et al., "Orally active aminopyridines as inhibitors of tetrameric fructose-1,6-bisphosphatase," Bioorganic & Medicinal Chemistry Lettters, 21(11): 3237-3242, (2011).
Hill, et al., "Dual Action Sulfonylureas: NLRP3 Inhibition and Insulin Secretion," 1st Queensland Annual Chemistry Symposium, Poster p. 20, Nov. 25, 2016 (and accompanying programme).
Hill, et al., "Sulfonylureas as Concomitant Insulin Secretagogues and NLRP3 Inflammasome Inhibitors," Chem Med Chem, 12(17): 1449-1457, (2017).
Holland, "Preparation of some additional sulfonylureas," Journal of Organic Chemistry, 26(5): 1662-1665, (1961).

(56) References Cited

OTHER PUBLICATIONS

Hutton, et al., "The NLRP3 inflammasome in kidney disease and autoimmunity," Nephrology, 21(9): 736-744, (2016).
Kazuto, et al., "Design, synthesis and biological activity of novel non-peptidyl endothelin converting enzyme inhibitors, 1-phenyl-tetrazole-formazan analogues," Bioorganic & Medicinal Chemistry Letters, 12(9): 1275-1278, (2002).
Khelili, et al., "Synthesis and vasodilator effects of 3- and 7-sulfonylurea-1,2,4-benzothiadiazin-1,1-dioxides on rat aorta," Bioorganic & Medicinal Chemistry, 3(5): 495-503, (1995).
Khuntwal, et al., "Credential role of van derwaal volumes and atomic masses in modeling Hepatitis C virus NS5B polymerase inhibition by tetrahydrobenzo-thiophenes using SVM and MLR aided QSAR studies," Current Bioinformatics, 8(4): 465-471, (2013).
Kim, et al., "Role for NLRP3 Inflammasome-mediated, IL-1β-Dependent Responses in Severe, Steroid-Resistant Asthma," 196(3): 283-297, (2017).
Krishnan, et al., "Inflammasome activity is essential for one kidney/deoxycorticosterone acetate/salt-induced hypertension in mice," British Journal of Pharmacology, 173(4): 752-765, (2016).
Laliberte, et al., "Glutathione S-transferase omega 1-1 is a target of cytokine release inhibitory drugs and may be responsible for their effect on interleukin-1B posttranslational processing," Journal of Biological Chemistry, 278(19): 16567-16578, (2003).
Laporte, et al., "Tetrahydrobenzothiophene inhibitors of hepatitis C virus NS5B polymerase," Bioorganic & Medicinal Chemistry Letters, 16(1): 100-103, (2006).
Lerner, et al. "*Mycobacterium tuberculosis* replicates within necrotic human macrophages," Journal of Cell Biology, 216(3): 583-594, (2017).
Li, et al., "Discovery of the first SecA inhibitors using structure-based virtual screening," Biochemical and Biophysical Research Communications, 368(4): 839-845, (2008).
Luckhurst, et al., "A convenient synthesis of sulfonylureas from carboxylic acids and sulfonamides via an in situ Curtius rearrangement," Tetrahedron Letters, 48(50): 8878-8882, (2007).
Ludwig-Portugall, et al., "An NLRP3-specific inflammasome inhibitor attenuates crystal-induced kidney fibrosis in mice," Kidney International, 90(3): 525-539, (2016).
Mokhtar, et al., "Synthesis of nitrogenous compounds. Part III," Pakistan Journal of Scientific and Industrial Research, 34(1): pp. 9-15, (1991).
Monnerat, et al.,"Macrophage-dependent IL-1β production induces cardiac arrhythmias in diabetic mice," Nature Communications, 7(13344): 1-15, (2016).
Mridha, et al., "NLRP3 inflammasome blockade reduces iiver inflammation and fibrosis in experimental NASH in mice," Journal of Hepatology, 66(5): 1037-1046, (2017).
Ouf, et al., "Sulphonyl Ureas and Thioureas of 1,3,4-Thiodiazole to be Tested as Hypoglycomic Agents," Egyptian Journal of Pharmaceutical Sciences, 21(3-4): 189-198, (1980).
Ouf, et al., "Thiophene sulphonylureas structurally related to antidiabetic drugs," Journal of Drug Research Egypt, 6(2): 123-129, (1974).
Pacini, et al., "2-(3-Thienyl)-5,6-dihydroxypyrimidine-4-carboxylic acids as inhibitors of HCV NS5B RdRp," Bioorganic & Medicinal Chemistry Letters, 19(21): 6245-6249, (2009).
Pinar, et al., "PB1-F2 Peptide Derived from Avian influenza A Virus H7N9 Induces Inflammation via Activation of the NLRP3 Inflammasome," Journal of Biological Chemistry, 292(3): 826-836, (2017).
Proks, et al., "Sulfonylurea stimulation of insulin secretion," Diabetes, 51(3): S368-S376, (2002).
Rotroff, et al., "Predictive Endocrine Testing in the 21st Century Using in Vitro Assays of Estrogen Receptor Signaling Responses," Environmental Science & Technology, 48(15): 8706-8716, (2014).
Saczewski, et al., "Synthesis of Novel Aryl(heteroaryl)suifonyl Ureas of Possible Biological Interest," Molecules, 15(3): 1113-1126, (2010).
Salla, et al., "identification, Synthesis, and Biological Evaluation of the Major Human Metabolite of NLRP3 Inflammasome Inhibitor MCC950," ACS Medicinal Chemistry Letters, 7(12): 1034-1038, (2016).
Sarges, et al., "Sulfamylurea hypoglycemic agents. 6. High potency derivatives," Journal of Medicinal Chemistry, 19(5): 695-709, (1976).
Shah, et al., "Analysis of Pfizer Compounds in EPA's ToxCast Chemicals-Assay Space," Chemical Research in Toxicology, 2014, 27(1), 86-98: (2014).
Shah, et al., "Setting Clinical Exposure Levels of Concern for Drug-Induced Liver Injury (DILI) Using Mechanistic in vitro Assays," Toxicological Sciences, 147(2): 500-514, (2015).
Sipes, et al., "Profiling 976 ToxCast Chemicals across 331 Enzymatic and Receptor Signaling Assays," Chemical Research in Toxicology, 26(6): 878-895, (2013).
Urban, et al., "Novel Synthesis of 1-(1,2,3,5,6,7-Hexahydro-s-indacen-4-yl)-3-[4-(1-hydroxy-1-methyl-ethyl)-furan-2-sulfonyl]urea, an Anti-inflammatory Agent," Synthetic Communications, 33(12): 2029-2043, (2003).
Wambaugh, et al., "High-Throughput Models for Exposure-Based Chemical Prioritization in the ExpoCast Project," Environmental Science & Technology, 47(15): 8479-8488, (2013).
Waterman, et al. "Improved Protocol and Data Analysis for Accelerated Shelf-Life Estimation of Solid Dosage Forms," Pharmaceutical Research, 24(4): 780-790, (2007).
Youssef, et al., "N1,N3-Diaryl sulfonylureas as possible anticancer agents," Alexandria Journal of Pharmaceutical Sciences, 8(3): 223-225, (1994).
Youssef, et al., "Synthesis of sulofenur analogues as antitumour agents: part II," Medicinal Chemistry Research, 11(9): 481-503, (2002).
Zhen, et al., "Recent advances in discovery and development of promising therapeutics against Hepatitis C virus NS5B RNA-dependent RNA polymerase," Mini Reviews in Medicinal Chemistry, 5(12): 1103-1112, (2005).
GB Application No. 061713082.4 Search Report under Section 17(5) dated Apr. 30, 2018.
G8 Application No. 061721727.4 Search Report under Section 17(5) dated Sep. 17, 2018.
GB Application No. GB1721729.0 Search Report under Section 17(5) dated Aug. 30, 2018.
GB Application No. 061721731.6 Search Report under Section 17(5) dated Sep. 3, 2018.
GB Application No. 061721732.4 Search Report under Section 17(5) dated Sep. 3, 2018.
G8 Application No. 061721735.7 Search Report under Section 17(5) dated Aug. 30, 2018.
G6 Application No. 061721736.5 Search Report under Section 17(5) dated Aug. 30, 2018.
G6 Application No. 061803391.6 Search Report under Section 17(5) dated Oct. 16, 2018.
GB Application No. GB1803392.8 Search Report under Section 17(5) dated Oct. 16, 2018.
WIPO Application No. PCT/EP2018/072111, PCT International Preliminary Report on Patentability dated Feb. 27, 2020.
WIPO Application No. PCT/EP2018/072111, PCT International Search Report and Written Opinion of the International Searching Authority dated Nov. 6, 2018.
WIPO Application No. PCT/EP2018/072115, PCT International Preliminary Report on Patentability dated Feb. 27, 2020.
WIPO Application No. PCT/EP2018/072115, PCT International Search Report and Written Opinion of the International Searching Authority dated Oct. 24, 2018.
WIPO Application No. PCT/EP2018/072119, PCT International Preliminary Report on Patentability dated Feb. 27, 2020.
WIPO Application No. PCT/EP2018/072119, PCT International Search Report and Written Opinion of the International Searching Authority dated Dec. 11, 2018.
WIPO Application No. PCT/EP2018/072123, PCT International Preliminary Report on Patentability dated Feb. 27, 2020.
WIPO Application No. PCT/EP2018/072123, PCT International Search Report and Written Opinion of the International Searching Authority dated Nov. 14, 2018.

(56) References Cited

OTHER PUBLICATIONS

WIPO Application No. PCT/EP2018/072125, PCT International Preliminary Report on Patentability dated Feb. 27, 2020.
WIPO Application No. PCT/EP2018/072125, PCT International Search Report and Written Opinion of the International Searching Authority dated Oct. 22, 2018.
WIPO Application No. PCT/EP2018/080737, PCT International Preliminary Report on Patentability dated May 22, 2020.
WIPO Application No. PCT/EP2018/080737, PCT International Search Report and Written Opinion of the International Searching Authority dated Jan. 30, 2019.
WIPO Application No. PCT/EP2018/686739, PCT International Preliminary Report on Patentability dated May 22, 2020.
WIPO Application No. PCT/EP2018/080739, PCT International Search Report and Written Opinion of the International Searching Authority dated Jan. 25, 2019.
WIPO Application No. PCT/EP2018/080746, PCT International Preliminary Report on Patentability dated May 22, 2020.
WIPO Application No. PCT/EP2018/080746, PCT International Search Report and Written Opinion of the International Searching Authority dated Jan. 25, 2019.
WIPO Application No. PCT/EP2019/055127, PCT International Search Report and Written Opinion of the International Searching Authority dated Apr. 24, 2019.
WIPO Application No. PCT/IB2017/053059, PCT International Preliminary Reporton Patentability dated Dec. 5, 2019.
WIPO Application No. PCT/IB2017/053059, PCT International Search Report and Written Opinion of the International Searching Authority dated Aug. 8, 2017.
Belikov, et al., "The interconnection between chemical structure, properties of substances and their effect on the body", MEDpress-inform, Pharmaceutical Chemistry, Text Book, 4th Edition, Moscow, Chap. 2.6, 27-29, (2007), Brief.
Disease—Wikipedia, retrieved from the internet on Jan. 5, 2022 at: https://en.wikipedia.org/wiki/Disease.
Parajuli, et al., "Prodrug as a novei approach of drug delivery—a review," Journal of Drug Delivery & Therapeutics, 5(3), pp. 5-9, (2015).
Solvation—Wikipedia, retrieved from the internet on Jan. 5, 2022 at: https://en.wikipedia.org/wiki/Solvation.
Zawilska, et al., "Prodrugs: a challenge for the drug development," Pharmacological reports: PR, vol. 65, No. 1, pp. 1-14, (Apr. 2013).
RU Application No. 2020110219/04(017079) Office Action and Search Report dated Feb. 15, 2022, English tranlsation of office action.
Balant, et al., "Metabolic Considerations in Prodrug Design," Burger's Medicinal Chemistry and Drug Discovery, 5th Edition, vol. 1; Principles and Practice, pp. 949-982, Editied by Manfred E. Wolff, © 1995 John Wiley & Sons, Inc.
Banker, et al., Prodrugs, Modern Pharmaceutics, 3rd edition, Revised and Expanded, pp. 451 and 596, (1995).
Bundgaard, "Design of Prodrugs," Chapter1, p. 1, (1985).
Ettmayer, et al., "Perspective, Lessons Learned from Marketed and Investigational Prodrugs," Journal of Medicinal Chemistry, vol. 47, No. 10, 2393-2404, (May 6, 2004).
Jordan, "Tamoxifen: A Most Unlikely Pioneering Medicine," Nature Reviews, Drug Discovery, vol. 2, 205-213, (Mar. 2003).
Silverman, "The Organic Chemistry of Drug Design and Drug Action," Prodrugs and Drug Delivery Stystem, The Organic Chemistry of Drug Design and Drug Action, Chapter 8, pp. 352-400, (1992).
Stella, "Prodrugs as therapeutics," Xpert Opin. Ther. Patients, 14(3): 277-280, (2004).
Testa, "Prodrug research: futile or fertile," Biochemical Pharmacology, 68, 2097-2106, (2004).
U.S. Appl. No. 16/638,648, Non-Final Office Action dated Oct. 12, 2021.
U.S. Appl. No. 16/638,700, Non-Final Office Action dated Sep. 10, 2021.
U.S. Appl. No. 16/761,993, Non-Final Office Action dated Aug. 16, 2021.
U.S. Appl. No. 16/762,000, Requirement for Restriction/Election dated Nov. 1, 2021.
U.S. Appl. No. 16/977,241, Requirement for Restriction/Election dated Nov. 30, 2021.
Himiceskij, Chemical Encyclopedia, (1983), p. 130-131, Brief.
Belikov, et al., "MEDpress-inform," Pharmaceutical Chemistry, Text Book, 4 th Edition, Moscow, 622 pages, 11, 27-29, (2007), Brief statement of relevance.
Gavrilov, et al., Pharmaceutical Technology, Preparation of Medicaments, Text Book, Moscow Publishing group "GEOTAR-Media", 2010, 624, p. 20, Brief statement of relevance.
Guidelines for Conducting Preclinical Drug Studies. Partone. M.: Grifand K, 2012, 944 p., ed. Mironova A.N, Brief statement of relevance.
Han," Targeted Prodrug Design to Optimize Drug Delivery," AAPS Pharmsci, 2 (1) article 6, 1-11, (2000).
Mashkovskiy, "Medicaments," Moscow, "Medicine", 1993, chapter 1, p. 8, Brief statement of relevance.
Zhulenko, et ai., "Pharmacology", Moscow: KolosS, p. 34-35, (2008), Brief statement of relevance.
U.S. Appl. No. 16/638,648, Final Office Action dated May 27, 2022.
U.S. Appl. No. 16/638,700, Final Office Action dated May 16, 2022.
U.S. Appl. No. 16/761,993, Non-Final Office Action dated Apr. 6, 2022.
U.S. Appl. No. 16/762,000, Non-Final Office Action dated Apr. 4, 2022.
U.S. Appl. No. 16/977,241, Non-Final Office Action dated Jun. 13, 2022.
U.S. Appl. No. 16/638,704, Final Office Action dated Jul. 8, 2022.
U.S. Appl. No. 16/761,993, Non-Final Office Action dated Oct. 12, 2022.
U.S. Appl. No. 16/638,648, Notice of Allowance dated Oct. 18, 2022.
U.S. Appl. No. 16/638,700, Non-Final Office Action dated Oct. 19, 2022.
U.S. Appl. No. 16/762,000, Final Office Action dated Nov. 15, 2022.

* cited by examiner

SULFONYLUREAS AND SULFONYLTHIOUREAS AS NLRP3 INHIBITORS

CROSS-REFERENCE TO RELATED APPLICATION

This application is the US national stage of PCT/EP2018/072123 filed Aug. 15, 2018, which claims priority to GB 1713082.4 filed Aug. 15, 2017; GB 1718563.8 filed Nov. 9, 2017; GB 1721726.6 filed Dec. 22, 2017; GB 1721732.4 filed Dec. 22, 2017; and GB 1810983.5 filed Jul. 4, 2018.

FIELD OF THE INVENTION

The present invention relates to sulfonylureas and sulfonylthioureas comprising a 5-membered heteroaryl ring attached to the sulfonyl group, wherein the heteroaryl ring is di-substituted at the 3- and 4-positions relative to the point of attachment of the sulfonyl group, wherein at least one of the di-substituents contains a nitrogen atom.

The present invention further relates to associated salts, solvates, prodrugs and pharmaceutical compositions, and to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R$^2$ resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3−/− mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1β receptor antagonist anakinra, the neutralizing IL-1β antibody canakinumab and the soluble decoy IL-1β receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1, WO 2018/136890 A1 and WO 2018/015445 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

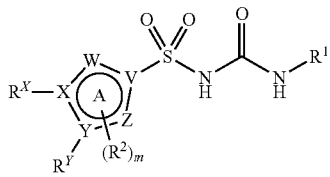

Formula (I)

wherein:
Q is selected from O or S;
V, X and Y are each independently selected from C and N, and W and Z are each independently selected from N, O, S, NH and CH, provided that at least one of V, W, X, Y and Z is N, O, S or NH;
$R^X$ and $R^Y$ are each independently any saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally $R^X$ and $R^Y$ together with the atoms X and Y to which they are attached may form a 3- to 12-membered saturated or unsaturated cyclic group, wherein the cyclic group may optionally be substituted;
$R^1$ is a cyclic group substituted at the α-position, wherein $R^1$ may optionally be further substituted;
m is 0, 1 or 2;
each $R^2$ is independently a halo, —OH, —NO₂, —NH₂, —N₃, —SH, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally $R^X$ and any $R^2$ attached to W may together with the atoms W and X to which they are attached form a 3- to 12-membered saturated or unsaturated cyclic group, wherein the cyclic group may optionally be substituted; and
optionally $R^Y$ and any $R^2$ attached to Z may together with the atoms Y and Z to which they are attached form a 3- to 12-membered saturated or unsaturated cyclic group, wherein the cyclic group may optionally be substituted;
provided that at least one of $R^X$ and $R^Y$ comprises a nitrogen atom; and
provided that the compound is not:

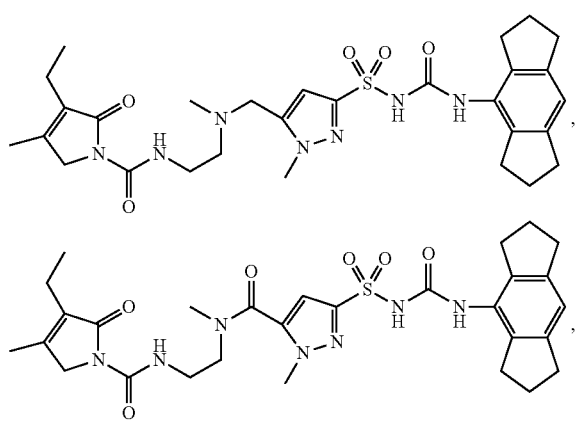

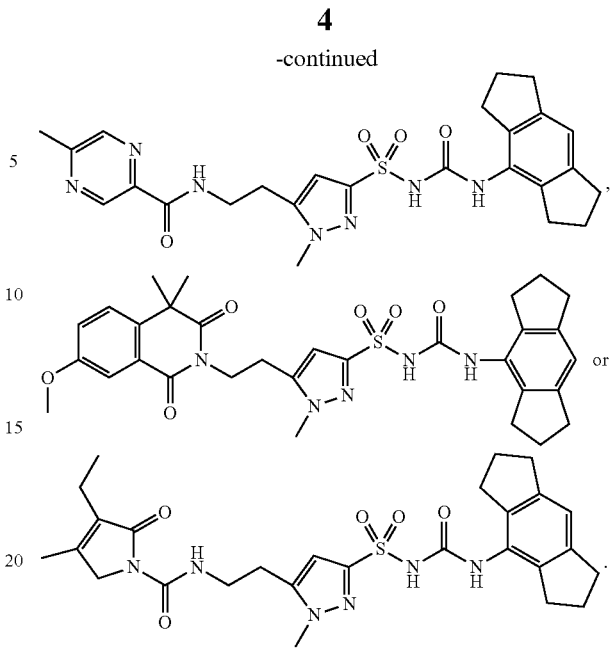

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{20}$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear (i.e. straight-chained) or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

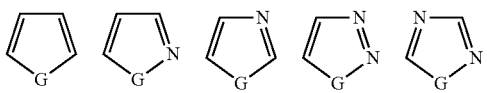

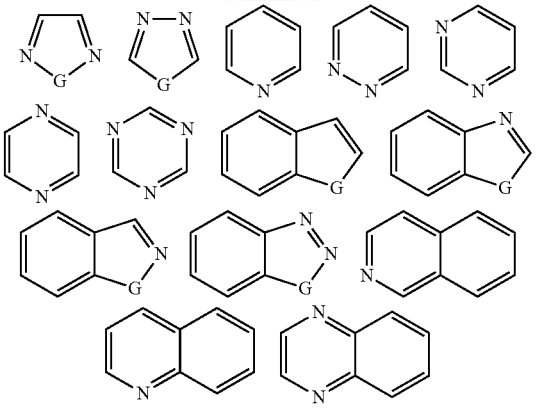

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SORB; —SO$_2$H; —SO$_2$R$^\beta$; —SO$_2$NH$_2$; —SO$_2$NHR$^\beta$; SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or (ii) any two hydrogen atoms attached to the same atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$—.

Where reference is made to a —R$^\alpha$—C(N$_2$)R$^\beta$ group, what is intended is:

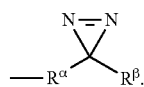

Typically, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SORB; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; or —NR$^\beta$—R$^\alpha$—N(R$^\beta$)$_2$; and/or (ii) any two hydrogen atoms attached to the same carbon atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

Alternately in the optionally substituted groups or moieties defined immediately above, each —R$^\beta$ may be independently selected from a C$_1$-C$_6$ alkyl, C$_2$-C$_6$ alkenyl, C$_2$-C$_6$ alkynyl or C$_2$-C$_6$ cyclic group, or any two —R$^\beta$ attached to the same nitrogen atom may, together with the nitrogen atom to which they are attached, form a C$_2$-C$_7$ cyclic group, wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), halo, —OH, —NH$_2$, —CN, —C≡CH, oxo (=O), or 4- to 6-membered heterocyclic group.

More typically, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$;
—R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$; and/or (ii) any two hydrogen atoms attached to the same carbon atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N($R^\beta$)— or —$R^\alpha$—;
  wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
  wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (=O), or 4- to 6-membered heterocyclic group.

Alternately in the optionally substituted groups or moieties defined immediately above, each —$R^\beta$ may be independently selected from a $C_1$-$C_6$ alkyl, $C_2$-$C_6$ alkenyl, $C_2$-$C_6$ alkynyl or $C_2$-$C_6$ cyclic group, or any two —$R^\beta$ attached to the same nitrogen atom may, together with the nitrogen atom to which they are attached, form a $C_2$-$C_7$ cyclic group, wherein any —$R^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), halo, —OH, —$NH_2$, —CN, —C≡CH, oxo (=O), or 4- to 6-membered heterocyclic group.

More typically still, in an optionally substituted group or moiety:
  (i) each hydrogen atom may optionally be replaced by a group independently selected from halo; —CN; —$R^\beta$; —OH; —O$R^\beta$; —$R^\alpha$-halo; —$R^\alpha$—CN; —$R^\alpha$—$R^\beta$; —$R^\alpha$—OH; —$R^\alpha$—O$R^\beta$; —S$R^\beta$; —SO$R^\beta$; —$SO_2$H; —$SO_2R^\beta$; —$SO_2NH_2$; —$SO_2NHR^\beta$; —$SO_2N(R^\beta)_2$; —$R^\alpha$—S$R^\beta$; —$R^\alpha$—SO$R^\beta$; —$R^\alpha$—$SO_2$H; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —NH$R^\beta$; N($R^1$)$_2$; —$R^\alpha$—$NH_2$; —$R^\alpha$—NH$R^\beta$; —$R^\alpha$—N($R^\beta$)$_2$; —CHO; —COR$^\beta$; —COOH; —COOR$^\beta$; —OCOR$^\beta$; —$R^\alpha$—CHO; —$R^\alpha$—CORI; —$R^\alpha$—COOH; —$R^\alpha$—COOR$^\beta$; or —$R^\alpha$—OCOR$^\beta$; and/or
  (ii) any two hydrogen atoms attached to the same carbon atom may optionally be replaced by a π-bonded substituent independently selected from oxo (=O), =S, =NH or =N$R^\beta$; and/or
  (iii) any two hydrogen atoms attached to the same or different atoms, within the same optionally substituted group or moiety, may optionally be replaced by a bridging substituent independently selected from —O—, —S—, —NH—, —N($R^\beta$)— or —$R^\alpha$—;
  wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and
  wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, halo, —OH, or 4- to 6-membered heterocyclic group.

Alternately in the optionally substituted groups or moieties defined immediately above, each —$R^\beta$ may be independently selected from a $C_1$-$C_6$ alkyl, $C_2$-$C_6$ alkenyl, $C_2$-$C_6$ alkynyl or $C_2$-$C_6$ cyclic group, or any two —$R^\beta$ attached to the same nitrogen atom may, together with the nitrogen atom to which they are attached, form a $C_2$-$C_7$ cyclic group, wherein any —$R^\beta$ may optionally be substituted with one or more $C_1$-$C_4$ alkyl, $C_1$-$C_4$ haloalkyl, halo, —OH, or 4- to 6-membered heterocyclic group.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —N($R^\beta$)—, —N(O)($R^\beta$)—, —$N^+(R^\beta)_2$— or —$R^\alpha$—) of an optionally substituted group or moiety (e.g. $R^1$) must only be attached to the specified group or moiety and may not be attached to a second group or moiety (e.g. $R^2$), even if the second group or moiety can itself be optionally substituted.

The term "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

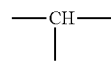

is replaced by

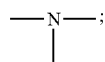

—$CH_2$— is replaced by —NH—, —O— or —S—;
—$CH_3$ is replaced by —$NH_2$, —OH or —SH;
—CH= is replaced by —N=;
$CH_2$= is replaced by NH=, O= or S=; or
CH≡ is replaced by N≡;
provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —$CH_2$— group in the backbone of a hydrocarbyl or other group being replaced by a —N(O)($R^β$)— or —$N^+(R^β)_2$— group, what is intended is that:

—$CH_2$— is replaced by

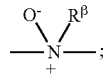

or
—$CH_2$— is replaced by

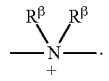

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are not to be counted as carbon atoms when calculating the number of carbon atoms in a $C_x$-$C_y$ group. For example, a morpholinyl group is to be considered a $C_4$ heterocyclic group, not a $C_6$ heterocyclic group.

As will be understood, ring A is a 5-membered heteroaryl group.

In one embodiment, at least one of $R^X$ and $R^Y$ is monovalent.

In a further embodiment, ring A is monocyclic. In such an embodiment, the groups $R^X$, $R^Y$ and, if present, $R^2$ are monovalent, but may be or include cyclic groups. Examples of monocyclic 5-membered heteroaryl groups include furanyl, thiophenyl, pyrrolyl, imidazolyl, pyrazolyl, triazolyl, tetrazolyl, oxazolyl, isoxazolyl, oxadiazolyl, thiazolyl, isothiazolyl and thiadiazolyl groups.

As stated, V, X and Y are each independently selected from C and N, and W and Z are each independently selected from N, O, S, NH and CH, provided that at least one of V, W, X, Y and Z is N, O, S or NH. For the purposes of the present specification, where it is stated that W or Z may be NH or CH, it is to be understood that this refers to W and Z before possible substitution with $R^2$ is considered. Thus, where it is stated that W or Z may be NH, it is to be understood that W or Z may be NH or N—$R^2$ after substitution is considered. Similarly, where it is stated that W or Z may be CH, it is to be understood that W or Z may be CH or C—$R^2$ after substitution is considered.

Typically, at least two of V, W, X, Y and Z are C or CH. More typically, two or three of V, W, X, Y and Z are C or CH. Most typically, three of V, W, X, Y and Z are C or CH.

In one embodiment, at least one of V, W, X, Y and Z is N or NH. It will be understood that in such an embodiment ring A is a 5-membered heteroaryl group containing at least one nitrogen atom in the 5-membered ring structure. Examples of such 5-membered heteroaryl groups include pyrrolyl, imidazolyl, pyrazolyl, triazolyl, tetrazolyl, oxazolyl, isoxazolyl, oxadiazolyl, thiazolyl, isothiazolyl and thiadiazolyl groups. Typically, one of X and Y is N and one of X and Y is C.

In a further embodiment, V is C, X and Y are each independently selected from C and N, and W and Z are each independently selected from N, O, S, NH and CH, provided that at least one of W, X, Y and Z is N, O, S or NH. Typically, V is C, X and Y are each independently selected from C and N, and W and Z are each independently selected from N, O, S, NH and CH, provided that at least one of W, X, Y and Z is N or NH.

Typically in such an embodiment, at least one of W, X, Y and Z is C or CH. More typically, one or two of W, X, Y and Z are C or CH. More typically still, two of W, X, Y and Z are C or CH. More typically in such an embodiment, one of X and Y is N and one of X and Y is C.

In another embodiment, V, X and Y are each independently selected from C and N, and W and Z are each independently selected from N, O, S, NH and CH, provided that at least two of V, W, X, Y and Z are N or NH. Typically in such an embodiment, two of V, W, X, Y and Z are N or NH. Typically in such an embodiment, V is C. Typically in such an embodiment, one or two of W, X, Y and Z are C or CH. More typically, two of W, X, Y and Z are C or CH. Typically, one of X and Y is N and one of X and Y is C.

In yet another embodiment, V, X and Y are each independently selected from C and N, and W and Z are each independently selected from N, NH and CH, provided that at least one of V, W, X, Y and Z is N or NH. Typically in such an embodiment, V is C. Typically in such an embodiment, at least one of W, X, Y and Z is C or CH. More typically, one or two of W, X, Y and Z are C or CH. More typically still, two of W, X, Y and Z are C or CH. Typically, at least two of V, W, X, Y and Z are N or NH. More typically, V is C and at least two of W, X, Y and Z are N or NH. More typically, two of V, W, X, Y and Z are N or NH. More typically still, V is C and two of W, X, Y and Z are N or NH. Typically, one of X and Y is N and one of X and Y is C. Most typically, ring A is an imidazolyl or pyrazolyl group. For example, in one embodiment V is C, X is C, Y is N, one of W and Z is CH and one of W and Z is N.

Typically, $R^X$ comprises at least one nitrogen atom.

Typically, $R^X$ is a monovalent group comprising at least one nitrogen atom, wherein $R^X$ contains from 1 to 11 atoms other than hydrogen or halogen. More typically, $R^X$ contains from 3 to 9 atoms other than hydrogen or halogen. Most typically, $R^X$ contains from 4 to 7 atoms other than hydrogen or halogen.

Where $R^X$ is monovalent, $R^X$ may be any saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton. Typically the hydrocarbyl group of $R^X$ includes at least one heteroatom N in its carbon skeleton, wherein the hydrocarbyl group may optionally include one or more further heteroatoms N, O or S in its carbon skeleton. Where the hydrocarbyl group of $R^X$ is optionally substituted, typically it is substituted with one or more groups selected from halo, —CN, —OH, —$NH_2$, oxo (=O) and =NH.

More typically, where $R^X$ is a monovalent group, $R^X$ is a saturated hydrocarbyl group, wherein the hydrocarbyl group is straight-chained or branched, or is or includes cyclic groups, wherein the hydrocarbyl group may optionally be substituted with one or more groups selected from halo, —CN, —OH, —$NH_2$ and oxo (=O), wherein the hydrocarbyl group includes at least one heteroatom N in its carbon skeleton, and wherein the hydrocarbyl group may optionally include one or two further heteroatoms independently selected from N and O in its carbon skeleton.

In one embodiment, where $R^X$ is a monovalent group, $R^X$ is a saturated hydrocarbyl group, wherein the hydrocarbyl group is straight-chained or branched, or is or includes cyclic groups, wherein the hydrocarbyl group may optionally be substituted with one or more groups selected from fluoro, chloro and —CN, wherein the hydrocarbyl group includes at least one heteroatom N in its carbon skeleton, and wherein the hydrocarbyl group may optionally include one or two further heteroatoms independently selected from N and O in its carbon skeleton.

In one embodiment, where $R^X$ is a monovalent group, $R^X$ has the formula:

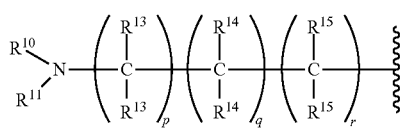

wherein:
p is 0 or 1;
q is 0 or 1;
r is 0 or 1;
$R^{10}$ and $R^{11}$ are each independently selected from hydrogen or an alkyl, cycloalkyl, saturated heterocyclic, aryl, heteroaryl, arylalkyl or heteroarylalkyl group, or $R^{10}$ and $R^{11}$ together with the nitrogen atom to which they are attached form a saturated heterocyclic group;
each $R^{13}$, $R^{14}$ and $R^{15}$ is independently selected from hydrogen or a halo, —CN, —OH, alkyl, —O-alkyl, cycloalkyl, —O-cycloalkyl, saturated heterocyclic or —O-(saturated heterocyclic) group, and/or any two $R^{13}$, two $R^{14}$ or two $R^{15}$ may together with the carbon atom to which they are attached form a C=O group, and/or any two $R^{13}$, $R^{14}$ or $R^{15}$ may together with the carbon atom or carbon atoms to which they are attached form a cycloalkyl or saturated heterocyclic group;
wherein optionally $R^{11}$ together with any $R^{13}$, $R^{14}$ or $R^{15}$ may together with the carbon and nitrogen atoms to which they are attached form a saturated heterocyclic group;
wherein any alkyl, cycloalkyl, saturated heterocyclic, arylalkyl or heteroarylalkyl group may optionally be substituted with one or more halo, —CN, —OH, —$NH_2$, oxo (=O), alkyl, haloalkyl, —O-alkyl, —O-haloalkyl, —NH(alkyl), —NH(haloalkyl), —N(alkyl)$_2$, —N(alkyl)(haloalkyl) and/or —N(haloalkyl)$_2$ groups; and
wherein any aryl or heteroaryl group may optionally be substituted with one or more halo, —CN, —OH, —$NH_2$, alkyl, haloalkyl, —O-alkyl, —O-haloalkyl, —NH(alkyl), —NH(haloalkyl), —N(alkyl)$_2$, —N(alkyl)(haloalkyl) and/or —N(haloalkyl)$_2$ groups.

Typically, p is 1, q is 0 or 1 and r is 0, i.e. $R^X$ has the formula:

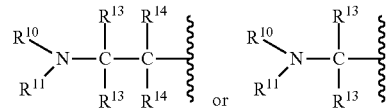

wherein $R^{10}$, $R^{11}$, $R^{13}$ and $R^{14}$ are as defined above.
In one embodiment:
$R^{10}$ is hydrogen or a $C_1$-$C_4$ alkyl or $C_3$-$C_4$ cycloalkyl group;
$R^{11}$ is a $C_1$-$C_4$ alkyl or $C_3$-$C_4$ cycloalkyl group, or $R^{11}$ together with any one of $R^{13}$, $R^{14}$ or $R^{15}$ forms a $C_1$-$C_4$ alkylene group; or
$R^{10}$ and $R^{11}$ together form a $C_2$-$C_5$ alkylene group;
wherein any alkylene group may optionally include one or two heteroatoms independently selected from O and N in its carbon skeleton;
wherein any alkyl or alkylene group may optionally be substituted with one or more halo, —CN, —OH, —$NH_2$, oxo (=O), —OMe, —O-halomethyl, —NHMe, —NH(halomethyl), —NMe$_2$, —NMe(halomethyl) and/or —N(halomethyl)$_2$ groups; and
wherein any cycloalkyl group may optionally be substituted with one or more halo, —CN, —OH, —$NH_2$, oxo (=O), methyl, halomethyl, —OMe, —O-halomethyl, —NHMe, —NH(halomethyl), —NMe$_2$, —NMe(halomethyl) and/or —N(halomethyl)$_2$ groups.

Typically:
$R^{10}$ is a $C_1$-$C_3$ alkyl or cyclopropyl group;
$R^{11}$ is a $C_1$-$C_3$ alkyl or cyclopropyl group, or $R^{11}$ together with any one of $R^{13}$, $R^{14}$ or $R^{15}$ forms a $C_1$-$C_3$ alkylene group; or
$R^{10}$ and $R^{11}$ together form a $C_2$-$C_4$ alkylene group;
wherein any alkylene group may optionally include an oxygen atom in its carbon skeleton;
wherein any alkyl or alkylene group may optionally be substituted with one or more fluoro, chloro, —CN, —OH, oxo (=O) and/or —OMe groups, wherein any cyclopropyl group may optionally be substituted with one or more fluoro, chloro, —CN, —OH, methyl and/or —OMe groups, and wherein any methyl (e.g. Me) group may optionally be substituted with one or more fluoro and/or chloro groups.

More typically:
$R^{10}$ is a $C_1$-$C_3$ alkyl or cyclopropyl group;
$R^{11}$ is a $C_1$-$C_3$ alkyl or cyclopropyl group, or $R^{11}$ together with any one of $R^{13}$ or $R^{14}$ forms a $C_1$-$C_3$ alkylene group; or
$R^{10}$ and $R^{11}$ together form a $C_2$-$C_4$ alkylene group, wherein the $C_2$-$C_4$ alkylene group may optionally include an oxygen atom in its carbon skeleton;
wherein any alkyl or alkylene group may optionally be substituted with one or more fluoro, chloro, —CN, —OH, oxo (=O) and/or —OMe groups, wherein any cyclopropyl group may optionally be substituted with one or more fluoro, —CN, —OH, methyl and/or —OMe groups, and wherein any methyl group may optionally be substituted with one or more fluoro and/or chloro groups.

More typically still:

$R^{10}$ is a methyl or ethyl group;

$R^{11}$ is a methyl, ethyl, isopropyl or cyclopropyl group; or $R^{10}$ and $R^{11}$ together form a $C_2$-$C_4$ alkylene group;

wherein any methyl, ethyl, isopropyl or alkylene group may optionally be substituted with one or more fluoro, —OH, —OMe, —OCH$_2$F, —OCF$_2$H, —OCF$_3$ or oxo (=O) groups, and wherein any cyclopropyl group may optionally be substituted with one or more fluoro, —OH, —OMe, —OCH$_2$F, —OCF$_2$H or —OCF$_3$ groups.

In one aspect of any of the above embodiments, $R^{10}R^{11}N$— is monovalent. Typically, where $R^{10}R^{11}N$— is monovalent, $R^{10}R^{11}N$— contains from 2 to 10 atoms other than hydrogen or halogen. More typically, where $R^{10}R^{11}N$— is monovalent, $R^{10}R^{11}N$— contains from 3 to 6 atoms other than hydrogen or halogen.

Most typically, $R^{10}$ and $R^{11}$ are both methyl groups, or $R^{10}$ and $R^{11}$ together form a —CH$_2$CH$_2$— or —CH$_2$CH$_2$CH$_2$— group.

In one embodiment:

each $R^{13}$, $R^{14}$ and $R^{15}$ is independently selected from hydrogen or a halo, —CN, —OH, $C_1$-$C_4$ alkyl, $C_3$-$C_4$ cycloalkyl, —O—($C_1$-$C_4$ alkyl) or —O—($C_3$-$C_4$ cycloalkyl) group, and/or any two $R^{13}$, two $R^{14}$ or two $R^{15}$ may together with the carbon atom to which they are attached form a C=O group, and/or any two $R^{13}$, $R^{14}$ or $R^{15}$ may together form a $C_1$-$C_4$ alkylene group, and/or $R^{11}$ together with any one of $R^{13}$, $R^{14}$ or $R^{15}$ may form a $C_1$-$C_4$ alkylene group;

wherein any alkylene group may optionally include one or two heteroatoms independently selected from 0 and N in its carbon skeleton;

wherein any alkyl or alkylene group may optionally be substituted with one or more halo, —CN, —OH, —NH$_2$, oxo (=O), —OMe, —O-halomethyl, —NHMe, —NH(halomethyl), —NMe$_2$, —NMe(halomethyl) and/or —N(halomethyl)$_2$ groups; and wherein any cycloalkyl group may optionally be substituted with one or more halo, —CN, —OH, —NH$_2$, oxo (=O), methyl, halomethyl, —OMe, —O-halomethyl, —NHMe, —NH(halomethyl), —NMe$_2$, —NMe(halomethyl) and/or —N(halomethyl)$_2$ groups.

In another embodiment:

each $R^{13}$, $R^{14}$ and $R^{15}$ is independently selected from hydrogen or a fluoro, chloro, —CN, —OH, $C_1$-$C_3$ alkyl, cyclopropyl, —O—($C_1$-$C_3$ alkyl) or —O-(cyclopropyl) group, and/or any two $R^{13}$, two $R^{14}$ or two $R^{15}$ may together with the carbon atom to which they are attached form a C=O group, and/or any two $R^{13}$, $R^{14}$ or $R^{15}$ may together form a $C_1$-$C_3$ alkylene group, and/or $R^{11}$ together with any one of $R^{13}$, $R^{14}$ or $R^{15}$ may form a $C_1$-$C_3$ alkylene group;

wherein any alkylene group may optionally include an oxygen atom in its carbon skeleton;

wherein any alkyl or alkylene group may optionally be substituted with one or more fluoro, chloro, —CN, —OH, oxo (=O) and/or —OMe groups, wherein any cyclopropyl group may optionally be substituted with one or more fluoro, chloro, —CN, —OH, methyl and/or —OMe groups, and wherein any methyl (e.g. Me) group may optionally be substituted with one or more fluoro and/or chloro groups.

In one embodiment, each $R^{13}$, $R^{14}$ and $R^{15}$ is independently selected from hydrogen or a halo, —OH, $C_1$-$C_3$ alkyl, or —O—($C_1$-$C_3$ alkyl) group, and/or any two $R^{13}$, two $R^{14}$ or two $R^{15}$ may together with the carbon atom to which they are attached form a C=O group, and/or any two $R^{13}$, $R^{14}$ or $R^{15}$ may together form a $C_1$-$C_3$ alkylene group, wherein the $C_1$-$C_3$ alkylene group may optionally include an oxygen atom in its carbon skeleton, and wherein any alkyl or alkylene group may optionally be substituted with one or more halo, —OH or oxo (=O) groups. Alternatively or in addition, $R^{11}$ together with any of $R^{13}$, $R^{14}$ or $R^{15}$ may form a $C_1$-$C_4$ alkylene group, wherein the $C_1$-$C_4$ alkylene group may optionally include one or two heteroatoms independently selected from 0 and N in its carbon skeleton, and wherein the $C_1$-$C_4$ alkylene group may optionally be substituted with one or more halo, —CN, —OH, oxo (=O), —OMe and/or —O-halomethyl groups.

In another embodiment, p is 1, q is 0 or 1 and r is 0, and each $R^{13}$ and $R^{14}$ is independently selected from hydrogen or a fluoro, chloro, —OH, methyl, ethyl, —OMe or —OEt group, and/or any two $R^{13}$ or two $R^{14}$ may together with the carbon atom to which they are attached form a C=O group, and/or any two $R^{13}$ or $R^{14}$ may together form a $C_1$-$C_2$ alkylene group, wherein the $C_1$-$C_2$ alkylene group may optionally include an oxygen atom in its carbon skeleton, and wherein any methyl, ethyl or alkylene group may optionally be substituted with one or more fluoro, chloro, —OH or oxo (=O) groups. Alternatively or in addition, $R^{11}$ together with any one of $R^{13}$ or $R^{14}$ may form a $C_1$-$C_3$ alkylene group, wherein the $C_1$-$C_3$ alkylene group may optionally be substituted with one or more fluoro, chloro, —CN, —OH, oxo (=O) and/or —OMe groups.

More typically, p is 1, q is 0 or 1 and r is 0, $R^{10}R^{11}N$— is monovalent, and each $R^{13}$ and $R^{14}$ is independently selected from hydrogen or a fluoro, methyl, ethyl, fluoromethyl or fluoroethyl group, and/or any two $R^{13}$ or two $R^{14}$ may together with the carbon atom to which they are attached form a C=O or cyclopropyl group, and wherein the cyclopropyl group may optionally be substituted with one or more fluoro groups.

Typically in any of the above embodiments, all or all but any one or two of $R^{13}$, $R^{14}$ and $R^{15}$ are hydrogen or halogen. More typically, all or all but any one or two of $R^{13}$, $R^{14}$ and $R^{15}$ are hydrogen or fluoro. Most typically, all or all but any one or two of $R^{13}$, $R^{14}$ and $R^{15}$ are hydrogen.

Typically, where $R^{10}R^{11}N$— is monovalent, the group:

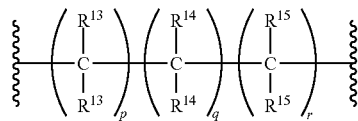

contains from 1 to 6 atoms other than hydrogen or halogen. More typically, the group contains from 1 to 4 atoms other than hydrogen or halogen.

In another embodiment, where $R^X$ is a monovalent group, $R^X$ has the formula:

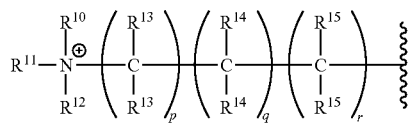

wherein p, q, r, $R^{10}$, $R^{11}$, $R^{13}$, $R^{14}$ and $R^{15}$ are as defined above, with the exception that $R^{10}$ and $R^{11}$ are not hydrogen, and wherein $R^{12}$ is selected from an alkyl, cycloalkyl, saturated heterocyclic, aryl, heteroaryl, arylalkyl or heteroarylalkyl group, wherein the alkyl, cycloalkyl, saturated heterocyclic, arylalkyl or heteroarylalkyl group may optionally be substituted with one or more halo, —CN, —OH, —$NH_2$, oxo (=O), alkyl, haloalkyl, —O-alkyl, —O-haloalkyl, —NH(alkyl), —NH(haloalkyl), —N(alkyl)$_2$, —N(alkyl)(haloalkyl) and/or —N(haloalkyl)$_2$ groups, and wherein the aryl or heteroaryl group may optionally be substituted with one or more halo, —CN, —OH, —$NH_2$, alkyl, haloalkyl, —O-alkyl, —O-haloalkyl, —NH(alkyl), —NH(haloalkyl), —N(alkyl)$_2$, —N(alkyl)(haloalkyl) and/or —N(haloalkyl)$_2$ groups. As will be understood, any optional or typical embodiment in relation to the definition of any of p, q, r, $R^{10}$, $R^{11}$, $R^{13}$, $R^{14}$ and $R^{15}$ is equally applicable to the present embodiment, provided that $R^{10}$ and $R^{11}$ are not hydrogen.

Alternatively in the above embodiment, $R^{10}$, $R^{11}$ and $R^{12}$ may, together with the nitrogen atom to which they are attached, form a cyclic group such as a saturated $C_5$-$C_8$ cyclic group.

In one embodiment, $R^{10}R^{11}R^{12}N^+$— is monovalent. Typically, where $R^{10}R^{11}R^{12}N^+$— is monovalent, $R^{10}R^{11}R^{12}N^+$— contains from 4 to 15 atoms other than hydrogen or halogen. More typically, where $R^{10}R^{11}R^{12}N^+$— is monovalent, $R^{10}R^{11}R^{12}N^+$— contains from 4 to 7 atoms other than hydrogen or halogen.

Typically, $R^{12}$ is a $C_1$-$C_4$ alkyl or $C_3$-$C_4$ cycloalkyl group, wherein the alkyl group may optionally be substituted with one or more halo, —CN, —OH, —$NH_2$, oxo (=O), —OMe, —O-halomethyl, —NHMe, —NH(halomethyl), —NMe$_2$, —NMe(halomethyl) and/or —N(halomethyl)$_2$ groups, and wherein the cycloalkyl group may optionally be substituted with one or more halo, —CN, —OH, —$NH_2$, oxo (=O), methyl, halomethyl, —OMe, —O-halomethyl, —NHMe, —NH(halomethyl), —NMe$_2$, —NMe(halomethyl) and/or —N(halomethyl)$_2$ groups.

Typically, $R^{12}$ is a $C_1$-$C_3$ alkyl or a cyclopropyl group, wherein the alkyl group may optionally be substituted with one or more fluoro, chloro, —CN, —OH, oxo (=O) and/or —OMe groups, wherein the cyclopropyl group may optionally be substituted with one or more fluoro, chloro, —CN, —OH, methyl and/or —OMe groups, and wherein any methyl group may optionally be substituted with one or more fluoro and/or chloro groups.

More typically, $R^{12}$ is a $C_1$-$C_3$ alkyl or a cyclopropyl group, wherein the alkyl group may optionally be substituted with one or more fluoro, chloro, —CN, —OH, oxo (=O) and/or —OMe groups, wherein the cyclopropyl group may optionally be substituted with one or more fluoro, —CN, —OH, methyl and/or —OMe groups, and wherein any methyl group may optionally be substituted with one or more fluoro and/or chloro groups.

More typically still, $R^{12}$ is a methyl, fluoromethyl, ethyl or fluoroethyl group.

Most typically, $R^{12}$ is a methyl group. Most typically, where $R^{12}$ is a methyl group, $R^{10}$ and $R^{11}$ are also methyl groups, i.e. $R^{10}R^{11}R^{12}N^+$— is Me$_3$N$^+$—.

In one embodiment, where $R^X$ is a monovalent group, $R^X$ is selected from the group consisting of:

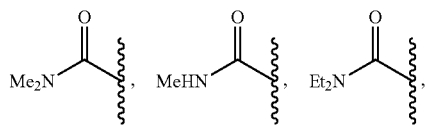

-continued

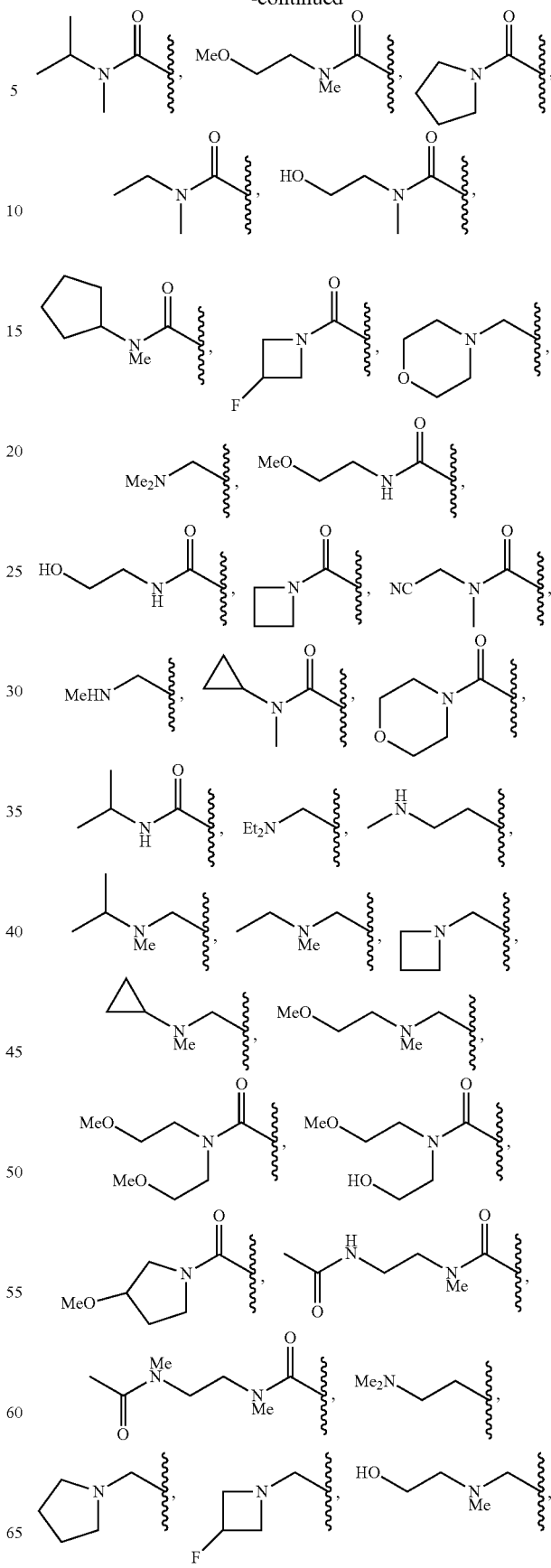

-continued

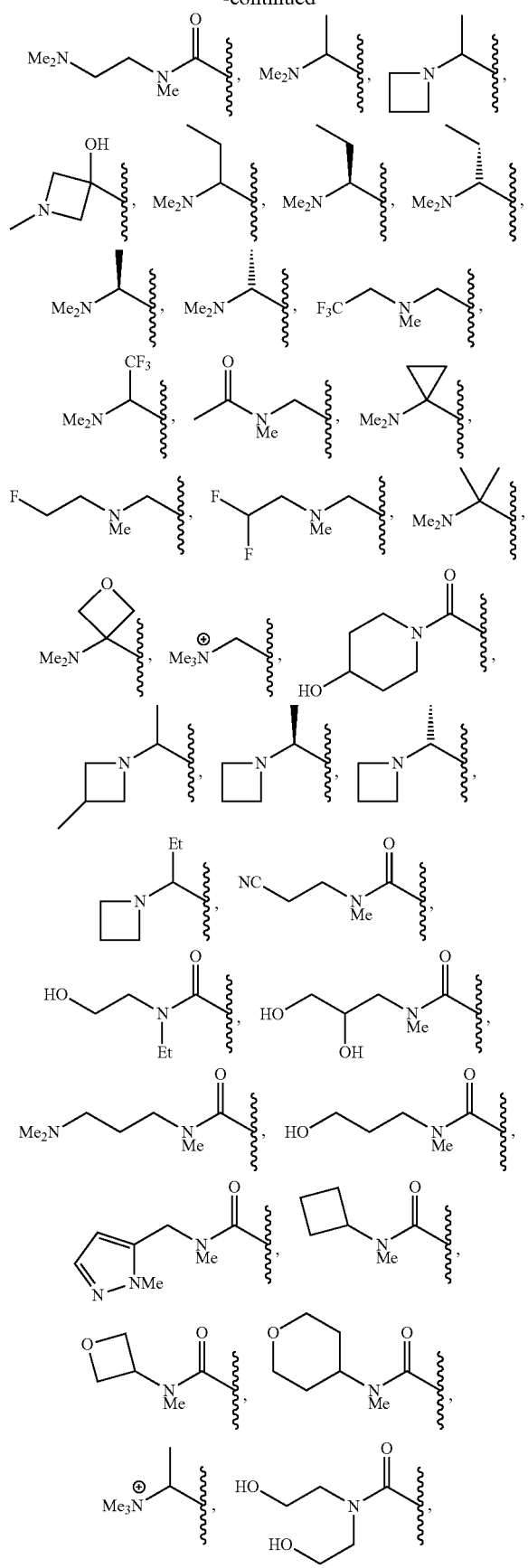

-continued

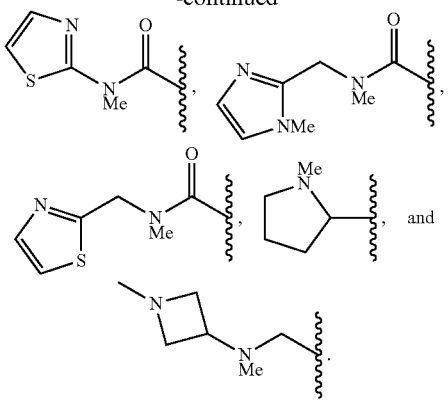

Typically $R^Y$ is a monovalent group. Typically, where $R^Y$ is a monovalent group, $R^Y$ contains from 1 to 11 atoms other than hydrogen or halogen. More typically, $R^Y$ contains from 1 to 8 atoms other than hydrogen or halogen. Most typically, $R^Y$ contains from 1 to 6 atoms other than hydrogen or halogen.

In one embodiment, each $R^Y$ is a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton. Where the hydrocarbyl group of $R^Y$ is optionally substituted, typically it is substituted with one or more groups selected from halo, —CN, —OH, —NH$_2$, oxo (=O) and =NH.

Typically, each $R^Y$ is a saturated hydrocarbyl group, wherein the saturated hydrocarbyl group may be straight-chained or branched, or is or includes cyclic groups, wherein the saturated hydrocarbyl group may optionally be substituted with one or more groups selected from halo, —CN, —OH, —NH$_2$ and oxo (=O), and wherein the saturated hydrocarbyl group may optionally include one or two heteroatoms N or O in its carbon skeleton.

In one embodiment, $R^Y$ is a saturated hydrocarbyl group, wherein the hydrocarbyl group may be straight-chained or branched, or may be or include cyclic groups, wherein the saturated hydrocarbyl group may be unsubstituted or optionally substituted with one or more halo (e.g. fluoro and/or chloro) groups, and wherein the saturated hydrocarbyl group may optionally include one or two oxygen atoms in its carbon skeleton.

In one embodiment, $R^Y$ may be any group as defined in relation to $R^X$. In such an embodiment, $R^Y$ may be the same as or different to $R^X$.

More typically, each $R^Y$ is independently selected from a $C_1$-$C_6$ alkyl or $C_3$-$C_6$ cycloalkyl group, wherein any $C_1$-$C_6$ alkyl or $C_3$-$C_6$ cycloalkyl group may optionally be substituted with one or more fluoro, chloro, —CN, —OH, —NH$_2$, —OMe, —NHMe and/or —NMe$_2$ groups, wherein any methyl (Me) group may optionally be substituted with one or more fluoro and/or chloro groups.

More typically still, each $R^Y$ is independently selected from a $C_1$-$C_5$ alkyl or $C_3$-$C_5$ cycloalkyl group, wherein any $C_1$-$C_5$ alkyl or $C_3$-$C_5$ cycloalkyl group may optionally be substituted with one or more fluoro, chloro, —CN, —OH, —NH$_2$, —OMe, —NHMe and/or —NMe$_2$ groups, wherein any methyl (Me) group may optionally be substituted with one or more fluoro and/or chloro groups.

Yet more typically, each $R^Y$ is independently selected from a $C_1$-$C_4$ alkyl or $C_3$-$C_4$ cycloalkyl group, wherein any $C_1$-$C_4$ alkyl or $C_3$-$C_4$ cycloalkyl group may optionally be substituted with one or more fluoro and/or chloro groups.

Most typically each $R^Y$ is independently selected from a methyl, ethyl, isopropyl or cyclopropyl group.

In one embodiment, where $R^Y$ is a monovalent group, $R^Y$ is selected from the group consisting of methyl, ethyl, isopropyl, cyclopropyl, t-butyl, —$CO_2H$, —$CH_2CH_2NMe_2$, —$CH_2NMe_2$, —$CH_2CMe_3$ and —$CMe_2OH$.

In one embodiment, any monovalent $R^X$ or $R^Y$ contains from 1 to 7 carbon atoms. Typically, any monovalent $R^X$ or $R^Y$ contains from 1 to 6 carbon atoms. More typically, any monovalent $R^X$ or $R^Y$ contains from 1 to 5 carbon atoms.

In an alternative embodiment, $R^X$ and $R^Y$ together with the atoms X and Y to which they are attached may form a 3- to 12-membered saturated or unsaturated cyclic group, wherein the cyclic group may optionally be substituted. Typically in such an embodiment, $R^X$ and $R^Y$ together with the atoms X and Y to which they are attached form a 5- or 6-membered saturated or unsaturated cyclic group, wherein the cyclic group may optionally be substituted.

In one embodiment, for example where $R^X$ and $R^Y$ together with the atoms X and Y to which they are attached form a saturated or unsaturated cyclic group as discussed above, $R^X$ and $R^Y$ together form a divalent group —$R^{XY}$—, wherein —$R^{XY}$— comprises at least one nitrogen atom, and wherein —$R^{XY}$— is directly attached to the ring atoms X and Y.

For the purposes of the present specification, where it is stated that a first atom or group is "directly attached" to a second atom or group it is to be understood that the first atom or group is covalently bonded to the second atom or group with no intervening atom(s) or groups being present. So, for example, for the group —(C=O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

Typically, —$R^{XY}$— contains from 1 to 12 atoms other than hydrogen or halogen. More typically, —$R^{XY}$— contains from 3 to 10 atoms other than hydrogen or halogen. Most typically, —$R^{XY}$— contains from 4 to 8 atoms other than hydrogen or halogen.

In one embodiment, —$R^{XY}$— is a saturated or unsaturated hydrocarbylene group, wherein the hydrocarbylene group may be straight-chained or branched, or be or include cyclic groups, wherein the hydrocarbylene group may optionally be substituted, wherein the hydrocarbylene group includes at least one heteroatom N in its carbon skeleton, and wherein the hydrocarbylene group may optionally include one or more further heteroatoms N, O or S in its carbon skeleton. Where the hydrocarbylene group of —$R^{XY}$— is optionally substituted, typically it is substituted with one or more groups selected from halo, —CN, —OH, —$NH_2$, oxo (=O) and =NH.

More typically, —$R^{XY}$— is a saturated hydrocarbylene group, wherein the saturated hydrocarbylene group is straight-chained or branched, wherein the saturated hydrocarbylene group may optionally be substituted with one or more groups selected from halo, —CN, —OH, —$NH_2$ and oxo (=O), wherein the saturated hydrocarbylene group includes at least one heteroatom N in its carbon skeleton, and wherein the saturated hydrocarbylene group may optionally include one further heteroatom N or O in its carbon skeleton.

In one embodiment, —$R^{XY}$— is a $C_2$-$C_5$ alkylene group, wherein the alkylene group is substituted with a monovalent group —$NR^{10}R^{11}$ or a monovalent group $R^{10}R^{11}R^{12}N^+$—, wherein $R^{10}$, $R^{11}$ and $R^{12}$ are as defined above, and wherein the alkylene group may optionally be further substituted with one or more halo, —CN, —OH, oxo (=O), —O-alkyl and/or —O-haloalkyl groups.

More typically, —$R^{XY}$— is a $C_3$-$C_4$ alkylene group, wherein the alkylene group is substituted with a monovalent group —$NR^{10}R^{11}$, wherein:

$R^{10}$ is hydrogen or a $C_1$-$C_4$ alkyl or $C_3$-$C_4$ cycloalkyl group;

$R^{11}$ is a $C_1$-$C_4$ alkyl or $C_3$-$C_4$ cycloalkyl group; or $R^{10}$ and $R^{11}$ together form a $C_2$-$C_4$ alkylene group;

wherein any alkyl or alkylene group may optionally be substituted with one or more halo, —CN, —OH, oxo (=O), —OMe and/or —O-halomethyl groups, and wherein any cycloalkyl group may optionally be substituted with one or more halo, —CN, —OH, oxo (=O), methyl, halomethyl, —OMe and/or —O-halomethyl groups.

More typically still, —$R^{XY}$— is a $C_3$-$C_4$ alkylene group, wherein the alkylene group is substituted with a monovalent group —$NR^{10}R^{11}$, wherein:

$R^{10}$ is a methyl or ethyl group;

$R^{11}$ is a methyl, ethyl, isopropyl or cyclopropyl group; or $R^{10}$ and $R^{11}$ together form a $C_2$-$C_4$ alkylene group;

wherein any methyl, ethyl, isopropyl or alkylene group may optionally be substituted with one or more fluoro, —OH or oxo (=O) groups, and wherein any cyclopropyl group may optionally be substituted with one or more fluoro or —OH groups.

In another embodiment, —$R^{XY}$— has the formula:

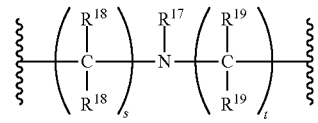

wherein:

s is 0, 1 or 2;

t is 0, 1 or 2;

s+t≥2;

$R^{17}$ is hydrogen or an alkyl, cycloalkyl or saturated heterocyclic group;

each $R^{18}$ and $R^{19}$ is independently selected from hydrogen or a halo, —CN, —OH, alkyl, —O-alkyl, cycloalkyl, —O-cycloalkyl, saturated heterocyclic or —O-(saturated heterocyclic) group, and/or any two $R^{18}$ or two $R^{19}$ attached to the same carbon atom may together with the carbon atom to which they are attached form a C=O group, and/or any two $R^{18}$ or two $R^{19}$ may together with the carbon atom or carbon atoms to which they are attached form a cycloalkyl or saturated heterocyclic group;

wherein optionally $R^{17}$ together with any $R^{18}$ or $R^{19}$ may together with the carbon and nitrogen atoms to which they are attached form a saturated heterocyclic group;

wherein any alkyl, cycloalkyl or saturated heterocyclic group may optionally be substituted with one or more halo, —CN, —OH, oxo (=O), alkyl, haloalkyl, —O-alkyl and/or —O-haloalkyl groups.

Typically, s is 1 or 2 and t is 1 or 2.

In one embodiment:
R$^{17}$ is a C$_1$-C$_4$ alkyl or C$_3$-C$_4$ cycloalkyl group, or R$^{17}$ together with any one of R$^{18}$ or R$^{19}$ forms a C$_1$-C$_4$ alkylene group;
each R$^{18}$ and R$^{19}$ is independently selected from hydrogen or a halo, —OH, C$_1$-C$_3$ alkyl, or —O—(C$_1$-C$_3$ alkyl) group, and/or any two R$^{18}$ or two R$^{19}$ attached to the same carbon atom may together with the carbon atom to which they are attached form a C=O group, and/or any two R$^{18}$ or two R$^{19}$ may together with the carbon atom or carbon atoms to which they are attached form a C$_1$-C$_3$ alkylene group; and
wherein any alkyl or alkylene group may optionally be substituted with one or more halo, —CN, —OH, oxo (=O), —OMe and/or —O-halomethyl groups, and wherein any cycloalkyl group may optionally be substituted with one or more halo, —CN, —OH, oxo (=O), methyl, halomethyl, —OMe and/or —O-halomethyl groups.

More typically:
R$^{17}$ is a C$_1$-C$_3$ alkyl or a cyclopropyl group;
each R$^{18}$ and R$^{19}$ is independently selected from hydrogen or a fluoro, chloro, —OH, methyl, ethyl, —OMe or —OEt group, and/or any two R$^{18}$ or two R$^{19}$ attached to the same carbon atom may together with the carbon atom to which they are attached form a C=O group or a cyclopropyl group;
wherein the C$_1$-C$_3$ alkyl group may optionally be substituted with one or more fluoro, chloro, —OH, oxo (=O), —OMe and/or —OEt groups;
wherein any cyclopropyl group may optionally be substituted with one or more fluoro, chloro, —OH or methyl groups; and
wherein any methyl or ethyl group may optionally be substituted with one or more fluoro and/or chloro groups.

More typically still:
R$^{17}$ is a methyl, ethyl, isopropyl or cyclopropyl group;
each R$^{18}$ and R$^{19}$ is independently selected from hydrogen or a fluoro, methyl or ethyl group, and/or any two R$^{18}$ or two R$^{19}$ attached to the same carbon atom may together with the carbon atom to which they are attached form a C=O or cyclopropyl group; and
any methyl, ethyl, isopropyl or cyclopropyl group may optionally be substituted with one or more fluoro groups.

In one embodiment, —R$^{XY}$— is selected from the group consisting of:

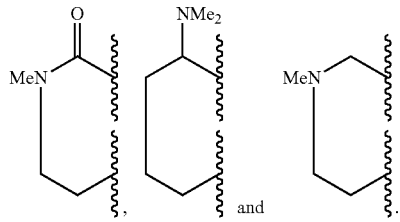

In one embodiment, R$^X$ and R$^Y$ do not comprise an amide group. In a further embodiment, R$^X$ and R$^Y$ do not comprise a carbonyl group.

For the purposes of the present specification, an "amide group" is considered to be any group comprising the structure:

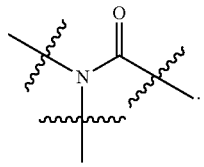 [SMILES: *C(=O)N(*)*]

Accordingly, the term "amide group" includes urea groups.

In one embodiment, R$^X$ and R$^Y$ do not comprise an oxygen atom that is directly attached to a sp$^2$ hybridised atom.

In one embodiment, at least one of R$^X$ and R$^Y$ comprises a nitrogen atom that is not directly attached to a sp$^2$ hybridised carbon atom. Typically in such an embodiment, at least one of R$^X$ and R$^Y$ comprises a nitrogen atom that is not directly attached to a sp$^2$ hybridised atom. More typically, where R$^X$ is monovalent, R$^X$ comprises a nitrogen atom that is not directly attached to a sp$^2$ hybridised atom.

In one embodiment, R$^X$ and R$^Y$ do not comprise a nitrogen atom that is directly attached to a sp$^2$ hybridised carbon atom. Typically in such an embodiment, R$^X$ and R$^Y$ do not comprise a nitrogen atom that is directly attached to a sp$^2$ hybridised atom. More typically in such an embodiment, R$^X$ and R$^Y$ do not comprise a nitrogen atom that is directly attached to a sp$^2$ or sp$^3$ hybridised atom.

In another embodiment, no oxygen or nitrogen atom within the groups R$^X$ and R$^Y$ is directly attached to a sp$^2$ or sp$^3$ hybridised atom.

Without wishing to be bound by theory, it is currently believed that where the groups R$^X$ and R$^Y$ do not comprise an amide group, and/or R$^X$ and R$^Y$ do not comprise a nitrogen atom that is directly attached to a sp$^2$ hybridised atom, the compounds of the invention are particularly suitable for administration via oral or intravenous routes due to their pharmacokinetic properties. This is thought to apply particularly where:
(i) R$^1$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein R$^1$ may optionally be further substituted, as discussed below; or
(ii) R$^1$ is a fused aryl or a fused heteroaryl group, wherein a cycloalkyl, cycloalkenyl, non-aromatic heterocyclic, aryl or heteroaryl ring is fused to the aryl or heteroaryl group across the α,β positions, wherein the aryl or heteroaryl group is further substituted at the α' position with an alkyl or cycloalkyl group, and wherein R$^1$ may optionally be further substituted; or
(iii) R$^1$ is an aryl or a heteroaryl group, wherein the aryl or the heteroaryl group is substituted at the α and α' positions, wherein the substituents at the α and α' positions are independently selected from alkyl and cycloalkyl groups, and wherein R$^1$ may optionally be further substituted.

Typically, where the groups R$^X$ and R$^Y$ do not comprise an amide group, and/or R$^X$ and R$^Y$ do not comprise a nitrogen atom that is directly attached to a sp$^2$ hybridised atom:
R$^X$ is a saturated hydrocarbyl group, wherein the hydrocarbyl group is straight-chained or branched, or is or includes cyclic groups, wherein the hydrocarbyl group may optionally be substituted with one or more groups selected from halo, —CN, —OH, —NH$_2$ and oxo (=O), wherein the hydrocarbyl group includes at least one heteroatom N in its carbon skeleton, and wherein the hydrocarbyl group may optionally include one or two further heteroatoms independently selected from N and O in its carbon skeleton; and $R^Y$ is a saturated hydrocarbyl group, wherein the saturated hydrocarbyl group may be straight-chained or branched, or is or includes cyclic groups, wherein the saturated hydrocarbyl group may optionally be substituted with one or more groups selected from halo, —CN, —OH, —NH$_2$ and oxo (=O), and wherein the saturated hydrocarbyl group may optionally include one or two heteroatoms N or O in its carbon skeleton.

For example, in such an embodiment:

$R^X$ may be a saturated hydrocarbyl group, wherein the hydrocarbyl group may be straight-chained or branched, or may be or include cyclic groups, wherein the saturated hydrocarbyl group may be unsubstituted or optionally substituted with one or more fluoro and/or chloro groups, wherein the saturated hydrocarbyl group includes at least one heteroatom N in its carbon skeleton, and wherein the saturated hydrocarbyl group may optionally include one or two further heteroatoms independently selected from N and O in its carbon skeleton; and $R^Y$ may be a saturated hydrocarbyl group, wherein the hydrocarbyl group may be straight-chained or branched, or may be or include cyclic groups, wherein the saturated hydrocarbyl group may be unsubstituted or optionally substituted with one or more fluoro and/or chloro groups, and wherein the saturated hydrocarbyl group may optionally include one or two oxygen atoms in its carbon skeleton.

Typically, where the groups $R^X$ and $R^Y$ do not comprise an amide group, and/or $R^X$ and $R^Y$ do not comprise a nitrogen atom that is directly attached to a sp$^2$ hybridised atom, no oxygen or nitrogen atom within the groups $R^X$ and $R^Y$ is directly attached to a sp$^2$ or sp$^3$ hybridised atom. Typically, where the groups $R^X$ and $R^Y$ do not comprise an amide group, and/or $R^X$ and $R^Y$ do not comprise a nitrogen atom that is directly attached to a sp$^2$ hybridised atom, ring A is monocyclic.

Typically, where the groups $R^X$ and $R^Y$ do not comprise an amide group, and/or $R^X$ and $R^Y$ do not comprise a nitrogen atom that is directly attached to a sp$^2$ hybridised atom,

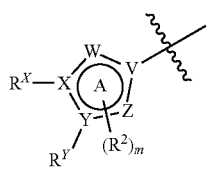

including any optional substituents, contains from 8 to 25 atoms other than hydrogen or halogen. Typically, m is 0.

In contrast, where at least one of the groups $R^X$ and $R^Y$ includes an amide group, it is currently believed that the compounds of the invention are particularly suitable for administration via topical routes due to their pharmacokinetic properties.

In one embodiment, $R^X$ and $R^Y$ contain only atoms selected from the group consisting of carbon, hydrogen, nitrogen, oxygen and halogen atoms. In a further embodiment, $R^X$ and $R^Y$ contain only atoms selected from the group consisting of carbon, hydrogen, nitrogen and halogen atoms.

As stated above, m is 0, 1 or 2. More typically, m is 0 or 1. Most typically, m is 0, i.e. the compound has the formula (Ia):

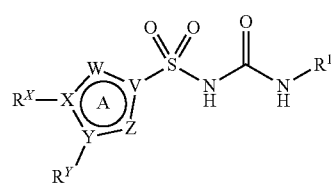

Formula (Ia)

wherein Q, V, W, X, Y, Z, $R^1$, $R^X$ and $R^Y$ are as defined above.

As will be understood, each $R^2$ where present may be directly attached to either ring atom W or Z.

In one embodiment:

each $R^2$ is independently a halo, —OH, —NO$_2$, —NH$_2$, —N$_3$, —SH, —SO$_2$H, —SO$_2$NH$_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

optionally $R^X$ and any $R^2$ attached to W may together with the atoms W and X to which they are attached form a 3- to 12-membered saturated or unsaturated cyclic group, wherein the cyclic group may optionally be substituted; and optionally $R^Y$ and any $R^2$ attached to Z may together with the atoms Y and Z to which they are attached form a 3- to 12-membered saturated or unsaturated cyclic group, wherein the cyclic group may optionally be substituted.

Typically, each $R^2$ where present is monovalent.

In any of the above embodiments, any monovalent $R^2$ may be independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—

$R^\alpha$—$N^+(R^\beta)_3$; —$NR^\beta$—$R^\alpha$—OH; —$NR^\beta$—$R^\alpha$—$OR^\beta$; —$NR^\beta$—$R^\alpha$—$NH_2$; —$NR^\beta$—$R^\alpha$—$NHR^\beta$; —$NR^\beta$—$R^\alpha$—$N(R^\beta)_2$; —$NR^\beta$—$R^\alpha$—$N(O)(R^\beta)_2$; —$NR^\beta$—$R^\alpha$—$N^+(R^\beta)_3$; —$N(O)R^\beta$—$R^\alpha$—OH; —$N(O)R^\beta$—$R^\alpha$—$OR^\beta$; —$N(O)R^\beta$—$R^\alpha$—$NH_2$; —$N(O)R^\beta$—$R^\alpha$—$NHR^\beta$; —$N(O)R^\beta$—$R^\alpha$—$N(R^\beta)_2$; —$N(O)R^\beta$—$R^\alpha$—$N(O)(R^\beta)_2$; —$N(O)R^\beta$—$R^\alpha$—$N^+(R^\beta)_3$; —$N^+(R^\beta)_2$—$R^\alpha$—OH; —$N^+(R^\beta)_2$—$R^\alpha$—$OR^\beta$; —$N^+(R^\beta)_2$—$R^\alpha$—$NH_2$; —$N^+(R^\beta)_2$—$R^\alpha$—$NHR^\beta$; —$N^+(R^\beta)_2$—$R^\alpha$—$N(R^\beta)_2$; or —$N^+(R^\beta)_2$—$R^\alpha$—$N(O)(R^\beta)_2$;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —$CH_2$— groups in the backbone of the alkylene, alkenylene or alkynylene group may optionally be replaced by one or more —$N(O)(R^\beta)$— or —$N^+(R^\beta)_2$— groups, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, or wherein any two or three —$R^\beta$ attached to the same nitrogen atom may, together with the nitrogen atom to which they are attached, form a $C_2$-$C_7$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —$O(C_1$-$C_4$ alkyl), —$O(C_1$-$C_4$ haloalkyl), —$O(C_3$-$C_7$ cycloalkyl), —$O(C_3$-$C_7$ halocycloalkyl), —$CO(C_1$-$C_4$ alkyl), —$CO(C_1$-$C_4$ haloalkyl), —$COO(C_1$-$C_4$ alkyl), —$COO(C_1$-$C_4$ haloalkyl), halo, —OH, —$NH_2$, —CN, —C≡CH, oxo (═O), or 4- to 6-membered heterocyclic group.

In one embodiment, each monovalent $R^2$ is independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; —$R^\alpha$—$OCOR^\beta$; —NH—CHO; —$NR^\beta$—CHO; —NH—$COR^\beta$; —$NR^\beta$—$COR^\beta$; —$CONH_2$; —$CONHR^\beta$; —$CON(R^\beta)_2$; —$R^\alpha$—NH—CHO; —$R^\alpha$—$NR^\beta$—CHO; —$R^\alpha$—NH—$COR^\beta$; —$R^\alpha$—$NR^\beta$—$COR^\beta$; —$R^\alpha$—$CONH_2$; —$R^\alpha$—$CONHR^\beta$; —$R^\alpha$—$CON(R^\beta)_2$; —O—$R^\alpha$—OH; —O—$R^\alpha$—$OR^\beta$; —O—$R^\alpha$—$NH_2$; —O—$R^\alpha$—$NHR^\beta$; —O—$R^\alpha$—$N(R^\beta)_2$; —NH—$R^\alpha$—OH; —NH—$R^\alpha$—$OR^\beta$; —NH—$R^\alpha$—$NH_2$; —NH—$R^\alpha$—$NHR^\beta$; —NH—$R^\alpha$—$N(R^\beta)_2$; —$NR^\beta$—$R^\alpha$—OH; —$NR^\beta$—$R^\alpha$—$OR^\beta$; —$NR^\beta$—$R^\alpha$—$NH_2$; —$NR^\beta$—$R^\alpha$—$NHR^\beta$; or —$NR^\beta$—$R^\alpha$—$N(R^\beta)_2$;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —$O(C_1$-$C_4$ alkyl), —$O(C_1$-$C_4$ haloalkyl), —$O(C_3$-$C_7$ cycloalkyl), halo, —OH, —$NH_2$, —CN, —C≡CH, oxo (═O), or 4- to 6-membered heterocyclic group.

In one embodiment, each $R^2$ is independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —$O(C_1$-$C_4$ alkyl), —$O(C_1$-$C_4$ haloalkyl), —$O(C_3$-$C_7$ cycloalkyl), halo, —OH, —$NH_2$, —CN, —C≡CH, oxo (═O), or 4- to 6-membered heterocyclic group.

Alternatively, each $R^2$ may be independently selected from halo; —CN; —$R^\beta$; —OH; —$OR^\beta$; —$R^\alpha$-halo; —$R^\alpha$—CN; —$R^\alpha$—$R^\beta$; —$R^\alpha$—OH; —$R^\alpha$—$OR^\beta$; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, halo, —OH, or 4- to 6-membered heterocyclic group.

Typically, each $R^2$ where present is a halo group or contains from 1 to 6 atoms other than hydrogen or halogen. Typically, where any $R^2$ contains from 1 to 6 atoms other than hydrogen or halogen, the $R^2$ is a saturated hydrocarbyl group, wherein the saturated hydrocarbyl group may be straight-chained or branched, or be or include cyclic groups, wherein the saturated hydrocarbyl group may optionally be substituted with one or more groups selected from halo, —CN, —OH, —NH$_2$ and oxo (=O), and wherein the saturated hydrocarbyl group may optionally include one or two heteroatoms N or O in its carbon skeleton.

More typically, each R$^2$ where present is independently selected from a fluoro, chloro, C$_1$-C$_4$ alkyl or C$_3$-C$_4$ cycloalkyl group, wherein any C$_1$-C$_4$ alkyl or C$_3$-C$_4$ cycloalkyl group may optionally be substituted with one or more fluoro and/or chloro groups.

Most typically each R$^2$ where present is independently selected from a fluoro, methyl, ethyl, isopropyl or cyclopropyl group.

Typically, where any R$^2$ is a halo group, such as a fluoro or chloro group, the halo group is directly attached to a ring carbon atom of ring A.

In one embodiment, the group:

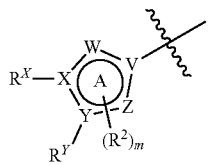

including any optional substituents, contains from 8 to 25 atoms other than hydrogen or halogen. More typically, the group contains from 8 to 17 atoms other than hydrogen or halogen. Most typically, the group contains from 10 to 15 atoms other than hydrogen or halogen.

As stated, R$^1$ is a cyclic group substituted at the α-position, wherein R$^1$ may optionally be further substituted. For the avoidance of doubt, it is noted that it is a ring atom of the cyclic group of R$^1$ that is directly attached to the nitrogen atom of the urea or thiourea group, not any substituent.

In one embodiment of the first aspect of the invention, R$^1$ is an aryl or a heteroaryl group, wherein the aryl or the heteroaryl group is substituted at the α-position, and wherein R$^1$ may optionally be further substituted. Typically, R$^1$ is a phenyl or a 5- or 6-membered heteroaryl group, wherein the phenyl or the heteroaryl group is substituted at the α-position, and wherein R$^1$ may optionally be further substituted. Typically, R$^1$ is an aryl or a heteroaryl group, wherein the aryl or the heteroaryl group is substituted at the α and α' positions, and wherein R$^1$ may optionally be further substituted. Typically, R$^1$ is a phenyl or a 5- or 6-membered heteroaryl group, wherein the phenyl or the heteroaryl group is substituted at the α and α' positions, and wherein R$^1$ may optionally be further substituted. For example, R$^1$ may be a phenyl group substituted at the 2- and 6-positions or a phenyl group substituted at the 2-, 4- and 6-positions.

In one embodiment, the parent phenyl or 5- or 6-membered heteroaryl group of R$^1$ may be selected from phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl. Typically, the parent phenyl or 5- or 6-membered heteroaryl group of R$^1$ may be selected from phenyl, pyridinyl, pyridazinyl, pyrimidinyl, pyrrolyl, pyrazolyl, imidazolyl or triazolyl. Typically, the parent phenyl or 5- or 6-membered heteroaryl group of R$^1$ may be selected from phenyl, pyridinyl, pyridazinyl, pyrimidinyl or pyrazolyl.

As used herein, the nomenclature α, β, α', β' refers to the position of the atoms of a cyclic group, such as —R$^1$, relative to the point of attachment of the cyclic group to the remainder of the molecule. For example, where —R$^1$ is a 1,2,3,5,6,7-hexahydro-s-indacen-4-yl moiety, the α, β, α' and β' positions are as follows:

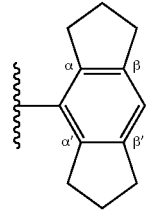 [SMILES: *c1c2c(cc3c1CCC3)CCC2]

For the avoidance of doubt, where it is stated that a cyclic group, such as an aryl or a heteroaryl group, is substituted at the α and/or α' positions, it is to be understood that one or more hydrogen atoms at the α and/or α' positions respectively are replaced by one or more substituents, such as any optional substituent as defined above. Unless stated otherwise the term 'substituted' does not include the replacement of one or more ring carbon atoms by one or more ring heteroatoms.

In another embodiment, R$^1$ is a cyclic group substituted at the α and α' positions, wherein R$^1$ may optionally be further substituted. For example, R$^1$ may be a cycloalkyl, cycloalkenyl or non-aromatic heterocyclic group substituted at the α and α' positions.

In any of the above embodiments, typical substituents at the α and/or α' positions of the parent cyclic group of R$^1$ comprise a carbon atom. For example, typical substituents at the α and/or α' positions may be independently selected from —R$^4$, —OR$^4$ and —COR$^4$ groups, wherein each R$^4$ is independently selected from a C$_1$-C$_6$ alkyl, C$_2$-C$_6$ alkenyl, C$_2$-C$_6$ alkynyl or C$_2$-C$_6$ cyclic group and wherein each R$^4$ is optionally further substituted with one or more halo groups. More typically, the substituents at the α and/or α' positions are independently selected from alkyl and cycloalkyl groups, such as C$_3$-C$_6$ branched alkyl and C$_3$-C$_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

Other typical substituents at the α and/or α' positions of the parent cyclic group of R$^1$ may include cycloalkyl, cycloalkenyl, non-aromatic heterocyclic, aryl or heteroaryl rings which are fused to the parent cyclic group across the α,β and/or α',β' positions respectively. Such fused cyclic groups are described in greater detail below.

In one embodiment, R$^1$ is a fused aryl or a fused heteroaryl group, wherein the aryl or heteroaryl group is fused to one or more cycloalkyl, cycloalkenyl, non-aromatic heterocyclic, aryl or heteroaryl rings, wherein R$^1$ may optionally be further substituted. Typically, a cycloalkyl, cycloalkenyl, non-aromatic heterocyclic, aryl or heteroaryl ring is fused to the aryl or heteroaryl group across the α,β positions. Typically, the aryl or heteroaryl group is also substituted at the α' position, for example with a substituent selected from —R$^4$, —OR$^4$ and —COR$^4$, wherein each R$^4$ is independently selected from a C$_1$-C$_6$ alkyl, C$_2$-C$_6$ alkenyl, C$_2$-C$_6$ alkynyl or C$_2$-C$_6$ cyclic group and wherein each R$^4$ is optionally further substituted with one or more halo groups. Typically in such an embodiment, $R^1$ is bicyclic or tricyclic.

More typically, $R^1$ is a fused phenyl or a fused 5- or 6-membered heteroaryl group, wherein the phenyl or the 5- or 6-membered heteroaryl group is fused to one or more cycloalkyl, cycloalkenyl, non-aromatic heterocyclic, aryl or heteroaryl rings, wherein $R^1$ may optionally be further substituted. Typically, a cycloalkyl, cycloalkenyl, non-aromatic heterocyclic, aryl or heteroaryl ring is fused to the phenyl or the 5- or 6-membered heteroaryl group across the α,β positions so as to form a 4- to 6-membered fused ring structure. Typically, the phenyl or the 5- or 6-membered heteroaryl group is also substituted at the α' position, for example with a substituent selected from —$R^4$, —$OR^4$ and —$COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^1$ is bicyclic or tricyclic.

In another embodiment, $R^1$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^1$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically, $R^1$ is tricyclic.

In yet another embodiment, $R^1$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^1$ may optionally be further substituted. Typically in such an embodiment, $R^1$ is tricyclic.

More typically, $R^1$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the phenyl or the 5- or 6-membered heteroaryl group across the α',β' positions so as to form a second 4- to 6-membered fused ring structure, wherein $R^1$, may optionally be further substituted. Typically in such an embodiment, $R^1$ is tricyclic.

In one embodiment —$R^1$ has a formula selected from:

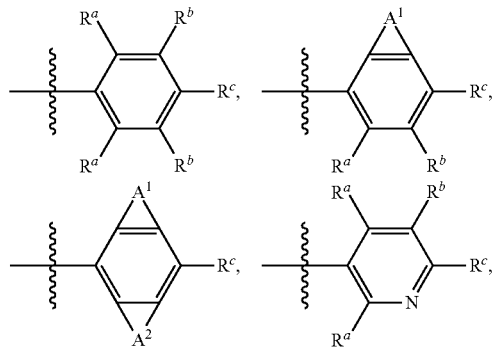

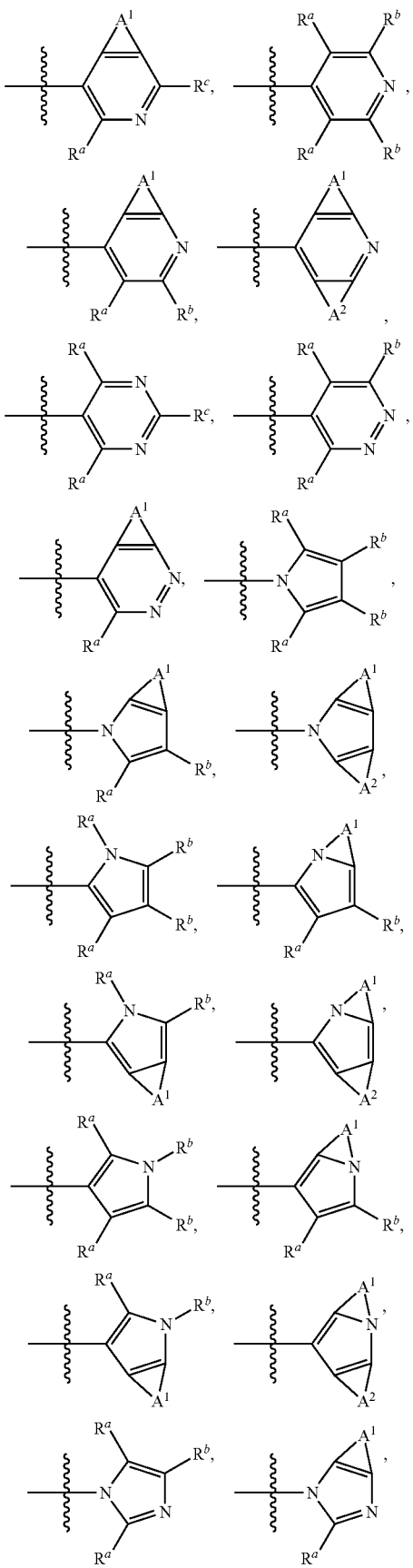

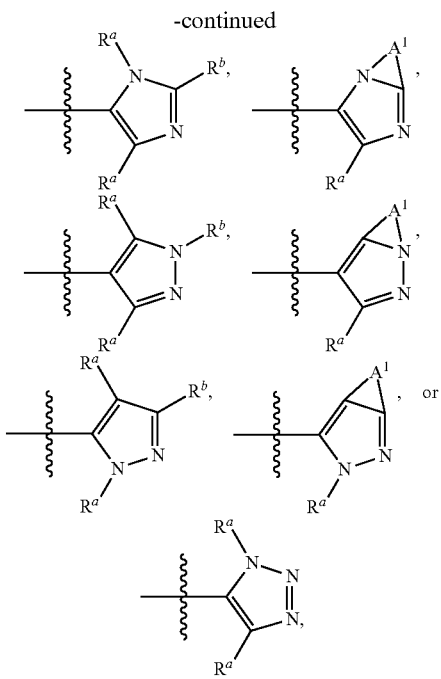

wherein:
A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S;
each R$^a$ is independently selected from —R$^{aa}$, —OR$^{aa}$ or —COR$^{aa}$;
each R$^b$ is independently selected from hydrogen, halo, —NO$_2$, —CN, —R$^{aa}$, —OR$^{aa}$ or —COR$^{aa}$;
provided that any R$^a$ or R$^b$ that is directly attached to a ring nitrogen atom is not halo, —NO$_2$, —CN, or —OR$^{aa}$;
each R$^c$ is independently selected from hydrogen, halo, —OH, —NO$_2$, —CN, —R$^{cc}$, —OR$^{cc}$, —COR$^c$, —COOR$^c$, —CONH$_2$, —CONHR$^{cc}$ or —CON(R$^e$)$_2$;
each R$^{aa}$ is independently selected from a C$_1$-C$_6$ alkyl, C$_2$-C$_6$ alkenyl, C$_2$-C$_6$ alkynyl or a 3- to 7-membered cyclic group, wherein each R$^{aa}$ is optionally substituted; and
each R$^c$ is independently selected from a C$_1$-C$_6$ alkyl, C$_2$-C$_6$ alkenyl, C$_2$-C$_6$ alkynyl or a 3- to 7-membered cyclic group, or any two R$^{cc}$ attached to the same nitrogen atom may, together with the nitrogen atom to which they are attached, form a 3- to 7-membered heterocyclic group, wherein each R$^{aa}$ is optionally substituted.

Typically, any ring containing A$^1$ or A$^2$ is a 5- or 6-membered ring. Typically, A$^1$ and A$^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A$^1$ and A$^2$ are each independently selected from an optionally substituted straight-chained alkylene group, wherein one carbon atom in the backbone of the alkylene group may optionally be replaced by an oxygen atom. Typically, no heteroatom in A$^1$ or A$^2$ is directly attached to another ring heteroatom. Typically, A$^1$ and A$^2$ are unsubstituted or substituted with one or more substituents independently selected from halo, —OH, —CN, —NO$_2$, C$_1$-C$_4$ alkyl, C$_1$-C$_4$ haloalkyl, —O(C$_1$-C$_4$ alkyl) or —O(C$_1$-C$_4$ haloalkyl). More typically, A$^1$ and A$^2$ are unsubstituted or substituted with one or more fluoro and/or chloro groups. Where R$^1$ contains both A$^1$ and A$^2$ groups, A$^1$ and A$^2$ may be the same or different. Typically, A$^1$ and A$^2$ are the same.

Where R$^{aa}$ is a substituted C$_1$-C$_6$ alkyl, C$_2$-C$_6$ alkenyl or C$_2$-C$_6$ alkynyl group, typically the C$_1$-C$_6$ alkyl, C$_2$-C$_6$ alkenyl or C$_2$-C$_6$ alkynyl group is substituted with one or more (e.g. one or two) substituents independently selected from halo, —OH, —CN, —NO$_2$, —O(C$_1$-C$_4$ alkyl) or —O(C$_1$-C$_4$ haloalkyl).

Where R$^{aa}$ is a substituted 3- to 7-membered cyclic group, typically the 3- to 7-membered cyclic group is substituted with one or more (e.g. one or two) substituents independently selected from halo, —OH, —NH$_2$, —CN, —NO$_2$, —B$^1$, —OB$^1$, —NHB$^1$, —N(B)$_2$, —CONH$_2$, —CONHB$^1$, —CON(B)$_2$, —NHCOB$^1$, —NBCOB$^1$, or —B$^{11}$—;
  wherein each B is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^1$ together with the nitrogen atom to which they are attached may form a 4- to 6-membered heterocyclic group containing one or two ring heteroatoms N and/or O, wherein any B$^1$ may optionally be halo-substituted and/or substituted with one or two substituents independently selected from —OH, —NH$_2$, —OB$^{12}$, —NHB$^{12}$ or —N(B$^{12}$)$_2$;
  wherein each B$^{11}$ is independently selected from a C$_1$-C$_8$ alkylene or C$_2$-C$_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{12}$, —NHB$^{12}$ or —N(B$^{12}$)$_2$; and
  wherein each B$^{12}$ is independently selected from a C$_1$-C$_3$ alkyl or C$_1$-C$_3$ haloalkyl group. Typically, any divalent group —B$^{11}$— forms a 4- to 6-membered fused ring.

Typically, each R$^a$ is —R$^{aa}$. More typically, each R$^a$ is independently selected from a C$_1$-C$_6$ alkyl (in particular C$_3$-C$_6$ branched alkyl) or C$_3$-C$_6$ cycloalkyl group, wherein each R$^a$ is optionally further substituted with one or more halo groups. More typically, each R$^a$ is independently selected from a C$_1$-C$_4$ alkyl, C$_1$-C$_4$ haloalkyl, C$_3$-C$_4$ cycloalkyl or C$_3$-C$_4$ halocycloalkyl group. Where a group R$^a$ is present at both the α- and α'-positions, each R$^a$ may be the same or different. Typically, each R$^a$ is the same.

Typically, each R$^b$ is independently selected from hydrogen or halo. More typically, each R$^b$ is hydrogen.

Typically, each R$^c$ is independently selected from hydrogen, halo, —OH, —NO$_2$, —CN, —R$^{cc}$ or —OR$^{cc}$. More typically, each R$^c$ is independently selected from hydrogen, halo, —CN, C$_1$-C$_3$ alkyl, C$_1$-C$_3$ haloalkyl, cyclopropyl or halocyclopropyl. Most typically, each R$^c$ is independently selected from hydrogen or halo.

Typically, each R$^{cc}$ is independently selected from a C$_1$-C$_4$ alkyl or C$_3$-C$_6$ cycloalkyl group, or any two R$^{cc}$ attached to the same nitrogen atom may, together with the nitrogen atom to which they are attached, form a 3- to 6-membered saturated heterocyclic group, wherein each R$^c$ is optionally substituted. Where R$^{cc}$ is substituted, typically R$^{cc}$ is substituted with one or more halo, —OH, —CN, —NO$_2$, —O(C$_1$-C$_4$ alkyl) or —O(C$_1$-C$_4$ haloalkyl) groups. More typically, each R$^{cc}$ is independently selected from a C$_1$-C$_4$ alkyl, C$_1$-C$_4$ haloalkyl, C$_3$-C$_4$ cycloalkyl or C$_3$-C$_4$ halocycloalkyl group.

In one embodiment, —R$^1$ has a formula selected from:

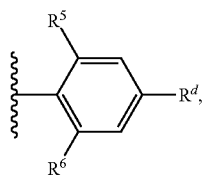

wherein R$^5$ and R$^6$ are independently selected from C$_1$-C$_4$ alkyl, C$_1$-C$_4$ haloalkyl, C$_3$-C$_4$ cycloalkyl and C$_3$-C$_4$ halocycloalkyl, and R$^d$ is hydrogen, halo, —OH, —NO$_2$, —CN, —R$^{dd}$, —OR$^{dd}$, —COR$^{dd}$, —COOR$^{dd}$, —CONH$_2$, —CONHR$^{dd}$ or —CON(R$^{dd}$)$_2$, wherein each —R$^{dd}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, R$^5$ and R$^6$ are independently selected from C$_1$-C$_4$ alkyl, and R$^d$ is hydrogen, halo, —CN, C$_1$-C$_3$ alkyl, C$_1$-C$_3$ haloalkyl, cyclopropyl or halocyclopropyl. More typically, R$^5$ and R$^6$ are independently selected from C$_1$-C$_4$ alkyl, and R$^d$ is hydrogen or halo. In one aspect of such an embodiment, R$^5$ and R$^6$ are independently selected from C$_1$-C$_4$ alkyl and G is halo.

Typically, —R$^1$ has a formula selected from:

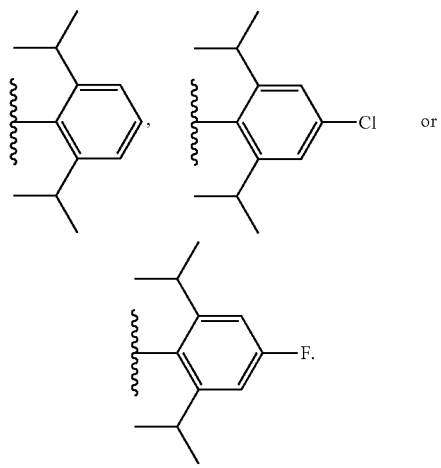

In one embodiment, —R$^1$ has a formula selected from:

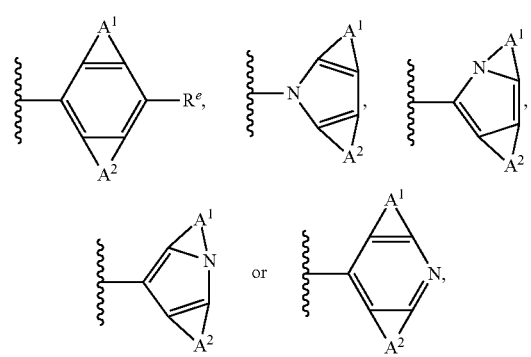

wherein A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S, and wherein R$^e$ is hydrogen or any optional substituent. R$^e$ and any optional substituent attached to A$^1$ or A$^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to A$^1$ and any optional substituent attached to A$^2$ may also together with the atoms to which they are attached form a further fused cycloalkyl, cycloalkenyl, non-aromatic heterocyclic, aryl or heteroaryl ring which may itself be optionally substituted.

In one embodiment, R$^e$ is hydrogen, halo, —OH, —NO$_2$, —CN, —R$^{ee}$, —OR$^{ee}$, —COR$^{ee}$, —COOR$^{ee}$, —CONH$_2$, —CONHR$^{ee}$ or —CON(R$^{ee}$)$_2$, wherein each —R$^{ee}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, R$^e$ is hydrogen or a halo, hydroxyl, —CN, —NO$_2$, —R$^{ee}$ or —OR$^{ee}$ group, wherein R$^{ee}$ is a C$_1$-C$_4$ alkyl group which may optionally be halo-substituted. More typically, R$^{ee}$ is hydrogen or a halo, hydroxyl, —CN, —R$^{ee}$ or —OR$^{ee}$ group, wherein R$^{ee}$ is a C$_1$-C$_4$ alkyl group which may optionally be halo-substituted. More typically still, R$^e$ is hydrogen or halo.

Typically, any ring containing A$^1$ or A$^2$ is a 5- or 6-membered ring.

Typically, A$^1$ and A$^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A$^1$ and A$^2$ are each independently selected from an optionally substituted straight-chained alkylene group, wherein one carbon atom in the backbone of the alkylene group may optionally be replaced by an oxygen atom. Typically, no heteroatom in A$^1$ or A$^2$ is directly attached to another ring heteroatom. Typically, A$^1$ and A$^2$ are unsubstituted or substituted with one or more halo, hydroxyl, —CN, —NO$_2$, —B$_3$ or —OB$_3$ groups, wherein B$_3$ is a C$_1$-C$_4$ alkyl group which may optionally be halo-substituted. More typically, A$^1$ and A$^2$ are unsubstituted or substituted with one or more halo, hydroxyl, —CN, —B$_3$ or —OB$_3$ groups, wherein B$_3$ is a C$_1$-C$_4$ alkyl group which may optionally be halo-substituted. More typically, A$^1$ and A$^2$ are unsubstituted or substituted with one or more fluoro and/or chloro groups. Where R$^1$ contains both A$^1$ and A$^2$ groups, A$^1$ and A$^2$ may be the same or different. Typically, A$^1$ and A$^2$ are the same.

In a further embodiment, —R$^1$ has a formula selected from:

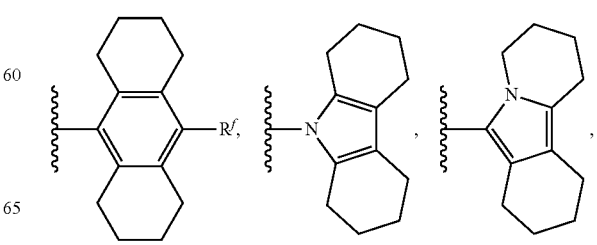

-continued
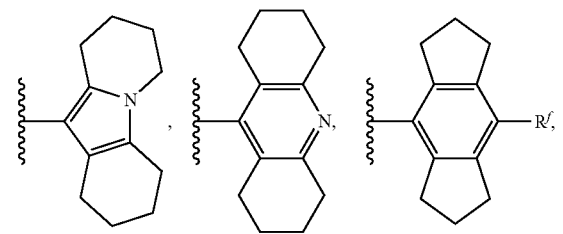
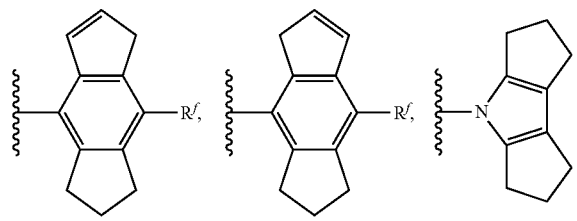
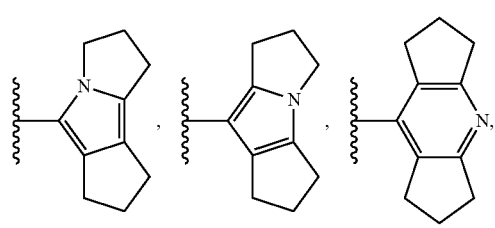
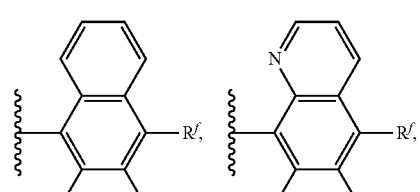
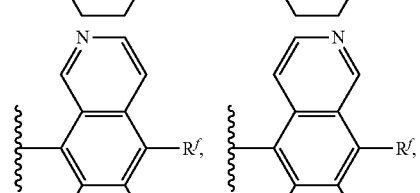
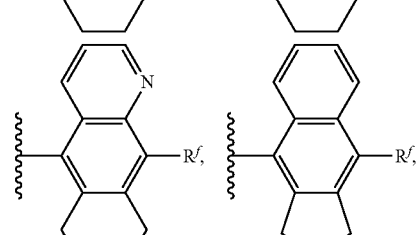
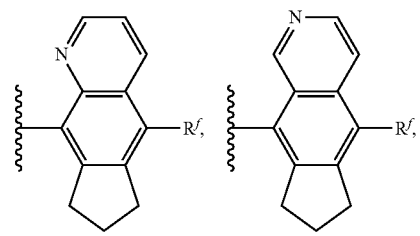
-continued
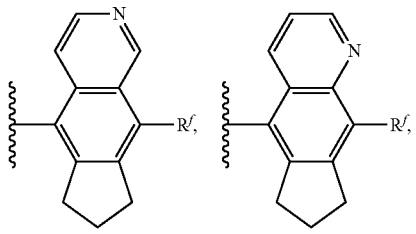
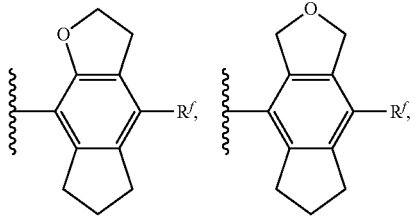
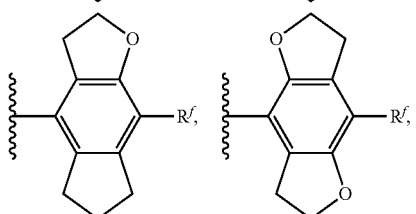
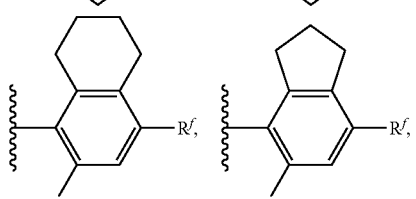
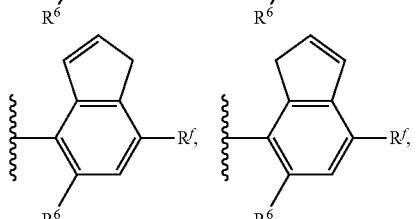
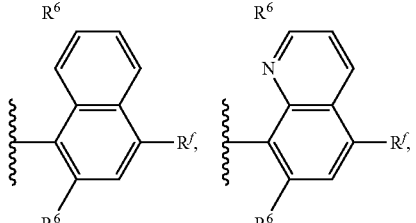
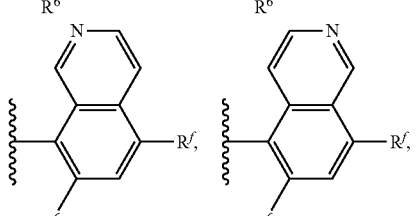
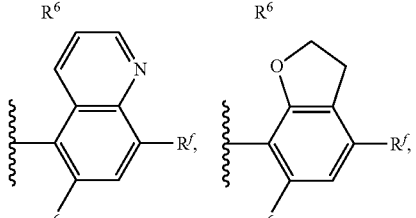

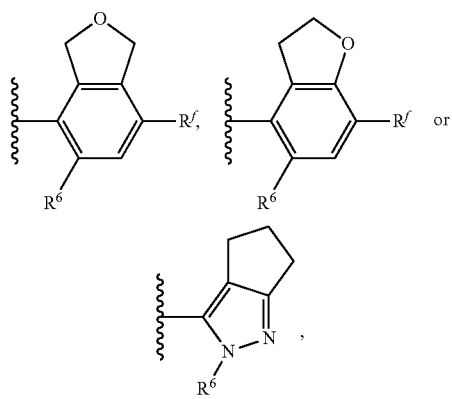

wherein $R^6$ is $C_1$-$C_4$ alkyl, $C_1$-$C_4$ haloalkyl, $C_3$-$C_4$ cycloalkyl or $C_3$-$C_4$ halocycloalkyl, and $R^f$ is hydrogen, halo, —OH, —NO$_2$, —CN, —R$^{ff}$, —OR$^{ff}$, —COR$^{ff}$, —CO-OR$^{ff}$, —CONH$_2$, —CONHR$^{ff}$ or —CON(R$^{ff}$)$_2$, wherein each —R$^{ff}$ is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^6$ is $C_1$-$C_4$ alkyl, and $R^f$ is hydrogen, halo, —CN, $C_1$-$C_3$ alkyl, $C_1$-$C_3$ haloalkyl, cyclopropyl or halocyclopropyl. Typically, $R^6$ is $C_1$-$C_4$ alkyl, and $R^f$ is hydrogen or halo.

Typically, —$R^1$ has the formula:

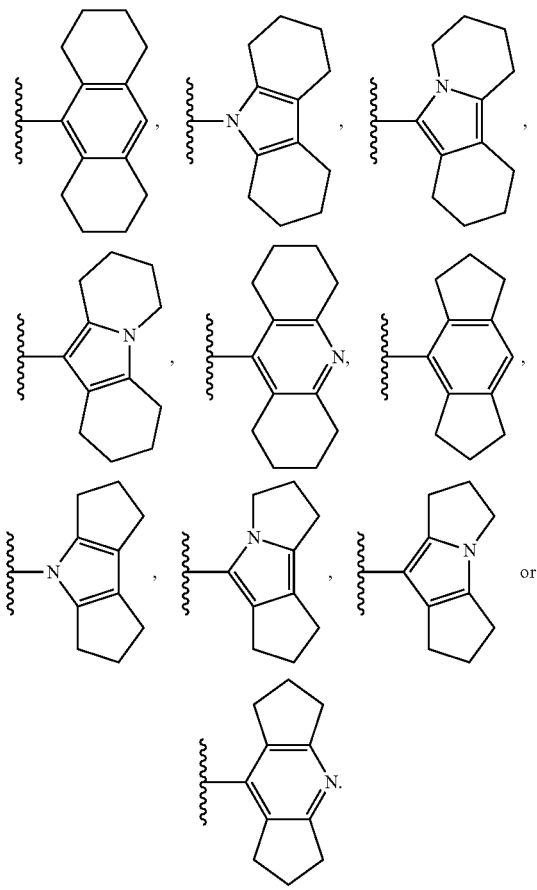

More typically, —$R^1$ has the formula:

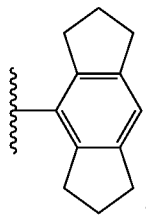

Yet other typical substituents at the α-position of the parent cyclic group of $R^1$ may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such $R^1$ groups are described in greater detail below.

In one embodiment, the α-substituted parent cyclic group of $R^1$ is a 5- or 6-membered cyclic group, wherein the cyclic group may optionally be further substituted. In one embodiment, the α-substituted parent cyclic group of $R^1$ is an aryl or a heteroaryl group, all of which may optionally be further substituted. In one embodiment, the α-substituted parent cyclic group of $R^1$ is a phenyl or a 5- or 6-membered heteroaryl group, all of which may optionally be further substituted. In one embodiment, the α-substituted parent cyclic group of $R^1$ is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α-substituted parent cyclic group of $R^1$ is a phenyl or pyrazolyl group, both of which may optionally be further substituted. In a further embodiment, the α-substituted parent cyclic group of $R^2$ is a phenyl group, which may optionally be further substituted.

In one embodiment, the α-substituted parent cyclic group of $R^1$ is substituted at the α and α' positions, and may optionally be further substituted. For example, the α-substituted parent cyclic group of $R^1$ may be a phenyl group substituted at the 2- and 6-positions or a phenyl group substituted at the 2-, 4- and 6-positions.

In one embodiment, $R^1$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, piperazinyl, 1,4-dioxanyl, thianyl, morpholinyl, thiomorpholinyl or 1-methyl-2-oxo-1,2-dihydropyridinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyridazinyl, pyrimidinyl, pyrazolyl, imidazolyl, isoxazolyl, thiazolyl, tetrahydropyranyl or 1-methyl-2-oxo-1,2-dihydropyridinyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted. In one embodiment, the monovalent heterocyclic group at the α-position is an unsubstituted pyridin-3-yl group or an optionally substituted pyridin-4-yl group.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH$_2$, —CN, —NO$_2$, —B$^4$, —OB$^4$, —NHB$^4$, —N(B$^4$)$_2$, —CONH$_2$, —CONHB$^4$, —CON(B$^4$)$_2$, —NHCOB$^4$, —NB$^4$COB$^4$, or —B$^{44}$—;

wherein each B$^4$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^4$ together with the nitrogen atom to which they are attached may form a 4- to 6-membered heterocyclic group containing one or two ring heteroatoms N and/or O, wherein any B$^4$ may optionally be halo-substituted and/or substituted with one or two substituents independently selected from —OH, —NH$_2$, —OB$^{45}$, —NHB$^{45}$ or —N(B$^{45}$)$_2$;

wherein each B$^{44}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{45}$, —NHB$^{45}$ or —N(B$^{45}$)$_2$; and wherein each B$^{45}$ is independently selected from a C$_1$-C$_3$ alkyl or C$_1$-C$_3$ haloalkyl group.

Typically, any divalent group —B$^{44}$— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted.

In one embodiment, R$^1$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of R$^1$. Such further substituents may be independently selected from halo, —R$^\delta$, —OR$^\delta$ or —COR$^\delta$ groups, wherein each R$^\delta$ is independently selected from a C$_1$-C$_6$ alkyl, C$_2$-C$_6$ alkenyl, C$_2$-C$_6$ alkynyl or C$_2$-C$_6$ cyclic group and wherein each R$^\delta$ is optionally further substituted with one or more halo groups. Typically, such further substituents on the α-substituted parent cyclic group of R$^1$ are independently selected from halo, C$_1$-C$_6$ alkyl (in particular C$_3$-C$_6$ branched alkyl) or C$_3$-C$_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —R$^1$ has a formula selected from:

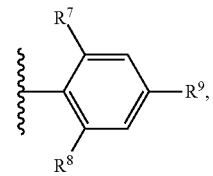

wherein R$^7$ is C$_1$-C$_4$ alkyl, C$_1$-C$_4$ haloalkyl, C$_3$-C$_6$ cycloalkyl or C$_3$-C$_6$ halocycloalkyl, R$^8$ is a 5- or 6-membered, optionally substituted heterocyclic or aromatic group, and R$^g$ is hydrogen, halo, —OH, —NO$_2$, —CN, —R$^{gg}$, —OR$^{gg}$, —COR$^{gg}$, —COOR$^{gg}$, —CONH$_2$, —CONHR$^{gg}$ or —CON(R$^{gg}$)$_2$, wherein each —R$^{gg}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group are independently selected from halo, —OH, —NH$_2$, —CN, —NO$_2$, —B$^5$, —OB$^5$, —NHB$^5$, —N(B$^5$)$_2$, —CONH$_2$, —CONHB$^5$, —CON(B$^5$)$_2$, —NHCOB$^5$, —NB$^5$COB$^5$, or —B$^{55}$—;

wherein each B$^5$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two $B^5$ together with the nitrogen atom to which they are attached may form a 4- to 6-membered heterocyclic group containing one or two ring heteroatoms N and/or O, wherein any $B^5$ may optionally be halo-substituted and/or substituted with one or two substituents independently selected from —OH, —NH$_2$, —OB$^{56}$, —NHB$^{56}$ or —N(B$^{56}$) wherein each $B^{55}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{56}$, —NHB$^{56}$ or —N(B$^{56}$)$_2$; and wherein each $B^{56}$ is independently selected from a $C_1$-$C_3$ alkyl or $C_1$-$C_3$ haloalkyl group.

Typically, any divalent group —$B^{55}$— forms a 4- to 6-membered fused ring. Typically, $R^7$ is $C_1$-$C_4$ alkyl, $R^8$ is a 5- or 6-membered, optionally substituted heterocyclic or aromatic group, and $R^g$ is hydrogen, halo, —CN, $C_1$-$C_3$ alkyl, $C_1$-$C_3$ haloalkyl, cyclopropyl or halocyclopropyl. More typically, $R^7$ is $C_1$-$C_4$ alkyl, $R^8$ is a 5- or 6-membered, optionally substituted heterocyclic or aromatic group, and $R^g$ is hydrogen or halo. In one embodiment, the optional substituents on the heterocyclic or aromatic group are independently selected from halo, —OH, —NH$_2$, —CN, —B$^5$, —OB$^5$, —NHB$^5$ or —N(B$^5$)$_2$, wherein each $B^5$ is independently selected from a $C_1$-$C_4$ alkyl, $C_2$-$C_4$ alkenyl or $C_2$-$C_4$ alkynyl group all of which may optionally be halo-substituted.

Typically, —$R^1$ has a formula selected from:

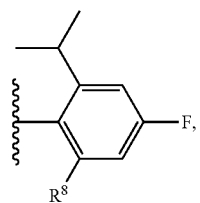

wherein $R^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —B$^6$, —OB$^6$, —NHB$^6$, —N(B$^6$)$_2$, —CONH$_2$, —CONHB$^6$, —CON(B$^6$)$_2$, —NHCOB$^6$, —NB$^6$COB$^6$, or —B$^{66}$—;

wherein each $B^6$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^6$ together with the nitrogen atom to which they are attached may form a 4- to 6-membered heterocyclic group containing one or two ring heteroatoms N and/or O, wherein any $B^6$ may optionally be halo-substituted and/or substituted with one or two substituents independently selected from —OH, —NH$_2$, —OB$^{67}$, —NHB$^{67}$ or —N(B$^{67}$)$_2$;

wherein each $B^{66}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{67}$, —NHB$^{67}$ or —N(B$^{67}$)$_2$; and wherein each $B^{67}$ is independently selected from a $C_1$-$C_3$ alkyl or $C_1$-$C_3$ haloalkyl group.

Typically, any divalent group —$B^{66}$— forms a 4- to 6-membered fused ring. Typically, the optional substituents on the heterocyclic or aromatic group are independently selected from halo, —OH, —NH$_2$, —CN, —B$^6$, —OB$^6$, —NHB$^6$ or —N(B$^6$)$_2$, wherein each $B^6$ is independently selected from a $C_1$-$C_4$ alkyl, $C_2$-$C_4$ alkenyl or $C_2$-$C_4$ alkynyl group all of which may optionally be halo-substituted.

In one embodiment, $R^1$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the α-substituted parent cyclic group of $R^1$ also include cycloalkyl, cycloalkenyl, non-aromatic heterocyclic, aryl or heteroaryl rings which are fused to the α-substituted parent cyclic group of $R^1$. Typically, the cycloalkyl, cycloalkenyl, non-aromatic heterocyclic, aryl or heteroaryl rings are ortho-fused to the α-substituted parent cyclic group of $R^1$, i.e. each fused cycloalkyl, cycloalkenyl, non-aromatic heterocyclic, aryl or heteroaryl ring has only two atoms and one bond in common with the α-substituted parent cyclic group of $R^1$. Typically, the cycloalkyl, cycloalkenyl, non-aromatic heterocyclic, aryl or heteroaryl rings are ortho-fused to the α-substituted parent cyclic group of $R^1$ across the α′,β′ positions.

In one embodiment, —$R^1$ has a formula selected from:

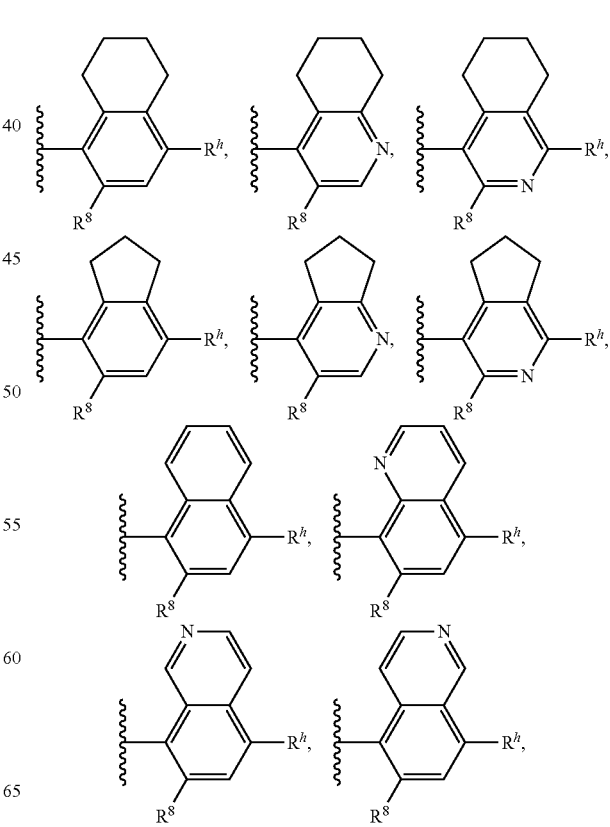

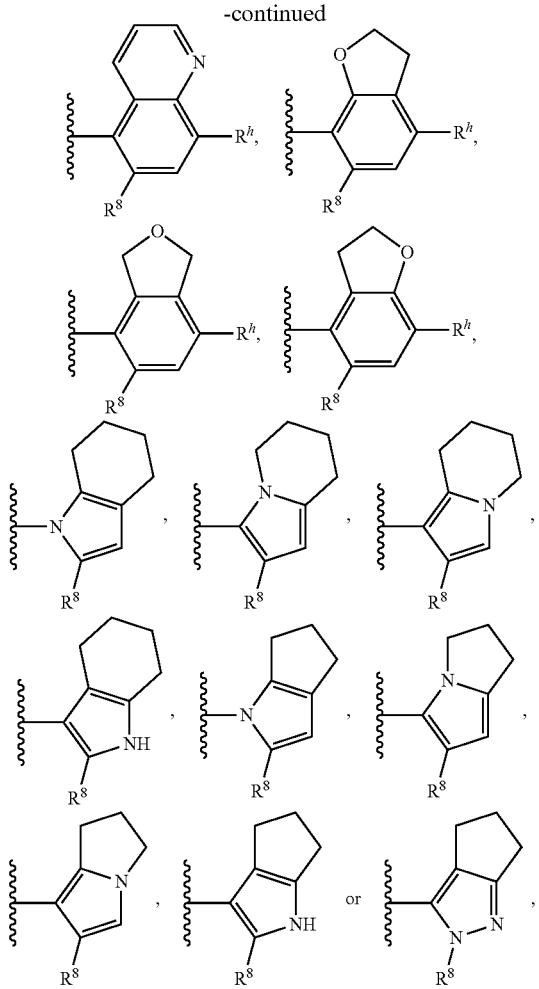

wherein $R^8$ is a 5- or 6-membered, optionally substituted heterocyclic or aromatic group, and $R^h$ is hydrogen, halo, —OH, —NO$_2$, —CN, —R$^{hh}$, —OR$^{hh}$, —COR$^{hh}$, —CO-OR$^{hh}$, —CONH$_2$, —CONHR$^{hh}$ or —CON(R$^{hh}$)$_2$, wherein each —R$^{hh}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group are independently selected from halo, —OH, —NH$_2$, —CN, —NO$_2$, —B$^7$, —OB$^7$, —NHB$^7$, —N(B$^7$)$_2$, —CONH$_2$, —CONHB$^7$, —CON(B$^7$)$_2$, —NHCOB$^7$, —NB$^7$COB$^7$, or —B$^{77}$—;

wherein each B$^7$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O or two B$^7$ together with the nitrogen atom to which they are attached may form a 4- to 6-membered heterocyclic group containing one or two ring heteroatoms N and/or O, wherein any B$^7$ may optionally be halo-substituted and/or substituted with one or two substituents independently selected from —OH, —NH$_2$, —OB$^{78}$, —NHB$^{78}$ or —N(B$^{78}$) wherein each B$^{77}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{78}$, —NHB$^{78}$ or —N(B$^{78}$)$_2$; and wherein each B$^{78}$ is independently selected from a C$_1$-C$_3$ alkyl or C$_1$-C$_3$ haloalkyl group.

Typically, any divalent group —B$^{77}$— forms a 4- to 6-membered fused ring. Typically, R$^h$ is hydrogen, halo, —CN, C$_1$-C$_3$ alkyl, C$_1$-C$_3$ haloalkyl, cyclopropyl or halocyclopropyl. More typically, R$^h$ is hydrogen or halo. Typically, the optional substituents on the heterocyclic or aromatic group are independently selected from halo, —OH, —NH$_2$, —CN, —B$^7$, —OB$^7$, —NHB$^7$ or —N(B$^7$)$_2$, wherein each B$^7$ is independently selected from a C$_1$-C$_4$ alkyl, C$_2$-C$_4$ alkenyl or C$_2$-C$_4$ alkynyl group all of which may optionally be halo-substituted.

In one embodiment, —R$^1$ has a formula selected from:

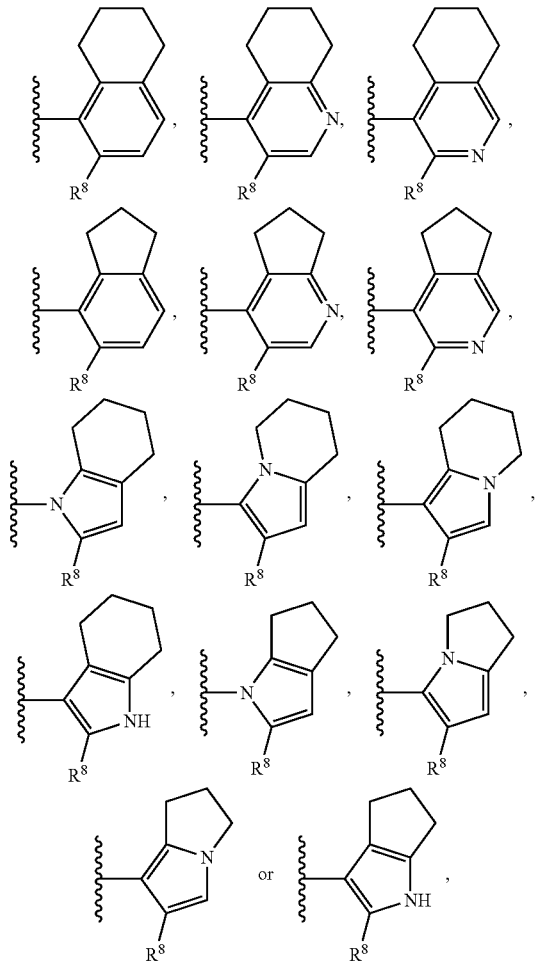

wherein R$^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —B$^8$, —OB$^8$, —NHB$^8$, —N(B$^8$)$_2$, —CONH$_2$, —CONHB$^8$, —CON(B$^8$)$_2$, —NHCOB$^8$, —NB$^8$COB$^8$, or —B$^{88}$—;

wherein each B$^8$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B⁸ together with the nitrogen atom to which they are attached may form a 4- to 6-membered heterocyclic group containing one or two ring heteroatoms N and/or O, wherein any B⁸ may optionally be halo-substituted and/or substituted with one or two substituents independently selected from —OH, —NH$_2$, —OB$^{89}$, —NHB$^{89}$ or —N(B$^{89}$)$_2$;

wherein each B$^{88}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{89}$, —NHB$^{89}$ or —N(B$^{89}$)$_2$; and wherein each B$^{89}$ is independently selected from a $C_1$-$C_3$ alkyl or $C_1$-$C_3$ haloalkyl group.

Typically, any divalent group —B$^{88}$— forms a 4- to 6-membered fused ring. Typically, the optional substituents on the heterocyclic or aromatic group are independently selected from halo, —OH, —NH$_2$, —CN, —B⁸, —OB⁸, —NHB⁸ or —N(B⁸)$_2$, wherein each B⁸ is independently selected from a $C_1$-$C_4$ alkyl, $C_2$-$C_4$ alkenyl or $C_2$-$C_4$ alkynyl group all of which may optionally be halo-substituted.

Typically, —R¹ has a formula selected from:

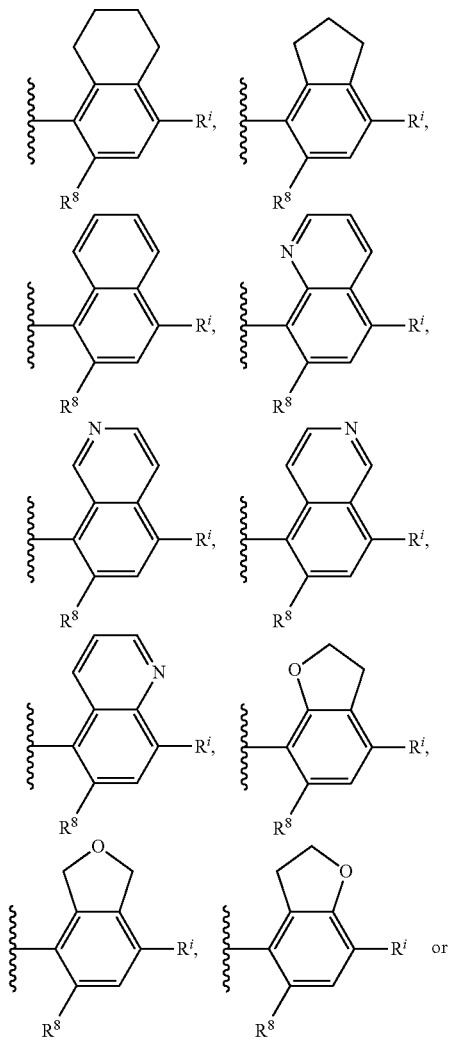

-continued

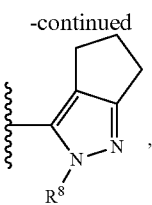

wherein R⁸ is a 5- or 6-membered, optionally substituted heterocyclic or aromatic group, and R$^i$ is hydrogen, halo, —OH, —NO$_2$, —CN, —R$^{ii}$, —OR$^{ii}$, —COR$^{ii}$, —COOR$^{ii}$, —CONH$_2$, —CONHR$^{ii}$ or —CON(R$^{ii}$)$_2$, wherein each —R$^{ii}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —NH$_2$, —CN, —NO$_2$, —B⁹, —OB⁹, —NHB⁹, —N(B⁹)$_2$, —CONH$_2$, —CONHB⁹, —CON(B⁹)$_2$, —NHCOB⁹, —NB⁹COB⁹, or —B$^{99}$—;

wherein each B⁹ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B⁹ together with the nitrogen atom to which they are attached may form a 4- to 6-membered heterocyclic group containing one or two ring heteroatoms N and/or O, wherein any B⁹ may optionally be halo-substituted and/or substituted with one or two substituents independently selected from —OH, —NH$_2$, —OB$^{98}$, —NHB$^{98}$ or —N(B$^{98}$) wherein each B$^{99}$ is independently selected from a $C_1$-$C_5$ alkylene or $C_2$-$C_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{98}$, —NHB$^{98}$ or —N(B$^{98}$)$_2$; and wherein each B$^{98}$ is independently selected from a $C_1$-$C_3$ alkyl or $C_1$-$C_3$ haloalkyl group.

Typically, any divalent group —B$^{99}$-forms a 4- to 6-membered fused ring. Typically, R¹ is hydrogen, halo, —CN, $C_1$-$C_3$ alkyl, $C_1$-$C_3$ haloalkyl, cyclopropyl or halocyclopropyl. More typically, R¹ is hydrogen or halo. Typically, the optional substituents on the heterocyclic or aromatic group are independently selected from halo, —OH, —NH$_2$, —CN, —B⁹, —OB⁹, —NHB⁹ or —N(B⁹)$_2$, wherein each B⁹ is independently selected from a $C_1$-$C_4$ alkyl, $C_2$-$C_4$ alkenyl or $C_2$-$C_4$ alkynyl group all of which may optionally be halo-substituted.

In one embodiment, R¹ is phenyl or a 5- or 6-membered heteroaryl group (such as phenyl, pyridinyl, pyridazinyl, pyrimidinyl or pyrazinyl); wherein
(i) the phenyl or 5- or 6-membered heteroaryl group is substituted at the α position with a substituent selected from —R⁴, —OR⁴ and —COR⁴, wherein R⁴ is selected from a $C_1$-$C_6$ alkyl, $C_2$-$C_6$ alkenyl, $C_2$-$C_6$ alkynyl or $C_2$-$C_6$ cyclic group and wherein R⁴ is optionally substituted with one or more halo groups; and optionally the phenyl or 5- or 6-membered heteroaryl group is further substituted at the α' position with a substituent selected from —R$^{44}$, —OR$^{44}$ and —COR$^{44}$, wherein R$^{44}$ is selected from a $C_1$-$C_6$ alkyl, $C_2$-$C_6$ alkenyl, $C_2$-$C_6$ alkynyl or $C_2$-$C_6$ cyclic group and wherein $R^{44}$ is optionally substituted with one or more halo groups; and optionally the phenyl or 5- or 6-membered heteroaryl group is further substituted (typically with one, two or three substituents independently selected from halo, —$NO_2$, —CN, —$COOR^{45}$, —$CONH_2$, —$CONHR^{45}$ or —$CON(R^{45})_2$, wherein each —$R^{45}$ is independently selected from a $C_1$-$C_4$ alkyl or $C_1$-$C_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one or two substituents independently selected from halo, —$NO_2$, —CN, —$COOR^{45}$, —$CONH_2$, —$CONHR^{45}$ or —$CON(R^{45})_2$, wherein each —$R^{45}$ is independently selected from a $C_1$-$C_4$ alkyl or $C_1$-$C_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —$NO_2$, —CN, —$COOR^{45}$, —$CONH_2$, —$CONHR^{45}$ or —$CON(R^{45})_2$, wherein each —$R^{45}$ is independently selected from a $C_1$-$C_4$ alkyl or $C_1$-$C_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{42}$—$OR^{43}$, —$R^{42}$—$N(R^{43})_2$, —$R^{42}$—CN or —$R^{42}$—C≡$CR^{43}$, and wherein a ring atom of the monovalent heterocyclic or aromatic group is directly attached to the α-ring atom of the parent phenyl or 5- or 6-membered heteroaryl group; wherein $R^{42}$ is independently selected from a bond or a $C_1$-$C_3$ alkylene group; and $R^{43}$ is independently selected from hydrogen or a $C_1$-$C_3$ alkyl or $C_1$-$C_3$ haloalkyl group; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one, two or three substituents independently selected from halo, —$NO_2$, —CN, —$COOR^{45}$, —$CONH_2$, —$CONHR^{45}$ or —$CON(R^{45})_2$, wherein each —$R^{45}$ is independently selected from a $C_1$-$C_4$ alkyl or $C_1$-$C_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{42}$—$OR^{43}$, —$R^{42}$—$N(R^{43})_2$, —$R^{42}$—CN or —$R^{42}$—C≡$CR^{43}$, and wherein a ring atom of the monovalent heterocyclic or aromatic group is directly attached to the α-ring atom of the parent phenyl or 5- or 6-membered heteroaryl group; wherein $R^{42}$ is independently selected from a bond or a $C_1$-$C_3$ alkylene group; and $R^{43}$ is independently selected from hydrogen or a $C_1$-$C_3$ alkyl or $C_1$-$C_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —$NO_2$, —CN, —$COOR^{45}$, —$CONH_2$, —$CONHR^{45}$ or —$CON(R^{45})_2$, wherein each —$R^{45}$ is independently selected from a $C_1$-$C_4$ alkyl or $C_1$-$C_4$ haloalkyl group).

In the embodiment directly above, where a group or moiety is optionally substituted with one or more halo groups, it may be substituted for example with one, two, three, four, five or six halo groups.

In one aspect of any of the above embodiments, $R^1$ contains from 5 to 30 atoms other than hydrogen or halogen. More typically, $R^1$ contains from 7 to 25 atoms other than hydrogen or halogen. More typically, $R^1$ contains from 9 to 20 atoms other than hydrogen or halogen. Most typically, $R^1$ contains from 12 to 18 atoms other than hydrogen or halogen.

In one aspect of any of the above embodiments, $R^1$ contains from 10 to 50 atoms other than hydrogen. More typically, $R^1$ contains from 10 to 40 atoms other than hydrogen. More typically, $R^1$ contains from 10 to 35 atoms other than hydrogen. Most typically, $R^1$ contains from 12 to 30 atoms other than hydrogen.

Q is selected from O or S. In one embodiment of the first aspect of the invention, Q is O.

In one aspect of any of the above embodiments, the compound of formula (I) has a molecular weight of from 250 to 2000 Da. Typically, the compound of formula (I) has a molecular weight of from 300 to 900 Da. More typically, the compound of formula (I) has a molecular weight of from 325 to 650 Da. More typically still, the compound of formula (I) has a molecular weight of from 350 to 600 Da.
A second aspect of the invention provides a compound selected from the group consisting of:
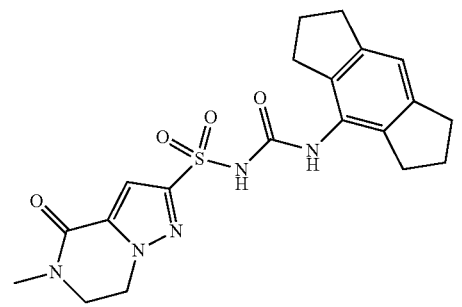
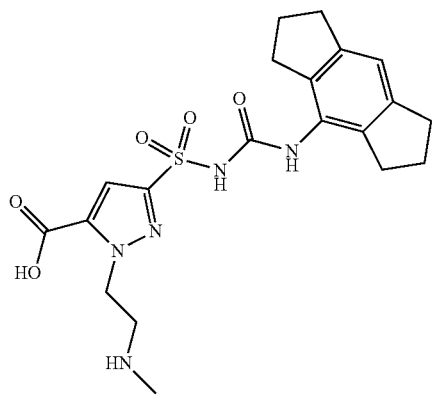
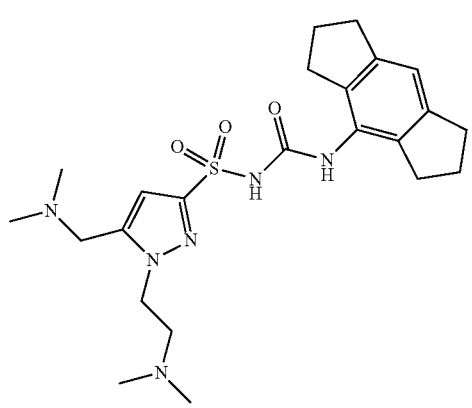
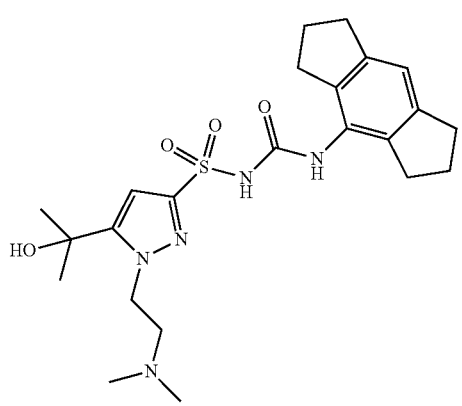
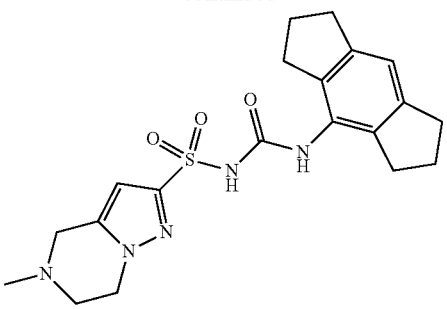
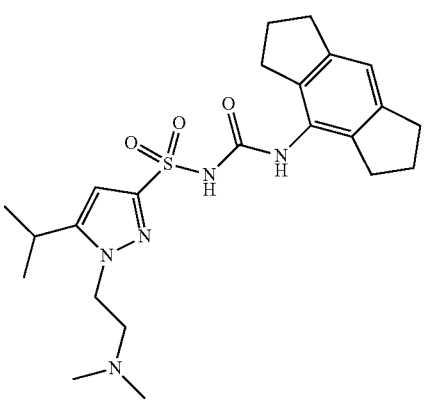
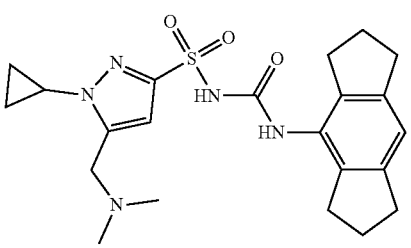
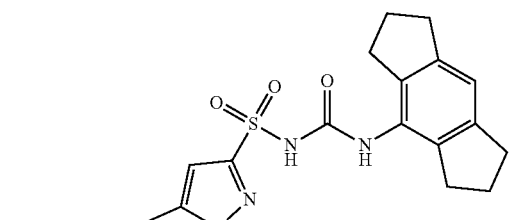
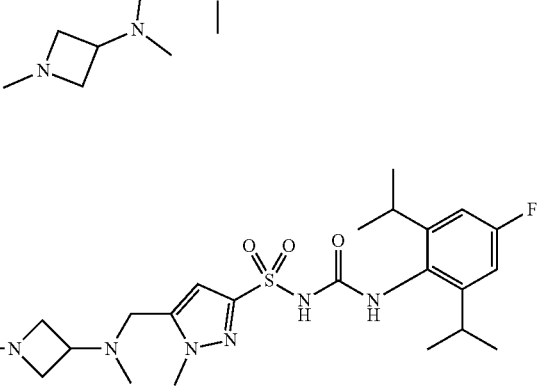

53
-continued
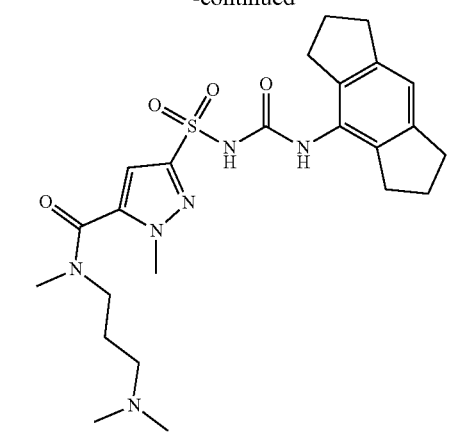
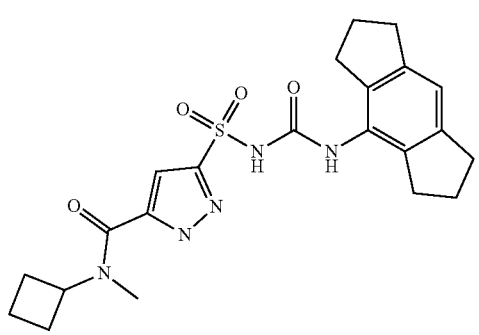
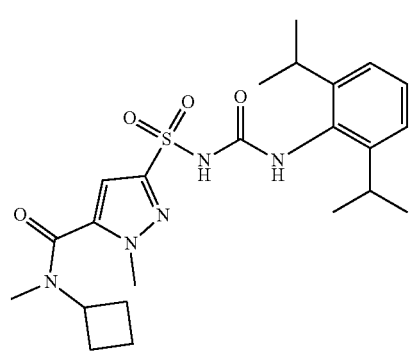
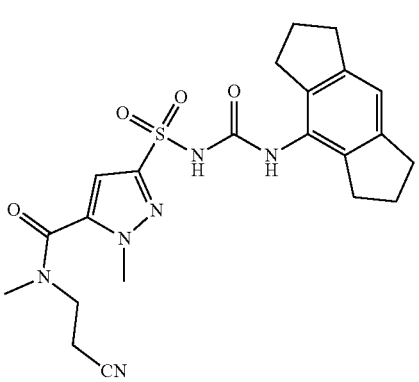
54
-continued
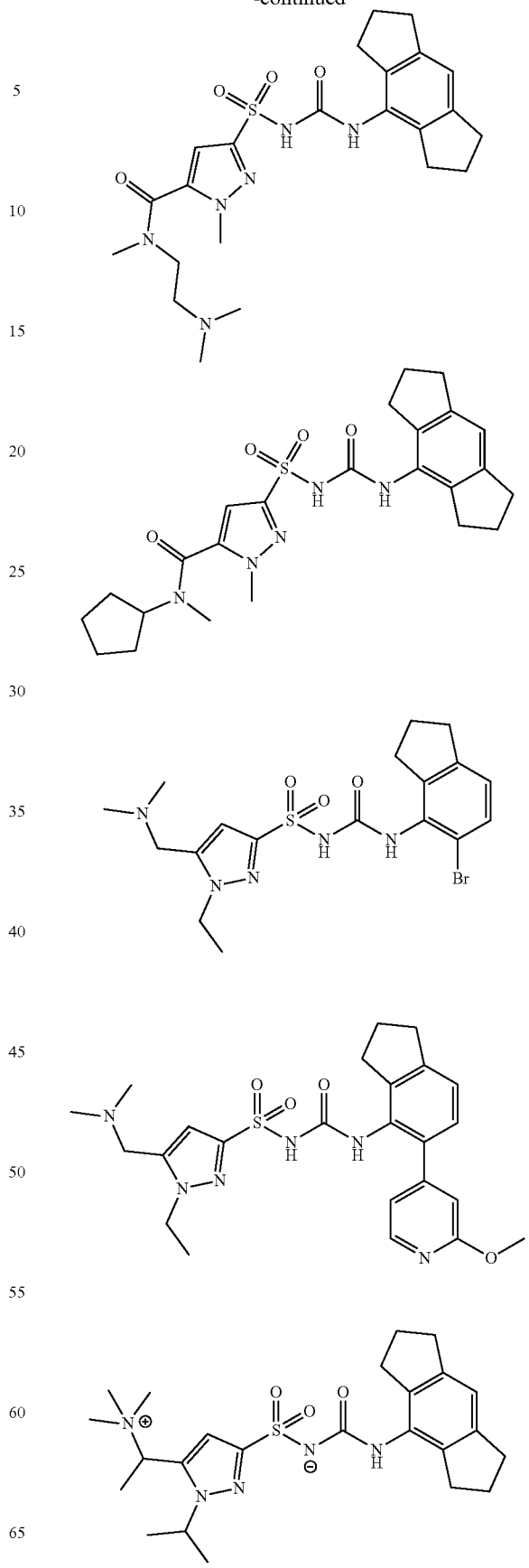

55
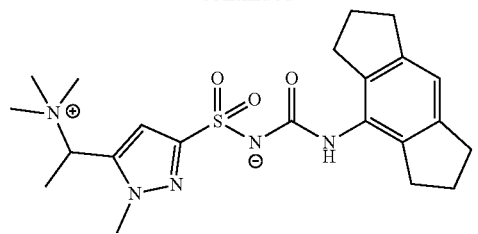
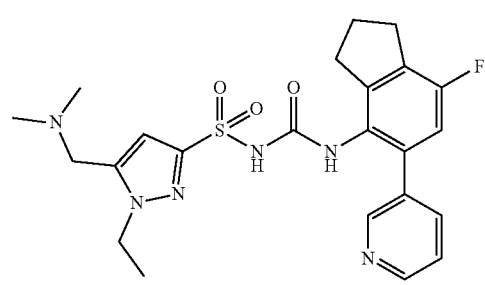
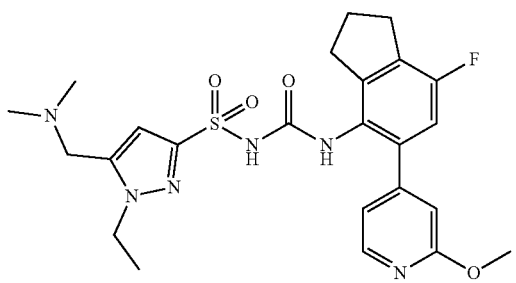
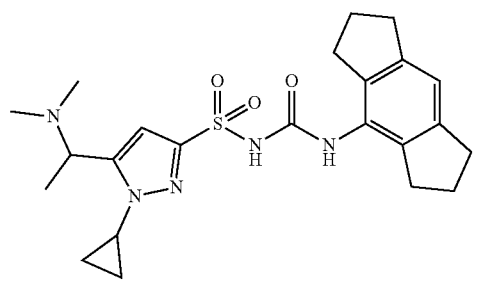
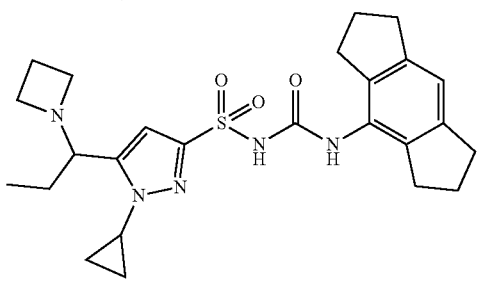
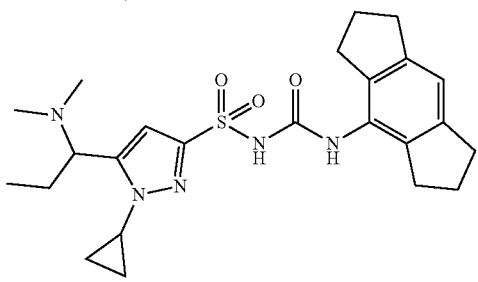
56
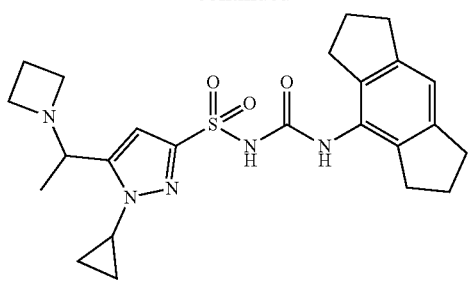
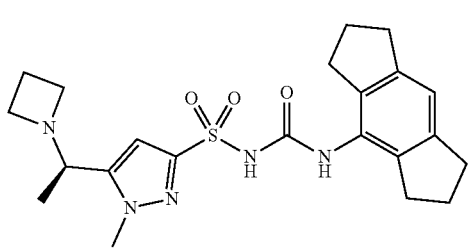
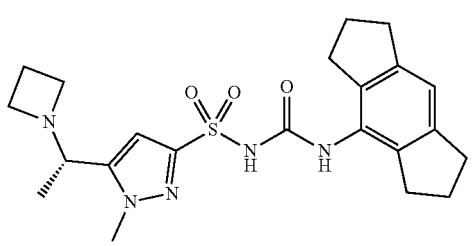
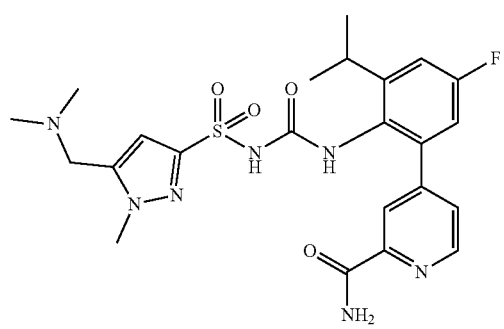
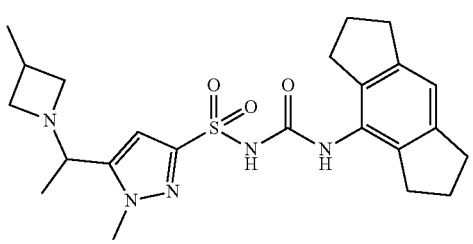
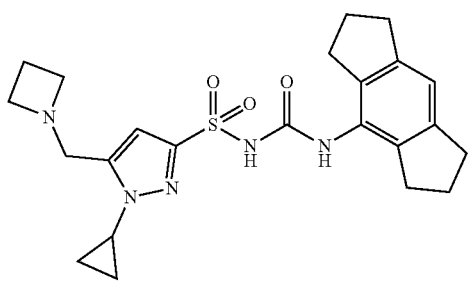

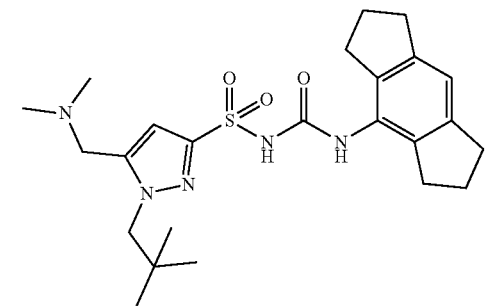
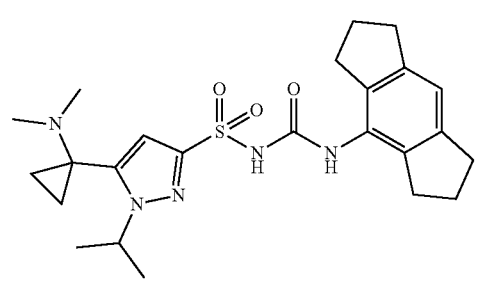
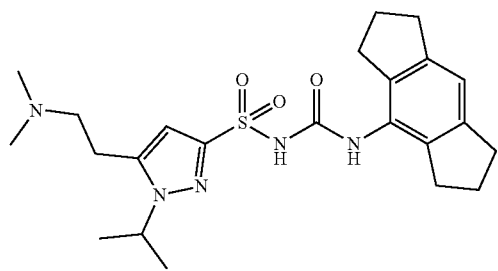
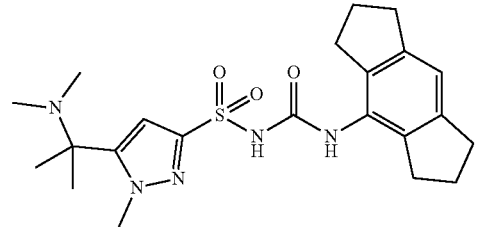
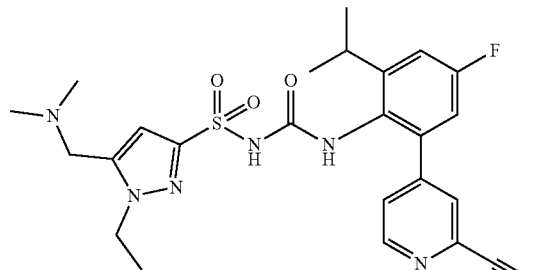
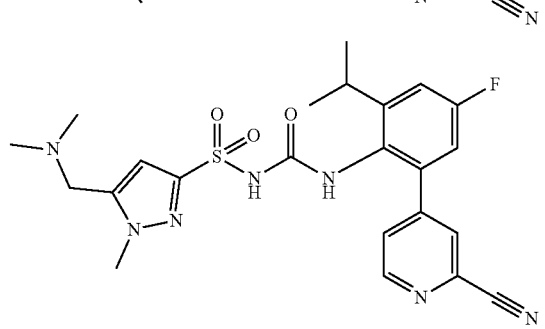
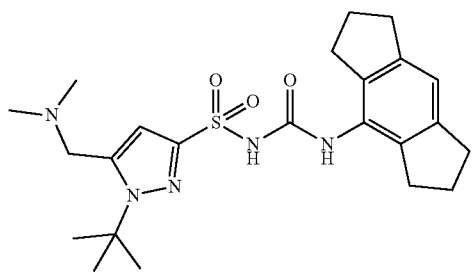
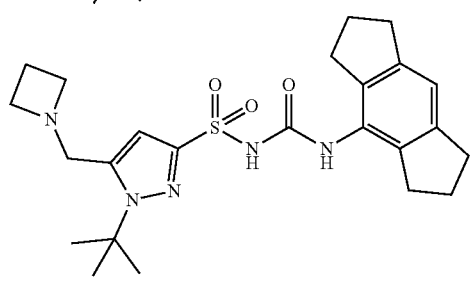
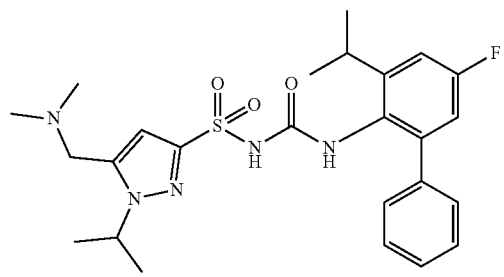
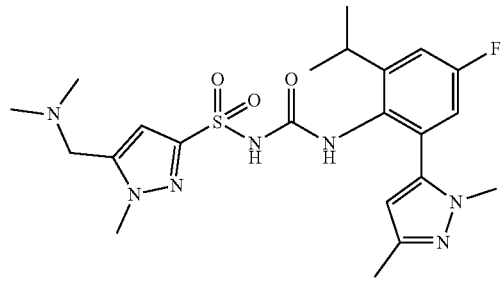
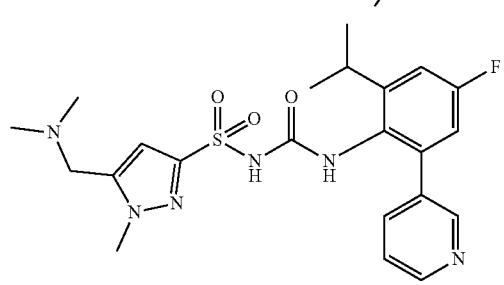
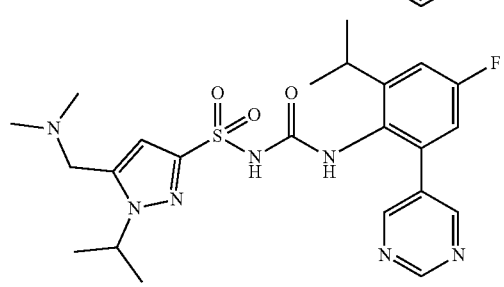

59
-continued
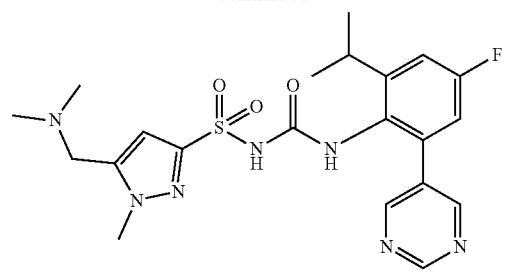
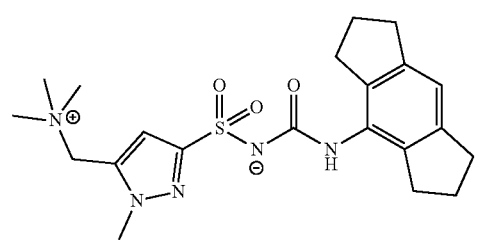
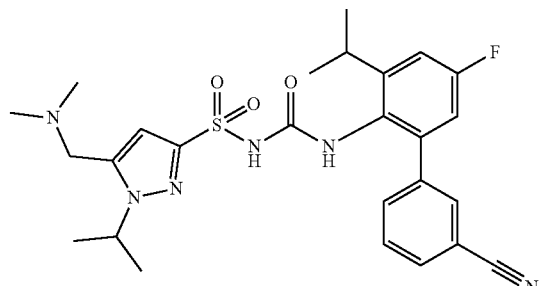
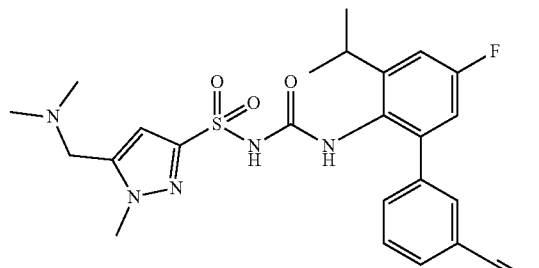
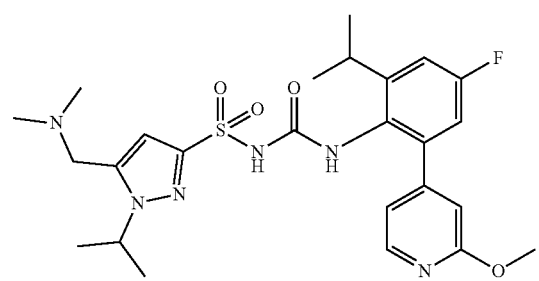
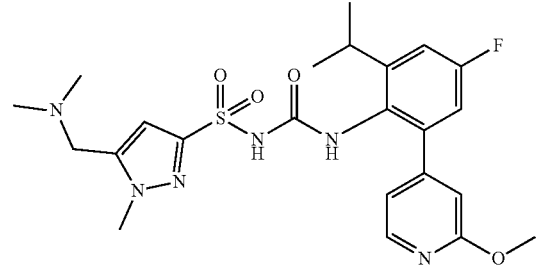
60
-continued
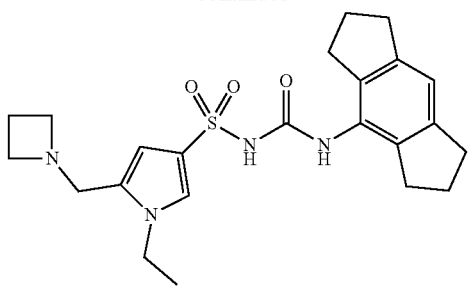
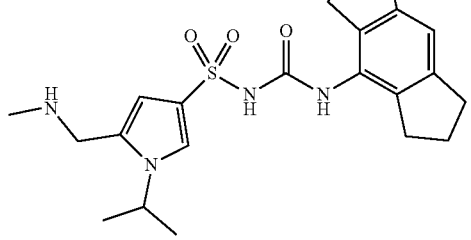
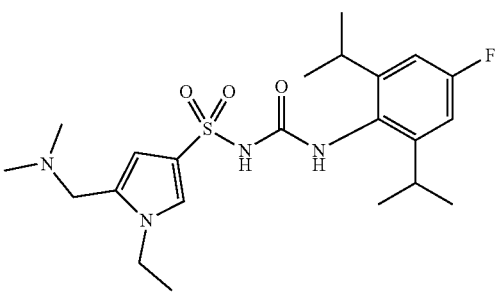
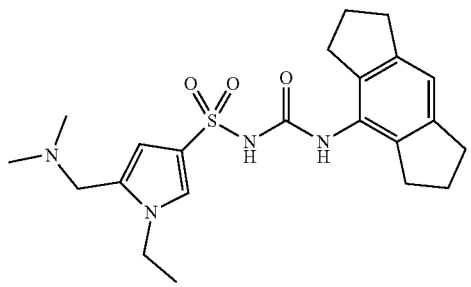
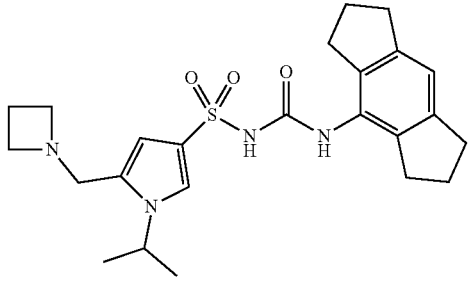
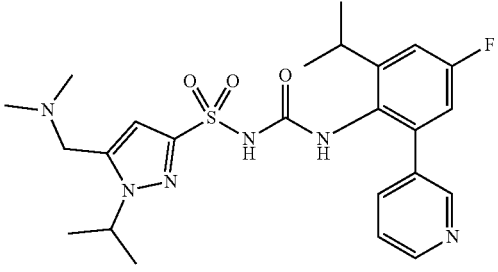

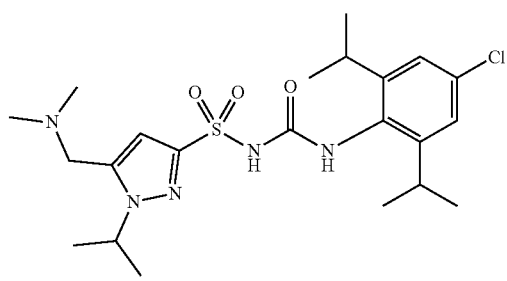
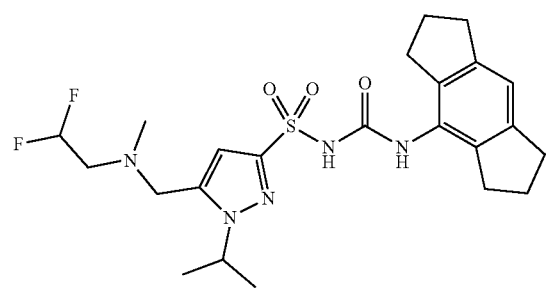
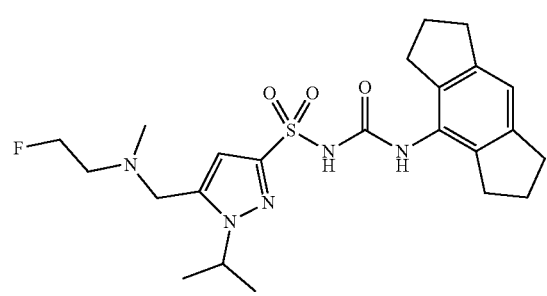
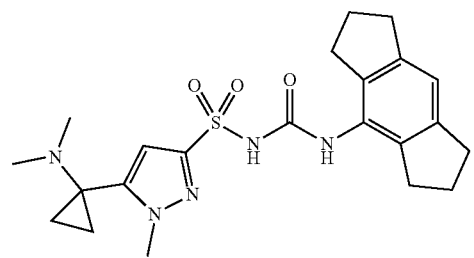
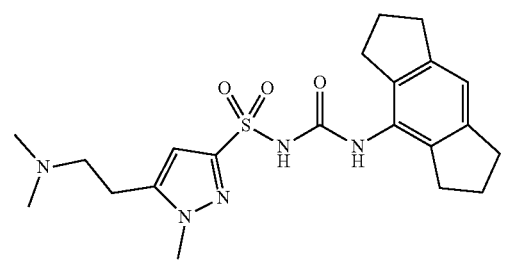
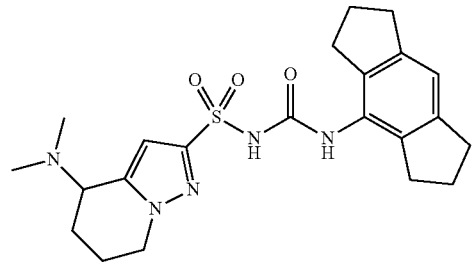
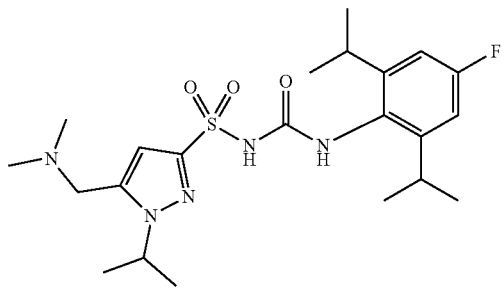
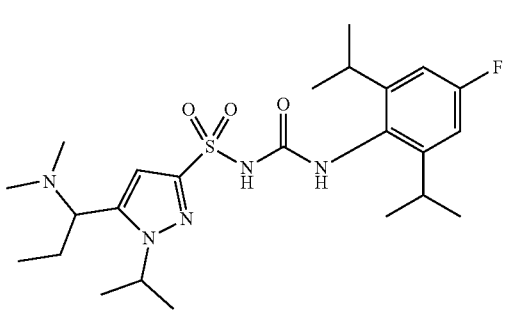
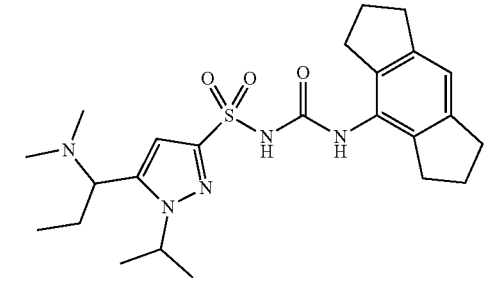
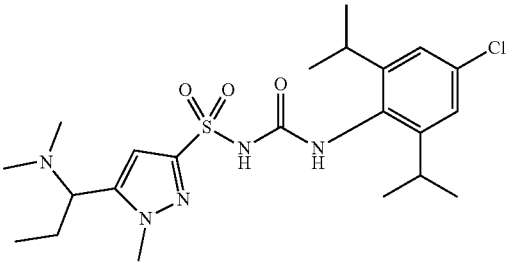
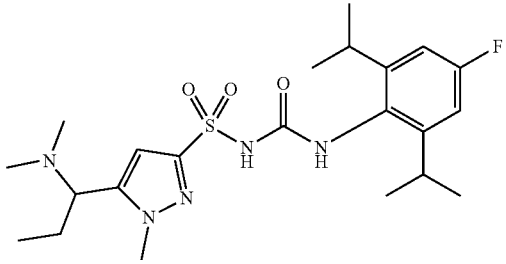
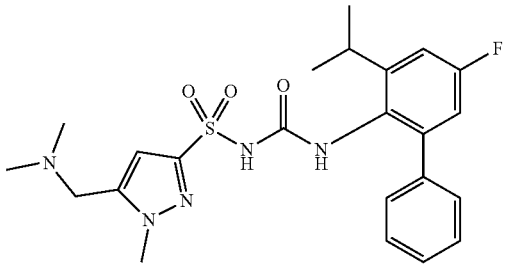

63
-continued
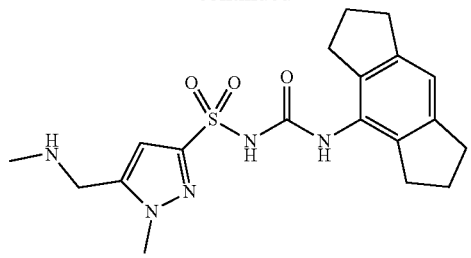
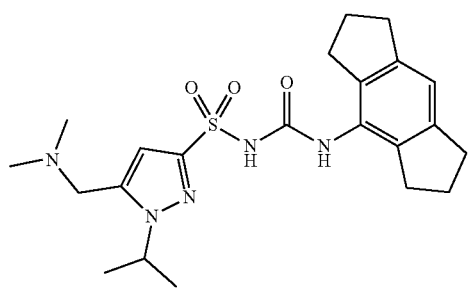
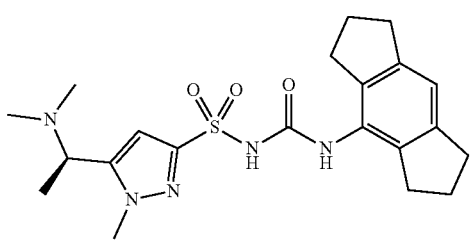
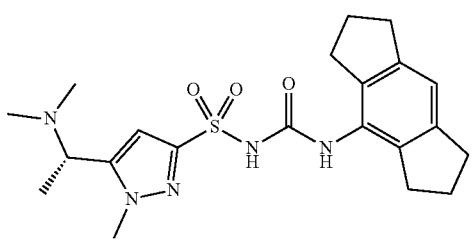
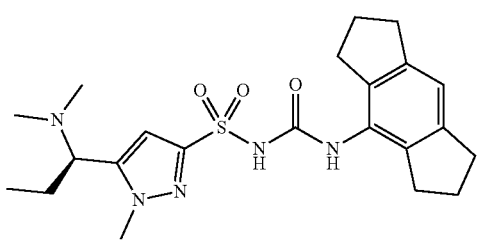
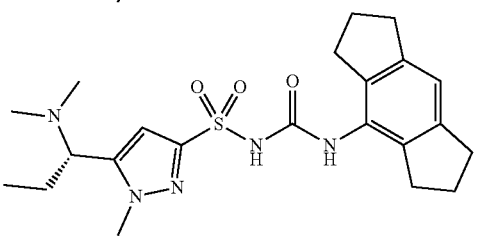
64
-continued
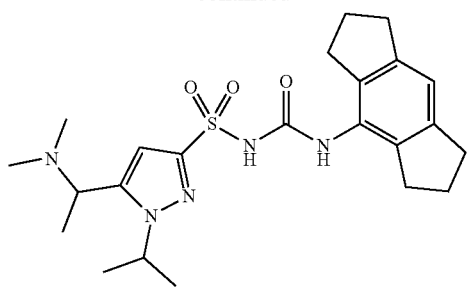
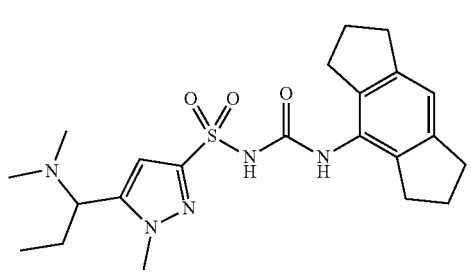
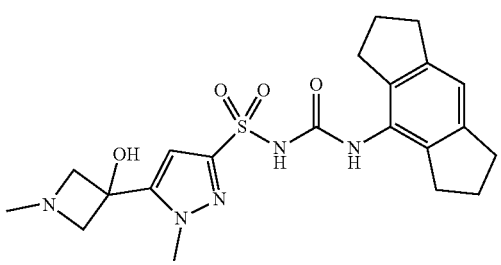
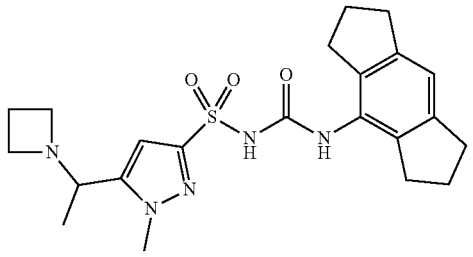
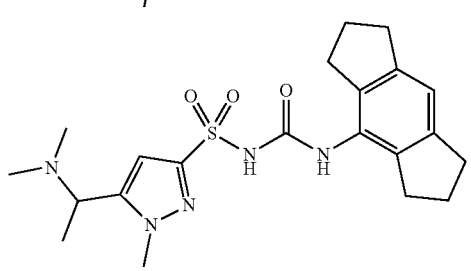
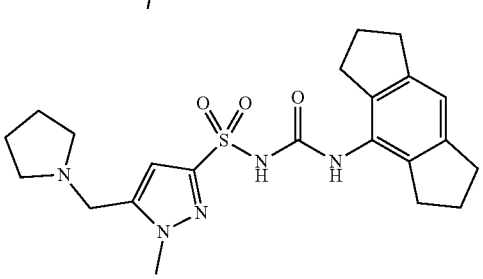

65
-continued
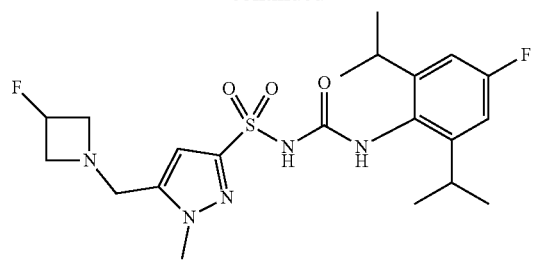
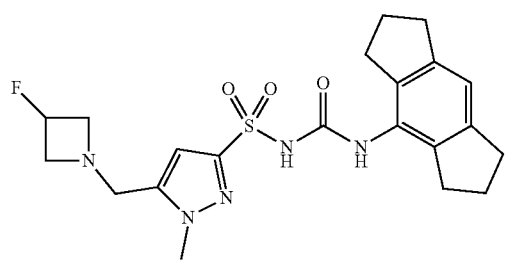
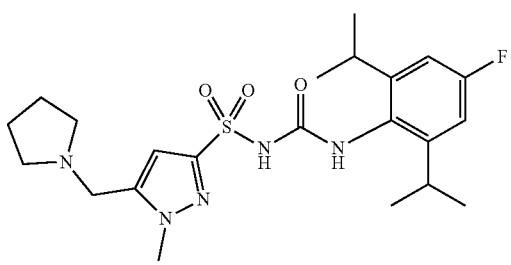
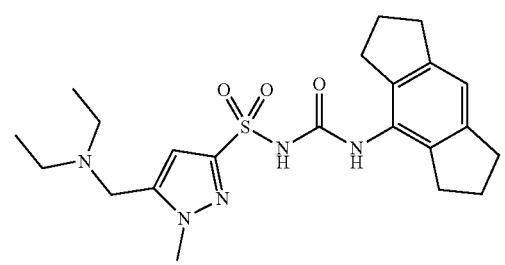
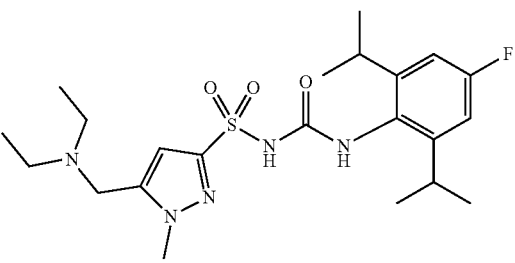
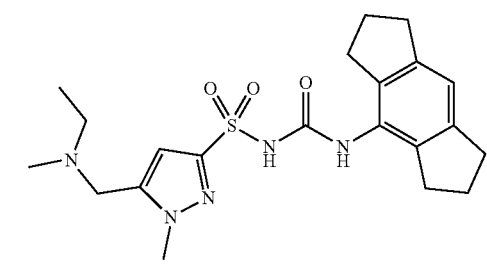
66
-continued
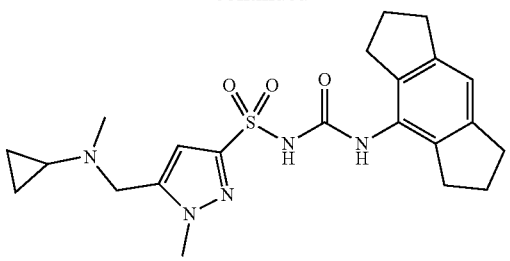
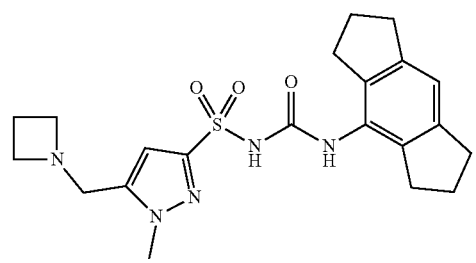
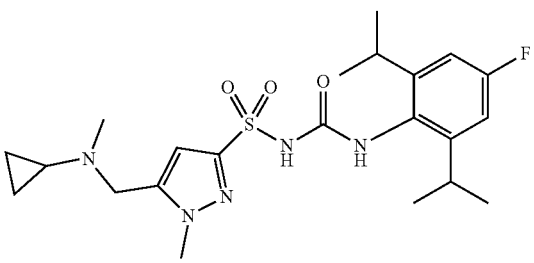
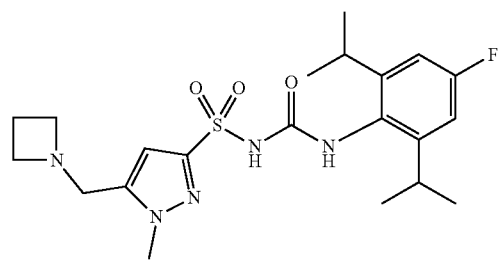
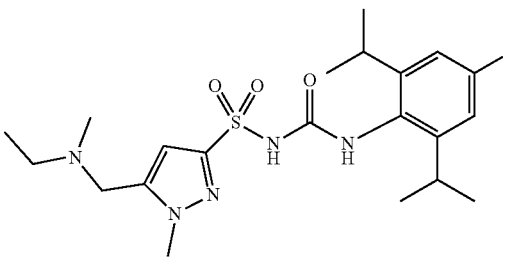
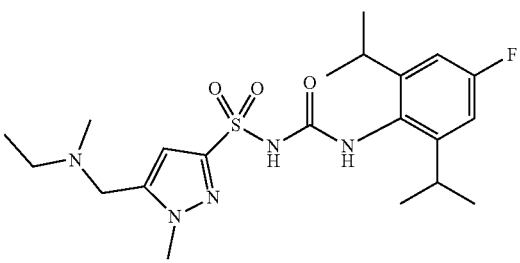

67
-continued
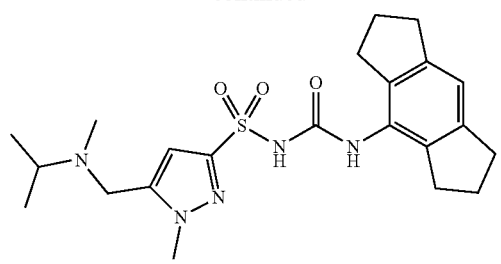
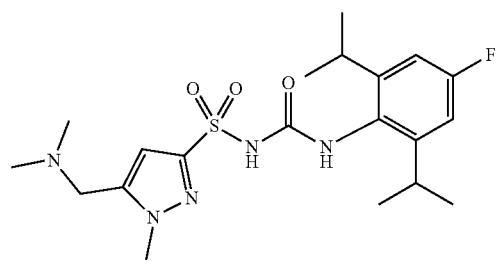
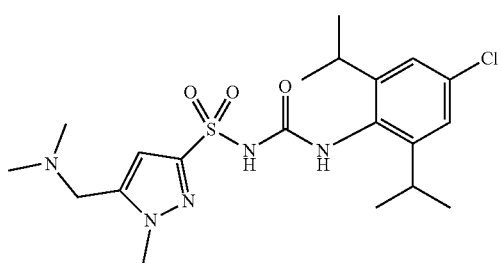
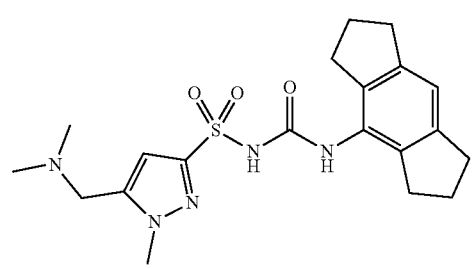
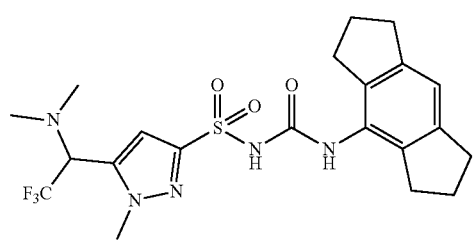
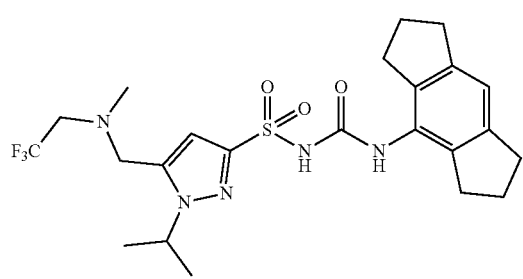
68
-continued
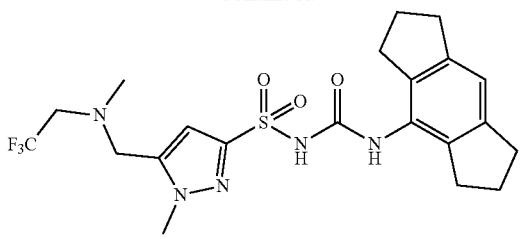
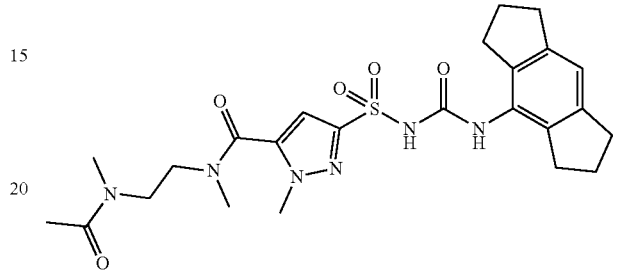
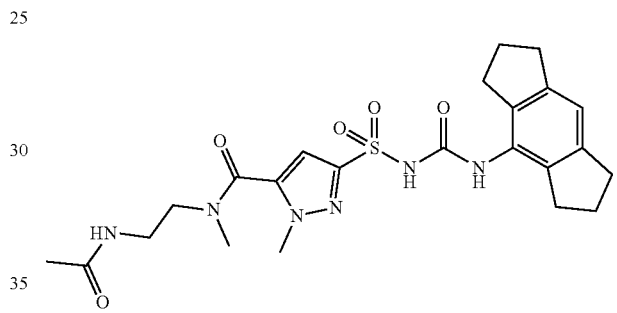
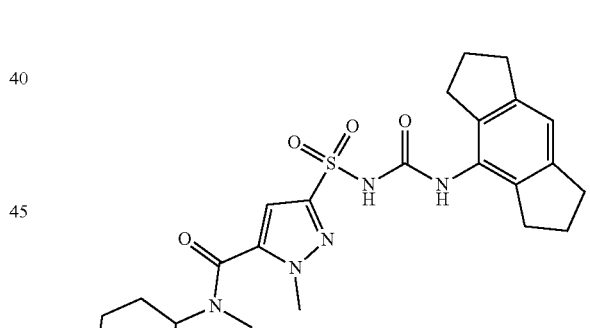
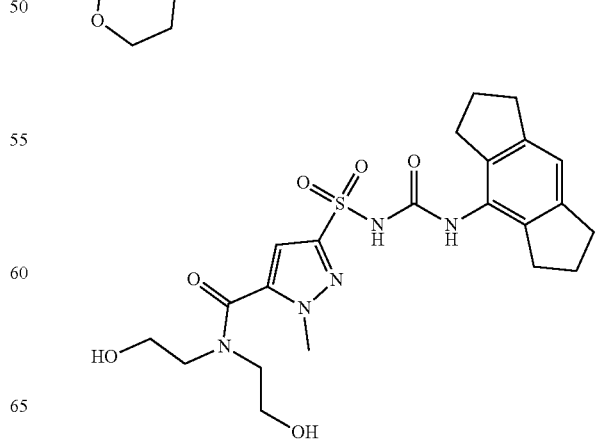

69
-continued
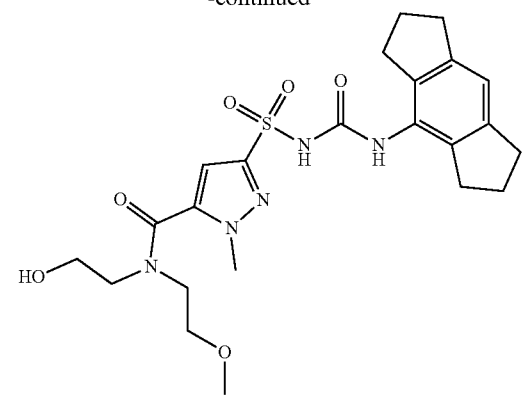
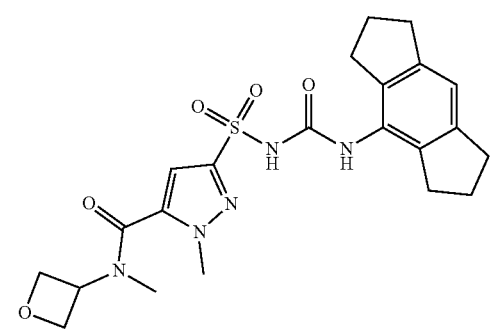
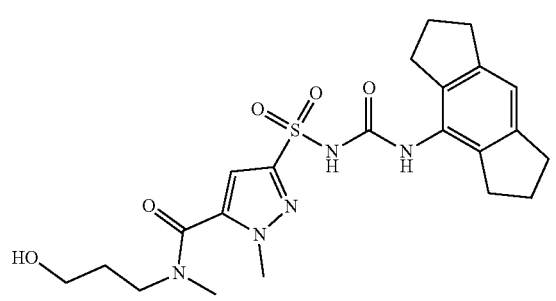
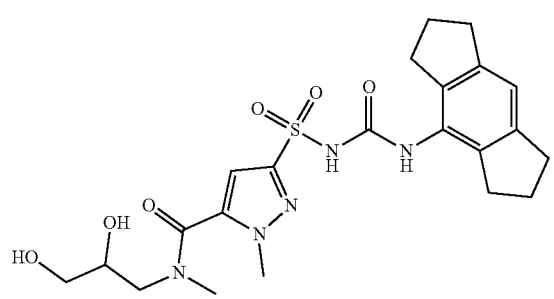
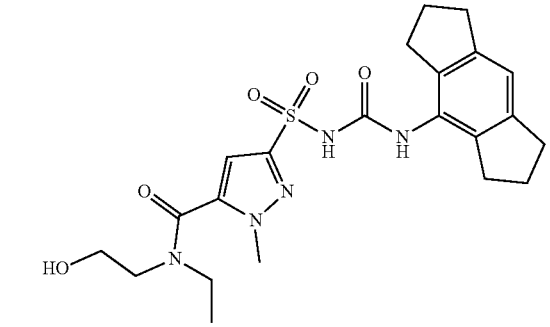
70
-continued
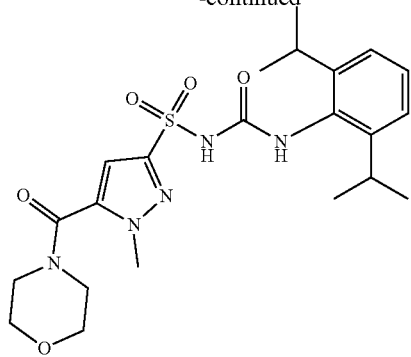
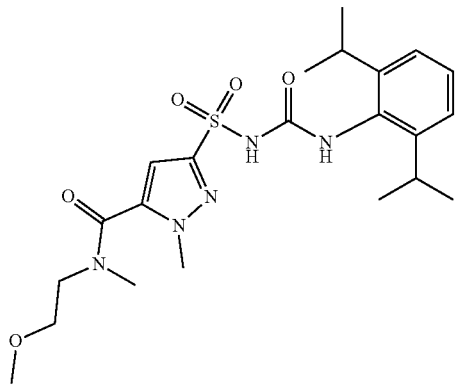
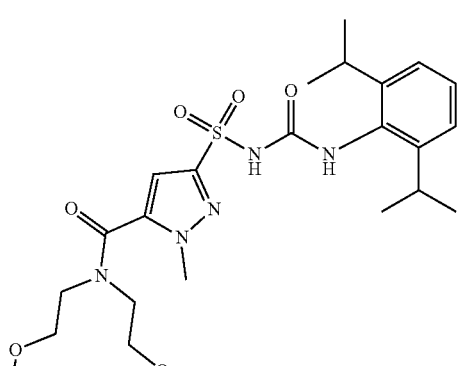
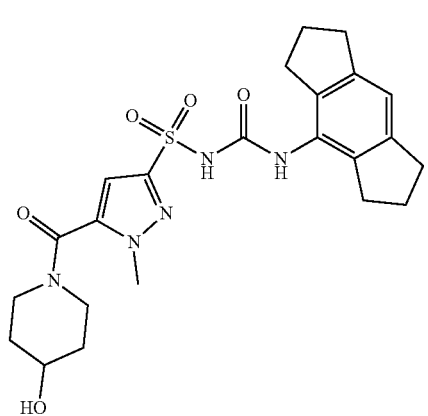

71
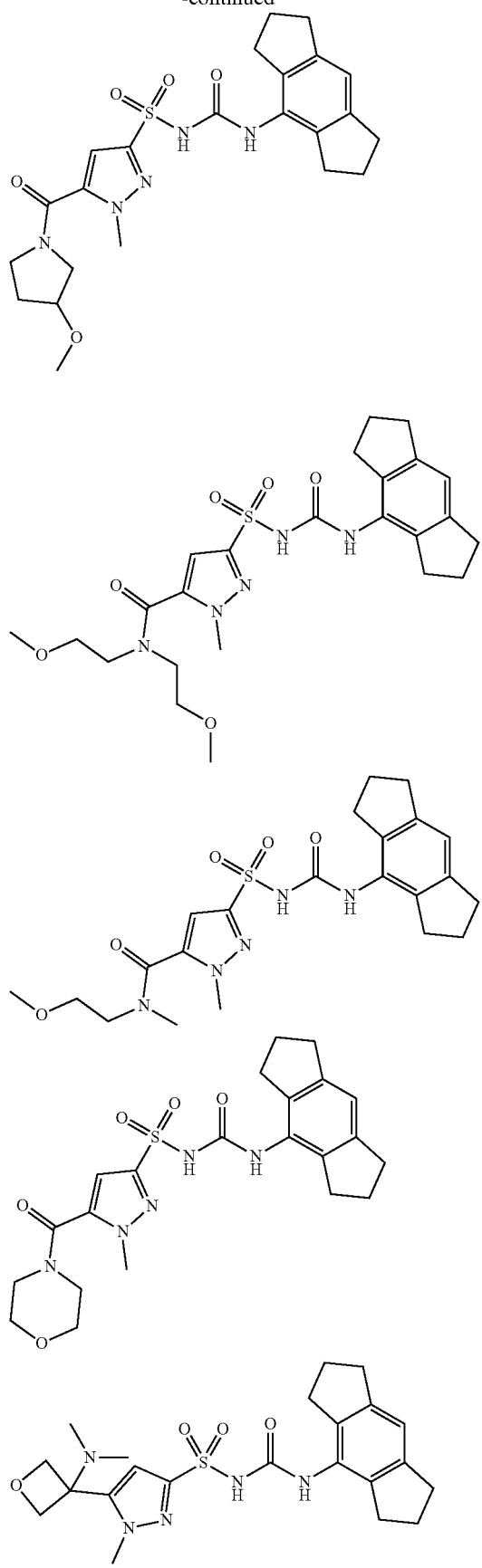
72
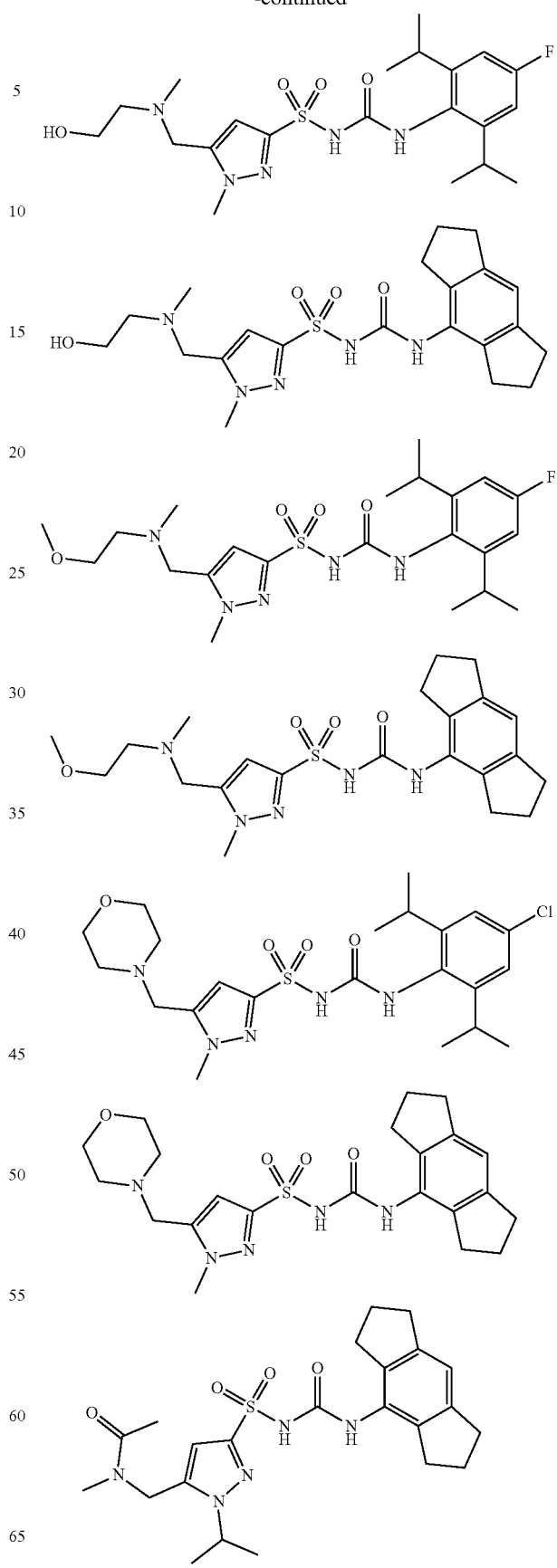

-continued
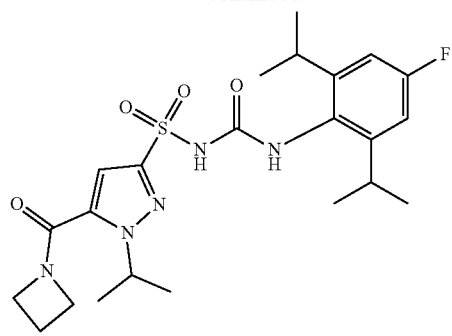
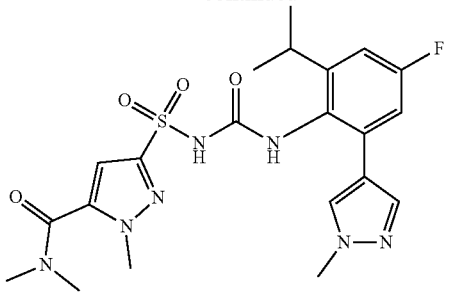
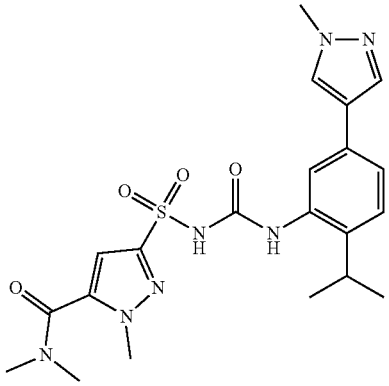
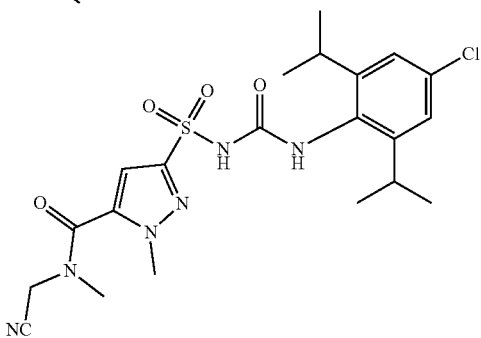
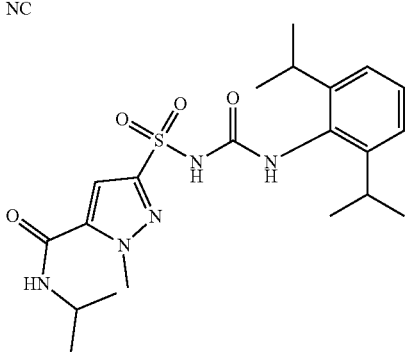
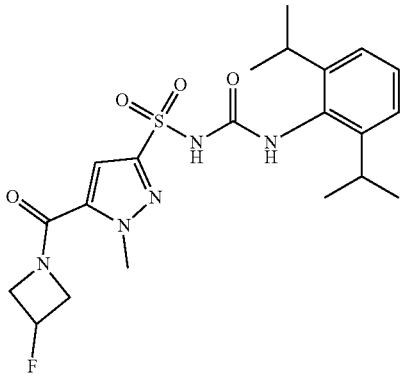

75
-continued
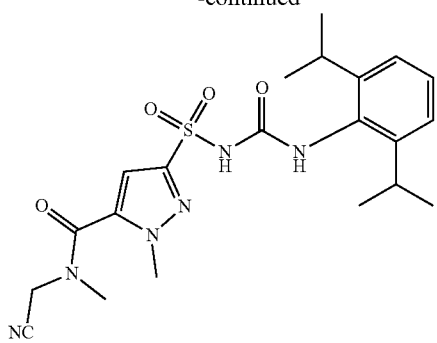
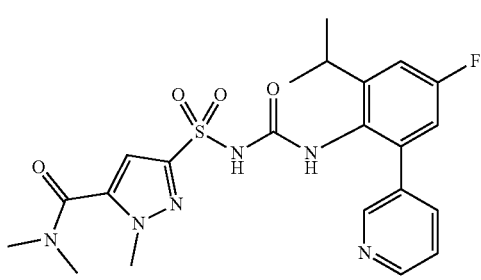
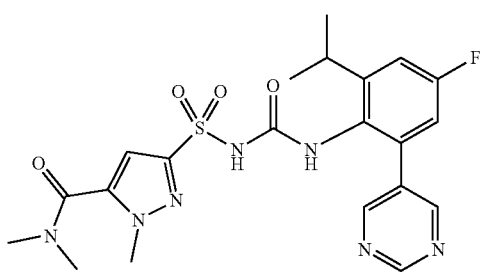
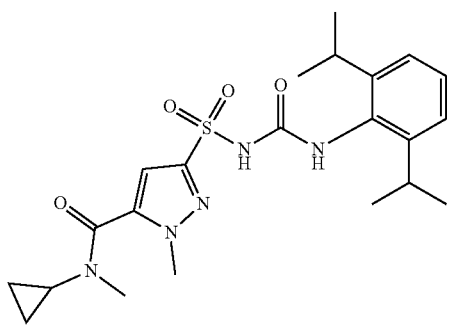
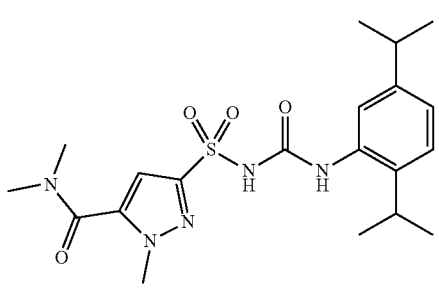
76
-continued
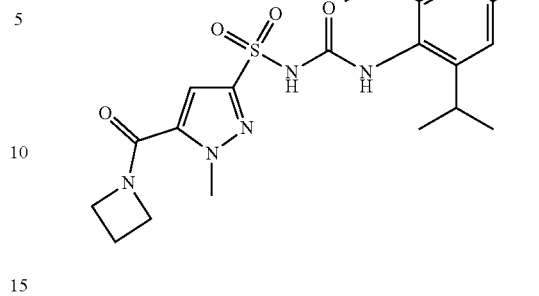
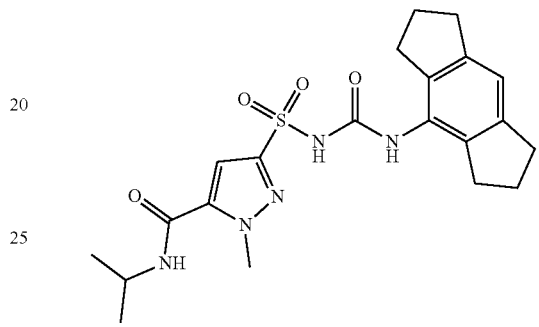
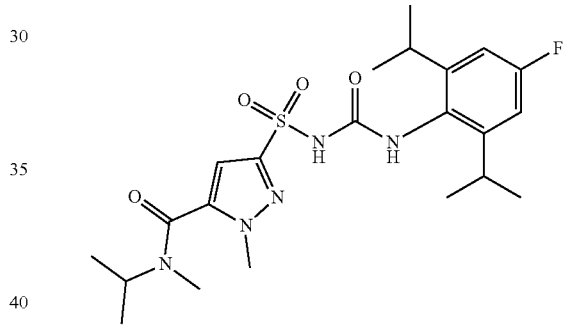
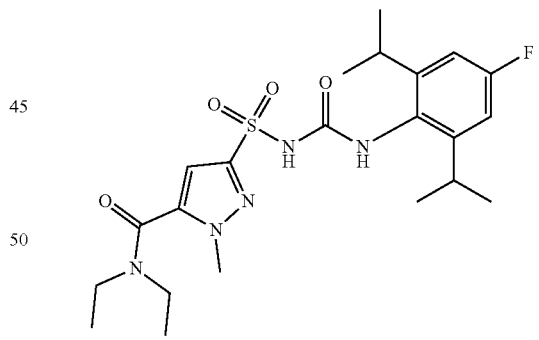
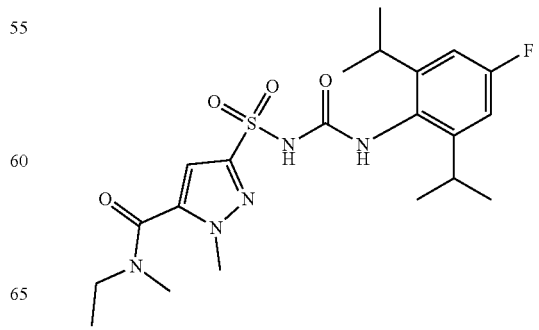

77
-continued
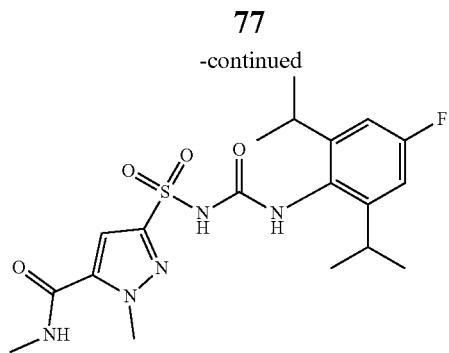
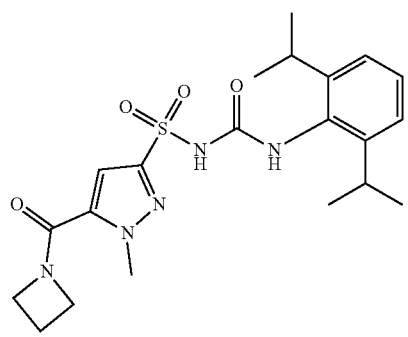
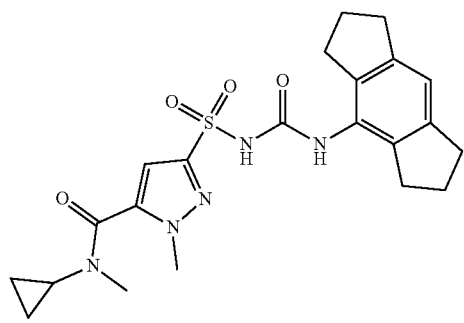
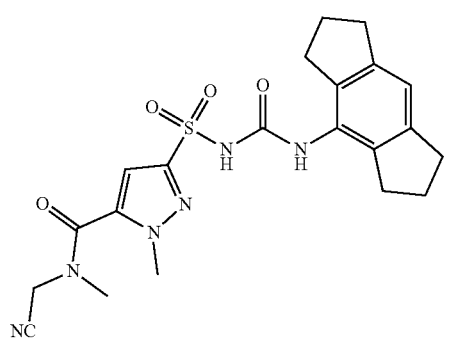
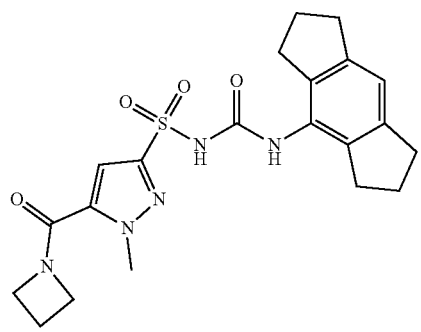
78
-continued
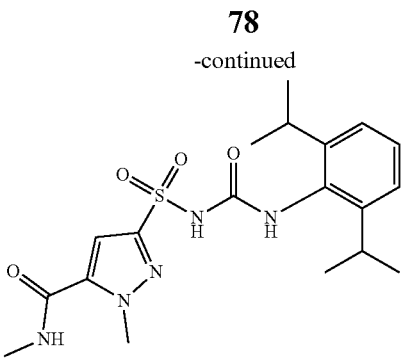
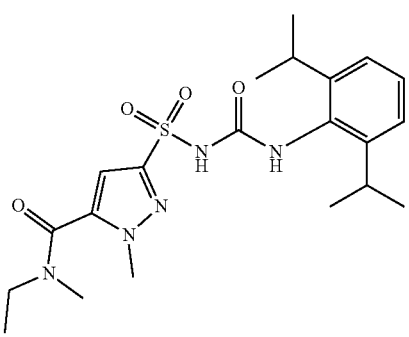
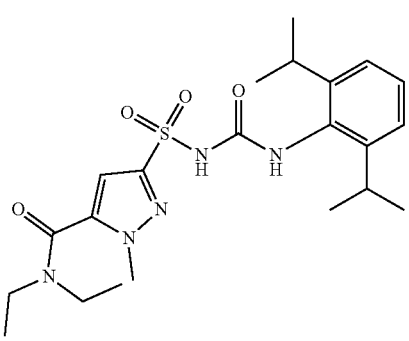
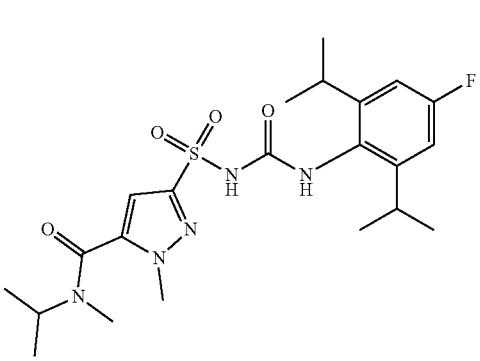
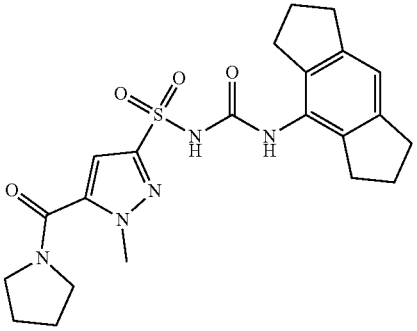

79
-continued
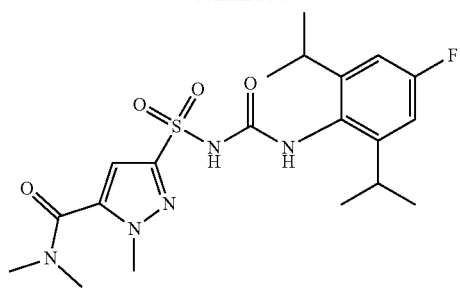
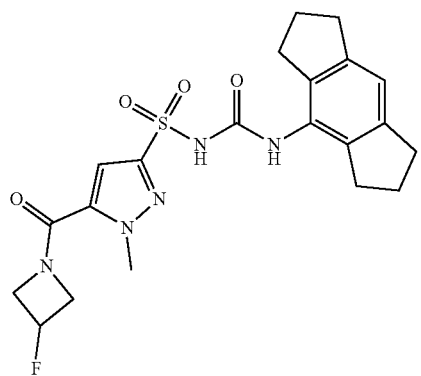
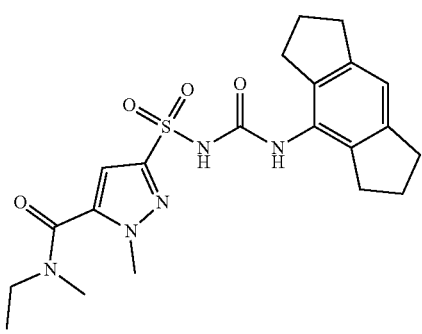
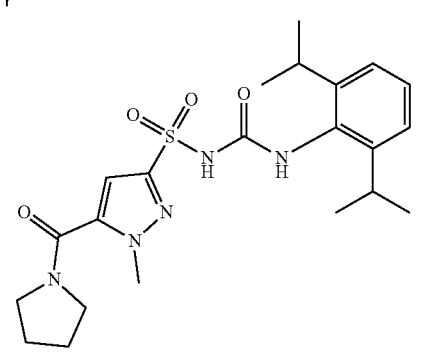
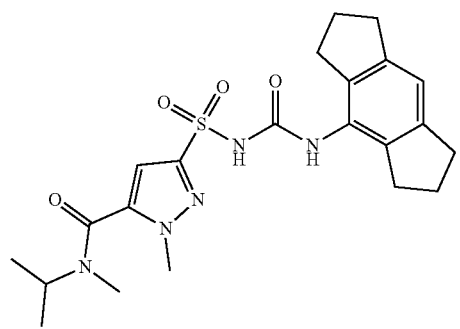
80
-continued
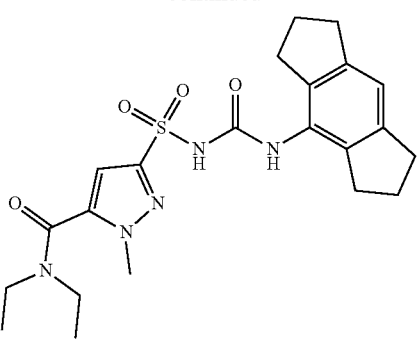
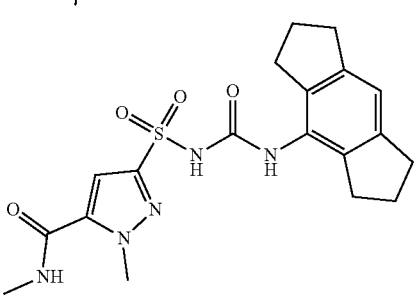
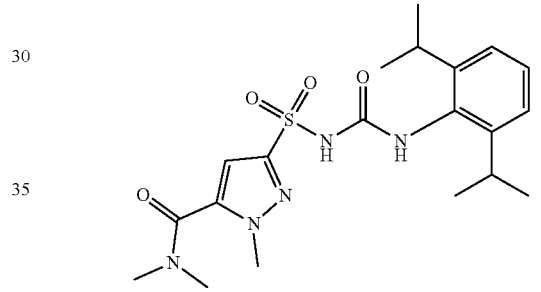
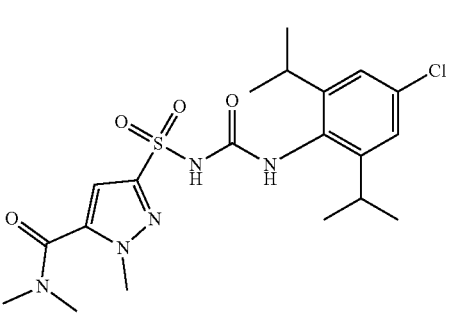
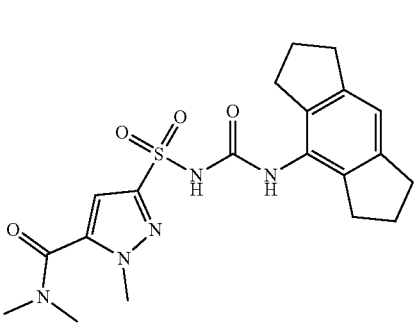

81
-continued
82
-continued
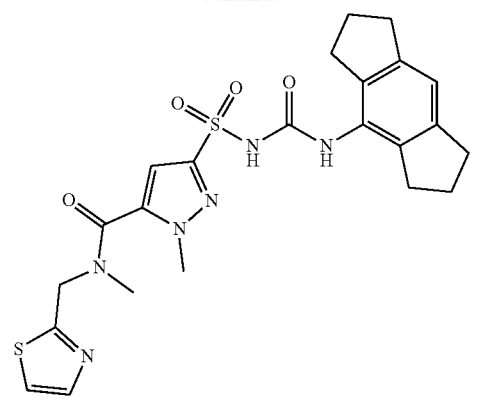
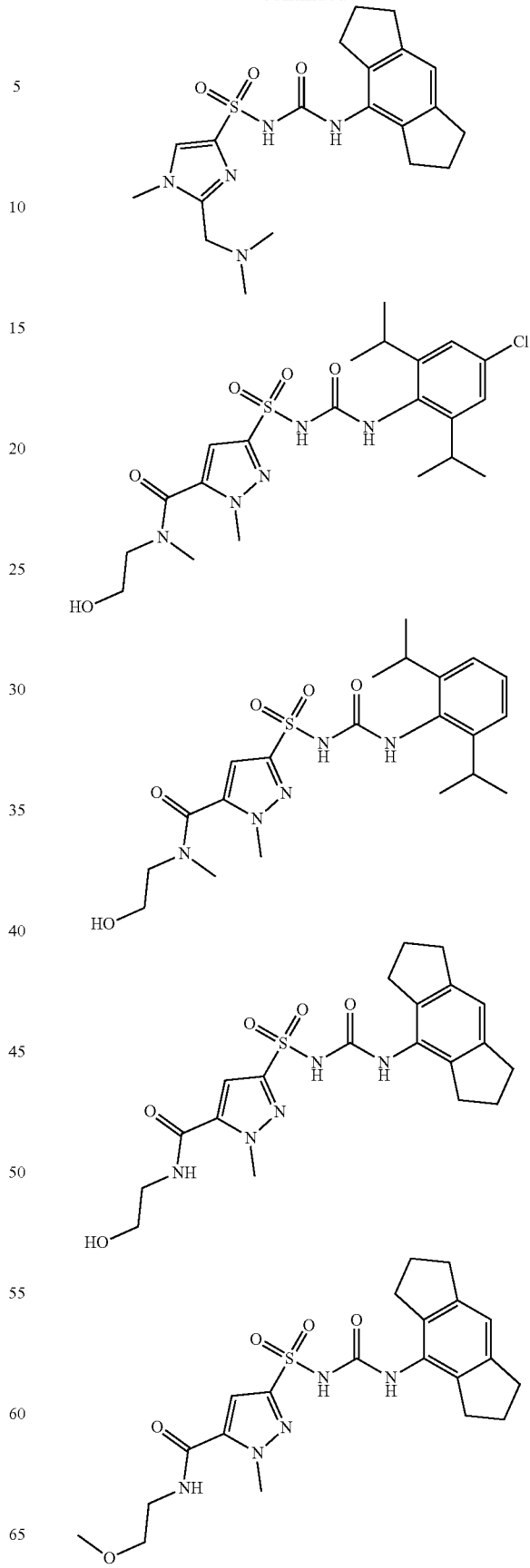

83
-continued
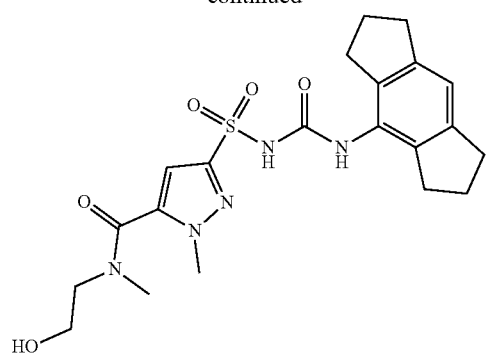
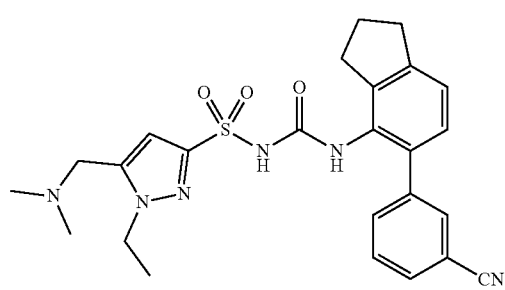
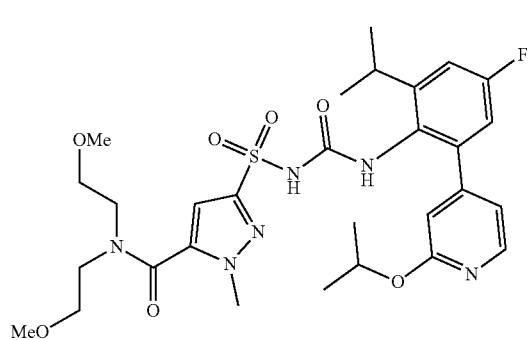
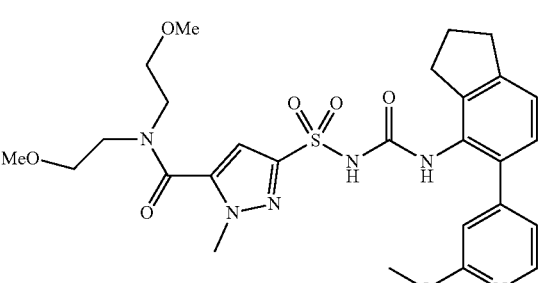
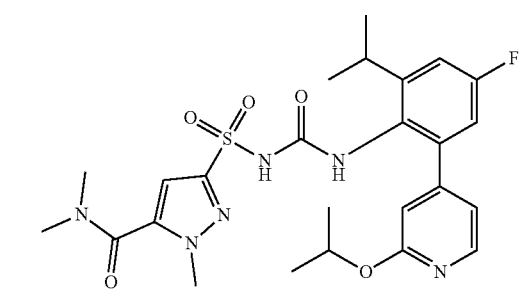
84
-continued
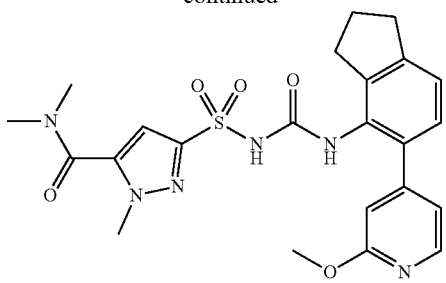
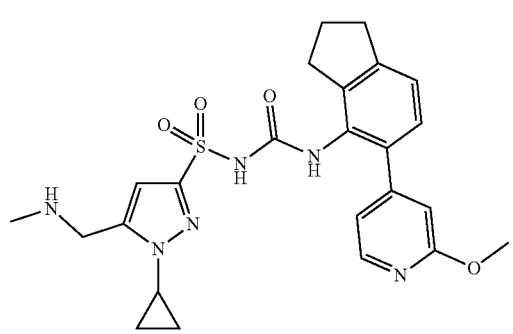
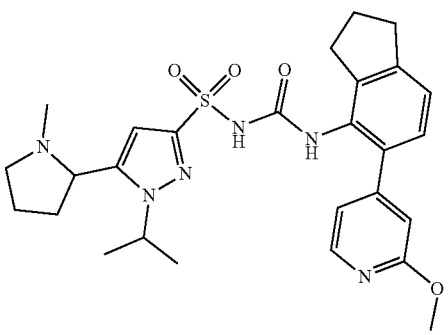
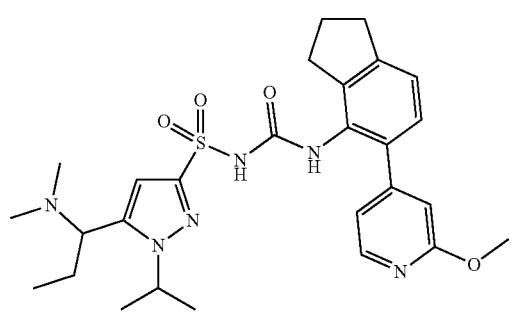
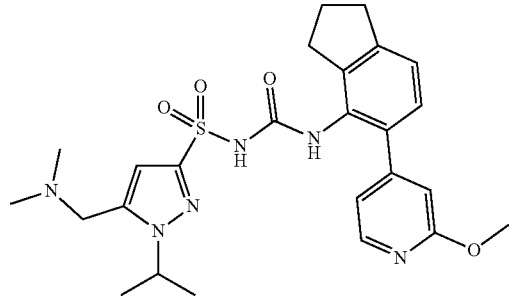

-continued

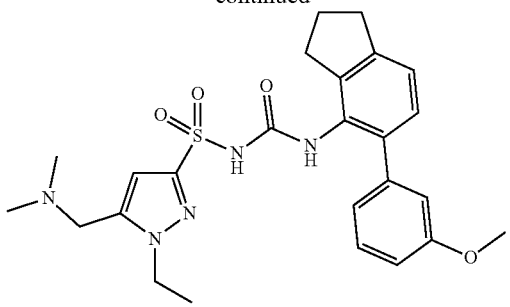

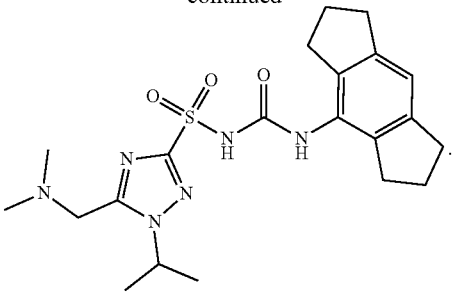

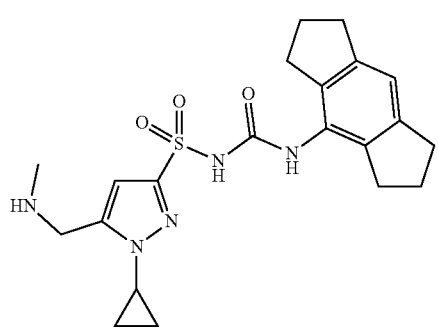

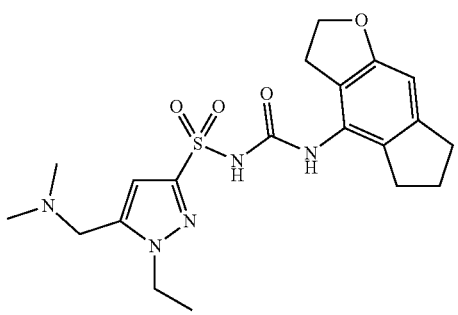

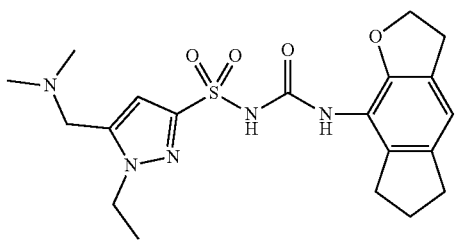

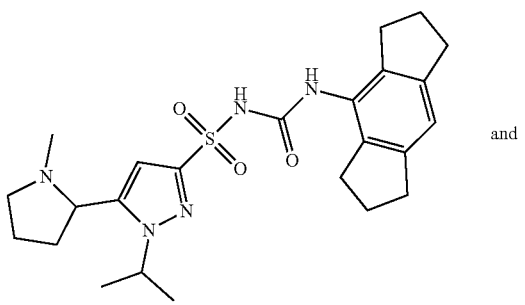 and

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound.

Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the present invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198

(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012149(4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): eo122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13:1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (TiD), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behget's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;

(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or *Trypanosomes*), helminth infections (e.g. from schistosoma, roundworms, tapeworms or flukes) and prion infections;

(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;

(vi) metabolic diseases such as type 2 diabetes (T2D), atherosclerosis, obesity, gout, and pseudo-gout;

(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;

(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;

(ix) liver diseases including non-alcoholic fatty liver disease (NAFLD), and non-alcoholic steatohepatitis (NASH) including advanced fibrosis stages F3 and F4, alcoholic fatty liver disease (AFLD), and alcoholic steatohepatitis (ASH);

(x) renal diseases including chronic kidney disease, oxalate nephropathy, nephrocalcinosis, glomerulonephritis, and diabetic nephropathy;

(xi) ocular diseases including those of the ocular epithelium, age-related macular degeneration (AMD) (dry and wet), uveitis, corneal infection, diabetic retinopathy, optic nerve damage, dry eye, and glaucoma;

(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;

(xiii) lymphatic conditions such as lymphangitis and Castleman's disease;

(xiv) psychological disorders such as depression and psychological stress;

(xv) graft versus host disease;

(xvi) allodynia including mechanical allodynia; and (xvii) any disease where an individual has been determined to carry a germline or somatic non-silent mutation in NLRP3.

In one embodiment, the disease, disorder or condition is selected from:
(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease; and
(xvi) any disease where an individual has been determined to carry a germline
or somatic non-silent mutation in NLRP3.

In another embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:

(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);

(iii) a muscular condition such as polymyositis or myasthenia gravis;

(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *Legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;
(xvi) a burn, wound, trauma, haemorrhage or stroke;
(xvii) radiation exposure; and/or
(xviii) obesity; and/or
(xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention.

Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3. In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:

(i) chemotherapeutic agents;
(ii) antibodies;
(iii) alkylating agents;
(iv) anti-metabolites;
(v) anti-angiogenic agents;
(vi) plant alkaloids and/or terpenoids;

(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPRio9881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PR$^\beta$), various retinoids, tetrahydrocortisol-S, thrombospondin-1 (TSP-1), transforming growth factor-beta (TGF-$\beta$), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a *Vinca* alkaloid, a podophyllotoxin and/or a taxane. In some embodiments, the one or more *Vinca* alkaloids may be derived from the Madagascar periwinkle, *Catharanthus roseus* (formerly known as *Vinca rosea*), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —N$_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30. CD39, CD73, CXCR4, and/or CXCL12. In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCBo24360, galunisertib, ulocuplumab, BKT140, bavituximab, CC-90002, bevacizumab, and/or MNR$^\beta$1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse, etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the present invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disease, disorder or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

By way of example, combinations of aspects and embodiments that are typical of the present invention include the following.

In a first combination, a compound of the first aspect of the invention is provided wherein ring A is monocyclic and wherein $R^1$ is a cyclic group substituted at the $\alpha$ and $\alpha'$ positions, wherein $R^1$ may optionally be further substituted.

In a second combination, a compound of the first aspect of the invention is provided wherein at least one of V, W, X, Y and Z is N or NH, and wherein $R^1$ is a cyclic group substituted at the $\alpha$ and $\alpha'$ positions, wherein $R^1$ may optionally be further substituted.

In a third combination, a compound of the first aspect of the invention is provided wherein $R^X$ and $R^Y$ do not comprise an amide group, and wherein $R^1$ is a cyclic group substituted at the $\alpha$ and $\alpha'$ positions, wherein $R^1$ may optionally be further substituted.

In a fourth combination, a compound of the first aspect of the invention is provided wherein $R^X$ and $R^Y$ do not comprise a nitrogen atom that is directly attached to a $sp^2$ hybridised atom, and wherein $R^1$ is a cyclic group substituted at the $\alpha$ and $\alpha'$ positions, wherein $R^1$ may optionally be further substituted.

In a fifth combination, a compound of the first aspect of the invention is provided wherein $R^X$ and $R^Y$ do not comprise an amide group, and wherein $R^1$ is a fused aryl or a fused heteroaryl group, wherein a first cycloalkyl, cycloalkenyl, non-aromatic heterocyclic, aryl or heteroaryl ring is fused to the aryl or heteroaryl group across the $\alpha,\beta$ positions and a second cycloalkyl, cycloalkenyl, non-aromatic heterocyclic, aryl or heteroaryl ring is fused to the aryl or heteroaryl group across the $\alpha',\beta'$ positions, and wherein $R^1$ may optionally be further substituted.

In a sixth combination, a compound of the first aspect of the invention is provided wherein $R^X$ and $R^Y$ do not comprise a nitrogen atom that is directly attached to a $sp^2$ hybridised atom, and wherein $R^1$ is a fused aryl or a fused heteroaryl group, wherein a first cycloalkyl, cycloalkenyl, non-aromatic heterocyclic, aryl or heteroaryl ring is fused to the aryl or heteroaryl group across the $\alpha,\beta$ positions and a second cycloalkyl, cycloalkenyl, non-aromatic heterocyclic, aryl or heteroaryl ring is fused to the aryl or heteroaryl group across the α',β' positions, and wherein $R^1$ may optionally be further substituted.

In a seventh combination, a compound of the first aspect of the invention is provided wherein:
- $R^X$ is a saturated or unsaturated hydrocarbyl group, wherein the hydrocarbyl group may be straight-chained or branched, or be or include cyclic groups, wherein the hydrocarbyl group may optionally be substituted with one or more groups selected from halo, —CN, —OH, —NH$_2$, oxo (=O) and =NH, wherein the hydrocarbyl group includes at least one heteroatom N in its carbon skeleton, and wherein the hydrocarbyl group may optionally include one or more further heteroatoms N, O or S in its carbon skeleton;
- $R^Y$ is a saturated or unsaturated hydrocarbyl group, wherein the hydrocarbyl group may be straight-chained or branched, or be or include cyclic groups, wherein the hydrocarbyl group may optionally be substituted with one or more groups selected from halo, —CN, —OH, —NH$_2$, oxo (=O) and =NH, and wherein the hydrocarbyl group may optionally include one or more heteroatoms N, O or S in its carbon skeleton;
- $R^X$ contains from 1 to 11 atoms other than hydrogen or halogen;
- $R^Y$ contains from 1 to 11 atoms other than hydrogen or halogen;
- m is 0;
- $R^1$ is an aryl or a heteroaryl group, wherein the aryl or the heteroaryl group is substituted at the α and α' positions, and wherein $R^1$ may optionally be further substituted; and
- $R^1$ contains from 9 to 20 atoms other than hydrogen or halogen.

In an eighth combination, a compound of the first aspect of the invention is provided wherein:
- $R^X$ is a saturated hydrocarbyl group, wherein the hydrocarbyl group is straight-chained or branched, or is or includes cyclic groups, wherein the saturated hydrocarbyl group is unsubstituted or optionally substituted with one or more fluoro and/or chloro groups, wherein the saturated hydrocarbyl group includes at least one heteroatom N in its carbon skeleton, and wherein the saturated hydrocarbyl group may optionally include one or two further heteroatoms independently selected from N and O in its carbon skeleton; and
- $R^Y$ is a saturated hydrocarbyl group, wherein the hydrocarbyl group is straight-chained or branched, or is or includes cyclic groups, wherein the saturated hydrocarbyl group is unsubstituted or optionally substituted with one or more fluoro and/or chloro groups, and wherein the saturated hydrocarbyl group may optionally include one or two oxygen atoms in its carbon skeleton; and
- $R^1$ is an aryl or a heteroaryl group, wherein the aryl or the heteroaryl group is substituted at the α and α' positions, and wherein $R^1$ may optionally be further substituted. Typically in such a combination, ring A is monocyclic. Typically in such a combination, $R^1$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein $R^1$ may optionally be further substituted.

A ninth combination provides a compound of the first or second aspect of the invention, or a pharmaceutically acceptable salt, solvate or prodrug of the third aspect of the invention, or a pharmaceutical composition of the fourth aspect of the invention, wherein at least one of V, W, X, Y and Z is N or NH, for use in medicine.

A tenth combination provides a compound of the first or second aspect of the invention, or a pharmaceutically acceptable salt, solvate or prodrug of the third aspect of the invention, or a pharmaceutical composition of the fourth aspect of the invention, wherein ring A is monocyclic, for use in medicine.

Typically, in any of the above exemplary combinations, Q is O.

Typically, in any of the above exemplary combinations, $R^1$ is an aryl or a heteroaryl group, wherein the aryl or the heteroaryl group is substituted at the α and α' positions, and wherein $R^1$ may optionally be further substituted. Typically, each substituent at the α and α' positions comprises a carbon atom. Typically in any of the above exemplary combinations, $R^1$ contains from 9 to 20 atoms other than hydrogen or halogen.

Typically, in any of the above exemplary combinations, at least one of V, W, X, Y and Z is N or NH. More typically, V, X and Y are each independently selected from C and N, and W and Z are each independently selected from N, NH and CH, provided that at least one of V, W, X, Y and Z is N or NH.

Typically, in any of the above exemplary combinations, $R^X$ is a monovalent group comprising at least one nitrogen atom, wherein $R^X$ contains from 1 to 11 atoms other than hydrogen or halogen, and $R^Y$ is a monovalent group, wherein $R^Y$ contains from 1 to 11 atoms other than hydrogen or halogen.

Most typically, in any of the above exemplary combinations, Q is O, m is 0, V is C, X and Y are each independently selected from C and N, and W and Z are each independently selected from N, NH and CH, provided that at least one of W, X, Y and Z is N or NH, and provided that the group:

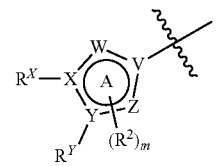

including any optional substituents, contains from 8 to 17 atoms other than hydrogen or halogen.

As will be appreciated the above combinations are exemplary only and other combinations of aspects and embodiments, including combinations of the above combinations, may readily be envisaged.

EXAMPLES—COMPOUND SYNTHESIS

All solvents, reagents and compounds were purchased and used without further purification unless stated otherwise.

Abbreviations

2-MeTHF 2-methyltetrahydrofuran
Ac$_2$O acetic anhydride
AcOH acetic acid aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMA dimethylacetamide
DMAP 4-dimethylaminopyridine, also called N,N-dimethylpyridin-4-amine
DME dimethoxyethane
DMF N,N-dimethylformamide
DMSO dimethyl sulfoxide
eq or equiv equivalent
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaOtBu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
NMR nuclear magnetic resonance (spectroscopy)
Pd(dba)$_3$ tris(dibenzylideneacetone) dipalladium(0)
Pd(dppf)Cl$_2$ [1,1'-bis(diphenylphosphino)ferrocene] dichloropalladium(II)
PE petroleum ether
Ph phenyl
PMB p-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated
SCX solid supported cation exchange (resin)
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight Experimental Methods Nuclear Magnetic Resonance NMR spectra were recorded at 300, 400 or 500 MHz. Spectra were measured at 298 K, unless indicated otherwise, and were referenced relative to the solvent resonance. The chemical shifts are reported in parts per million. Spectra were recorded using one of the following machines:
  a Bruker Avance III spectrometer at 400 MHz fitted with a BBO 5 mm liquid probe,
  a Bruker 400 MHz spectrometers using ICON-NMR, under TopSpin program control,
  a Bruker Avance III HD spectrometer at 500 MHz, equipped with a Bruker 5 mm SmartProbe™,
  an Agilent VNMRS 300 instrument fitted with a 7.05 Tesla magnet from Oxford instruments, indirect detection probe and direct drive console including PFG module, or
  an Agilent MercuryPlus 300 instrument fitted with a 7.05 Tesla magnet from Oxford instruments, 4 nuclei auto-switchable probe and Mercury plus console.

LC-MS

LC-MS Methods: Using SHIMADZU LCMS-2020, Agilent 1200 LC/G1956A MSD and Agilent 1200\G6110A, Agilent 1200 LC & Agilent 6110 MSD. Mobile Phase: A: 0.025% NH$_3$.H$_2$O in water (v/v); B: acetonitrile. Column: Kinetex EVO C18 2.1×30 mm, 5 µm.

Reversed Phase HPLC Conditions for the LCMS Analytical Methods

Methods 1a and 1b: Waters Xselect CSH C18 XP column (4.6×30 mm, 2.5 µm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method 1b) over 4 min employing UV detection at 254 nm. Gradient information: 0-3.00 min, ramped from 95% water-5% acetonitrile to 5% water-95% acetonitrile; 3.00-3.01 min, held at 5% water-95% acetonitrile, flow rate increased to 4.5 mL min$^{-1}$; 3.01-3.50 min, held at 5% water-95% acetonitrile; 3.50-3.60 min, returned to 95% water-5% acetonitrile, flow rate reduced to 3.50 mL min$^{-1}$; 3.60-3.90 min, held at 95% water-5% acetonitrile;
  3.90-4.00 min, held at 95% water-5% acetonitrile, flow rate reduced to 2.5 mL min$^{-1}$.
  Method 1c: Agilent 1290 series with UV detector and HP 6130 MSD mass detector using Waters XBridge BEH C18 XP column (2.1×50 mm, 2.5 µm) at 35° C.; flow rate 0.6 mL/min; mobile phase A: ammonium acetate (10 mM); water/MeOH/acetonitrile (900:60:40); mobile phase B: ammonium acetate (10 mM); water/MeOH/acetonitrile (100:540:360); over 4 min employing UV detection at 215 and 238 nm. Gradient information: 0-0.5 min, held at 80% A-20% B; 0.5-2.0 min, ramped from 80% A-20% B to 100% B.

Reversed Phase HPLC Conditions for the UPLC Analytical Methods

Methods 2a and 2b: Waters BEH C18 (2.1×30 mm, 1.7 µm) at 40° C.; flow rate 0.77 mL min-1 eluted with a H$_2$O-MeCN gradient containing either 0.1% v/v formic acid (Method 2a) or 10 mM NH₄HCO₃ in water (Method 2b) over 3 min employing UV detection at 254 nm. Gradient information: 0-0.11 min, held at 95% water-5% acetonitrile, flow rate 0.77 mL min⁻¹; 0.11-2.15 min, ramped from 95% water-5% acetonitrile to 5% water-95% acetonitrile; 2.15-2.49 min, held at 5% water-95% acetonitrile, flow rate 0.77 mL min⁻¹; 2.49-2.56 min, returned to 95% water-5% acetonitrile; 2.56-3.00 min, held at 95% water-5% acetonitrile, flow rate reduced to 0.77 mL min⁻¹.

Preparative Reversed Phase HPLC General Methods

Method 1 (acidic preparation): Waters X-Select CSH column C18, 5 μm (19×50 mm), flow rate 28 mL min-1 eluting with a H₂O-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Method 2 (basic preparation): Waters X-Bridge Prep column C18.5 μm (19×50 mm), flow rate 28 mL min-1 eluting with a 10 mM NH₄HCO₃-MeCN gradient over 6.5 min using UV detection at 254 nm. Gradient information: 0.0-0.2 min, 10% MeCN; 0.2-5.5 min, ramped from 10% MeCN to 40% MeCN; 5.5-5.6 min, ramped from 40% MeCN to 95% MeCN; 5.6-6.5 min, held at 95% MeCN.

Method 3: Phenomenex Gemini column, 10 μm (150×25 mm), flow rate=25 mL/min eluting with a water-acetonitrile gradient containing 0.04% NH₃ at pH 10 over 9 minutes using UV detection at 220 and 254 nm. Gradient information: 0-9 minutes, ramped from 8% to 35% acetonitrile; 9-9.2 minutes, ramped from 35% to 100% acetonitrile; 9.2-15.2 minutes, held at 100% acetonitrile.

Method 4: Revelis C18 reversed-phase 12 g cartridge [carbon loading 18%; surface area 568 m²/g; pore diameter 65 Angstrom; pH (5% slurry) 5.1; average particle size 40 μm], flow rate=30 mL/min eluting with a water-methanol gradient over 35 minutes using UV detection at 215, 235, 254 and 280 nm. Gradient information: 0-5 minutes, held at 0% methanol; 5-30 minutes, ramped from 0% to 70% methanol; 30-30.1 minutes, ramped from 70% to 100% methanol; 30.1-35 minutes, held at 100% methanol.

Synthesis of Intermediates

Intermediate P1: 5-Methyl-4-oxo-4,5,6,7-tetrahydropyrazolo[1,5-a]pyrazine-2-sulfonamide Step A: 2-Amino-5-methyl-6,7-dihydropyrazolo[1,5-a]pyrazin-4(5H)-one

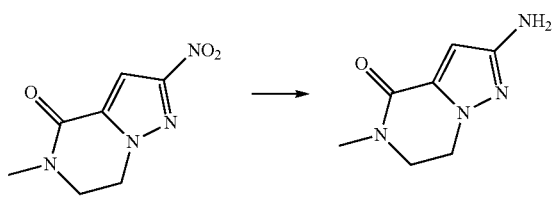

Zinc (167 mg, 2.55 mmol) was added portionwise to 5-methyl-2-nitro-6,7-dihydropyrazolo[1,5-a]pyrazin-4(5H)-one (1.4 g, 7.14 mmol) in AcOH (1.0 mL) and THF (1.5 mL). The reaction mixture was left to stir at room temperature for 2 days. The reaction mixture was filtered through a pad of Celite®, washed with DCM (2×15 mL) and the filtrate concentrated under reduced pressure to give a yellow solid. The solid was suspended in DCM (5 mL), filtered and the filtrate was evaporated to dryness to give the title compound (2.2 g, 74%) as a yellow solid.

¹H NMR (DMSO-d₆) δ 5.80 (s, 1H), 4.83 (s, 2H), 4.10-3.93 (m, 2H), 3.72-3.55 (m, 2H), 2.97 (s, 3H).

LCMS; m/z 167 (M+H)⁺ (ES⁺).

Step B: 5-Methyl-4-oxo-4,5,6,7-tetrahydropyrazolo[1,5-a]pyrazine-2-sulfonyl Chloride

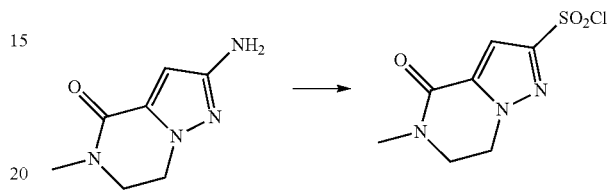

A mixture of aqueous HCl (2.2 mL) in water (8 mL) and acetonitrile (8 mL) was cooled to −10° C. and treated with a solution of NaNO₂ (0.50 g, 7.25 mmol) in water (0.9 mL) dropwise maintaining the internal temperature below 0° C. The solution was stirred for 10 minutes and then treated with a solution of 2-amino-5-methyl-6,7-dihydropyrazolo[1,5-a]pyrazin-4(5H)-one (0.997 g, 6 mmol) in acetonitrile (8 mL) (which was pre-cooled to 0° C.) at 0° C. The resulting reaction mixture was stirred at 0° C. for 50 minutes. Cold AcOH (4.8 mL), CuCl₂ dihydrate (0.30 g, 2.23 mmol) and CuCl (0.03 g, 0.30 mmol) were sequentially added to the reaction mixture and the reaction mixture was purged with SO₂ gas for 20 minutes at 0° C. The reaction was stirred for a further 45 minutes, diluted with water (20 mL) and extracted with EtOAc (2×20 mL). The organic phase was washed with water (25 mL) and saturated brine (25 mL), dried (MgSO₄), filtered and concentrated in vacuo to afford a brown oil. The brown oil was purified by chromatography on silica gel (40 g column, 0-100% EtOAc/isohexane) to afford the title compound (577 mg, 30%) as a yellow crystalline solid.

¹H NMR (CDCl₃) δ 7.39 (s, 1H), 4.63-4.45 (m, 2H), 3.95-3.83 (m, 2H), 3.19 (s, 3H).

Step C: 5-Methyl-4-oxo-4,5,6,7-tetrahydropyrazolo[1,5-a]pyrazine-2-sulfonamide

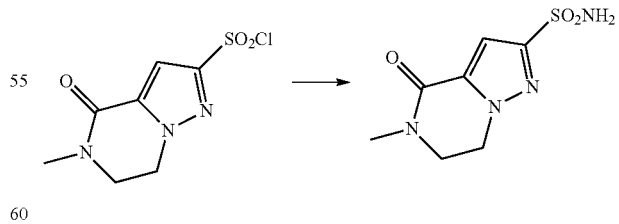

5-Methyl-4-oxo-4,5,6,7-tetrahydropyrazolo[1,5-a]pyrazine-2-sulfonyl chloride (577 mg, 1.826 mmol) in THF (4 mL) was treated with 0.5 M ammonia in 1,4-dioxane (11.00 mL, 5.50 mmol). The reaction mixture was stirred at room temperature for 2 hours and concentrated to dryness. The residue was suspended in water (10 mL) and filtered. The yellow powder obtained was then washed with DCM (2×5 mL) and dried under vacuum to afford the title compound (332 mg, 77%) as a white powder.

¹H NMR (DMSO-d₆) δ 7.57 (s, 2H), 6.93 (s, 1H), 4.59-4.34 (m, 2H), 3.90-3.71 (m, 2H), 3.01 (s, 3H).

LCMS; m/z 231 (M+H)⁺ (ES⁺).

Intermediate P2: 1-(2-(Dimethylamino)ethyl)-5-((dimethylamino)methyl)-1H-pyrazole-3-sulfonamide Step A: Lithium 1-(tetrahydro-2H-pyran-2-yl)-1H-pyrazole-5-sulfinate

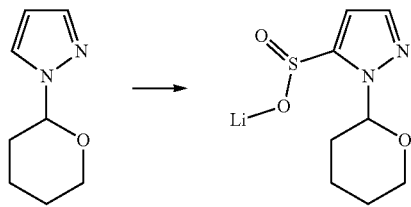

A solution of BuLi (100 mL, 250 mmol, 2.5M in hexanes) was added slowly to a solution of 1-(tetrahydro-2H-pyran-2-yl)-1H-pyrazole (36.2 g, 238 mmol) in THF (500 mL) keeping the temperature below −65° C. The mixture was stirred for 1.5 hours, then sulfur dioxide was bubbled through for 10 minutes. The mixture was allowed to warm to room temperature, the solvent evaporated and the residue triturated with TBME (300 mL) and filtered. The solid was washed with TBME and isohexane and dried to afford the crude title compound (54.89 g, 99%).

¹H NMR (DMSO-d₆) δ 7.26 (d, J=1.6 Hz, 1H), 6.10 (d, J=1.7 Hz, 1H), 5.99 (dd, J=10.0, 2.5 Hz, 1H), 3.92-3.87 (m, 1H), 3.56-3.49 (m, 1H), 2.25-2.15 (m, 1H), 2.00-1.91 (m, 1H), 1.75-1.69 (m, 1H), 1.66-1.46 (m, 3H).

LCMS; m/z 215 (M−H)⁻ (ES⁻).

Step B: N,N-Bis(4-methoxybenzyl)-1-(tetrahydro-2H-pyran-2-yl)-1H-pyrazole-5-sulfonamide

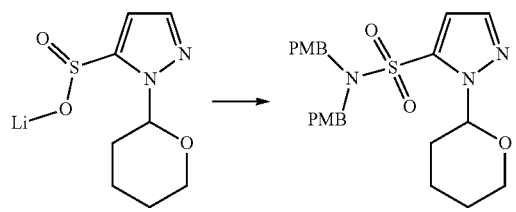

NCS (12.0 g, 90 mmol) was added to a suspension of lithium 1-(tetrahydro-2H-pyran-2-yl)-1H-pyrazole-5-sulfinate (20 g, 90 mmol) in DCM (250 mL) cooled in an ice bath. The mixture was stirred for 4 hours, quenched with water (100 mL), and then partitioned between DCM (300 mL) and water (200 mL. The organic phase was washed with water (200 mL), dried (MgSO₄), filtered and evaporated to ~50 mL. The solution was added to a mixture of bis(4-methoxybenzyl)amine (24 g, 93 mmol) and triethylamine (40 mL, 287 mmol) in DCM (300 mL) cooled in an ice bath. After stirring for 1 hour, the mixture was warmed to room temperature, and then partitioned between DCM (300 mL) and water (250 mL). The organic layer was washed with water (250 mL), aq 1M HCl (2×250 mL), water (250 mL), dried (MgSO₄), filtered, and evaporated to afford the crude title compound (41.02 g, 97%) as a brown oil.

LCMS; m/z 494.2 (M+Na)⁺ (ES⁺).

Step C: N,N-Bis(4-methoxybenzyl)-1H-pyrazole-3-sulfonamide

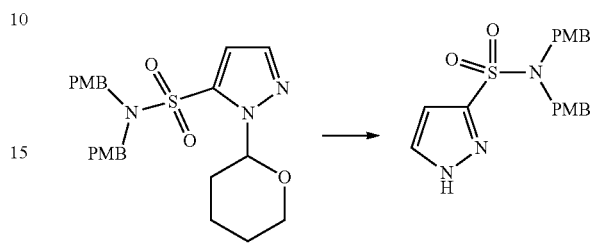

A mixture of N,N-bis(4-methoxybenzyl)-1-(tetrahydro-2H-pyran-2-yl)-1H-pyrazole-5-sulfonamide (41 g, 87 mmol) and aq 1M HCl (30 mL) in THF (300 mL) and MeOH (50 mL) was stirred at room temperature for 18 hours. The solvent was evaporated and the residue partitioned between EtOAc (400 mL) and aq 1M HCl (200 mL). The organic layer was washed with 10% brine (200 mL), dried (MgSO₄), filtered and evaporated. The residue was triturated with TBME, filtered and dried to afford the title compound (24.87 g, 69%) as an off white solid.

¹H NMR (CDCl₃) δ 7.88 (d, J=2.4 Hz, 1H), 7.06-7.02 (m, 4H), 6.79-6.75 (m, 4H), 6.63 (d, J=2.4 Hz, 1H), 4.31 (s, 4H), 3.78 (s, 6H). Exchangeable proton not visible.

LCMS; m/z 388 (M+H)⁺ (ES⁺); 386 (M−H)⁻ (ES⁻).

Step D: 1-(2-Hydroxyethyl)-N,N-bis(4-methoxybenzyl)-1H-pyrazole-3-sulfonamide

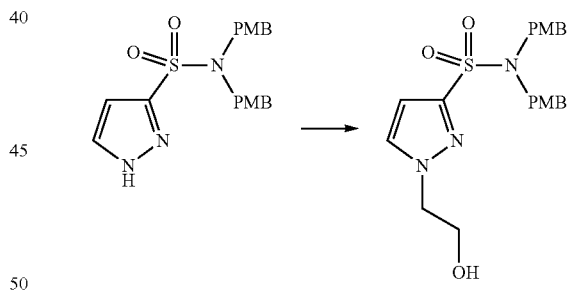

N,N-Bis(4-methoxybenzyl)-1H-pyrazole-3-sulfonamide (3.94 g, 10.17 mmol) and potassium carbonate (4.22 g, 30.5 mmol) were suspended in dry acetonitrile (30 mL). 2-Bromoethanol (0.937 mL, 13.22 mmol) was added, the mixture was warmed to 50° C. overnight, then water (20 mL) was added and the organic layer was collected. The aqueous layer was extracted with EtOAc (3×20 mL) and the combined organic layers were dried (MgSO₄) and concentrated in vacuo. The crude product was purified by chromatography on silica (80 g column, 0-75% EtOAc/isohexane) to afford the title compound (3 g, 66%) as a clear colourless oil.

¹H NMR (CDCl₃) δ 7.50 (d, J=2.3 Hz, 1H), 7.12-7.01 (m, 4H), 6.82-6.74 (m, 4H), 6.66 (d, J=2.3 Hz, 1H), 4.32 (s, 4H), 4.30-4.24 (m, 2H), 4.01-3.94 (m, 2H), 3.78 (s, 6H).

OH proton not visible.

LCMS; m/z 454.4 (M+Na)⁺ (ES⁺).

Step E: 1-(2-(Dimethylamino)ethyl)-N,N-bis(4-methoxybenzyl)-1H-pyrazole-3-sulfonamide

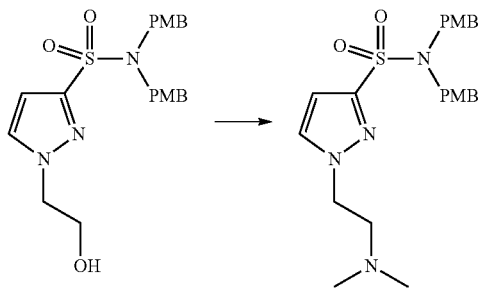

1-(2-Hydroxyethyl)-N,N-bis(4-methoxybenzyl)-1H-pyrazole-3-sulfonamide (2.00 g, 4.63 mmol) and DIPEA (1.4 mL, 8.04 mmol) were dissolved in THF (20 mL) and cooled to 0° C. Methanesulfonyl chloride (0.40 mL, 5.17 mmol) was added and the mixture was stirred at 0° C. for 1 hour. Dimethylamine (40% in water) (3 mL, 23.69 mmol) was added and the reaction mixture was stirred at room temperature over the weekend. The mixture was concentrated to dryness and the yellow residue partitioned between water (30 mL) and EtOAc (70 mL). The organic layer was separated and the aqueous layer was extracted with EtOAc (2×70 mL). The combined organic layers were dried (MgSO$_4$) and evaporated to give a yellow oil. The crude product was loaded onto a column of SCX (7 g) in MeOH. The column was washed with DCM:MeOH (9:1) and then the product was eluted with 0.7 M ammonia in MeOH. The resultant mixture was concentrated in vacuo to afford the title compound (1.36 g, 61%) as a thick orange oil.

$^1$H NMR (CDCl$_3$) δ 7.54 (d, J=2.3 Hz, 1H), 7.14-6.97 (m, 4H), 6.81-6.71 (m, 4H), 6.62 (d, J=2.3 Hz, 1H), 4.35-4.21 (m, 6H), 3.78 (s, 6H), 2.77 (t, J=6.5 Hz, 2H), 2.29 (s, 6H).
LCMS; m/z 459.5 (M+H)$^+$ (ES$^+$).

Step F: 1-(2-(Dimethylamino)ethyl)-5-((dimethylamino)methyl)-N,N-bis(4-methoxybenzyl)-1H-pyrazole-3-sulfonamide

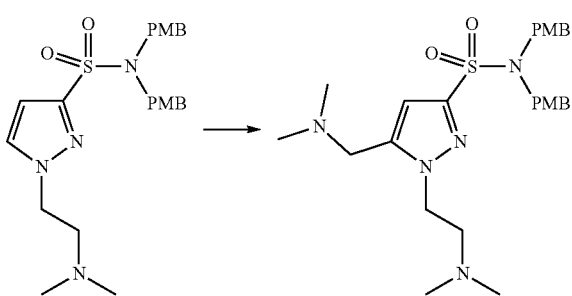

A solution of n-BuLi (2.5M in hexanes) (0.44 mL, 1.100 mmol) was added dropwise to a stirred solution of 1-(2-(dimethylamino)ethyl)-N,N-bis(4-methoxybenzyl)-1H-pyrazole-3-sulfonamide (0.5 g, 1.090 mmol) in THF (14 mL) at −78° C. The reaction was stirred for 1 hour and N-methyl-N-methylenemethanaminium iodide (0.403 g, 2.181 mmol) was added. The reaction mixture was left at −78° C. for 1 hour. Then the reaction mixture was quenched with water (20 mL) and extracted with EtOAc (2×20 mL). The organic layer was separated, dried over MgSO$_4$, filtered and concentrated to dryness. The crude product was purified by chromatography on silica gel (24 g column, 0-10% MeOH/DCM) to afford the title compound (208 mg, 35%) as a yellow oil.

$^1$H NMR (DMSO-d$_6$) δ 7.09-6.94 (m, 4H), 6.89-673 (m, 4H), 6.56 (s, 1H), 4.28 (t, J=6.9 Hz, 2H), 4.20 (s, 4H), 3.71 (s, 6H), 3.48 (s, 2H), 2.63 (t, J=6.9 Hz, 2H), 2.19 (s, 6H), 2.16 (s, 6H).
LCMS; m/z 517 (M+H)$^+$ (ES$^+$).

Step G: 1-(2-(Dimethylamino)ethyl)-5-((dimethylamino)methyl)-1H-pyrazole-3-sulfonamide

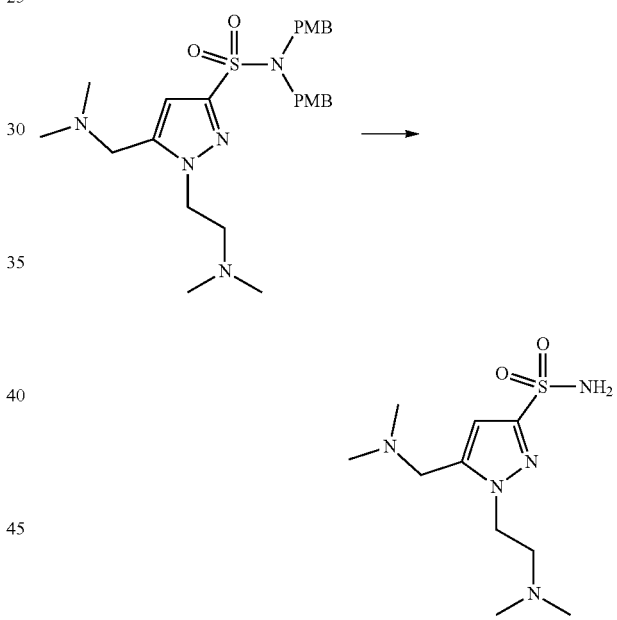

1-(2-(Dimethylamino)ethyl)-5-((dimethylamino)methyl)-N,N-bis(4-methoxybenzyl)-1H-pyrazole-3-sulfonamide (207 mg, 0.401 mmol) was dissolved in TFA (3 mL) and stirred at room temperature for 17 hours. The mixture was evaporated to dryness, dissolved in DCM:MeOH (9:1) and loaded onto SCX (1 g). The column was washed with DCM:MeOH (9:1) (2×20 mL), then the product was eluted with 0.7 NH$_3$ in DCM:MeOH (9:1) (2×10 mL). The resultant mixture was concentrated in vacuo to afford the title compound (82 mg, 73%) as a white solid.

$^1$H NMR (DMSO-d$_6$) δ 7.35 (s, 2H), 6.46 (s, 1H), 4.25 (t, J=7.0 Hz, 2H), 3.47 (s, 2H), 2.64 (t, J=7.0 Hz, 2H), 2.19 (s, 6H), 2.16 (s, 6H).
LCMS; m/z 276 (M+H)$^+$ (ES$^+$).

Intermediate P3: 1-(2-(Dimethylamino)ethyl)-5-(2-hydroxypropan-2-yl)-1H-pyrazole-3-sulfonamide Step A: 1-(2-(Dimethylamino)ethyl)-5-(2-hydroxypropan-2-yl)-N,N-bis(4-methoxybenzyl)-1H-pyrazole-3-sulfonamide

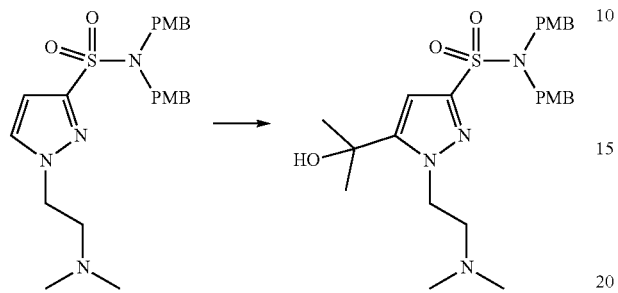

Prepared according to the general procedure of 1-(2-(dimethylamino)ethyl)-5-((dimethylamino)methyl)-N,N-bis(4-methoxybenzyl)-1H-pyrazole-3-sulfonamide (Intermediate P2, Step F) from 1-(2-(dimethylamino)ethyl)-N,N-bis(4-methoxybenzyl)-1H-pyrazole-3-sulfonamide (Intermediate P2, Step E) and acetone to afford the title compound (373 mg, 33%) as a white solid.

$^1$H NMR (DMSO-$d_6$) δ 7.10-6.94 (m, 4H), 6.88-6.72 (m, 4H), 6.40 (s, 1H), 5.63 (s, 1H), 4.54-4.45 (m, 2H), 4.20 (s, 4H), 3.72 (s, 6H), 2.69 (t, J=7.3 Hz, 2H), 2.20 (s, 6H), 1.50 (s, 6H).
LCMS; m/z 518 (M+H)$^+$ (ES$^+$).

Step B: 1-(2-(Dimethylamino)ethyl)-5-(2-hydroxypropan-2-yl)-1H-pyrazole-3-sulfonamide

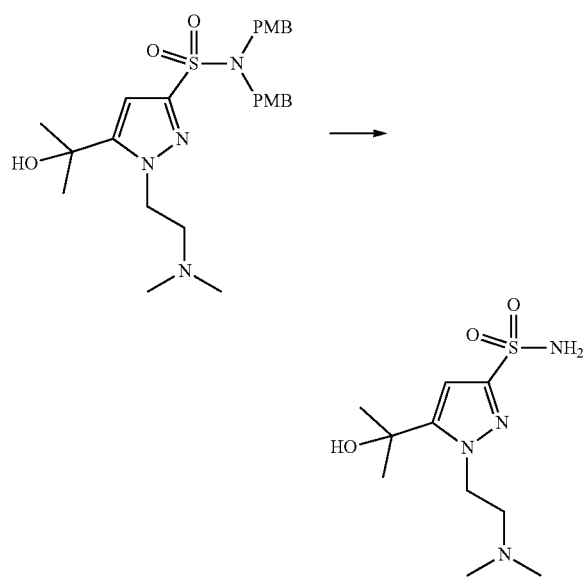

Prepared according to the general procedure of 1-(2-(dimethylamino)ethyl)-5 ((dimethylamino)methyl)-1H-pyrazole-3-sulfonamide (Intermediate P2, Step G) from 1-(2-(dimethylamino)ethyl)-5-(2-hydroxypropan-2-yl)-N,N-bis(4-methoxybenzyl)-1H-pyrazole-3-sulfonamide to afford the title compound (140 mg, 67%) as pale yellow solid on standing.

$^1$H NMR (DMSO-d6) δ 7.34 (s, 2H), 6.38 (s, 1H), 5.63 (s, 1H), 4.64-4.35 (m, 2H), 2.79-2.65 (m, 2H), 2.21 (s, 6H), 1.52 (s, 6H).
LCMS; m/z 277 (M+H)$^+$ (ES$^+$).

Intermediate P4: 5-Methyl-4,5,6,7-tetrahydropyrazolo[1,5-a]pyrazine-2-sulfonamide

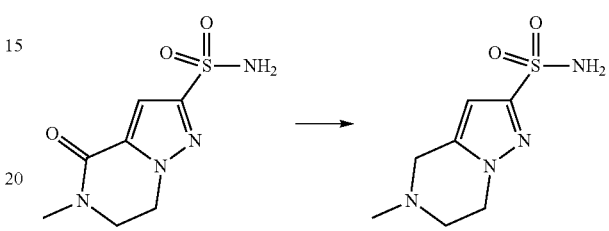

Borane tetrahydrofuran complex (0.87 mL, 0.87 mmol) was added to a solution of 5-methyl-4-oxo-4,5,6,7-tetrahydropyrazolo[1,5-a]pyrazine-2-sulfonamide (Intermediate P1) (50 mg, 0.217 mmol) in THF (5 mL) at room temperature. The mixture was stirred for 5 minutes and then heated to reflux overnight for 2 days. The reaction mixture was cooled to room temperature, MeOH (10 mL) was added dropwise and the reaction mixture was stirred at room temperature for 1 hour. The solvent was removed in vacuo and the crude product was loaded onto a column of SCX (2 g) in MeOH. The column was washed with MeOH and then the product was eluted with 0.7 M ammonia in MeOH. The resultant mixture was concentrated in vacuo to afford the title compound (30 mg, 61%) as a colourless solid.

$^1$H NMR (DMSO-$d_6$) δ 7.35 (s, 2H), 6.36 (s, 1H), 4.14 (t, J=5.6 Hz, 2H), 3.60 (s, 2H), 2.87 (t, J=5.6 Hz, 2H), 2.40 (s, 3H).

Intermediate P5: 1-(2-(Dimethylamino)ethyl)-5-isopropyl-1H-pyrazole-3-sulfonamide Step A: 1-(2-(Dimethylamino)ethyl)-5-iodo-N,N-bis(4-methoxybenzyl)-1H-pyrazole-3-sulfonamide

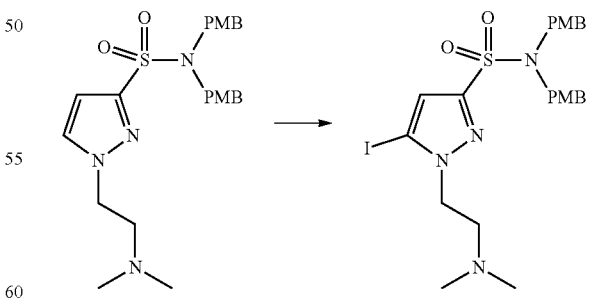

n-BuLi (2.5 M in hexanes) (0.951 mL, 2.377 mmol) was added dropwise to a solution of 1-(2-(dimethylamino)ethyl)-N,N-bis(4-methoxybenzyl)-1H-pyrazole-3-sulfonamide (Intermediate P2, Step E) (1.09 g, 2.377 mmol) in anhydrous THF (15 mL) at −78° C., maintaining the temperature below −65° C. The solution was stirred for 1 hour at −78° C., before a solution of diiodine (0.784 g, 3.09 mmol) in THF (5 mL) was added. The mixture was stirred for 5 minutes at this temperature, then the temperature was raised to room temperature and the reaction mixture was stirred for 1 hour. The reaction mixture was quenched with saturated aqueous ammonium chloride (15 mL) and diluted with DCM (20 mL), then the mixture was poured onto 10 wt % aqueous sodium thiosulfate (30 mL). The organic layer was separated and the aqueous layer was extracted with DCM (2×20 mL). The combined organic layers were dried (Na₂SO₄), filtered and concentrated to dryness to give a yellow oil. The crude product was purified by chromatography on silica gel (24 g column, 0-5% MeOH/DCM) to afford the title compound (0.48 g, 32%) as a yellow wax.

¹H NMR (DMSO-d₆) δ 7.07-7.00 (m, 4H), 6.84 (s, 1H), 6.83-6.77 (m, 4H), 4.28 (t, J=6.8 Hz, 2H), 4.20 (s, 4H), 3.72 (s, 6H), 2.63 (t, J=6.8 Hz, 2H), 2.20 (s, 6H).

LCMS; m/z 585.4 (M+H)⁺ (ES⁺).

Step B: 1-(2-(Dimethylamino)ethyl)-N,N-bis(4-methoxybenzyl)-5-(prop-1-en-2-yl)-1H-pyrazole-3-sulfonamide

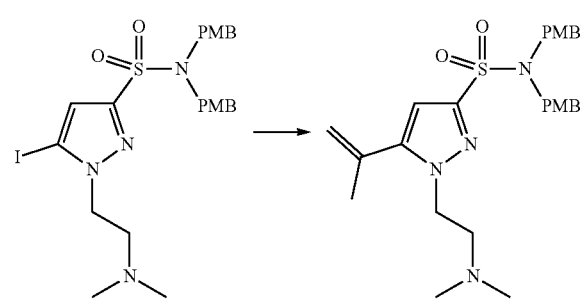

Nitrogen was bubbled through a mixture of 1-(2-(dimethylamino)ethyl)-5-iodo-N,N—bis(4-methoxybenzyl)-1H-pyrazole-3-sulfonamide (0.48 g, 0.772 mmol), 4,4,5,5-tetramethyl-2-(prop-1-en-2-yl)-1,3,2-dioxaborolane (0.185 mL, 0.984 mmol), palladium acetate (0.037 g, 0.164 mmol), tricyclohexylphosphine in toluene (20 wt %) (0.460 g, 0.328 mmol), and caesium carbonate (2.67 g, 8.20 mmol) in toluene (10 mL) and water (5 mL) for 15 minutes and then the reaction mixture was heated at 100° C. for 18 hours. Then the reaction mixture was cooled to room temperature and filtered through a pad of Celite®. The filter cake was washed with DCM (3×10 mL) and the organic layer was separated, dried (Na₂SO₄), filtered and evaporated to give a brown residue which was purified by chromatography on silica gel (24 g column, 0-10% MeOH/DCM) to afford the title compound (191 mg, 35%) as an orange oil.

¹H NMR (DMSO-d₆) δ 7.09-7.01 (m, 4H), 6.84-6.76 (m, 4H), 6.65 (s, 1H), 5.53-5.40 (m, 1H), 5.35-5.21 (m, 1H), 4.26 (t, J=6.7 Hz, 2H), 4.21 (s, 4H), 3.71 (s, 6H), 2.61 (t, J=6.7 Hz, 2H), 2.13 (s, 6H), 2.07-2.02 (m, 3H).

LCMS; m/z 499.5 (M+H)⁺ (ES⁺).

Step C: 1-(2-(Dimethylamino)ethyl)-5-isopropyl-N,N-bis(4-methoxybenzyl)-1H-pyrazole-3-sulfonamide

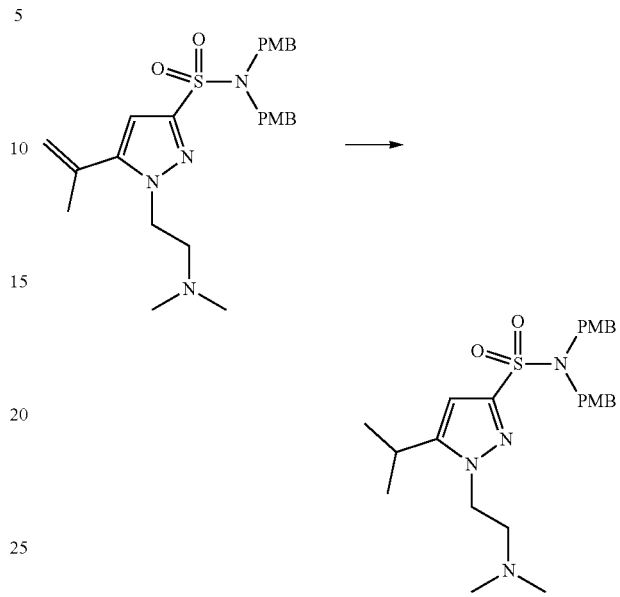

1-(2-(Dimethylamino)ethyl)-N,N-bis(4-methoxybenzyl)-5-(prop-1-en-2-yl)-1H-pyrazole-3-sulfonamide (191 mg, 0.287 mmol) and 5% palladium on carbon (61 mg, 0.014 mmol) were suspended in EtOH (3 mL) and hydrogenated at 5 bar for 17 hours. The reaction mixture was filtered through a pad of Celite® and washed with EtOH (2×5 mL). The filtrate was evaporated to dryness, redissolved in MeOH (3 mL) and loaded onto a column of SCX (1 g) in MeOH. The column was washed with MeOH and then the product was eluted with 0.7 M ammonia in MeOH. The resultant mixture was concentrated in vacuo to afford the title compound (174 mg, 92%) as a thick orange oil.

¹H NMR (DMSO-d₆) δ 7.15-6.96 (m, 4H), 6.90-6.77 (m, 4H), 6.44 (s, 1H), 4.29-4.15 (m, 6H), 3.72 (s, 6H), 3.09 (sept, J=6.8 Hz, 1H), 2.63 (t, J=6.6 Hz, 2H), 2.19 (s, 6H), 1.21 (d, J=6.8 Hz, 6H).

LCMS; m/z 501.5 (M+H)⁺ (ES⁺).

Step D: 1-(2-(Dimethylamino)ethyl)-5-isopropyl-1H-pyrazole-3-sulfonamide

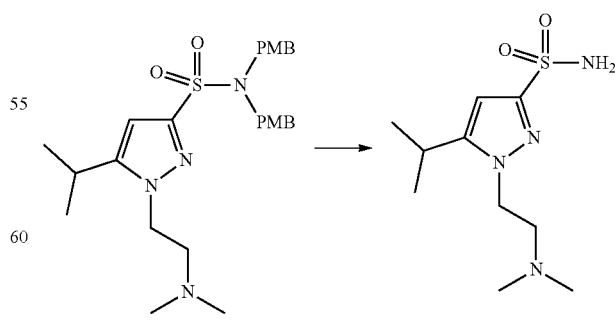

Prepared according to the general procedure of 1-(2-(dimethylamino)ethyl)-5-((dimethylamino)methyl)-1H-pyrazole-3-sulfonamide (Intermediate P2, Step G) from 1-(2-(dimethylamino)ethyl)-5-isopropyl-N,N-bis(4-methoxybenzyl)-1H-pyrazole-3-sulfonamide to afford the title compound (68 mg, 73%) as a colourless glass.

$^1$H NMR (DMSO-d$_6$) δ 7.33 (s, 2H), 6.39 (s, 1H), 4.16 (t, J=6.9 Hz, 2H), 3.08 (sept, J=6.7 Hz, 1H), 2.63 (t, J=6.9 Hz, 2H), 2.18 (s, 6H), 1.21 (d, J=6.8 Hz, 6H).

LCMS; m/z 261.3 (M+H)$^+$ (ES$^+$).

Intermediate P6: 1-Cyclopropyl-5-((dimethylamino)methyl)-1H-pyrazole-3-sulfonamide Step A: 1-cyclopropyl-3-nitro-1H-pyrazole

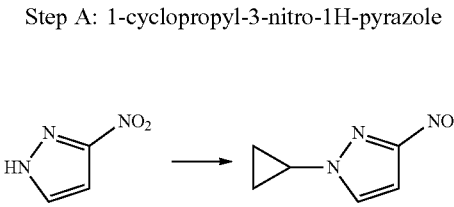

To a solution of cyclopropylboronic acid (36.77 g, 428.04 mmol, 1.1 eq) in 1,2-dichloroethane (500 mL) was added 3-nitro-1H-pyrazole (44 g, 389.12 mmol, 1 eq), 2,2-bipyridine (60.77 g, 389.12 mmol, 1 eq) and Na$_2$CO$_3$ (64.59 g, 609.44 mmol, 1.57 eq) at 25° C. The mixture was stirred at 25° C. for 30 minutes. Then Cu(OAc)$_2$ (70.68 g, 389.12 mmol, 1 eq) was added and the reaction mixture was warmed to 70° C. and stirred at 70° C. for 15.5 hours. Then the reaction mixture was concentrated under reduced pressure to remove the solvent. The residue was purified by column chromatography (SiO$_2$, petroleum ether:ethyl acetate=30:1 to 3:1) to give crude product (26.7 g). The crude product was dissolved in pyrrolidine (10 mL) and the resulting mixture was stirred at 70° C. for 2 hours. The reaction mixture was concentrated under reduced pressure to remove pyrrolidine. The residue was diluted with H$_2$O (33 mL) and the pH was adjusted to 5-6 with aqueous HCl solution (1N). The mixture was extracted with EtOAc (3×50 mL). The combined organic layers were washed with brine (2×33 mL), dried over Na$_2$SO$_4$, filtered and concentrated under reduced pressure to give the title compound (17.7 g, 29.7%) as a yellow oil.

$^1$H NMR (CDCl$_3$) δ 7.54 (d, 1H), 6.84 (d, 1H), 3.73-3.67 (m, 1H), 1.24-1.22 (m, 2H), 1.13-1.07 (m, 2H).

Step B: 1-Cyclopropyl-1H-pyrazol-3-amine

To a solution of 1-cyclopropyl-3-nitro-1H-pyrazole (36 g, 235.08 mmol, 1 eq) in EtOH (400 mL) was added a solution of NH$_4$Cl (62.87 g, 1.18 mol, 41.09 mL, 5 eq) in H$_2$O (150 mL). Then the reaction mixture was warmed to 60° C. and iron powder (39.38 g, 705.24 mmol, 3 eq) was added to the reaction mixture in portions. The reaction mixture was stirred at 60° C. for 16 hours and then concentrated under reduced pressure. The residue was diluted with H$_2$O (500 mL) and extracted with EtOAc (3×500 mL). The combined organic layers were washed with brine (2×250 mL), dried over Na$_2$SO$_4$, filtered and concentrated under reduced pressure. The residue was purified by column chromatography (SiO$_2$, petroleum ether:ethyl acetate=30:1 to 1:1) to give the title compound (20 g, 69.08%) as a yellow oil.

$^1$H NMR (CDCl$_3$) δ 7.14 (d, 1H), 5.11 (d, 1H), 3.57 (br s, 2H), 3.38-3.32 (m, 1H), 0.99-0.95 (m, 2H), 0.90-0.87 (m, 2H).

LCMS: m/z 124.2 (M+H)$^+$ (ES$^+$).

Step C: 1-Cyclopropyl-1H-pyrazole-3-sulfonyl Chloride

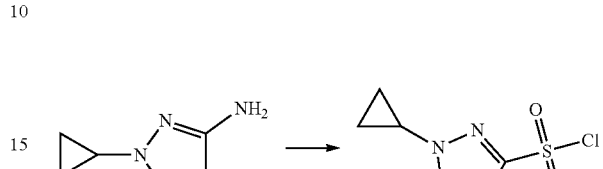

To a solution of 1-cyclopropyl-1H-pyrazol-3-amine (19 g, 154.28 mmol, 1 eq) in acetonitrile (500 mL) and H$_2$O (50 mL) at 0° C. was added concentrated HCl solution (50 mL). Then an aqueous solution of NaNO$_2$ (12.77 g, 185.13 mmol, 1.2 eq) in H$_2$O (50 mL) was added slowly. The resulting solution was stirred at 0° C. for 40 minutes. AcOH (50 mL), CuCl$_2$ (10.37 g, 77-14 mmol, 0.5 eq) and CuCl (763 mg, 7.71 mmol, 0.05 eq) were added into the reaction mixture. Then SO$_2$ gas (15 psi) was bubbled into the reaction mixture for 20 minutes at 0° C. The reaction mixture was stirred at 0° C. for 1 hour and then concentrated under reduced pressure. The residue was diluted with H$_2$O (250 mL) and extracted with EtOAc (3×250 mL). The combined organic layers were washed with brine (2×150 mL), dried over Na$_2$SO$_4$, filtered and concentrated under reduced pressure. The residue was purified by column chromatography (SiO$_2$, petroleum ether:ethyl acetate=100:0 to 1:1) to give the title compound (14 g, 43.91%) as a yellow oil.

$^1$H NMR (CDCl$_3$) δ 7.62 (d, 1H), 6.83 (d, 1H), 3.78-3.72 (m, 1H), 1.28-1.24 (m, 2H), 1.16-1.12 (m, 2H).

Step D: 1-Cyclopropyl-N,N-bis(4-methoxybenzyl)-1H-pyrazole-3-sulfonamide

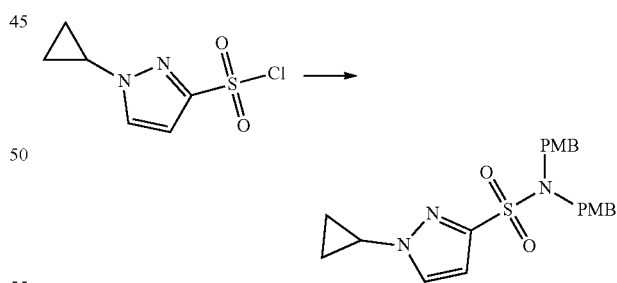

To a solution of 1-cyclopropyl-1H-pyrazole-3-sulfonyl chloride (28 g, 135.49 mmol, 1 eq) in THF (300 mL) was added triethylamine (27.42 g, 270.99 mmol, 37.72 mL, 2 eq) and bis(4-methoxybenzyl)amine (34.87 g, 135.49 mmol, 1 eq). The mixture was stirred at 25° C. for 1 hour. Then the reaction mixture was diluted with H$_2$O (500 mL) and extracted with EtOAc (3×500 mL). The combined organic layers were washed with brine (2×500 mL), dried over Na$_2$SO$_4$, filtered and concentrated under reduced pressure. The residue was purified by reversed phase flash chromatography (acetonitrile/NH$_3$. H$_2$O (0.5% NH$_3$. H$_2$O)) and the collected eluting solution was concentrated under reduced pressure to remove most of the acetonitrile. Then the mixture was extracted with EtOAc (3×1000 mL). The combined organic layers were washed with brine (2×500 mL), dried over Na$_2$SO$_4$, filtered and concentrated under reduced pressure to give the title compound (30 g, 51.69% yield, 99.8% HPLC purity).

$^1$H NMR (CDCl$_3$) δ 7.49 (d, 1H), 7.08-7.06 (m, 4H), 6.79-6.77 (m, 4H), 6.62 (d, 1H), 4.32 (s, 4H), 3.80 (s, 6H), 3.68-3.64 (m, 1H), 1.15-1.13 (m, 2H), 1.09-1.06 (m, 2H).

LCMS: m/z 428.2 (M+H)$^+$ (ES$^+$).

Step E: 1-Cyclopropyl-5-((dimethylamino)methyl)-N,N-bis(4-methoxybenzyl)-1H-pyrazole-3-sulfonamide

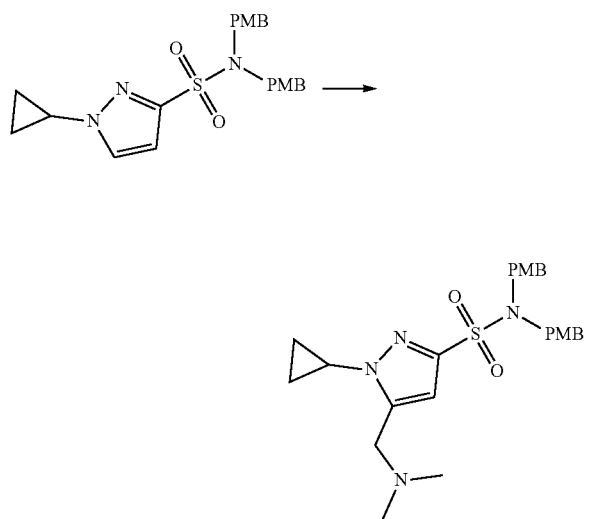

A solution of n-BuLi (2.5 M, 8.89 mL, 1 eq) was added dropwise to a stirred solution of 1-cyclopropyl-N,N-bis(4-methoxybenzyl)-1H-pyrazole-3-sulfonamide (10 g, 22.22 mmol, 1 eq) in THF (250 mL) at −78° C. The reaction mixture was stirred for 1 hour at −78° C. Then N-methyl-N-methylenemethanaminium iodide (8.22 g, 44.44 mmol, 2 eq) was added. The reaction mixture was stirred at −78° C. for 30 minutes and warmed to 25° C. for 30 minutes. Then the reaction mixture was diluted with saturated aqueous NH$_4$Cl solution (150 mL) and extracted with EtOAc (3×250 mL). The combined organic layers were washed with brine (2×100 mL), dried over Na$_2$SO$_4$, filtered and concentrated under reduced pressure. The residue was purified by column chromatography (SiO$_2$, petroleum ether:ethyl acetate=10:1 to 0:1) to give the title compound (9 g, 81.82% yield, 97.9% LCMS purity) as a yellow oil.

$^1$H NMR (DMSO-d$_6$) δ 7.03-7.00 (m, 4H), 6.83-6.78 (m, 4H), 6.56 (s, 1H), 4.20 (s, 4H), 3.82-3.76 (m, 1H), 3.71 (s, 6H), 3.57 (s, 2H), 2.19 (s, 6H), 1.09-0.99 (m, 4H).

LCMS: m/z 485.2 (M+H)$^+$ (ES$^+$).

Step F: 1-Cyclopropyl-5-((dimethylamino)methyl)-1H-pyrazole-3-sulfonamide

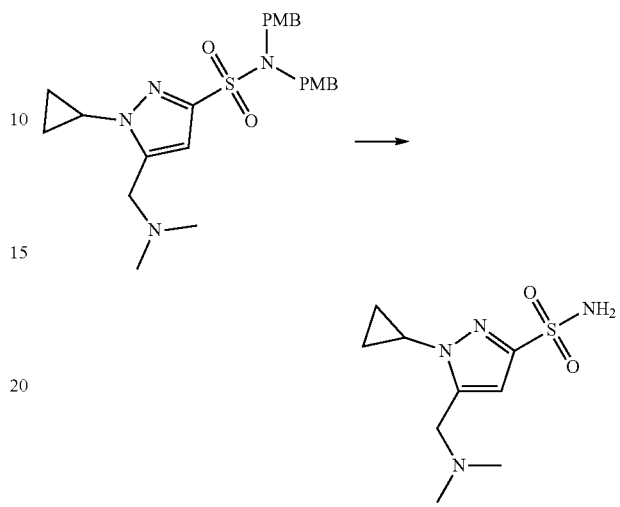

To a solution of 1-cyclopropyl-5-((dimethylamino)methyl)-N,N-bis(4-methoxybenzyl)-1H-pyrazole-3-sulfonamide (9 g, 18.57 mmol, 1 eq) in DCM (30 mL) was added TFA (154.0 g, 1.35 mol, 100 mL, 72.73 eq). The reaction mixture was stirred at 25° C. for 12 hours and then concentrated under reduced pressure. The residue was treated with MeOH (300 mL) and a solid formed. The mixture was filtered and the filtrate was collected. The pH of the filtrate was adjusted to 8-9 with ion exchange resin (Amberlyst® A-21). The mixture was filtered and the filtrate was concentrated. The residue was purified by reversed phase prep-HPLC (column: Phenomenex Gemini; C18 250 mm*50 mm*10 μm; mobile phase: [water (0.05% ammonium hydroxide v/v)-MeCN]; B %: 1%-45%, 35 minutes) to give the title compound (3.97 g, 87.6% yield, 100% $^1$H NMR purity) as a white solid.

$^1$H NMR (DMSO-d$_6$) δ 7.34 (br s, 2H), 6.48 (s, 1H), 3.78-3.74 (m, 1H), 3.56 (s, 2H), 2.20 (s, 6H), 1.11-1.02 (m, 4H).

LCMS: m/z 245.2 (M+H)$^+$ (ES$^+$).

Intermediate P7: 5-((Dimethylamino)methyl)-1-ethyl-1H-pyrazole-3-sulfonamide

Step A: N,N-Bis-(4-methoxybenzyl)-1-ethyl-1H-pyrazole-3-sulfonamide

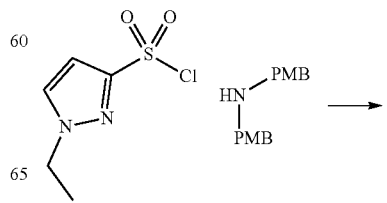

-continued

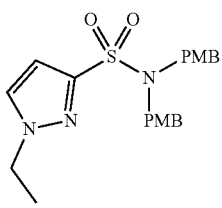

To a solution of 1-ethyl-1H-pyrazole-3-sulfonyl chloride (41.0 g, 210 mmol) in THF (400 mL) was added TEA (63.9 g, 631 mmol) and bis(4-methoxybenzyl)amine (10.8 g, 42.1 mmol). The mixture was stirred at 25° C. for 1.5 hours. The reaction mixture was diluted with water (800 mL) and extracted with EtOAc (3×800 mL). The combined organic layers were dried over $Na_2SO_4$, filtered and concentrated in vacuo. The residue was purified by reversed phase flash chromatography (0.1% $NH_3$ in water/MeCN) to give the title compound (18.7 g, 21%) as a yellow oil.

$^1$H NMR ($CDCl_3$) δ 7.44 (d, 1H), 7.06 (d, 4H), 6.77 (d, 4H), 6.64 (d, 1H), 4.32 (s, 4H), 4.27-4.21 (m, 2H), 3.79 (s, 6H), 1.52 (t, 3H).

LCMS: m/z 416.1 $(M+H)^+$ $(ES^+)$.

Step B: 5-((Dimethylamino)methyl)-N,N-bis(4-methoxybenzyl)-1-ethyl-1H-pyrazole-3-sulfonamide

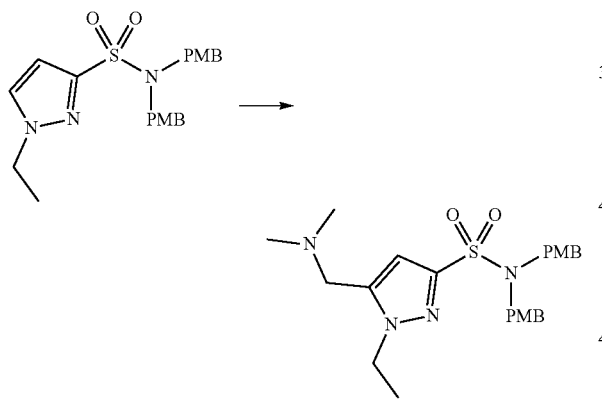

A solution of n-BuLi (2.5 M in hexanes) (3 mL, 7.50 mmol) was added dropwise to a stirred solution of 1-ethyl-N,N-bis(4-methoxybenzyl)-1H-pyrazole-3-sulfonamide (3 g, 7.22 mmol) in THF (45 mL) at −78° C. The reaction was stirred for 1 hour and then N,N— dimethylmethyleneiminium iodide (2.67 g, 14.44 mmol) was added. The reaction mixture was left at −78° C. for 1 hour, quenched with water (20 mL) and extracted with EtOAc (2×20 mL). The combined organic layers were dried over $MgSO_4$, filtered and concentrated in vacuo. The crude product was purified by chromatography on the $SiO_2$ (120 g column, 0-10% MeOH/DCM) to afford the title compound (1.75, 49%) as a yellow solid.

$^1$H NMR (DMSO-$d_6$) δ 7.06-6.99 (m, 4H), 6.85-6.78 (m, 4H), 6.57 (s, 1H), 4.27-4.17 (m, 6H), 3.72 (s, 6H), 3.47 (s, 2H), 2.16 (s, 6H), 1.35 (t, J=7.2 Hz, 3H).

LCMS; m/z 473.5 $(M+H)^+$ $(ES^+)$.

Step C: 5-((Dimethylamino)methyl)-1-ethyl-1H-pyrazole-3-sulfonamide

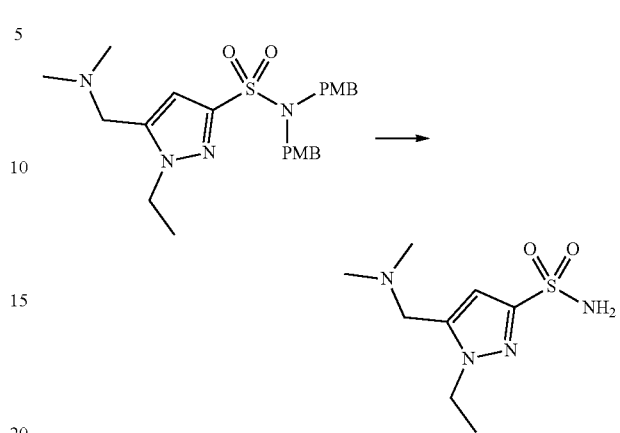

5-((Dimethylamino)methyl)-1-ethyl-N,N-bis(4-methoxybenzyl)-1H-pyrazole-3-sulfonamide (1.75 g, 3.70 mmol) was dissolved in DCM (5 mL) and TFA (5 mL) was added. The solution was stirred for 16 hours, concentrated in vacuo, suspended in toluene (5 mL) and concentrated again. The residue was dissolved in a mixture of DCM (10 mL) and MeOH (20 mL). SCX (14 g) was added and the suspension was stirred at room temperature for 1 hour. The SCX was filtered off and washed with MeOH (3×10 mL) and then the product was eluted with 0.7 M ammonia in MeOH. The resultant mixture was concentrated in vacuo to afford the title compound (705 mg, 81%) as a white solid.

$^1$H NMR (DMSO-$d_6$) δ 7.35 (s, 2H), 6.47 (s, 1H), 4.19 (q, J=7.2 Hz, 2H), 3.47 (s, 2H), 2.17 (s, 6H), 1.35 (t, J=7.2 Hz, 3H).

LCMS; m/z 233.4 $(M+H)^+$ $(ES^+)$.

Intermediate P8: 1-(1-Isopropyl-3-sulfamoyl-1H-pyrazol-5-yl)-N,N,N-trimethylethan-1-aminium 2,2,2-trifluoroacetate Step A: N,N-Bis-(4-methoxybenzyl)-1-isopropyl-1H-pyrazole-3-sulfonamide

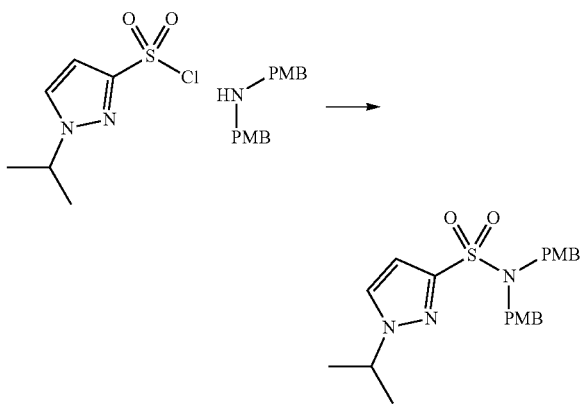

Prepared according to the general procedure of N,N-bis-(4-methoxybenzyl)-1-ethyl-1H-pyrazole-3-sulfonamide (Intermediate P7, Step A) from 1-isopropyl-H-pyrazole-3-sulfonyl chloride to afford the title compound (16.6 g, 80%) as a white solid.

¹H NMR (DMSO-d₆) δ 8.00 (d, J=2.4 Hz, 1H), 7.07-6.96 (m, 4H), 6.85-6.76 (m, 4H), 6.70 (d, J=2.4 Hz, 1H), 4.61 (sept, J=6.7 Hz, 1H), 4.20 (s, 4H), 3.71 (s, 6H), 1.44 (d, J=6.7 Hz, 6H).

LCMS; m/z 452.2 (M+Na)+(ES⁺).

Step B: 5-(1-Hydroxyethyl)-1-isopropyl-N,N-bis(4-methoxybenzyl)-1H-pyrazole-3-sulfonamide

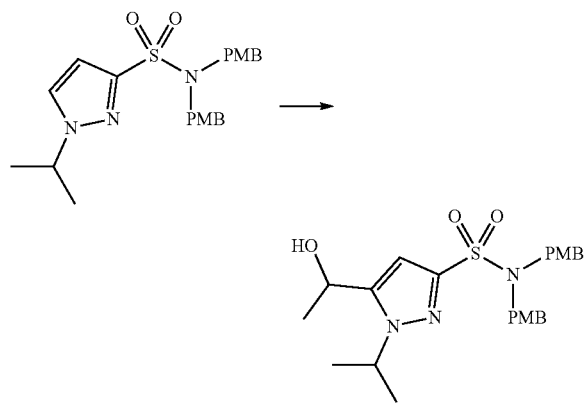

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis-(4-methoxybenzyl)-1-isopropyl-1H-pyrazole-3-sulfonamide and acetaldehyde to afford the title compound (2.14 g, 65%) as a white solid.

¹H NMR (DMSO-d₆) δ 7.07-6.99 (m, 4H), 6.84-6.78 (m, 4H), 6.51 (s, 1H), 5.49 (d, J=6.0 Hz, 1H), 4.96-4.76 (m, 2H), 4.19 (s, 4H), 3.72 (s, 6H), 1.44 (d, J=6.5 Hz, 3H), 1.39 (t, J=6.4 Hz, 6H).

LCMS; m/z 496.4 (M+Na)+(ES⁺).

Step C: 5-(1-(Dimethylamino)ethyl)-1-isopropyl-N,N-bis(4-methoxybenzyl)-1H-pyrazole-3-sulfonamide

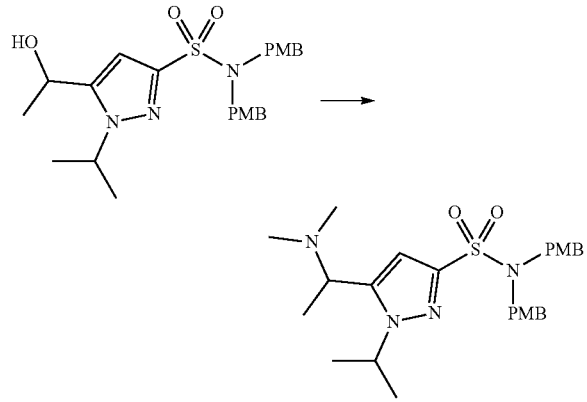

5-(1-Hydroxyethyl)-1-isopropyl-N,N-bis(4-methoxybenzyl)-1H-pyrazole-3-sulfonamide (1 g, 2.112 mmol) and N-ethyl-N-isopropylpropan-2-amine (1.103 mL, 6.33 mmol) were dissolved in THF (20 mL) and cooled to 0° C. MsCl (0.327 mL, 4.22 mmol) was added and the mixture was stirred at 0° C. for 1 hour. Dimethylamine (2 M in THF) (10 mL, 20.00 mmol) and KI (0.175 g, 1.056 mmol) were added and the reaction mixture was stirred at room temperature over the weekend. The mixture was concentrated to dryness and the yellow residue partitioned between water (20 mL) and EtOAc (30 mL). The organic layer was separated and the aqueous layer was extracted with EtOAc (2×20 mL). The combined organic layers were dried (MgSO₄) and evaporated to give a yellow oil. The crude product was purified by chromatography on SiO₂ (40 g column, 0-10% MeOH/DCM) to afford impure product (800 mg) as a brown oil. The impure product was loaded onto a column of SCX (4 g) in MeOH. The column was washed with MeOH and then the product was eluted with 0.7 M ammonia in MeOH. The resultant mixture was concentrated in vacuo to afford the title compound (555 mg, 52%) as a yellow oil.

¹H NMR (DMSO-d₆) δ 7.07-6.96 (m, 4H), 6.86-6.76 (m, 4H), 6.49 (s, 1H), 4.93-4.84 (m, 1H), 4.21 (s, 4H), 4.01-3.90 (m, 1H), 3.72 (s, 6H), 2.13 (s, 6H), 1.43-1.32 (m, 6H), 1.24 (d, J=6.7 Hz, 3H).

LCMS; m/z 501.5 (M+H)⁺ (ES⁺).

Step D: 1-(3-(N,N-Bis(4-methoxybenzyl)sulfamoyl)-1-isopropyl-1H-pyrazol-5-yl)-N,N,N-trimethylethan-1-aminium Iodide

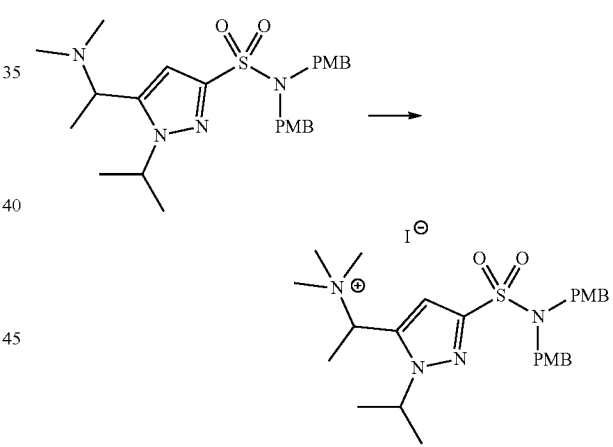

MeI (0.139 mL, 2.217 mmol) was added to a stirred solution of 5-(1-(dimethylamino)ethyl)-1-isopropyl-N,N-bis(4-methoxybenzyl)-1H-pyrazole-3-sulfonamide (555 mg, 1.109 mmol) in MeCN (75 mL). The reaction mixture was stirred at room temperature for 16 hours. The resultant colourless precipitate was collected by filtration, washing with MeCN (5 mL), and dried in vacuo to afford the title compound (241 mg, 34%) as a colourless solid. The filtrate and washing were combined and concentrated to afford additional material (450 mg, 60%) as a yellow solid.

¹H NMR (DMSO-d₆) δ 7.26 (s, 1H), 7.12-7.02 (m, 4H), 6.88-6.80 (m, 4H), 5.13 (q, J=6.8 Hz, 1H), 5.09-4.97 (m, 1H), 4.31 (d, J=15.4 Hz, 2H), 4.23 (d, J=15.4 Hz, 2H), 3.73 (s, 6H), 3.02 (s, 9H), 1.69 (d, J=6.8 Hz, 3H), 1.51 (d, J=6.4 Hz, 3H), 1.29 (d, J=6.3 Hz, 3H).

LCMS; m/z 515.5 (M)+(ES⁺).

Step E: 1-(1-Isopropyl-3-sulfamoyl-1H-pyrazol-5-yl)-N,N,N-trimethylethan-1-aminium 2,2,2-trifluoroacetate

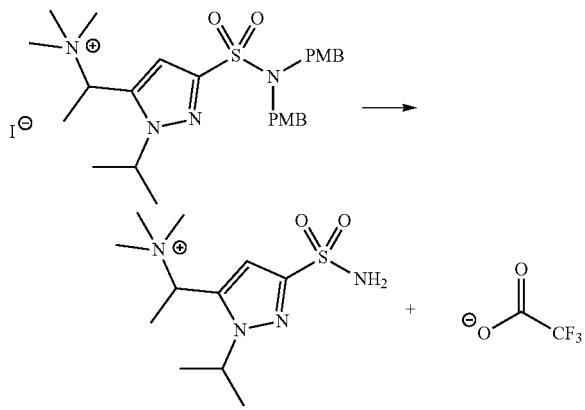

1-(3-(N,N-Bis(4-methoxybenzyl)sulfamoyl)-1-isopropyl-1H-pyrazol-5-yl)-N,N,N-trimethylethan-1-aminium iodide (150 mg, 0.233 mmol) was dissolved in DCM (1.5 mL) and TFA (1.5 mL) was added. The solution was stirred for 16 hours at room temperature. The reaction mixture was concentrated in vacuo, suspended in toluene (5 mL) and concentrated again. The crude was dissolved in MeOH, filtered and dried under vacuum to afford the title compound (100 mg, 99%) as a solid.

$^1$H NMR (DMSO-$d_6$) δ 7.52 (s, 2H), 7.15 (s, 1H), 5.22-5.08 (m, 1H), 5.08-4.98 (m, 1H), 3.04 (s, 9H), 1.73 (d, J=6.8 Hz, 3H), 1.53 (d, J=6.4 Hz, 3H), 1.32 (d, J=6.3 Hz, 3H).

LCMS; m/z 275.4 (M)+(ES$^+$).

Intermediate P9: N,N,N-Trimethyl-1-(1-methyl-3-sulfamoyl-1H-pyrazol-5-yl)ethan-1-aminium 2,2,2-trifluoroacetate Step A: N,N-Bis-(4-methoxybenzyl)-1-methyl-1H-pyrazole-3-sulfonamide

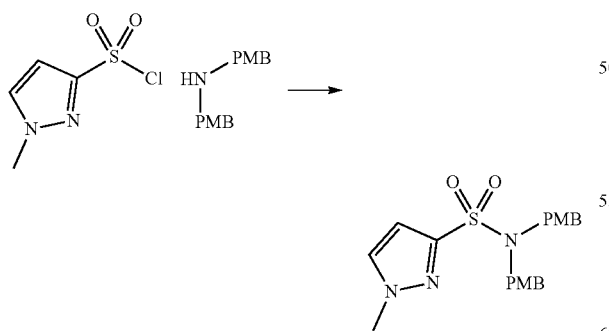

A solution of 1-methyl-1H-pyrazole-3-sulfonyl chloride (13.0 g, 72.0 mmol) in DCM (30 mL) was added slowly to a solution of bis-(4-methoxybenzyl)amine (20 g, 78 mmol) and triethylamine (20 mL, 143 mmol) in DCM (250 mL) cooled in an ice bath. The mixture was stirred for 30 minutes, warmed to room temperature and stirred for 2 hours. The mixture was washed with water (200 mL), hydrochloric acid (aqueous, 1 M, 200 mL) and water (200 mL), then dried (magnesium sulfate), filtered and concentrated in vacuo. The residue was triturated with TBME (250 mL), filtered and then purified by chromatography on silica gel (330 g column, 0-60% EtOAc/iso-hexane) to afford the title compound (27.7 g, 93%) as a white solid.

$^1$H NMR (CDCl$_3$) δ 7.42 (d, J=2.3 Hz, 1H), 7.11-7.07 (m, 4H), 6.81-6.77 (m, 4H), 6.65 (d, J=2.3 Hz, 1H), 4.33 (s, 4H), 3.99 (s, 3H) and 3.81 (s, 6H).

LCMS; m/z 402 (M+H)$^+$ (ES$^+$).

Step B: 5-(1-Hydroxyethyl)-N,N-bis(4-methoxybenzyl)-1-methyl-1H-pyrazole-3-sulfonamide

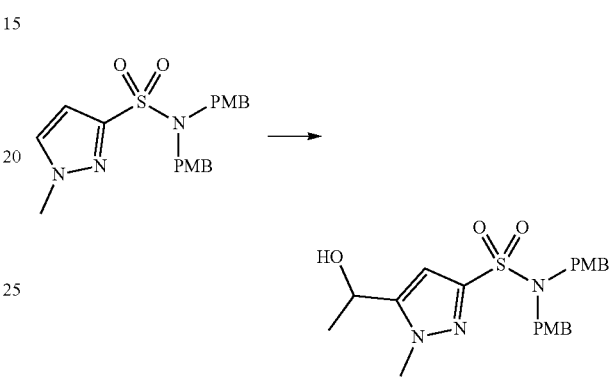

Prepared according to the general procedure of 5-((dimethylamino)methyl)-N,N-bis(4-methoxybenzyl)-1-ethyl-1H-pyrazole-3-sulfonamide (Intermediate P7, Step B) from N,N-bis-(4-methoxybenzyl)-1-methyl-1H-pyrazole-3-sulfonamide and acetaldehyde to afford the title compound (1.9 g, 38%) as a colourless oil.

$^1$H NMR (DMSO-$d_6$) δ 7.11-6.90 (m, 4H), 6.86-6.74 (m, 4H), 6.53 (s, 1H), 5.49 (d, J=5.7 Hz, 1H), 4.86 (dt, J=12.5, 6.4 Hz, 1H), 4.20 (s, 4H), 3.91 (s, 3H), 3.71 (s, 6H), 1.42 (d, J=6.5 Hz, 3H).

Step C: 5-(1-(Dimethylamino)ethyl)-N,N-bis(4-methoxybenzyl)-1-methyl-1H-pyrazole-3-sulfonamide

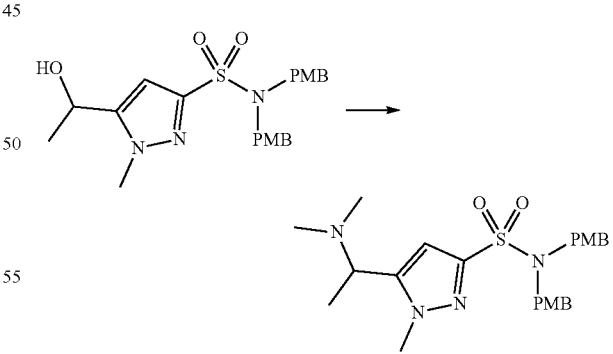

Prepared according to the general procedure of 5-(1-(dimethylamino)ethyl)-1-isopropyl-N,N-bis(4-methoxybenzyl)-1H-pyrazole-3-sulfonamide (Intermediate P8, Step C) from 5-(1-hydroxyethyl)-N,N-bis(4-methoxybenzyl)-1-methyl-1H-pyrazole-3-sulfonamide and 2 M dimethylamine in THF to afford the title compound (0.39 g, 96%) as a very pale yellow viscous oil.

LCMS; m/z 473.5 (M+H)$^+$ (ES$^+$).

Step D: 1-(3-(N,N-Bis(4-methoxybenzyl)sulfamoyl)-1-methyl-1H-pyrazol-5-yl)-N,N,N-trimethylmethanaminium Iodide

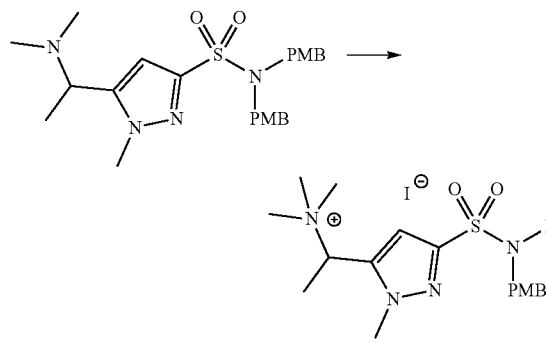

Prepared according to the general procedure of 1-(3-(N,N-bis(4-methoxybenzyl)sulfamoyl)-1-isopropyl-1H-pyrazol-5-yl)-N,N,N-trimethylethan-1-aminium iodide (Intermediate P8, Step D) from 5-(1-(dimethylamino)ethyl)-N,N—bis(4-methoxybenzyl)-1-methyl-1H-pyrazole-3-sulfonamide to afford the title compound (435 mg, 82%) as a yellow solid.

$^1$H NMR (DMSO-d$_6$) δ 7.28 (s, 1H), 7.10-7.05 (m, 4H), 6.87-6.81 (m, 4H), 5.04 (q, J=6.8 Hz, 1H), 4.28 (d, J=15.4 Hz, 2H), 4.23 (d, J=15.3 Hz, 2H), 4.04 (s, 3H), 3.73 (s, 6H), 3.02 (s, 9H), 1.68 (d, J=6.8 Hz, 3H).

LCMS; m/z 487.4 (M)+(ES$^+$).

Step E: N,N,N-Trimethyl-1-(1-methyl-3-sulfamoyl-1H-pyrazol-5-yl)ethan-1-aminium 2,2,2-trifluoroacetate

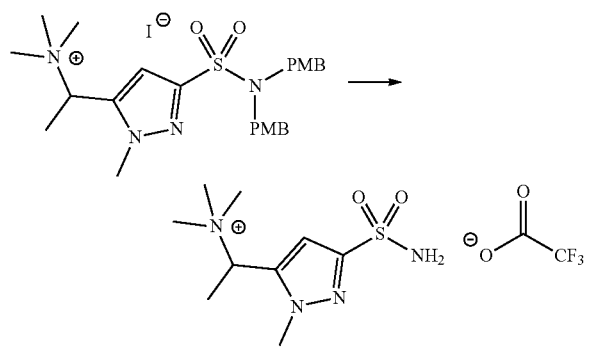

Prepared according to the general procedure of 1-(1-isopropyl-3-sulfamoyl-H-pyrazol-5-yl)-N,N,N-trimethylethan-1-aminium 2,2,2-trifluoroacetate (Intermediate P8, Step E) from 1-(3-(N,N-bis(4-methoxybenzyl)sulfamoyl)-1-methyl-1H-pyrazol-5-yl)-N,N,N-trimethylmethanaminium iodide to afford the title compound (70 mg, 101%) as an orange oil.

$^1$H NMR (DMSO-d$_6$) δ 7.51 (s, 2H), 7.16 (s, 1H), 5.04 (q, J=6.8 Hz, 1H), 4.02 (s, 3H), 3.04 (s, 9H), 1.71 (d, J=6.8 Hz, 3H).

LCMS; m/z 247.3 (M)+(ES$^+$).

Intermediate P10: 1-Cyclopropyl-5-(1-(dimethylamino)ethyl)-1H-pyrazole-3-sulfonamide

Step A: 1-Cyclopropyl-5-(1-hydroxyethyl)-N,N-bis(4-methoxybenzyl)-1H-pyrazole-3-sulfonamide

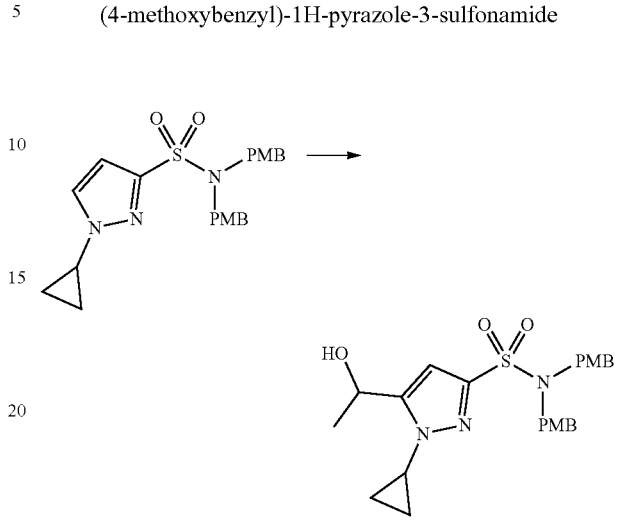

Prepared according to the general procedure of 5-((dimethylamino)methyl)-N,N-bis(4-methoxybenzyl)-1-ethyl-H-pyrazole-3-sulfonamide (Intermediate P7, Step B) from 1-cyclopropyl-N,N-bis(4-methoxybenzyl)-1H-pyrazole-3-sulfonamide (Intermediate P6, Step D) and acetaldehyde to afford the title compound (0.61 g, 31%) as an orange oil.

$^1$H NMR (DMSO-d$_6$) δ 7.06-7.01 (m, 4H), 6.83-6.78 (m, 4H), 6.55 (s, 1H), 5.50 (d, J=5.7 Hz, 1H), 5.01 (p, J=6.4 Hz, 1H), 4.19 (s, 4H), 3.85-3.77 (m, 1H), 3.72 (s, 6H), 1.46 (d, J=6.5 Hz, 3H), 1.18-0.95 (m, 4H).

LCMS; m/z 494.4 (M+Na)+(ES$^+$).

Step B: 1-Cyclopropyl-5-(1-(dimethylamino)ethyl)-N,N-bis(4-methoxybenzyl)-1H-pyrazole-3-sulfonamide

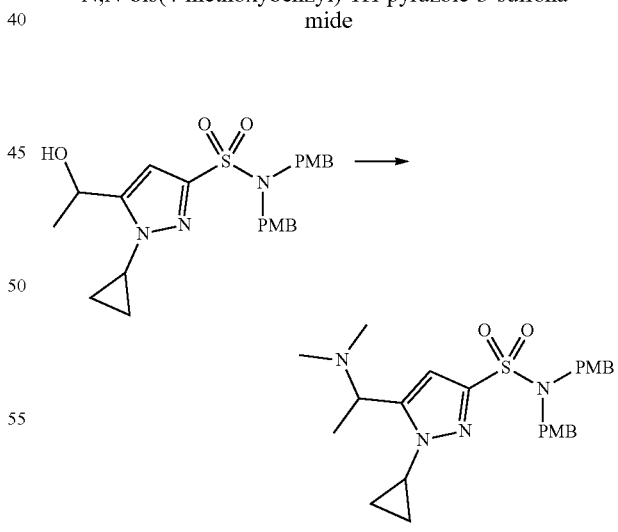

MsCl (0.11 mL, 1.47 mmol) was added to a solution of 1-cyclopropyl-5-(1-hydroxyethyl)-N,N-bis(4-methoxybenzyl)-1H-pyrazole-3-sulfonamide (0.60 g, 1.221 mmol) and DIPEA (0.30 mL, 1.71 mmol) in anhydrous DCM (6 mL) at 0° C. The reaction mixture was stirred for 1 hour at 0° C. Then the temperature was raised to room temperature and the reaction mixture stirred overnight. The reaction was quenched by addition of saturated aqueous NaHCO₃ solution (1 mL), then diluted with DCM (40 mL), and the layers were separated. The aqueous phase was extracted with further portions of DCM (2×40 mL), and the combined organic layers were washed with saturated aqueous NaHCO₃ solution (20 mL), H₂O (20 mL) and brine (20 mL), dried over MgSO₄, filtered, and concentrated in vacuo to give an orange oil (0.523 g). The oil was dissolved in anhydrous THF (4 mL) at room temperature, treated with dimethylamine (2 M in THF) (2.27 mL, 4.55 mmol), heated to 50° C. and stirred overnight. The mixture was transferred into a microwave vial and stirred at 60° C. over the weekend. The mixture was quenched with aqueous NaHCO₃ (15 mL) and extracted with EtOAc (3×25 mL). The combined organic extracts were washed with brine (20 mL), passed through a phase separator and the solvent was removed in vacuo. The residue was dissolved in MeOH (20 mL), SCX (~8 g) was added and the suspension was stirred for 30 minutes at room temperature. The mixture was transferred to a cartridge, washed with MeOH and the product was eluted with 0.7 M NH₃ in MeOH to afford the title compound (217 mg, 81%) as a brown oil.

¹H NMR (DMSO-d₆) δ 7.03 (d, J=8.6 Hz, 4H), 6.81 (d, J=8.6 Hz, 4H), 6.53 (s, 1H), 4.19 (s, 4H), 4.05 (q, J=6.8 Hz, 1H), 3.91-3.82 (m, 1H), 3.72 (s, 6H), 2.15 (s, 6H), 1.27 (d, J=6.8 Hz, 3H), 1.18-1.09 (m, 1H), 1.08-1.01 (m, 2H), 1.01-0.92 (m, 1H).

LCMS; m/z 499.5 (M+H)⁺ (ES⁺).

Step C: 1-Cyclopropyl-5-(1-(dimethylamino)ethyl)-1H-pyrazole-3-sulfonamide

A mixture of 1-cyclopropyl-5-(1-(dimethylamino)ethyl)-N,N-bis(4-methoxybenzyl)-1H-pyrazole-3-sulfonamide (215 mg, 0.431 mmol) and TFA (2.5 mL) in DCM (2 mL) was stirred at room temperature overnight. The volatiles were evaporated, the residue dissolved in MeOH (25 mL), SCX (~8 g) was added and the suspension was stirred at room temperature for 30 minutes. The mixture was transferred to a cartridge, washed sequentially with DCM/MeOH (9:1) and MeOH, and the product was eluted with 0.7 M NH₃ in MeOH to afford the title compound (103 mg, 80%) as a brown oil.

¹H NMR (DMSO-d₆) δ 7.33 (s, 2H), 6.48 (s, 1H), 4.05 (q, J=6.8 Hz, 1H), 3.88-3.78 (m, 1H), 2.16 (s, 6H), 1.28 (d, J=6.8 Hz, 3H), 1.23-1.15 (m, 1H), 1.08-0.96 (m, 3H).

LCMS m/z 259.3 (M+H)⁺ (ES⁺).

Intermediate P11: 5-(1-(Azetidin-1-yl)propyl)-1-cyclopropyl-1H-pyrazole-3-sulfonamide Step A: 1-Cyclopropyl-5-(1-hydroxypropyl)-N,N-bis(4-methoxybenzyl)-1H-pyrazole-3-sulfonamide

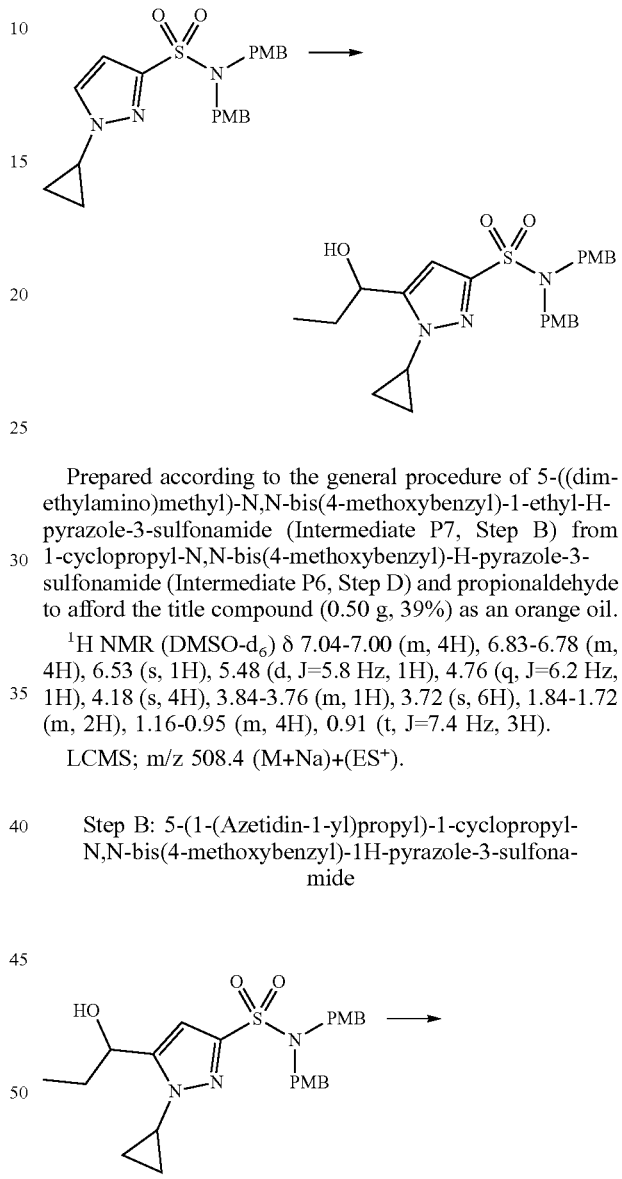

Prepared according to the general procedure of 5-((dimethylamino)methyl)-N,N-bis(4-methoxybenzyl)-1-ethyl-H-pyrazole-3-sulfonamide (Intermediate P7, Step B) from 1-cyclopropyl-N,N-bis(4-methoxybenzyl)-H-pyrazole-3-sulfonamide (Intermediate P6, Step D) and propionaldehyde to afford the title compound (0.50 g, 39%) as an orange oil.

¹H NMR (DMSO-d₆) δ 7.04-7.00 (m, 4H), 6.83-6.78 (m, 4H), 6.53 (s, 1H), 5.48 (d, J=5.8 Hz, 1H), 4.76 (q, J=6.2 Hz, 1H), 4.18 (s, 4H), 3.84-3.76 (m, 1H), 3.72 (s, 6H), 1.84-1.72 (m, 2H), 1.16-0.95 (m, 4H), 0.91 (t, J=7.4 Hz, 3H).

LCMS; m/z 508.4 (M+Na)+(ES⁺).

Step B: 5-(1-(Azetidin-1-yl)propyl)-1-cyclopropyl-N,N-bis(4-methoxybenzyl)-1H-pyrazole-3-sulfonamide

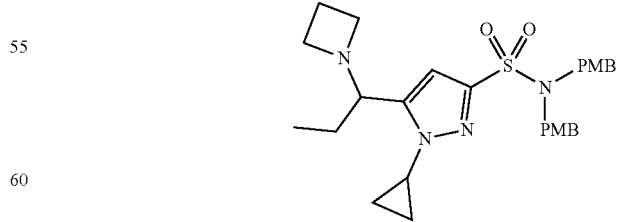

Prepared according to the general procedure of 1-cyclopropyl-5-(1-(dimethylamino) ethyl)-N,N-bis(4-methoxybenzyl)-1H-pyrazole-3-sulfonamide (Intermediate P10, Step B) from 1-cyclopropyl-5-(1-hydroxypropyl)-N,N-bis (4-methoxybenzyl)-1H-pyrazole-3-sulfonamide and azetidine to afford the title compound as a pale yellow oil (178 mg, 72%).

¹H NMR (DMSO-d₆) δ 7.00 (d, J=8.7 Hz, 4H), 6.80 (d, J=8.7 Hz, 4H), 6.47 (s, 1H), 4.19 (s, 4H), 3.96-3.87 (m, 1H), 3.72 (s, 6H), 3.68 (dd, J=8.2, 4.1 Hz, 1H), 3.10 (q, J=6.7 Hz, 2H), 3.03-2.96 (m, 2H), 1.99-1.85 (m, 2H), 1.77-1.63 (m, 1H), 1.61-1.49 (m, 1H), 1.14-0.98 (m, 4H), 0.69 (t, J=7.4 Hz, 3H).

LCMS; m/z 525.5 (M+Na)+(ES⁺).

Step C: 5-(1-(Azetidin-1-yl)propyl)-1-cyclopropyl-1H-pyrazole-3-sulfonamide

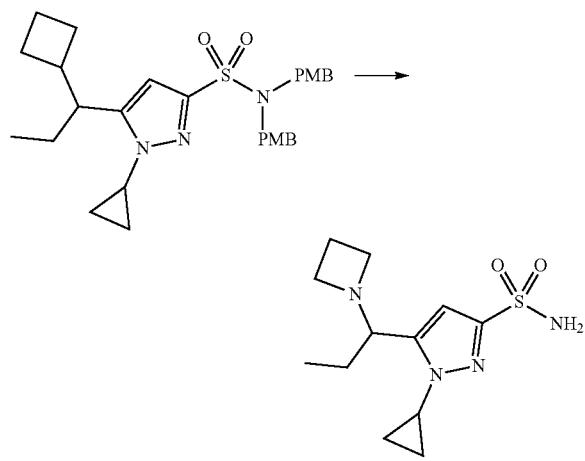

Prepared according to the general procedure of 1-cyclopropyl-5-(1-(dimethylamino) ethyl)-1H-pyrazole-3-sulfonamide (Intermediate P10, Step C) from 5-(1-(azetidin-1-yl)propyl)-1-cyclopropyl-N,N-bis(4-methoxybenzyl)-1H-pyrazole-3-sulfonamide to afford the title compound as a white foam (70 mg, 78%).

¹H NMR (DMSO-d₆) δ 7.34 (s, 2H), 6.41 (s, 1H), 3.92-3.81 (m, 1H), 3.68 (dd, J=8.0, 4.1 Hz, 1H), 3.11 (q, J=6.8 Hz, 2H), 3.03 (q, J=6.8 Hz, 2H), 1.93 (p, J=6.8 Hz, 2H), 1.74-1.62 (m, 1H), 1.62-1.49 (m, 1H), 1.23-1.13 (m, 1H), 1.12-1.00 (m, 3H), 0.70 (t, J=7.4 Hz, 3H).

LCMS; m/z 285.3 (M+H)⁺ (ES⁺).

Intermediate P12: 1-Cyclopropyl-5-(1-(dimethylamino)propyl)-1H-pyrazole-3-sulfonamide Step A: 1-Cyclopropyl-5-(1-(dimethylamino)propyl)-N,N-bis(4-methoxybenzyl)-1H-pyrazole-3-sulfonamide

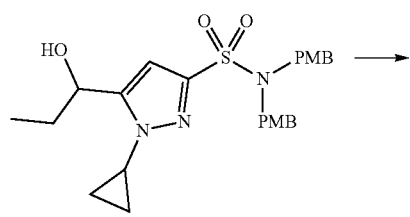

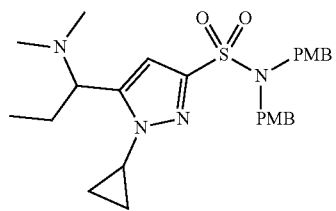

Prepared according to the general procedure of 1-cyclopropyl-5-(1-(dimethylamino) ethyl)-N,N-bis(4-methoxybenzyl)-1H-pyrazole-3-sulfonamide (Intermediate P10, Step B) from 1-cyclopropyl-5-(1-hydroxypropyl)-N,N-bis(4-methoxybenzyl)-1H-pyrazole-3-sulfonamide (Intermediate P11, Step A) and dimethylamine (2 M in THF) to afford the title compound (147 mg, 62%) as a brown oil.

¹H NMR (DMSO-d₆) δ 7.01 (d, J=8.7 Hz, 4H), 6.81 (d, J=8.7 Hz, 4H), 6.55 (s, 1H), 4.20 (s, 4H), 3.91-3.84 (m, 1H), 3.84-3.78 (m, 1H), 3.72 (s, 6H), 2.14 (s, 6H), 1.87-1.77 (m, 1H), 1.76-1.63 (m, 1H), 1.16-0.94 (m, 4H), 0.79 (t, J=7.3 Hz, 3H).

LCMS; m/z 513.5 (M+H)⁺ (ES⁺).

Step B: 1-Cyclopropyl-5-(1-(dimethylamino)propyl)-1H-pyrazole-3-sulfonamide

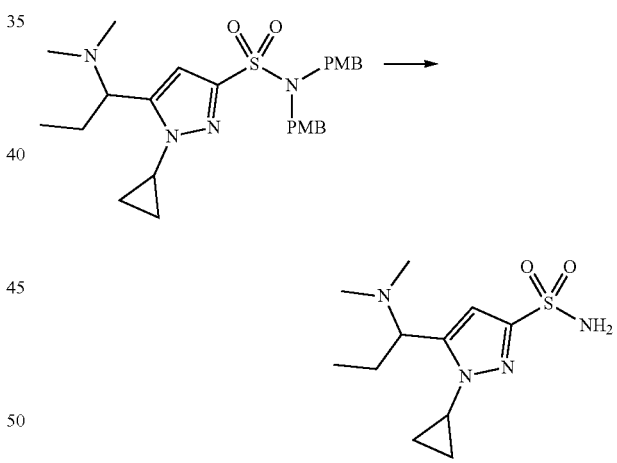

Prepared according to the general procedure of 1-cyclopropyl-5-(1-(dimethylamino) ethyl)-1H-pyrazole-3-sulfonamide (Intermediate P10, Step C) from 1-cyclopropyl-5-(1-(dimethylamino)propyl)-N,N-bis(4-methoxybenzyl)-1H-pyrazole-3-sulfonamide to afford the title compound (77 mg, 100%) as a tan solid.

¹H NMR (DMSO-d₆) δ 7.35 (s, 2H), 6.47 (s, 1H), 3.86 (dd, J=9.2, 5.4 Hz, 1H), 3.82-3.74 (m, 1H), 2.16 (s, 6H), 1.90-1.77 (m, 1H), 1.76-1.62 (m, 1H), 1.20-1.11 (m, 1H), 1.11-0.98 (m, 3H), 0.80 (t, J=7.3 Hz, 3H).

LCMS; m/z 273.3 (M+H)⁺ (ES⁺).

Intermediate P13: 5-(1-(Azetidin-1-yl)ethyl)-1-cyclopropyl-1H-pyrazole-3-sulfonamide Step A: 5-(1-(Azetidin-1-yl)ethyl)-1-cyclopropyl-N,N-bis(4-methoxybenzyl)-1H-pyrazole-3-sulfonamide

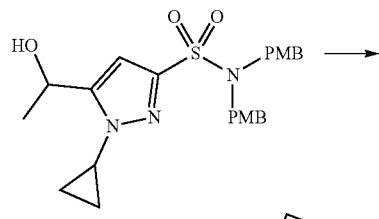

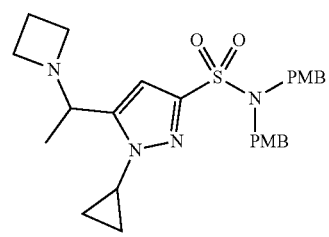

Prepared according to the general procedure of 1-cyclopropyl-5-(1-(dimethylamino) ethyl)-N,N-bis(4-methoxybenzyl)-1H-pyrazole-3-sulfonamide (Intermediate P10, Step B) from 1-cyclopropyl-5-(1-hydroxyethyl)-N,N-bis(4-methoxybenzyl)-1H-pyrazole-3-sulfonamide (Intermediate P10, Step A) and azetidine to afford the title compound (246 mg, 91%) as a brown oil.

$^1$H NMR (DMSO-$d_6$) δ 7.00 (d, J=8.7 Hz, 4H), 6.80 (d, J=8.7 Hz, 4H), 6.44 (s, 1H), 4.19 (s, 4H), 3.92-3.81 (m, 1H), 3.77 (q, J=6.5 Hz, 1H), 3.72 (s, 6H), 3.16-3.00 (m, 4H), 1.93 (p, J=6.9 Hz, 2H), 1.17 (d, J=6.5 Hz, 3H), 1.15-0.95 (m, 4H).
LCMS; m/z 511.5 (M+H)$^+$ (ES$^+$).

Step B: 5-(1-(Azetidin-1-yl)ethyl)-1-cyclopropyl-1H-pyrazole-3-sulfonamide

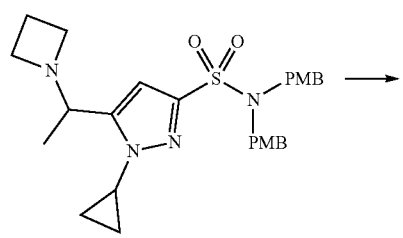

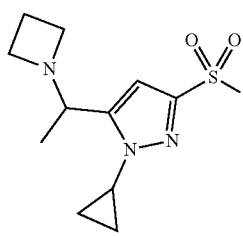

Prepared according to the general procedure of 1-cyclopropyl-5-(1-(dimethylamino) ethyl)-1H-pyrazole-3-sulfonamide (Intermediate P10, Step C) from 5-(1-(azetidin-1-yl)ethyl)-1-cyclopropyl-N,N-bis(4-methoxybenzyl)-1H-pyrazole-3-sulfonamide to afford the title compound (108 mg, 86%) as a beige foam.

$^1$H NMR (DMSO-$d_6$) δ 7.33 (s, 2H), 6.40 (s, 1H), 3.87-3.80 (m, 1H), 3.77 (q, J=6.5 Hz, 1H), 3.16-3.02 (m, 4H), 1.93 (p, J=7.0 Hz, 2H), 1.17 (d, J=6.5 Hz, 3H), 1.16-1.01 (m, 4H).
LCMS; m/z 271.3 (M+H)$^+$ (ES$^+$).

Intermediate P14: 5-(1-(Azetidin-1-yl)ethyl)-1-methyl-1H-pyrazole-3-sulfonamide, Enantiomer A and

Intermediate P15: 5-(1-(Azetidin-1-yl)ethyl)-1-methyl-1H-pyrazole-3-sulfonamide, Enantiomer B

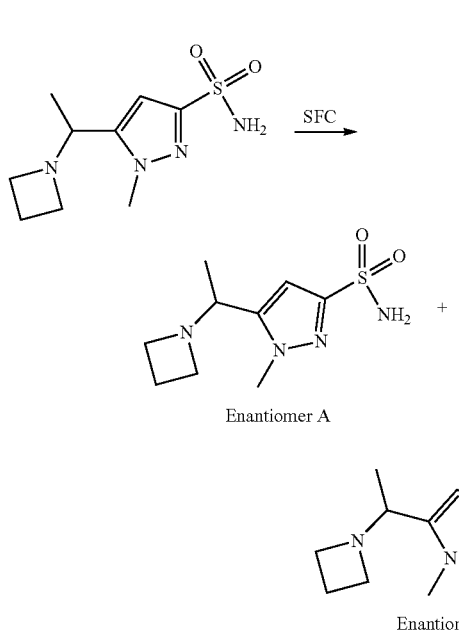

Prepared by chiral resolution of 5l-(azetidin-1-yl)ethyl)-1-methyl-1H-pyrazole-3-sulfonamide (Intermediate P41): racemic 5-(1-(azetidin-1-yl)ethyl)-1-methyl-1H-pyrazole-3-sulfonamide (Intermediate P41) (16 g) was separated by SFC to give Intermediate P14, Enantiomer A (5.45 g, 98.34% ee) and Intermediate P15, Enantiomer B (5.49 g, 99.72% ee).

SFC Separation Method:
Instrument: Waters UPC$^2$ analytical SFC (SFC-H)
Column: ChiralPak AD, 150×4.6 mm I.D., 3 μm
Mobile phase: A for CO$_2$ and B for MeOH (0.05% DEA)
Gradient: B 5-40%
Flow rate: 2.5 mL/min
Back pressure: 100 bar
Column temperature: 35° C.
Wavelength: 220 nm Intermediate P14: $^1$H NMR (DMSO-$d_6$) δ 7.39 (br s, 2H), 6.46 (s, 1H), 3.90 (s, 3H), 3.80-3.60 (m, 1H), 3.18-2.96 (m, 4H), 2.05-1.90 (m, 2H), 1.10 (s, 3H).
LCMS; m/z 245.0 (M+H)$^+$ (ES$^+$).
SFC: retention time: 3.026 min.

Intermediate P15: $^1$HNMR (DMSO-$d_6$) δ 7.36 (s, 2H), 6.42 (s, 1H), 3.89 (s, 3H), 3.75-3.61 (m, 1H), 3.10-2.96 (m, 4H), 1.96-1.92 (m, 2H), 1.13 (d, 3H).
LCMS; m/z 245.0 (M+H)$^+$ (ES$^+$).
SFC: retention time: 3.132 min.

Intermediate P16: 5-((Dimethylamino)methyl)-1-methyl-1H-pyrazole-3-sulfonamide Step A: 5-((Dimethylamino)methyl)-N,N-bis(4-methoxybenzyl)-1-methyl-1H-pyrazole-3-sulfonamide

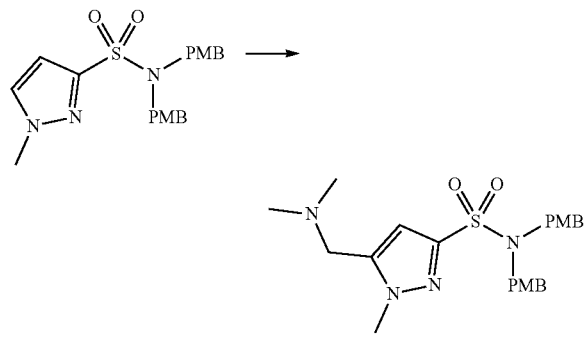

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis-(4-methoxybenzyl)-1-methyl-H-pyrazole-3-sulfonamide (Intermediate P9, Step A) and N-methyl-N-methylenemethanaminium iodide to afford the title compound (1.9 g, 38%) as a colourless oil.

$^1$H NMR (DMSO-$d_6$) δ 7.07-7.01 (m, 4H), 6.84-6.78 (m, 4H), 6.58 (s, 1H), 4.21 (s, 4H), 3.89 (s, 3H), 3.72 (s, 6H), 3.47 (s, 2H) and 2.16 (s, 6H).

LCMS; m/z 459.8 (M+H)$^+$ (ES$^+$).

Step B: 5-((Dimethylamino)methyl)-1-methyl-1H-pyrazole-3-sulfonamide

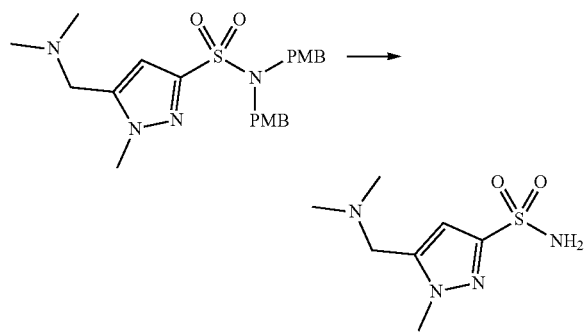

Prepared according to the general procedure of 1-cyclopropyl-5-(1-(dimethylamino) ethyl)-1H-pyrazole-3-sulfonamide (Intermediate P10, Step C) from 5-((dimethylamino)methyl)-N,N-bis(4-methoxybenzyl)-1-methyl-1H-pyrazole-3-sulfonamide to afford the title compound (337 mg, 79%) as a white solid.

$^1$H NMR (DMSO-$d_6$) δ 7.36 (br s, 2H), 6.51 (s, 1H), 3.86 (s, 3H), 3.32 (s, 2H) and 2.23 (s, 6H).

LCMS; m/z 219.3 (M+H)$^+$ (ES$^+$).

Intermediate P17: 1-Methyl-5-(1-(3-methylazetidin-1-yl)ethyl)-1H-pyrazole-3-sulfonamide Step A: N,N-Bis(4-methoxybenzyl)-1-methyl-5-(1-(3-methylazetidin-1-yl)ethyl)-1H-pyrazole-3-sulfonamide

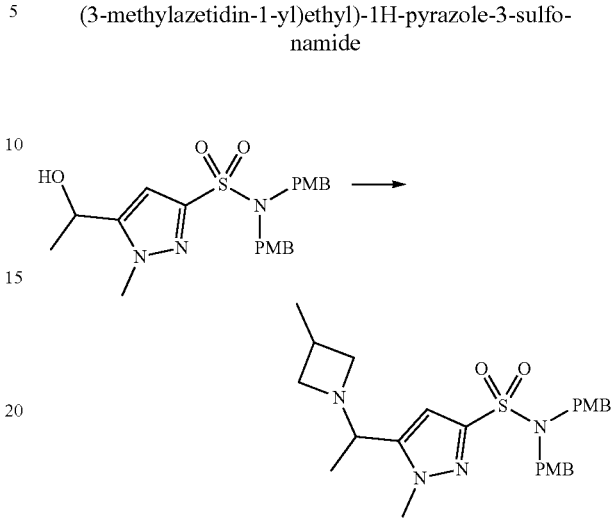

Prepared according to the general procedure of 5-(1-(dimethylamino)ethyl)-1-isopropyl-N,N-bis(4-methoxybenzyl)-1H-pyrazole-3-sulfonamide (Intermediate P8, Step C) from 5-(1-hydroxyethyl)-N,N-bis(4-methoxybenzyl)-1-methyl-H-pyrazole-3-sulfonamide (Intermediate P9, Step B) and 3-methylazetidine hydrochloride to afford the title compound (867 mg, 67%) as a yellow oil.

$^1$H NMR (DMSO-$d_6$) δ 7.01 (d, J=8.7 Hz, 4H), 6.81 (d, J=8.7 Hz, 4H), 6.43 (s, 1H), 4.19 (s, 4H), 3.91 (s, 3H), 3.71 (s, 6H), 3.59 (q, J=6.5 Hz, 1H), 3.35-3.31 (m, 1H), 3.21-3.14 (m, 1H), 2.67-2.58 (m, 2H), 2.44-2.32 (m, 1H), 1.12 (d, J=6.5 Hz, 3H), 1.10 (d, J=6.7 Hz, 3H).

LCMS; m/z 499.5 (M+H)$^+$ (ES$^+$).

Step B: 1-Methyl-5-(1-(3-methylazetidin-1-yl)ethyl)-1H-pyrazole-3-sulfonamide

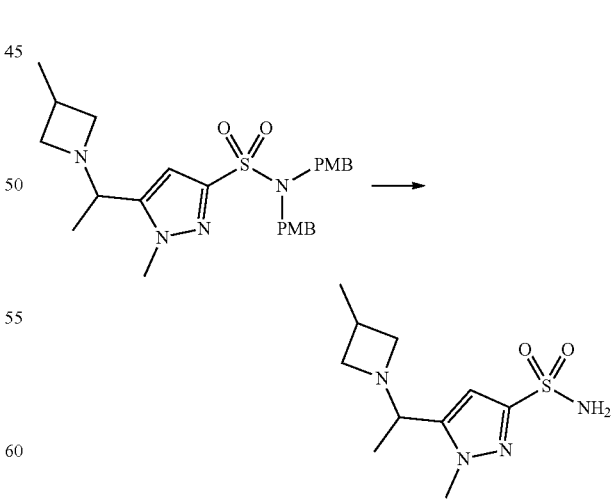

Prepared according to the general procedure of 1-cyclopropyl-5-(1-(dimethylamino) ethyl)-1H-pyrazole-3-sulfonamide (Intermediate P10, Step C) from N,N-bis(4-methoxybenzyl)-1-methyl-5-(1-(3-methylazetidin-1-yl)ethyl)-1H- pyrazole-3-sulfonamide to afford the title compound (283 mg, 66%) as a pale tan solid.

$^1$H NMR (DMSO-$d_6$) δ 7.35 (s, 2H), 6.39 (s, 1H), 3.88 (s, 3H), 3.58 (q, J=6.6 Hz, 1H), 3.38-3.30 (m, 1H), 3.24-3.16 (m, 1H), 2.64 (app. q, J=6.8 Hz, 2H), 2.44-2.32 (m, 1H), 1.12 (d, J=6.6 Hz, 3H), 1.10 (d, J=6.7 Hz, 3H).

LCMS; m/z 259.3 (M+H)$^+$ (ES$^+$).

Intermediate P18: 5-(Azetidin-1-ylmethyl)-1-cyclopropyl-1H-pyrazole-3-sulfonamide Step A: 1-Cyclopropyl-5-formyl-N,N-bis(4-methoxybenzyl)-1H-pyrazole-3-sulfonamide

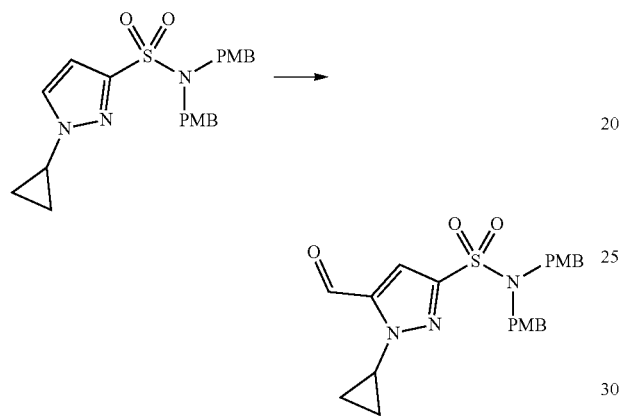

Prepared according to the general procedure of 5-((dimethylamino)methyl)-N,N-bis(4-methoxybenzyl)-1-ethyl-H-pyrazole-3-sulfonamide (Intermediate P7, Step B) from 1-cyclopropyl-N,N-bis(4-methoxybenzyl)-1H-pyrazole-3-sulfonamide (Intermediate P6, Step D) and morpholine-4-carbaldehyde to afford the title compound (732 mg, 33%) as a colourless oil that solidified slowly.

$^1$H NMR (DMSO-$d_6$) δ 10.02 (s, 1H), 7.35 (s, 1H), 7.05 (d, J=8.7 Hz, 4H), 6.82 (d, J=8.7 Hz, 4H), 4.32-4.25 (m, 1H), 4.24 (s, 4H), 3.72 (s, 6H), 1.14 (s, 2H), 1.13-1.11 (m, 2H).

LCMS; m/z 456.2 (M+H)$^+$ (ES$^+$).

Step B: 5-(Azetidin-1-ylmethyl)-1-cyclopropyl-N,N-bis(4-methoxybenzyl)-1H-pyrazole-3-sulfonamide

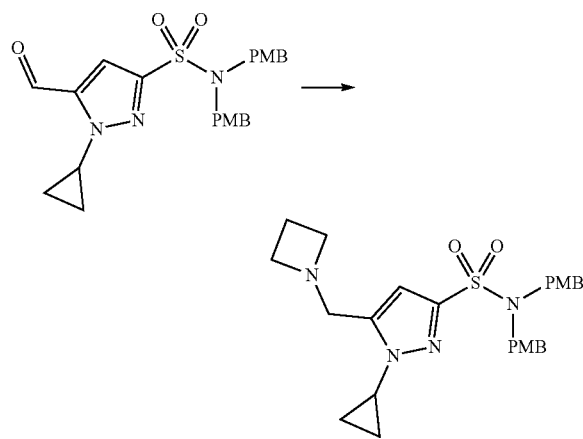

To a solution of 1-cyclopropyl-5-formyl-N,N-bis(4-methoxybenzyl)-1H-pyrazole-3-sulfonamide (730 mg, 1.603 mmol) in THF (10 mL) was added azetidine hydrochloride (300 mg, 3.21 mmol), triethylamine (0.44 mL, 3.16 mmol) and 4 Å molecular sieves. The mixture was stirred for 1 hour before NaBH(OAc)$_3$ (509 mg, 2.404 mmol) was added and stirring was continued overnight. The mixture was filtered over a pad of Celite® with EtOAc and the solvent was removed in vacuo. The residue was dissolved in MeOH (10 mL), SCX was added, and the suspension was stirred for 30 minutes and transferred into a cartridge. The solid was washed with MeOH and the product was eluted with 0.7 M NH$_3$ in MeOH. The solvent was evaporated to afford the title compound (691 mg, 84%) as a pale yellow oil.

$^1$H NMR (DMSO-$d_6$) δ 7.01 (d, J=8.7 Hz, 4H), 6.81 (d, J=8.7 Hz, 4H), 6.50 (s, 1H), 4.17 (s, 4H), 3.76-3.70 (m, 7H), 3.68 (s, 2H), 3.18 (t, J=7.0 Hz, 4H), 2.00 (p, J=7.0 Hz, 2H), 1.04 (s, 2H), 1.02 (s, 2H).

LCMS; m/z 497.6 (M+H)$^+$ (ES$^+$).

Step C: 5-(Azetidin-1-ylmethyl)-1-cyclopropyl-1H-pyrazole-3-sulfonamide

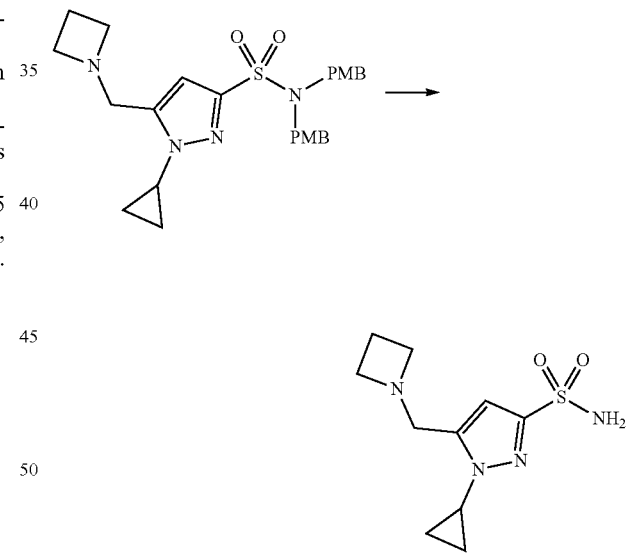

Prepared according to the general procedure of 1-cyclopropyl-5-(1-(dimethylamino) ethyl)-1H-pyrazole-3-sulfonamide (Intermediate P10, Step C) from 5-(azetidin-1-ylmethyl)-1-cyclopropyl-N,N-bis(4-methoxybenzyl)-1H-pyrazole-3-sulfonamide to afford the title compound (345 mg, 95%) as a beige solid.

$^1$H NMR (DMSO-$d_6$) δ 7.36 (s, 2H), 6.43 (s, 1H), 3.78-3.62 (m, 4H), 3.26-3.16 (m, 3H), 2.01 (p, J=7.0 Hz, 2H), 1.11-0.97 (m, 4H).

LCMS; m/z 257.3 (M+H)$^+$ (ES$^+$).

Intermediate P19: 5-((Dimethylamino)methyl)-1-neopentyl-1H-pyrazole-3-sulfonamide Step A: N,N-Bis(4-methoxybenzyl)-1-neopentyl-1H-pyrazole-3-sulfonamide

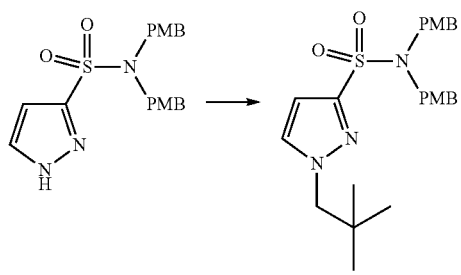

A mixture of N,N-bis(4-methoxybenzyl)-1H-pyrazole-3-sulfonamide (Intermediate P2, Step C) (500 mg, 1.290 mmol), K$_2$CO$_3$ (360 mg, 2.60 mmol), KI (214 mg, 1.290 mmol) and 1-bromo-2,2-dimethylpropane (300 mg, 1.986 mmol) in DMF (10 mL) was heated at 100° C. for 24 hours. The mixture was cooled and partitioned between EtOAc (80 mL) and water (60 mL). The organic layer was washed with water (50 mL), dried (MgSO$_4$), filtered and evaporated. The residue was purified by chromatography on silica gel (40 g column, 0-40% EtOAc/isohexane) to afford the title compound (426 mg, 69%) as an oil.

$^1$H NMR (CDCl$_3$) δ 7.38 (d, J=2.3 Hz, 1H), 7.11-7.07 (m, 4H), 6.80-6.76 (m, 4H), 6.68 (d, J=2.3 Hz, 1H), 4.34 (s, 4H), 3.98 (s, 2H), 3.80 (s, 6H), 0.97 (s, 9H).

Step B: 5-((Dimethylamino)methyl)-N,N-bis(4-methoxybenzyl)-1-neopentyl-1H-pyrazole-3-sulfonamide

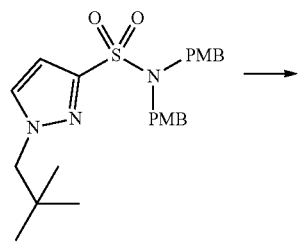

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis(4-methoxybenzyl)-1-neopentyl-1H-pyrazole-3-sulfonamide and N-methyl-N— methylenemethanaminium iodide to afford the title compound (198 mg, 42%) as a thick colourless oil.

$^1$H NMR (CDCl$_3$) δ 7.14-7.06 (m, 4H), 6.83-6.75 (m, 4H), 6.68 (s, 1H), 4.36 (s, 4H), 4.13 (s, 2H), 3.80 (s, 6H), 3.76 (s, 2H), 2.42 (s, 6H), 0.97 (s, 9H).

LCMS; m/z 515.3 (M+H)$^+$ (ES$^+$); 513.5 (M–H)$^-$ (ES$^-$).

Step C: 5-((Dimethylamino)methyl)-1-neopentyl-1H-pyrazole-3-sulfonamide

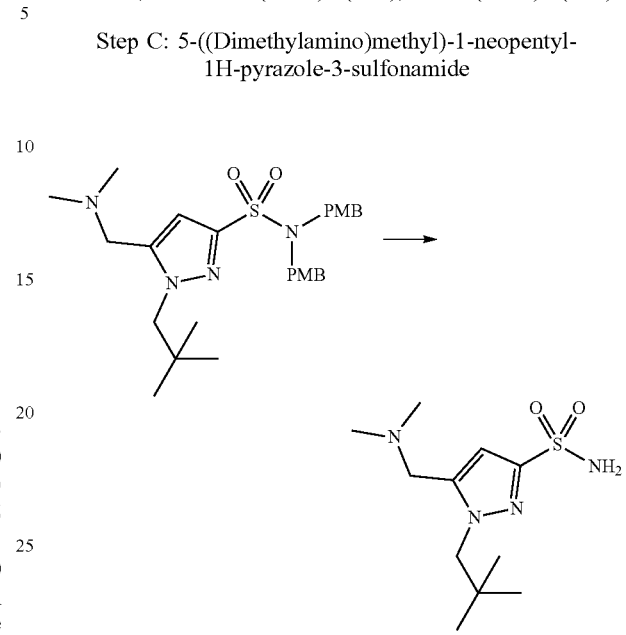

Prepared according to the general procedure of 1-cyclopropyl-5-(1-(dimethylamino)ethyl)-1H-pyrazole-3-sulfonamide (Intermediate P10, Step C) from 5-((dimethylamino)methyl)-N,N-bis(4-methoxybenzyl)-1-neopentyl-1H-pyrazole-3-sulfonamide to afford the title compound (94 mg, 90%) as a colourless oil.

$^1$H NMR (CDCl$_3$) δ 6.60 (s, 1H), 4.95 (s, 2H), 4.07 (s, 2H), 3.45 (s, 2H), 2.23 (s, 6H), 0.99 (s, 9H).

LCMS; m/z 275.3 (M+H)$^+$ (ES$^+$).

Intermediate P20: 5-(1-(Dimethylamino)cyclopropyl)-1-isopropyl-1H-pyrazole-3-sulfonamide Step A: 3-(N,N-Bis(4-methoxybenzyl)sulfamoyl)-1-isopropyl-N,N-dimethyl-1H-pyrazole-5-carboxamide

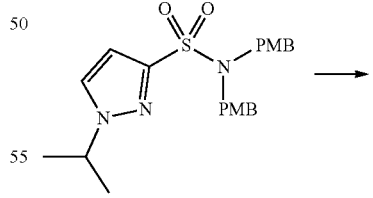

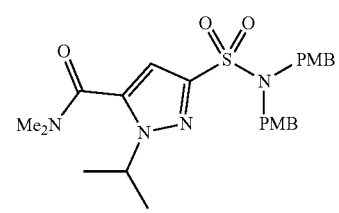

Prepared according to the general procedure of 5-((dimethylamino)methyl)-N,N-bis(4-methoxybenzyl)-1-ethyl-H- pyrazole-3-sulfonamide (Intermediate P7, Step B) from N,N-bis-(4-methoxybenzyl)-1-isopropyl-1H-pyrazole-3-sulfonamide (Intermediate P8, Step A) and carbamoyl chloride to afford the title compound (0.6 g, 50%) as a yellow gum.

$^1$H NMR (DMSO-$d_6$) δ 7.09-6.98 (m, 4H), 6.88 (s, 1H), 6.85-6.77 (m, 4H), 4.69 (sept, J=6.6 Hz, 1H), 4.24 (s, 4H), 3.72 (s, 6H), 3.01 (s, 3H), 2.95 (s, 3H), 1.39 (d, J=6.6 Hz, 6H).

LCMS; m/z 523.4 (M+Na)+(ES$^+$).

Step B: 5-(1-(Dimethylamino)cyclopropyl)-1-isopropyl-N,N-bis(4-methoxybenzyl)-1H-pyrazole-3-sulfonamide

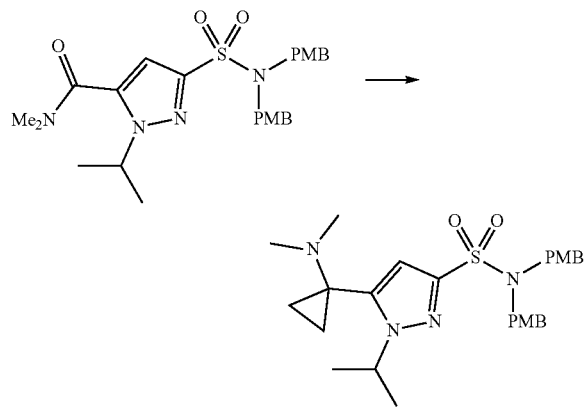

1 M Ethylmagnesium bromide in THF (2.0 mL, 2.000 mmol) was added dropwise over seconds to a stirred solution of 3-(N,N-bis(4-methoxybenzyl)sulfamoyl)-1-isopropyl-N,N-dimethyl-1H-pyrazole-5-carboxamide (0.5 g, 0.999 mmol) and 1 M triisopropoxy(methyl)titanium (1.2 mL, 1.200 mmol) in THF (15 mL) at room temperature. The mixture was then left to stir at room temperature for 23 hours. The reaction mixture was quenched with water (5 mL) and the reaction mixture filtered. The filtrate was partitioned between EtOAc (30 mL) and brine (50 mL) and the organic layer separated. The aqueous layer was extracted with EtOAc (2×20 mL). The combined organic layers were dried (MgSO$_4$), filtered and evaporated to dryness. The crude product was loaded onto a column of SCX (3 g) in 9:1 DCM:MeOH. The column was washed with MeOH:DCM (1:9) and then the product was eluted with 0.7 M ammonia in MeOH:DCM (1:9). The resultant mixture was concentrated in vacuo to afford the title compound (0.37 g, 52%) as a pale yellow solid.

$^1$H NMR (DMSO-$d_6$) δ 7.07-6.95 (m, 4H), 6.82-6.73 (m, 4H), 6.47 (s, 1H), 4.92 (sept, J=6.0 Hz, 1H), 4.22 (s, 4H), 3.71 (s, 6H), 2.15 (s, 6H), 1.38 (d, J=6.5 Hz, 6H), 1.06-0.97 (m, 2H), 0.86-0.77 (m, 2H).

LCMS; m/z 513.3 (M+H)$^+$ (ES$^+$).

Step C: 5-(1-(Dimethylamino)cyclopropyl)-1-isopropyl-1H-pyrazole-3-sulfonamide

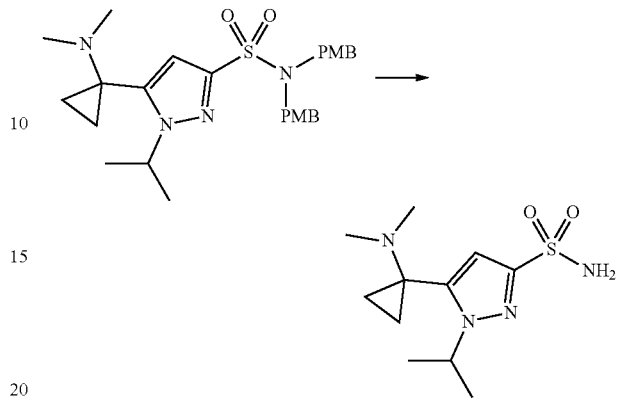

5-(1-(Dimethylamino)cyclopropyl)-1-isopropyl-N,N-bis(4-methoxybenzyl)-1H-pyrazole-3-sulfonamide (0.37 g, 0.520 mmol) was dissolved in TFA (5 mL) and stirred at room temperature for 17 hours. The mixture was evaporated to dryness, dissolved in 9:1 DCM:MeOH and loaded onto SCX (2 g). The column was washed with 9:1 DCM:MeOH (20 mL), then the product was eluted with 0.7 NH$_3$ in 1:9 MeOH:DCM (20 mL). The resultant mixture was concentrated in vacuo to afford crude product as a pale yellow solid. The crude product was purified by reversed phase prep-HPLC (General Methods, basic prep) to afford the title compound (79 mg, 55%) as a white solid.

$^1$H NMR (DMSO-$d_6$) δ 7.36 (s, 2H), 6.43 (s, 1H), 4.92 (sept, J=6.5 Hz, 1H), 2.17 (s, 6H), 1.40 (d, J=6.5 Hz, 6H), 1.10-0.96 (m, 2H), 0.86-0.73 (m, 2H).

LCMS; m/z 273.3 (M+H)$^+$ (ES$^+$).

Intermediate P21: 5-(2-(Dimethylamino)ethyl)-1-isopropyl-H-pyrazole-3-sulfonamide Step A: 5-(2-Hydroxyethyl)-1-isopropyl-N,N-bis(4-methoxybenzyl)-1H-pyrazole-3-sulfonamide

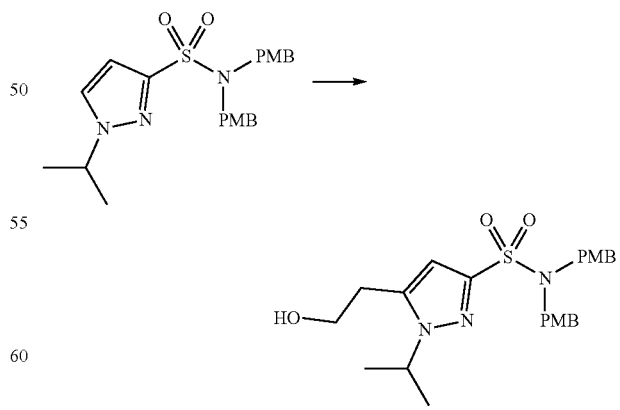

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis-(4-methoxybenzyl)-1-isopropyl-1H-pyrazole-3- sulfonamide (Intermediate P8, Step A) and oxirane (2.5 M in THF) to afford the title compound (1.33 g, 56%) as a yellow oil.

$^1$H NMR (DMSO-d$_6$) δ 7.06-6.97 (m, 4H), 6.85-6.78 (m, 4H), 6.51 (s, 1H), 4.87 (t, J=5.2 Hz, 1H), 4.68 (sept, J=6.6 Hz, 1H), 4.19 (s, 4H), 3.72 (s, 6H), 3.70-3.63 (m, 2H), 2.84 (t, J=6.5 Hz, 2H), 1.38 (d, J=6.6 Hz, 6H).

LCMS; m/z 496.4 (M+Na)+(ES+).

Step B: 5-(2-(Dimethylamino)ethyl)-1-isopropyl-N,N-bis(4-methoxybenzyl)-1H-pyrazole-3-sulfonamide

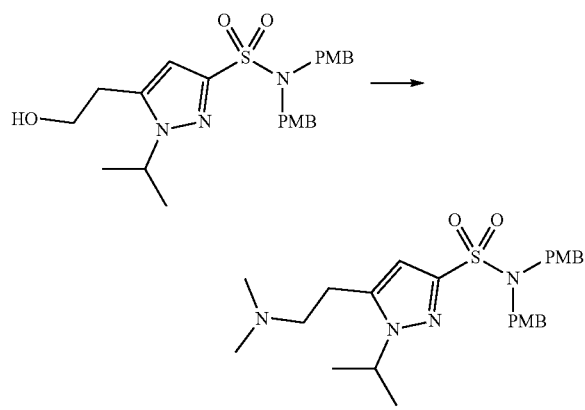

Dess-Martin periodinane (220 mg, 0.492 mmol) was added to a solution of 5-(2-hydroxyethyl)-1-isopropyl-N,N-bis(4-methoxybenzyl)-1H-pyrazole-3-sulfonamide (212 mg, 0.448 mmol) in anhydrous DCM (4 mL) at room temperature. The reaction mixture was stirred for 1 hour at room temperature. Then dimethylamine (2 M in THF) (671 μL, 1.343 mmol) was added and the reaction mixture stirred for 20 minutes, before NaBH(OAc)$_3$ (142 mg, 0.671 mmol) was added. The reaction mixture was stirred for 48 hours. The crude product was loaded onto a column of SCX (1 g) in MeOH. The column was washed with MeOH and then the product was eluted with 0.7 M ammonia in MeOH. The MeOH fraction was concentrated in vacuo. The crude product was purified by chromatography on silica gel (12 g column, 0-10% MeOH/DCM) to afford the title compound (162 mg, 61%) as a colourless oil.

$^1$H NMR (DMSO-d$_6$) δ 7.05-6.97 (m, 4H), 6.86-6.77 (m, 4H), 6.48 (s, 1H), 4.65 (sept, J=6.7 Hz, 1H), 4.19 (s, 4H), 3.72 (s, 6H), 2.84 (t, J=7.4 Hz, 2H), 2.55 (t, J=7.5 Hz, 2H), 2.24 (s, 6H), 1.39 (d, J=6.5 Hz, 6H).

LCMS m/z 501.5 (M+H)+ (ES+).

Step C: 5-(2-(Dimethylamino)ethyl)-1-isopropyl-1H-pyrazole-3-sulfonamide

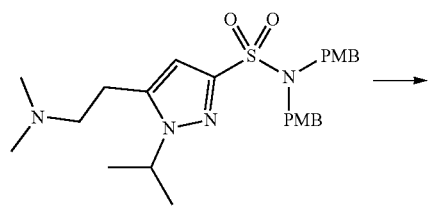

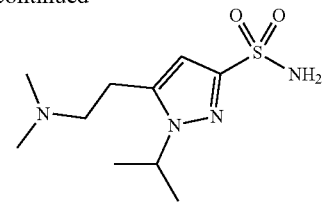

Prepared according to the general procedure of 1-cyclopropyl-5-(1-(dimethylamino) ethyl)-1H-pyrazole-3-sulfonamide (Intermediate P10, Step C) from 5-(2-(dimethylamino) ethyl)-1-isopropyl-N,N-bis(4-methoxybenzyl)-1H-pyrazole-3-sulfonamide to afford the title compound (55 mg, 84%) as a colourless oil.

$^1$H NMR (DMSO-d$_6$) δ 7.31 (s, 2H), 6.41 (s, 1H), 4.61 (sept, J=6.5 Hz, 1H), 2.81 (t, J=7.3 Hz, 2H), 2.19 (s, 6H), 1.38 (d, J=6.5 Hz, 6H). CH$_2$ triplet cannot be observed, under DMSO.

LCMS; m/z 261.3 (M+H)+ (ES+).

Intermediate P22: 5-(2-(Dimethylamino)propan-2-yl)-1-methyl-1H-pyrazole-3-sulfonamide Step A: Ethyl 3-(N,N-bis(4-methoxybenzyl)sulfamoyl)-1-methyl-1H-pyrazole-5-carboxylate

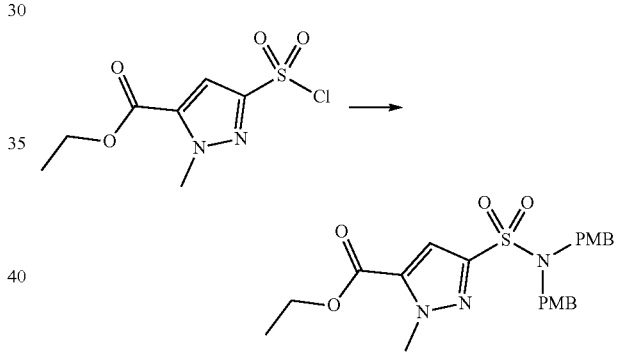

Prepared according to the general procedure of N,N-bis-(4-methoxybenzyl)-1-methyl-1H-pyrazole-3-sulfonamide (Intermediate P9, Step A) from ethyl 3-(chlorosulfonyl)-1-methyl-1H-pyrazole-5-carboxylate to afford the title compound (15.9 g, 91%) as a white solid.

$^1$H NMR (DMSO-d$_6$) δ 7.19-7.00 (m, 5H), 6.85-6.77 (m, 4H), 4.33 (q, J=7.1 Hz, 2H), 4.25 (s, 4H), 4.15 (s, 3H), 3.71 (s, 6H), 1.33 (t, J=7.1 Hz, 3H).

LCMS; m/z 496.4 (M+Na)+(ES+).

Step B: 5-(2-Hydroxypropan-2-yl)-N,N-bis(4-methoxybenzyl)-1-methyl-1H-pyrazole-3-sulfonamide

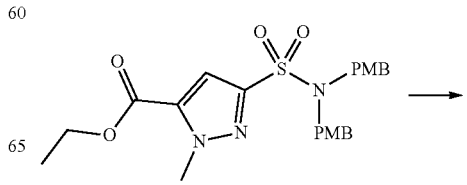

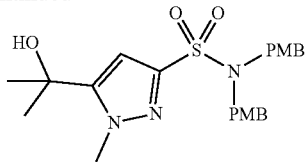

Ethyl 3-(N,N-bis(4-methoxybenzyl)sulfamoyl)-1-methyl-1H-pyrazole-5-carboxylate (2 g, 3.67 mmol) was dissolved in dry THF (70 mL) under nitrogen atmosphere and cooled to −78° C. (bath temperature). Methylmagnesium chloride (3 M in THF) (6.2 mL, 18.60 mmol) was added via syringe over the course of 5 minutes and the mixture was warmed to room temperature and stirred over the weekend. The yellow reaction mixture was cooled in an ice bath and quenched by cautious addition of saturated aqueous ammonium chloride (20 mL). Water (20 mL) and EtOAc (80 mL) were added and the phases separated. The aqueous layer was extracted with EtOAc (2×80 mL). The combined organic extracts were passed through a phase separator and concentrated in vacuo to give a pale yellow oil. The crude product was loaded onto silica and purified by chromatography on $SiO_2$ (40 g column, 0-70% EtOAc/isohexane) to afford the title compound (1.56 g, 87%) as a clear colourless crystalline solid after drying in the desiccator overnight.

$^1$H NMR (DMSO-$d_6$) δ 7.05 (d, J=8.7 Hz, 4H), 6.81 (d, J=8.7 Hz, 4H), 6.41 (s, 1H), 5.48 (s, 1H), 4.21 (s, 4H), 4.03 (s, 3H), 3.72 (s, 6H), 1.49 (s, 6H).

LCMS; m/z 482.1 (M+Na)+(ES$^+$).

Step C: 5-(2-Aminopropan-2-yl)-N,N-bis(4-methoxybenzyl)-1-methyl-1H-pyrazole-3-sulfonamide

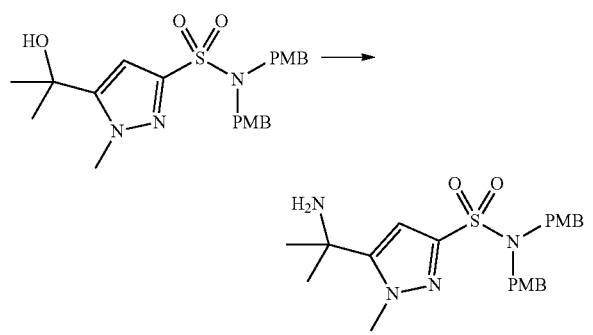

To a mixture of 5-(2-hydroxypropan-2-yl)-N,N-bis(4-methoxybenzyl)-1-methyl-1H-pyrazole-3-sulfonamide (1 g, 2.176 mmol) and azidotrimethylsilane (0.58 mL, 4.37 mmol) in toluene (5 mL) was added $BF_3.OEt_2$ (4 mL, 15.07 mmol) via syringe. The resulting mixture was stirred at room temperature for 2 hours. The mixture was quenched with aqueous $NaHCO_3$ (30 mL) and extracted with DCM (3×30 mL). The combined organic extracts were passed through a phase separator and the solvent was removed in vacuo to give a brown oil. The residue was dissolved in EtOH (45 mL) and hydrogenated using an H-Cube (10% Pd/C at 35° C., 1 cycle). After evaporation of the solvent, the residue was loaded onto SCX with MeOH, washed with MeOH and the product was eluted with 0.7 M $NH_3$ in MeOH to afford the title compound (322 mg, 29%) as a clear colourless oil.

$^1$H NMR (DMSO-$d_6$) δ 7.05 (d, J=8.7 Hz, 4H), 6.81 (d, J=8.7 Hz, 4H), 6.36 (s, 1H), 4.21 (s, 4H), 4.12 (s, 3H), 3.72 (s, 6H), 2.00 (s, 2H), 1.42 (s, 6H).

LCMS; m/z 459.2 (M+H)$^+$ (ES$^+$).

Step D: 5-(2-(Dimethylamino)propan-2-yl)-N,N-bis(4-methoxybenzyl)-1-methyl-1H-pyrazole-3-sulfonamide

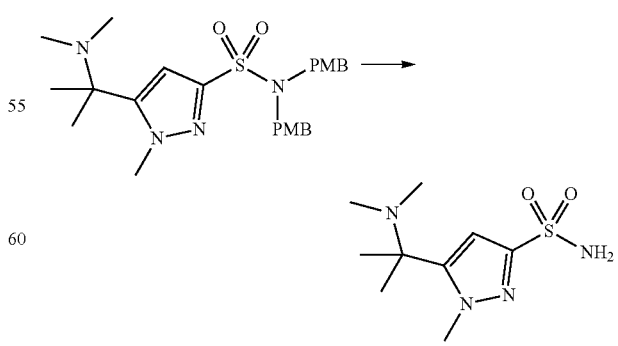

A mixture of 5-(2-aminopropan-2-yl)-N,N-bis(4-methoxybenzyl)-1-methyl-1H-pyrazole-3-sulfonamide (320 mg, 0.698 mmol), formaldehyde (37% in $H_2O$, 10% MeOH) (1.1 mL, 14.77 mmol) and formic acid (0.54 mL, 14.08 mmol) was stirred at 60° C. overnight. Upon cooling to room temperature, the mixture was diluted with EtOAc (15 mL), basified with 2 M aqueous NaOH (2 mL) and diluted with $H_2O$ (5 mL). The layers were separated and the aqueous layer extracted with EtOAc (2×15 mL). The combined organic extracts were passed through a phase separator and the solvent was removed in vacuo. To the residue was added SCX and the mixture was stirred for 30 minutes before being transferred into a cartridge. The suspension was washed with MeOH and the product subsequently eluted with 0.7 M $NH_3$ in MeOH. The solvent was evaporated to afford the title compound (275 mg, 75%) as a pale yellow oil.

$^1$H NMR (DMSO-$d_6$) δ 7.06 (d, J=8.7 Hz, 4H), 6.81 (d, J=8.7 Hz, 4H), 6.36 (s, 1H), 4.21 (s, 4H), 4.06 (s, 3H), 3.71 (s, 6H), 2.08 (s, 6H), 1.31 (s, 6H).

LCMS; m/z 487.6 (M+H)$^+$ (ES$^+$).

Step E: 5-(2-(Dimethylamino)propan-2-yl)-1-methyl-1H-pyrazole-3-sulfonamide

Prepared according to the general procedure of 1-cyclopropyl-5-(1-(dimethylamino) ethyl)-1H-pyrazole-3-sulfonamide (Intermediate P10, Step C) from 5-(2-(dimethylamino)propan-2-yl)-N,N-bis(4-methoxybenzyl)-1-methyl-1H-pyrazole-3-sulfonamide to afford the title compound (135 mg, 78%) as a sticky yellow oil.

$^1$H NMR (DMSO-$d_6$) δ 7.32 (s, 2H), 6.40 (s, 1H), 4.05 (s, 3H), 2.10 (s, 6H), 1.34 (s, 6H).

LCMS; m/z 247.4 (M+H)$^+$ (ES$^+$).

Intermediate P23: 1-Cyclopropyl-5-((dimethylamino)methyl)-1H-pyrazole-3-sulfonamide Step A: 1-Cyclopropyl-5-((dimethylamino)methyl)-N,N-bis(4-methoxybenzyl)-1H-pyrazole-3-sulfonamide

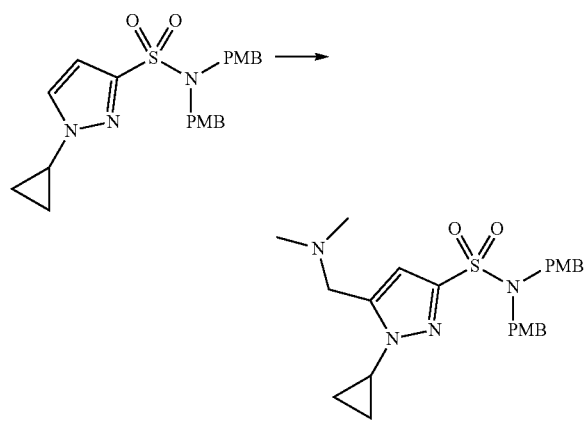

Prepared according to the general procedure of 5-((dimethylamino)methyl)-N,N-bis(4-methoxybenzyl)-1-ethyl-H-pyrazole-3-sulfonamide (Intermediate P7, Step B) from 1-cyclopropyl-N,N-bis(4-methoxybenzyl)-H-pyrazole-3-sulfonamide (Intermediate P6, Step D) and N-methyl-N-methylenemethanaminium iodide to afford the title compound (9 g, 82%) as a yellow oil.

$^1$H NMR (DMSO-$d_6$) δ 7.06-6.98 (m, 4H), 6.85-6.77 (m, 4H), 6.57 (s, 1H), 4.20 (s, 4H), 3.80 (tt, J=6.6, 4.5 Hz, 1H), 3.73 (s, 6H), 3.57 (s, 2H), 2.20 (s, 6H), 1.10-1.00 (m, 4H).

LCMS m/z 485.5 (M+H)$^+$ (ES$^+$).

Step B: 1-Cyclopropyl-5-((dimethylamino)methyl)-1H-pyrazole-3-sulfonamide

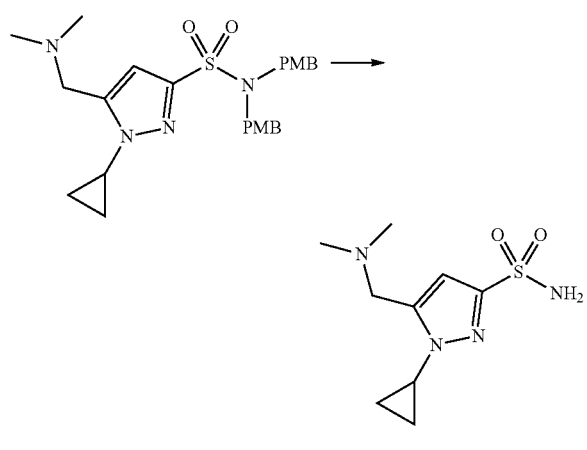

To a solution 1-cyclopropyl-5-((dimethylamino)methyl)-N,N-bis(4-methoxybenzyl)-1H-pyrazole-3-sulfonamide (9 g, 18.57 mmol, 1 eq) in DCM (30 mL) was added TFA (154.0 g, 1.35 mol, 100 mL, 72.73 eq). The reaction mixture was stirred at 25° C. for 12 hours and then concentrated under reduced pressure. The residue was treated with MeOH (300 mL) and a solid formed. The mixture was filtered and the filtrate was collected. The pH of the filtrate was adjusted to 8-9 with ion exchange resin (Amberlyst® A-21). The mixture was filtered and the filtrate was concentrated. The residue was purified by reversed phase prep-HPLC (General Methods, basic prep) to afford the title compound (3.97 g, 88%) as a white solid.

$^1$H NMR (DMSO-$d_6$) δ 7.34 (br s, 2H), 6.48 (s, 1H), 3.78-3.74 (m, 1H), 3.56 (s, 2H), 2.20 (s, 6H), 1.11-1.02 (m, 4H).

LCMS m/z 245.2 (M+H)$^+$ (ES$^+$).

Intermediate P24: 1-(tert-Butyl)-5-((dimethylamino)methyl)-1H-pyrazole-3-sulfonamide Step A: 1-(tert-Butyl)-N,N-bis(4-methoxybenzyl)-1H-pyrazole-3-sulfonamide

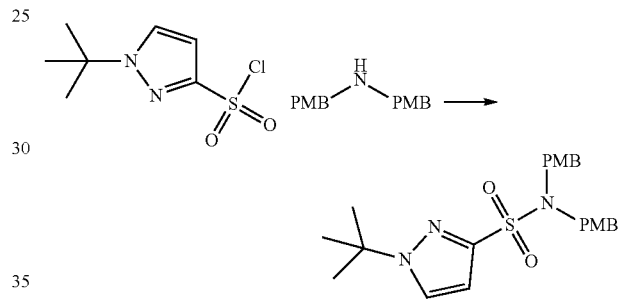

To a solution of 1-(tert-butyl)-1H-pyrazole-3-sulfonyl chloride (40 g, 179.6 mmol) in THF (400 mL) was added TEA (54.53 g, 538.9 mmol, 75.00 mL) and bis(4-methoxybenzyl)amine (13.87 g, 53.9 mmol). The mixture was stirred at 25° C. for 16 hours. The reaction mixture was poured into H$_2$O (1 L) and extracted with EtOAc (3×1 L). The combined organic layers were dried (Na$_2$SO$_4$), filtered and concentrated in vacuo. The residue was purified by column chromatography on silica gel (30:1 to 2:1 petroleum ether/EtOAc) and then purified by reversed phase flash chromatography (0.1% NH$_3$.H$_2$O/CH$_3$CN) to give the title compound (15 g, 19%) as a yellow oil.

$^1$H NMR (CDCl$_3$) δ 7.54 (d, 1H), 7.07 (d, 4H), 6.77 (d, 4H), 6.66 (d, 1H), 4.32 (s, 4H), 3.79 (s, 6H), and 1.60 (s, 9H).

Step B: 1-(tert-Butyl)-5-((dimethylamino)methyl)-N,N-bis(4-methoxybenzyl)-1H-pyrazole-3-sulfonamide

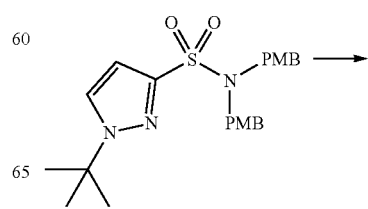

-continued

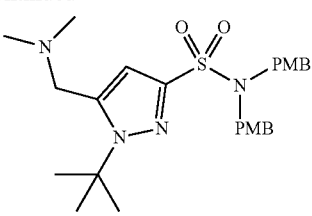

Prepared according to the general procedure of 5-((dimethylamino)methyl)-N,N-bis(4-methoxybenzyl)-1-ethyl-H-pyrazole-3-sulfonamide (Intermediate P7, Step B) from 1-(tert-butyl)-N,N-bis(4-methoxybenzyl)-1H-pyrazole-3-sulfonamide and N-methyl-N— methylenemethanaminium iodide to afford the title compound (266 mg, 23%).

$^1$H NMR (DMSO-$d_6$) δ 7.05-7.00 (m, 4H), 6.83-6.78 (m, 4H), 6.60 (s, 1H), 4.22 (s, 4H), 3.72 (s, 6H), 3.52 (s, 2H), 2.17 (s, 6H), 1.60 (s, 9H).

LCMS; m/z 501.6 (M+H)$^+$ (ES$^+$).

Step C: 1-(tert-Butyl)-5-((dimethylamino)methyl)-1H-pyrazole-3-sulfonamide

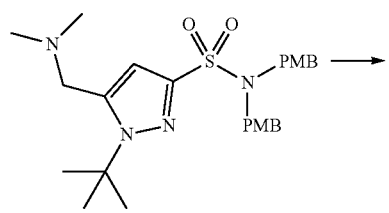

1-(tert-Butyl)-5-((dimethylamino)methyl)-N,N-bis(4-methoxybenzyl)-1H-pyrazole-3-sulfonamide (266 mg, 0.531 mmol) was dissolved in DCM (1.5 mL) and TFA (1.5 mL) was added. The solution was stirred for 16 hours at room temperature. The reaction mixture was concentrated in vacuo, suspended in toluene (5 mL) and concentrated again. The crude product was loaded onto a column of SCX (2 g) in MeOH. The column was washed with MeOH and then the product was eluted with 0.7 M ammonia in MeOH. The crude product was purified by chromatography on SiO$_2$ (12 g column, 0-10% MeOH/DCM) to afford the title compound (30 mg, 19%) as a white solid.

$^1$H NMR (DMSO-$d_6$) δ 7.42 (s, 2H), 6.62 (s, 1H), 3.61 (s, 2H), 2.26 (s, 6H), 1.71 (s, 9H).

LCMS; m/z 261.3 (M+H)$^+$ (ES$^+$).

Intermediate P25: 5-(Azetidin-1-ylmethyl)-1-(tert-butyl)-1H-pyrazole-3-sulfonamide Step A: 1-(tert-Butyl)-5-formyl-N,N-bis(4-methoxybenzyl)-1H-pyrazole-3-sulfonamide

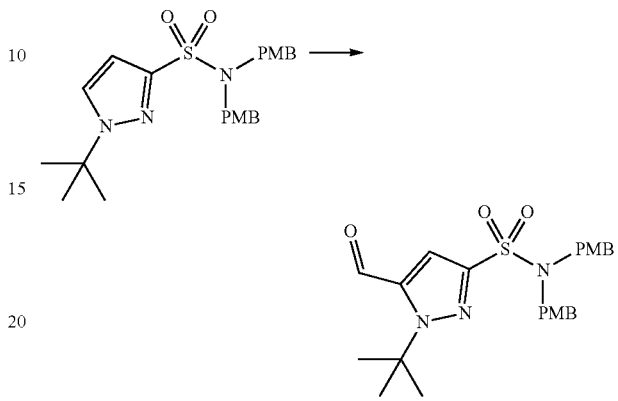

Prepared according to the general procedure of 5-((dimethylamino)methyl)-N,N-bis(4-methoxybenzyl)-1-ethyl-H-pyrazole-3-sulfonamide (Intermediate P7, Step B) from 1-(tert-butyl)-N,N-bis(4-methoxybenzyl)-1H-pyrazole-3-sulfonamide (Intermediate P24, Step A) and morpholine-4-carbaldehyde to afford the title compound (713 mg, 31%) as a colourless oil.

$^1$H NMR (DMSO-$d_6$) δ 9.97 (s, 1H), 7.54 (s, 1H), 7.14-7.03 (m, 4H), 6.91-6.75 (m, 4H), 4.29 (s, 4H), 3.72 (s, 6H), 1.61 (s, 9H).

LCMS; m/z 494.5 (M+Na)+(ES$^+$).

Step B: 5-(Azetidin-1-ylmethyl)-1-(tert-butyl)-N,N-bis(4-methoxybenzyl)-1H-pyrazole-3-sulfonamide

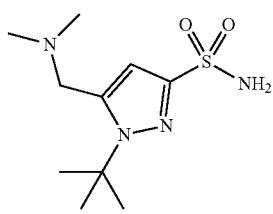

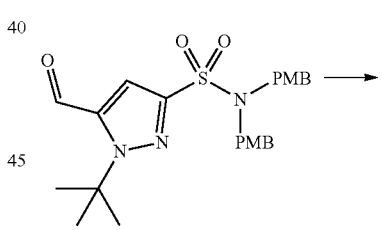

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 1-(tert-butyl)-5-formyl-N,N-bis(4-methoxybenzyl)-1H-pyrazole-3-sulfonamide and azetidine hydrochloride to afford the title compound (690 mg, 73%) as a white oil.

$^1$H NMR (DMSO-$d_6$) δ 7.05-6.99 (m, 4H), 6.84-6.78 (m, 4H), 6.57 (s, 1H), 4.20 (s, 4H), 3.72 (s, 6H), 3.70 (s, 2H), 3.16 (t, J=7.0 Hz, 4H), 2.01 (p, J=7.0 Hz, 2H), 1.59 (s, 9H).

LCMS; m/z 513.5 (M+H)$^+$ (ES$^+$).

Step C: 5-(Azetidin-1-ylmethyl)-1-(tert-butyl)-1H-pyrazole-3-sulfonamide

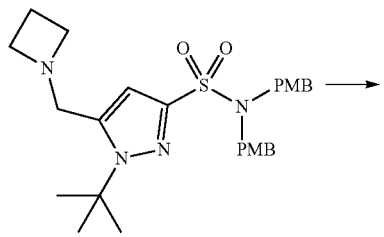

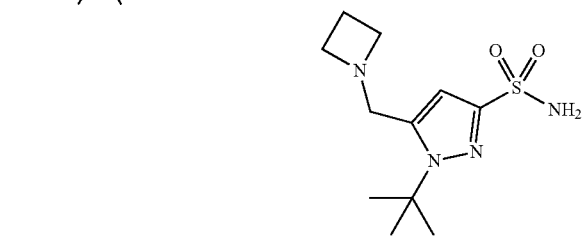

Prepared according to the general procedure of 1-cyclopropyl-5-(1-(dimethylamino)ethyl)-1H-pyrazole-3-sulfonamide (Intermediate P10, Step C) from 5-(azetidin-1-ylmethyl)-1-(tert-butyl)-N,N-bis(4-methoxybenzyl)-1H-pyrazole-3-sulfonamide to afford the title compound (284 mg, 63%).

$^1$H NMR (DMSO-d$_6$) δ 7.31 (s, 2H), 6.51 (s, 1H), 3.70 (s, 2H), 3.18 (t, J=7.0 Hz, 4H), 2.01 (p, J=7.0 Hz, 2H), 1.60 (s, 9H).

LCMS; m/z 273.4 (M+H)$^+$ (ES$^+$).

Intermediate P26: 5-((Dimethylamino)methyl)-1-isopropyl-H-pyrazole-3-sulfonamide Step A: 5-((Dimethylamino)methyl)-1-isopropyl-N,N-bis(4-methoxybenzyl)-1H-pyrazole-3-sulfonamide

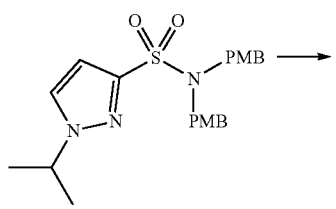

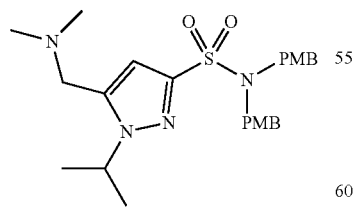

Prepared according to the general procedure of 5-((dimethylamino)methyl)-N,N-bis(4-methoxybenzyl)-1-ethyl-1H-pyrazole-3-sulfonamide (Intermediate P7, Step B) from N,N-bis-(4-methoxybenzyl)-1-isopropyl-1H-pyrazole-3-sulfonamide (Intermediate P8, Step A) and N-methyl-N-methylenemethanaminium iodide to afford the title compound (2.43 g, 69%) as a white solid.

$^1$H NMR (CDCl$_3$) δ 7.13-7.04 (m, 4H), 6.83-6.76 (m, 4H), 6.58 (s, 1H), 4.86 (sept, J=6.5 Hz, 1H), 4.34 (s, 4H), 3.81 (s, 6H), 3.51 (s, 2H) 2.38 (s, 6H), 1.51 (d, J=6.5 Hz, 6H).

LCMS; m/z 487 (M+H)$^+$ (ES$^+$); 485 (M−H)$^-$ (ES$^-$).

Step B: 5-((Dimethylamino)methyl)-1-isopropyl-1H-pyrazole-3-sulfonamide

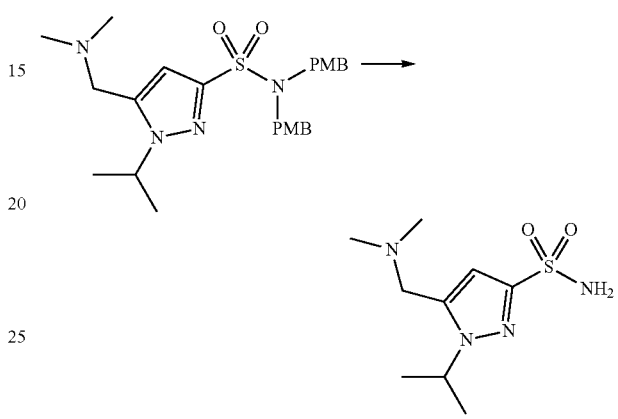

5-((Dimethylamino)methyl)-1-isopropyl-N,N-bis(4-methoxybenzyl)-1H-pyrazole-3-sulfonamide (2.43 g, 4.84 mmol) was dissolved in DCM (20 mL) and TFA (10 mL, 130 mmol) was added. The mixture was stirred over the weekend at room temperature. The reaction solvent was removed in vacuo. DCM (50 mL) and MeOH (50 mL) were added along with SCX (25 g, ~3 eq). The mixture was stirred for 2 hours at room temperature. The SCX was filtered and washed with MeOH (3×100 mL). The product was then eluted with 0.7 M ammonia in MeOH (3×100 mL). Concentration of the ammoniacal washings in vacuo gave a pale yellow semi-solid. This residue was dissolved in a minimum amount of DCM/MeOH (9:1, ~10 mL). Then the product was precipitated by adding an excess of iso-hexanes (100 mL). After filtration, the title compound (1.04 g, 86%) was isolated as a colourless solid that was dried in vacuo and used without further purification.

$^1$H NMR (DMSO-d$_6$) δ 7.35 (s, 2H), 6.46 (s, 1H), 4.78 (sept, J=6.6 Hz, 1H), 3.47 (s, 2H), 2.16 (s, 6H), 1.38 (d, J=6.6 Hz, 6H).

LCMS; m/z 247 (M+H)$^+$ (ES$^+$); 245 (M−H)$^-$ (ES$^-$).

Intermediate P27: N,N,N-Trimethyl-1-(1-methyl-3-sulfamoyl-1H-pyrazol-5-yl)methanaminium 2,2,2-trifluoroacetate Step A: 1-(3-(N,N-Bis(4-methoxybenzyl)sulfamoyl)-1-methyl-1H-pyrazol-5-yl)-N,N,N-trimethylmethanaminium iodide

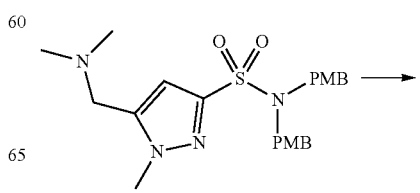

-continued

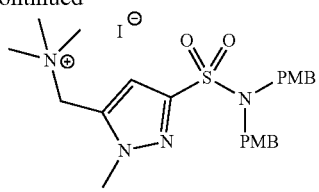

MeI (0.136 mL, 2.181 mmol) was added to a stirred solution of 5-((dimethylamino)methyl)-N,N-bis(4-methoxybenzyl)-1-methyl-1H-pyrazole-3-sulfonamide (Intermediate P16, Step A) (500 mg, 1.090 mmol) in MTBE (5 mL). The reaction mixture was stirred at room temperature 16 hours. Additional MeI (0.136 mL, 2.181 mmol) was added and the reaction mixture stirred for 48 hours. The precipitate was filtered and washed with MTBE (10 mL) to afford the title compound (490 mg, 69%).

$^1$H NMR (DMSO-$d_6$) δ 7.12-7.03 (m, 5H), 6.87-6.78 (m, 4H), 4.74 (s, 2H), 4.26 (s, 4H), 4.04 (s, 3H), 3.73 (s, 6H), 3.09 (s, 9H).

LCMS; m/z 473.3 (M)+(ES$^+$).

Step B: N,N,N-Trimethyl-1-(1-methyl-3-sulfamoyl-1H-pyrazol-5-yl)methanaminium 2,2,2-trifluoroacetate


Prepared according to the general procedure of 1-(1-isopropyl-3-sulfamoyl-H-pyrazol-5-yl)-N,N,N-trimethylethan-1-aminium 2,2,2-trifluoroacetate (Intermediate P8, Step E) from 1-(3-(N,N-bis(4-methoxybenzyl)sulfamoyl)-1-methyl-1H-pyrazol-5-yl)-N,N,N-trimethylmethanaminium iodide to afford the title compound (182 mg, 47%) as a brown solid.

$^1$H NMR (DMSO-$d_6$) δ 7.61 (s, 2H), 7.01 (s, 1H), 4.81 (s, 2H), 4.08 (s, 3H), 3.18 (s, 9H).

LCMS; m/z 233.0 (M)+(ES$^+$).

Intermediate P28: 5-(Azetidin-1-ylmethyl)-1-ethyl-1H-pyrazole-3-sulfonamide

Step A: 1-Ethyl-5-formyl-N,N-bis(4-methoxybenzyl)-1H-pyrazole-3-sulfonamide

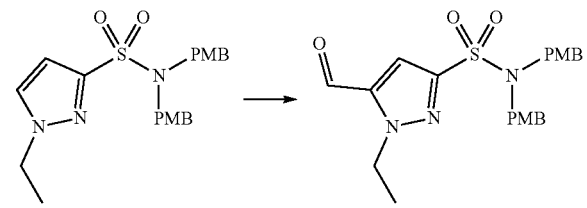

Prepared according to the general procedure of 5-((dimethylamino)methyl)-N,N-bis(4-methoxybenzyl)-1-ethyl-1H-pyrazole-3-sulfonamide (Intermediate P7, Step B) from 1-ethyl-N,N-bis(4-methoxybenzyl)-1H-pyrazole-3-sulfonamide (Intermediate P7, Step A) and morpholine-4-carbaldehyde to afford the title compound (960 mg, 45%) as a white solid.

$^1$H NMR (DMSO-$d_6$) δ 9.90 (s, 1H), 7.44 (s, 1H), 7.10-7.04 (m, 4H), 6.85-6.79 (m, 4H), 4.54 (q, J=7.2 Hz, 2H), 4.26 (s, 4H), 3.72 (s, 6H), 1.36 (t, J=7.2 Hz, 3H).

LCMS; m/z 466.3 (M+Na)+(ES$^+$).

Step B: 5-(Azetidin-1-ylmethyl)-1-ethyl-N,N-bis(4-methoxybenzyl)-1H-pyrazole-3-sulfonamide

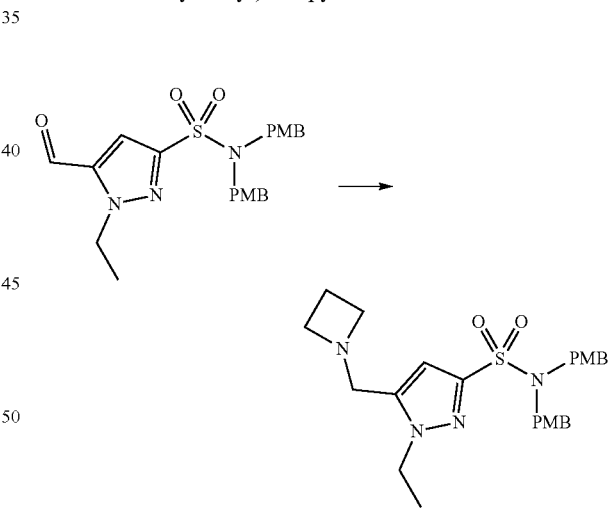

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 1-ethyl-5-formyl-N,N-bis(4-methoxybenzyl)-1H-pyrazole-3-sulfonamide and azetidine hydrochloride to afford the title compound (555 mg, 49%) as a white oil.

$^1$H NMR (DMSO-$d_6$) δ 7.04-6.99 (m, 4H), 6.84-6.78 (m, 4H), 6.53 (s, 1H), 4.23-4.15 (m, 6H), 3.72 (s, 6H), 3.60 (s, 2H), 3.14 (t, J=7.0 Hz, 4H), 1.99 (p, J=7.0 Hz, 2H), 1.35 (t, J=7.2 Hz, 3H).

LCMS; m/z 485.3 (M+H)$^+$ (ES$^+$).

Step C: 5-(Azetidin-1-ylmethyl)-1-ethyl-1H-pyrazole-3-sulfonamide

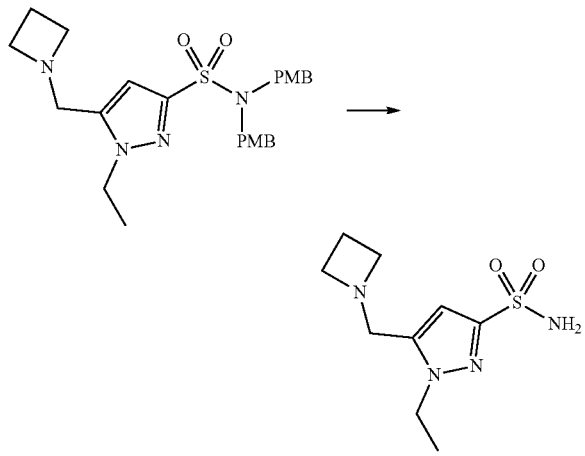

Prepared according to the general procedure of 1-cyclopropyl-5-(1-(dimethylamino) ethyl)-1H-pyrazole-3-sulfonamide (Intermediate P10, Step C) from 5-(azetidin-1-ylmethyl)-1-ethyl-N,N-bis(4-methoxybenzyl)-1H-pyrazole-3-sulfonamide to afford the title compound (255 mg, 98%).

$^1$H NMR (DMSO-d$_6$) δ 7.34 (s, 2H), 6.45 (s, 1H), 4.16 (q, J=7.2 Hz, 2H), 3.60 (s, 2H), 3.21-3.10 (m, 4H), 2.00 (p, J=7.0 Hz, 2H), 1.35 (t, J=7.2 Hz, 3H).
LCMS; m/z 245.4 (M+H)$^+$ (ES$^+$).

Intermediate P29: 2,2,2-Trifluoro-N-((1-isopropyl-3-sulfamoyl-H-pyrazol-5-yl)methyl)-N-methylacetamide

Step A: 5-Formyl-1-isopropyl-N,N-bis(4-methoxybenzyl)-1H-pyrazole-3-sulfonamide

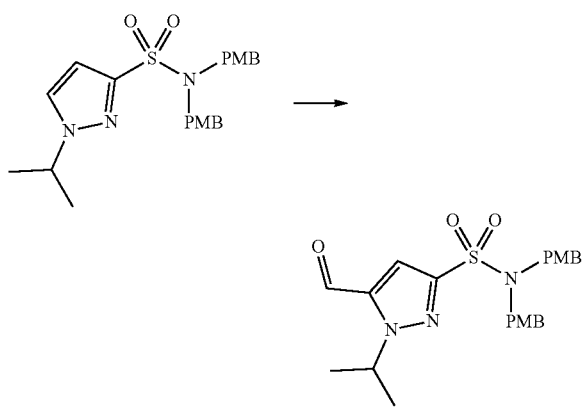

Prepared according to the general procedure of 5-((dimethylamino)methyl)-N,N-bis(4-methoxybenzyl)-1-ethyl-1H-pyrazole-3-sulfonamide (Intermediate P7, Step B) from 1-isopropyl-N,N-bis(4-methoxybenzyl)-1H-pyrazole-3-sulfonamide (Intermediate P8, Step A) and morpholine-4-carbaldehyde to afford the title compound (3.45 g, 80%) as a white solid.

$^1$H NMR (DMSO-d$_6$) δ 9.90 (s, 1H), 7.44 (s, 1H), 7.10-7.03 (m, 4H), 6.86-6.80 (m, 4H), 5.34 (sept, J=6.6 Hz, 1H), 4.26 (s, 4H), 3.72 (s, 6H), 1.42 (d, J=6.5 Hz, 6H).
LCMS; m/z 480.3 (M+Na)+(ES$^+$).

Step B: 1-Isopropyl-N,N-bis(4-methoxybenzyl)-5-((methylamino)methyl)-1H-pyrazole-3-sulfonamide

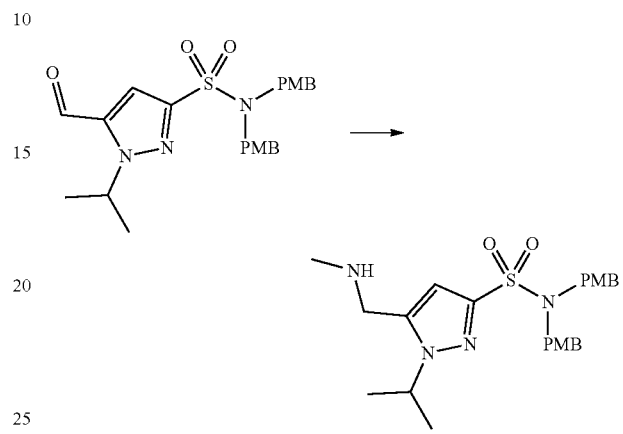

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-1-isopropyl-N,N-bis(4-methoxybenzyl)-1H-pyrazole-3-sulfonamide and methylamine (2 M in THF) to afford the title compound (388 mg, 68%) as a yellow oil.

$^1$H NMR (DMSO-d$_6$) δ 7.05-6.98 (m, 4H), 6.84-6.78 (m, 4H), 6.56 (s, 1H), 4.78 (sept, J=6.6 Hz, 1H), 4.19 (s, 4H), 3.73 (s, 2H), 3.72 (s, 6H), 3.32 (br s, 1H), 2.27 (s, 3H), 1.39 (d, J=6.6 Hz, 6H).
LCMS; m/z 473.3 (M+H)$^+$ (ES$^+$).

Step C: N-((3-(N,N-Bis(4-methoxybenzyl)sulfamoyl)-1-isopropyl-1H-pyrazol-5-yl)methyl)-2,2,2-trifluoro-N-methylacetamide

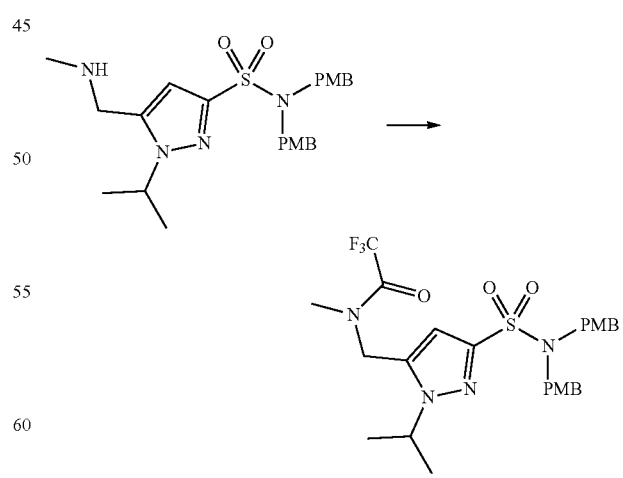

To a solution of 1-isopropyl-N,N-bis(4-methoxybenzyl)-5-((methylamino)methyl)-1H-pyrazole-3-sulfonamide (388 mg, 0.739 mmol) in DCM (2.5 mL) was added pyridine (0.131 mL, 1.626 mmol) and the mixture was cooled to 0°

C. Trifluoroacetic anhydride (0.157 mL, 1.108 mmol) was added dropwise and the resultant mixture was stirred at 0° C. for 15 minutes before warming to room temperature for 2 hours. The mixture was quenched with saturated aqueous sodium bicarbonate (5 mL) and the layers were separated. The aqueous layer was extracted with DCM (2×10 mL) and EtOAc (10 mL) and the combined organics were dried with MgSO$_4$. The solvent was removed under reduced pressure. The crude product was purified by chromatography on SiO$_2$ (24 g column, 0-100% EtOAc/isohexane) to afford the title compound (366 mg, 86%) as a white solid.

$^1$H NMR (DMSO-d$_6$) δ 7.02 (d, J=8.7 Hz, 4H), 6.85-6.79 (m, 4H), 6.73 (s, 1H), 4.81 (s, 2H), 4.70-4.62 (m, 1H), 4.22 (s, 4H), 3.72 (s, 6H), 3.11-3.07 (m, 3H), 1.36 (d, J=6.5 Hz, 6H).

LCMS; m/z 591.3 (M+Na)+(ES$^+$).

Step D: 2,2,2-Trifluoro-N-((1-isopropyl-3-sulfamoyl-1H-pyrazol-5-yl)methyl)-N-methylacetamide

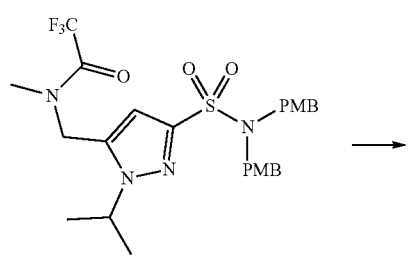

N-((3-(N,N-Bis(4-methoxybenzyl)sulfamoyl)-1-isopropyl-1H-pyrazol-5-yl)methyl)-2,2,2-trifluoro-N-methylacetamide (366 mg, 0.644 mmol) was dissolved in DCM (2 mL) and TFA (2 mL) was added. The reaction mixture was stirred for 16 hours, concentrated in vacuo, suspended in toluene (5 mL) and concentrated again. The crude product was purified by chromatography on silica gel (24 g column, 0-10% MeOH/DCM) to afford the title compound (186 mg, 85%) as a brown solid.

$^1$H NMR (DMSO-d$_6$) δ 7.42 (br s, 2H), 6.57 (s, 1H), 4.80 (s, 2H), 4.70-4.56 (m, 1H), 3.13-3.10 (m, 3H), 1.38 (d, J=6.5 Hz, 6H).

LCMS m/z 329.6 (M+H)$^+$ (ES$^+$).

Intermediate P30: 5-(Azetidin-1-ylmethyl)-1-isopropyl-1H-pyrazole-3-sulfonamide

Step A: 5-(Hydroxymethyl)-1-isopropyl-N,N-bis(4-methoxybenzyl)-1H-pyrazole-3-sulfonamide

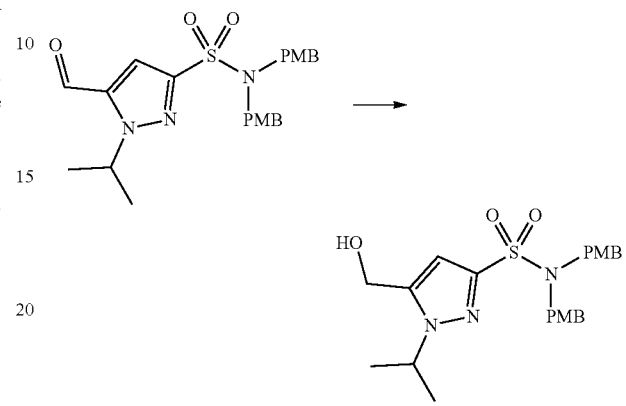

A suspension of 5-formyl-1-isopropyl-N,N-bis(4-methoxybenzyl)-1H-pyrazole-3-sulfonamide (Intermediate P29, Step A) (500 mg, 1.093 mmol) in MeOH (11 mL) was treated with NaBH$_4$ (70.3 mg, 1.858 mmol). The solution was stirred at room temperature for 3 hours and then evaporated in vacuo. The crude product was redissolved in EtOAc (10 mL) and washed with brine (5 mL). The organic phase was dried (MgSO$_4$) and evaporated in vacuo to afford the title compound (514 mg, 98%).

$^1$H NMR (DMSO-d$_6$) δ 7.04-7.00 (m, 4H), 6.83-6.79 (m, 4H), 6.60 (s, 1H), 5.48 (d, J=5.3 Hz, 1H), 4.73 (sept, J=6.4 Hz, 1H), 4.57 (d, J=5.0 Hz, 2H), 4.19 (s, 4H), 3.72 (s, 6H), 1.41 (d, J=6.6 Hz, 6H).

LCMS; m/z 482.3 (M+Na)+(ES$^+$).

Step B: 5-(Azetidin-1-ylmethyl)-1-isopropyl-N,N-bis(4-methoxybenzyl)-1H-pyrazole-3-sulfonamide

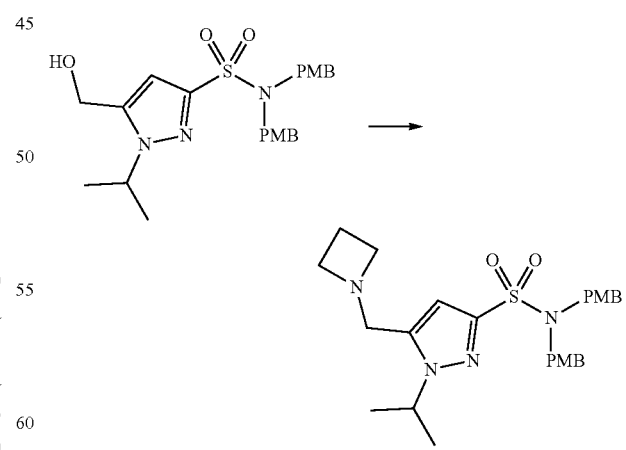

MsCl (62.0 μL, 0.796 mmol) was added to a solution of 5-(hydroxymethyl)-1-isopropyl-N,N-bis(4-methoxybenzyl)-1H-pyrazole-3-sulfonamide (305 mg, 0.663 mmol) and DIPEA (151 μL, 0.862 mmol) in anhydrous DCM (3 mL) at 0° C. The mixture was stirred at room temperature for 3 hours. The reaction mixture was diluted with DCM (10 mL) and saturated aqueous NaHCO₃ solution was added (10 mL). The phases were separated and the aqueous phase was extracted with a further portion of DCM (10 mL). The combined organic phases were washed with brine (10 mL), dried over MgSO₄, filtered and concentrated in vacuo to give crude intermediate as a brown oil. The crude intermediate was redissolved in anhydrous THF (3 mL) and azetidine (303 mg, 5.30 mmol) was added. The mixture was heated to 60° C. and stirred for 1 hour. The solvent was removed in vacuo. The crude product was loaded onto a column of SCX (2 g) in MeOH. The column was washed with MeOH and then the product was eluted with 0.7 M ammonia in MeOH. The crude product was purified by chromatography on SiO₂ (12 g column, 0-10% MeOH/DCM) to afford the title compound (212 mg, 55%) as a white solid.

¹H NMR (DMSO-d₆) δ 7.03-6.98 (m, 4H), 6.84-6.79 (m, 4H), 6.53 (s, 1H), 4.74 (sept, J=6.6 Hz, 1H), 4.19 (s, 4H), 3.72 (s, 6H), 3.61 (s, 2H), 3.13 (t, J=7.0 Hz, 4H), 1.99 (p, J=7.0 Hz, 2H), 1.39 (d, J=6.6 Hz, 6H).

LCMS; m/z 499.5 (M+H)⁺ (ES⁺).

Step C: 5-(Azetidin-1-ylmethyl)-1-isopropyl-1H-pyrazole-3-sulfonamide

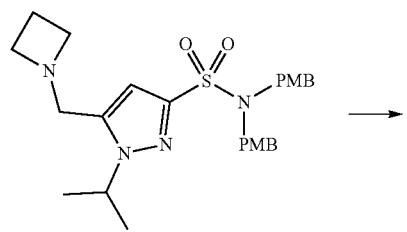

Prepared according to the general procedure of 1-cyclopropyl-5-(1-(dimethylamino) ethyl)-1H-pyrazole-3-sulfonamide (Intermediate P10, Step C) from 5-(azetidin-1-ylmethyl)-1-isopropyl-N,N-bis(4-methoxybenzyl)-1H-pyrazole-3-sulfonamide to afford the title compound (91 mg, 94%) as a white solid.

¹H NMR (DMSO-d₆) δ 7.34 (s, 2H), 6.43 (s, 1H), 4.71 (sept, J=6.6 Hz, 1H), 3.60 (s, 2H), 3.14 (t, J=7.0 Hz, 4H), 1.99 (p, J=7.0 Hz, 2H), 1.38 (d, J=6.6 Hz, 6H).

LCMS; m/z 259.4 (M+H)⁺ (ES⁺).

Intermediate P31:5-(((2,2-Difluoroethyl)(methyl)amino)methyl)-1-isopropyl-1H-pyrazole-3-sulfonamide Step A: 5-(((2,2-Difluoroethyl)(methyl)amino)methyl)-1-isopropyl-N,N-bis(4-methoxybenzyl)-1H-pyrazole-3-sulfonamide

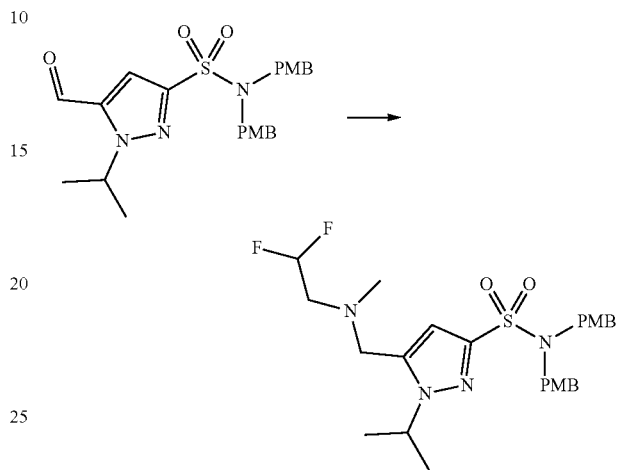

Prepared according to the general procedure of 5-(azetidin-1-ylmethyl)-1-cyclopropyl-N,N-bis(4-methoxybenzyl)-H-pyrazole-3-sulfonamide (Intermediate P18, Step B) from 5-formyl-1-isopropyl-N,N-bis(4-methoxybenzyl)-1H-pyrazole-3-sulfonamide (Intermediate P29, Step A) and 2,2-difluoro-N-methylethanamine hydrochloride to afford the title compound (374 mg, 60%) as a colourless oil.

¹H NMR (DMSO-d₆) δ 7.03-6.97 (m, 4H), 6.85-6.78 (m, 4H), 6.62 (s, 1H), 6.16 (tt, J=55.6, 4.2 Hz, 1H), 4.80 (sept, J=6.5 Hz, 1H), 4.20 (s, 4H), 3.72 (s, 8H), 2.83 (td, J=15.6, 4.2 Hz, 2H), 2.26 (s, 3H), 1.39 (d, J=6.6 Hz, 6H).

LCMS; m/z 57.5 (M+H)⁺ (ES⁺).

Step B: 5-(((2,2-Difluoroethyl)(methyl)amino)methyl)-1-isopropyl-1H-pyrazole-3-sulfonamide

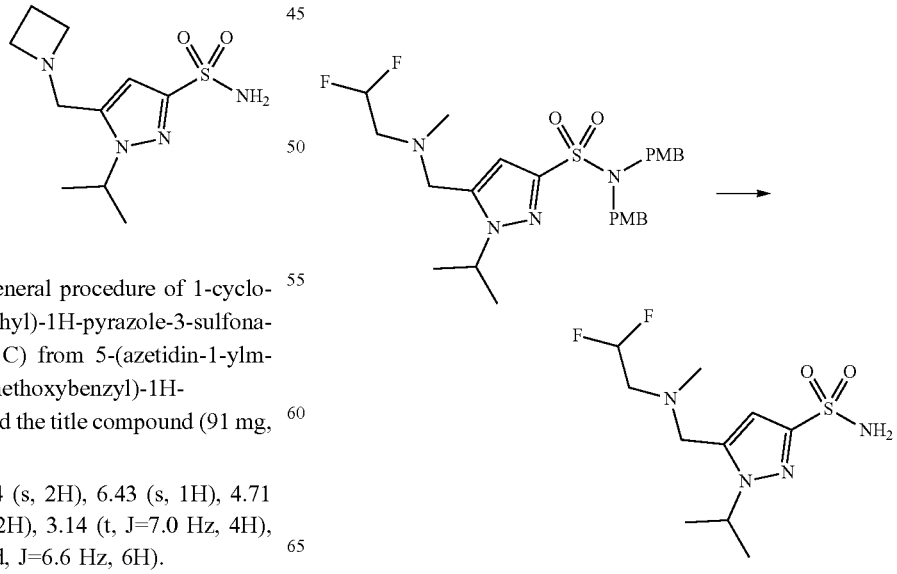

Prepared according to the general procedure of 1-cyclopropyl-5-(1-(dimethylamino) ethyl)-1H-pyrazole-3-sulfonamide (Intermediate P10, Step C) from 5-(((2,2-difluoroethyl)(methyl)amino)methyl)-1-isopropyl-N,N-bis(4-methoxybenzyl)-1H-pyrazole-3-sulfonamide to afford the title compound (145 mg, 81%) as a white solid.

$^1$H NMR (DMSO-d$_6$) δ 7.37 (s, 2H), 6.50 (s, 1H), 6.15 (tt, J=55.7, 4.3 Hz, 1H), 4.76 (sept, J=6.6 Hz, 1H), 3.71 (s, 2H), 2.81 (td, J=15.6, 4.3 Hz, 2H), 2.27 (s, 3H), 1.38 (d, J=6.6 Hz, 6H).

LCMS; m/z 297.3 (M+H)$^+$ (ES$^+$).

Intermediate P32: 5-(((2-Fluoroethyl)(methyl)amino)methyl)-1-isopropyl-1H-pyrazole-3-sulfonamide Step A: 5-(((2-Fluoroethyl)(methyl)amino)methyl)-1-isopropyl-N,N-bis(4-methoxybenzyl)-1H-pyrazole-3-sulfonamide

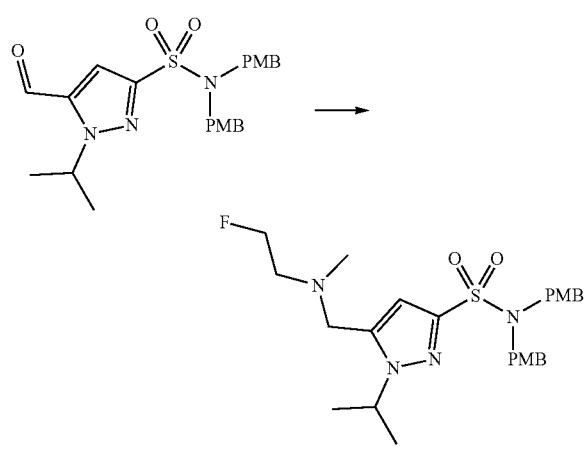

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-1-isopropyl-N,N-bis(4-methoxybenzyl)-1H-pyrazole-3-sulfonamide (Intermediate P29, Step A) and 2-fluoro-N-methylethanamine hydrochloride to afford the title compound (279 mg, 48%) as a colourless oil.

$^1$H NMR (DMSO-d$_6$) δ 7.06-6.97 (m, 4H), 6.86-6.77 (m, 4H), 6.59 (s, 1H), 4.83 (sept, J=6.5 Hz, 1H), 4.55 (dt, J=47.8, 4.8 Hz, 2H), 4.20 (s, 4H), 3.72 (s, 6H), 3.65 (s, 2H), 2.68 (dt, J=28.4, 4.9 Hz, 2H), 2.21 (s, 3H), 1.39 (d, J=6.6 Hz, 6H).

LCMS; m/z 519.2 (M+H)$^+$ (ES$^+$).

Step B: 5-(((2-Fluoroethyl)(methyl)amino)methyl)-1-isopropyl-1H-pyrazole-3-sulfonamide

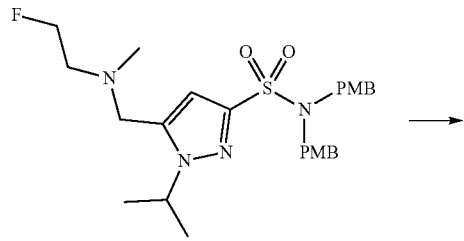

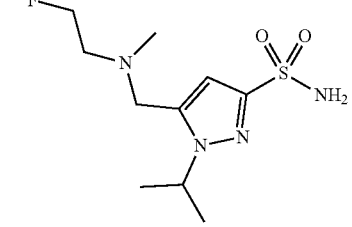

Prepared according to the general procedure of 1-cyclopropyl-5-(1-(dimethylamino) ethyl)-1H-pyrazole-3-sulfonamide (Intermediate P10, Step C) from 5-(((2-fluoroethyl)(methyl)amino)methyl)-1-isopropyl-N,N-bis(4-methoxybenzyl)-1H-pyrazole-3-sulfonamide to afford the title compound (129 mg, 100%).

$^1$H NMR (DMSO-d$_6$) δ 7.36 (s, 2H), 6.48 (s, 1H), 4.79 (sept, J=6.6 Hz, 1H), 4.54 (dt, J=47.8, 4.9 Hz, 2H), 3.63 (s, 2H), 2.68 (dt, J=28.3, 4.9 Hz, 2H), 2.22 (s, 3H), 1.38 (d, J=6.6 Hz, 6H).

LCMS; m/z 279.4 (M+H)$^+$ (ES$^+$).

Intermediate P33: 5-(1-(Dimethylamino)cyclopropyl)-1-methyl-1H-pyrazole-3-sulfonamide Step A: 3-(N,N-Bis(4-methoxybenzyl)sulfamoyl)-N,N,1-trimethyl-1H-pyrazole-5-carboxamide

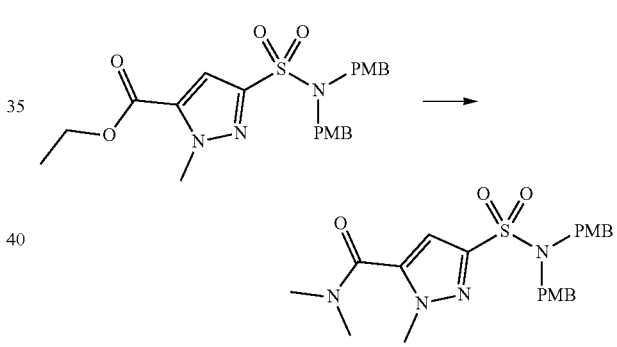

Ethyl 3-(N,N-bis(4-methoxybenzyl)sulfamoyl)-1-methyl-1H-pyrazole-5-carboxylate (Intermediate P22, Step A) (2 g, 4.22 mmol) was suspended in EtOH (20 mL) and THF (5 mL) and 2 M aqueous NaOH (4.22 mL, 8.45 mmol). The reaction was left to stir at room temperature for 20.5 hours. The reaction was then evaporated to dryness under reduced pressure to give a white solid. The solid obtained was suspended in THF (25 mL) to which T3P, 50 wt % in EtOAc (4.8 mL, 8.06 mmol), 2 M dimethylamine in THF (2.5 mL, 5.00 mmol) and DIPEA (1.4 mL, 8.02 mmol) were added. The reaction mixture was stirred at room temperature for 90 minutes. A gel was obtained, so further THF (10 mL) was added and the mixture stirred for a further 17 hours. Further T3P, 50 wt % in EtOAc (4.8 mL, 8.06 mmol), DIPEA (1.4 mL, 8.02 mmol) and 2 M dimethylamine in THF (2.5 mL, 5.00 mmol) were added and the mixture was stirred for a further 24 hours at room temperature. The mixture was quenched with 1 M aqueous HCl (50 mL) and extracted with EtOAc (50 mL). The organic layer was washed with 1 M aqueous HCl (50 mL), dried (MgSO$_4$), filtered and concentrated to dryness to give a yellow oil. The yellow oil was dissolved in THF (25 mL) and 2 M dimethylamine in THF (2.5 mL, 5.00 mmol), DIPEA (1.4 mL, 8.02 mmol) and T3P, 50 wt % in EtOAc (4.8 mL, 8.06 mmol) were added sequentially. The mixture was stirred at room temperature for a further 1 hour. The mixture was quenched with 1 M aqueous HCl (50 mL) and extracted with EtOAc (50 mL). The organic layer was washed with 1 M aqueous HCl (50 mL), 2 M aqueous NaOH and then dried (MgSO$_4$), filtered and concentrated to dryness to give an orange oil. The crude product was purified by chromatography on SiO$_2$ (40 g column, 0-100% EtOAc/isohexane) to afford the title compound (1.64 g, 85%) as a beige solid.

$^1$H NMR (DMSO-d$_6$) δ 7.20-7.01 (m, 4H), 6.95 (s, 1H), 6.88-6.70 (m, 4H), 4.23 (s, 4H), 3.91 (s, 3H), 3.71 (s, 6H), 3.01 (s, 3H), 3.00 (s, 3H).

LCMS; m/z 495.2 (M+Na)+(ES$^+$).

Step B: 5-(1-(Dimethylamino)cyclopropyl)-N,N-bis (4-methoxybenzyl)-1-methyl-1H-pyrazole-3-sulfonamide

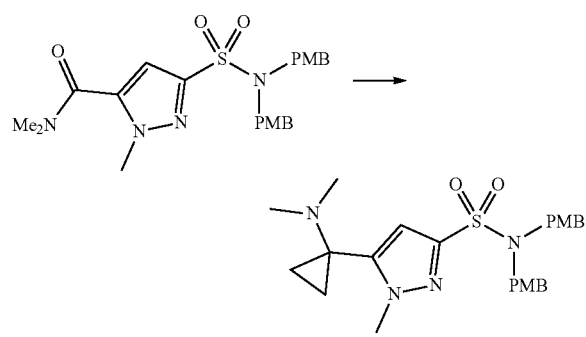

Prepared according to the general procedure 5-(1-(dimethylamino)cyclopropyl)-1-isopropyl-N,N-bis(4-methoxybenzyl)-1H-pyrazole-3-sulfonamide (Intermediate P20, Step B) from 3-(N,N-bis(4-methoxybenzyl)sulfamoyl)-N,N,1-trimethyl-1H-pyrazole-5-carboxamide to afford the title compound (345 mg, 48.3%) as a white solid.

$^1$H NMR (DMSO-d$_6$) δ 7.08-6.97 (m, 4H), 6.85-6.74 (m, 4H), 6.49 (s, 1H), 4.22 (s, 4H), 3.94 (s, 3H), 3.72 (s, 6H), 2.15 (s, 6H), 1.04-0.95 (m, 2H), 0.88-0.80 (m, 2H).

LCMS; m/z 485.6 (M+H)$^+$ (ES$^+$).

Step C: 5-(1-(Dimethylamino)cyclopropyl)-1-methyl-1H-pyrazole-3-sulfonamide

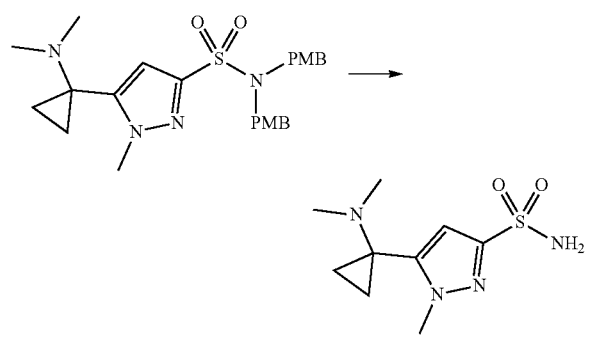

Prepared according to the general procedure of 5-(1-(dimethylamino)cyclopropyl)-1-methyl-1H-pyrazole-3-sulfonamide (Intermediate P20, Step C) from 5-(1-(dimethylamino)cyclopropyl)-N,N-bis(4-methoxybenzyl)-1-methyl-1H-pyrazole-3-sulfonamide to afford the title compound (140 mg, 68%) as a white solid.

$^1$H NMR (DMSO-d$_6$) δ 7.32 (br s, 2H), 6.47 (s, 1H), 3.93 (s, 3H), 2.18 (s, 6H), 1.07-0.95 (m, 2H), 0.93-0.71 (m, 2H).

LCMS; m/z 245.4 (M+H)$^+$ (ES$^+$).

Intermediate P34: 5-(2-(Dimethylamino)ethyl)-1-methyl-1H-pyrazole-3-sulfonamide

Step A: 5-(2-Hydroxyethyl)-N,N-bis(4-methoxybenzyl)-1-methyl-1H-pyrazole-3-sulfonamide

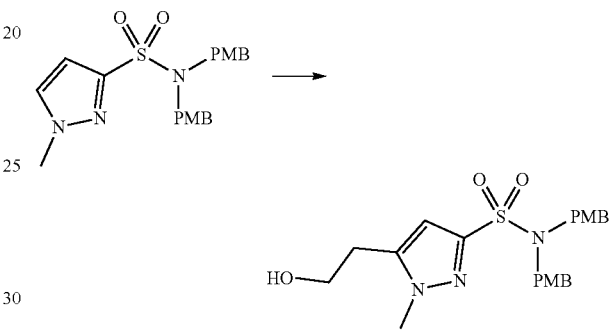

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis-(4-methoxybenzyl)-1-methyl-H-pyrazole-3-sulfonamide (Intermediate P9, Step A) and oxirane (2.5 M in THF) to afford the title compound (0.55 g, 25%) as a yellow oil.

$^1$H NMR (CDCl$_3$) δ 7.10-7.05 (m, 4H), 6.80-6.74 (m, 4H), 6.41 (d, J=0.6 Hz, 1H), 4.30 (s, 4H), 3.88 (t, J=6.3 Hz, 2H), 3.87 (s, 3H), 3.78 (s, 6H), 2.87 (t, J=6.3 Hz, 2H).

OH signal not observed.

LCMS; m/z 468.4 (M+Na)+(ES$^+$).

Step B: 5-(2-(Dimethylamino)ethyl)-N,N-bis(4-methoxybenzyl)-1-methyl-1H-pyrazole-3-sulfonamide

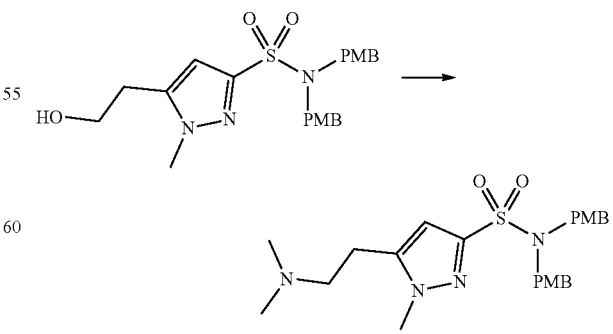

Dess-Martin periodinane 0.540 g, 1.210 mmol) was added to a solution of 5-(2-hydroxyethyl)-N,N-bis(4-methoxybenzyl)-1-methyl-1H-pyrazole-3-sulfonamide (0.50 g, 1.100 mmol) in anhydrous DCM (8 mL) at room temperature. The mixture was stirred for 2.5 hours at room temperature and then quenched by addition of a 5% aqueous $NaS_2O_3$ solution (3 mL), followed by a saturated aqueous $NaHCO_3$ solution (5 mL). This mixture was then stirred for 15 minutes and extracted with EtOAc (3×25 mL). The combined organic phases were washed with saturated aqueous $NaHCO_3$ solution (2×10 mL), $H_2O$ (10 mL), and brine (10 mL), dried over $MgSO_4$, filtered, and concentrated in vacuo to give a yellow oil. $NaCNBH_3$ (0.086 g, 1.299 mmol) was added to a pre-stirred solution (10 minutes at room temperature) of this oil and dimethylamine (2 M in THF) (2.71 mL, 5.41 mmol) in anhydrous MeOH (5 mL) at room temperature. The mixture was stirred at room temperature over the weekend. The mixture was concentrated under reduced pressure, redissolved in MeOH (3 mL) and loaded onto SCX (ca. 5 g), which was then rinsed with MeOH (15 mL) and eluted with 0.7 M $NH_3$/MeOH (15 mL). The eluent was concentrated in vacuo to give a pale yellow oil. The residue was re-dissolved in anhydrous MeOH (5 mL), $NaBH_4$ (0.082 g, 2.165 mmol) was added and the mixture was stirred at room temperature for 20 hours. The reaction mixture was quenched with 14% w/v aqueous NaOH (0.928 mL, 3.25 mmol) and stirred for 20 minutes at room temperature before being concentrated under reduced pressure. The residue was partitioned between EtOAc (30 mL) and brine (10 mL), and the layers were separated. The aqueous phase was extracted with EtOAc (2×30 mL). The combined organic phases were washed with brine (2×10 mL), dried over $MgSO_4$, filtered, and concentrated in vacuo to give a pale yellow oil. The crude product was purified by chromatography on $SiO_2$ (12 g column, 0-10% (0.7 M ammonia/MeOH)/DCM) to afford the title compound (0.24 g, 43%) as a very pale yellow oil.

$^1$H NMR (DMSO-$d_6$) δ 7.06-7.00 (m, 4H), 6.84-6.77 (m, 4H), 6.48 (s, 1H), 4.18 (s, 4H), 3.84 (s, 3H), 3.71 (s, 6H), 2.79 (t, J=7.4 Hz, 2H), 2.20 (s, 6H). 2H triplet directly underneath DMSO peak.

LCMS; m/z 473.5 (M+H)$^+$ (ES$^+$).

Step C: 5-(2-(Dimethylamino)ethyl)-1-methyl-1H-pyrazole-3-sulfonamide

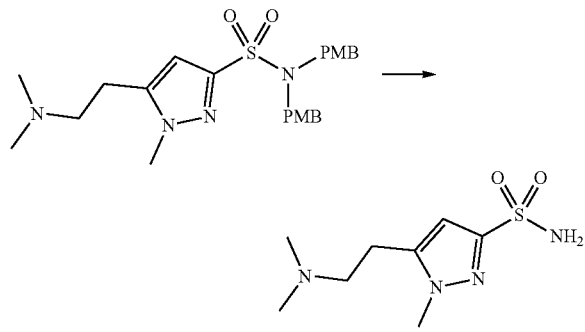

Prepared according to the general procedure of 1-cyclopropyl-5-(1-(dimethylamino) ethyl)-1H-pyrazole-3-sulfonamide (Intermediate P10, Step C) from 5-(2-(dimethylamino) ethyl)-N,N-bis(4-methoxybenzyl)-1-methyl-1H-pyrazole-3-sulfonamide to afford the title compound (0.07 g, 85%) as a colourless oil.

LCMS; m/z 233.4 (M+H)$^+$ (ES$^+$).

Intermediate P35: 4-(Dimethylamino)-4,5,6,7-tetrahydropyrazolo[1,5-a]pyridine-2-sulfonamide Step A: Ethyl 3-(N,N-bis(4-methoxybenzyl)sulfamoyl)-1H-pyrazole-5-carboxylate

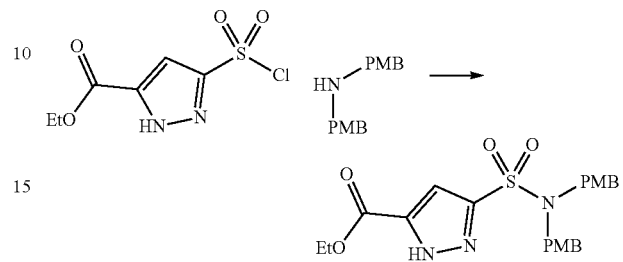

Prepared according to the general procedure of N,N-bis-(4-methoxybenzyl)-1-methyl-1H-pyrazole-3-sulfonamide (Intermediate P9, Step A) from ethyl 3-(chlorosulfonyl)-1H-pyrazole-5-carboxylate to afford the title compound (5.7 g, 81%) as a white solid.

$^1$H NMR (DMSO-$d_6$) δ 14.87 (s, 1H), 7.28-6.98 (m, 5H), 6.98-6.47 (m, 4H), 4.35 (q, J=7.1 Hz, 2H), 4.24 (br s, 4H), 3.71 (s, 6H), 1.33 (t, J=7.1 Hz, 3H).

LCMS; m/z 482.1 (M+Na)+(ES$^+$).

Step B: Ethyl 3-(N,N-bis(4-methoxybenzyl)sulfamoyl)-1-(4-methoxy-4-oxobutyl)-1H-pyrazole-5-carboxylate

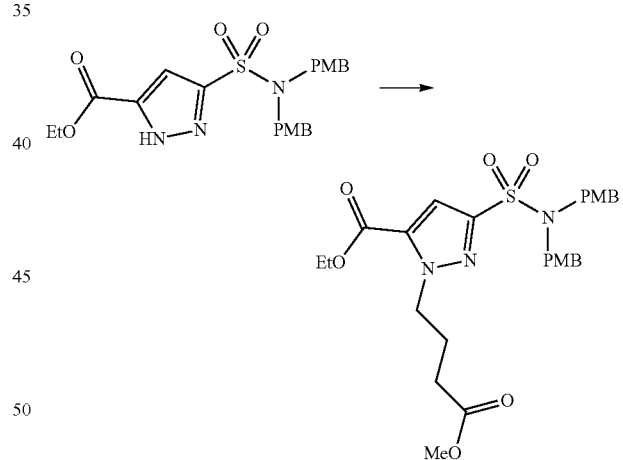

A mixture of ethyl 3-(N,N-bis(4-methoxybenzyl)sulfamoyl)-1H-pyrazole-5-carboxylate (1 g, 2.176 mmol), ethyl 4-bromobutanoate (0.509 g, 2.61 mmol) and $K_2CO_3$ (600 mg, 4.34 mmol) in DMF (10 mL) was stirred at room temperature for 72 hours. The mixture was partitioned between EtOAc (100 mL) and water (100 mL), the organic layer washed with water (100 mL), dried (MgSO$_4$), filtered and evaporated to afford the title compound (1.09 g, 85%) as an oil.

$^1$H NMR (CDCl$_3$) δ 7.14 (s, 1H), 7.13-7.09 (m, 4H), 6.82-6.78 (m, 4H), 4.67 (t, J=6.9 Hz, 2H), 4.39 (q, J=7.2 Hz, 2H), 4.34 (s, 4H), 3.80 (s, 6H), 3.70 (s, 3H), 2.35 (t, J=7.2 Hz, 2H), 2.24-2.16 (m, 2H), 1.42 (t, J=7.1 Hz, 3H).

LCMS; m/z 582 (M+Na)+(ES$^+$).

Step C: Methyl 2-(N,N-bis(4-methoxybenzyl)sulfamoyl)-4-oxo-4,5,6,7-tetrahydropyrazolo[1,5-a]pyridine-5-carboxylate and ethyl 2-(N,N-bis(4-methoxybenzyl)sulfamoyl)-4-oxo-4,5,6,7-tetrahydropyrazolo[1,5-a]pyridine-5-carboxylate

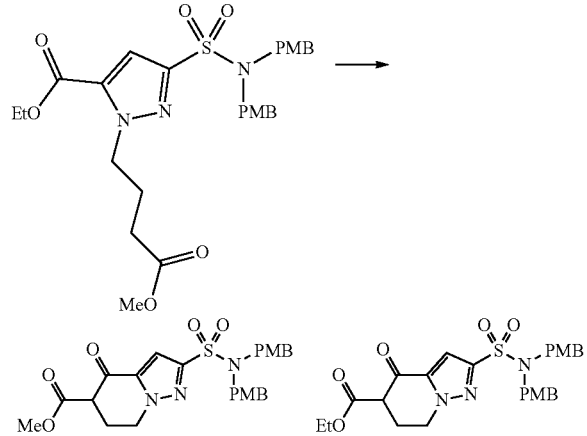

Toluene (15 mL) was added to ethyl 3-(N,N-bis(4-methoxybenzyl)sulfamoyl)-1-(4-methoxy-4-oxobutyl)-1H-pyrazole-5-carboxylate (1.06 g, 1.894 mmol) and the solution evaporated under reduced pressure. A solution of sodium tert-butoxide (1 mL, 2.000 mmol) (2 M in THF) was added to a solution of ethyl 3-(N,N-bis(4-methoxybenzyl)sulfamoyl)-1-(4-methoxy-4-oxobutyl)-1H-pyrazole-5-carboxylate (1.06 g, 1.894 mmol) in toluene (15 mL). The reaction mixture was stirred at room temperature for 10 minutes and then heated at 80° C. for 3 hours. The mixture was cooled, and partitioned between EtOAc (80 mL) and 1 M aqueous HCl (50 mL). The organic layer was washed with water (40 mL), dried (MgSO₄), filtered and evaporated. The residue was purified by chromatography on silica gel (40 g column, 0-50% EtOAc/isohexane) to afford methyl 2-(N,N-bis(4-methoxybenzyl)sulfamoyl)-4-oxo-4,5,6,7-tetrahydropyrazolo[1,5-a]pyridine-5-carboxylate (510 mg, 45%) and ethyl 2-(N,N-bis(4-methoxybenzyl)sulfamoyl)-4-oxo-4,5,6,7-tetrahydropyrazolo[1,5-a]pyridine-5-carboxylate (264 mg, 24%) as solids.

Methyl ester: ¹H NMR (CDCl₃) δ 11.93 (s, 1H), 7.13-709 (m, 4H), 6.92 (s, 1H), 6.82-6.78 (m, 4H), 4.35 (s, 4H), 4.28 (t, J=7.5 Hz, 2H), 3.90 (s, 3H), 3.80 (s, 6H), 2.93 (t, J=7.4 Hz, 2H).

LCMS; m/z 514 (M+H)⁺ (ES⁺); 512 (M−H)⁻ (ES⁻).

Ethyl ester: LCMS; m/z 528 (M+H)⁺ (ES⁺); 526 (M−H)⁻ (ES⁻).

Step D: N,N-Bis(4-methoxybenzyl)-4-oxo-4,5,6,7-tetrahydropyrazolo[1,5-a]pyridine-2-sulfonamide

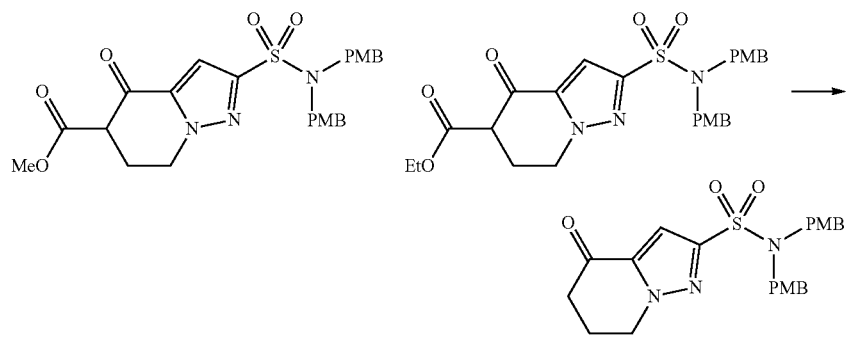

A mixture of methyl 2-(N,N-bis(4-methoxybenzyl)sulfamoyl)-4-oxo-4,5,6,7-tetrahydropyrazolo[1,5-a]pyridine-5-carboxylate (450 mg, 0.876 mmol), ethyl 2-(N,N— bis(4-methoxybenzyl)sulfamoyl)-4-oxo-4,5,6,7-tetrahydropyrazolo[1,5-a]pyridine-5-carboxylate (260 mg, 0.493 mmol) and LiCl (120 mg, 2.83 mmol) in DMSO (10 mL) and water (1 mL) was heated at 120° C. for 3 hours. The mixture was partitioned between EtOAc (80 mL) and 10% brine (50 mL), the organic layer separated, dried (MgSO₄), filtered and evaporated. The crude product was purified by chromatography on silica gel (40 g column, 0-70% EtOAc/isohexane) to afford the title compound (525 mg, 80%) as a solid.

¹H NMR (CDCl₃) δ 7.13-7.10 (m, 5H), 6.81-6.77 (m, 4H), 4.42-4.39 (m, 2H), 4.36 (s, 4H), 3.80 (s, 6H), 2.77-2.73 (m, 2H), 2.45-2.39 (m, 2H).

LCMS; m/z 478 (M+Na)+(ES⁺); 454.3 (M−H)⁻ (ES⁻).

Step E: 4-(Dimethylamino)-N,N-bis(4-methoxybenzyl)-4,5,6,7-tetrahydropyrazolo[1,5-a]pyridine-2-sulfonamide

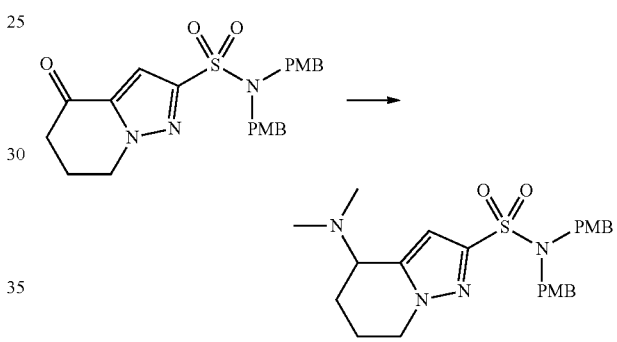

To a mixture of N,N-bis(4-methoxybenzyl)-4-oxo-4,5,6,7-tetrahydropyrazolo[1,5-a]pyridine-2-sulfonamide (200 mg, 0.439 mmol), dimethylamine (2 M in THF) (280 μL, 0.560 mmol) and triethylamine (200 μL, 1.435 mmol) in DCM (4 mL) at 0° C. was added titanium(IV) chloride (1 M in DCM) (220 μL, 0.220 mmol) slowly via syringe. The resulting mixture was warmed to room temperature and stirred overnight. NaBH(OAc)₃ (240 mg, 1.132 mmol) and MeOH (1 mL) were added and stirring was continued over the weekend. The reaction was quenched with H₂O (5 mL) and brine (10 mL) and the mixture was extracted with EtOAc (3×30 mL). The combined organic extracts were washed with brine (15 mL), passed through a phase separator and the solvent was removed under reduced pressure. The residue was loaded onto a SCX column with MeOH and the product eluted with 0.7 M NH₃ in MeOH to afford the title compound (133 mg, 59%) as a yellow oil.

¹H NMR (DMSO-d₆) δ 7.03 (d, J=8.7 Hz, 4H), 6.81 (d, J=8.7 Hz, 4H), 6.44 (d, J=0.9 Hz, 1H), 4.28-4.11 (m, 5H), 4.12-3.96 (m, 1H), 3.94-3.85 (m, 1H), 3.71 (s, 6H), 2.21 (s, 6H), 2.21-2.11 (m, 1H), 2.03-1.82 (m, 2H), 1.76-1.61 (m, 1H).

LCMS; m/z 485.2 (M+H)⁺ (ES⁺).

Step F: 4-(Dimethylamino)-4,5,6,7-tetrahydropyrazolo[1,5-a]pyridine-2-sulfonamide

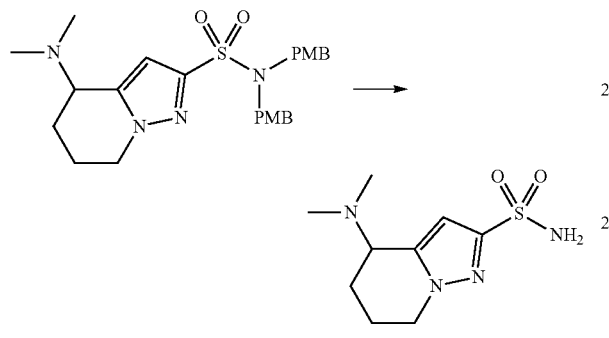

Prepared according to the general procedure of 1-cyclopropyl-5-(1-(dimethylamino)ethyl)-1H-pyrazole-3-sulfonamide (Intermediate P10, Step C) from 4-(dimethylamino)-N,N-bis(4-methoxybenzyl)-4,5,6,7-tetrahydropyrazolo[1,5-a]pyridine-2-sulfonamide to afford the title compound (58 mg, 81%) as a beige solid.

¹H NMR (DMSO-d₆) δ 7.33 (s, 2H), 6.42 (s, 1H), 4.18-4.07 (m, 1H), 4.07-3.94 (m, 1H), 3.93-3.85 (m, 1H), 2.23 (s, 6H), 2.19-2.08 (m, 1H), 1.99-1.80 (m, 2H), 1.75-1.60 (m, 1H).

LCMS; m/z 245.4 (M+H)⁺ (ES⁺).

Intermediate P36: 5-(1-(Dimethylamino)propyl)-1-isopropyl-1H-pyrazole-3-sulfonamide Step A: 5-(1-Hydroxypropyl)-1-isopropyl-N,N-bis(4-methoxybenzyl)-1H-pyrazole-3-sulfonamide

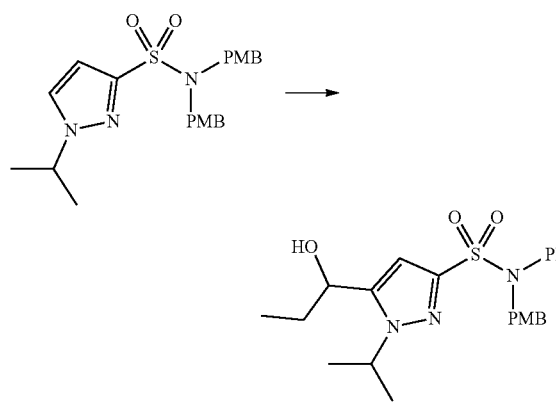

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis-(4-methoxybenzyl)-1-isopropyl-1H-pyrazole-3-sulfonamide (Intermediate P8, Step A) and propionaldehyde to afford the title compound (1.79 g, 77%) as a very pale yellow oil.

LCMS; m/z 488.3 (M+H)⁺ (ES⁺).

Step B: 5-(1-(Dimethylamino)propyl)-1-isopropyl-N,N-bis(4-methoxybenzyl)-1H-pyrazole-3-sulfonamide

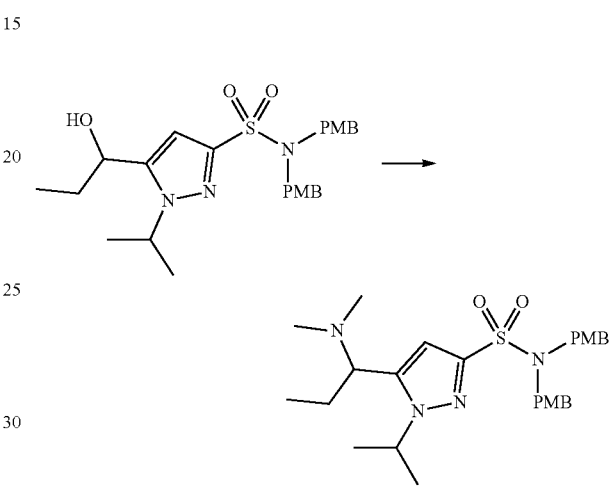

MsCl (0.158 mL, 2.026 mmol) was added to a solution of 5-(1-hydroxypropyl)-1-isopropyl-N,N-bis(4-methoxybenzyl)-1H-pyrazole-3-sulfonamide (0.84 g, 1.688 mmol) and DIPEA (0.413 mL, 2.364 mmol) in anhydrous DCM (8 mL) at 0° C. After 20 minutes, the solution was allowed to warm to room temperature and stirred overnight. Dimethylamine (2 M in THF) (5.06 mL, 10.13 mmol) was added and the mixture was heated to 40° C. for 23 hours. The mixture was concentrated under reduced pressure and the flask was recharged with dimethylamine (2 M in THF) (5.06 mL, 10.13 mmol) and heated to 50° C. overnight. After a further 24 hours, the reaction mixture was transferred to a microwave vial, dimethylamine (2 M in THF) (1.688 mL, 3.38 mmol) was added, and the vessel was sealed and heated at 40° C. over the weekend. To the reaction mixture was added saturated aqueous NaHCO₃ (20 mL) and EtOAc (30 mL). The layers were separated and the aqueous layer extracted with EtOAc (2×30 mL). The combined organic extracts were washed with brine (30 mL), passed through a phase separator and the solvent was removed in vacuo to give a brown oil. The residue was loaded onto a SCX column with MeOH and the column was washed with further MeOH (15 mL). The product was eluted with 0.7 M NH₃ in MeOH (~20 mL) and the solvent was removed in vacuo to afford the title compound (428 mg, 48%) as a light brown oil.

¹H NMR (DMSO-d₆) δ 6.99 (d, J=8.7 Hz, 4H), 6.80 (d, J=8.7 Hz, 4H), 6.53 (s, 1H), 4.89-4.80 (m, 1H), 4.21 (s, 2H), 4.20 (s, 2H), 3.71 (s, 6H), 3.70-3.65 (m, 1H), 2.10 (s, 6H), 1.88-1.76 (m, 1H), 1.72-1.61 (m, 1H), 1.40 (d, J=6.5 Hz, 3H), 1.33 (d, J=6.5 Hz, 3H), 0.76 (t, J=7.3 Hz, 3H).

LCMS; m/z 515.5 (M+H)⁺ (ES⁺).

Step C: 5-(1-(Dimethylamino)propyl)-1-isopropyl-1H-pyrazole-3-sulfonamide

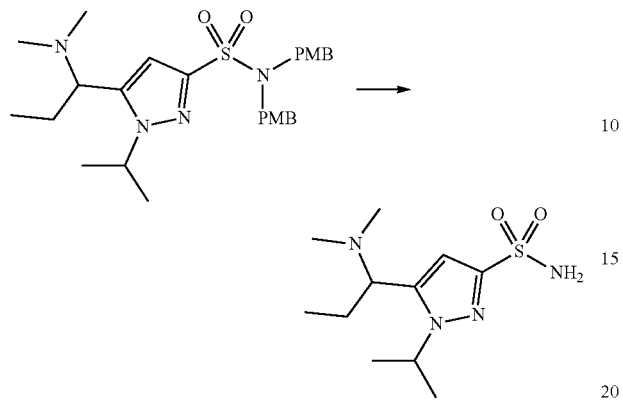

Prepared according to the general procedure of 1-cyclopropyl-5-(1-(dimethylamino)ethyl)-1H-pyrazole-3-sulfonamide (Intermediate P10, Step C) from 5-(1-(dimethylamino)propyl)-1-isopropyl-N,N-bis(4-methoxybenzyl)-1H-pyrazole-3-sulfonamide to afford the title compound (202 mg, 91%) as a light tan solid.

$^1$H NMR (DMSO-d$_6$) δ 7.35 (s, 2H), 6.43 (s, 1H), 4.88-4.75 (m, 1H), 3.66 (dd, J=4.8, 9.8 Hz, 1H), 2.12 (s, 6H), 1.91-1.78 (m, 1H), 1.71-1.59 (m, 1H), 1.40 (d, J=6.5 Hz, 3H), 1.35 (d, J=6.5 Hz, 3H), 0.79 (t, J=7.3 Hz, 3H).

LCMS; m/z 275.1 (M+H)$^+$ (ES$^+$).

Intermediate P37: 5-(1-(Dimethylamino)propyl)-1-methyl-1H-pyrazole-3-sulfonamide

Step A: 5-(1-Hydroxypropyl)-N,N-bis(4-methoxybenzyl)-1-methyl-1H-pyrazole-3-sulfonamide

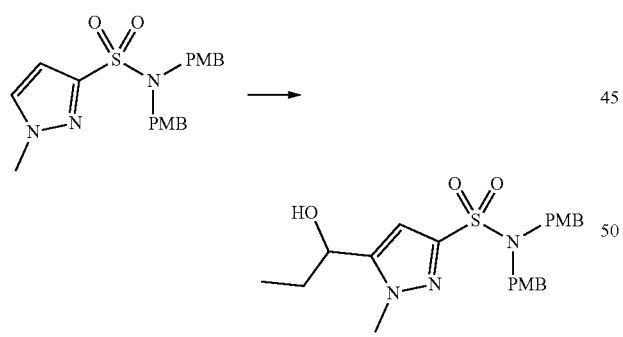

Prepared according to the general procedure of 5-((dimethylamino)methyl)-N,N-bis(4-methoxybenzyl)-1-ethyl-1H-pyrazole-3-sulfonamide (Intermediate P7, Step B) from N,N-bis-(4-methoxybenzyl)-1-methyl-1H-pyrazole-3-sulfonamide (Intermediate P9, Step A) and propionaldehyde to afford the title compound (3.4 g, 84%) as a viscous colourless oil.

$^1$H NMR (DMSO-d$_6$) δ 7.08-7.02 (m, 4H), 6.84-6.80 (m, 4H), 6.53 (s, 1H), 5.50 (d, J=5.8 Hz, 1H), 4.60 (q, J=6.4 Hz, 1H), 4.20 (s, 4H), 3.91 (s, 3H), 3.72 (s, 6H), 1.73 (td, J=7.7, 6.5 Hz, 2H), 0.95-0.81 (m, 3H).

LCMS; m/z 460 (M+H)$^+$ (ES$^+$).

Step B: 5-(1-(Dimethylamino)propyl)-1-methyl-N,N-bis(4-methoxybenzyl)-1H-pyrazole-3-sulfonamide

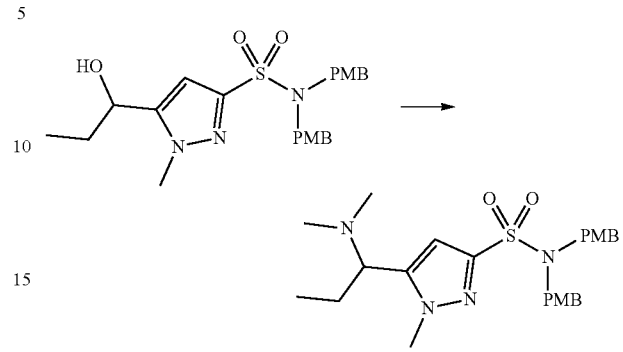

MsCl (0.094 mL, 1.200 mmol) was added to a solution of 5-(1-hydroxypropyl)-N,N—bis(4-methoxybenzyl)-1-methyl-1H-pyrazole-3-sulfonamide (0.484 g, 1.000 mmol) and DIPEA (0.245 mL, 1.400 mmol) in anhydrous DCM (5 mL) at 0° C. The mixture was warmed to room temperature and stirred for 2.5 hours. Then the pale yellow solution was cooled to 0° C. and dimethylamine (2 M in THF) (12.50 mL, 25.00 mmol) was added. The reaction mixture was warmed to 40° C. and stirred for 17 hours. A further portion of dimethylamine (2 M in THF) (1.0 mL, 2.000 mmol) was added and the reaction was stirred at 40° C. for a further 2 hours. The mixture was cooled to room temperature and evaporated to dryness. The residue was taken up in EtOAc (50 mL) and saturated aqueous NaHCO$_3$ solution (10 mL), the layers were separated, and the aqueous phase was extracted with further portions of EtOAc (2×20 mL). The combined organic phases were washed with saturated aqueous NaHCO$_3$ solution (10 mL) and brine (2×10 mL), dried over MgSO$_4$, filtered, and concentrated in vacuo to give crude product as a yellow oil. The crude product was re-dissolved in MeOH (3 mL) and loaded onto SCX (ca. 4 g), which was then washed with MeOH (15 mL) and eluted with 0.7 M NH$_3$/MeOH (15 mL) and concentrated in vacuo to afford the title compound (0.27 g, 48%) as a pale yellow oil.

LCMS; m/z 487.5 (M+H)$^+$ (ES$^+$).

Step C: 5-(1-(Dimethylamino)propyl)-1-methyl-1H-pyrazole-3-sulfonamide

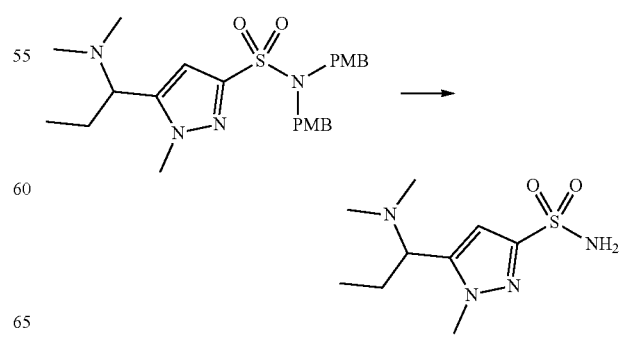

TFA (1.412 mL, 18.45 mmol) was added to a solution of 5-(1-(dimethylamino)propyl)-N,N-bis(4-methoxybenzyl)-1-methyl-1H-pyrazole-3-sulfonamide (0.630 g, 1.230 mmol) in anhydrous DCM (4 mL) at room temperature. The mixture was stirred at room temperature for 19 hours. A second portion of TFA (0.471 mL, 6.15 mmol) was added and the reaction was stirred for a further 2 hours at room temperature. The reaction mixture was concentrated in vacuo and co-evaporated with portions of MeCN (2×10 mL). The residue was then redissolved in MeOH (3 mL) and loaded onto SCX (ca. 5 g), which was rinsed with MeOH (15 mL) and eluted with 0.7 M NH$_3$/MeOH (15 mL) to give a yellow solid after concentration in vacuo. This material was pre-adsorbed onto silica and purified by chromatography on SiO$_2$ (12 g column, 0-10% (0.7 M ammonia/MeOH)/DCM) to afford the title compound (0.14 g, 45%) as an off-white solid.

LCMS; m/z 247.4 (M+H)$^+$ (ES$^+$).

Intermediate P38: 2,2,2-Trifluoro-N-methyl-N-((1-methyl-3-sulfamoyl-1H-pyrazol-5-yl)methyl)acetamide Step A: 5-Formyl-N,N-bis(4-methoxybenzyl)-1-methyl-1H-pyrazole-3-sulfonamide

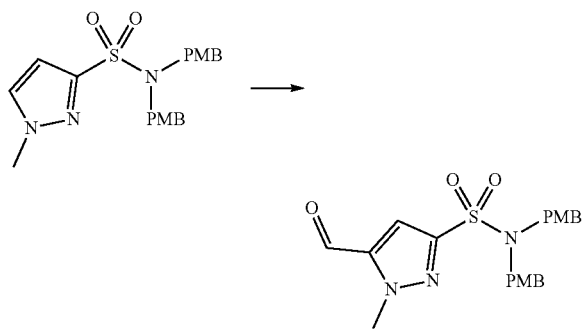

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis-(4-methoxybenzyl)-1-methyl-H-pyrazole-3-sulfonamide (Intermediate P9, Step A) and DMF to afford the title compound (4 g, 93%) as a white solid.

$^1$H NMR (DMSO-d$_6$) δ 9.90 (s, 1H), 7.41 (s, 1H), 7.11-7.02 (m, 4H), 6.87-6.78 (m, 4H), 4.25 (s, 4H), 4.17 (s, 3H), 3.72 (s, 6H).

LCMS; m/z 452.4 (M+Na)+(ES$^+$).

Step B: N,N-Bis(4-methoxybenzyl)-1-methyl-5-((methylamino)methyl)-1H-pyrazole-3-sulfonamide

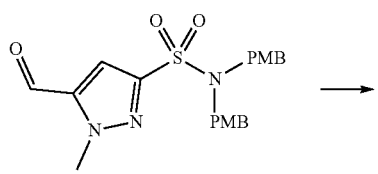

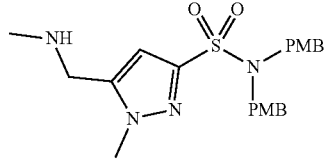

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide and methylamine (2 M in THF) to afford the title compound (251 mg, 44%).

$^1$H NMR (DMSO-d$_6$) δ 7.06-7.01 (m, 4H), 6.83-6.78 (m, 4H), 6.59 (s, 1H), 4.19 (s, 4H), 3.90 (s, 3H), 3.72 (s, 8H), 3.34 (br s, 1H), 2.27 (s, 3H).

LCMS; m/z 445771 (M+H)$^+$ (ES$^+$).

Step C: 1-Methyl-5-((methylamino)methyl)-1-H-pyrazole-3-sulfonamide

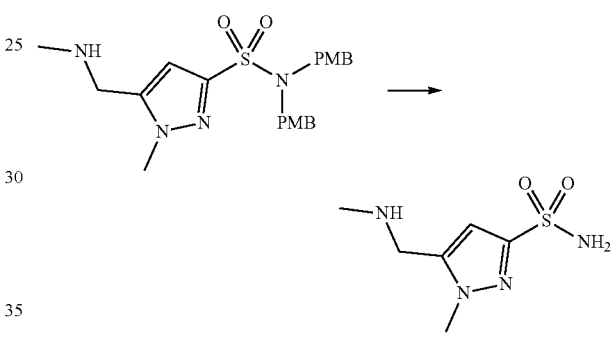

Prepared according to the general procedure of 1-cyclopropyl-5-(1-(dimethylamino) ethyl)-1H-pyrazole-3-sulfonamide (Intermediate P10, Step C) from N,N-bis(4-methoxybenzyl)-1-methyl-5-((methylamino)methyl)-1H-pyrazole-3-sulfonamide to afford the title compound (110 mg, 91%) as a tan solid.

$^1$H NMR (DMSO-d$_6$) δ 7.33 (br s, 2H), 6.47 (s, 1H), 3.84 (s, 3H), 3.69 (s, 2H), 2.27 (s, 3H). N—H not observed.

LCMS; m/z 205.3 (M+H)$^+$ (ES$^+$).

Step D: 2,2,2-Trifluoro-N-methyl-N-((1-methyl-3-sulfamoyl-1H-pyrazol-5-yl)methyl)acetamide

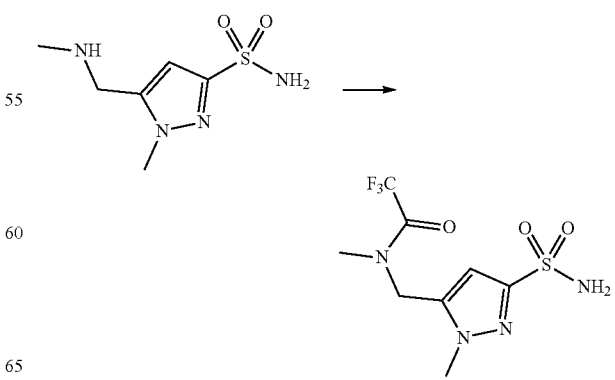

Prepared according to the general procedure of N-((3-(N,N-bis(4-methoxybenzyl)sulfamoyl)-1-isopropyl-1H-pyrazol-5-yl)methyl)-2,2,2-trifluoro-N— methylacetamide (Intermediate P29, Step C) from 1-methyl-5-((methylamino)methyl)-1H-pyrazole-3-sulfonamide to afford the title compound (27 mg, 21%) as a white solid.

$^1$H NMR (DMSO-d$_6$) δ 7.42 (br s, 2H), 6.56 (s, 1H), 4.75 (s, 2H), 3.86 (s, 3H), 3.18-3.07 (m, 3H).

LCMS; m/z 301.2 (M+H)$^+$ (ES$^+$).

Intermediate P39: 5-(1-(Dimethylamino)ethyl)-1-isopropyl-1H-pyrazole-3-sulfonamide

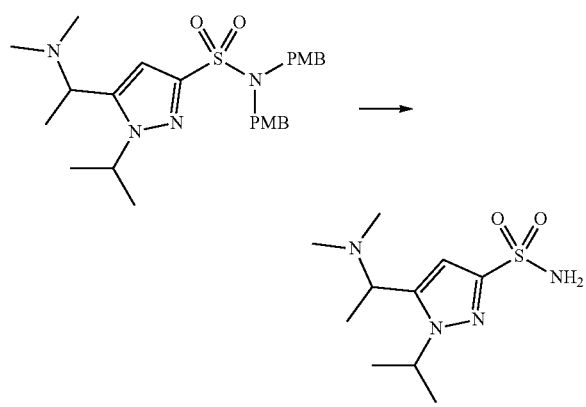

5-(1-(Dimethylamino)ethyl)-1-isopropyl-N,N-bis(4-methoxybenzyl)-1H-pyrazole-3-sulfonamide (Intermediate P8, Step C) (88 mg, 0.176 mmol) was dissolved in TFA (5 mL) and stirred for 16 hours. The reaction mixture was concentrated and the crude product was loaded onto a column of SCX (2 g) in MeOH. The column was washed with MeOH and then the product was eluted with 0.7 M ammonia in MeOH. The resultant mixture was concentrated in vacuo to afford the title compound (38 mg, 76%) as a tan solid.

$^1$H NMR (DMSO-d$_6$) δ 7.34 (s, 2H), 6.45 (s, 1H), 4.86 (sept, J=6.6 Hz, 1H), 3.94 (q, J=6.8 Hz, 1H), 2.14 (s, 6H), 1.38 (app t, J=6.2 Hz, 6H), 1.25 (d, J=6.8 Hz, 3H).

LCMS; m/z 261.5 (M+H)$^+$ (ES$^+$).

Intermediate P40: 5-(3-Hydroxy-1-methylazetidin-3-yl)-1-methyl-1H-pyrazole-3-sulfonamide Step A: Benzyl 3-(3-(N,N-bis(4-methoxybenzyl)sulfamoyl)-1-methyl-1H-pyrazol-5-yl)-3-hydroxyazetidine-1-carboxylate

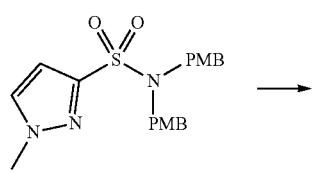

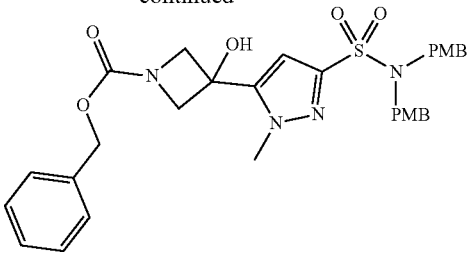

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis(4-methoxybenzyl)-1-methyl-H-pyrazole-3-sulfonamide (Intermediate P9, Step A) and benzyl 3-oxoazetidine-1-carboxylate to afford the title compound (4.20 g, 83%) as a pale yellow oil.

$^1$H NMR (DMSO-d$_6$) δ 7.39-7.35 (m, 4H), 7.07-7.02 (m, 4H), 6.91 (s, 1H), 6.82-6.79 (m, 5H), 5.07 (s, 2H), 4.42 (br d, J=9.4 Hz, 2H), 4.22 (s, 4H), 4.15 (br d, J=9.4 Hz, 2H), 3.85 (s, 3H), 3.71 (s, 1H), 3.70 (s, 6H).

LCMS; m/z 607.0 (M+H)$^+$ (ES$^+$).

Step B: 5-(3-Hydroxyazetidin-3-yl)-N,N-bis(4-methoxybenzyl)-1-methyl-1H-pyrazole-3-sulfonamide

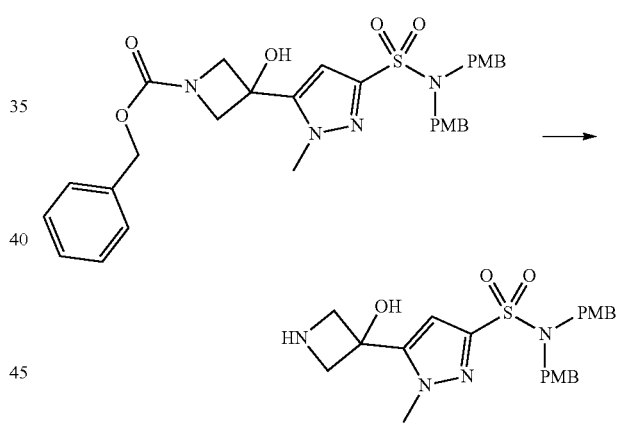

A slurry of Pd/C (J&M Type 39, 50% paste with water) (0.631 g, 2.97 mmol) in EtOH (2 mL) was added to a solution of benzyl 3-(3-(N,N-bis(4-methoxybenzyl)sulfamoyl)-1-methyl-1H-pyrazol-5-yl)-3-hydroxyazetidine-1-carboxylate (2.00 g, 2.97 mmol) in EtOH (18 mL). The vessel was charged with hydrogen (5 bar) and stirred at room temperature for 17 hours. The mixture was filtered through a plug of Celite® (ca. 6 g), rinsed with further portions of EtOH (3×20 mL), and concentrated in vacuo to give a pale yellow oil. The residue was redissolved in MeOH (5 mL) and loaded onto SCX (ca. 5 g), which was washed with MeOH (15 mL) and then eluted with 0.7 M NH$_3$/MeOH (15 mL) and concentrated in vacuo to give a colourless oil, which solidified upon standing to afford the title compound (0.61 g, 41%) as a white solid.

$^1$H NMR (DMSO-d$_6$) δ 7.18-6.97 (m, 4H), 6.84-6.78 (m, 4H), 6.77 (s, 1H), 6.34 (br s, 1H), 4.22 (br s, 4H), 3.84 (s, 3H), 3.75 (br s, 3H), 3.71 (s, 6H), 3.17 (s, 2H).

LCMS; m/z 473.0 (M+H)$^+$ (ES$^+$).

Step C: 5-(3-Hydroxy-1-methylazetidin-3-yl)-N,N-bis(4-methoxybenzyl)-1-methyl-1H-pyrazole-3-sulfonamide

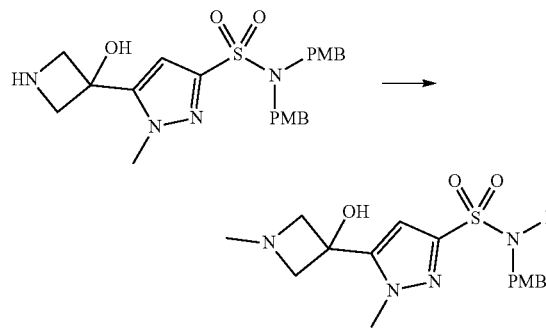

NaCNBH₃ (0.160 g, 2.54 mmol) was added to a mixture of 5-(3-hydroxyazetidin-3-yl)-N,N-bis(4-methoxybenzyl)-1-methyl-1H-pyrazole-3-sulfonamide (0.60 g, 1.270 mmol) and formaldehyde (37% aqueous solution) (0.473 mL, 6.35 mmol) in anhydrous DCM (8 mL) at room temperature. The reaction mixture was stirred for 4 days at room temperature. The mixture was diluted with MeOH (~2 mL) and the flask was rinsed with DCM (~2 mL). The product was loaded onto SCX (ca. 6 g), which was washed with MeOH (18 mL) and eluted with 0.7 M NH₃/MeOH (18 mL) and then concentrated in vacuo to give an opaque viscous oil. The crude product was purified by chromatography on SiO₂ (24 g column, 0-10% (0.7 M ammonia/MeOH)/DCM) to afford the title compound (0.18 g, 25%) as a viscous colourless oil.

LCMS; m/z 487.4 (M+H)⁺ (ES⁺).

Step D: 5-(3-Hydroxy-1-methylazetidin-3-yl)-1-methyl-1H-pyrazole-3-sulfonamide

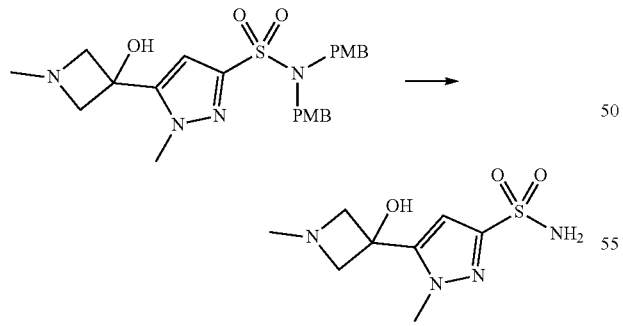

Prepared according to the general procedure of 1-cyclopropyl-5-(1-(dimethylamino) ethyl)-1H-pyrazole-3-sulfonamide (Intermediate P10, Step C) from 5-(3-hydroxy-1-methylazetidin-3-yl)-N,N-bis(4-methoxybenzyl)-1-methyl-1H-pyrazole-3-sulfonamide to afford the title compound (0.09 g, 107%) as a white solid.

LCMS; m/z 247.3 (M+H)⁺ (ES⁺).

Intermediate P41: 5-(1-(Azetidin-1-yl)ethyl)-1-methyl-1H-pyrazole-3-sulfonamide

Step A: 5-(1-(Azetidin-1-yl)ethyl)-N,N-bis(4-methoxybenzyl)-1-methyl-1H-pyrazole-3-sulfonamide

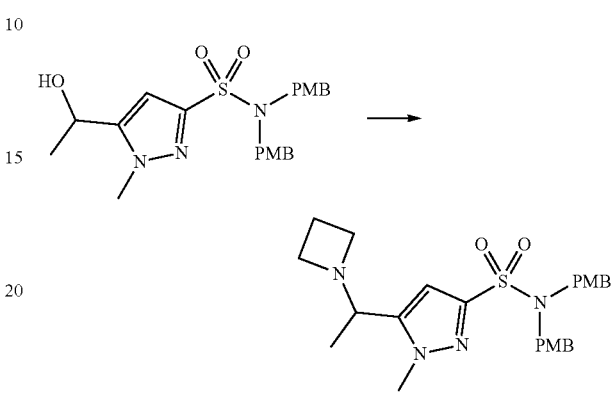

Prepared according to the general procedure of 5-(azetidin-1-ylmethyl)-1-isopropyl N,N-bis(4-methoxybenzyl)-1H-pyrazole-3-sulfonamide (Intermediate P30, Step B) from 5-(1-hydroxyethyl)-N,N-bis(4-methoxybenzyl)-1-methyl-1H-pyrazole-3-sulfonamide (Intermediate P9, Step B) and azetidine to afford the title compound (0.58 g, 55%) as a yellow oil.

LCMS; m/z 485.1 (M+H)⁺ (ES⁺).

Step B: 5-(~(Azetidin-1-yl)ethyl)-1-methyl-1H-pyrazole-3-sulfonamide

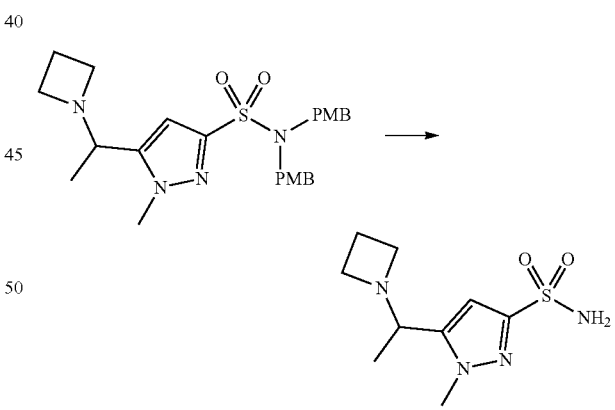

Prepared according to the general procedure of 1-cyclopropyl-5-(~(dimethylamino) ethyl)-1H-pyrazole-3-sulfonamide (Intermediate P10, Step C) from 5-(1-(azetidin-1-yl) ethyl)-N,N-bis(4-methoxybenzyl)-1-methyl-1H-pyrazole-3-sulfonamide to afford the title compound (0.26 g, 89%) as a cream coloured solid.

¹H NMR (DMSO-d₆) δ 7.33 (s, 2H), 6.40 (s, 1H), 3.89 (s, 3H), 3.65-3.56 (m, 1H), 3.18-2.98 (m, 4H), 1.97-1.89 (m, 2H), 1.12 (d, J=6.6 Hz, 3H).

LCMS; m/z 245.1 (M+H)⁺ (ES⁺).

Intermediate P42: 5-(1-(Dimethylamino)ethyl)-1-methyl-1H-pyrazole-3-sulfonamide

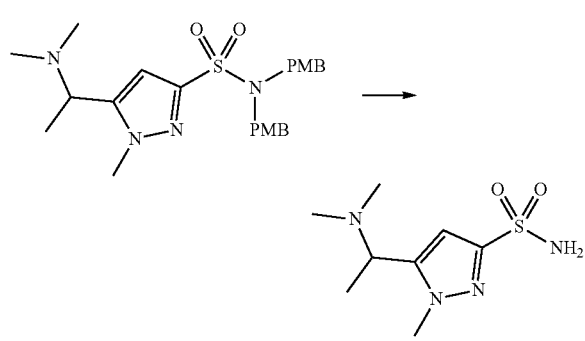

Prepared according to the general procedure of 1-cyclopropyl-5-(1-(dimethylamino) ethyl)-1H-pyrazole-3-sulfonamide (Intermediate P10, Step C) from 5-(1-(dimethylamino)ethyl)-N,N-bis(4-methoxybenzyl)-1-methyl-1H-pyrazole-3-sulfonamide (Intermediate P9, Step C) to afford the title compound (0.17 g, 83%) as a cream coloured solid.

$^1$H NMR (MeOH-d$_4$) δ 6.51 (s, 1H), 3.84 (s, 3H), 3.83 (q, J=6.8 Hz, 1H), 2.16 (s, 6H), 1.27 (d, J=6.8 Hz, 3H). NH$_2$ signal not observed.

LCMS; m/z 233.1 (M+H)$^+$ (ES$^+$).

Intermediate P43: 1-Methyl-5-(pyrrolidin-1-ylmethyl)-1H-pyrazole-3-sulfonamide Step A: N,N-Bis(4-methoxybenzyl)-1-methyl-5-(pyrrolidin-1-ylmethyl)-1H-pyrazole-3-sulfonamide

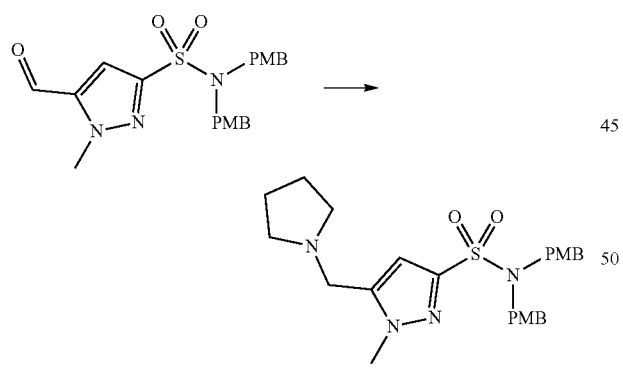

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and pyrrolidine to afford the title compound (211 mg, 46%) as a clear colourless gum.

$^1$H NMR (DMSO-d$_6$) δ 7.10-6.95 (m, 4H), 6.87-6.73 (m, 4H), 6.56 (s, 1H), 4.19 (s, 4H), 3.88 (s, 3H), 3.71 (s, 6H), 3.65 (s, 2H), 2.45-2.35 (m, 4H), 1.77-1.62 (m, 4H).

LCMS; m/z 485.2 (M+H)$^+$ (ES$^+$).

Step B: 1-Methyl-5-(pyrrolidin-1-ylmethyl)-1H-pyrazole-3-sulfonamide

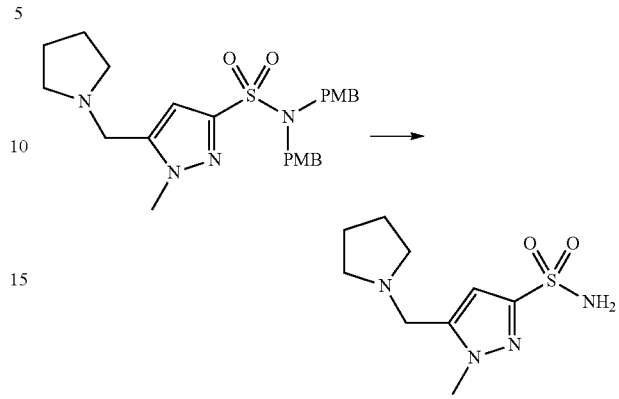

Prepared according to the general procedure of 5-(1-(dimethylamino)ethyl)-1-isopropyl-1H-pyrazole-3-sulfonamide (Intermediate P39) from N,N-bis(4-methoxybenzyl)-1-methyl-5-(pyrrolidin-1-ylmethyl)-1H-pyrazole-3-sulfonamide to afford the title compound (100 mg, 84%) as a waxy orange solid.

$^1$H NMR (DMSO-d$_6$) δ 7.31 (s, 2H), 6.46 (s, 1H), 3.84 (s, 3H), 3.64 (s, 2H), 2.47-2.40 (m, 4H), 1.73-1.64 (m, 4H).

LCMS; m/z 245.1 (M+H)$^+$ (ES$^+$).

Intermediate P44: 5-((3-Fluoroazetidin-1-yl)methyl)-1-methyl-1H-pyrazole-3-sulfonamide Step A: 5-((3-Fluoroazetidin-1-yl)methyl)-N,N-bis(4-methoxybenzyl)-1-methyl-1H-pyrazole-3-sulfonamide

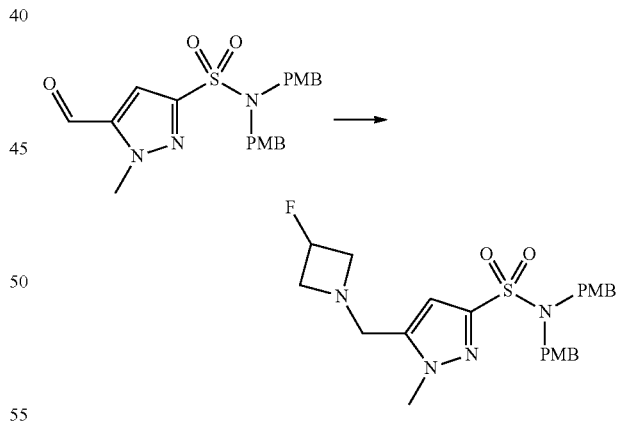

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and 3-fluoroazetidine hydrochloride to afford the title compound (0.34 g, 73%) as a colourless gum.

$^1$H NMR (DMSO-d$_6$) δ 7.10-6.97 (m, 4H), 6.85-6.75 (m, 4H), 6.57 (s, 1H), 5.30-5.04 (m, 1H), 4.18 (s, 4H), 3.85 (s, 3H), 3.71 (s, 8H), 3.65-3.49 (m, 2H), 3.25-3.11 (m, 2H).

LCMS; m/z 489.2 (M+H)$^+$ (ES$^+$).

Step B: 5-((3-Fluoroazetidin-1-yl)methyl)-1-methyl-1H-pyrazole-3-sulfonamide

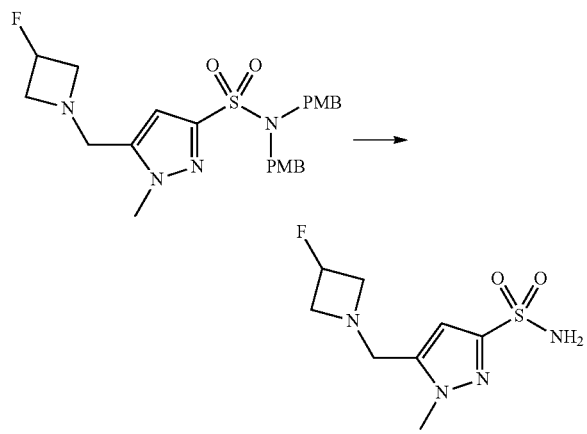

5-((3-Fluoroazetidin-1-yl)methyl)-N,N-bis(4-methoxybenzyl)-1-methyl-1H-pyrazole-3-sulfonamide (0.34 g, 0.696 mmol) was dissolved in TFA (5 mL, 64.9 mmol) and stirred for 4 hours. The solution was diluted with toluene (20 mL) and evaporated in vacuo to afford a colourless gum. The gum was dissolved in THF, absorbed onto SCX and eluted with THF/MeOH/DCM (1:1:3) followed by (1 M $NH_3$/MeOH)/THF/DCM (1:1:3). The solvent was evaporated in vacuo to afford the title compound (0.17 g, 95%) as a white solid.

$^1$H NMR (DMSO-$d_6$) δ 7.35 (s, 2H), 6.49 (s, 1H), 5.32-5.04 (m, 1H), 3.82 (s, 3H), 3.71 (s, 2H), 3.57 (m, 2H), 3.21 (m, 2H).
LCMS; m/z 249.1 (M+H)$^+$ (ES$^+$).

Intermediate P45: 5-((Diethylamino)methyl)-1-methyl-1H-pyrazole-3-sulfonamide

Step A: 5-((Diethylamino)methyl)-N,N-bis(4-methoxybenzyl)-1-methyl-1H-pyrazole-3-sulfonamide

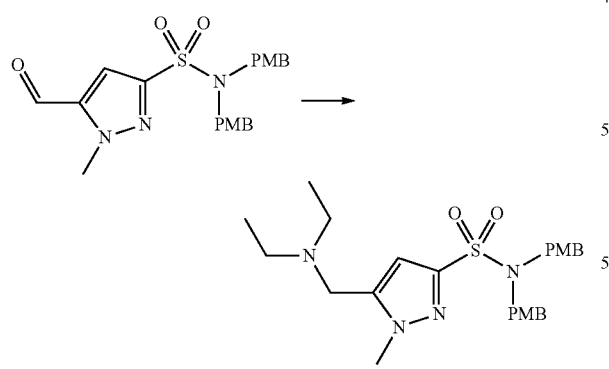

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and diethylamine to afford the title compound (0.35 g, 72%) as a colourless oil.

$^1$H NMR (DMSO-$d_6$) δ 7.08-6.99 (m, 4H), 6.86-6.77 (m, 4H), 6.59 (s, 1H), 4.20 (s, 4H), 3.90 (s, 3H), 3.72 (s, 6H), 3.61 (s, 2H), 2.47 (q, J=7.1 Hz, 4H), 0.98 (t, J=7.1 Hz, 6H).
LCMS; m/z 487.2 (M+H)$^+$ (ES$^+$).

Step B: 5-((Diethylamino)methyl)-1-methyl-1H-pyrazole-3-sulfonamide

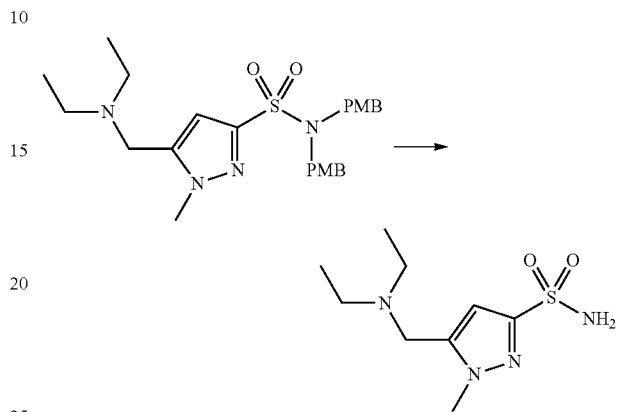

Prepared according to the general procedure of 5-((3-fluoroazetidin-1-yl)methyl)-1-methyl-1H-pyrazole-3-sulfonamide (Intermediate P44, Step B) from 5-((diethylamino)methyl)-N,N-bis(4-methoxybenzyl)-1-methyl-1H-pyrazole-3-sulfonamide to afford the title compound (0.17 g, 94%) as a white solid.

$^1$H NMR (DMSO-$d_6$) δ 7.33 (s, 2H), 6.49 (s, 1H), 3.86 (s, 3H), 3.59 (s, 2H), 2.47 (q, J=7.1 Hz, 4H), 0.98 (t, J=7.1 Hz, 6H).
LCMS; m/z 247.1 (M+H)$^+$ (ES$^+$).

Intermediate P46: 5-((Ethyl(methyl)amino)methyl)-1-methyl-1H-pyrazole-3-sulfonamide

Step A: 5-((Ethyl(methyl)amino)methyl)-N,N-bis(4-methoxybenzyl)-1-methyl-1H-pyrazole-3-sulfonamide

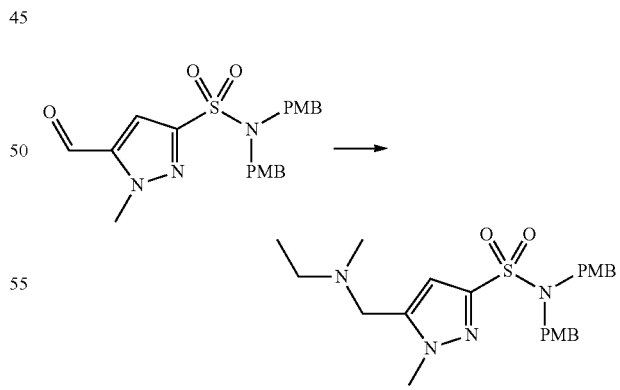

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and N-methylethanamine to afford the title compound (0.42 g, 76%) as a colourless gum.

¹H NMR (DMSO-d₆) δ 7.03 (m, 4H), 6.81 (m, 4H), 6.58 (s, 1H), 4.20 (s, 4H), 3.89 (s, 3H), 3.72 (s, 6H), 3.53 (s, 2H), 2.40 (q, J=7.1 Hz, 2H), 2.11 (s, 3H), 1.03 (t, J=7.1 Hz, 3H). LCMS; m/z 473.2 (M+H)⁺ (ES⁺).

Step B: 5-((Ethyl(methyl)amino)methyl)-1-methyl-1H-pyrazole-3-sulfonamide

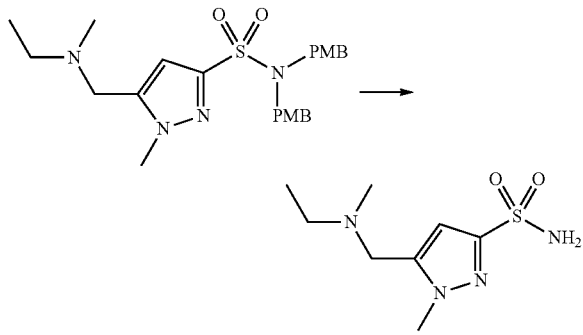

Prepared according to the general procedure of 5-((3-fluoroazetidin-1-yl)methyl)-1-methyl-1H-pyrazole-3-sulfonamide (Intermediate P44, Step B) from 5-((ethyl(methyl)amino)methyl)-N,N-bis(4-methoxybenzyl)-1-methyl-1H-pyrazole-3-sulfonamide to afford the title compound (0.23 g, 103%) as a white solid.

¹H NMR (DMSO-d₆) δ 7.34 (s, 2H), 6.48 (s, 1H), 3.85 (s, 3H), 3.52 (s, 2H), 2.40 (q, J=7.1 Hz, 2H), 2.12 (s, 3H), 1.02 (t, J=7.1 Hz, 3H).
LCMS; m/z 233.1 (M+H)⁺ (ES⁺).

Intermediate P47: 5-((Cyclopropyl(methyl)amino)methyl)-1-methyl-1H-pyrazole-3-sulfonamide Step A: 5-((Cyclopropyl(methyl)amino)methyl)-N,N-bis(4-methoxybenzyl)-1-methyl-1H-pyrazole-3-sulfonamide

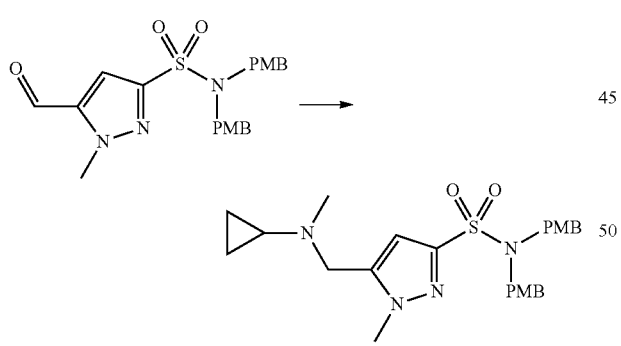

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and N-methylcyclopropanamine hydrochloride to afford the title compound (0.42 g, 72%) as a colourless gum.

¹H NMR (DMSO-d₆) δ 7.10-7.00 (m, 4H), 6.85-6.77 (m, 4H), 6.59 (s, 1H), 4.19 (s, 4H), 3.85 (s, 3H), 3.72 (s, 6H), 3.71 (m, 2H), 2.20 (s, 3H), 1.72 (tt, J=3.6, 6.6 Hz, 1H), 0.44 (m, 2H), 0.31 (m, 2H).
LCMS; m/z 485.2 (M+H)⁺ (ES⁺).

Step B: 5-((Cyclopropyl(methyl)amino)methyl)-1-methyl-1H-pyrazole-3-sulfonamide

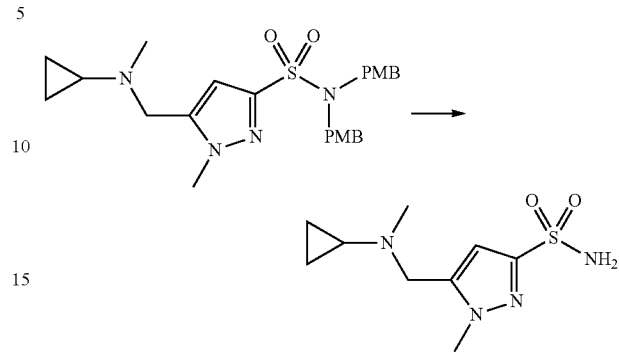

Prepared according to the general procedure of 5-((3-fluoroazetidin-1-yl)methyl)-1-methyl-1H-pyrazole-3-sulfonamide (Intermediate P44, Step B) from 5-((cyclopropyl(methyl)amino)methyl)-N,N-bis(4-methoxybenzyl)-1-methyl-1H-pyrazole-3-sulfonamide to afford the title compound (200 mg, 94%) as a colourless gum.

¹H NMR (DMSO-d₆) δ 7.34 (s, 2H), 6.48 (s, 1H), 3.80 (s, 3H), 3.70 (s, 2H), 2.21 (s, 3H), 1.73 (tt, J=3.6, 6.7 Hz, 1H), 0.45 (m, 2H), 0.31 (m, 2H).
LCMS; m/z 245.1 (M+H)⁺ (ES⁺).

Intermediate P48: 5-(Azetidin-1-ylmethyl)-1-methyl-1H-pyrazole-3-sulfonamide

Step A: 5-(Azetidin-1-ylmethyl)-N,N-bis(4-methoxybenzyl)-1-methyl-1H-pyrazole-3-sulfonamide

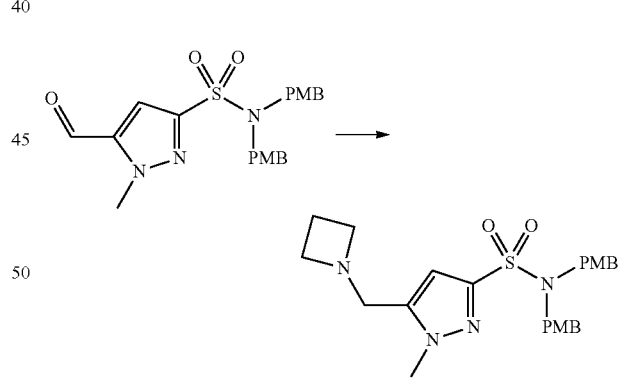

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and azetidine hydrochloride to afford the title compound (0.46 g, 84%) as a colourless gum.

¹H NMR (DMSO-d₆) δ 7.08-6.98 (m, 4H), 6.85-6.77 (m, 4H), 6.54 (s, 1H), 4.19 (s, 4H), 3.86 (s, 3H), 3.72 (s, 6H), 3.59 (s, 2H), 3.15 (t, J=7.0 Hz, 4H), 1.99 (p, J=7.0 Hz, 2H).
LCMS; m/z 471.2 (M+H)⁺ (ES⁺).

Step B: 5-(Azetidin-1-ylmethyl)-1-methyl-1H-pyrazole-3-sulfonamide

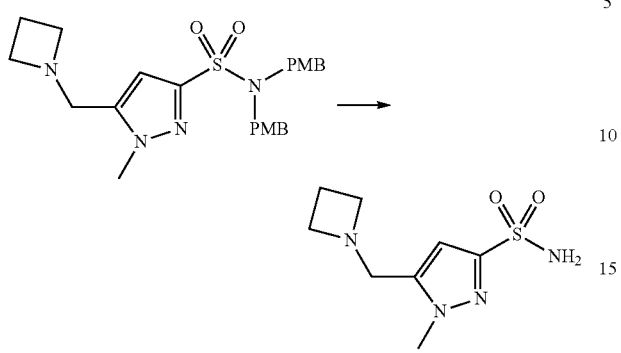

Prepared according to the general procedure of 5-((3-fluoroazetidin-1-yl)methyl)-1-methyl-1H-pyrazole-3-sulfonamide (Intermediate P44, Step B) from 5-(azetidin-1-ylmethyl)-N,N-bis(4-methoxybenzyl)-1-methyl-1H-pyrazole-3-sulfonamide to afford the title compound (220 mg, 98%) as a white solid.

$^1$H NMR (DMSO-$d_6$) δ 7.33 (s, 2H), 6.44 (s, 1H), 3.82 (s, 3H), 3.58 (s, 2H), 3.15 (t, J=7.0 Hz, 4H), 1.99 (p, J=7.0 Hz, 2H).

LCMS; m/z 231.0 (M+H)$^+$ (ES$^+$).

Intermediate P49: 5-((Isopropyl(methyl)amino)methyl)-1-methyl-1H-pyrazole-3-sulfonamide Step A: 5-((Isopropyl(methyl)amino)methyl)-N,N-bis(4-methoxybenzyl)-1-methyl-1H-pyrazole-3-sulfonamide

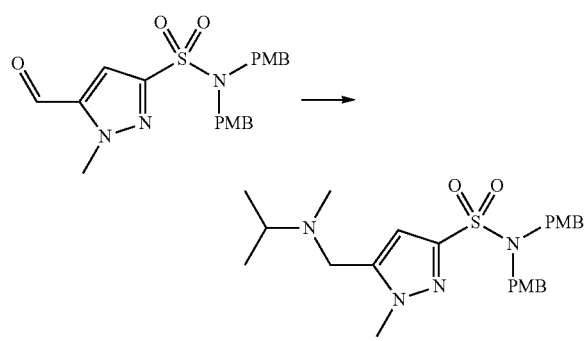

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and N-methylpropan-2-amine to afford the title compound (0.46 g, 88%) as a colourless gum.

$^1$H NMR (DMSO-$d_6$) δ 7.03 (m, 4H), 6.81 (m, 4H), 6.57 (s, 1H), 4.20 (s, 4H), 3.89 (s, 3H), 3.72 (s, 6H), 3.57 (s, 2H), 2.84 (sept, J=6.6 Hz, 1H), 2.05 (s, 3H), 1.02 (d, J=6.5 Hz, 6H).

LCMS; m/z 487.2 (M+H)$^+$ (ES$^+$).

Step B: 5-((Isopropyl(methyl)amino)methyl)-1-methyl-1H-pyrazole-3-sulfonamide

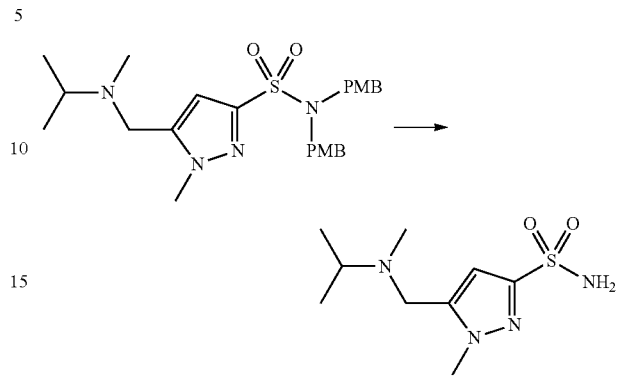

Prepared according to the general procedure of 5-((3-fluoroazetidin-1-yl)methyl)-1-methyl-1H-pyrazole-3-sulfonamide (Intermediate P44, Step B) from 5-((isopropyl(methyl)amino)methyl)-N,N-bis(4-methoxybenzyl)-1-methyl-1H-pyrazole-3-sulfonamide to afford the title compound (0.24 g, 104%) as a white solid.

$^1$H NMR (DMSO-$d_6$) δ 7.33 (s, 2H), 6.47 (s, 1H), 3.85 (s, 3H), 3.56 (s, 2H), 2.83 (sept, J=6.6 Hz, 1H), 2.07 (s, 3H), 1.01 (d, J=6.6 Hz, 6H).

LCMS; m/z 247.1 (M+H)$^+$ (ES$^+$).

Intermediate P50: N,N,1-Trimethyl-3-sulfamoyl-1H-pyrazole-5-carboxamide

Step A: 1-Methyl-3-sulfamoyl-1H-pyrazole-5-carboxylic acid, Sodium Salt

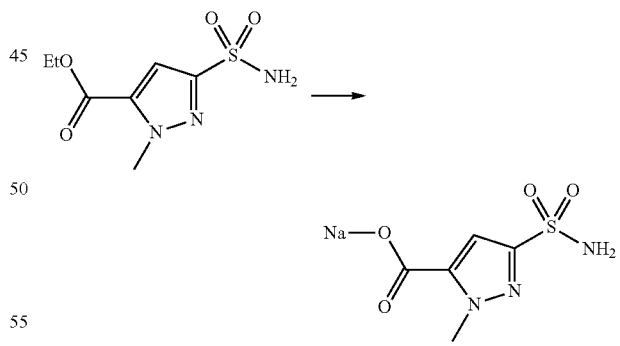

To a suspension of ethyl 1-methyl-3-sulfamoyl-1H-pyrazole-5-carboxylate (3 g, 12.86 mmol) in ethanol (60 mL) was added a solution of sodium hydroxide (2.0 M, 13.5 mL) and the mixture was stirred at room temperature for 2 hours. The resulting precipitate was filtered off, washed with ethanol and dried to afford the title compound (2.92 g, 99%) as a white solid.

$^1$H NMR (D$_2$O) δ 6.79 (s, 1H), 4.01 (s, 3H). NH$_2$ not observed.

Step B: N,N,1-Trimethyl-3-sulfamoyl-1H-pyrazole-5-carboxamide

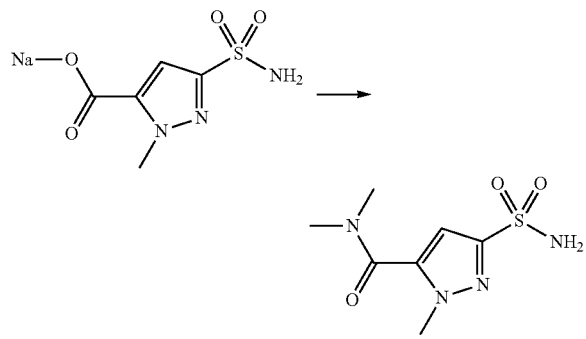

To a mixture of 1-methyl-3-sulfamoyl-1H-pyrazole-5-carboxylic acid, sodium salt (2.38 g, 10.48 mmol) was added T3P (50% in EtOAc, 12.47 mL, 20.95 mmol) and DIPEA (Hunig's Base, 3.66 mL, 20.95 mmol) in THF (50 mL). A solution of 2.0 M dimethylamine in THF (15.71 mL, 31.4 mmol) was added and the reaction stirred for 20 hours, before being quenched with saturated aqueous ammonium chloride (10 mL) and extracted with EtOAc (3×20 mL). The combined organic extracts were dried (magnesium sulfate), filtered and evaporated in vacuo to afford a yellow gum. The crude product was triturated in DCM (20 mL) and filtered to obtain the title compound (900 mg) as a white solid. The mother layers were evaporated, dissolved in DCM/MeOH and purified by chromatography (Companion apparatus, 40 g column, 0-10% MeOH/DCM with product eluting at ~5% MeOH) to afford a further batch of the title compound (457 mg) as a white solid. The solids were combined to afford the title compound (1.36 g, 55%).

$^1$H NMR (DMSO-$d_6$) δ 7.50 (s, 2H), 6.82 (s, 1H), 3.90 (s, 3H), 3.03 (s, 3H) and 3.01 (s, 3H).

LCMS; m/z 233.0 (M+H)$^+$ (ES$^+$).

Intermediate P51: 3-(N-((1,2,3,5,6,7-Hexahydro-s-indacen-4-yl)carbamoyl)sulfamoyl)-1-methyl-1H-pyrazole-5-carboxylic Acid

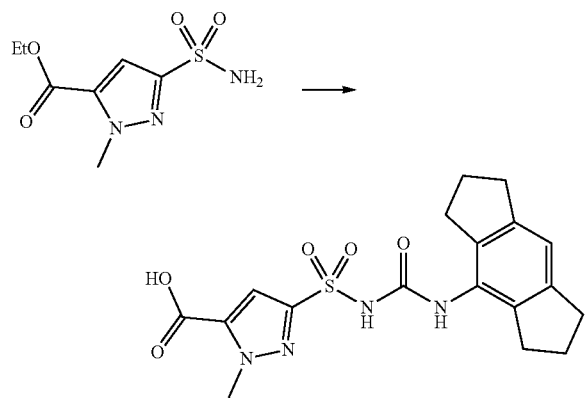

Triphosgene (170 mg, 0.573 mmol) was added to a mixture of 1,2,3,5,6,7-hexahydro-s-indacen-4-amine (165 mg, 0.952 mmol) and triethylamine (0.36 mL, 2.58 mmol) in THF (8 mL) and stirred for 15 hours. The reaction mixture was evaporated in vacuo and azeotroped with toluene (3×1 mL). THF (8 mL) was added and the reaction mixture was filtered. The filtrate was added to a mixture of ethyl 1-methyl-3-sulfamoyl-1H-pyrazole-5-carboxylate (200 mg, 0.857 mmol) and sodium hydride (86 mg, 2.150 mmol) in THF (8 mL) and stirred for 20 hours. The reaction was quenched with aqueous Na$_2$CO$_3$ (3.5 mL, 1.295 mmol), and evaporated in vacuo to remove the THF. The residual aqueous was washed with MTBE (2×5 mL). The solid that precipitated from the aqueous was filtered off and dried to afford ethyl 3-(N-((1,2,3,5,6,7-hexahydro-s-indacen-4-yl)carbamoyl)sulfamoyl)-1-methyl-1H-pyrazole-5-carboxylate, sodium (100 mg) as a solid. The filtrate was purified by chromatography on RP Flash C18 (12 g column, 5-50% MeCN/10 mM ammonium bicarbonate) to afford the title compound (180 mg) as a white solid. The solids were combined and dissolved in MeOH (3 mL). Aq. NaOH (0.25 mL, 0.500 mmol) was added and the reaction mixture was stirred for 20 hours. The MeOH was evaporated in vacuo. The remaining aqueous was adjusted to pH 8 with NaH$_2$PO$_4$ and purified by chromatography on RP Flash C18 (12 g column, 5-50% MeCN/10 mM ammonium bicarbonate) to afford the title compound (140 mg, 39%) as a white solid.

$^1$H NMR (DMSO-$d_6$) δ 7.65 (s, 2H), 6.31 (s, 1H), 6.15 (s, 1H), 3.41 (s, 3H), 2.05 (t, J=7.4 Hz, 4H), 1.90 (t, J=7.3 Hz, 4H), 1.24 (quin, J=7.4 Hz, 4H). One exchangeable proton not observed.

LCMS; m/z 405.0 (M+H)$^+$ (ES$^+$).

Intermediate P52: 1-Methyl-5-(pyrrolidine-1-carbonyl)-1H-pyrazole-3-sulfonamide

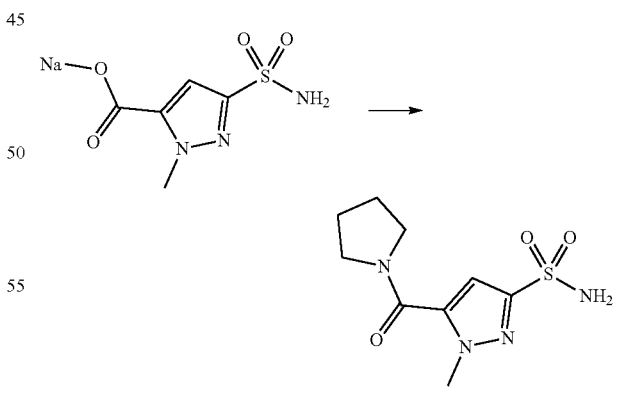

Prepared according to the general procedure for N,N,1-trimethyl-3-sulfamoyl-H-pyrazole-5-carboxamide (Intermediate P50, Step B) from 1-methyl-3-sulfamoyl-1H-pyrazole-5-carboxylic acid, sodium salt (Intermediate P50, Step A) and pyrrolidine to afford the title compound (204 mg, 54%) as a cream solid.

LCMS; m/z 259.3 (M+H)$^+$ (ES$^+$).

Intermediate P53: 3-(N-((1,2,3,5,6,7-Hexahydro-s-indacen-4-yl)carbamoyl) sulfamoyl)-1-methyl-1H-pyrazole-5-carboxylic Acid, disodium Salt Step A: Ethyl 3-(N-((1,2,3,5,6,7-hexahydro-s-indacen-4-yl)carbamoyl)sulfamoyl)-1-methyl-1H-pyrazole-5-carboxylate, sodium salt

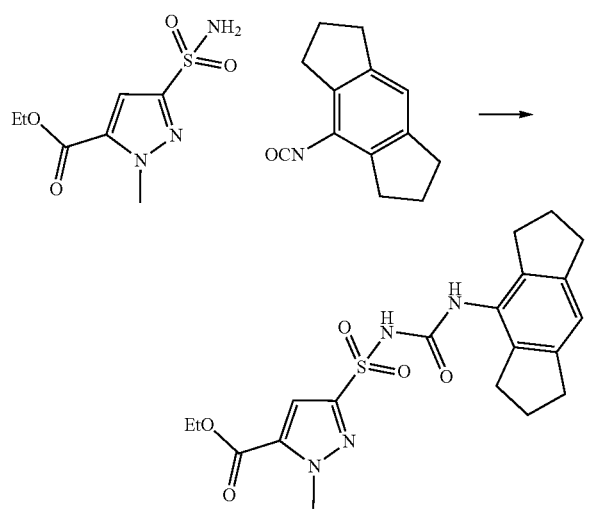

2 M Sodium tert-butoxide in THF (1.005 mL, 2.009 mmol) was added to a solution of ethyl 1-methyl-3-sulfamoyl-1H-pyrazole-5-carboxylate (0.5 g, 1·914 mmol) in THF (15 mL) and stirred at room temperature for 1 hour to give a white suspension. Then 4-isocyanato-1,2,3,5,6,7-hexahydro-s-indacene (Intermediate A1) (0.419 g, 2.105 mmol) in THF (5 mL) was added and stirred at room temperature overnight. The resultant colourless precipitate was collected by filtration, washing with THF (4 mL), and dried in vacuo to afford the title compound (930 mg, 91%) as a colourless solid.

$^1$H NMR (DMSO-$d_6$) δ 7.51 (s, 1H), 6.96 (s, 1H), 6.77 (s, 1H), 4.28 (q, J=7.1 Hz, 2H), 4.05 (s, 3H), 2.74 (t, J=7.4 Hz, 4H), 2.66 (t, J=7.3 Hz, 4H), 1.90 (p, J=7.4 Hz, 4H), 1.30 (t, J=7.1 Hz, 3H).

LCMS; m/z 433.4 (M+H)$^+$ (ES$^+$).

Step B: 3-(N-((1,2,3,5,6,7-Hexahydro-s-indacen-4-yl)carbamoyl) sulfamoyl)-1-methyl-1H-pyrazole-5-carboxylic Acid, disodium Salt

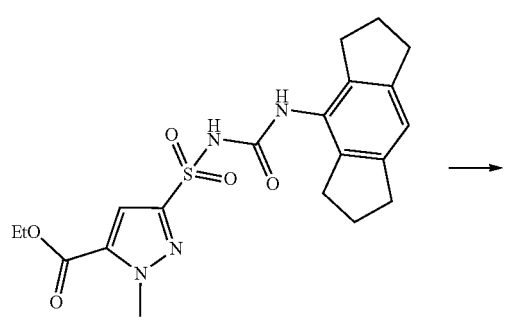

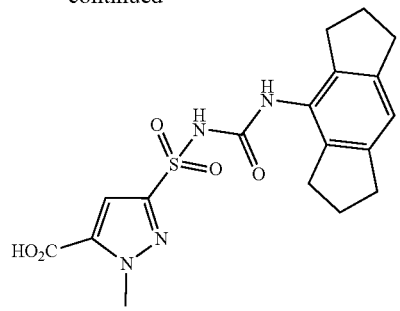

Ethyl 3-(N-((1,2,3,5,6,7-hexahydro-s-indacen-4-yl)carbamoyl)sulfamoyl)-1-methyl-1H-pyrazole-5-carboxylate, sodium salt (3.15 g, 6.24 mmol) was dissolved in MeOH (20 mL), 2 M aqueous NaOH (3.12 mL, 6.24 mmol) was added and stirred for 6 hours. The reaction mixture was concentrated under reduced pressure to afford the title compound (2.80 g, 99%) as a colourless solid.

$^1$H NMR (DMSO-$d_6$) δ 7.57 (s, 1H), 6.76 (s, 1H), 6.44 (s, 1H), 4.02 (s, 3H), 2.74 (t, J=7.4 Hz, 4H), 2.65 (t, J=7.4 Hz, 4H), 1.89 (p, J=7.4 Hz, 4H).

LCMS; m/z 405.4 (M+H)$^+$ (ES$^+$).

Intermediate P54: 3-(N-((2,6-Diisopropylphenyl)carbamoyl)sulfamoyl)-1-methyl-1H-pyrazole-1-carboxylic Acid, disodium Salt Step A: Ethyl 3-(N-((2,6-diisopropylphenyl)carbamoyl)sulfamoyl)-1-methyl-1H-pyrazole-5-carboxylate, Sodium Salt

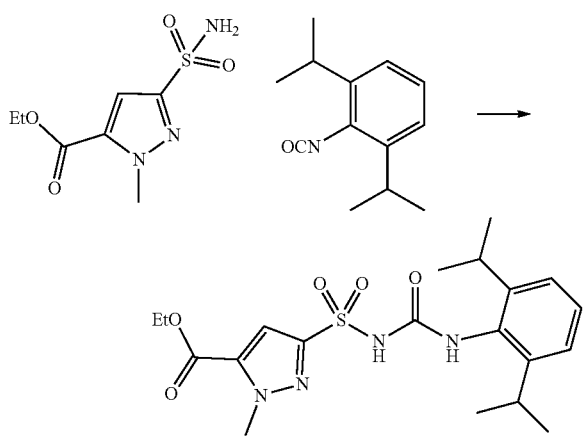

Ethyl 1-methyl-3-sulfamoyl-1H-pyrazole-5-carboxylate (2 g, 7.65 mmol) was dissolved in THF (80 mL, 986 mmol). Sodium hydride (0.367 g, 9.18 mmol) was added and stirred at room temperature for 30 minutes to give a white suspension. Then 2-isocyanato-1,3-diisopropylbenzene (Intermediate A19) (1.712 g, 8.42 mmol) in THF (20 mL) was added and stirred at room temperature overnight. The resultant colourless precipitate was collected by filtration, washing with THF (2×20 mL), and dried in vacuo to afford the title compound (2.16 g, 60%) as a colourless solid.

$^1$H NMR (DMSO-$d_6$) δ 7.35 (s, 1H), 7.15-7.05 (m, 1H), 7.05-6.95 (m, 2H), 6.93 (s, 1H), 4.28 (q, J=7.1 Hz, 2H), 4.05 (s, 3H), 3.20-3.02 (m, 2H), 1.28 (t, J=7.1 Hz, 3H), 1.03 (d, J=6.9 Hz, 12H).

LCMS; m/z 437.4 (M+H)$^+$ (ES$^+$).

Step B: 3-(N-((2,6-Diisopropylphenyl)carbamoyl)sulfamoyl)-1-methyl-1H-pyrazole-5-carboxylic Acid, disodium Salt

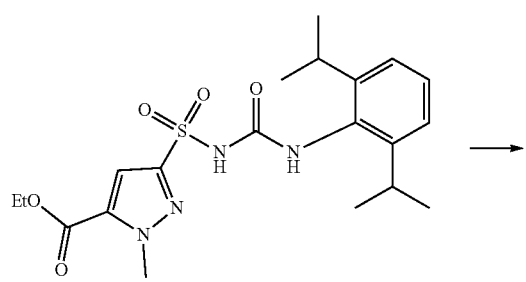

↓

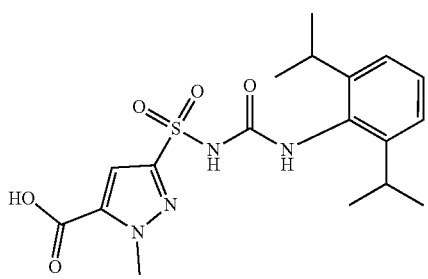

Prepared according to the general procedure for 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53, Step B) from ethyl 3-(N-((2,6-diisopropylphenyl)carbamoyl) sulfamoyl)-1-methyl-1H-pyrazole-5-carboxylate, sodium salt to afford the title compound (2.0 g, 99%) as a colourless solid.

$^1$H NMR (DMSO-$d_6$) δ 7.44 (s, 1H), 7.13-7.05 (m, 1H), 7.05-6.94 (m, 2H), 6.42 (s, 1H), 4.00 (s, 3H), 3.16-3.03 (m, 2H), 1.01 (d, J=6.8 Hz, 12H).

LCMS; m/z 409.4 (M+H)$^+$ (ES$^+$).

Intermediate P55: 3-(N-((4-Fluoro-2,6-diisopropylphenyl)carbamoyl) sulfamoyl)-1-methyl-1H-pyrazole-5-carboxylic Acid, disodium Salt Step A: Ethyl 3-(N-((4-fluoro-2,6-diisopropylphenyl)carbamoyl)sulfamoyl)-1-methyl-1H-pyrazole-5-carboxylate, Sodium Salt

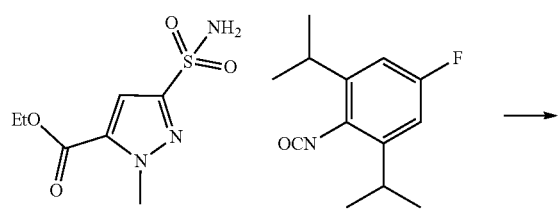

↓

-continued

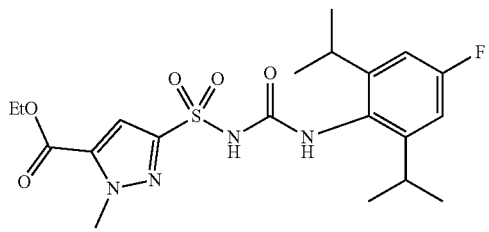

Prepared according to the general procedure for ethyl 3-(N-((1,2,3,5,6,7-hexahydro-s-indacen-4-yl)carbamoyl)sulfamoyl)-1-methyl-1H-pyrazole-5-carboxylate, sodium salt (Intermediate P53, Step A) from ethyl 1-methyl-3-sulfamoyl-H-pyrazole-5-carboxylate and 5-fluoro-2-isocyanato-1,3-diisopropylbenzene (Intermediate A2) to afford the title compound (1.7 g, 92%) as a colourless solid.

$^1$H NMR (DMSO-$d_6$) δ 7.32 (s, 1H), 6.93 (s, 1H), 6.79 (d, J=10.1 Hz, 2H), 4.29 (q, J=7.1 Hz, 2H), 4.05 (s, 3H), 3.21-2.94 (m, 2H), 1.29 (t, J=7.1 Hz, 3H), 1.03 (d, J=6.8 Hz, 12H).

LCMS; m/z 455.4 (M+H)$^+$ (ES$^+$).

Step B: 3-(N-((4-Fluoro-2,6-diisopropylphenyl)carbamoyl)sulfamoyl)-1-methyl-1H-pyrazole-5-carboxylic Acid, disodium Salt

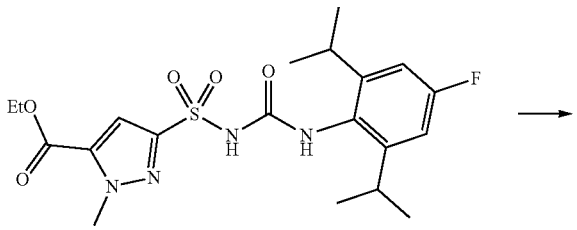

↓

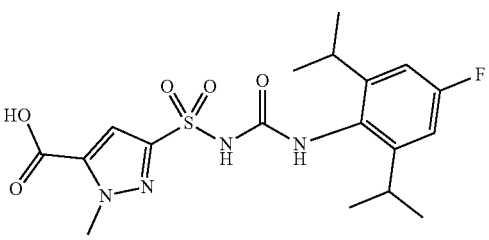

Prepared according to the general procedure for 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53, Step B) from ethyl 3-(N-((4-fluoro-2,6-diisopropylphenyl)carbamoyl) sulfamoyl)-1-methyl-1H-pyrazole-5-carboxylate, sodium salt to afford the title compound (1.65 g, 98%) as a colourless solid.

$^1$H NMR (DMSO-$d_6$) δ 7.41 (s, 1H), 6.77 (d, J=10.1 Hz, 2H), 6.45 (s, 1H), 4.01 (s, 3H), 3.15-3.02 (m, 2H), 1.10-0.93 (m, 12H).

LCMS; m/z 427.4 (M+H)$^+$ (ES$^+$).

Intermediate P56: 3-(N-((4-Chloro-2,6-diisopropylphenyl)carbamoyl) sulfamoyl)-1-methyl-1H-pyrazole-5-carboxylic Acid, Disodium Salt Step A: Ethyl 3-(N-((4-chloro-2,6-diisopropylphenyl)carbamoyl) sulfamoyl)-1-methyl-1H-pyrazole-5-carboxylate, Sodium Salt

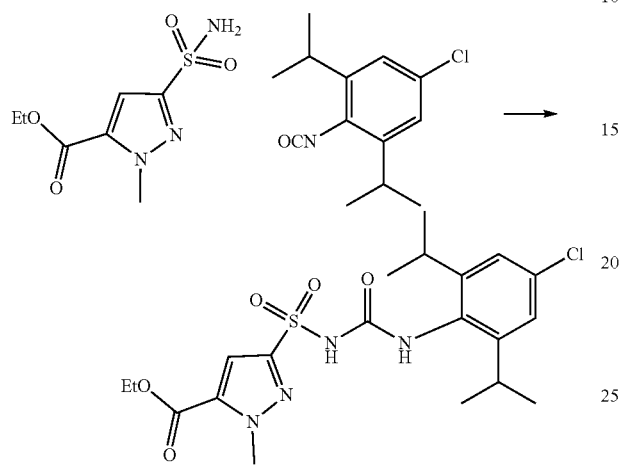

Prepared according to the general procedure for ethyl 3-(N-((1,2,3,5,6,7-hexahydro-s-indacen-4-yl)carbamoyl) sulfamoyl)-1-methyl-1H-pyrazole-5-carboxylate, sodium salt (Intermediate P53, Step A) from ethyl 1-methyl-3-sulfamoyl-H-pyrazole-5-carboxylate and 5-chloro-2-isocyanato-1,3-diisopropylbenzene (Intermediate A22) to afford the title compound (1.32 g, 92%) as a colourless solid.

$^1$H NMR (DMSO-d$_6$); δ 7.41 (s, 1H), 7.01 (s, 2H), 6.92 (s, 1H), 4.29 (q, J=7.1 Hz, 2H), 4.05 (s, 3H), 3.13 (br s, 2H), 1.29 (t, J=7.1 Hz, 3H), 1.04 (d, J=6.8 Hz, 12H).

LCMS; m/z 471.4 (M+H)$^+$ (ES$^+$).

Step B: 3-(N-((4-Chloro-2,6-diisopropylphenyl)carbamoyl)sulfamoyl)-1-methyl-1H-pyrazole-5-carboxylic Acid, Disodium Salt

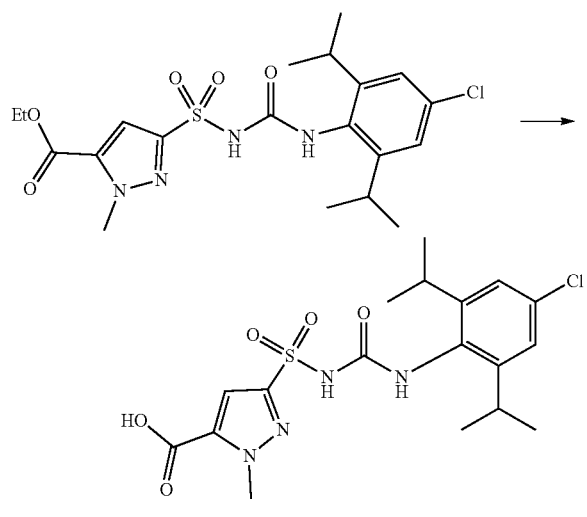

Prepared according to the general procedure for 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53, Step B) from ethyl 3-(N-((4-chloro-2,6-diisopropylphenyl)carbamoyl) sulfamoyl)-1-methyl-1H-pyrazole-5-carboxylate, sodium salt (Intermediate P56, Step A) to afford the title compound (1.0 g, 77%) as a colourless solid.

$^1$H NMR (DMSO-d$_6$) δ 7.49 (s, 1H), 7.00 (s, 2H), 6.42 (s, 1H), 4.01 (s, 3H), 3.09 (br s, 2H), 1.02 (d, J=6.8 Hz, 12H).

LCMS; m/z 443.4 (M+H)$^+$ (ES$^+$).

Intermediate P57: 5-(Azetidine-1-carbonyl)-1-isopropyl-1H-pyrazole-3-sulfonamide Step A: Ethyl 3-(N,N-bis(4-methoxybenzyl)sulfamoyl)-1-isopropyl-1H-pyrazole-5-carboxylate

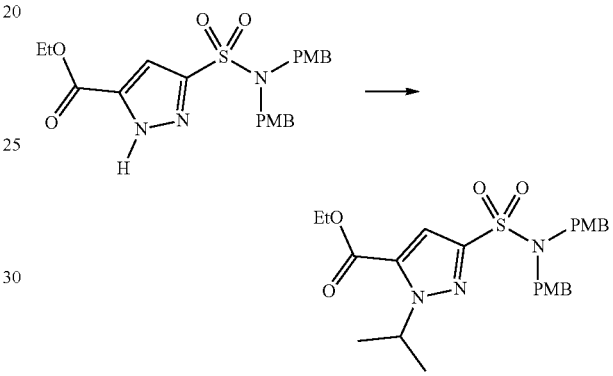

Ethyl 3-(N,N-bis(4-methoxybenzyl)sulfamoyl)-1H-pyrazole-5-carboxylate (Intermediate P35, Step A) (1 g, 2.176 mmol), K$_2$CO$_3$ (0.391 g, 2.83 mmol) and 2-iodopropane (0.26 mL, 2.61 mmol) were stirred in DMF (10 mL) under a nitrogen atmosphere for 18 hours. The reaction was poured onto brine (100 mL) and EtOAc (50 mL). The aqueous layer was discarded and the organic layer washed with brine (2×100 mL), dried (MgSO$_4$), filtered and concentrated to dryness to give a yellow oil which was purified by chromatography on silica gel (80 g column, 0-40% EtOAc/isohexane) to afford the title compound (1.0 g, 85%) as a clear colourless oil which solidified on standing.

$^1$H NMR (DMSO-d$_6$) δ 7.22-6.93 (m, 5H), 6.93-6.68 (m, 4H), 5.45 (sept, J=6.6 Hz, 1H), 4.32 (q, J=7.1 Hz, 2H), 4.25 (s, 4H), 3.71 (s, 6H), 1.42 (d, J=6.6 Hz, 6H), 1.32 (t, J=7.1 Hz, 3H).

LCMS; m/z 524.2 (M+Na)+(ES$^+$).

Step B: 3-(N,N-Bis(4-methoxybenzyl)sulfamoyl)-1-isopropyl-1H-pyrazole-5-carboxylic Acid, Sodium Salt

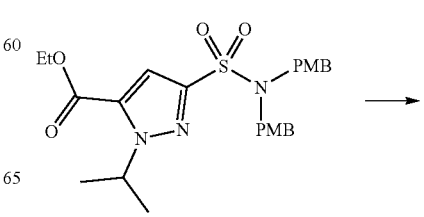

-continued

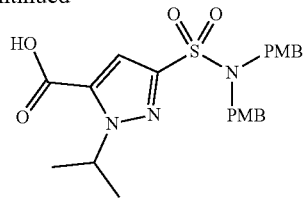

Ethyl 3-(N,N-bis(4-methoxybenzyl)sulfamoyl)-1-isopropyl-1H-pyrazole-5-carboxylate (1 g, 1.994 mmol) was suspended in EtOH (10 mL) and 2 M aqueous sodium hydroxide (1.994 ml, 3.99 mmol). The reaction was left to stir at room temperature for 17 hours, then evaporated to dryness under reduced pressure to afford the title compound as a colourless foam which was used without further purification.

LCMS; m/z 496.1 (M+Na)+(ES$^+$).

Step C: 5-(Azetidine-1-carbonyl)-1-isopropyl-N,N-bis(4-methoxybenzyl)-1H-pyrazole-3-sulfonamide

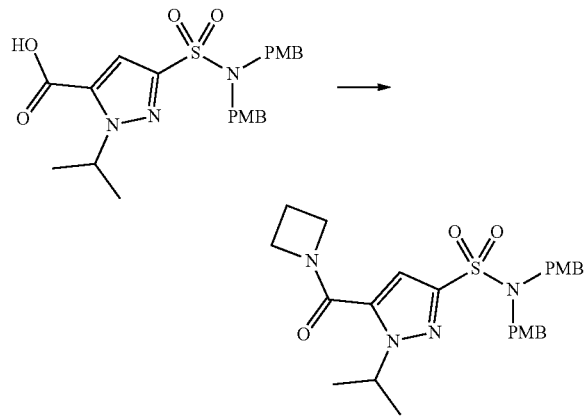

T3P (50 wt % in EtOAc) (2.28 mL, 3.83 mmol) was added to a mixture of sodium 3-(N,N-bis(4-methoxybenzyl)sulfamoyl)-1-isopropyl-1H-pyrazole-5-carboxylate (0.99 g, 1.913 mmol) and azetidine hydrochloride (0.215 g, 2.296 mmol) in THF (10 mL). DIPEA (0.67 mL, 3.84 mmol) was added and the reaction stirred at room temperature for 5 hours. Additional T3P (50 wt % in EtOAc) (2.28 mL, 3.83 mmol), DIPEA (0.67 mL, 3.84 mmol) and azetidine hydrochloride (0.215 g, 2.296 mmol) were added and the reaction was stirred at room temperature for a further 2 days. The reaction mixture was diluted with EtOAc (20 mL) and washed with 2 M aqueous NaOH (2×20 mL) followed by 1 M aqueous HCl (20 mL). The organic layer was dried (MgSO$_4$), filtered and concentrated to dryness to give crude product still containing starting acid. The mixture was subjected to the reaction procedure above, stirred for 2 days, then diluted with EtOAc (20 mL) and washed with water (2×30 mL) followed by 1 M aqueous HCl (20 mL). The organic layer was dried (MgSO$_4$), filtered and concentrated to dryness to afford the title compound (786 mg, 75%) as an orange oil which was used without further purification in the next step.

$^1$H NMR (CDCl$_3$) δ 7.17-6.99 (m, 4H), 6.85-6.73 (m, 4H), 6.70 (s, 1H), 5.46 (sept, J=6.6 Hz, 1H), 4.37-4.24 (m, 6H), 4.20 (t, J=7.8 Hz, 2H), 3.78 (s, 6H), 2.50-2.29 (m, 2H), 1.47 (d, J=6.6 Hz, 6H).

LCMS; m/z 513.2 (M+H)$^+$ (ES$^+$).

Step D: 5-(Azetidine-1-carbonyl)-1-isopropyl-1H-pyrazole-3-sulfonamide

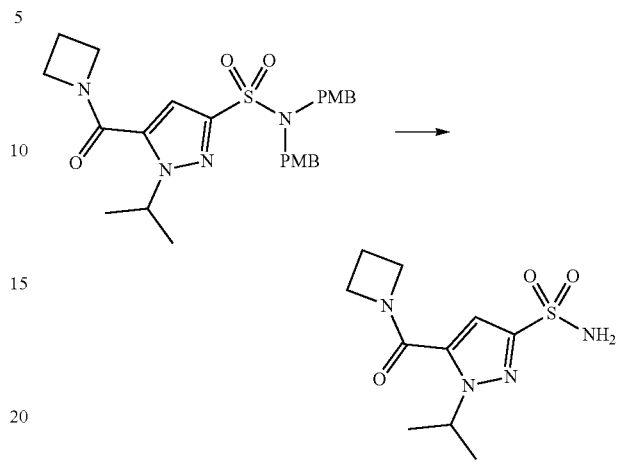

5-(Azetidine-1-carbonyl)-1-isopropyl-N,N-bis(4-methoxybenzyl)-1H-pyrazole-3-sulfonamide (0.79 g, 1.54 mmol) was dissolved in DCM:TFA (5:1.12 mL) and stirred for 18 hours at room temperature. The solvent was removed under reduced pressure and the purple residue obtained was purified by chromatography on silica gel (24 g column, 0-5% MeOH/DCM) to afford the title compound (201 mg, 47%) as a colourless foam.

$^1$H NMR (DMSO-d$_6$) δ 7.51 (s, 2H), 6.85 (s, 1H), 5.28 (sept, J=6.6 Hz, 1H), 4.30 (t, J=7.7 Hz, 2H), 4.04 (t, J=7.8 Hz, 2H), 2.27 (p, J=7.8 Hz, 2H), 1.40 (d, J=6.6 Hz, 6H).

LCMS; m/z 273.1 (M+H)$^+$ (ES$^+$).

Intermediate P58: (4-(Dimethylamino)pyridin-1-ium-1-carbonyl)((5-(dimethylcarbamoyl)-1-methyl-1H-pyrazol-3-yl)sulfonyl)amide

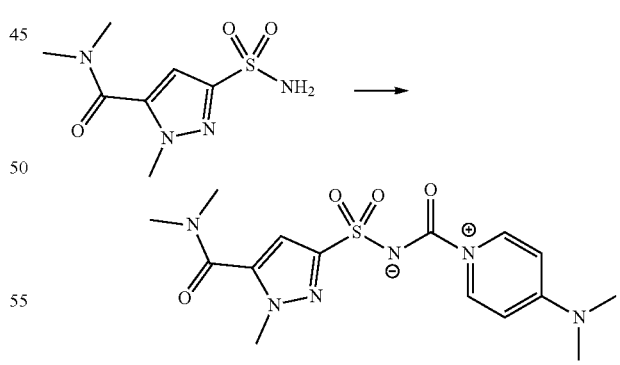

A solution of N,N,1-trimethyl-3-sulfamoyl-1H-pyrazole-5-carboxamide (Intermediate P50) (459 mg, 1.976 mmol) in MeCN (2.3 mL) was treated with N,N-dimethylpyridin-4-amine (483 mg, 3.95 mmol) and the reaction mixture was stirred at room temperature until the sulfonamide had dissolved. Diphenyl carbonate (466 mg, 2.174 mmol) was added and the reaction mixture was left for 16 hours at room temperature. The resulting precipitate was separated by filtration, washed with MeCN and dried to afford the title compound (578 mg, 77%) which was used in the next step without further purification.

$^1$H NMR (DMSO-d$_6$) δ 8.77-8.73 (m, 2H), 7.02-6.98 (m, 2H), 6.83 (s, 1H), 3.85 (s, 3H), 3.26 (s, 6H), 3.05 (s, 3H), 3.00 (s, 3H).

Intermediate P59:5-(1-(Dimethylamino)-2,2,2-trifluoroethyl)-1-methyl-1H-pyrazole-3-sulfonamide Step A: N,N-Bis(4-methoxybenzyl)-1-methyl-5-(2,2,2-trifluoroacetyl)-1H-pyrazole-3-sulfonamide

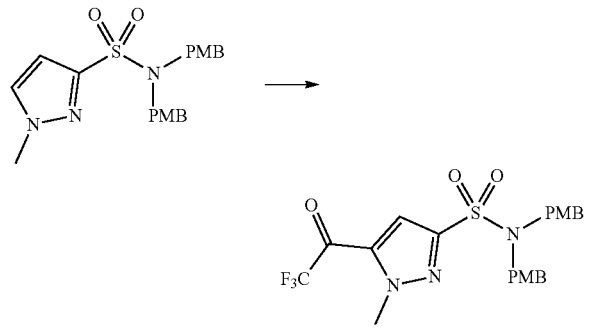

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis(4-methoxybenzyl)-1-methyl-H-pyrazole-3-sulfonamide (Intermediate P9, Step A) and ethyl 2,2,2-trifluoroacetate to afford the title compound (1.23 g, 53%) as a colourless solid.

$^1$H NMR (DMSO-d$_6$) δ 7.06-7.00 (m, 4H), 6.83-6.79 (m, 4H), 6.74 (s, 1H), 4.22 (s, 4H), 4.01 (s, 3H), 3.72 (s, 6H).
LCMS; m/z not found, no ionisation.

Step B: N,N-Bis(4-methoxybenzyl)-1-methyl-5-(2,2,2-trifluoro-1-hydroxyethyl)-1H-pyrazole-3-sulfonamide

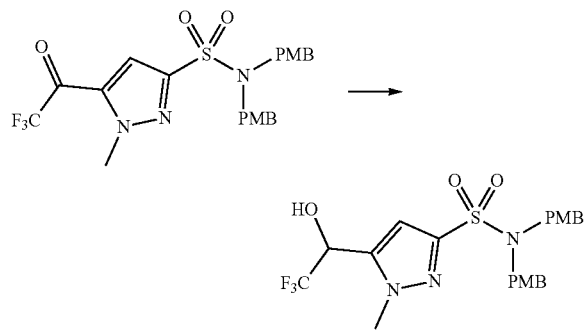

A solution of N,N-bis(4-methoxybenzyl)-1-methyl-5-(2,2,2-trifluoroacetyl)-1H-pyrazole-3-sulfonamide (0.6 g, 1.206 mmol) in MeOH (5 mL) was stirred at 0° C. under nitrogen. NaBH$_4$ (0.046 g, 1.206 mmol) was added in small portions over 5 minutes, then the reaction was left at 0° C. for 1 hour. After concentration under reduced pressure, the residue was treated with a concentrated solution of aqueous ammonium chloride, taken up in EtOAc (50 mL), dried over MgSO$_4$, and concentrated under reduced pressure. The crude product was purified by chromatography on silica gel (12 g column, 0-50% EtOAc/isohexane) to afford the title compound (510 mg, 82%) as a sticky colourless gum.

$^1$H NMR (DMSO-d$_6$) δ 7.32 (d, J=6.6 Hz, 1H), 7.07-6.98 (m, 4H), 6.87-6.77 (m, 4H), 6.74 (s, 1H), 5.71-5.53 (m, 1H), 4.28-4.16 (m, 4H), 3.97 (s, 3H), 3.72 (s, 6H).
LCMS; m/z 522.4 (M+H)$^+$ (ES$^+$).

Step C: 5-(1-(Dimethylamino)-2,2,2-trifluoroethyl)-N,N-bis(4-methoxybenzyl)-1-methyl-1H-pyrazole-3-sulfonamide

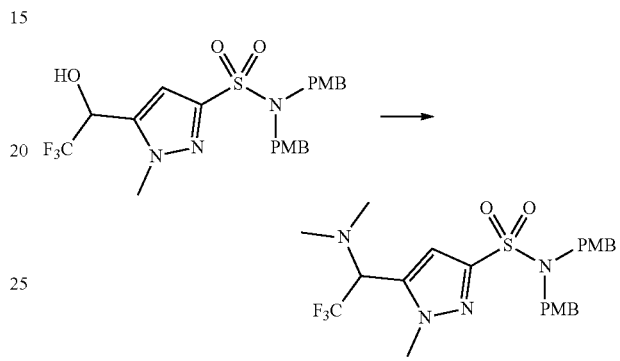

Triflic anhydride (1 M in DCM) (2 mL, 2.000 mmol) was added to a solution of N,N— bis(4-methoxybenzyl)-1-methyl-5-(2,2,2-trifluoro-1-hydroxyethyl)-1H-pyrazole-3-sulfonamide (500 mg, 1.001 mmol) and 2,6-dimethylpyridine (0.233 mL, 2.002 mmol) in anhydrous DCM (5 mL) at 0° C. The reaction was allowed to warm to room temperature, stirred for 2 hour and then cooled to 0° C. A solution of dimethylamine (5 mL, 10.00 mmol) was added and the mixture was stirred at 40° C. for 18 hours. The mixture was cooled to room temperature and evaporated to dryness. The residue was taken up in EtOAc (50 mL) and saturated aqueous NaHCO$_3$ solution (10 mL), the layers were separated, and the aqueous phase was extracted with further portions of EtOAc (2×20 mL). The combined organic phases were washed with saturated aqueous NaHCO$_3$ solution (10 mL) and brine (2×10 mL), dried over MgSO$_4$, filtered, and concentrated in vacuo to give crude product as a yellow oil. The crude product was re-dissolved in MeOH (3 mL) and loaded onto SCX (ca. 4 g), which was then washed with MeOH (15 mL) and eluted with 0.7 M NH$_3$/MeOH (15 mL) and concentrated in vacuo to give the title compound (200 mg, 32%) as a pale yellow solid.

$^1$H NMR (DMSO-d$_6$) δ 7.10-6.99 (m, 4H), 6.86-6.77 (m, 4H), 6.59 (s, 1H), 5.15 (q, J=8.5 Hz, 1H), 4.24 (s, 4H), 3.95 (s, 3H), 3.72 (s, 6H), 2.36 (s, 6H).
LCMS; m/z 549.4 (M+Na)+(ES$^+$).

Step D: 5-(1-(Dimethylamino)-2,2,2-trifluoroethyl)-1-methyl-1H-pyrazole-3-sulfonamide

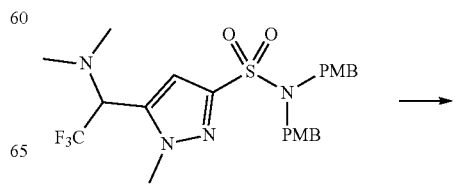

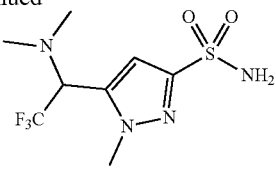

5-(1-(Dimethylamino)-2,2,2-trifluoroethyl)-N,N-bis(4-methoxybenzyl)-1-methyl-1H-pyrazole-3-sulfonamide (200 mg, 0.304 mmol) was dissolved in TFA (5 mL) and stirred for 16 hours. The reaction mixture was concentrated and the crude product was loaded onto a column of SCX (2 g) in MeOH. The column was washed with MeOH and then the product was eluted with 0.7 M ammonia in MeOH. The resultant mixture was concentrated in vacuo to afford the title compound (85 mg, 98%) as a yellow oil.

LCMS; m/z 287.5 (M+H)⁺ (ES⁺).

Intermediate P60: 1-Isopropyl-5-((methyl(2,2,2-trifluoroethyl)amino)methyl)-1H-pyrazole-3-sulfonamide Step A: 1-Isopropyl-N,N-bis(4-methoxybenzyl)-5-((methyl(2,2,2-trifluoroethyl)amino)methyl)-1H-pyrazole-3-sulfonamide

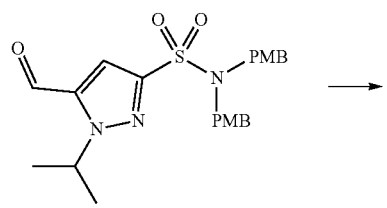

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-1-isopropyl-N,N-bis(4-methoxybenzyl)-1H-pyrazole-3-sulfonamide (Intermediate P29, Step A) and 2,2,2-trifluoro-N-methylethanamine (114 mg, 1.005 mmol) and sodium triacetoxyborohydride to afford the title compound (170 mg, 60%) as a colourless oil.

¹H NMR (DMSO-d₆) 7.04-6.99 (m, 4H), 6.84-6.78 (m, 4H), 6.64 (s, 1H), 4.78 (sept, J=6.6 Hz, 1H), 4.20 (s, 4H), 3.82 (s, 2H), 3.72 (s, 6H), 3.37-3.25 (m, 2H), 2.31 (s, 3H), 1.39 (d, J=6.6 Hz, 6H).

LCMS; m/z 577.9 (M+Na)+(ES⁺).

Step B: 1-Isopropyl-5-((methyl(2,2,2-trifluoroethyl)amino)methyl)-1H-pyrazole-3-sulfonamide

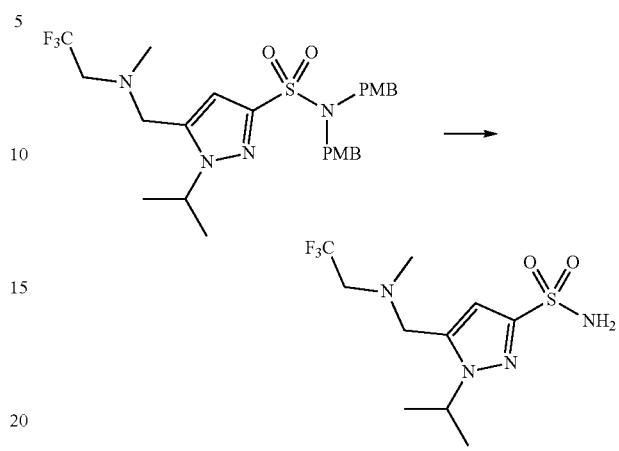

1-Isopropyl-N,N-bis(4-methoxybenzyl)-5-((methyl(2,2,2-trifluoroethyl)amino)methyl)-1H-pyrazole-3-sulfonamide (168 mg, 0.303 mmol) was dissolved in DCM (0.4 mL) and TFA (0.6 mL) was added. The reaction mixture was stirred for 16 hours, concentrated in vacuo, suspended in toluene (5 mL) and concentrated again. The crude product was purified by chromatography on RP Flash C18 (12 g column, 5-50% MeCN/10 mM ammonium bicarbonate) to afford the title compound (15 mg, 14%) as a white solid.

¹H NMR (DMSO-d₆) δ 7.38 (bs, 2H), 6.53 (s, 1H), 4.74 (sept, J=6.6 Hz, 1H), 3.81 (s, 2H), 3.32-3.25 (m, 2H), 2.33 (s, 3H), 1.39 (d, J=6.6 Hz, 6H).

LCMS m/z 315.1 (M+H)⁺ (ES⁺).

Intermediate P61: 1-Methyl-5-((methyl(2,2,2-trifluoroethyl)amino)methyl)-1H-pyrazole-3-sulfonamide Step A: N,N-Bis(4-methoxybenzyl)-1-methyl-5-((methyl(2,2,2-trifluoroethyl)amino)methyl)-1H-pyrazole-3-sulfonamide

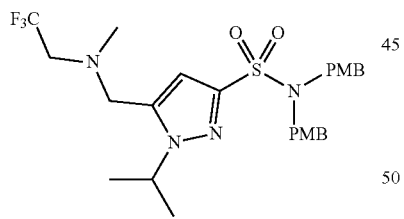

Prepared according to the general procedure of 5-(azetidin-1-ylmethyl)-1-cyclopropyl-N,N-bis(4-methoxybenzyl)-H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and 2,2,2-trifluoro-N-methylethanamine to afford the title compound (148 mg, 50%) as a colourless oil.

¹H NMR (DMSO-d₆) δ 7.06-7.00 (m, 4H), 6.84-6.78 (m, 4H), 6.66 (s, 1H), 4.20 (s, 4H), 3.89 (s, 3H), 3.82 (s, 2H), 3.72 (s, 6H), 3.30 (q, J=10.1 Hz, 2H), 2.34 (s, 3H).
LCMS; m/z 549.4 (M+Na)+(ES⁺).

Step B: 1-Methyl-5-((methyl(2,2,2-trifluoroethyl)amino)methyl)-1H-pyrazole-3-sulfonamide

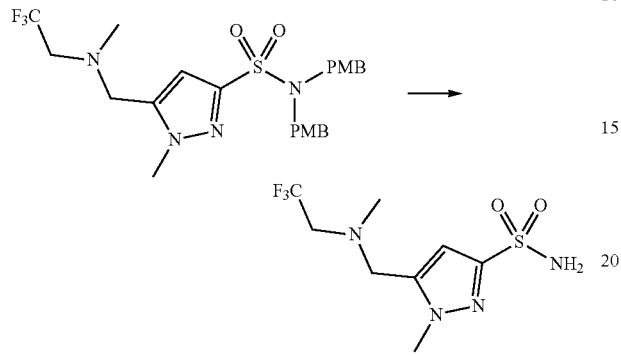

Prepared according to the general procedure of 1-isopropyl-5-((methyl(2,2,2-trifluoroethyl)amino)methyl)-1H-pyrazole-3-sulfonamide (Intermediate P60, Step B) from N,N-bis(4-methoxybenzyl)-1-methyl-5-((methyl(2,2,2-trifluoroethyl)amino)methyl)-1H-pyrazole-3-sulfonamide to afford the title compound (74 mg, 39%) as a white solid.
¹H NMR (DMSO-d₆) δ 7.37 (bs, 2H), 6.55 (s, 1H), 3.85 (s, 3H), 3.80 (s, 2H), 3.30-3.24 (m, 2H), 2.35 (s, 3H).
LCMS; m/z 287.2 (M+H)⁺ (ES⁺).

Intermediate P62: 5-(3-(Dimethylamino)oxetan-3-yl)-1-methyl-1H-pyrazole-3-sulfonamide Step A: 5-(3-Aminooxetan-3-yl)-N,N-bis(4-methoxybenzyl)-1-methyl-1H-pyrazole-3-sulfonamide

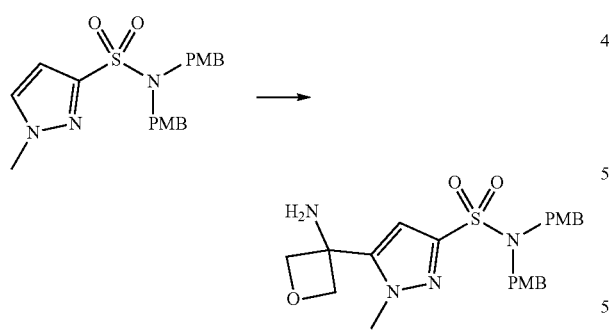

A solution of n-BuLi (2.5 M in hexanes; 0.70 mL, 1.750 mmol) was added dropwise to a stirred solution of N,N-bis(4-methoxybenzyl)-1-methyl-1H-pyrazole-3-sulfonamide (Intermediate P9, Step A) (0.70 g, 1.74 mmol) in THF (15 mL) at −78° C. The reaction was stirred for 1 hour, then a solution of 2-methyl-N-(oxetan-3-ylidene)propane-2-sulfinamide (0.40 g, 2.28 mmol) in THF (5 mL) was added. The reaction mixture was left at −78° C. for 5 minutes and then allowed to warm to room temperature and stirred for 1 hour. The reaction was quenched with saturated aqueous ammonium chloride (15 mL) and extracted with DCM (3×20 mL). The organic extracts were dried (MgSO₄), filtered and concentrated in vacuo. The resultant orange gum was dissolved in MeOH (18 mL) and HCl (3.7 M in 1,4-dioxane, 1.7 mL, 6.29 mmol) was added. The solution was stirred for 16 hours and then concentrated in vacuo. The crude product was loaded onto a column (SCX; 5 g) in MeOH and the column was washed with MeOH and then the product was eluted with 0.7 M ammonia in MeOH. The resultant mixture was concentrated in vacuo to afford the title compound (0.25 g, 41%) as a thick brown gum.
¹H NMR (DMSO-d₆) δ 7.09-7.04 (m, 4H), 6.86-6.80 (m, 4H), 6.79 (s, 1H), 4.87 (d, J=6.4 Hz, 2H), 4.65 (d, J=6.4 Hz, 2H), 4.22 (s, 4H), 3.84 (s, 3H), 3.71 (s, 6H), 3.16 (s, 2H).
LCMS; m/z 473.5 (M+H)⁺ (ES⁺).

Step B: 5-(3-(Dimethylamino)oxetan-3-yl)-N,N-bis(4-methoxybenzyl)-1-methyl-1H-pyrazole-3-sulfonamide

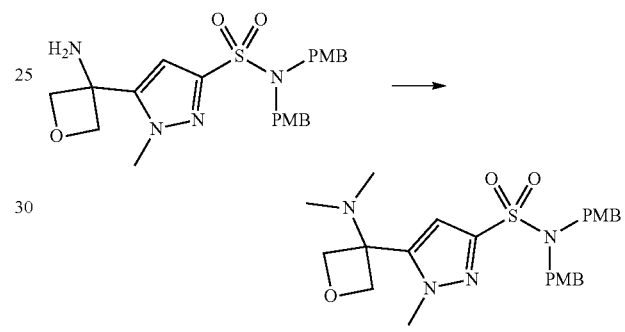

Prepared according to the general procedure of 5-(2-(dimethylamino)propan-2-yl)-N,N-bis(4-methoxybenzyl)-1-methyl-1H-pyrazole-3-sulfonamide (Intermediate P22, Step D) from 5-(3-aminooxetan-3-yl)-N,N-bis(4-methoxybenzyl)-1-methyl-1H-pyrazole-3-sulfonamide to afford the title compound (0.17 g, 61%) as an orange oil.
¹H NMR (DMSO-d₆) δ 7.11-7.03 (m, 4H), 6.86-6.78 (m, 4H), 6.77 (s, 1H), 4.93 (d, J=7.2 Hz, 2H), 4.74 (d, J=7.2 Hz, 2H), 4.23 (s, 4H), 3.75 (s, 3H), 3.72 (s, 6H), 2.19 (s, 6H).
LCMS; m/z 501.4 (M+H)⁺ (ES⁺).

Step C: 5-(3-(Dimethylamino)oxetan-3-yl)-1-methyl-1H-pyrazole-3-sulfonamide

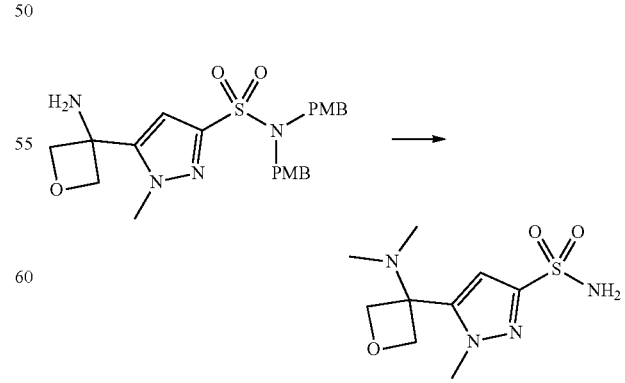

5-(3-(Dimethylamino)oxetan-3-yl)-N,N-bis(4-methoxybenzyl)-1-methyl-1H-pyrazole-3-sulfonamide (0.17 g, 0.25 mmol) was dissolved in TFA (3 mL) and stirred at room temperature for 23 hours. Additional TFA (3 mL) was added and the mixture was stirred for a further 3 hours at room temperature. The mixture was then evaporated to dryness and purified by chromatography on silica gel (12 g column, 0-10% MeOH/DCM) to afford an orange solid. The product was further purified by precipitation on addition of isohexane to a solution of the product in 19:1 DCM:MeOH.

The product was collected by filtration to afford the title compound (65 mg, 84%) as an orange solid.

¹H NMR (DMSO-d₆) δ 7.46 (s, 2H), 6.79 (s, 1H), 5.00 (d, J=7.6 Hz, 2H), 4.85 (d, J=7.6 Hz, 2H), 3.76 (s, 3H), 2.38 (br s, 6H).

LCMS; m/z 261.1 (M+H)⁺ (ES⁺).

Intermediate P63: 5-(((2-Hydroxyethyl)(methyl)amino)methyl)-1-methyl-1H-pyrazole-3-sulfonamide Step A: 5-(((2-Hydroxyethyl)(methyl)amino)methyl)-N,N-bis(4-methoxybenzyl)-1-methyl-1H-pyrazole-3-sulfonamide

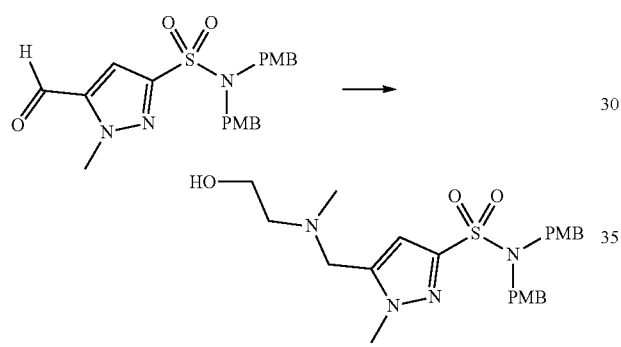

2-(Methylamino)ethanol (112 μL, 1.40 mmol) was added to a solution of 5-formyl-N,N— bis(4-methoxybenzyl)-1-methyl-H-pyrazole-3-sulfonamide (Intermediate P38, Step A) (0.40 g, 0.93 mmol) in dry THF (20 mL) containing 4 Å molecular sieves and stirred for 1 hour. Sodium triacetoxyborohydride (0.30 g, 1.42 mmol) and acetic acid (6 μL, 0.1 mmol) were added and the reaction was stirred at room temperature for 3 days. An additional portion of acetic acid (54 μL, 0.94 mmol) was added and the reaction mixture stirred for 20 hours at 60° C. Then 2-(methylamino)ethanol (112 μL, 1.39 mmol) and more sodium triacetoxyborohydride (0.30 g, 1.42 mmol) were added and the reaction was heated at 60° C. for another 20 hours. The reaction was quenched with water (1 mL) and loaded onto a column (SCX). The column was washed with 20% MeOH in DCM and then the crude product was eluted with 0.7M ammonia in DCM:MeOH (9:1, 50 mL). The resultant mixture was concentrated in vacuo and the crude product was further purified by chromatography on silica gel (12 g column, 0-20% (0.7M ammonia in MeOH)/DCM) to afford the title compound (0.19 g, 41%) as a colourless gum.

¹H NMR (DMSO-d₆) δ 7.07-6.99 (m, 4H), 6.86-6.77 (m, 4H), 6.61 (s, 1H), 4.49 (t, J=5.3 Hz, 1H), 4.20 (s, 4H), 3.91 (s, 3H), 3.72 (s, 6H), 3.60 (s, 2H), 3.54 (td, J=5.2, 6.1 Hz, 2H), 2.47 (t, J=6.1 Hz, 2H), 2.17 (s, 3H).

LCMS; m/z 489.2 (M+H)⁺ (ES⁺).

Step B: 5-(((2-Hydroxyethyl)(methyl)amino)methyl)-1-methyl-1H-pyrazole-3-sulfonamide

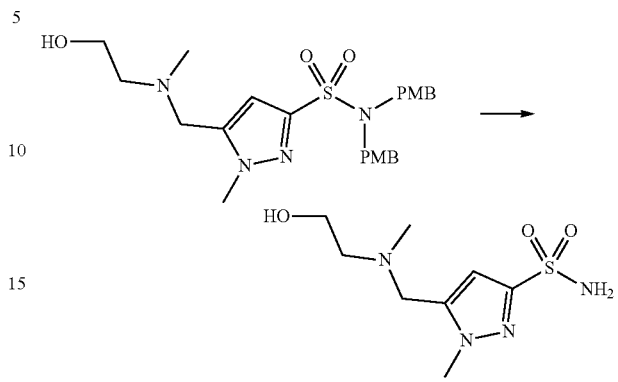

Prepared according to the general procedure of 1-cyclopropyl-5-(1-(dimethylamino) ethyl)-1H-pyrazole-3-sulfonamide (Intermediate P10, Step C) from 5-(((2-hydroxyethyl)(methyl)amino) methyl)-N,N-bis(4-methoxybenzyl)-1-methyl-1H-pyrazole-3-sulfonamide to afford the title compound (95 mg, 95%) as a colourless gum.

¹H NMR (DMSO-d₆) δ 7.34 (s, 2H), 6.49 (s, 1H), 4.47 (t, J=5.3 Hz, 1H), 3.87 (s, 3H), 3.58 (s, 2H), 3.56-3.48 (m, 2H), 2.45 (t, J=6.1 Hz, 2H), 2.17 (s, 3H).

LCMS; m/z 249.1 (M+H)⁺ (ES⁺).

Intermediate P64: 5-(((2-Methoxyethyl)(methyl)amino)methyl)-1-methyl-1H-pyrazole-3-sulfonamide Step A: N,N-Bis(4-methoxybenzyl)-5-(((2-methoxyethyl)(methyl)amino) methyl)-1-methyl-1H-pyrazole-3-sulfonamide

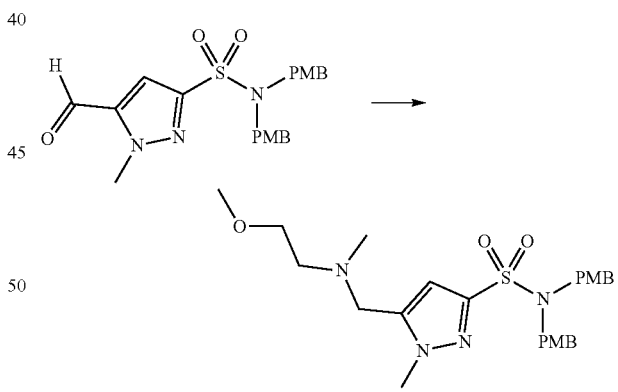

Prepared according to the general procedure of 5-(azetidin-1-ylmethyl)-1-cyclopropyl-N,N-bis(4-methoxybenzyl)-H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and 2-methoxy-N-methylethanamine to afford the title compound (0.41 g, 86%) as a pale colourless oil.

¹H NMR (DMSO-d₆) δ 7.08-6.99 (m, 4H), 6.86-6.77 (m, 4H), 6.59 (s, 1H), 4.20 (s, 4H), 3.90 (s, 3H), 3.72 (s, 6H), 3.60 (s, 2H), 3.46 (t, J=5.7 Hz, 2H), 3.24 (s, 3H), 2.55 (t, J=5.7 Hz, 2H), 2.17 (s, 3H).

LCMS; m/z 503.4 (M+H)⁺ (ES⁺).

Step B: 5-(((2-Methoxyethyl)(methyl)amino)methyl)-1-methyl-1H-pyrazole-3-sulfonamide

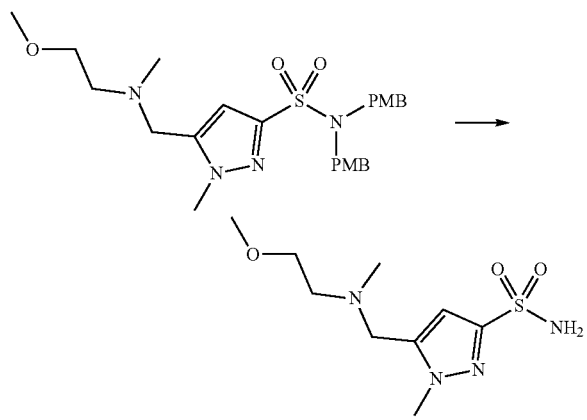

Prepared according to the general procedure of 1-cyclopropyl-5-(1-(dimethylamino)ethyl)-1H-pyrazole-3-sulfonamide (Intermediate P10, Step C) from N,N-bis(4-methoxybenzyl)-5-(((2-methoxyethyl)(methyl)amino)methyl)-1-methyl-H-pyrazole-3-sulfonamide to afford the title compound (0.20 g, 91%) as a white solid.

$^1$H NMR (DMSO-$d_6$) δ 7.34 (s, 2H), 6.49 (s, 1H), 3.86 (s, 3H), 3.58 (s, 2H), 3.45 (t, J=5.8 Hz, 2H), 3.24 (s, 3H), 2.54 (t, J=5.8 Hz, 2H), 2.18 (s, 3H).

LCMS; m/z 263.1 (M+H)$^+$ (ES$^+$).

Intermediate P65: 1-Methyl-5-(morpholinomethyl)-1H-pyrazole-3-sulfonamide

Step A: 5-(Hydroxymethyl)-1-methyl-1H-pyrazole-3-sulfonamide

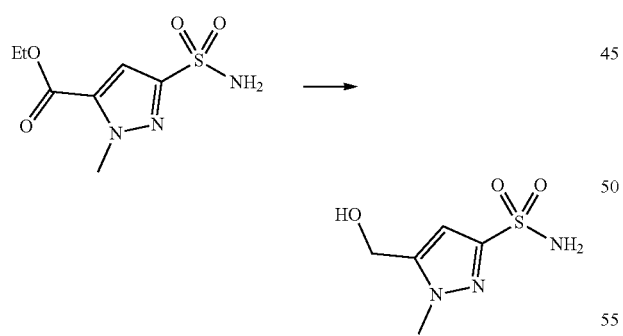

A solution of LiBH$_4$ (2 M in THF; 4.3 mL, 8.6 mmol) was added dropwise over 5 minutes to a stirred solution of ethyl 1-methyl-3-sulfamoyl-H-pyrazole-5-carboxylate (1.00 g, 4.29 mmol) in THF (10 mL) at 0° C. The reaction was allowed to warm to room temperature, stirred for 3 hours and then heated at 40° C. for 20 hours. The reaction was cooled to 0° C. LiAlH$_4$ (2 M in THF; 0.55 mL, 1.10 mmol) was added and the reaction was stirred for a further 2 days at 40° C. The reaction was cooled to 0° C. and aqueous saturated ammonium chloride (10 mL) was cautiously added dropwise over 10 minutes. The mixture was allowed to warm to room temperature and EtOAc (30 mL) was added. The reaction mixture was stirred vigorously for 10 minutes and then filtered through a pad of Celite®. The layers were separated and the aqueous layer was saturated with NaCl and extracted further with EtOAc (5×20 mL). The combined organic extracts were dried (MgSO$_4$), filtered and evaporated in vacuo to afford the title compound (0.67 g, 78%) as a white solid.

$^1$H NMR (DMSO-$d_6$) δ 5.70 (s, 1H), 3.73 (s, 2H), 3.02 (s, 3H). Three exchangeable protons not observed.

LCMS; m/z 192.0 (M+H)$^+$ (ES$^+$).

Step B: 5-Formyl-1-methyl-1H-pyrazole-3-sulfonamide

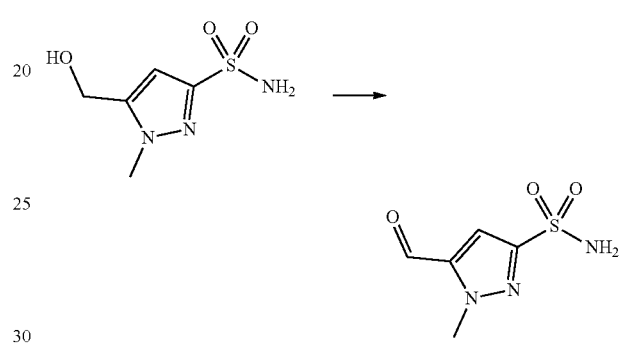

Manganese(IV) oxide (1.00 g, 11.5 mmol) was added to a solution of 5-(hydroxymethyl)-1-methyl-H-pyrazole-3-sulfonamide (0.55 g, 2.88 mmol) in 1,2-dimethoxyethane (30 mL). The reaction mixture was stirred for 20 hours at room temperature and then at 40° C. for a further 6 hours. Further manganese(IV) oxide (0.50 g, 5.75 mmol) was added and the reaction was heated at 40° C. for 2 days. The mixture was cooled to room temperature and filtered through a pad of Celite®, washing with 1,2-dimethoxyethane. The filtrate was concentrated in vacuo to afford the title compound (0.29 g, 52%), as a yellow gum.

$^1$H NMR (DMSO-$d_6$) δ 9.92 (s, 1H), 7.64 (s, 2H), 7.31 (s, 1H), 4.16 (s, 3H).

LCMS; m/z 189.9 (M+H)$^+$ (ES$^+$).

Step C: 1-Methyl-5-(morpholinomethyl)-1H-pyrazole-3-sulfonamide

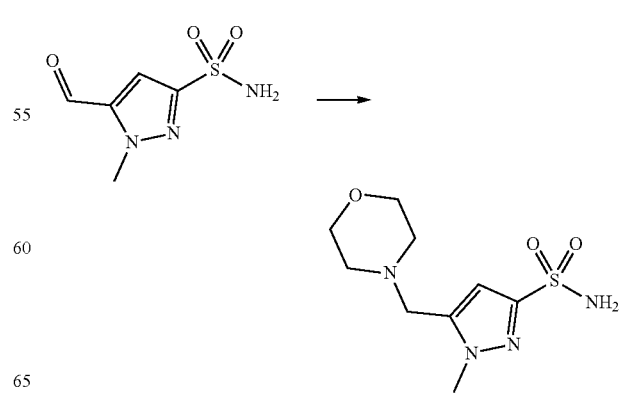

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-1-methyl-1H-pyrazole-3-sulfonamide and morpholine to afford the title (73 mg, 25%) as a colourless gum.

$^1$H NMR (DMSO-d$_6$) δ 7.36 (s, 2H), 6.50 (s, 1H), 3.87 (s, 3H), 3.57 (m, 4H), 3.56 (s, 2H), 2.37 (m, 4H).

LCMS; m/z 261.0 (M+H)$^+$ (ES$^+$).

Intermediate P66: 2-((Dimethylamino)methyl)-1-methyl-1H-imidazole-4-sulfonamide, and Intermediate P67: 5-((Dimethylamino)methyl)-1-methyl-1H-imidazole-4-sulfonamide Step A: N,N-Bis(4-methoxybenzyl)-1-methyl-1H-imidazole-4-sulfonamide

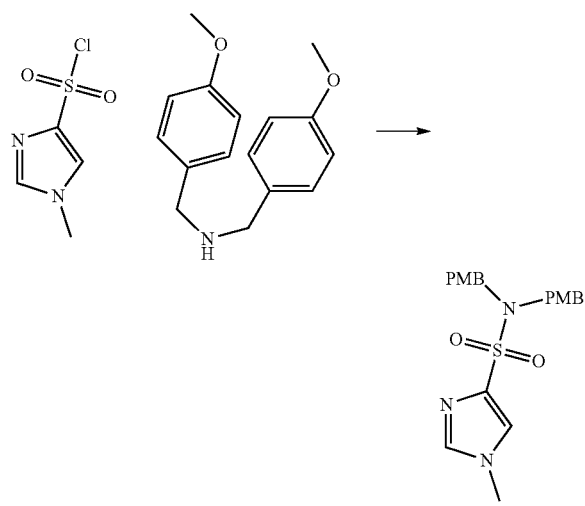

1-Methyl-1H-imidazole-4-sulfonyl chloride (4 g, 22.15 mmol) was added portionwise to a solution of bis(4-methoxybenzyl)amine (5.98 g, 23.25 mmol) and triethylamine (6.17 ml, 44.3 mmol) in DCM (100 mL) cooled in an ice bath. The mixture was stirred for 30 minutes, warmed to room temperature and stirred for 16 hours. The mixture was washed with water (2×50 mL), aq 1 M HCl (50 mL), water (50 mL), and brine (50 mL), then dried over MgSO$_4$, filtered and evaporated to dryness to give crude product as a cream coloured solid. The crude product was dissolved in a minimum amount of DCM to load, then purified by column chromatography on silica gel (220 g column, 0-80% EtOAc/isohexane) to afford the title compound (5-1, 55%) as a white solid.

$^1$H NMR (DMSO-d$_6$) δ 7.87-7.78 (m, 2H), 7.09-6.99 (m, 4H), 6.91-6.73 (m, 4H), 4.19 (s, 4H), 3.72 (s, 6H), 3.33 (s, 3H).

LCMS; m/z 402.3 (M+H)$^+$ (ES$^+$).

Step B: 2-((Dimethylamino)methyl)-N,N-bis(4-methoxybenzyl)-1-methyl-1H-imidazole-4-sulfonamide and 5-((dimethylamino)methyl)-N,N-bis(4-methoxybenzyl)-1-methyl-1H-imidazole-4-sulfonamide

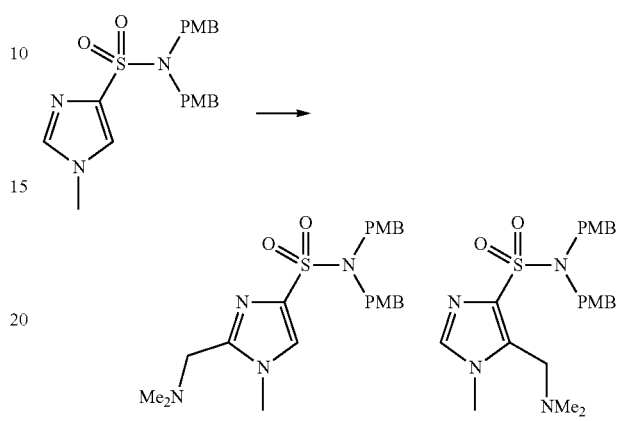

Prepared according to the general procedure of 5-((dimethylamino)methyl)-N,N-bis(4-methoxybenzyl)-1-ethyl-H-pyrazole-3-sulfonamide (Intermediate P7, Step B) from N,N-bis(4-methoxybenzyl)-1-methyl-1H-imidazole-4-sulfonamide and N-methyl-N— methylenemethanaminium iodide to afford the title compounds as a 85:15 mixture (374 mg, 28%) as a yellow oil.

$^1$H NMR (major product) (DMSO-d$_6$) δ 7.83 (s, 1H), 7.05-6.98 (m, 4H), 6.83-6.74 (m, 4H), 4.24 (s, 4H), 3.71 (s, 6H), 3.70 (s, 3H), 3.68 (s, 2H), 2.16 (s, 6H).

LCMS; m/z 459.4 (M+H)$^+$ (ES$^+$).

Step C: 2-((Dimethylamino)methyl)-1-methyl-1H-imidazole-4-sulfonamide and 5-((dimethylamino)methyl)-1-methyl-1H-imidazole-4-sulfonamide

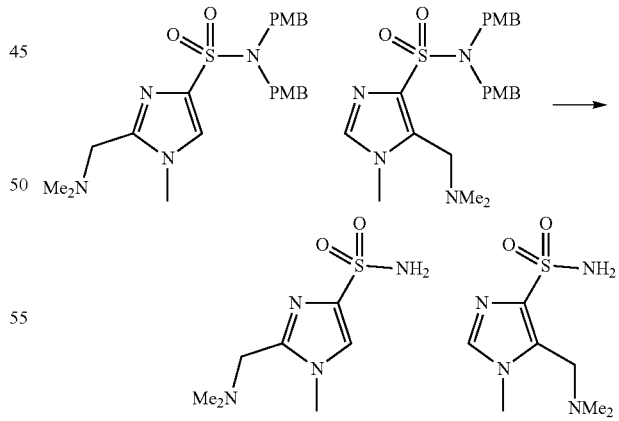

A 85:15 mixture of 2-((dimethylamino)methyl)-N,N-bis(4-methoxybenzyl)-1-methyl-1H-imidazole-4-sulfonamide and 5-((dimethylamino)methyl)-N,N-bis(4-methoxybenzyl)-1-methyl-1H-imidazole-4-sulfonamide (552 mg, 1.204 mmol) was dissolved in TFA (5 ml, 1.204 mmol) and stirred overnight. Additional TFA (2 mL) was added and stirred for a further 24 hours at room temperature. The mixture was concentrated in vacuo and the residue was suspended in a mixture of MeOH (50 mL) and DCM (1 mL). SCX (3 eq.) was added and the suspension was stirred at room temperature for 1 hour. The SCX was filtered and washed with MeOH (50 mL) and the product was then eluted with 0.7% ammonia in MeOH (50 mL). After concentration in vacuo, a 85:15 mixture of 2-((dimethylamino)methyl)-1-methyl-H-imidazole-4-sulfonamide and 5-((dimethylamino)methyl)-1-methyl-H-imidazole-4-sulfonamide (222 mg, 84%) was isolated as a pale yellow oil.

$^1$H NMR (major product) (DMSO-$d_6$) δ 7.72 (s, 1H), 7.10 (s, 2H), 3.66 (s, 3H), 3.65 (s, 2H), 2.15 (s, 6H).

Intermediate P68: N-((1-Isopropyl-3-sulfamoyl-1H-pyrazol-5-yl)methyl)-N— methylacetamide Step A: 1-Isopropyl-N,N-bis(4-methoxybenzyl)-5-((methylamino)methyl)-1H-pyrazole-3-sulfonamide, acetic Acid Salt

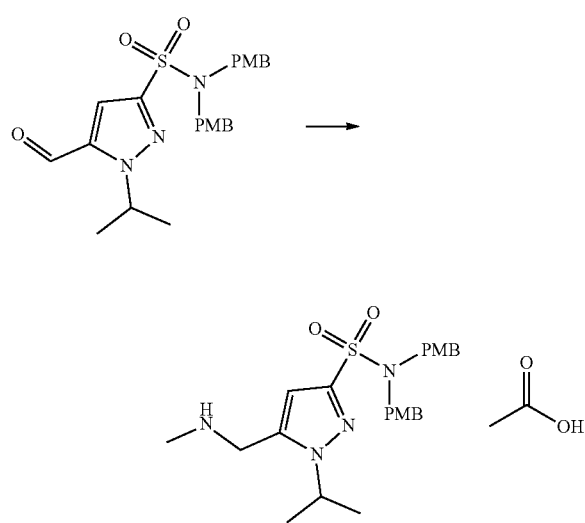

Acetic acid (10 μL, 0.175 mmol) was added to a stirred suspension of 5-formyl-1-isopropyl-N,N-bis(4-methoxy-benzyl)-1H-pyrazole-3-sulfonamide (Intermediate P29, Step A) (400 mg, 0.874 mmol), methylamine (2 M in THF) (874 μL, 1.748 mmol) and sodium triacetoxyborohydride (278 mg, 1.311 mmol) in THF (14 mL). The reaction mixture was left to stir at room temperature for 16 hours. Water (1 mL) was added and volatiles were evaporated. The crude product was purified by chromatography on SiO$_2$ (24 g column, 0-10% MeOH/DCM) to afford the title compound (130 mg, 24%) as a colourless oil.

$^1$H NMR (DMSO-$d_6$) δ 7.05-6.98 (m, 4H), 6.85-6.79 (m, 4H), 6.57 (s, 1H), 4.77 (sept, J=6.5 Hz, 1H), 4.19 (s, 4H), 3.74 (s, 2H), 3.72 (s, 6H), 3.37 (bs, 1H), 2.27 (s, 3H), 1.90 (s, 3H), 1.39 (d, J=6.5 Hz, 6H). OH not observed.

LCMS; m/z 473.5 (M+H)$^+$ (ES$^+$).

Step B: N-((3-(N,N-Bis(4-methoxybenzyl)sulfamoyl)-1-isopropyl-1H-pyrazol-5-yl)methyl)-N-methylacetamide

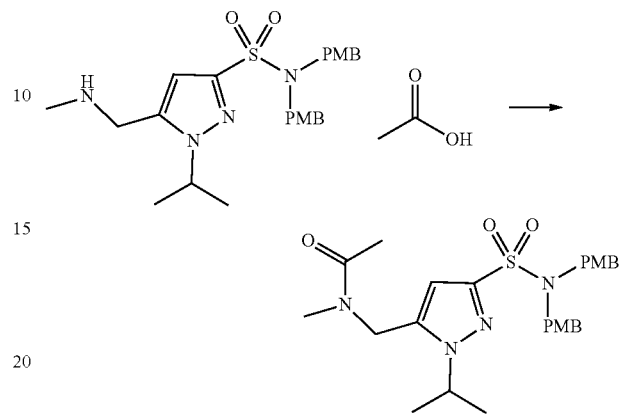

To a solution of 1-isopropyl-N,N-bis(4-methoxybenzyl)-5-((methylamino)methyl)-1H-pyrazole-3-sulfonamide, acetic acid salt (130 mg, 0.248 mmol) in DCM (1 mL) was added pyridine (45 μL, 0.556 mmol) and the mixture was cooled to 0° C. Trifluoroacetic anhydride (53 μL, 0.375 mmol) was added dropwise and the resultant mixture was stirred at 0° C. for 15 minutes, before warming to room temperature for 16 hours. Additional pyridine (45 μL, 0.556 mmol) and trifluoroacetic anhydride (53 μL, 0.375 mmol) were added and the mixture was stir for another 16 hours. The mixture was quenched with saturated sodium bicarbonate (5 mL) and the layers were separated. The aqueous layer was extracted with DCM (2×10 mL) and EtOAc (10 mL) and the combined organic phases were dried with magnesium sulfate. The solvent was removed under reduced pressure. The crude product was purified by chromatography on SiO$_2$ (12 g column, 0-10% MeOH/DCM) to afford the title compound (88 mg, 57%) as a brown oil.

$^1$H NMR (DMSO-$d_6$); rotamers: δ 7.05-6.99 (m, 4H), 6.85-6.79 (m, 4H), 6.63 (s, 1H), 4.75-4.66 (m, 1H), 4.63 (s, 2H), 4.21 (s, 4H), 3.73 (s, 6H), 3.32 (s, 3H), 2.07 (s, 3H), 1.35 (d, J=6.5 Hz, 6H).

LCMS; m/z 537.1 (M+Na)+(ES$^+$).

Step C: N-((1-Isopropyl-3-sulfamoyl-1H-pyrazol-5-yl)methyl)-N— methylacetamide

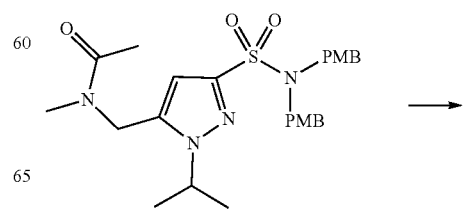

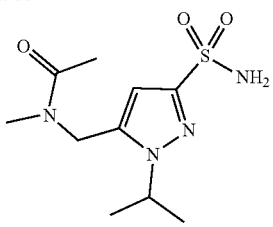

Prepared according to the general procedure of 1-isopropyl-5-((methyl(2,2,2-trifluoroethyl)amino)methyl)-1H-pyrazole-3-sulfonamide (Intermediate P60, Step B) from N-((3-(N,N-bis(4-methoxybenzyl)sulfamoyl)-1-isopropyl-1H-pyrazol-5-yl)methyl)-N-methylacetamide to afford the title compound (30 mg, 78%) as a white solid.

$^1$H NMR (DMSO-$d_6$) δ 7.37 (bs, 2H), 6.51 (s, 1H), 4.73-4.66 (m, 1H), 4.61 (s, 2H), 2.95 (s, 3H), 2.06 (s, 3H), 1.35 (d, J=6.5 Hz, 6H).

LCMS; m/z 275.2 (M+H)$^+$ (ES$^+$).

Intermediate P69: 1-Methyl-5-((methyl(1-methylazetidin-3-yl)amino) methyl)-1H-pyrazole-3-sulfonamide Step A: N,N-bis(4-Methoxybenzyl)-1-methyl-5-((methyl(1-methylazetidin-3-yl)amino)methyl)-1H-pyrazole-3-sulfonamide

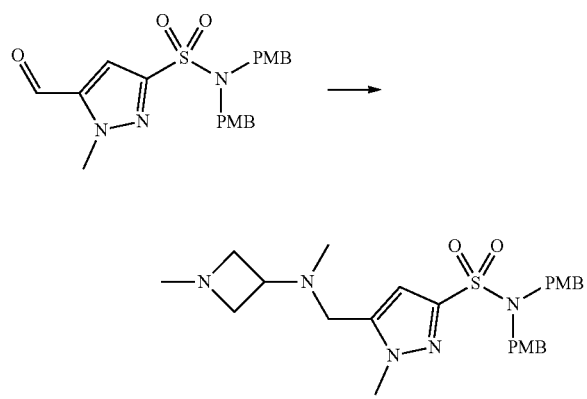

Prepared according to the general procedure of 5-(azetidin-1-ylmethyl)-1-cyclopropyl-N,N-bis(4-methoxybenzyl)-1H-pyrazole-3-sulfonamide (Intermediate P18, Step B) from 5-formyl-N,N-bis(4-methoxybenzyl)-1-methyl-1H-pyrazole-3-sulfonamide (Intermediate P38, Step A) and N,1-dimethylazetidin-3-amine to afford the title compound (195 mg, 38%) as a colourless oil.

$^1$H NMR (DMSO-$d_6$) δ 7.08-7.00 (m, 4H), 6.86-6.77 (m, 4H), 6.60 (s, 1H), 4.20 (s, 4H), 3.93 (s, 3H), 3.72 (s, 6H), 3.43 (s, 2H), 3.37 (m, 2H), 2.97 (p, J=6.5 Hz, 1H), 2.72 (m, 2H), 2.21 (s, 3H), 1.96 (s, 3H).

LCMS; m/z 514.2 (M+H)$^+$ (ES$^+$).

Step B: 1-Methyl-5-((methyl(1-methylazetidin-3-yl)amino)methyl)-1H-pyrazole-3-sulfonamide

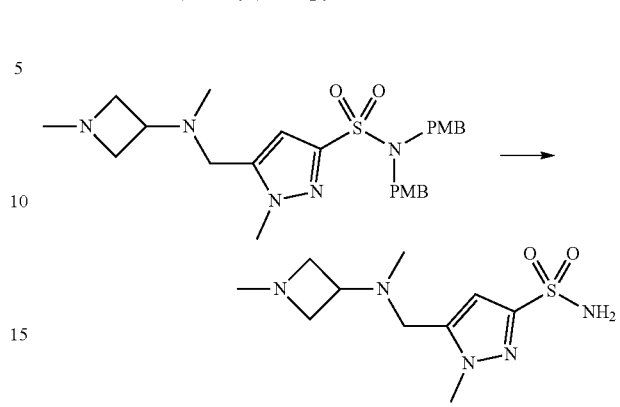

N,N-bis(4-Methoxybenzyl)-1-methyl-5-((methyl(1-methylazetidin-3-yl)amino)methyl)-1H-pyrazole-3-sulfonamide (190 mg, 0.370 mmol) was dissolved in TFA (5 ml, 64.9 mmol) and stirred for 4 hours. The solution was diluted with toluene (20 ml) and evaporated in vacuo to afford a colourless gum. The gum was dissolved in THF, absorbed onto SCX and eluted with THF/MeOH/DCM (1:1:3) followed by (1M NH$_3$/MeOH)/THF/DCM (1:1:3). The NH$_3$/THF/DCM was evaporated in vacuo to afford the title compound (96 mg, 93%) as a white solid.

$^1$H NMR (DMSO-$d_6$) δ 7.35 (s, 2H), 6.49 (s, 1H), 3.88 (s, 3H), 3.41 (s, 2H), 3.35 (m, 2H), 2.96 (p, J=6.6 Hz, 1H), 2.68 (m, 2H), 2.20 (s, 3H), 1.97 (s, 3H).

LCMS; m/z 274.1 (M+H)$^+$ (ES$^+$).

Intermediate P70: N,N-Bis(2-methoxyethyl)-1-methyl-3-sulfamoyl-1H-pyrazole-5-carboxamide Step A: 1-Methyl-1H-pyrazole-3-sulfonyl chloride

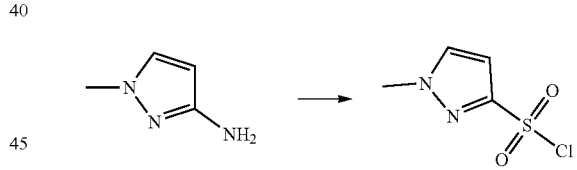

A solution of 1-methyl-1H-pyrazol-3-amine (25 g, 257.42 mmol, 1 eq) in MeCN (600 mL) at 0° C. was treated with concentrated HCl (60 mL) and H$_2$O (60 mL). Then an aqueous solution of NaNO$_2$ (21-31 g, 308.90 mmol, 1.2 eq) in H$_2$O (60 mL) was added slowly. The resulting mixture was stirred at 0° C. for 40 minutes. AcOH (6 mL), CuCl$_2$ (17-31 g, 128.71 mmol, 0.5 eq) and CuCl (1.27 g, 12.87 mmol, 307.78 μL, 0.05 eq) were added, then SO$_2$ gas (15 psi) was bubbled into the mixture for 15 minutes at 0° C. The reaction mixture was concentrated in vacuo to remove most of the MeCN. Then the reaction mixture was treated with H$_2$O (2.5 L) and extracted with EtOAc (2×1.2 L). The combined organic layers were washed with brine (3×2 L), dried over anhydrous Na$_2$SO$_4$ filtered and concentrated under reduced pressure. The residue was purified by silica gel column chromatography (petroleum ether:ethyl acetate=15:1 to 5:1) to give the title compound (19 g, 41%) as a yellow oil.

$^1$H NMR (CDCl$_3$): δ 7.52 (d, 1H), 6.89 (d, 1H) and 4.07 (s, 3H).

Step B: N,N-Bis(4-methoxybenzyl)-1-methyl-1H-pyrazole-3-sulfonamide

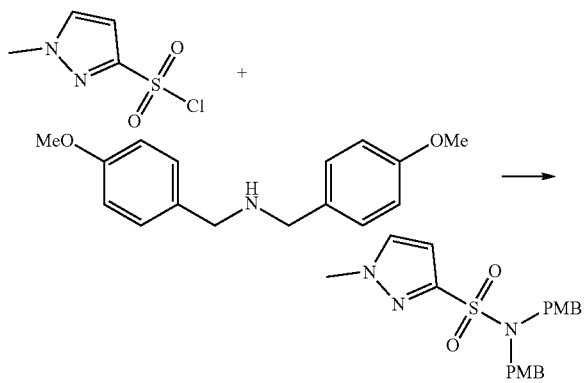

To a solution of bis(4-methoxybenzyl)amine (99.83 g, 387.96 mmol, 0.91 eq) in THF (1 L) was added TEA (86.28 g, 852.65 mmol, 118.68 mL, 2 eq), followed by 1-methyl-1H-pyrazole-3-sulfonyl chloride (77 g, 426.33 mmol, 1 eq). Then the reaction mixture was stirred at 25° C. for 12 hours. The reaction mixture was concentrated in vacuo to remove most of the THF. The reaction mixture was quenched by addition of aqueous HCl (1 M, 500 mL) and then extracted with EtOAc (2×500 mL). The combined organic layers were washed with brine (2×600 mL), dried over anhydrous $Na_2SO_4$, filtered and concentrated under reduced pressure. The residue was triturated with a mixture of petroleum ether and ethyl acetate (70 mL, v:v=5:1) to give the title compound (138 g, 81%) as a white solid.

$^1$H NMR ($CDCl_3$): δ 7.40 (d, 1H), 7.08 (d, 4H), 6.78 (d, 4H), 6.65-6.63 (m, 1H), 4.32 (s, 4H), 3.98 (s, 3H) and 3.79 (s, 6H).

LCMS: m/z 402.2 (M+H)$^+$ (ES$^+$).

Step C: 3-(N,N-Bis(4-methoxybenzyl)sulfamoyl)-1-methyl-1H-pyrazole-5-carboxylic Acid

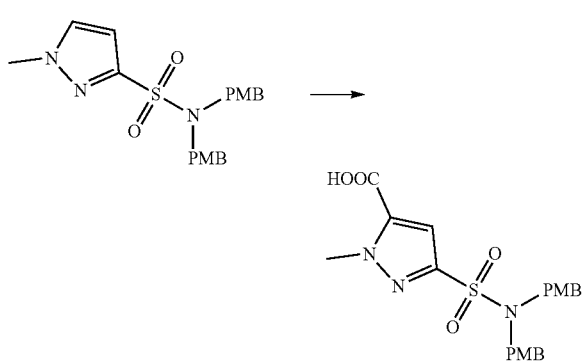

A solution of N,N-bis(4-methoxybenzyl)-1-methyl-1H-pyrazole-3-sulfonamide (100 g, 249.08 mmol, 1 eq) in THF (1.35 L) was cooled to −70° C. Then n-BuLi (2.5 M, 104.61 mL, 1.05 eq) was added dropwise. The reaction mixture was stirred at −70° C. for 1 hour, then $CO_2$ (15 psi) was bubbled into the mixture for 15 minutes. The reaction mixture was stirred at −70° C. for another 1 hour. The reaction mixture was quenched with $H_2O$ (1.2 L) and adjusted with aqueous HCl (1 M) to pH=3. Then the mixture was extracted with EtOAc (2×1). The combined organic layers were washed with brine (2×1 L), dried over $Na_2SO_4$, filtered and concentrated in vacuo. The residue was triturated with a mixture of petroleum ether and ethyl acetate (300 mL, v:v=1:1) to give the title compound (94 g, 84% yield, 99% purity on LCMS) as a white solid.

$^1$H NMR (DMSO-$d_6$): δ 6.98-7.16 (m, 5H), 6.82 (d, 4H), 4.25 (s, 4H), 4.15 (s, 3H) and 3.72 (s, 6H).

LCMS: m/z 468.2 (M+Na)+(ES$^+$).

Step D: 3-(N,N-Bis(4-methoxybenzyl)sulfamoyl)-N,N-bis(2-methoxyethyl)-1-methyl-1H-pyrazole-5-carboxamide

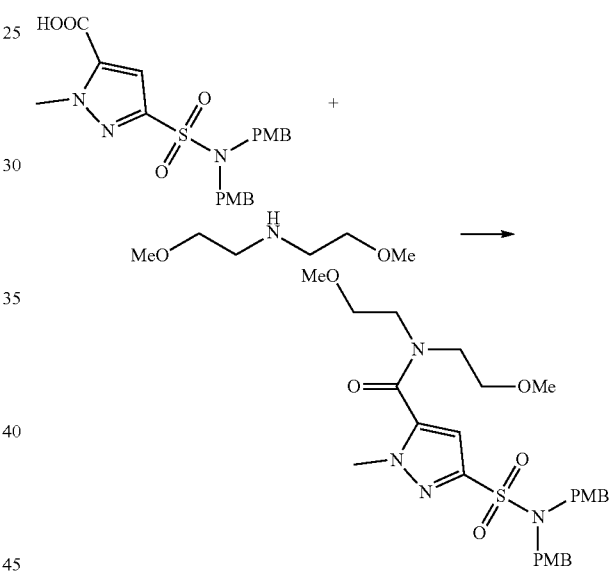

To a solution of 3-(N,N-bis(4-methoxybenzyl)sulfamoyl)-1-methyl-1H-pyrazole-5-carboxylic acid (8 g, 17.96 mmol, 1 eq) in DMF (100 mL) was added with HATU (10.24 g, 26.94 mmol, 1.5 eq), DIPEA (6.96 g, 53.87 mmol, 3 eq) and bis(2-methoxyethyl)amine (2.87 g, 21.55 mmol, 1.2 eq). The reaction mixture was stirred at 25° C. for 1 hour. Then the reaction mixture was diluted with EtOAc (50 mL), washed with saturated aqueous $NH_4C$ solution (3×50 mL) and brine (3×50 mL). The organic layer was dried over anhydrous $Na_2SO_4$, filtered and concentrated in vacuo. The residue was purified by reversed phase flash chromatography (0.05% $NH_3.H_2O$-MeCN) to give the title compound (8 g, 79%) as a red oil.

$^1$H NMR ($CD_3OD$): δ 7.05 (d, 4H), 6.81-6.77 (m, 5H), 4.29 (s, 4H), 3.90 (s, 3H), 3.79-3.72 (m, 8H), 3.68-3.57 (m, 4H), 3.48-3.46 (m, 2H), 3.38 (s, 3H) and 3.27 (s, 3H).

LCMS: m/z 561.3 (M+H)$^+$ (ES$^+$).

Step E: N,N-Bis(2-methoxyethyl)-1-methyl-3-sulfamoyl-1H-pyrazole-5-carboxamide

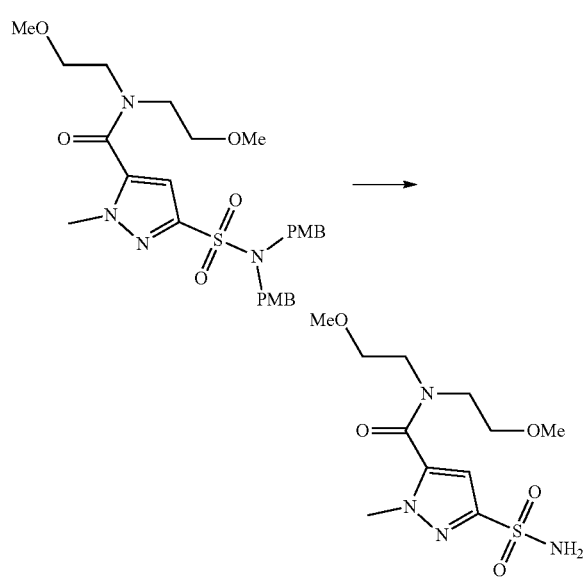

To a solution of 3-(N,N-bis(4-methoxybenzyl)sulfamoyl)-N,N-bis(2-methoxyethyl)-1-methyl-1H-pyrazole-5-carboxamide (8 g, 14.27 mmol, 1 eq) in DCM (50 mL) was added TFA (56 g, 491.13 mmol, 34.42 eq). The reaction mixture was stirred at 25° C. for 12 hours and then concentrated in vacuo. The residue was triturated with a mixture of EtOAc and PE (50 mL, v:v=3:2) to give the title compound (4.0 g, 88%) as a white solid.

$^1$H NMR (DMSO-$d_6$): δ 7.50 (s, 2H), 6.74 (s, 1H), 3.84 (s, 3H), 3.63 (t, 4H), 3.43-3.40 (m, 4H), 3.28 (s, 3H) and 3.18 (s, 3H).

Intermediate A1:
4-Isocyanato-1,2,3,5,6,7-hexahydro-s-indacene

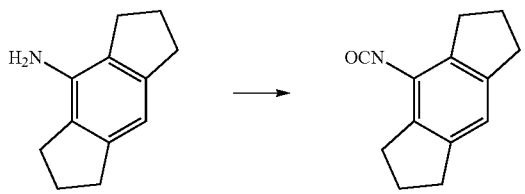

To a solution of phosgene (4.45 mL, 20% weight in toluene, 8.4 mmol) in EtOAc (90 mL) was added dropwise a solution of 1,2,3,5,6,7-hexahydro-s-indacen-4-amine (589 mg, 3.4 mmol) in EtOAc (45 mL) at ambient temperature. The resulting reaction mixture was then heated to reflux for 3 hours and upon cooling was filtered and concentrated in vacuo to afford the title compound as a brown oil (756 mg, 100%). The crude product was used directly in the next step without further purification.

$^1$H NMR (CDCl$_3$) δ 6.8 (s, 1H), 2.89 (m, 8H) and 2.09 (m, 4H).

Intermediate A2:
5-Fluoro-2-isocyanato-1,3-diisopropylbenzene

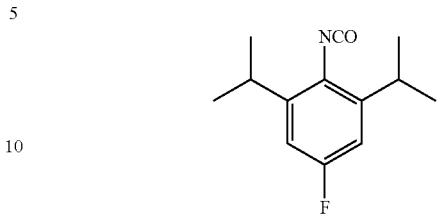

4-Fluoro-2,6-diisopropylaniline (1 g, 5.12 mmol) and triethylamine (0.785 mL, 5.63 mmol) were dissolved in THF (10 mL) and cooled to 0° C. Triphosgene (0.760 g, 2.56 mmol) was added to the mixture portionwise and the reaction mixture was stirred for 16 hours at room temperature. The mixture was concentrated in vacuo. Isohexane (so mL) was added and the suspension filtered through silica (3 g). The filtrate was dried under reduced pressure to afford the title compound (900 mg, 75%) as a colourless oil.

$^1$H NMR (DMSO-$d_6$) δ 6.8 (d, J=9.4 Hz, 2H), 3.27-3.12 (m, 2H), 1.23 (d, J=6.8 Hz, 12H).

Intermediate A3:
4-Fluoro-2-isopropyl-6-(pyridin-3-yl)aniline

Step A: 2-Bromo-4-fluoro-6-isopropylaniline

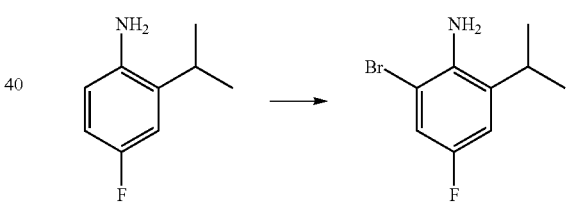

N-Bromosuccinimide (5.64 g, 31.7 mmol) was added portionwise to 4-fluoro-2-isopropylaniline (4.62 g, 30.2 mmol) in DCM (72 mL) at 0° C. The resulting mixture was stirred at 0° C. for 1 hour and then left to warm to room temperature over 21 hours. The reaction mixture was washed with a solution of aqueous sodium hydroxide (2 M, 2×50 mL), dried (MgSO$_4$), filtered and concentrated in vacuo to give a brown residue. The crude product was then filtered through a plug of silica (50 g) and washed through with 50% DCM in iso-hexane (500 mL). The red filtrate was concentrated to dryness and the crude product was purified by chromatography on silica gel (120 g column, 0-10% DCM/iso-hexane) to afford the title compound (4.99 g, 70%) as a red oil.

$^1$H NMR (CDCl$_3$) δ 7.07 (dd, 1H), 6.86 (dd, 1H), 4.14 (s, 2H), 2.93 (sept, 1H) and 1.25 (d, 6H). NH$_2$ not observed.

LCMS; m/z 232.2/234.3 (M+H)$^+$ (ES$^+$).

Step B: 4-Fluoro-2-isopropyl-6-(pyridin-3-yl)aniline

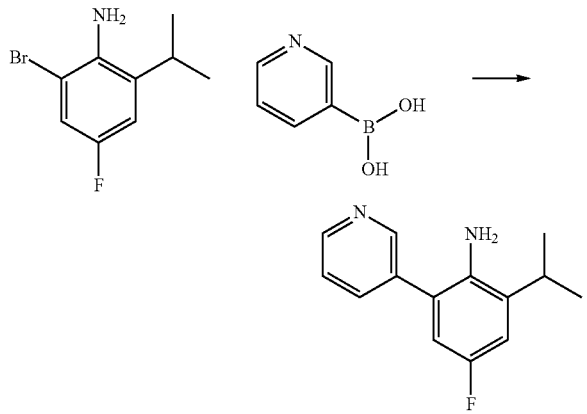

To a stirred, nitrogen-degassed mixture of 2-bromo-4-fluoro-6-isopropylaniline (1.00 g, 4.27 mmol) was added pyridin-3-ylboronic acid (0.577 g, 4.69 mmol), Pd(dppf)Cl$_2$ (0.156 g, 0.213 mmol) and potassium carbonate (1.769 g, 12.80 mmol) in a 10:1 mixture of 14-dioxane:water (33 mL). The reaction mixture was then heated to 80° C. under a nitrogen atmosphere for 2 days, left to cool to room temperature, filtered through a pad of Celite® (10 g) and the filter cake washed with EtOAc (2×30 mL). The filtrate was poured onto water (50 mL) and the organic layer collected. The aqueous layer was extracted with EtOAc (2×20 mL). The combined organic layers were dried (magnesium sulfate), filtered and evaporated to dryness. The crude product was purified by chromatography on silica gel (80 g column, 0-60% EtOAc/iso-hexane) to afford the title compound (273 mg, 27%) as a brown gum.

$^1$H NMR (CDCl$_3$) δ 8.70 (dd, 1H), 8.63 (dd, 1H), 7.82 (ddd, 1H), 7.48-7.34 (m, 1H), 6.94 (dd, 1H), 6.70 (dd, 1H), 2.93 (sept, 1H), 3.98-2.44 (br s, 2H) and 1.29 (d, 6H).

LCMS; m/z 231.1 (M+H)$^+$ (ES$^+$).

The following intermediates were synthesised following the general procedure for Intermediate A3:

| Intermediate | Structure | Analytical data |
|---|---|---|
| A4 | 5-Fluoro-3-isopropyl-[1,1'-biphenyl]-2-amine | $^1$H NMR (CDCl$_3$) δ 7.50-7.32 (m, 5H), 6.90 (dd, 1 H), 6.74 (dd, 1H), 4.11 (br s, 2H), 3.15-2.80 (m, 1H) and 1.29 (d, 6H). LCMS; m/z 230.1 (M + H)$^+$ (ES$^+$). (161 mg, 82%) |
| A5 | 2'-Amino-5'-fluoro-3'-isopropyl-[1,1'-biphenyl]-3-carbonitrile | $^1$H NMR (CDCl$_3$) δ 7.82-7.74 (m, 1H), 7.73-7.66 (m, 1H), 7.66-7.60 (m, 1H), 7.59-7.49 (m, 1H), 6.96 (dd, 1H), 6.69 (dd, 1 H), 3.10-2.84 (m, 1H), and 1.29 (d, 6H). LCMS; m/z 255.1 (M + H)$^+$ (ES$^+$). (182 mg, 81%) |
| A6 | 2-(1,3-Dimethyl-1H-pyrazol-5-yl)-4-fluoro-6-isopropylaniline | $^1$H NMR (CDCl$_3$) δ 6.95 (dd, 1H), 6.68 (dd, 1H), 6.09 (s, 1H), 3.69 (s, 3H), 2.98-2.81 (m, 1H), 2.33 (s, 3H) and 1.28 (d, 6H). LCMS; m/z 248.1 (M + H)$^+$ (ES$^+$). (72 mg, 34%) |

-continued

| Intermediate | Structure | Analytical data |
|---|---|---|
| A7 | 4-Fluoro-2-isopropyl-6-(2-methoxypyridin-4-yl)aniline | $^1$H NMR (CDCl$_3$) δ 8.25 (d, 1H), 7.00 (d, 1H), 6.93 (dd, 1H), 6.85 (s, 1H), 6.71 (dd, 1H), 4.01 (s, 3H), 2.92 (sept, 1H) and 1.28 (d, 6H). Exchangeable NH$_2$ observed as broad signal from 4.5-0.5 ppm. LCMS; m/z 261.1 (M + H)$^+$ (ES$^+$). (174 mg, 78%) |
| A8 | 4-Fluoro-2-isopropyl-6-(pyrimidin-5-yl)aniline | $^1$H NMR (CDCl$_3$) δ 9.23 (s, 1H), 8.86 (s, 2H), 6.98 (dd, 1H), 6.69 (dd, 1H), 3.55 (br s, 2H), 2.92 (sept, 1H) and 1.29 (d, 6H). (126 mg, 60%) |
| A9 | 4-(2-Amino-5-fluoro-3-isopropylphenyl)picolinonitrile | $^1$H NMR (CDCl$_3$) δ 8.78 (dd, 1H), 7.86 (dd, 1H), 7.65 (dd, 1H), 6.99 (dd, 1H), 6.69 (dd, 1H), 3.49 (br s, 2H), 2.93 (sept, 1H) and 1.29 (d, 6H). LCMS; m/z 256.5 (M + H)$^+$ (ES$^+$). (89 mg, 29%) |
| A10 | 4-Fluoro-2-isopropyl-6-(1-methyl-1H-pyrazol-4-yl)aniline | $^1$H NMR (CDCl$_3$) δ 7.68 (d, 1 H), 7.58 (d, 1 H), 6.86 (dd, 1 H), 6.78 (dd, 1 H), 3.99 (s, 3 H), 3.74 (br s, 2 H), 2.94 (sept, 1 H) and 1.29 (d, 6 H). (85 mg, 22%) |

Intermediate A11: 7-Fluoro-5-(2-methoxypyridin-4-yl)-2,3-dihydro-1H-inden-4-amine Step A:
N-(7-Fluoro-2,3-dihydro-1H-inden-4-yl)pivalamide

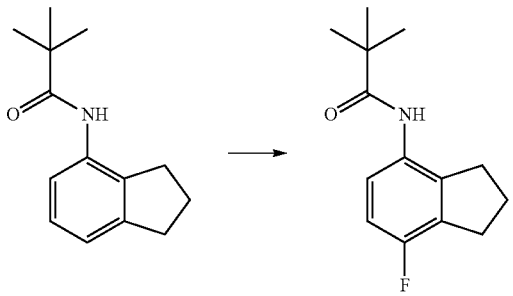 [SMILES: CC(C)(C)C(=O)Nc1cccc2c1CCC2 ; CC(C)(C)C(=O)Nc1ccc(F)c2c1CCC2]

To an ice-cooled solution of N-(2,3-dihydro-1H-inden-4-yl)pivalamide (2.5 g, 11.50 mmol) in dry DCM (50 mL) was added pyridine hydrofluoride (9 mL, 69.9 mmol). The pale yellow mixture was stirred for 30 minutes at 0° C. A solution of bis(tert-butylcarbonyloxy)iodobenzene (7.5 g, 17.91 mmol) in DCM (10 mL) was then slowly added over 10 minutes. The reaction was slowly allowed to reach room temperature and stirred overnight. It was then quenched with triethylamine (0.5 mL, 3.58 mmol) and the mixture was absorbed onto silica gel and purified by chromatography on silica gel (120 g column, 0-30% EtOAc/isohexane) to afford the title compound (0.64 g, 22%) as a yellow crystalline solid.

$^1$H NMR (CDCl$_3$) δ 7.68 (dd, J=8.8, 4.5 Hz, 1H), 7.14 (s, 1H), 6.87 (t, J=8.6 Hz, 1H), 3.01 (t, J=7.5 Hz, 2H), 2.85 (t, J=7.5 Hz, 2H), 2.18 (p, J=7.5 Hz, 2H), 1.34 (s, 9H).

LCMS; m/z 236.3 (M+H)$^+$ (ES$^+$); 234.2 (M−H)$^-$ (ES$^-$).

Step B: 7-Fluoro-2,3-dihydro-1H-inden-4-amine

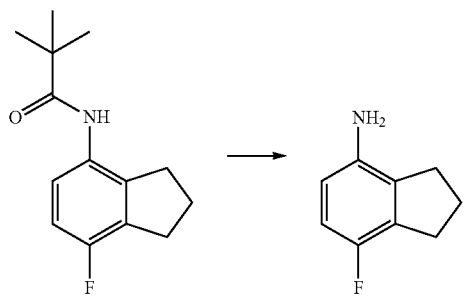 [SMILES: CC(C)(C)C(=O)Nc1ccc(F)c2c1CCC2 ; Nc1ccc(F)c2c1CCC2]

N-(7-Fluoro-2,3-dihydro-1H-inden-4-yl)pivalamide (0.632 g, 2.69 mmol) was dissolved in ethanol (5 mL) and stirred at room temperature. H$_2$SO$_4$ (95% aqueous) (5 mL, 89 mmol) was slowly added to water (5 mL) and this mixture was then added to the reaction mixture. The slurry was heated to 100° C. (bath temperature) over the weekend. The reaction mixture was cooled to room temperature, diluted with water (10 mL) and then basified with 2 M aqueous NaOH. The mixture was extracted with DCM (3×100 mL). The combined organic phases were washed, dried by passing through a hydrophobic frit and concentrated in vacuo. The crude product was purified by chromatography on silica gel (24 g column, 0-30% EtOAc/isohexane) to afford the title compound (350 mg, 82%) as a pale pink oil that solidified on standing.

$^1$H NMR (CDCl$_3$) δ 6.71 (dd, J=9.0, 8.2 Hz, 1H), 6.46 (dd, J=8.5, 3.9 Hz, 1H), 3.45 (s, 2H), 2.96 (t, J=7.6 Hz, 2H), 2.77 (t, J=7.5 Hz, 2H), 2.16 (p, J=7.6 Hz, 2H).

LCMS; m/z 152.3 (M+H)$^+$ (ES$^+$).

Step C:
5-Bromo-7-fluoro-2,3-dihydro-1H-inden-4-amine

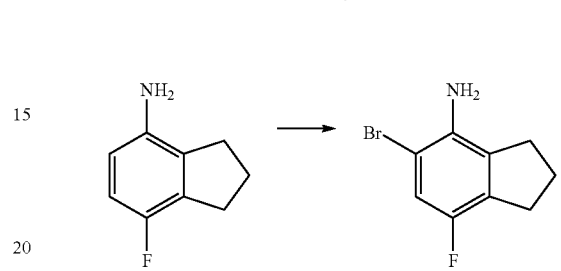

7-Fluoro-2,3-dihydro-1H-inden-4-amine (345 mg, 2.282 mmol) was dissolved in DCM (1 mL). NBS (450 mg, 2.53 mmol) was added at room temperature in a single portion. The mixture turned dark brown immediately and was stirred for 15 minutes at room temperature. The reaction mixture was partitioned between DCM (20 mL) and 1 M aqueous NaOH (20 mL) and stirred for 15 minutes. The organic phase was separated and washed with brine (10 mL), and then dried by passing through a hydrophobic frit. The solvent was removed in vacuo to give a dark brown oil. The crude product was purified by chromatography on silica gel (24 g column, 0-20% EtOAc/isohexane) to afford the title compound (323 mg, 82%) as a dark purple oil.

$^1$H NMR (CDCl$_3$) δ 7.08 (d, J=7.8 Hz, 1H), 3.06 (t, J=7.5 Hz, 2H), 2.95 (t, J=7.5 Hz, 2H), 2.20 (p, J=7.6 Hz, 2H). NH$_2$ not observed.

Step D: 7-Fluoro-5-(2-methoxypyridin-4-yl)-2,3-dihydro-1H-inden-4-amine

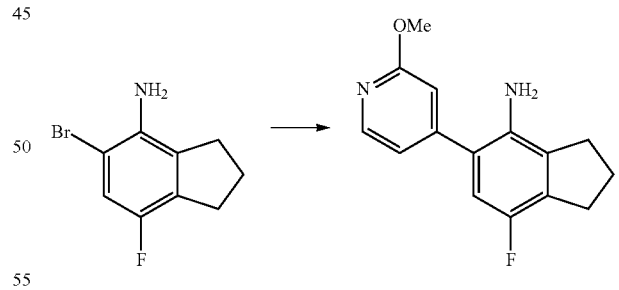

Prepared according to the general procedure of 5-(2-methoxypyridin-4-yl)-2,3-dihydro-1H-inden-4-amine (Intermediate A14) from 5-bromo-7-fluoro-2,3-dihydro-1H-inden-4-amine and (2-methoxypyridin-4-yl)boronic acid to afford the title compound (0.19 g, 49%) as a pale brown oil that crystallized on standing.

$^1$H NMR (CDCl$_3$) δ 8.27 (d, J=5.4 Hz, 1H), 7.06 (d, J=5.3 Hz, 1H), 6.95 (s, 1H), 6.73 (d, J=9.0 Hz, 1H), 4.03 (s, 3H), 3.00 (t, J=7.5 Hz, 2H), 2.85 (t, J=7.4 Hz, 2H), 2.23 (p, J=7.5 Hz, 2H). NH$_2$ not observed.

LCMS; m/z 259.3 (M+H)$^+$ (ES$^+$).

Intermediate A12: 7-Fluoro-5-(pyridin-3-yl)-2,3-dihydro-1H-inden-4-amine

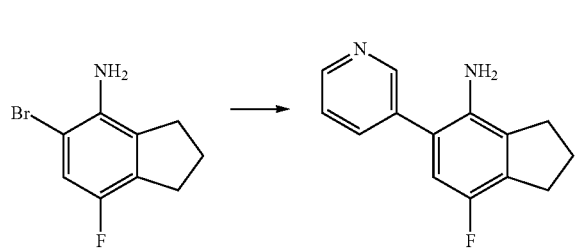 [SMILES: Nc1c(Br)cc(F)c2c1CCC2 ; Nc1c(-c2cccnc2)cc(F)c2c1CCC2]

Prepared according to the general procedure of 5-(2-methoxypyridin-4-yl)-2,3-dihydro-1H-inden-4-amine (Intermediate A14) from 5-bromo-7-fluoro-2,3-dihydro-1H-inden-4-amine (Intermediate A11, Step C) and pyridin-3-ylboronic acid to afford the title compound (0.32 g, 68%) as a green crystalline solid.

$^1$H NMR (CDCl$_3$) δ 8.79 (s, 1H), 8.65 (s, 1H), 8.00 (d, J=7.1 Hz, 1H), 7.56 (s, 1H), 6.71 (d, J=8.9 Hz, 1H), 3.04 (t, J=7.6 Hz, 2H), 2.83 (t, J=7.4 Hz, 2H), 2.24 (p, J=7.5 Hz, 2H). NH$_2$ not observed.

LCMS; m/z 229.3 (M+H)$^+$ (ES$^+$).

Intermediate A13: 5-Bromo-2,3-dihydro-1H-inden-4-amine

Step A: N-(5-Bromo-2,3-dihydro-1H-inden-4-yl)pivalamide

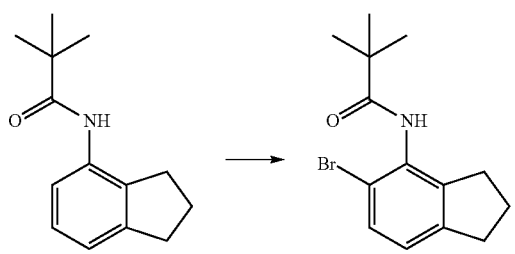 [SMILES: CC(C)(C)C(=O)Nc1cccc2c1CCC2 ; CC(C)(C)C(=O)Nc1c(Br)ccc2c1CCC2]

N-(2,3-dihydro-1H-inden-4-yl)pivalamide (1 g, 4.60 mmol), p-toluenesulfonic acid monohydrate (0.45 g, 2.366 mmol), Pd(OAc)$_2$ (0.05 g, 0.223 mmol), and NBS (0.9 g, 5.06 mmol) were suspended in toluene (20 mL) and stirred under air for 16 hours. The dark green mixture was diluted with EtOAc (20 mL), and then washed with saturated aqueous NaHCO$_3$ (2×10 mL), water (2×10 mL) and brine (10 mL). The organic phase was dried (Na$_2$SO$_4$), filtered and concentrated in vacuo to give a dark green amorphous solid. The crude product was purified by chromatography on silica gel (40 g column, 0-30% EtOAc/isohexane) to afford the title compound (1.662 g, 100%) as a colourless crystalline solid that was contaminated with a small amount of reaction byproducts.

LCMS; m/z 296.3/298.3 (M+H)$^+$ (ES$^+$).

Step B: 5-Bromo-2,3-dihydro-1H-inden-4-amine

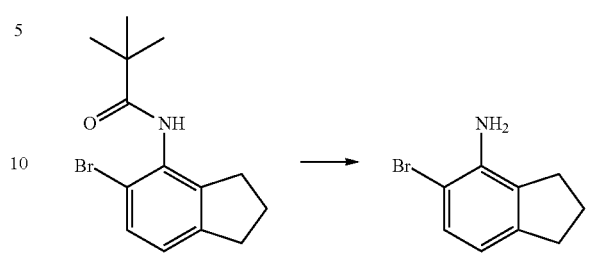

N-(5-Bromo-2,3-dihydro-1H-inden-4-yl)pivalamide (0.632 g, 2.134 mmol) was dissolved in ethanol (5 mL) and stirred at room temperature. H$_2$SO$_4$ (95% aqueous) (5 mL, 89 mmol) was slowly added to water (5 mL) and this mixture was then added to the reaction mixture. The slurry was heated to 100° C. (bath temperature) at which point the mixture became homogeneous and it was stirred at this temperature over the weekend. The mixture was cooled to room temperature and then basified with 2 M aqueous NaOH. The mixture was extracted with DCM (3×20 mL). The organic phases were dried by passing through a hydrophobic frit, and then concentrated in vacuo. The crude product was purified by chromatography on silica gel (40 g column, 0-50% EtOAc/isohexane) to afford the title compound (0.14 g, 29%).

$^1$H NMR (CDCl$_3$) δ 7.23 (d, J=7.9 Hz, 1H), 6.57 (d, J=8.0 Hz, 1H), 3.92 (s, 2H), 2.89 (t, J=7.6 Hz, 2H), 2.77 (t, J=7.4 Hz, 2H), 2.15 (p, J=7.5 Hz, 2H).

Intermediate A14: 5-(2-Methoxypyridin-4-yl)-2,3-dihydro-1H-inden-4-amine

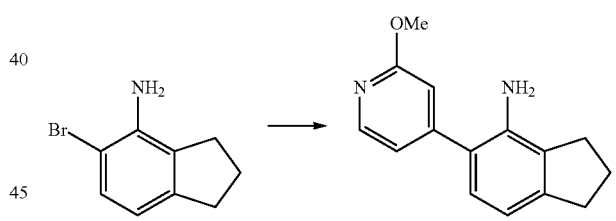

5-Bromo-2,3-dihydro-H-inden-4-amine (Intermediate A13) (280 mg, 1.320 mmol) was dissolved in dioxane (5 mL). A solution of potassium carbonate (600 mg, 4.34 mmol) in water (1 mL) and (2-methoxypyridin-4-yl)boronic acid (250 mg, 1.635 mmol) were added. The mixture was degassed with nitrogen for 15 minutes, before Pd(dppf)Cl$_2$·DCM (60 mg, 0.073 mmol) was added. The reaction mixture was heated to 80° C. (bath temperature) for 2 hours. The mixture was cooled to room temperature and partitioned between DCM (30 mL) and water (20 mL). The organic phase was dried by passing through a hydrophobic frit and concentrated in vacuo to give a brown oil. The crude product was purified by chromatography on silica gel (12 g column, 0-50% EtOAc/isohexane) to afford the title compound (0.29 g, 87%) as a pale yellow crystalline solid.

$^1$H NMR (CDCl$_3$) δ 8.26 (d, J=5.4 Hz, 1H), 7.11 (d, J=5.0 Hz, 1H), 7.01 (d, J=7.7 Hz, 1H), 6.97 (s, 1H), 6.80 (d, J=7.6 Hz, 1H), 4.06 (s, 3H), 2.98 (t, J=7.6 Hz, 2H), 2.80 (t, J=7.4 Hz, 2H), 2.19 (p, J=7.5 Hz, 2H). NH$_2$ not observed.

LCMS; m/z 241.3 (M+H)$^+$ (ES$^+$).

Intermediate A15: 4-Fluoro-2-isopropyl-6-(tetrahydro-2H-pyran-4-yl) aniline

Step A: 2-Bromo-4-fluoro-6-(prop-1-en-2-yl)aniline

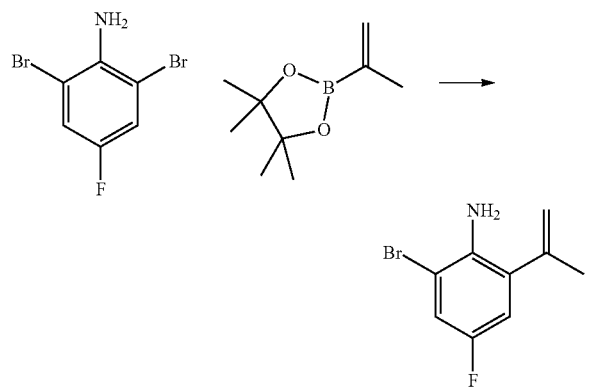

Nitrogen gas was bubbled through a mixture of 2,6-dibromo-4-fluoroaniline (5 g, 18.59 mmol), 4,4,5,5-tetramethyl-2-(prop-1-en-2-yl)-1,3,2-dioxaborolane (4.2 mL, 22.34 mmol) and potassium triphosphate (7.9 g, 37.2 mmol) in dioxane (50 mL) and water (8 mL) for 15 minutes. Then (2-dicyclohexylphosphino-2',4',6'-triisopropyl-1,1'-biphenyl)[2-(2'-amino-1,1'-biphenyl)]palladium(II) methanesulfonate [XPhos G3 Pd cat (500 mg, 0.591 mmol)] was added. The mixture was heated at 90° C. for 8 hours and then partitioned between hexane (200 mL) and water (100 mL). The organic layer was dried (magnesium sulfate), filtered, evaporated in vacuo and the residue purified by chromatography on silica gel (120 g column, 0-2% EtOAc/iso-hexane) to afford the title compound (1.95 g, 43%) as an oil.

$^1$H NMR (CDCl$_3$) δ 7.13 (dd, 1H), 6.77 (dd, 1H), 5.37-5.35 (m, 1H), 5.12-5.10 (m, 1H), 3.52 (br s, 2H) and 2.08-2.06 (m, 3H).

LCMS; m/z 230.2 (M+H)$^+$ (ES$^+$).

Step B: 2-(3,6-Dihydro-2H-pyran-4-yl)-4-fluoro-6-(prop-1-en-2-yl)aniline

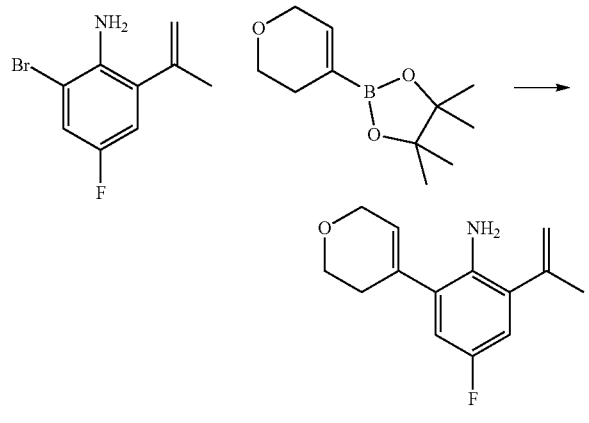

2-(3,6-Dihydro-2H-pyran-4-yl)-4,4,5,5-tetramethyl-1,3,2-dioxaborolane (457 mg, 2.176 mmol), tetrakis(triphenylphosphine)palladium(0) (251 mg, 0.218 mmol), sodium carbonate (923 mg, 8.70 mmol) and water (4 mL) were added to a sealed vial containing a solution of 2-bromo-4-fluoro-6-(prop-1-en-2-yl)aniline (500 mg, 2.173 mmol) in DMF (22 mL). The reaction mixture was heated under nitrogen at 100° C. overnight and then allowed to cool. The reaction mixture was diluted with EtOAc (50 mL), washed with brine (50 mL), dried (sodium sulfate) and concentrated in vacuo. The crude product was purified by chromatography on silica (40 g column, 0-20% EtOAc/iso-hexanes) to afford the title compound (355 mg, 65%) as a brownish oil.

$^1$H NMR (CDCl$_3$) δ 6.71 (dd, 1H), 6.67 (dd, 1H), 5.88 (m, 1H), 5.35-5.31 (m, 1H), 5.09 (m, 1H), 4.32 (m, 2H), 3.95 (t, J=5.4 Hz, 2H), 3.82 (br s, 2H), 2.42 (m, 2H) and 2.09-2.07 (m, 3H).

Step C: 4-Fluoro-2-isopropyl-6-(tetrahydro-2H-pyran-4-yl)aniline

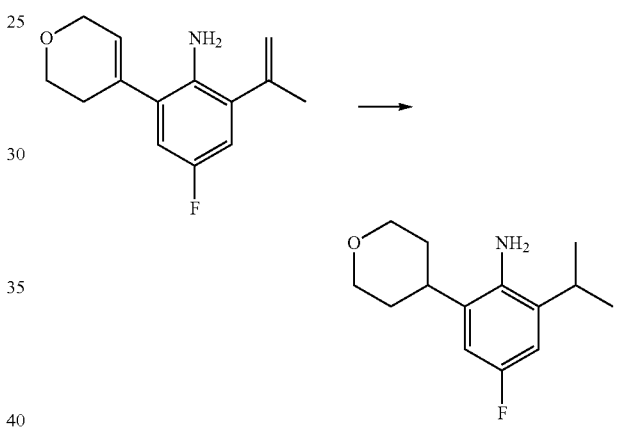

A mixture of 2-(3,6-dihydro-2H-pyran-4-yl)-4-fluoro-6-(prop-1-en-2-yl)aniline (355 mg, 1.522 mmol) and 5% palladium on carbon (156 mg, 0.03 mmol; type 87L (58.5% moisture)) in EtOAc (3.8 mL) was hydrogenated at 5 bar for 1 hour. The mixture was filtered through Celite® and evaporated to afford the title compound (340 mg, 91%).

$^1$H NMR (CDCl$_3$) δ 6.80 (dd, 1H), 6.75 (dd, 1H), 4.16-4.14 (m, 1H), 4.13-4.10 (m, 1H), 3.65-3.51 (m, 4H), 3.01-2.89 (m, 1H), 2.85-2.74 (m, 1H), 1.86-1.78 (m, 4H) and 1.28 (d, 6H).

LCMS; m/z 238.1 (M+H)$^+$ (ES$^+$).

Intermediate A16: 2-Isopropyl-5-(1-methyl-1H-pyrazol-4-yl)aniline

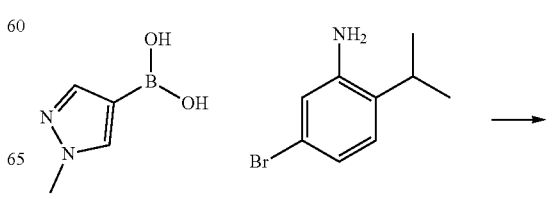

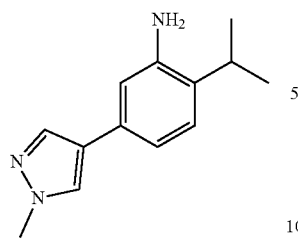

To a sealed vial was added 5-bromo-2-isopropylaniline (250 mg, 1.168 mmol) in DMF (11 mL), followed by the addition of (1-methyl-1H-pyrazol-4-yl)boronic acid (147 mg, 1.168 mmol), Pd(PPh$_3$)$_4$ (135 mg, 0.117 mmol) and aqueous 2 M Na$_2$CO$_3$ (2.335 mL, 4.67 mmol). The reaction mixture is heated under Argon at 100° C. overnight. The reaction mixture was diluted with EtOAc (20 mL), washed with brine (20 mL), dried over anhydrous Na$_2$SO$_4$, filtered, concentrated, and then purified by chromatography on silica gel (40 g column, 0-60% EtOAc/iso-hexane) to afford the title compound (90 mg, 36%) as a white solid.

$^1$H NMR (CDCl$_3$) δ 7.70 (d, J=0.9 Hz, 1H), 7.54 (s, 1H), 7.13 (d, J=7.9 Hz, 1H), 6.90 (dd, J=7.9, 1.8 Hz, 1H), 6.80 (d, J=1.8 Hz, 1H), 3.93 (s, 3H), 3.69 (bs, 2H), 2.90 (sept, J=6.8 Hz, 1H), 1.27 (d, J=6.8 Hz, 6H).

Intermediate A17:
2-Isopropyl-5-(pyrimidin-5-yl)aniline

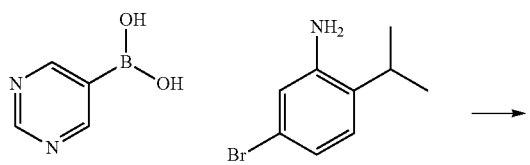

Prepared according to the general procedure for 2-isopropyl-5-(1-methyl-1H-pyrazol-4-yl)aniline (Intermediate A16) from 5-bromo-2-isopropylaniline and pyrimidin-5-ylboronic acid to afford the title compound (130 mg, 51%) as a white solid.

$^1$H NMR (CDCl$_3$) δ 9.16 (s, 1H), 8.91 (s, 2H), 7.28 (d, J=7.9 Hz, 1H), 6.98 (dd, J=8.0, 1.9 Hz, 1H), 6.87 (d, J=1.9 Hz, 1H), 3.84 (bs, 2H), 2.95 (sept, J=6.8 Hz, 1H), 1.31 (d, J=6.8 Hz, 6H).

Intermediate A18: 2,5-Diisopropylaniline

Step A: 2-Isopropyl-5-(prop-1-en-2-yl)aniline

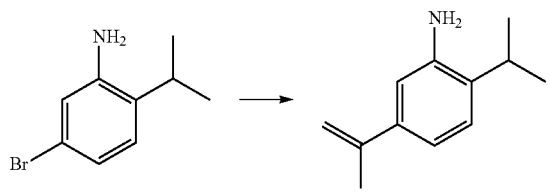

Nitrogen was bubbled through a mixture of 5-bromo-2-isopropylaniline (500 mg, 2.335 mmol), 4,4,5,5-tetramethyl-2-(prop-1-en-2-yl)-1,3,2-dioxaborolane (0.527 mL, 2.80 mmol) and Cs$_2$CO$_3$ (7609 mg, 23.35 mmol) in toluene (20 mL) and water (10 mL) for 15 minutes. Then palladium (II) acetate (157 mg, 0.701 mmol) and tricyclohexylphosphine (327 mg, 1.168 mmol) were added. The mixture was heated at 100° C. for 4 hours and then partitioned between hexane (50 mL) and water (20 mL). The organic layer was dried (MgSO$_4$), filtered and evaporated under reduced pressure. The crude product was purified by chromatography on silica gel (40 g column, 0-30% EtOAc/iso-hexane) to afford the title compound (227 mg, 53%) as an oil.

$^1$H NMR (CDCl$_3$) δ 7.13 (d, J=8.0 Hz, 1H), 6.94 (dd, J=8.0, 1.9 Hz, 1H), 6.83 (d, J=1.9 Hz, 1H), 5.37-5.30 (m, 1H), 5.03 (p, J=1.6 Hz, 1H), 3.69 (bs, 2H), 2.93 (sept, J=6.8 Hz, 1H), 2.17-2.11 (m, 3H), 1.29 (d, J=6.8 Hz, 6H).

Step B: 2,5-Diisopropylaniline

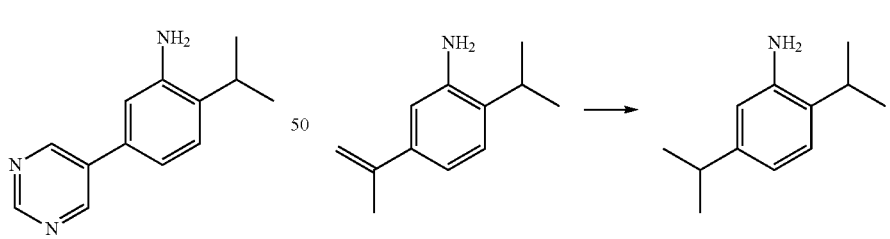

A mixture of 2-isopropyl-5-(prop-1-en-2-yl)aniline (227 mg, 1.295 mmol) and 5% Pd/C (0.133 g, 0.026 mmol) (Type 87 μL, 58-5% moisture) in EtOAc (3 mL) was hydrogenated at 5 bar for 16 hours. The mixture was filtered through Celite® and evaporated to afford the title compound (209 mg, 88%).

$^1$H NMR (CDCl$_3$) δ 7.06 (d, J=7.9 Hz, 1H), 6.66 (dd, J=7.9, 1.9 Hz, 1H), 6.56 (d, J=1.9 Hz, 1H), 3.71 (bs, 2H), 2.88 (sept, J=7.0 Hz, 1H), 2.78 (sept, J=7.0 Hz, 1H), 1.25 (d, J=7.1 Hz, 6H), 1.21 (d, J=6.9 Hz, 6H).

Intermediate A19:
2-Isocyanato-1,3-diisopropylbenzene

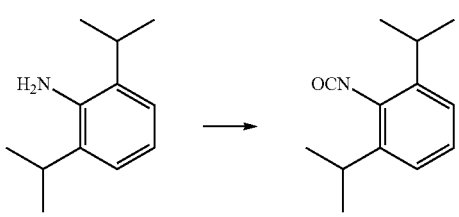

2,6-Diisopropylaniline (3.07 g, 17-14 mmol) was dissolved in dry THF (40 mL) and Et₃N (3 mL, 21.52 mmol) was added. A solution of triphosgene (4.26 g, 14.35 mmol) in dry THF (12 mL) was added over 5 minutes, resulting in the formation of a thick colourless precipitate. The reaction mixture was stirred at room temperature overnight.

The THF was removed in vacuo and toluene (50 mL) was added. The mixture was filtered through a short silica plug eluting with toluene (150 mL). The filtrate was concentrated in vacuo to afford the title compound (2.76 g, 92%) as a colourless oil.

$^1$H NMR (CDCl$_3$) δ 7.20-7.10 (m, 3H), 3.22 (hept, J=6.9 Hz, 2H), 1.26 (d, J=6.8 Hz, 12H).

Intermediate A20: 4-(4-Isocyanato-2,3-dihydro-1H-inden-5-yl)-2-methoxypyridine

Step A: 4-Nitro-2,3-dihydro-1H-indene

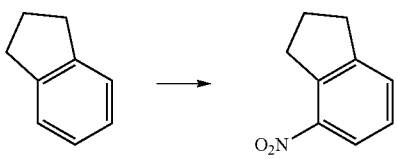 [SMILES: c1ccc2c(c1)CCC2 ; O=[N+]([O-])c1cccc2c1CCC2]

To a mixture of 2,3-dihydro-1H-indene (60 g, 507.72 mmol, 62.50 mL, 1 eq) in concentrated H$_2$SO$_4$ (30 mL) was added a mixture of HNO$_3$ (50 mL, 69 wt % in water) and concentrated H$_2$SO$_4$ (50 mL) dropwise at 0° C. over a period of 3.5 hours. The reaction mixture was stirred at 0° C. for 0.5 hour. Then the reaction mixture was poured into ice water (600 mL) and extracted with ethyl acetate (2×400 mL). The combined organic layers were washed with water (500 mL), saturated aqueous NaHCO$_3$ solution (500 mL) and brine (2×500 mL). The organic layer was dried over anhydrous Na$_2$SO$_4$, filtered and concentrated in vacuo. The residue was purified by silica gel column chromatography (SiO$_2$, petroleum ether:ethyl acetate, 1:0 to 100:1) to give the title compound (55 g, 66%) as a colourless oil.

$^1$H NMR (CDCl$_3$): δ 7.98 (d, 1H), 7.51 (d, 1H), 7.30 (t, 1H), 3.41 (t, 2H), 302 (t, 2H) and 2.22-2.20 (m, 2H).

Step B: 2,3-Dihydro-1H-inden-4-amine

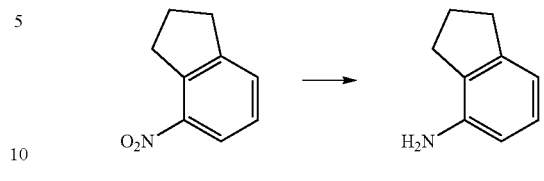

To a solution of 4-nitro-2,3-dihydro-1H-indene (55 g, contained another regio-isomer) in MeOH (500 mL) was added Pd/C (5 g, 10 wt % loading on activated carbon) under N$_2$ atmosphere. The suspension was degassed under vacuum and purged with H$_2$ several times. The reaction mixture was stirred under H$_2$ (50 psi) at 20° C. for 12 hours. The reaction mixture was filtered and the filtrate was concentrated in vacuo. The residue was purified by silica gel column chromatography (SiO$_2$, petroleum ether:ethyl acetate, 1:0 to 100:4) to give the title compound (19.82 g, 43% yield, 96.39% purity on LCMS) as a brown oil.

$^1$H NMR (CDCl$_3$): δ 7.01 (t, 1H), 6.71 (d, 1H), 6.51 (d, 1H), 3.57 (br s, 2H), 2.93 (t, 2H), 2.75 (t, 2H) and 2.16-2.08 (m, 2H).

LCMS: m/z 134.2 (M+H)$^+$ (ES$^+$).

Step C: N-(2,3-Dihydro-1H-inden-4-yl)acetamide

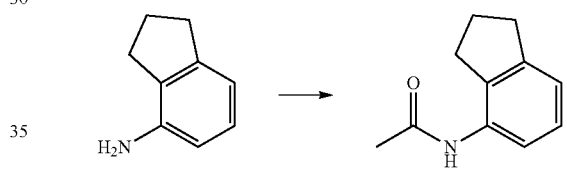

To a solution of 2,3-dihydro-1H-inden-4-amine (19.8 g, 148.66 mmol, 1 eq) and TEA (19.56 g, 193.26 mmol, 1.3 eq) in DCM (300 mL) was added dropwise Ac$_2$O (17.45 g, 170.96 mmol, 1.15 eq) over 6 minutes at 0° C. Then the reaction mixture was warmed to 16° C. and stirred for 1.4 hours. The mixture was poured into water (500 mL) and extracted with DCM (2×300 mL). The combined organic phases were washed with brine (2×500 mL), dried over anhydrous Na$_2$SO$_4$, filtered and concentrated in vacuo to give the title compound (25.74 g, 96% yield, 96.69% purity on LCMS) as a white solid.

$^1$H NMR (CDCl$_3$): δ 7.70 (d, 1H), 7.15 (t, 1H), 7.02 (d, 1H), 2.95 (t, 2H), 2.81 (t, 2H), 2.18 (s, 3H) and 2.15-2.08 (m, 2H).

LCMS: m/z 176.2 (M+H)$^+$ (ES$^+$)

Step D: N-(5-Bromo-2,3-dihydro-1H-inden-4-yl)acetamide

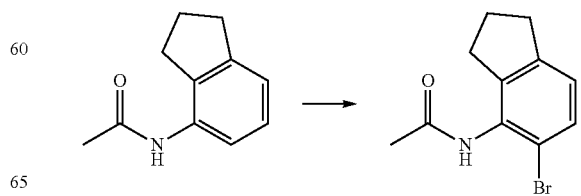

N-(2,3-dihydro-1H-inden-4-yl)acetamide (34.6 g, 197.46 mmol, 1 eq), p-toluenesulfonic acid (18.70 g, 108.60 mmol, 0.55 eq) and Pd(OAc)$_2$ (2.22 g, 9.87 mmol, 0.05 eq) were suspended in toluene (400 mL) and stirred at 20° C. for 0.5 hour under air atmosphere. NBS (38.66 g, 217.20 mmol, 1.1 eq) was added. Then the reaction mixture was stirred at 20° C. for 2 hours. The reaction mixture was poured into water (500 mL) and extracted with ethyl acetate (2×500 mL). The combined organic phases were washed with brine (2×500 mL), dried over anhydrous Na$_2$SO$_4$, filtered and concentrated in vacuo. The residue was purified by silica gel column chromatography (SiO$_2$, petroleum ether:ethyl acetate, 10:1 to 2:1) to give the title compound (13.9 g, 27% yield, 98.1% purity on LCMS) as a white solid.

$^1$H NMR (CDCl$_3$): δ 7.33 (d, 1H), 7.16 (s, 1H), 6.98 (d, 1H), 2.92-2.83 (m, 4H), 2.21 (s, 3H) and 2.10-2.02 (m, 2H).

LCMS: m/z 254.1 (M+H)$^+$ (ES$^+$).

Step E: 5-Bromo-2,3-dihydro-1H-inden-4-amine

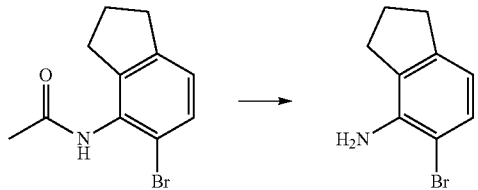

A mixture of N-(5-bromo-2,3-dihydro-1H-inden-4-yl)acetamide (45.68 g, 179.76 mmol, 1 eq) in EtOH (200 mL) and concentrated HCl (300 mL, 36 wt % in water) was stirred at 80° C. for 36 hours. The reaction mixture was cooled to 0° C. in an ice bath and some solid precipitated. The suspension was filtered. The filter cake was washed with ice water (50 mL) and dried in vacuo to give the title compound (34.1 g, 72% yield, 94.08% purity on LCMS, HCl salt) as a grey solid.

$^1$H NMR (DMSO-d$_6$): δ 7.67 (br S, 2H), 7.24 (d, 1H), 6.69 (d, 1H), 2.85 (t, 2H), 2.79 (t, 2H) and 2.04-1.96 (m, 2H).

LCMS: m/z 212.0 (M+H)$^+$ (ES$^+$).

Step F: 5-(2-Methoxypyridin-4-yl)-2,3-dihydro-1H-inden-4-amine

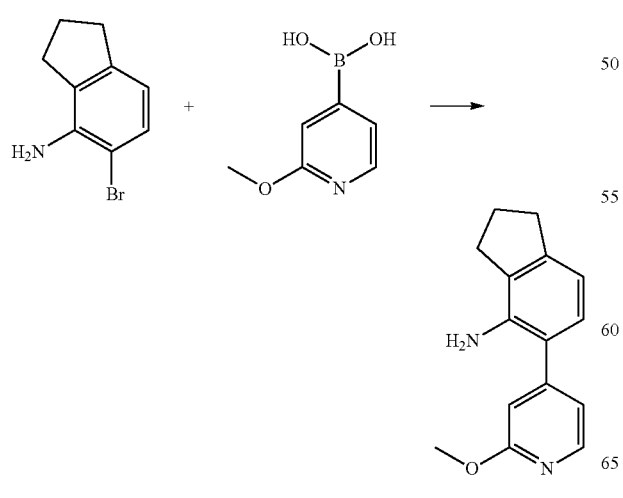

A solution of (2-methoxypyridin-4-yl)boronic acid (25.11 g, 164.15 mmol, 1.2 eq), 5-bromo-2,3-dihydro-1H-inden-4-amine (34 g, 136.80 mmol, 1 eq, HCl salt) and K$_2$CO$_3$ (60.50 g, 437-74 mmol, 3.2 eq) in dioxane (500 mL) and H$_2$O (100 mL) was degassed with nitrogen for 15 minutes before Pd(dppf)Cl$_2$.CH$_2$Cl$_2$ (6 g, 7.35 mmol, 0.053 eq) was added. The reaction mixture was heated to 80° C. for 12 hours. The mixture was poured into water (500 mL) and extracted with ethyl acetate (2×500 mL). The combined organic phases were washed with brine (2×700 mL), dried over anhydrous Na$_2$SO$_4$, filtered and concentrated in vacuo. The residue was purified by silica gel column chromatography (SiO$_2$, petroleum ether:ethyl acetate, 1:0 to 10:1) to give the title compound (27.4 g, 79% yield, 95% purity on LCMS) as a white solid.

$^1$H NMR (CDCl$_3$): δ 8.22 (d, 1H), 7.03-7.00 (m, 1H), 6.99 (d, 1H), 6.87 (s, 1H), 6.77 (d, 1H), 3.99 (s, 3H), 3.77 (br s, 2H), 2.97 (t, 2H), 2.77 (t, 2H) and 2.21-2.13 (m, 2H).

LCMS: m/z 241.2 (M+H)$^+$ (ES$^+$).

Step G: 4-(4-Isocyanato-2,3-dihydro-1H-inden-5-yl)-2-methoxypyridine

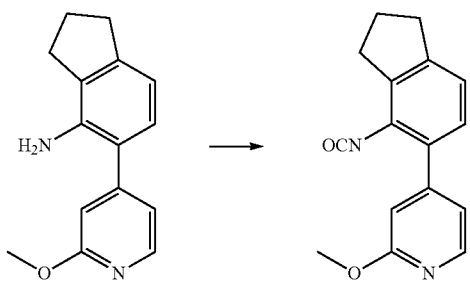

To a solution of 5-(2-methoxypyridin-4-yl)-2,3-dihydro-1H-inden-4-amine (11 g, 45.78 mmol, 1 eq) and TEA (5.10 g, 50-35 mmol, 1.1 eq) in THF (275 mL) was added bis(trichloromethyl) carbonate (4.93 g, 16.61 mmol, 0.36 eq) in portions at 0° C. Then the reaction mixture was stirred at 16° C. for 0.5 hour. The reaction mixture was filtered and the filter cake was washed with THF (2 L). The filtrate was concentrated in vacuo to give the title compound (9.04 g, 74%) as a light yellow solid.

$^1$H NMR (CDCl$_3$): δ 8.28 (d, 1H), 7.20-7.16 (m, 3H), 7.02 (s, 1H), 4.16 (s, 3H), 3.04-2.99 (m 4H) and 2.23-2.15 (m, 2H).

Intermediate A21: 4-(5-Fluoro-2-isocyanato-3-isopropylphenyl)-2-isopropoxypyridine Step A: 4-Fluoro-2-(prop-1-en-2-yl)aniline

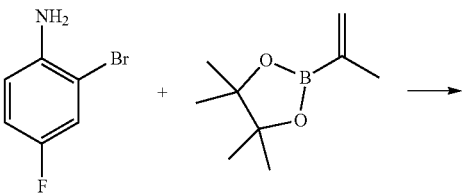

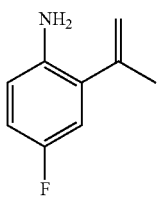

To a mixture of 2-bromo-4-fluoroaniline (39 g, 205.25 mmol, 1 eq), 4,4,5,5-tetramethyl-2-(prop-1-en-2-yl)-1,3,2-dioxaborolane (36.21 g, 215.51 mmol, 1.05 eq) and K$_2$CO$_3$ (70.92 g, 513.12 mmol, 2.5 eq) in dioxane (200 mL) and H$_2$O (40 mL) was added Pd(dppf)Cl$_2$ (7.51 g, 10.26 mmol, 0.05 eq) under N$_2$ atmosphere. Then the reaction mixture was stirred at 80° C. for 5 hours. The reaction mixture was quenched by addition of H$_2$O (600 mL) and extracted with EtOAc (2×500 mL). The combined organic layers were washed with brine (2×600 mL), dried over anhydrous Na$_2$SO$_4$, filtered and concentrated under reduced pressure. The residue was purified by silica gel column chromatography (petroleum ether:ethyl acetate=1:0 to 100:1) to give the title compound (27 g, 77% yield, 89% purity on LCMS) as a yellow oil.

$^1$H NMR (CDCl$_3$): δ 6.81-6.76 (m, 2H), 6.66-6.62 (m, 1H), 5.38 (s, 1H), 5.08 (s, 1H), 3.69 (br s, 2H) and 1.25 (s, 3H).

LCMS: m/z 152.2 (M+H)$^+$ (ES$^+$).

Step B: 4-Fluoro-2-isopropylaniline

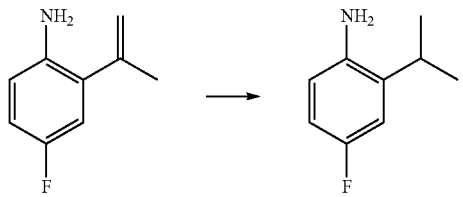

To a solution of 4-fluoro-2-(prop-1-en-2-yl)aniline (21 g, 138.91 mmol, 1 eq) in MeOH (300 mL) was added Pd/C (2.1 g, 178.59 mmol, 10 wt % loading on activated carbon) under N$_2$ atmosphere. The reaction mixture was degassed in vacuo and purged with H$_2$ several times. The reaction mixture was stirred at 25° C. for 12 hours under H$_2$ (50 psi). The reaction mixture was filtered and the filtrate was concentrated in vacuo to give the title compound (20 g, crude) as a yellow oil.

$^1$H NMR (CDCl$_3$): δ 6.86 (dd, 1H), 6.75-6.72 (m, 1H), 6.63-6.61 (m, 1H), 3.50 (br s, 2H), 2.95-2.84 (m, 1H) and 1.25 (d, 6H).

LCMS: m/z 154.2 (M+H)$^+$ (ES$^+$).

Step C: 2-Bromo-4-fluoro-6-isopropylaniline

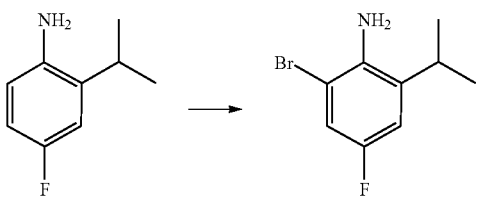

To a solution of 4-fluoro-2-isopropylaniline (20 g, 130.55 mmol, 1 eq) in toluene (250 mL) was added NBS (23.24 g, 130-55 mmol, 1 eq) at 25° C. The reaction mixture was stirred at 25° C. for 10 minutes. Then the reaction mixture was poured into H$_2$O (300 mL) and extracted with EtOAc (2×250 mL). The organic phases were washed with brine (2×400 mL), dried over anhydrous Na$_2$SO$_4$, filtered and concentrated in vacuo. The residue was purified by silica gel column chromatography (eluting only by using petroleum ether) to give the title compound (30 g, 99%) as a black brown oil.

$^1$H NMR (CDCl$_3$): δ 6.99 (dd, 1H), 6.78 (dd, 1H), 3.91 (br s, 2H), 2.88-2.71 (m, 1H) and 1.17 (d, 6H).

LCMS: m/z 232.1 (M+H)$^+$ (ES$^+$).

Step D: 4-Bromo-2-isopropoxypyridine

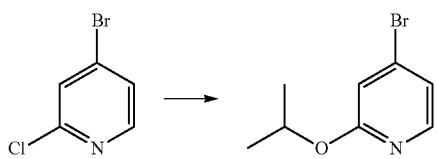

To a solution of 4-bromo-2-chloropyridine (20 g, 103.93 mmol, 1 eq) in THF (400 mL) was added NaH (6.24 g, 155.89 mmol, 60% purity, 1.5 eq) at 0° C. Then the mixture was stirred for 0.5 hour. Propan-2-ol (6.87 g, 114.32 mmol, 8.75 mL, 1.1 eq) was added and the resulting mixture was warmed to 50° C. and stirred for 12 hours. The reaction mixture was quenched with H$_2$O (1 L) at 25° C. and extracted with EtOAc (2×200 mL). The combined organic layers were washed with brine (200 mL), dried over Na$_2$SO$_4$, filtered and concentrated under reduced pressure. The residue was purified by column chromatography (SiO$_2$, petroleum ether:ethyl acetate=50:1 to 40:1) to give the title compound (22 g, 98%) as a light yellow oil.

$^1$H NMR (CDCl$_3$): δ 7.96 (d, 1H), 6.98 (dd, 1H), 6.89 (d, 1H), 5.44-5.24 (m, 1H) and 1.34 (d, 6H).

Step E: 2-Isopropoxy-4-(4,4,5,5-tetramethyl-1,3,2-dioxaborolan-2-yl)pyridine

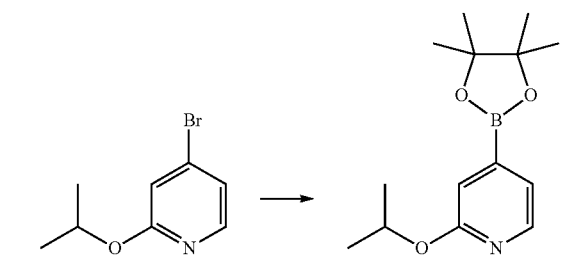 [SMILES: CC(C)Oc1cc(Br)ccn1 ; CC(C)Oc1cc(B2OC(C)(C)C(C)(C)O2)ccn1]

To a solution of 4-bromo-2-isopropoxypyridine (19 g, 87.93 mmol, 1 eq) and 4,4,4',4',5,5,5',5'-octamethyl-2,2'-bi(1,3,2-dioxaborolane) (22.33 g, 87.93 mmol, 1 eq) in 1,4-dioxane (300 mL) was added KOAc (25.89 g, 263.80 mmol, 3 eq) followed by Pd(dppf)Cl$_2$ (1.93 g, 2.64 mmol, 0.03 eq) under nitrogen. Then the reaction mixture was heated to 80° C. and stirred for 12 hours. The mixture was concentrated in vacuo. The residue was purified by silica gel column chromatography (SiO$_2$, petroleum ether:ethyl acetate=50:1 to 20:1) to give the title compound (22 g, 95%) as a light yellow oil.

$^1$H NMR (CDCl$_3$): δ 8.16 (d, 1H), 7.13 (d, 1H), 7.08 (s, 1H), 5.32-5.24 (m, 1H), 1.34 (s, 12H) and 1.27 (s, 6H).

LCMS: m/z 264.2 (M+H)$^+$ (ES$^+$).

Step F: 4-Fluoro-2-(2-isopropoxypyridin-4-yl)-6-isopropylaniline

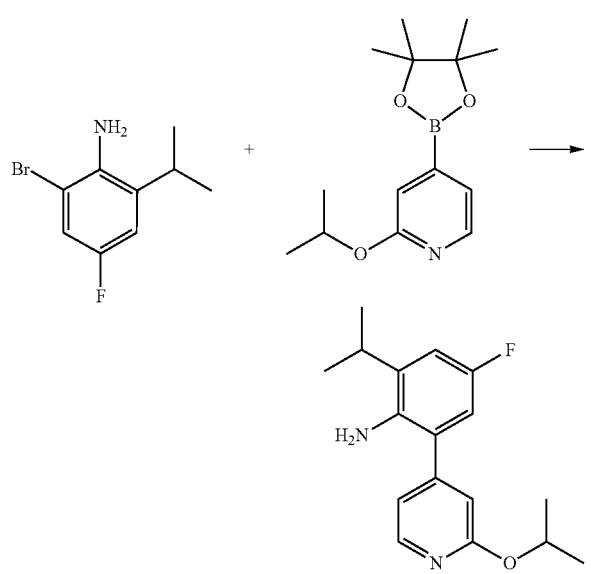

To a solution of 2-bromo-4-fluoro-6-isopropylaniline (10.94 g, 47.12 mmol, 1 eq) and 2-isopropoxy-4-(4,4,5,5-tetramethyl-1,3,2-dioxaborolan-2-yl)pyridine (12.4 g, 47.12 mmol, 1 eq) in 1,4-dioxane (200 mL) and H$_2$O (20 mL) was added Pd(dppf)Cl$_2$ (1.72 g, 2.36 mmol, 0.05 eq) followed by K$_2$CO$_3$ (19.54 g, 141-37 mmol, 3 eq) at 25° C. Then the reaction mixture was heated to 80° C. and stirred for 2 hours. The mixture was filtered and the filtrate was concentrated in vacuo. The residue was purified by silica gel column chromatography (SiO$_2$, petroleum ether:ethyl acetate=50:1 to 20:1) to give the title compound (10.3 g, 69% yield, 91% purity on LCMS) as a brown oil.

$^1$H NMR (CDCl$_3$): δ 8.21 (d, 1H), 6.94-6.91 (m, 2H), 6.76 (s, 1H), 6.72 (dd, 1H), 5.38-5.29 (m, 1H), 3.64 (br s, 2H), 2.98-2.89 (m, 1H), 1.38 (d, 6H) and 1.30-1.27 (m, 6H).

LCMS: m/z 289.2 (M+H)$^+$ (ES$^+$).

Step G: 4-(5-Fluoro-2-isocyanato-3-isopropylphenyl)-2-isopropoxypyridine

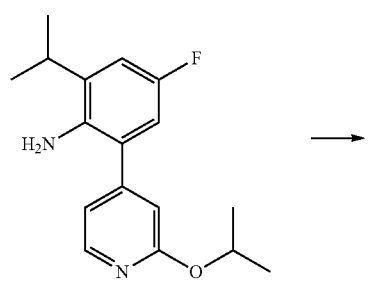

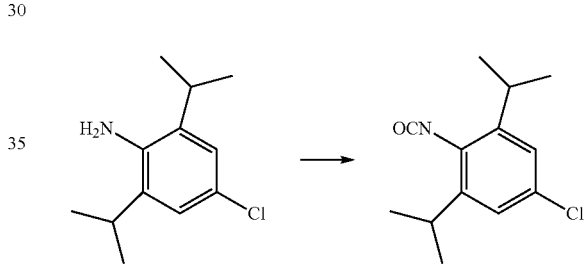

To a solution of 4-fluoro-2-(2-isopropoxypyridin-4-yl)-6-isopropylaniline (4 g, 13.87 mmol, 1 eq) in THF (80 mL) was added TEA (2.81 g, 27.74 mmol, 3.86 mL, 2 eq). The mixture was cooled to 0° C. and then triphosgene (1.65 g, 5.55 mmol, 0.4 eq) was added to the mixture. The resulting mixture was heated to 70° C. and stirred for 1 hour. The mixture was filtered and the filtrate was concentrated in vacuo. The residue was purified by silica gel column chromatography (SiO$_2$, petroleum ether:ethyl acetate=100:1 to 30:1) to give the title compound (1.9 g, 44% yield) as a yellow oil, which was used directly in the next step.

Intermediate A22:
5-Chloro-2-isocyanato-1,3-diisopropylbenzene

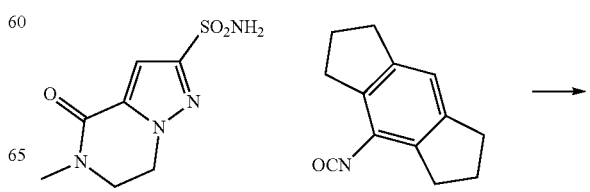

To a solution of 4-chloro-2,6-diisopropylaniline (0.105 g, 0.496 mmol) in toluene (1 mL) was added a phosgene solution (0.65 mL, 20 wt % in toluene, 1.22 mmol) and the reaction mixture was refluxed for 1 hour. Upon cooling, the mixture was concentrated in vacuo to afford the title compound as an orange oil (0.111 g, 94%).

$^1$H NMR (CDCl$_3$) δ 7.07 (d, 2H), 3.17 (h, 2H), 1.24 (d, 12H).

PREPARATION OF EXAMPLES

Example 1: N-((1,2,3,5,6,7-Hexahydro-s-indacen-4-yl)carbamoyl)-5-methyl-4-oxo-4,5,6,7-tetrahydropyrazolo[1,5-a]pyrazine-2-sulfonamide, Sodium Salt

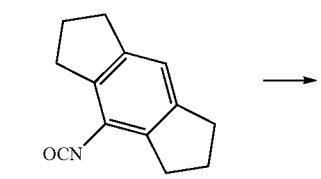

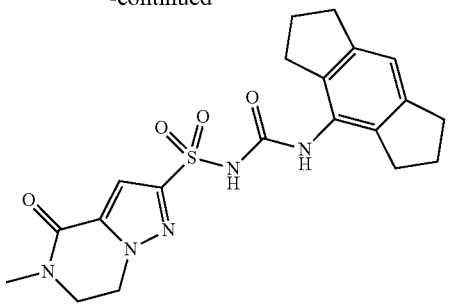

5-Methyl-4-oxo-4,5,6,7-tetrahydropyrazolo[1,5-a]pyrazine-2-sulfonamide (Intermediate P1) (59.8 mg, 0.26 mmol) was dissolved in THF:DMF (1:1) (4 mL) and sodium tert-butoxide (2M in THF) (0.136 ml, 0.273 mmol) was added. After stirring for 1 hour, 4-isocyanato-1,2,3,5,6,7-hexahydro-s-indacene (Intermediate A1) (54-3 mg, 0.273 mmol) was added and the reaction mixture was stirred at room temperature for 6 hours. Ethyl acetate (6 mL) was added and the suspension stirred for hours. The resultant precipitate was collected by filtration, washed with ethyl acetate (2 mL), triturated with ethyl acetate (5 mL) for 1 hour, filtered, and dried under reduced pressure to afford the title compound (73 mg, 60%) as a white solid.

$^1$H NMR (DMSO-$d_6$) δ 7.47 (s, 1H), 6.79-6.74 (m, 2H), 4.38-4.32 (m, 2H), 3.80-372 (m, 2H), 3.00 (s, 3H), 2.79-2.71 (m, 4H), 2.67 (t, J=7.2 Hz, 4H), 1.95-1.86 (m, 4H).

LCMS; m/z 430 (M+H)$^+$ (ES$^+$).

Example 2: 3-(N-((1,2,3,5,6,7-Hexahydro-s-indacen-4-yl)carbamoyl) sulfamoyl)-1-(2-(methylamino)ethyl)-1H-pyrazole-5-carboxylic Acid

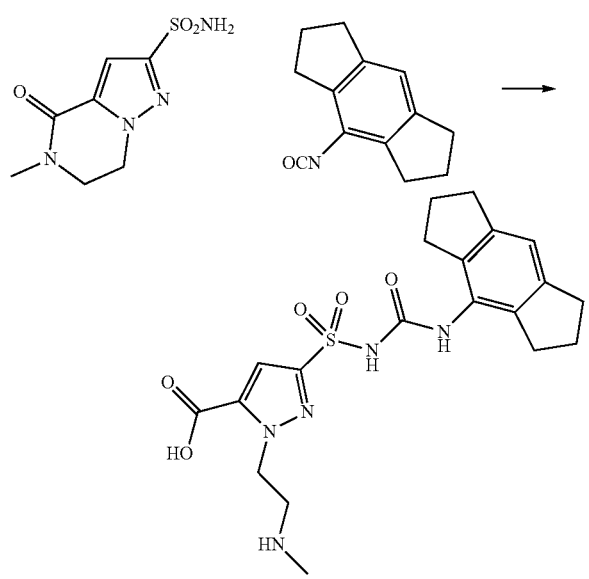

5-Methyl-4-oxo-4,5,6,7-tetrahydropyrazolo[1,5-a]pyrazine-2-sulfonamide (Intermediate P1) (80.5 mg, 0.350 mmol) was dissolved in THF (10 mL) and sodium tert-butoxide (2M in THF) (0.184 ml, 0.367 mmol) was added. After stirring for 1 hour, 4-isocyanato-1,2,3,5,6,7-hexahydro-s-indacene (Intermediate A1) (69.7 mg, 0.350 mmol) was added and the reaction mixture stirred at room temperature for 15 hours. The resultant precipitate was collected by filtration, washed with THF (1 mL), triturated with ethyl acetate (5 mL) for 1 hour, filtered, and purified by chromatography on silica gel (RP Flash C18) (13 g column, 0-50% acetonitrile/10 mM ammonium bicarbonate). The compound obtained was triturated with TBME (2 mL) for 2 hours, filtered and dried under reduced pressure to afford the title compound (91 mg, 56%) as a white solid. Ring opening occurred on purification.

$^1$H NMR (DMSO-$d_6$) δ 7.58 (s, 1H), 6.77 (s, 1H), 6.44 (s, 1H), 4.72-4.56 (m, 2H), 3.57-3.38 (m, 2H), 2.83-2.58 (m, 11H), 1.98-1.82 (m, 4H). Three exchangeable protons not visible.

LCMS; m/z 448 (M+H)$^+$ (ES$^+$).

Example 3: 1-(2-(Dimethylamino)ethyl)-5-((dimethylamino)methyl)-N-((1,2,3,5,6,7-hexahydro-s-indacen-4-yl)carbamoyl)-1H-pyrazole-3-sulfonamide

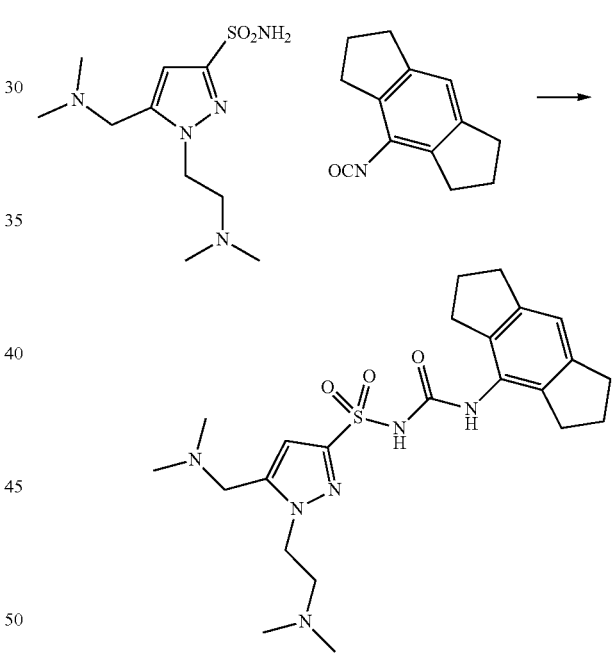

Prepared according to the general procedure of 3-(N-((1,2,3,5,6,7-hexahydro-s-indacen-4-yl)carbamoyl) sulfamoyl)-1-(2-(methylamino)ethyl)-1H-pyrazole-5-carboxylic acid (Example 2) from 1-(2-(dimethylamino)ethyl)-5-((dimethylamino)methyl)-1H-pyrazole-3-sulfonamide (Intermediate P2) and 4-isocyanato-1,2,3,5,6,7-hexahydro-s-indacene (Intermediate A1) to afford the title compound (40.1 mg, 46%) as a white solid.

$^1$H NMR (DMSO-$d_6$) δ 7.92 (s, 1H), 6.89 (s, 1H), 6.60 (s, 1H), 4.31 (t, J=6.8 Hz, 2H), 3.51 (s, 2H), 2.83-2.71 (m, 6H), 2.59 (t, J=7.4 Hz, 4H), 2.26 (s, 6H), 2.18 (s, 6H), 1.98-1.85 (m, 4H). One exchangeable proton not visible.

LCMS; m/z 475 (M+H)$^+$ (ES$^+$); 473 (M−H)$^−$ (ES$^−$).

Example 4: 1-(2-(Dimethylamino)ethyl)-N-((1,2,3,5,6,7-hexahydro-s-indacen-4-yl)carbamoyl)-5-(2-hydroxypropan-2-yl)-1H-pyrazole-3-sulfonamide

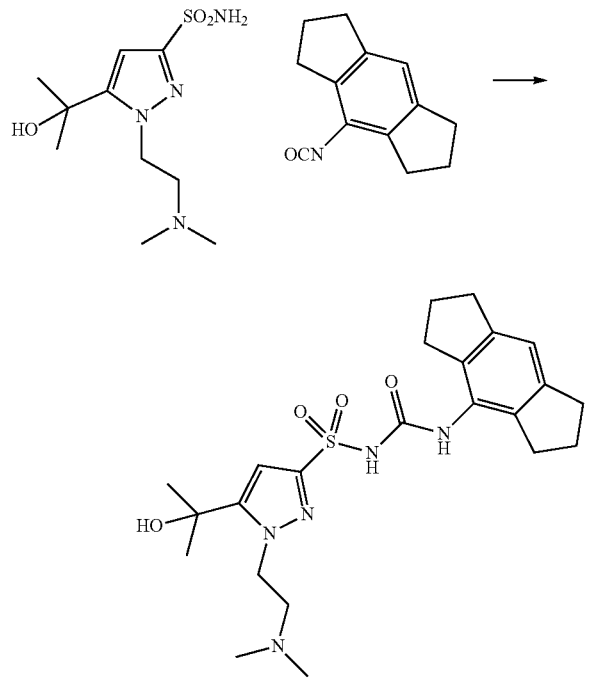

Prepared according to the general procedure of 3-(N-((1,2,3,5,6,7-hexahydro-s-indacen-4-yl)carbamoyl) sulfamoyl)-1-(2-(methylamino)ethyl)-1H-pyrazole-5-carboxylic acid (Example 2) from 1-(2-(dimethylamino)ethyl)-5-(2-hydroxypropan-2-yl)-1H-pyrazole-3-sulfonamide (Intermediate P3) and 4-isocyanato-1,2,3,5,6,7-hexahydro-s-indacene (Intermediate A1) to afford the title compound (23.7 mg, 27%) as a white solid.

$^1$H NMR (DMSO-d$_6$) δ 7.93 (s, 1H), 6.90 (s, 1H), 6.48 (s, 1H), 4.53 (t, J=7.2 Hz, 2H), 2.85 (t, J=7.1 Hz, 2H), 2.78 (t, J=7.4 Hz, 4H), 2.62 (t, J=7.3 Hz, 4H), 2.27 (s, 6H), 2.00-1.83 (m, 4H), 1.51 (s, 6H). Two exchangeable protons not visible.

LCMS; m/z 476 (M+H)$^+$ (ES$^+$); 474 (M–H)$^-$ (ES$^-$).

Example 5: N-((1,2,3,5,6,7-Hexahydro-s-indacen-4-yl)carbamoyl)-5-methyl-4,5,6,7-tetrahydropyrazolo[1,5-a]pyrazine-2-sulfonamide

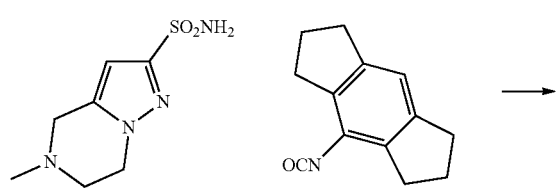

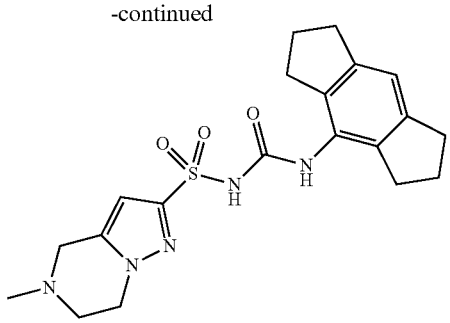

Prepared according to the general procedure of 3-(N-((1,2,3,5,6,7-hexahydro-s-indacen-4-yl)carbamoyl) sulfamoyl)-1-(2-(methylamino)ethyl)-1H-pyrazole-5-carboxylic acid (Example 2) from 5-methyl-4,5,6,7-tetrahydropyrazolo[1,5-a]pyrazine-2-sulfonamide (Intermediate P4) and 4-isocyanato-1,2,3,5,6,7-hexahydro-s-indacene (Intermediate A1) to afford the title compound (16 mg, 26%) as a colourless solid.

$^1$H NMR (DMSO-d$_6$) δ 10.78 (s, 1H), 7.94 (s, 1H), 6.92 (s, 1H), 6.49 (s, 1H), 4.15 (t, J=5.6 Hz, 2H), 3.60 (s, 2H), 2.88 (t, J=5.7 Hz, 2H), 2.79 (t, J=7.4 Hz, 4H), 2.61 (t, J=7.4 Hz, 4H), 2.39 (s, 3H), 2.05-1.86 (m, 4H).

LCMS; m/z 416 (M+H)$^+$ (ES$^+$).

Example 6: 1-(2-(Dimethylamino)ethyl)-N-((1,2,3,5,6,7-hexahydro-s-indacen-4-yl)carbamoyl)-5-isopropyl-1H-pyrazole-3-sulfonamide

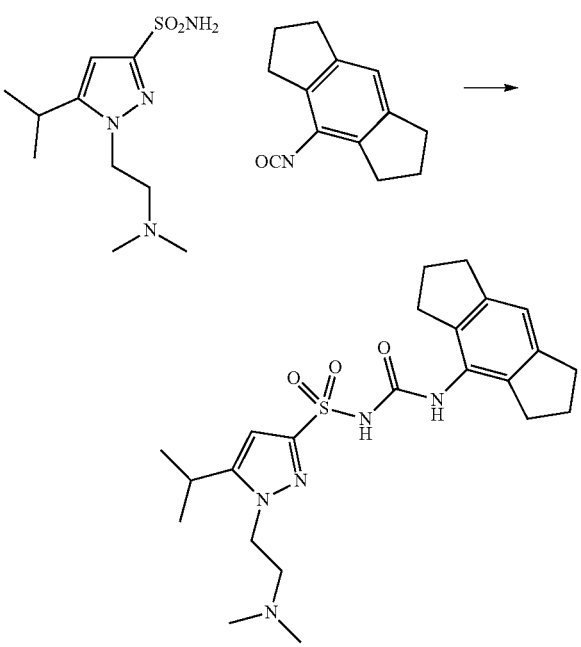

Prepared according to the general procedure of 3-(N-((1,2,3,5,6,7-hexahydro-s-indacen-4-yl)carbamoyl) sulfamoyl)-1-(2-(methylamino)ethyl)-1H-pyrazole-5-carboxylic acid (Example 2) from 1-(2-(dimethylamino)ethyl)-5-isopropyl-1H-pyrazole-3-sulfonamide (Intermediate P5) and 4-isocyanato-1,2,3,5,6,7-hexahydro-s-indacene (Intermediate A1) to afford the title compound (47 mg, 39%) as a white solid.

$^1$H NMR (DMSO-d$_6$) δ 11.28-9.98 (br s, 1H), 7.94 (s, 1H), 6.91 (s, 1H), 6.52 (s, 1H), 4.20 (t, J=6.8 Hz, 2H), 3.09

(sept, J=6.8 Hz, 1H), 2.78 (t, J=7.4 Hz, 4H), 2.70 (t, J=6.8 Hz, 2H), 2.60 (t, J=7.4 Hz, 4H), 2.20 (s, 6H), 1.93 (p, J=7.4 Hz, 4H), 1.21 (d, J=6.8 Hz, 6H).
LCMS; m/z 460.5 (M+H)⁺ (ES⁺); 458.3 (M−H)⁻ (ES⁻).

Example 7: 1-Cyclopropyl-5-((dimethylamino)methyl)-N-((1,2,3,5,6,7-hexahydro-s-indacen-4-yl)carbamoyl)-1H-pyrazole-3-sulfonamide

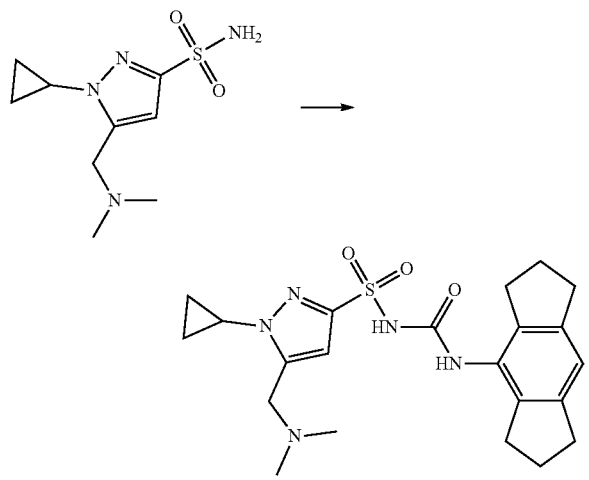

To a solution of 1-cyclopropyl-5-((dimethylamino)methyl)-1H-pyrazole-3-sulfonamide (Intermediate P6) (4.5 g, 18.42 mmol, 1 eq) in THF (50 mL) was added t-BuONa (1.86 g, 19.34 mmol, 1.05 eq). Then 4-isocyanato-1,2,3,5,6,7-hexahydro-s-indacene (Intermediate A1) (3.67 g, 18.42 mmol, 1 eq) was added. The reaction mixture was stirred at 70° C. for 10 minutes and then concentrated in vacuo. The residue was purified by reversed phase prep-HPLC (column: Synergi Max-Rᵝ; 250 mm*50 mm*10 μm; mobile phase: [water (10 mM NH₄HCO₃)-MeCN]; B %: 5%-35%, 20 minutes) to give the title compound (5.1 g, 61.8% yield, 99% HPLC purity, free acid) as a white solid.
¹H NMR (DMSO-d₆) δ 8.00 (s, 1H), 6.93 (s, 1H), 6.66 (s, 1H), 3.82-3.78 (m, 1H), 3.61 (s, 2H), 2.80-2.76 (m, 4H), 2.59-2.55 (m, 4H), 2.21 (s, 6H), 1.97-1.89 (m, 4H) and 1.11-1.04 (m, 4H).
LCMS: m/z 444.2 (M+H)⁺ (ES⁺).

Example 7B: 1-Cyclopropyl-5-((dimethylamino)methyl)-N-((1,2,3,5,6,7-hexahydro-s-indacen-4-yl)carbamoyl)-1H-pyrazole-3-sulfonamide, Sodium Salt

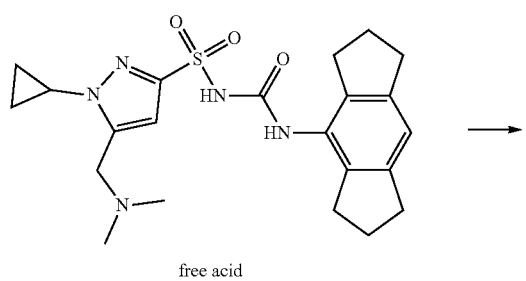
free acid

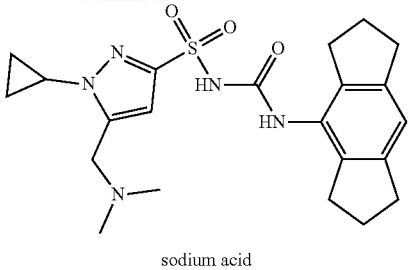
sodium acid

To a solution of 1-cyclopropyl-5-((dimethylamino)methyl)-N-((1,2,3,5,6,7-hexahydro-s-indacen-4-yl)carbamoyl)-1H-pyrazole-3-sulfonamide (Example 7) (3.7 g, 8.34 mmol, 1 eq) in THF (50 mL) was added t-BuONa (801 mg, 8.34 mmol, 1 eq). The reaction mixture was stirred at 25° C. for 1 hour and then concentrated in vacuo. The residue was triturated with TBME (25 mL). Then the mixture was filtered to give the title compound. The title compound combined with another batch (3.7 g) obtained in parallel was redissolved in H₂O (300 mL) and lyophilized to give the title compound (6.8 g, 87.36% yield, 100% HPLC purity, sodium salt) as a white solid.
¹H NMR (DMSO-d₆) δ 7.53 (s, 1H), 6.76 (s, 1H), 6.31 (s, 1H), 3.65-3.61 (m, 1H), 3.49 (s, 2H), 2.76-2.72 (m, 4H), 2.65-2.60 (m, 4H), 2.18 (s, 6H), 1.92-1.86 (m, 4H), 1.08-1.05 (m, 2H), 0.95-0.93 (m, 2H).
LCMS: m/z 444.2 (M+H)⁺ (ES⁺).

Example 8: N-((1,2,3,5,6,7-Hexahydro-s-indacen-4-yl)carbamoyl)-1-methyl-5-((methyl(1-methylazetidin-3-yl)amino)methyl)-1H-pyrazole-3-sulfonamide, Sodium Salt Prepared according to the general procedure of N-((1,2,3,5,6,7-hexahydro-s-indacen-4-yl)carbamoyl)-5-methyl-4-oxo-4,5,6,7-tetrahydropyrazolo[1,5-a]pyrazine-2-sulfonamide, sodium salt (Example 1) from 1-methyl-5-((methyl(1-methylazetidin-3-yl)amino)methyl)-1H-pyrazole-3-sulfonamide (Intermediate P69) and 4-isocyanato-1,2,3,5,6,7-hexahydro-s-indacene (Intermediate A1) to afford the title compound (13 mg, 23%) as a white solid.

$^1$H NMR (DMSO-d$_6$) δ 7.51 (s, 1H), 6.76 (s, 1H), 6.29 (s, 1H), 3.79 (s, 3H), 3.34 (m, 2H), 3.33 (s, 2H), 2.93 (p, J=6.5 Hz, 1H), 2.75 (t, J=7.4 Hz, 4H), 2.71-2.63 (m, 6H), 2.18 (s, 3H), 1.94 (s, 3H), 1.89 (p, J=7.4 Hz, 4H). NH not observed.

LCMS; m/z 473.5 (M+H)$^+$ (ES$^+$); 471.4 (M–H)$^-$ (ES$^-$).

Example 9: N-((4-Fluoro-2,6-diisopropylphenyl)carbamoyl)-1-methyl-5-((methyl(1-methylazetidin-3-yl)amino)methyl)-1H-pyrazole-3-sulfonamide, Sodium Salt

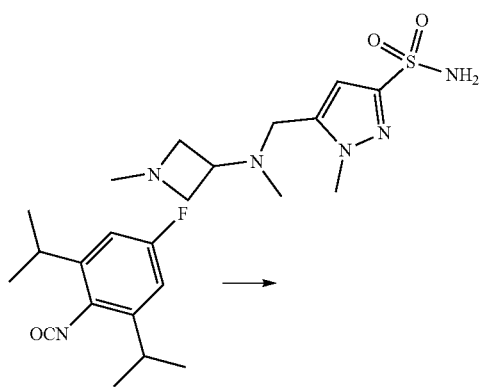

Prepared according to the general procedure of N-((1,2,3,5,6,7-hexahydro-s-indacen-4-yl)carbamoyl)-5-methyl-4-oxo-4,5,6,7-tetrahydropyrazolo[1,5-a]pyrazine-2-sulfonamide, sodium salt (Example 1) from 1-methyl-5-((methyl(1-methylazetidin-3-yl)amino)methyl)-1H-pyrazole-3-sulfonamide (Intermediate P69) and 5-fluoro-2-isocyanato-1,3-diisopropylbenzene (Intermediate A2) to afford the title compound (31 mg, 54%) as a white solid.

$^1$H NMR (DMSO-d$_6$) δ 7.37 (s, 1H), 6.79 (d, J=10.1 Hz, 2H), 6.28 (s, 1H), 3.78 (s, 3H), 3.38-3.33 (m, 2H), 3.14 (m, 2H), 2.93 (p, J=6.6 Hz, 1H), 2.69 (t, J=7.2 Hz, 2H), 2.20 (s, 3H), 1.94 (s, 3H), 1.03 (d, J=6.8 Hz, 12H). 2H under solvent.

LCMS; m/z 495.5 (M+H)$^+$ (ES$^+$); 493.3 (M–H)$^-$ (ES$^-$).

Example 10: N-(3-(Dimethylamino)propyl)-3-(N-((1,2,3,5,6,7-hexahydro-s-indacen-4-yl)carbamoyl)sulfamoyl)-N,1-dimethyl-1H-pyrazole-5-carboxamide

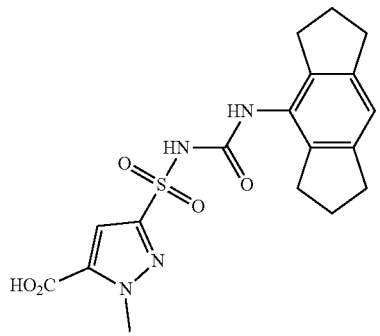

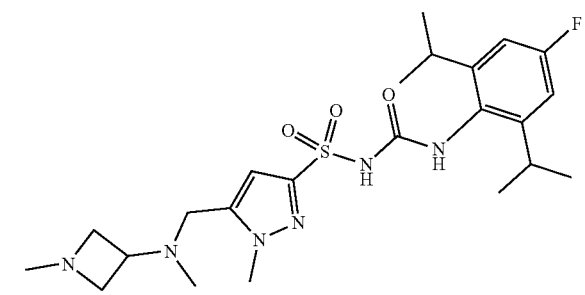

N1,N1,N3-Trimethylpropane-1,3-diamine (28 μl, 0.19 mmol), sodium bicarbonate (16 mg, 0.19 mmol) and HATU (72 mg, 0.19 mmol) were successively added to a suspension of 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) (70 mg, 0.156 mmol) in DMF (1 mL) and stirred at room temperature for 2 days. The reaction was quenched with water (1 mL) and purified by reversed phase prep-HPLC (General Methods, basic prep) to afford the title compound as a white solid (34 mg, 43%).

$^1$H NMR (DMSO-d$_6$) (rotamers) δ 7.77 (s, 1H), 6.83 (s, 1H), 6.80 & 6.72 (2×s, 1H), 3.85 & 3.81 (2×s, 3H), 3.47 & 3.30 (t, J=6.9 & 7.3 Hz, 2H), 3.01 & 2.96 (2×s, 3H), 2.84 & 2.76 (t, J=7.7 Hz, 2H), 2.76 (t, J=7.4 Hz, 4H), 2.64 (t, J=6.1 Hz, 4H), 2.60 & 2.32 (2×s, 6H), 1.89 (quin, J=7.2 Hz, 4H), 1.90 & 1.77 (2×m, 2H). NH not observed.

LCMS; m/z 503.5 (M+H)$^+$ (ES$^+$); 501.3 (M–H)$^-$ (ES$^-$).

Example 11: N-Cyclobutyl-3-(N-((1,2,3,5,6,7-hexahydro-s-indacen-4-yl) carbamoyl)sulfamoyl)-N,1-dimethyl-1H-pyrazole-5-carboxamide, Partial ammonium Salt

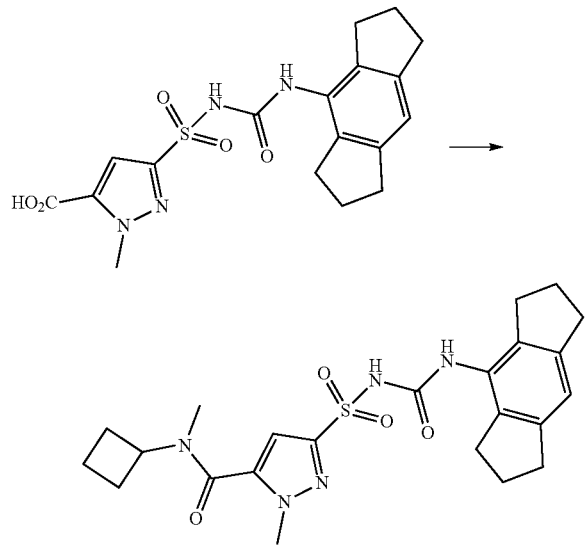

Prepared according to the general procedure of N-(3-(dimethylamino)propyl)-3-(N-((1,2,3,5,6,7-hexahydro-s-indacen-4-yl)carbamoyl)sulfamoyl)-N,1-dimethyl-1H-pyrazole-5-carboxamide (Example 10) from 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) and N-methylcyclobutanamine, HCl salt to afford the title compound (40 mg, 54%) as a white solid.

$^1$H NMR (DMSO-d$_6$), rotamers; δ 7.74 (s, 1H), 7.39 (br s, 1H), 6.83 (s, 1H), 6.80-6.32 (m, 1H), 5.00-4.14 (m, 1H), 3.83 (s, 3H), 2.98 (s, 3H), 2.77 (t, J=7.4 Hz, 4H), 2.64 (t, J=7.4 Hz, 4H), 2.36-2.12 (m, 2H), 2.13-1.85 (m, 6H), 1.81-1.24 (m, 2H).

LCMS; m/z 472.5 (M+H)$^+$ (ES$^+$); 470.3 (M−H)$^−$ (ES$^−$).

Example 12: N-Cyclobutyl-3-(N-((2,6-diisopropylphenyl)carbamoyl) sulfamoyl)-N,1-dimethyl-1H-pyrazole-5-carboxamide

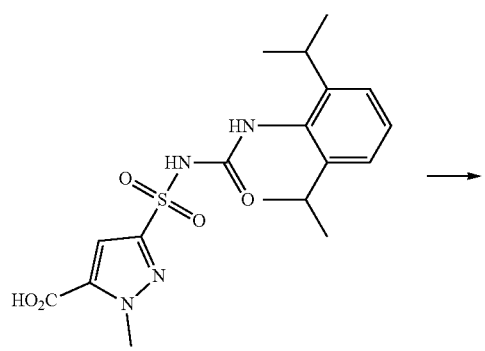

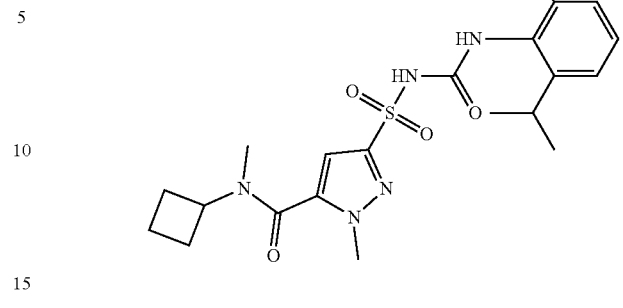

HATU (68.5 mg, 0.180 mmol) was added to a solution of 3-(N-((2,6-diisopropylphenyl) carbamoyl)sulfamoyl)-1-methyl-1H-pyrazole-5-carboxylic acid, disodium salt (Intermediate P54) (67.9 mg, 0.150 mmol) and N-methylcyclobutanamine, HCl (20.07 mg, 0.165 mmol) in DMF (1 mL). Triethylamine (23.01 µL, 0.165 mmol) was added and the mixture stirred for 20 hours. Water (1 mL) was slowly added and the suspension stirred for 1 hour. The suspension was filtered and the collected solid triturated in water (3 mL) for 0.5 hour. The suspension was filtered and the collected solid was purified by chromatography on RP Flash C18 (13 g column, 0-50% MeCN/10 mM ammonium bicarbonate) and triturated with TBME (2 mL) for 1 hour to afford the title compound (30 mg, 40%) as a white solid.

$^1$H NMR (DMSO-d$_6$), rotamers; δ 11.09 (s, 1H), 7.90 (s, 1H), 7.28-7.20 (m, 1H), 7.12 (d, J=7.7 Hz, 2H), 7.03-6.86 (2×m, 1H), 4.78-4.24 (2×m, 1H), 3.91 (s, 3H), 3.02-2.91 (m, 5H), 2.27-1.91 (m, 4H), 1.72-1.36 (m, 2H), 1.17-0.94 (m, 12H).

LCMS; m/z 476 (M+H)$^+$ (ES$^+$).

Example 13: N-(2-Cyanoethyl)-3-(N-((1,2,3,5,6,7-hexahydro-s-indacen-4-yl)carbamoyl)sulfamoyl)-N,1-dimethyl-1H-pyrazole-5-carboxamide

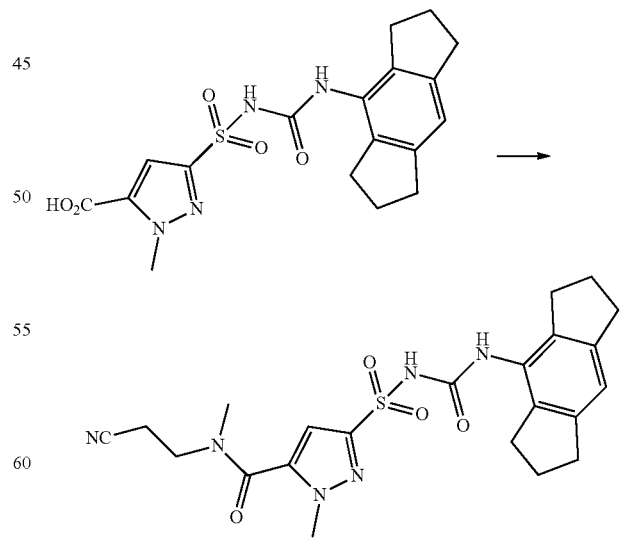

HATU (77 mg, 0.201 mmol) was added to a solution of 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) (75.2 mg, 0.168 mmol) and 3-(methylamino)propanenitrile (18.83 μL, 0.201 mmol) in DMF (1 mL) and the mixture stirred at room temperature for hours. Water (1 mL) was slowly added and the suspension stirred for 1 hour. The suspension was filtered and the collected solid triturated in water (3 mL) for 0.5 hour. The suspension was filtered and the collected solid was washed with water (0.5 mL) and TBME (1 mL). The solid was dried under reduced pressure for 6 hours to afford the title compound (25 mg, 31%) as a white solid.

$^1$H NMR (DMSO-d$_6$), rotamers; δ 10.96 (s, 1H), 8.09 (s, 1H), 7.06 (s, 1H), 6.95 (s, 1H), 3.95-3.92 (2×s, 3H), 3.80-3.65 (m, 2H), 3.07-2.87 (2×s, 3H), 2.88 (t, J=6.6 Hz, 2H), 2.79 (t, J=7.4 Hz, 4H), 2.60 (t, J=7.5 Hz, 4H), 1.99-1.92 (m, 4H).

LCMS: m/z 471 (M+H)$^+$ (ES$^+$).

Example 14: N-(2-(Dimethylamino)ethyl)-3-(N-((1,2,3,5,6,7-hexahydro-s-indacen-4-yl)carbamoyl)sulfamoyl)-N,1-dimethyl-1H-pyrazole-5-carboxamide

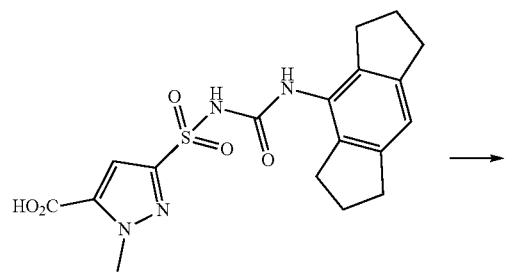

N1,N1,N2-Trimethylethane-1,2-diamine (29 μL, 0.223 mmol) and HATU (83 mg, 0.219 mmol) were successively added to a suspension of 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) (70 mg, 0.156 mmol) in DMF (1 mL) and stirred for 20 hours. The reaction was quenched with water (0.1 mL) and purified by reversed phase prep-HPLC (General Methods, basic prep) to afford the title compound (34 mg, 44%) as a white solid.

$^1$H NMR (DMSO-d$_6$), rotamers; δ10.36 (s, 1H), 7.87 & 7.80 (2×s, 1H), 6.91-6.80 (m, 2H), 3.88 & 3.83 (2×s, 3H), 3.70-3.62 & 3.48-3.40 (2×m, 2H), 3.04 & 2.96 (2×s, 3H), 2.86 & 2.40 (2×m, 2H), 2.77 (t, J=7.4 Hz, 4H), 2.62 (t, J=7.4 Hz, 4H), 2.01-1.85 (m, 7H). CH$_3$ not visible.

LCMS: m/z 489.4 (M+H)$^+$ (ES$^+$); 487.3 (M−H)$^−$ (ES$^−$).

Example 15: N-Cyclopentyl-3-(N-((1,2,3,5,6,7-hexahydro-s-indacen-4-yl)carbamoyl)sulfamoyl)-N,1-dimethyl-1H-pyrazole-5-carboxamide, sodium Salt

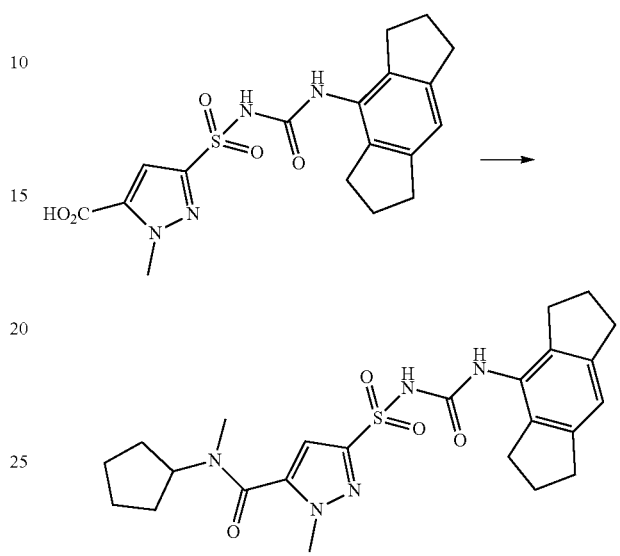

N-Methylcyclopentanamine (0.012 mL, 0.102 mmol) and HATU (39 mg, 0.103 mmol) were successively added to a suspension of 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) (60 mg, 0.134 mmol) in DMF (1 mL) and stirred for 20 hours. TBME (5 mL) was added and the resulting solid filtered off. The filtrate was treated with NaHCO$_3$ (5-7 mg, 0.068 mmol) and the solution purified by reversed phase chromatography (12 g column, 5-50% MeCN/10 mM ammonium bicarbonate) to afford the crude product as a white solid. This material (33 mg) was dissolved in MeOH (3 mL), 0.1 M aqueous NaHCO$_3$ (0.68 mL, 0.068 mmol) and water (1 mL), sonicated for 10 minutes, evaporated in vacuo and dried to afford the title compound (29 mg, 83%) as a white solid.

$^1$H NMR (DMSO-d$_6$), rotamers; δ 7.51 (s, 1H), 6.76 (s, 1H), 6.53 (br s, 1H), 4.31-414 (m, 1H), 3.78 (s, 3H), 2.86 (s, 3H), 2.74 (t, J=7.4 Hz, 4H), 2.64 (t, J=7.5 Hz, 4H), 1.89 (p, J=7.5 Hz, 4H), 1.82-1.47 (m, 8H).

LCMS; m/z 486.5 (M+H)$^+$ (ES$^+$); 484.3 (M−H)$^−$ (ES$^−$).

Example 16: N-((5-Bromo-2,3-dihydro-1H-inden-4-yl)carbamoyl)-5-((dimethylamino)methyl)-1-ethyl-1H-pyrazole-3-sulfonamide

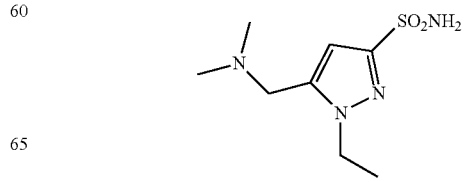

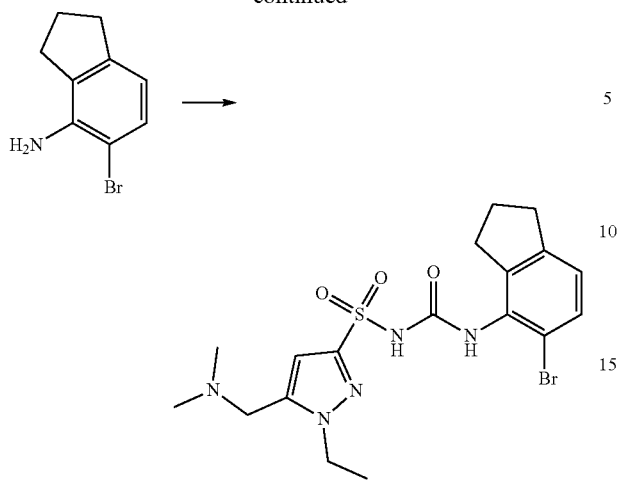

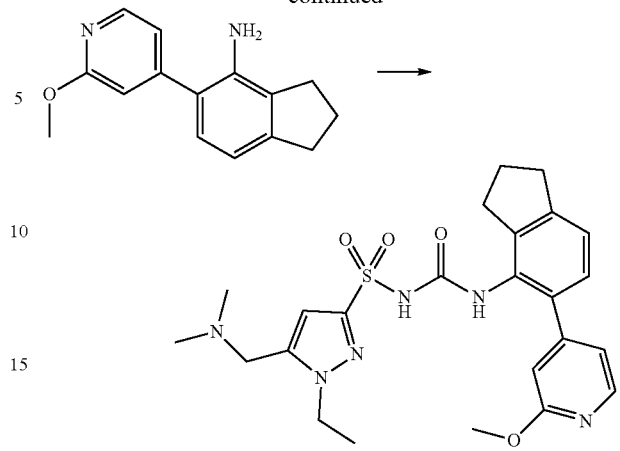

5-Bromo-2,3-dihydro-H-inden-4-amine (Intermediate A13) (45 mg, 0.212 mmol) was dissolved in THF (2 mL). Triethylamine (35 µL, 0.251 mmol) was added, followed by a solution of bis(trichloromethyl) carbonate (62 mg, 0.209 mmol) in THF (1 mL). The slurry was stirred at room temperature for 1 hour, before being concentrated in vacuo. The solid was washed with THF (5 mL) and DCM (mL. Then the filtrate was concentrated in vacuo to give 5-bromo-4-isocyanato-2,3-dihydro-1H-indene as a pale yellow solid that was used without further purification. The isocyanate was dissolved in dry DMF (1 mL). A solution of 5-((dimethylamino)methyl)-1-ethyl-H-pyrazole-3-sulfonamide (Intermediate P7) (50 mg, 0.215 mmol) in dry THF (2 mL) was treated with sodium tert-butoxide (2 M in THF) (110 µL, 0.220 mmol) and stirred at room temperature for 1 hour. The solution of 5-bromo-4-isocyanato-2,3-dihydro-1H-indene in DMF was added and the mixture was stirred overnight. The THF was removed in vacuo and DMSO (1 mL) was added. The mixture was purified by reversed phase prep-HPLC (General Methods, basic prep) to afford the title compound (24 mg, 24%) as a colourless powder.

$^1$H NMR (DMSO-$d_6$) δ 11.00 (s, 1H), 8.09 (s, 1H), 7.38 (d, J=8.0 Hz, 1H), 7.05 (d, J=7.9 Hz, 1H), 6.65 (s, 1H), 4.22 (q, J=7.2 Hz, 2H), 3.52 (s, 2H), 2.83 (t, J=7.4 Hz, 2H), 2.60 (t, J=7.5 Hz, 2H), 2.18 (s, 6H), 1.92 (p, J=7.6 Hz, 2H), 1.35 (t, J=7.2 Hz, 3H).

LCMS m/z 470.3/472.3 (M+H)$^+$ (ES$^+$); 468.4/470.2 (M–H)$^-$ (ES$^-$).

Example 17: 5-((Dimethylamino)methyl)-1-ethyl-N-((5-(2-methoxypyridin-4-yl)-2,3-dihydro-1H-inden-4-yl)carbamoyl)-1H-pyrazole-3-sulfonamide

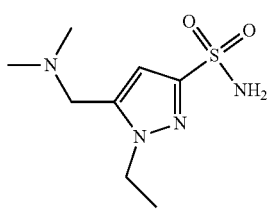

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-ethyl-H-pyrazole-3-sulfonamide (Intermediate P7) and 5-(2-methoxypyridin-4-yl)-2,3-dihydro-H-inden-4-amine (Intermediate A14) to afford the title compound (29 mg, 28%) as a colourless powder.

$^1$H NMR (DMSO-$d_6$) δ 10.81 (s, 1H), 8.13 (dd, J=5.3, 0.7 Hz, 1H), 7.92 (s, 1H), 7.22 (d, J=7.7 Hz, 1H), 7.12 (d, J=7.6 Hz, 1H), 6.87 (dd, J=5.3, 1.5 Hz, 1H), 6.73-6.71 (m, 1H), 6.56 (s, 1H), 4.22 (q, J=7.2 Hz, 2H), 3.89 (s, 3H), 3.50 (s, 2H), 2.91 (t, J=7.5 Hz, 2H), 2.62 (t, J=7.5 Hz, 2H), 2.17 (s, 6H), 1.96 (p, J=7.5 Hz, 2H), 1.36 (t, J=7.2 Hz, 3H).

LCMS; m/z 499.4 (M+H)$^+$ (ES$^+$); 497.3 (M–H)$^-$ (ES$^-$).

Example 18: ((1,2,3,5,6,7-Hexahydro-s-indacen-4-yl)carbamoyl)((1-isopropyl-5-(1-(trimethylammonio)ethyl)-1H-pyrazol-3-yl)sulfonyl)amide

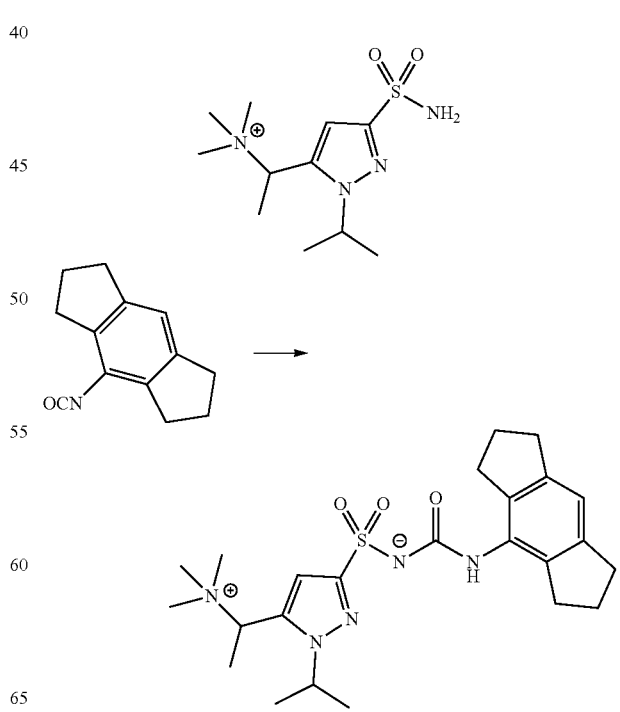

Sodium tert-butoxide (2 M in THF) (0.24 mL, 0.480 mmol) was added to a solution of 1-(1-isopropyl-3-sulfamoyl-1H-pyrazol-5-yl)-N,N,N-trimethylethanaminium trifluoroacetate (Intermediate P8) (90 mg, 0.233 mmol) in THF (2 mL) and stirred at room temperature for 1 hour. Then 4-isocyanato-1,2,3,5,6,7-hexahydro-s-indacene (Intermediate A1) (51.1 mg, 0.256 mmol) was added and stirred at room temperature overnight. Additional 4-isocyanato-1,2,3,5,6,7-hexahydro-s-indacene (Intermediate A1) (51.1 mg, 0.256 mmol) was added and the mixture stirred for 24 hours. Volatiles were evaporated and the residue was dissolved in DMSO (2 mL), filtered and purified by reversed phase prep-HPLC (General Methods, basic prep) to afford the title compound (35 mg, 31%) as a white solid.

$^1$H NMR (DMSO-$d_6$) δ 7.44 (s, 1H), 6.91 (s, 1H), 6.76 (s, 1H), 5.07 (q, J=6.8 Hz, 1H), 4.97-4.85 (m, 1H), 3.01 (s, 9H), 2.75 (t, J=7.4 Hz, 4H), 2.67-2.57 (m, 4H), 1.96-1.81 (m, 4H), 1.69 (d, J=6.8 Hz, 3H), 1.50 (d, J=6.4 Hz, 3H), 1.27 (d, J=6.3 Hz, 3H).

LCMS; m/z 474.5 (M+H)$^+$ (ES$^+$).

Example 19: ((1,2,3,5,6,7-Hexahydro-s-indacen-4-yl)carbamoyl)((1-methyl-5-(1-(trimethylammonio)ethyl)-1H-pyrazol-3-yl)sulfonyl)amide

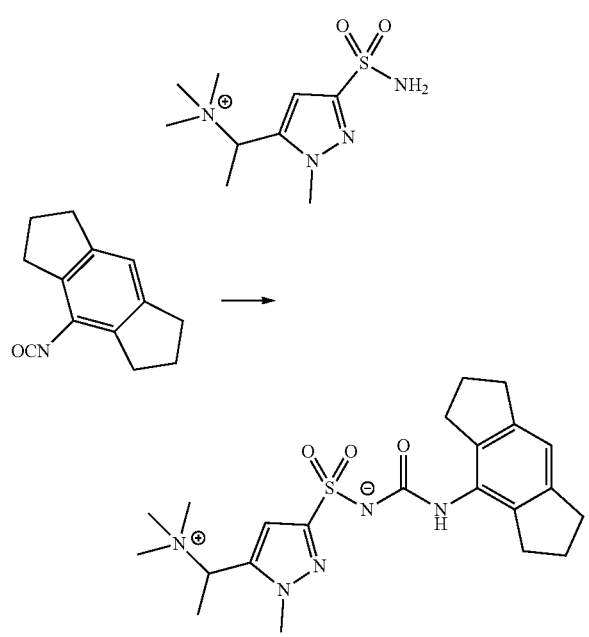

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from N,N,N-trimethyl-1-(1-methyl-3-sulfamoyl-1H-pyrazol-5-yl)ethan-1-aminium 2,2,2-trifluoroacetate (Intermediate P9) and 4-isocyanato-1,2,3,5,6,7-hexahydro-s-indacene (Intermediate A1) to afford the title compound (27 mg, 37%) as a white solid.

$^1$H NMR (DMSO-$d_6$) δ 7.45 (s, 1H), 6.91 (s, 1H), 6.76 (s, 1H), 4.99 (q, J=6.8 Hz, 1H), 3.93 (s, 3H), 3.01 (s, 9H), 2.75 (t, J=7.4 Hz, 4H), 2.72-2.57 (m, 4H), 1.98-1.80 (m, 4H), 1.68 (d, J=6.8 Hz, 3H).

LCMS; m/z 446.5 (M+H)$^+$ (ES$^+$).

Example 20: 5-((Dimethylamino)methyl)-1-ethyl-N-((7-fluoro-5-(pyridin-3-yl)-2,3-dihydro-1H-inden-4-yl)carbamoyl)-1H-pyrazole-3-sulfonamide

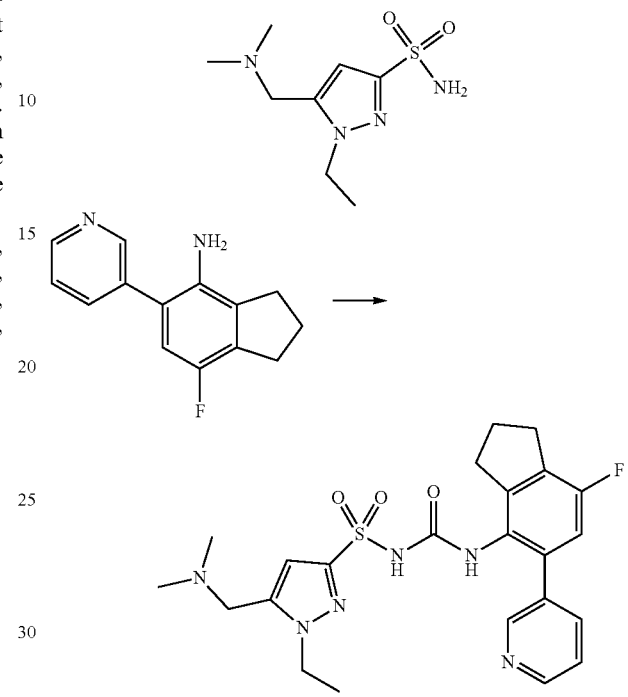

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-ethyl-H-pyrazole-3-sulfonamide (Intermediate P7) and 7-fluoro-5-(pyridin-3-yl)-2,3-dihydro-H-inden-4-amine (Intermediate A12) to afford the title compound (5 mg, 6%) as a colourless powder.

$^1$H NMR (DMSO-$d_6$) δ 10.83 (s, 1H), 8.56 (dd, J=4.8, 1.6 Hz, 1H), 8.50 (d, J=2.2 Hz, 1H), 7.90 (s, 1H), 7.72-7.68 (m, 1H), 7.43-7.39 (m, 1H), 7.03 (d, J=9.2 Hz, 1H), 6.54 (s, 1H), 4.23 (q, J=7.2 Hz, 2H), 3.51 (s, 2H), 2.95 (t, J=7.4 Hz, 2H), 2.68 (t, J=7.3 Hz, 2H), 2.18 (s, 6H), 2.03 (p, J=7.6 Hz, 2H), 1.36 (t, J=7.2 Hz, 3H).

LCMS; m/z 487.5 (M+H)$^+$ (ES$^+$); 485.3 (M−H)$^−$ (ES$^−$).

Example 21: 5-((Dimethylamino)methyl)-1-ethyl-N-((7-fluoro-5-(2-methoxypyridin-4-yl)-2,3-dihydro-1H-inden-4-yl)carbamoyl)-1H-pyrazole-3-sulfonamide

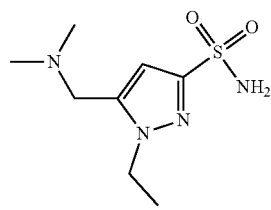

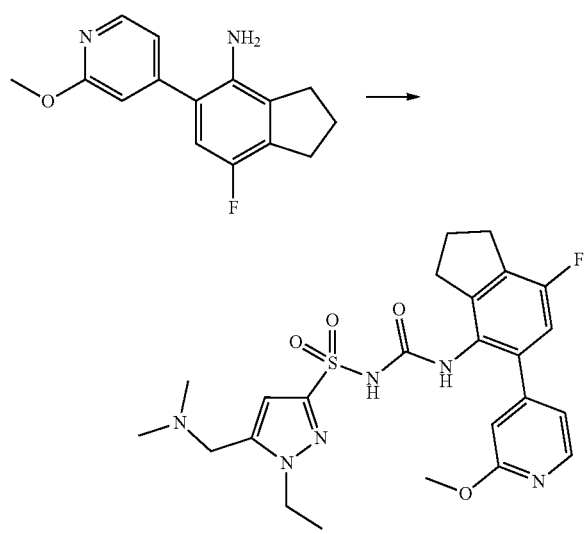

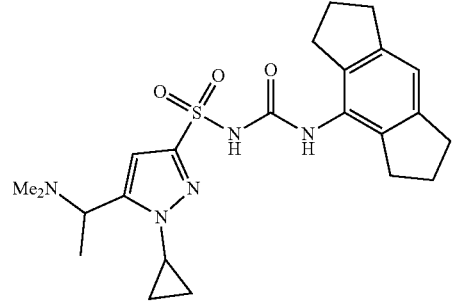

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-ethyl-H-pyrazole-3-sulfonamide (Intermediate P7) and 7-fluoro-5-(2-methoxypyridin-4-yl)-2,3-dihydro-1H-inden-4-amine (Intermediate A11) to afford the title compound (5 mg, 7%) as a colourless powder.

$^1$H NMR (DMSO-d$_6$) δ 1.85 (s, 1H), 8.14 (d, J=5.3 Hz, 1H), 7.90 (s, 1H), 7.02 (d, J=9.2 Hz, 1H), 6.89 (dd, J=5.3, 1.5 Hz, 1H), 6.75 (s, 1H), 6.56 (s, 1H), 4.22 (q, J=7.2 Hz, 2H), 3.89 (s, 3H), 3.51 (s, 2H), 2.94 (t, J=7.5 Hz, 2H), 2.66 (t, J=7.1 Hz, 2H), 2.18 (s, 6H), 2.02 (p, J=7.6 Hz, 2H), 1.35 (t, J=7.2 Hz, 3H).

LCMS; m/z 517.4 (M+H)$^+$ (ES$^+$); 515.3 (M−H)$^-$ (ES$^-$).

Example 22: 1-Cyclopropyl-5-(1-(dimethylamino)ethyl)-N-((1,2,3,5,6,7-hexahydro-s-indacen-4-yl)carbamoyl)-1H-pyrazole-3-sulfonamide

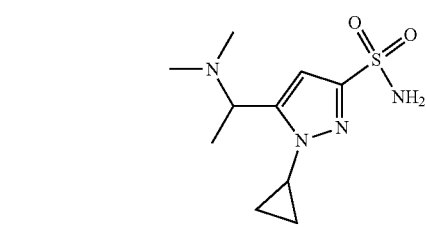

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl) amide (Example 18) from 1-cyclopropyl-5-(1-(dimethylamino)ethyl)-1H-pyrazole-3-sulfonamide (Intermediate P10) and 4-isocyanato-1,2,3,5,6,7-hexahydro-s-indacene (Intermediate A1) to afford the title compound (83 mg, 52%) as a white solid.

$^1$H NMR (DMSO-d$_6$) δ 10.76 (s, 1H), 8.00 (s, 1H), 6.93 (s, 1H), 6.67 (s, 1H), 4.09 (q, J=6.8 Hz, 1H), 3.92-3.84 (m, 1H), 2.78 (t, J=7.4 Hz, 4H), 2.56 (t, J=7.4 Hz, 4H), 2.17 (s, 6H), 1.93 (p, J=7.4 Hz, 4H), 1.29 (d, J=6.8 Hz, 3H), 1.22-1.14 (m, 1H), 1.08-0.97 (m, 3H).

LCMS; m/z 458.5 (M+H)$^+$ (ES$^+$).

Example 23: 5-(1-(Azetidin-1-yl)propyl)-1-cyclopropyl-N-((1,2,3,5,6,7-hexahydro-s-indacen-4-yl)carbamoyl)-1H-pyrazole-3-sulfonamide

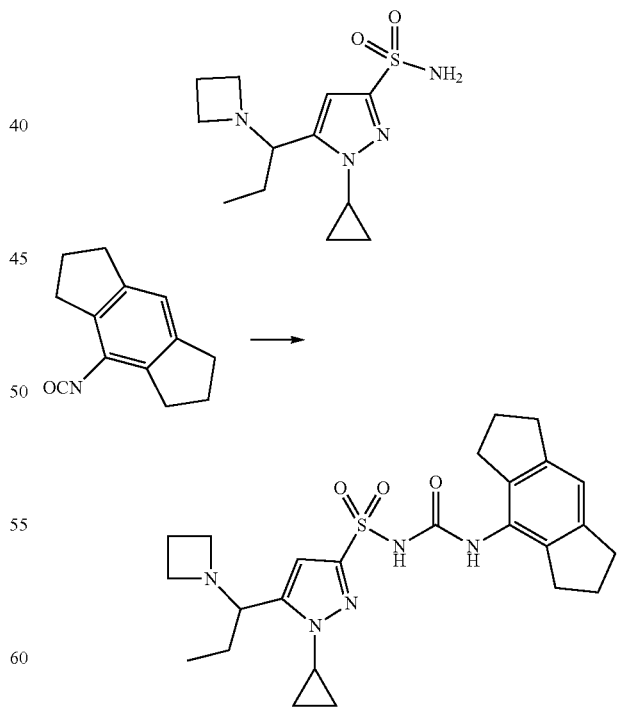

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl) amide (Example 18) from 5-(1-(azetidin-1-yl)propyl)-1- cyclopropyl-1H-pyrazole-3-sulfonamide (Intermediate P11) and 4-isocyanato-1,2,3,5,6,7-hexahydro-s-indacene (Intermediate A1) to afford the title compound (42 mg, 36%) as a white solid.

$^1$H NMR (DMSO-d$_6$) δ 10.77 (s, 1H), 7.98 (s, 1H), 6.91 (s, 1H), 6.58 (s, 1H), 3.96-3.87 (m, 1H), 3.81-3.73 (m, 1H), 3.16 (q, J=6.9 Hz, 2H), 3.09 (q, J=6.9 Hz, 2H), 2.78 (t, J=7.4 Hz, 4H), 2.56 (t, J=7.4 Hz, 4H), 2.00-1.87 (m, 6H), 1.77-1.63 (m, 1H), 1.63-1.49 (m, 1H), 1.20-1.12 (m, 1H), 1.12-1.01 (m, 3H), 0.69 (t, J=7.4 Hz, 3H).

LCMS; m/z 484.5 (M+H)$^+$ (ES$^+$).

Example 24: 1-Cyclopropyl-5-(1-(dimethylamino)propyl)-N-((1,2,3,5,6,7-hexahydro-s-indacen-4-yl)carbamoyl)-1H-pyrazole-3-sulfonamide

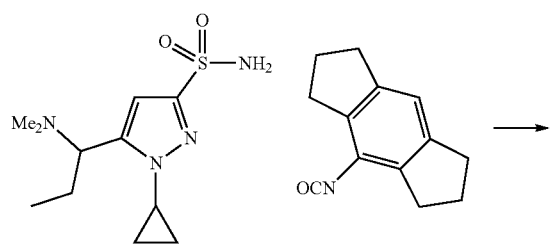

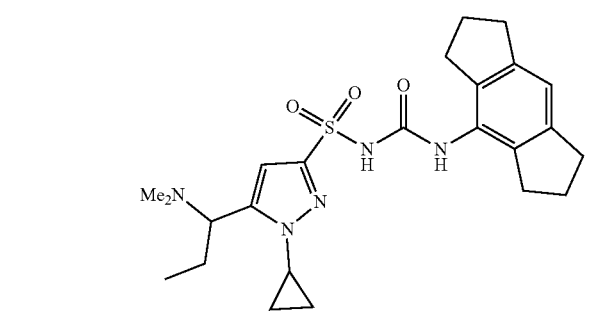

Prepared according to the general procedure of (((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 1-cyclopropyl-5-(1-(dimethylamino)propyl)-1H-pyrazole-3-sulfonamide (Intermediate P12) and 4-isocyanato-1,2,3,5,6,7-hexahydro-s-indacene (Intermediate A1) to afford the title compound (40 mg, 31%) as a white solid.

$^1$H NMR (DMSO-d$_6$) δ 10.77 (s, 1H), 7.99 (s, 1H), 6.92 (s, 1H), 6.66 (s, 1H), 3.90 (dd, J=9.3, 5.3 Hz, 1H), 3.87-3.79 (m, 1H), 2.78 (t, J=7.4 Hz, 4H), 2.55 (t, J=7.4 Hz, 4H), 2.16 (s, 6H), 1.92 (p, J=7.4 Hz, 4H), 1.88-1.78 (m, 1H), 1.77-1.63 (m, 1H), 1.20-0.98 (m, 4H), 0.78 (t, J=7.3 Hz, 3H).

LCMS; m/z 472.4 (M+H)$^+$ (ES$^+$).

Example 2t: 5-(~(Azetidin-1-yl)ethyl)-1-cyclopropyl-N-((1,2,3,5,6,7-hexahydro-s-indacen-4-yl)carbamoyl)-1H-pyrazole-3-sulfonamide

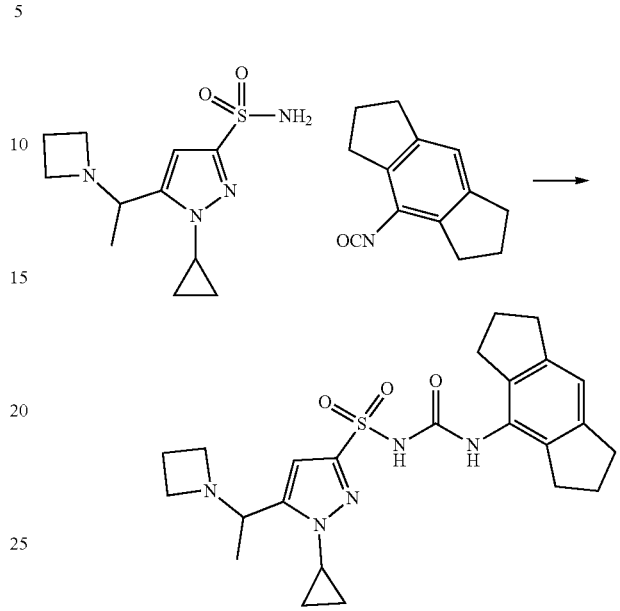

Prepared according to the general procedure of (((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-(1-(azetidin-1-yl)ethyl)-1-cyclopropyl-1H-pyrazole-3-sulfonamide (Intermediate P13) and 4-isocyanato-1,2,3,5,6,7-hexahydro-s-indacene (Intermediate A1) to afford the title compound (11 mg, 12%) as a white solid.

$^1$H NMR (DMSO-d$_6$) δ 1.8 (s, 1H), 7.96 (s, 1H), 6.91 (s, 1H), 6.55 (s, 1H), 3.92-3.79 (m, 2H), 3.24-3.05 (m, 4H), 2.78 (t, J=7.4 Hz, 4H), 2.57 (t, J=7.4 Hz, 4H), 2.01-1.87 (m, 6H), 1.19 (d, J=6.5 Hz, 3H), 1.15-1.02 (m, 4H).

LCMS; m/z 470.4 (M+H)$^+$ (ES$^+$).

Example 26: 5-(1-(Azetidin-1-yl)ethyl)-N-((1,2,3,5,6,7-hexahydro-s-indacen-4-yl)carbamoyl)-1-methyl-1H-pyrazole-3-sulfonamide, Sodium Salt (Enantiomer 1)

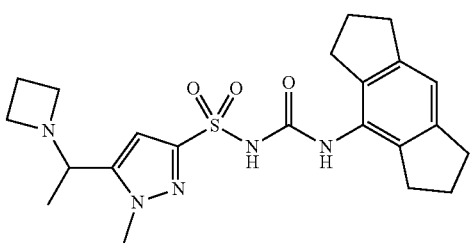

Enantiomer 1, sodium salt

Step A: 5-(1-(Azetidin-1-yl)ethyl)-N-((1,2,3,5,6,7-hexahydro-s-indacen-4-yl)carbamoyl)-1-methyl-1H-pyrazole-3-sulfonamide (Enantiomer 1)

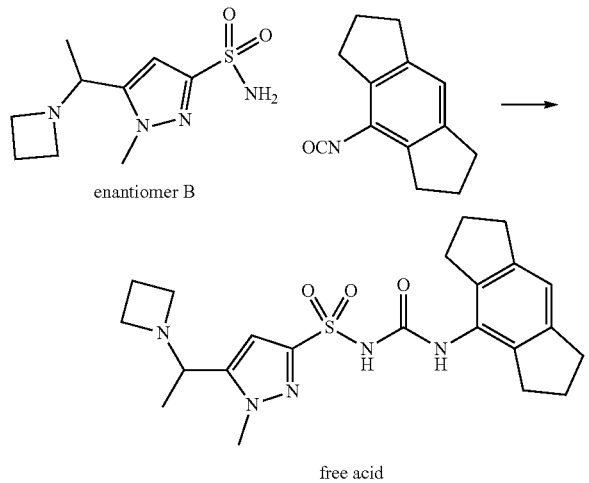

enantiomer B free acid

To a solution of 5-(1-(azetidin-1-yl)ethyl)-1-methyl-1H-pyrazole-3-sulfonamide, enantiomer B (Intermediate P15) (3.4 g, 13.92 mmol, 1 eq.) in THF (100 ml) and DMF (13 mL) was added t-BuONa (2 M, 6.96 mL, 1 eq) and the reaction mixture was stirred for 20 minutes. Then a solution of 4-isocyanato-1,2,3,5,6,7-hexahydro-s-indacene (Intermediate A1) (2.77 g, 13.92 mmol, 1 eq) in THF (20 mL) was added. The mixture was stirred at 25° C. for 20 minutes. LCMS showed the starting material was consumed completely and the desired mass was detected. The reaction mixture was concentrated in vacuo. The residue was triturated with MTBE (150 mL) and a solid was formed. The mixture was filtered. The filter cake was purified by reversed phase prep-HPLC (General Methods, basic prep) to afford the title compound (2.77 g, 43%) as a white solid.

¹H NMR (DMSO-d₆) δ 8.03 (s, 1H), 6.93 (s, 1H), 6.61 (s, 1H), 3.93 (s, 3H), 3.78-374 (m, 1H), 3.23-3.13 (m, 4H), 2.81-2.77 (t, 4H), 2.61-2.57 (m, 4H), 1.98-1.92 (m, 6H), 1.16 (d, 3H).

LCMS m/z 444.2 (M+H)⁺ (ES⁺).

Step B: 5-(1-(Azetidin-1-yl)ethyl)-N-((1,2,3,5,6,7-hexahydro-s-indacen-4-yl)carbamoyl)-1-methyl-1H-pyrazole-3-sulfonamide, Sodium Salt

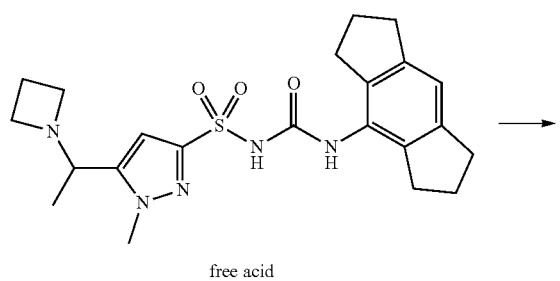

free acid

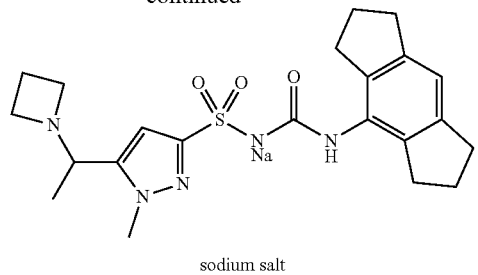

sodium salt

To a solution of 5-(1-(azetidin-1-yl)ethyl)-N-((1,2,3,5,6,7-hexahydro-s-indacen-4-yl)carbamoyl)-1-methyl-1H-pyrazole-3-sulfonamide (Enantiomer 1) (3.5 g, 7.89 mmol, 1 eq, free acid) in THF (20 mL) was added a solution of t-BuONa in THF (2 M, 3.95 mL, 1 eq). The mixture was stirred at 25° C. for 1 hour. The reaction mixture was concentrated in vacuo. The residue was triturated with MBTE (100 mL). The mixture was filtered and the filtrate was concentrated in vacuo. The residue was combined with another batch of product (350 mg, crude) and re-dissolved in H₂O and lyophilised to give the title compound (2.96 g, 69%) as a light yellow solid.

¹H NMR (DMSO-d₆) δ 7.58 (s, 1H), 6.77 (s, 1H), 6.24 (s, 1H), 3.80 (s, 3H), 3.56-3.50 (m, 1H), 3.09-3.00 (m, 4H), 2.75-2.71 (m, 4H), 2.63-2.60 (m, 4H), 1.91-1.86 (m, 6H), 1.09 (d, J=6.0 Hz, 3H).

LCMS; m/z 444.2 (M+H)⁺ (ES⁺).

Example 27: 5-(1-(Azetidin-1-yl)ethyl)-N-((1,2,3,5,6,7-hexahydro-s-indacen-4-yl)carbamoyl)-1-methyl-1H-pyrazole-3-sulfonamide, Sodium Salt (Enantiomer 2)

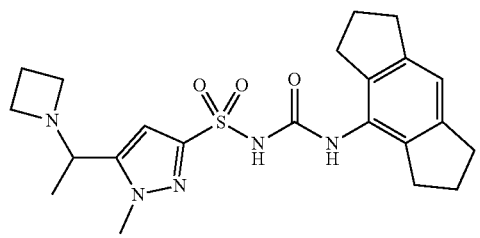

Enantiomer 2, sodium salt

Step A: 5-(1-(Azetidin-1-yl)ethyl)-N-((1,2,3,5,6,7-hexahydro-s-indacen-4-yl)carbamoyl)-1-methyl-1H-pyrazole-3-sulfonamide (Enantiomer 2)

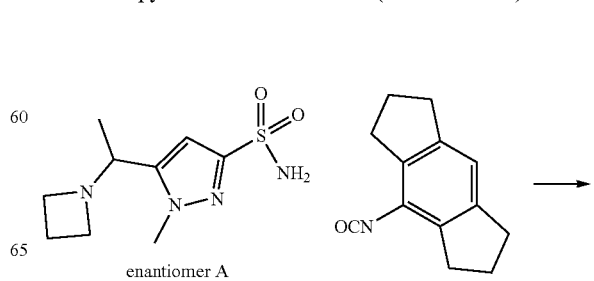

enantiomer A

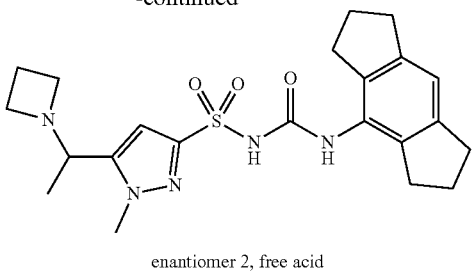

enantiomer 2, free acid

A solution of sodium tert-butoxide in THF (2 M, 3.27 mL) was added to a solution of 5-(1-(azetidin-1-yl)ethyl)-1-methyl-1H-pyrazole-3-sulfonamide, enantiomer A (Intermediate P14) (1.6 g, 6.55 mmol) in THF (20 mL) and DMF (20 mL) at 20° C. The reaction was stirred for 10 minutes at 20° C., before a solution of 4-isocyanato-1,2,3,5,6,7-hexahydro-s-indacene (Intermediate A1) (913 mg, 4.58 mmol, 0.7 eq) in THF (12 mL) was added dropwise. The resulting mixture was stirred at 20° C. for 1 hour. The reaction mixture was diluted with MTBE (96 mL) and the solid was filtered and purified by reversed phase prep-HPLC (General Methods, basic prep) to afford the title compound (581 mg, 20%) as a white solid.

$^1$H NMR (DMSO-$d_6$) δ 8.03 (s, 1H), 6.93 (s, 1H), 6.61 (s, 1H), 3.93 (s, 3H), 3.78-3.74 (m, 1H), 3.23-3.13 (m, 4H), 2.81-2.77 (t, 4H), 2.61-2.57 (m, 4H), 1.98-1.92 (m, 6H), 1.16 (d, 3H).

LCMS: m/z 444.2 (M+H)$^+$ (ES$^+$).

Step B: 5-(~(Azetidin-1-yl)ethyl)-N-((1,2,3,5,6,7-hexahydro-s-indacen-4-yl)carbamoyl)-1-methyl-1H-pyrazole-3-sulfonamide, Sodium Salt (Enantiomer 2)

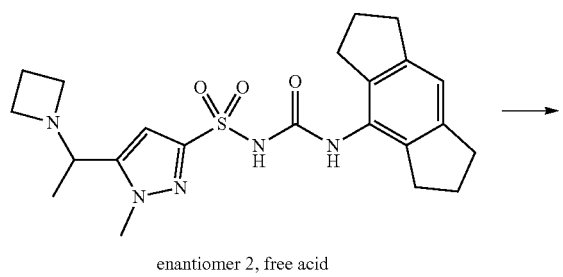

enantiomer 2, free acid

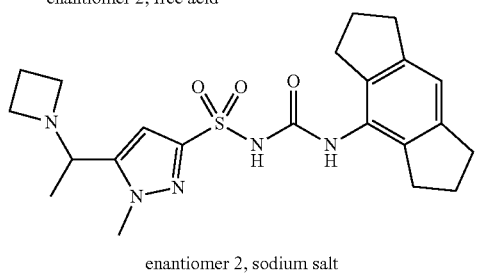

enantiomer 2, sodium salt

To a solution of 5-(1-(azetidin-1-yl)ethyl)-N-((1,2,3,5,6,7-hexahydro-s-indacen-4-yl)carbamoyl)-1-methyl-1H-pyrazole-3-sulfonamide (Enantiomer 2) (950 mg, 2.10 mmol) in THF (20 mL) was added a solution of t-BuONa in THF (2 M, 1.05 mL). The mixture was stirred at 20° C. for 1 hour and then concentrated in vacuo. The residue was triturated with MTBE (30 mL) and the solid was filtered. The filter cake was re-dissolved in THF (20 mL) and the resulting solution was added dropwise into 60 mL of MTBE. Some precipitate formed at the same time. The suspension was filtered to give the title compound (760 mg) as an off-white solid. The product combined with another batch of product (200 mg) was re-dissolved in deionized water (40 mL) and then lyophilized to give the title compound (841 mg, 78%).

$^1$H NMR (DMSO-$d_6$) δ 7.57 (s, 1H), 6.77 (s, 1H), 6.25 (s, 1H), 3.81 (s, 3H), 3.55-3.52 (m, 1), 3.11-3.01 (m, 4H), 2.76-2.73 (m, 4H), 2.64-2.61 (m, 4H), 1.93-1.86 (m, 6H), 1.10 (d, J=6.4 Hz, 3H).

LCMS m/z 444.2 (M+H)$^+$ (ES$^+$).

Example 28: 4-(2-(3-((5-((Dimethylamino)methyl)-1-methyl-1H-pyrazol-3-yl)sulfonyl)ureido)-5-fluoro-3-isopropylphenyl)picolinamide

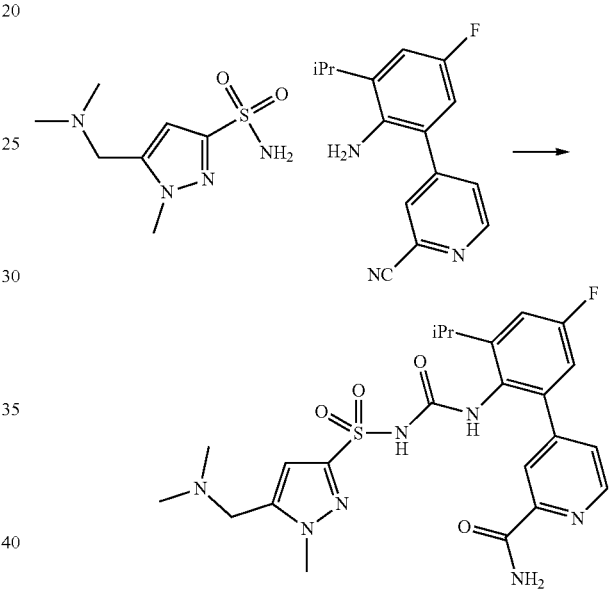

4-(2-Amino-5-fluoro-3-isopropylphenyl)picolinonitrile (Intermediate A9) (0.05 g, 0.196 mmol) was dissolved in dry THF (2 mL). Triethylamine (0.030 mL, 0.215 mmol) and a solution of bis(trichloromethyl) carbonate (0.058 g, 0.196 mmol) in THF (1 mL) was added. The thick, opaque mixture was stirred for two hours. The THF was removed in vacuo and the mixture was suspended in toluene (10 mL) and filtered through a phase separator cartridge washing with toluene (10 mL). After concentration in vacuo, 4-(5-fluoro-2-isocyanato-3-isopropylphenyl)picolinonitrile was isolated as a yellow oil that was used without further purification. The isocyanate was dissolved in dry THF (2 mL).

A suspension of 5-((dimethylamino)methyl)-1-methyl-H-pyrazole-3-sulfonamide (Intermediate P16) (0.043 g, 0.196 mmol) in dry THF (2 mL) was treated with sodium hydride (10 mg, 0.250 mmol), which had been previously washed with iso-hexanes (5 mL) to remove silicone oil. The suspension was stirred at room temperature for 30 minutes, before the previously prepared solution of 4-(5-fluoro-2-isocyanato-3-isopropylphenyl)picolinonitrile was added in a single portion. The reaction mixture was stirred at room temperature overnight. The THF was removed in vacuo and the residue was dissolved in DMSO (2 mL) and then purified by reversed phase prep-HPLC (General Methods, basic prep). After concentration of product containing fractions, the title compound (16 mg, 15%) was isolated as a colourless powder. Hydrolysis of the nitrile occurred during the reaction.

$^1$H NMR (DMSO-d$_6$) δ 10.86 (s, 1H), 8.53 (d, J=5.0 Hz, 1H), 8.16 (d, J=2.7 Hz, 1H), 7.96 (s, 2H), 7.69 (s, 1H), 7.49 (dd, J=5.1, 1.8 Hz, 1H), 7.25 (dd, J=10.1, 3.0 Hz, 1H), 7.10 (dd, J=8.8, 2.9 Hz, 1H), 6.41 (s, 1H), 3.86 (s, 3H), 3.47 (s, 2H), 3.17-2.96 (m, 1H), 2.16 (s, 6H), 1.11 (br s, 6H).

LCMS; m/z 518.4 (M+H)$^+$ (ES$^+$); 516.3 (M−H)$^−$ (ES$^−$).

Example 29: N-((1,2,3,5,6,7-Hexahydro-s-indacen-4-yl)carbamoyl)-1-methyl-5-(1-(3-methylazetidin-1-yl)ethyl)-1H-pyrazole-3-sulfonamide

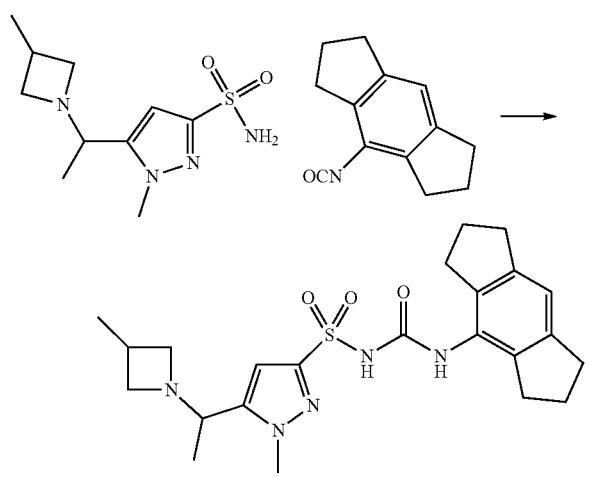

To a solution of 1-methyl-5-(1-(3-methylazetidin-1-yl)ethyl)-1H-pyrazole-3-sulfonamide (Intermediate P17) (75 mg, 0.290 mmol) in THF (2 mL) was added sodium tert-butoxide (2 M in THF) (0.15 mL, 0.300 mmol) and the mixture was stirred at room temperature for 1 hour. 4-Isocyanato-1,2,3,5,6,7-hexahydro-s-indacene (Intermediate A1) (58 mg, 0.291 mmol) in THF (2 mL) was added and stirring was continued overnight. The mixture was diluted with EtOAc (6 mL) and extracted twice with H$_2$O (2 mL) containing a few drops of 2 M NaOH. The combined aqueous extracts were loaded onto a reversed phase column and purified by chromatography on RP Flash C18 (13 g column, 5-75% MeCN/10 mM ammonium bicarbonate) to afford a clear colourless solid. The product was further purified by preparative HPLC to afford the title compound (72 mg, 54%) as a clear colourless solid.

$^1$H NMR (DMSO-d$_6$) δ 10.71 (s, 1H), 7.98 (s, 1H), 6.92 (s, 1H), 6.56 (s, 1H), 3.91 (s, 3H), 3.75-3.62 (m, 1H), 3.39 (d, J=6.0 Hz, 1H), 3.24 (t, J=6.9 Hz, 1H), 2.78 (t, J=7.5 Hz, 4H), 2.75-2.64 (m, 2H), 2.58 (t, J=7.5 Hz, 4H), 2.47-2.33 (m, 1H), 1.93 (p, J=7.5 Hz, 4H), 1.14 (d, J=6.6 Hz, 3H), 1.09 (d, J=6.7 Hz, 3H).

LCMS; m/z 458.5 (M+H)$^+$ (ES$^+$).

Example 30:5-(Azetidin-1-ylmethyl)-1-cyclopropyl-N-((1,2,3,5,6,7-hexahydro-s-indacen-4-yl)carbamoyl)-1H-pyrazole-3-sulfonamide

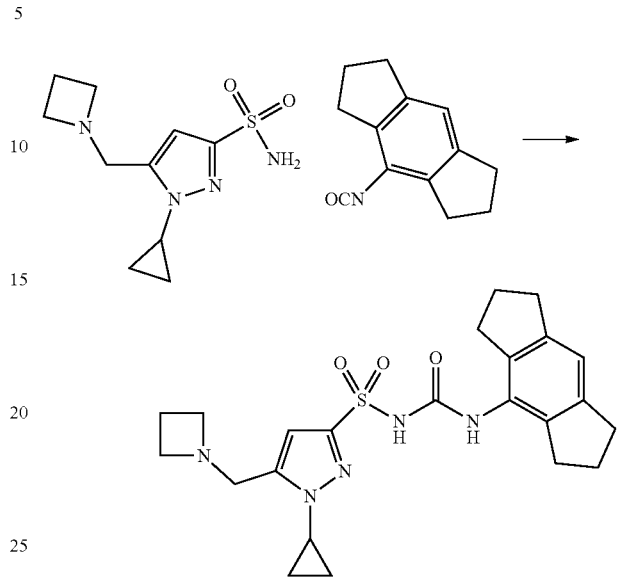

To a solution of 5-(azetidin-1-ylmethyl)-1-cyclopropyl-1H-pyrazole-3-sulfonamide (Intermediate P8) (75 mg, 0.293 mmol) in THF (1.5 mL) was added sodium tert-butoxide (2 M in THF) (0.16 mL, 0.320 mmol) and the mixture was stirred at room temperature for 1 hour. 4-Isocyanato-1,2,3,5,6,7-hexahydro-s-indacene (Intermediate A1) (61 mg, 0.306 mmol) in THF (1.5 mL) was added and the mixture was stirred at room temperature overnight. The mixture was diluted with EtOAc (6 mL) and extracted twice with H$_2$O (2 mL) containing a few drops of 2 M aqueous NaOH. The combined aqueous extracts were loaded onto a reversed phase column and purified by reversed phase chromatography (13 g column, 5-75% MeCN/10 mM ammonium bicarbonate) to afford the title compound (72 mg, 49%) as a clear colourless solid.

$^1$H NMR (DMSO-d$_6$) δ 10.78 (s, 1H), 7.98 (s, 1H), 6.92 (s, 1H), 6.59 (s, 1H), 3.79 (s, 2H), 3.76-3.68 (m, 1H), 3.28 (t, J=7.1 Hz, 4H), 2.78 (t, J=7.4 Hz, 4H), 2.58 (t, J=7.4 Hz, 4H), 2.03 (p, J=7.1 Hz, 2H), 1.93 (p, J=7.4 Hz, 4H), 1.10-0.98 (m, 4H).

LCMS; m/z 456.4 (M+H)$^+$ (ES$^+$).

Example 31: 5-((Dimethylamino)methyl)-N-((1,2,3,5,6,7-hexahydro-s-indacen-4-yl)carbamoyl)-1-neopentyl-1H-pyrazole-3-sulfonamide

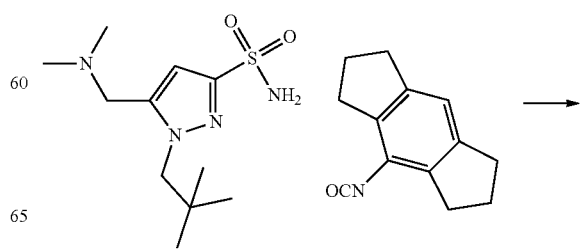

-continued

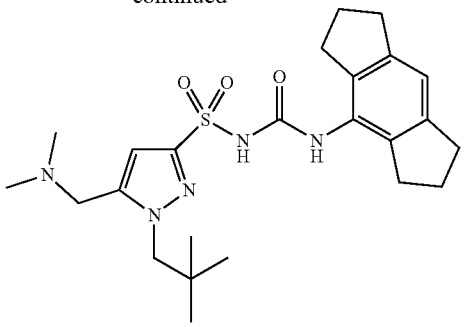

Prepared according to the general procedure of (((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-((dimethylamino)methyl)-1-neopentyl-1H-pyrazole-3-sulfonamide (Intermediate P19) and 4-isocyanato-1,2,3,5,6,7-hexahydro-s-indacene (Intermediate A1) to afford the title compound (16 mg, 28%) as a colourless powder.

$^1$H NMR (DMSO-d$_6$) δ 1.81 (s, 1H), 7.98 (s, 1H), 6.93 (s, 1H), 6.67 (s, 1H), 4.03 (s, 2H), 3.51 (s, 2H), 2.78 (t, J=7.4 Hz, 4H), 2.57 (t, J=7.3 Hz, 4H), 2.17 (s, 6H), 1.92 (p, J=7.4 Hz, 4H), 0.92 (s, 9H).

LCMS; m/z 474.2 (M+H)$^+$ (ES$^+$); 472.4 (M−H)$^−$ (ES$^−$).

Example 32: 5-(1-(Dimethylamino)cyclopropyl)-N-((1,2,3,5,6,7-hexahydro-s-indacen-4-yl)carbamoyl)-1-isopropyl-1H-pyrazole-3-sulfonamide

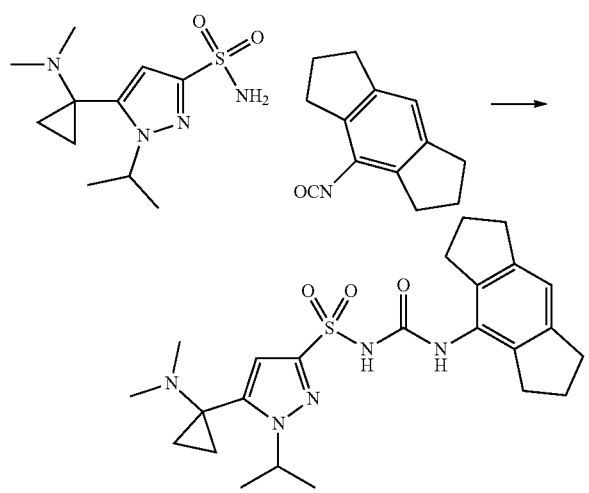

Prepared according to the general procedure of (((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-(1-(dimethylamino)cyclopropyl)-1-isopropyl-1H-pyrazole-3-sulfonamide (Intermediate P20) and 4-isocyanato-1,2,3,5,6,7-hexahydro-s-indacene (Intermediate A1) to afford the title compound (22 mg, 25%) as a white solid.

$^1$H NMR (DMSO-d$_6$) δ 10.84 (s, 1H), 8.03 (s, 1H), 6.93 (s, 1H), 6.62 (s, 1H), 4.96 (sept, J=6.5 Hz, 1H), 2.78 (t, J=7.4 Hz, 4H), 2.58-2.52 (m, 4H), 2.16 (s, 6H), 1.91 (p, J=7.5 Hz, 4H), 1.40 (d, J=6.5 Hz, 6H), 1.07-1.00 (m, 2H), 0.85-0.78 (m, 2H).

LCMS; m/z 472.5 (M+H)$^+$ (ES$^+$); 470.3 (M−H)$^−$ (ES$^−$).

Example 33: 5-(2-(Dimethylamino)ethyl)-N-((1,2,3,5,6,7-hexahydro-s-indacen-4-yl)carbamoyl)-1-isopropyl-1H-pyrazole-3-sulfonamide, Sodium Salt

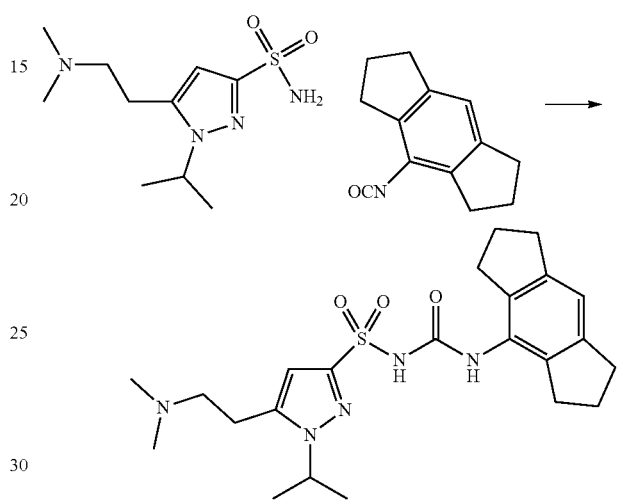

Sodium tert-butoxide (2 M in THF) (0.103 mL, 0.206 mmol) was added to a solution of 5-(2-(dimethylamino)ethyl)-1-isopropyl-1H-pyrazole-3-sulfonamide (Intermediate P21) (51 mg, 0.196 mmol) in THF (2 mL) and stirred at room temperature for 1 hour. Then 4-isocyanato-1,2,3,5,6,7-hexahydro-s-indacene (Intermediate A1) (43 mg, 0.216 mmol) was added and stirred at room temperature overnight. The suspension was filtered and the collected solid washed with THF (2 mL) and MTBE (4 mL). The solid was dissolved in MeCN and evaporated under vacuum to afford the title compound (63 mg, 64%).

$^1$H NMR (DMSO-d$_6$) δ 7.58 (s, 1H), 6.77 (s, 1H), 6.23 (s, 1H), 4.51 (sept, J=6.5 Hz, 1H), 2.79-2.70 (m, 6H), 2.64 (t, J=7.4 Hz, 4H), 2.47 (t, J=7.5 Hz, 2H), 2.19 (s, 6H), 1.89 (p, J=7.4 Hz, 4H), 1.36 (d, J=6.5 Hz, 6H).

LCMS; m/z 460.6 (M+H)$^+$ (ES$^+$).

Example 14: 5-(2-(Dimethylamino)propan-2-yl)-N-((1,2,3,5,6,7-hexahydro-s-indacen-4-yl)carbamoyl)-1-methyl-1H-pyrazole-3-sulfonamide

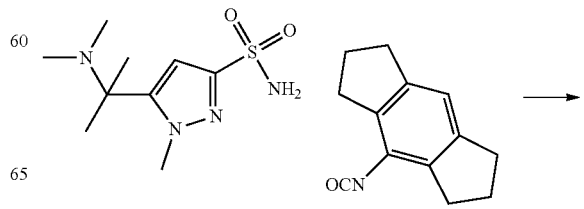

-continued

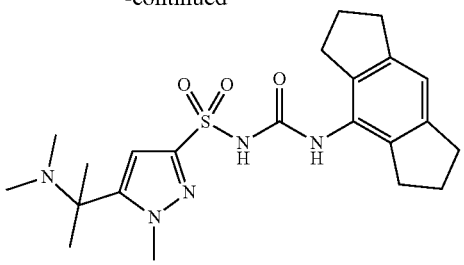

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(2-(dimethylamino)propan-2-yl)-1-methyl-1H-pyrazole-3-sulfonamide (Intermediate P22) and 4-isocyanato-1,2,3,5,6,7-hexahydro-s-indacene (Intermediate A1) to afford the title compound (4.8 mg, 4%) as a clear colourless solid.

$^1$H NMR (DMSO-d$_6$) δ 7.60 (s, 1H), 6.78 (s, 1H), 6.27 (s, 1H), 3.98 (s, 3H), 2.75 (t, J=7.4 Hz, 4H), 2.61 (t, J=7.4 Hz, 4H), 2.10 (s, 6H), 1.89 (p, J=7.4 Hz, 4H), 1.32 (s, 6H). NH not resolved.

LCMS; m/z 446.5 (M+H)$^+$ (ES$^+$).

Example 35: N-((2-(2-Cyanopyridin-4-yl)-4-fluoro-6-isopropylphenyl)carbamoyl)-5-((dimethylamino)methyl)-1-ethyl-1H-pyrazole-3-sulfonamide

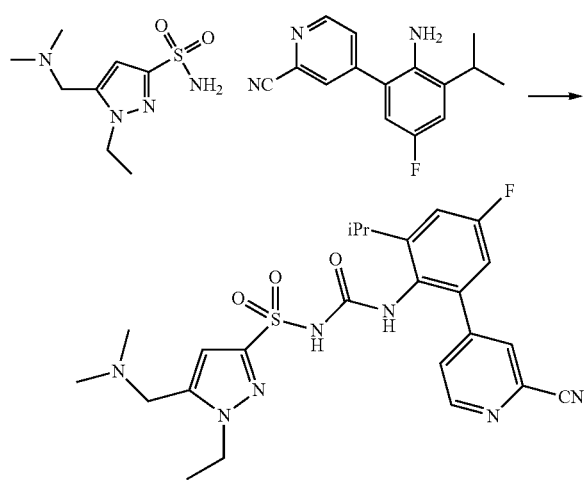

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-ethyl-H-pyrazole-3-sulfonamide (Intermediate P7) and 4-(2-amino-5-fluoro-3-isopropylphenyl)picolinonitrile (Intermediate A9) to afford the title compound (7 mg, 6%) as a colourless powder.

$^1$H NMR (DMSO-d$_6$) δ 11.02 (br s, 1H), 8.65 (d, J=5.0 Hz, 1H), 8.03 (d, J=1.7 Hz, 1H), 7.97 (s, 1H), 7.73-7.65 (m, 1H), 7.26 (dd, J=10.0, 3.0 Hz, 1H), 7.15 (dd, J=8.8, 3.0 Hz, 1H), 6.29 (s, 1H), 4.17 (q, J=7.2 Hz, 2H), 3.46 (s, 2H), 3.21-3.02 (m, 1H), 2.16 (s, 6H), 1.33 (t, J=7.2 Hz, 3H), 1.11 (d, J=6.8 Hz, 6H).

LCMS; m/z 514.6 (M+H)$^+$ (ES$^+$); 512.4 (M–H)$^-$ (ES$^-$).

Example 16: N-((2-(2-Cyanopyridin-4-yl)-4-fluoro-6-isopropylphenyl)carbamoyl)-5-((dimethylamino)methyl)-1-methyl-1H-pyrazole-3-sulfonamide

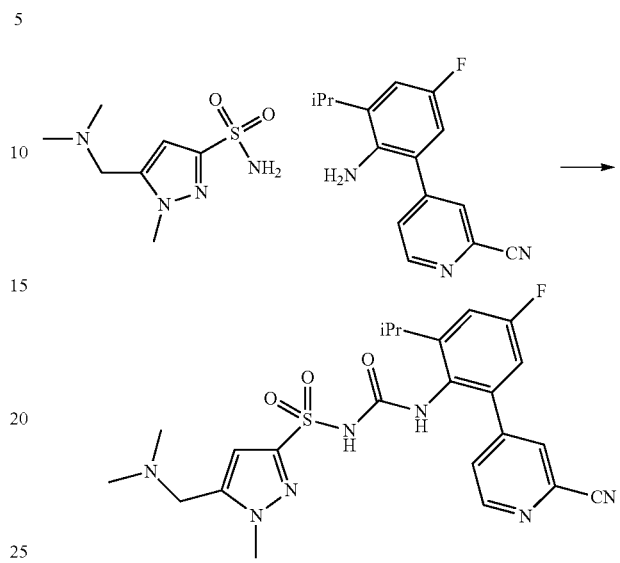

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 4-(2-amino-5-fluoro-3-isopropylphenyl)picolinonitrile (Intermediate Aq) to afford the title compound (8 mg, 7%) as a colourless powder.

$^1$H NMR (DMSO-d$_6$) δ 10.91 (s, 1H), 8.66 (d, J=5.1 Hz, 1H), 8.07-7.97 (m, 2H), 7.73-7.61 (m, 1H), 7.27 (dd, J=9.9, 3.0 Hz, 1H), 7.15 (dd, J=8.8, 2.9 Hz, 1H), 6.33 (s, 1H), 3.86 (s, 3H), 3.48 (s, 2H), 3.12 (sept, J=6.5 Hz, 1H), 2.17 (s, 6H), 1.12 (d, J=6.8 Hz, 6H).

LCMS; m/z 500.5 (M+H)$^+$ (ES$^+$); 498.4 (M–H)$^-$ (ES$^-$).

Example 37: 1-(tert-Butyl)-5-((dimethylamino)methyl)-N-((1,2,3,5,6,7-hexahydro-s-indacen-4-yl)carbamoyl)-1H-pyrazole-3-sulfonamide

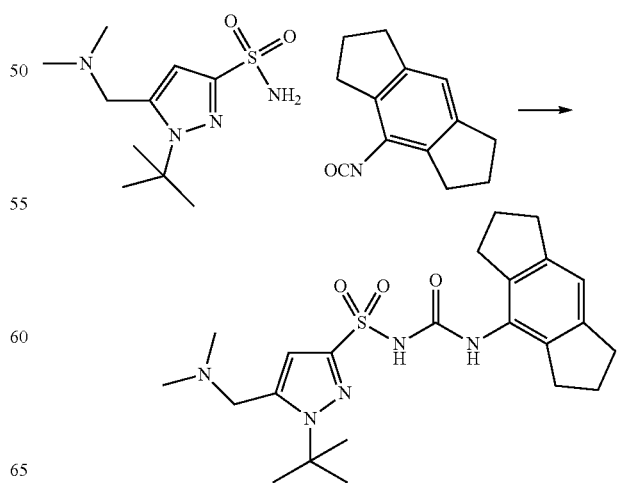

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 1-(tert-butyl)-5-((dimethylamino)methyl)-1H-pyrazole-3-sulfonamide (Intermediate P24) and 4-isocyanato-1,2,3,5,6,7-hexahydro-s-indacene (Intermediate A1) to afford the title compound (15 mg, 28%) as a white solid.

$^1$H NMR (DMSO-$d_6$) δ 10.78 (bs, 1H), 7.98 (s, 1H), 6.93 (s, 1H), 6.68 (s, 1H), 3.53 (s, 2H), 2.79 (t, J=7.4 Hz, 4H), 2.57 (t, J=7.4 Hz, 4H), 2.17 (s, 6H), 1.93 (p, J=7.4 Hz, 4H), 1.62 (s, 9H).

LCMS; m/z 460.5 (M+H)$^+$ (ES$^+$).

Example 38: 5-(Azetidin-1-ylmethyl)-1-(tert-butyl)-N-((1,2,3,5,6,7-hexahydro-s-indacen-4-yl)carbamoyl)-1H-pyrazole-3-sulfonamide

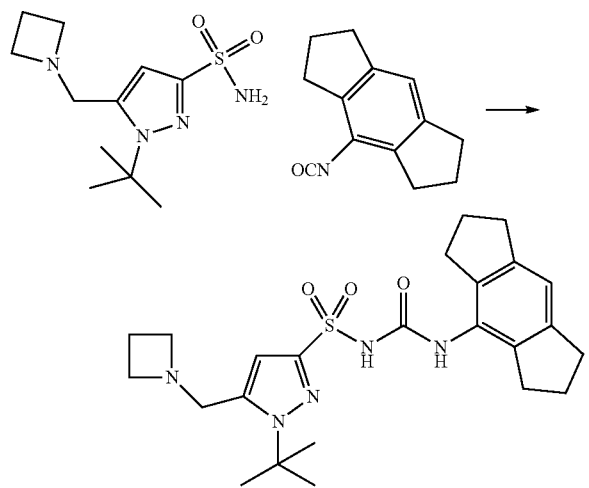

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(azetidin-1-ylmethyl)-1-(tert-butyl)-1H-pyrazole-3-sulfonamide (Intermediate P25) and 4-isocyanato-1,2,3,5,6,7-hexahydro-s-indacene (Intermediate A1) to afford the title compound (4 mg, 31%) as a white solid.

$^1$H NMR (DMSO-$d_6$) δ 10.78 (bs, 1H), 7.98 (s, 1H), 6.93 (s, 1H), 6.66 (s, 1H), 3.76 (s, 2H), 3.22 (t, J=7.0 Hz, 4H), 2.79 (t, J=7.4 Hz, 4H), 2.58 (t, J=7.4 Hz, 4H), 2.02 (p, J=7.1 Hz, 2H), 1.93 (p, J=7.4 Hz, 4H), 1.60 (s, 9H).

LCMS; m/z 472.8 (M+H)$^+$ (ES$^+$).

Example 39: 5-((Dimethylamino)methyl)-N-((5-fluoro-3-isopropyl-[1,1'-biphenyl]-2-yl)carbamoyl)-1-isopropyl-1-H-pyrazole-3-sulfonamide

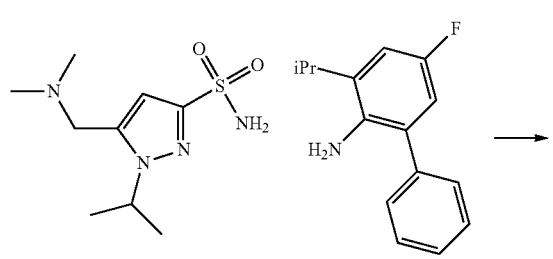

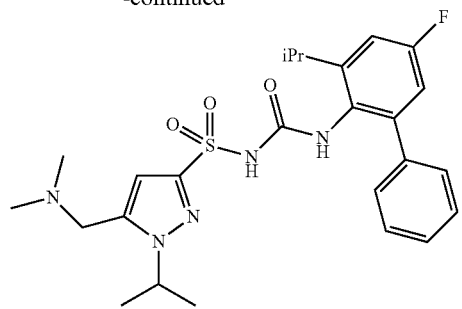

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-isopropyl-1H-pyrazole-3-sulfonamide (Intermediate P26) and 5-fluoro-3-isopropyl-[1,1'-biphenyl]-2-amine (Intermediate A4) to afford the title compound (36 mg, 32%) as a colourless powder.

$^1$H NMR (DMSO-$d_6$) δ 10.77 (s, 1H), 7.70 (s, 1H), 7.39-7.27 (m, 5H), 7.16 (dd, J=10.1, 3.0 Hz, 1H), 6.97 (dd, J=8.9, 3.0 Hz, 1H), 6.51 (s, 1H), 4.83 (sept, J=6.6 Hz, 1H), 3.50 (s, 2H), 2.95 (sept, J=7.9 Hz, 1H), 2.17 (s, 6H), 1.39 (d, J=6.5 Hz, 6H), 1.09 (d, J=6.8 Hz, 6H).

LCMS; m/z 502 (M+H)$^+$ (ES$^+$); 500 (M−H)$^-$ (ES$^-$).

Example 40: N-((2-(1,3-Dimethyl-1H-pyrazol-5-yl)-4-fluoro-6-isopropylphenyl)carbamoyl)-5-((dimethylamino)methyl)-1-methyl-1H-pyrazole-3-sulfonamide

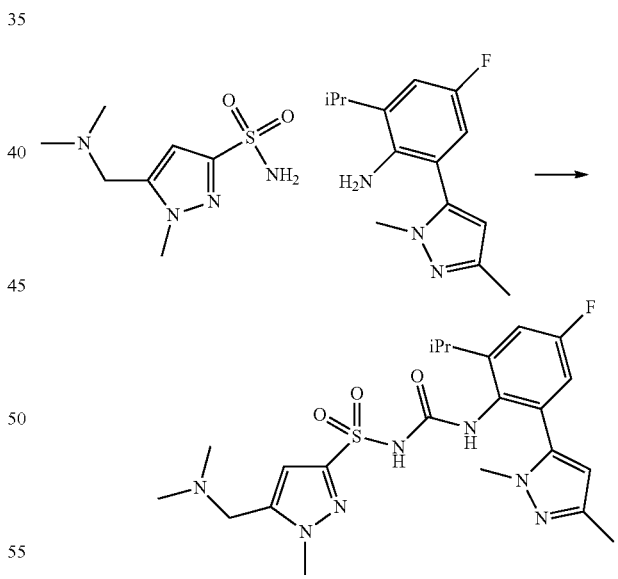

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 2-(1,3-dimethyl-H-pyrazol-5-yl)-4-fluoro-6-isopropylaniline (Intermediate A6) to afford the title compound (16 mg, 22%) as a colourless powder.

$^1$H NMR (DMSO-$d_6$) δ 10.84 (s, 1H), 7.68 (s, 1H), 7.24 (dd, J=10.1, 3.0 Hz, 1H), 7.04 (dd, J=8.7, 3.0 Hz, 1H), 6.52

(s, 1H), 5.93 (s, 1H), 3.89 (s, 3H), 3.50 (s, 2H), 3.45 (s, 3H), 3.08-2.92 (m, 1H), 2.17 (s, 6H), 2.14 (s, 3H), 1.09 (d, J=6.8 Hz, 6H).

LCMS; m/z 492 (M+H)$^+$ (ES$^+$); 490 (M−H)$^-$ (ES$^-$).

Example 41: 5-((Dimethylamino)methyl)-N-((4-fluoro-2-isopropyl-6-(pyridin-3-yl)phenyl)carbamoyl)-1-methyl-1H-pyrazole-3-sulfonamide

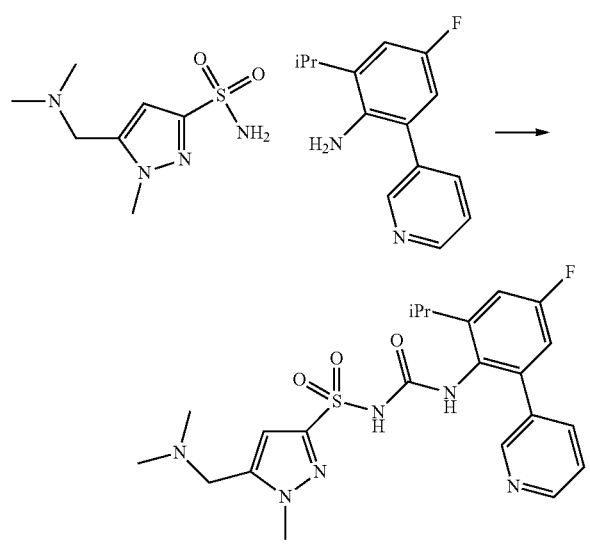

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 4-fluoro-2-isopropyl-6-(pyridin-3-yl)aniline (Intermediate A3) to afford the title compound (36 mg, 34%) as a colourless powder.

$^1$H NMR (DMSO-d$_6$) δ 10.84 (s, 1H), 8.57-8.52 (m, 1H), 8.49 (s, 1H), 7.83 (s, 1H), 7.73-7.67 (m, 1H), 7.35 (dd, J=8.0, 4.9 Hz, 1H), 7.21 (dd, J=10.1, 3.0 Hz, 1H), 7.06 (dd, J=8.9, 3.0 Hz, 1H), 6.47 (s, 1H), 3.89 (s, 3H), 3.49 (s, 2H), 3.04 (sept, J=6.4 Hz, 1H), 2.17 (s, 6H), 1.10 (d, J=6.6 Hz, 6H).

LCMS; m/z 475 (M+H)$^+$ (ES$^+$); 473 (M−H)$^-$ (ES$^-$).

Example 42: 5-((Dimethylamino)methyl)-N-((4-fluoro-2-isopropyl-6-(pyrimidin-5-yl)phenyl)carbamoyl)-1-isopropyl-1H-pyrazole-3-sulfonamide

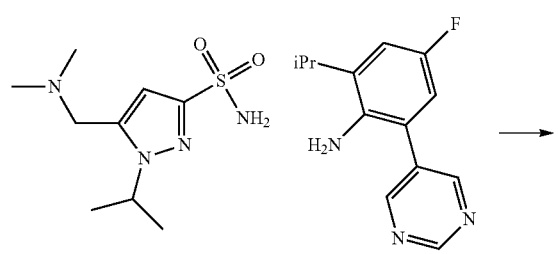

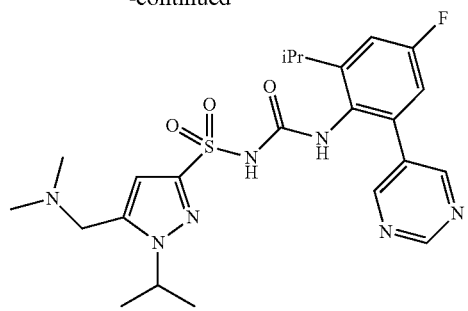

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-isopropyl-H-pyrazole-3-sulfonamide (Intermediate P26) and 4-fluoro-2-isopropyl-6-(pyrimidin-5-yl)aniline (Intermediate A8) to afford the title compound (17 mg, 12%) as a colourless powder.

$^1$H NMR (DMSO-d$_6$) δ 11.02 (s, 1H), 9.13 (s, 1H), 8.76 (s, 2H), 8.04 (s, 1H), 7.26 (dd, J=10.0, 3.0 Hz, 1H), 7.20 (dd, J=8.8, 3.0 Hz, 1H), 6.44 (s, 1H), 4.81 (sept, J=6.6 Hz, 1H), 3.51 (s, 2H), 3.03 (sept, J=7.0 Hz, 1H), 2.17 (s, 6H), 1.38 (d, J=6.6 Hz, 6H), 1.10 (d, J=6.8 Hz, 6H).

LCMS; m/z 504 (M+H)$^+$ (ES$^+$); 502 (M−H)$^-$ (ES$^-$).

Example 4: 5-((Dimethylamino)methyl)-N-((4-fluoro-2-isopropyl-6-(pyrimidin-5-yl)phenyl)carbamoyl)-1-methyl-1H-pyrazole-3-sulfonamide

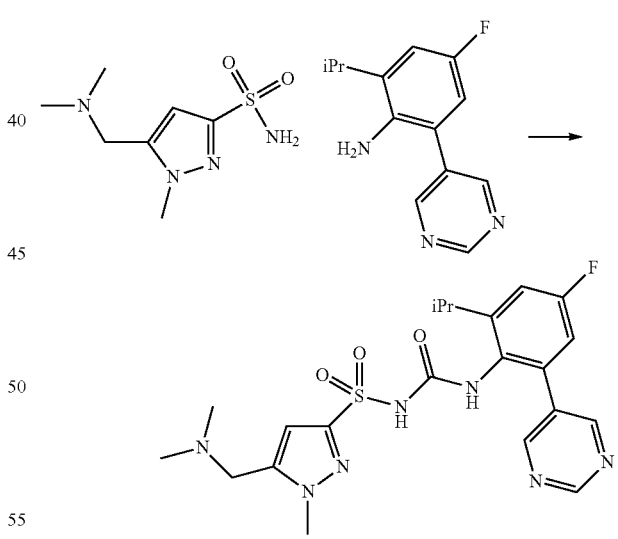

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 4-fluoro-2-isopropyl-6-(pyrimidin-5-yl)aniline (Intermediate A8) to afford the title compound (14 mg, 10%) as a colourless powder.

$^1$H NMR (DMSO-d$_6$) δ 10.93 (s, 1H), 9.15 (s, 1H), 8.73 (s, 2H), 8.02 (s, 1H), 7.27 (dd, J=10.0, 3.0 Hz, 1H), 7.19 (dd,

J=8.8, 3.0 Hz, 1H), 6.48 (s, 1H), 3.90 (s, 3H), 3.53 (s, 2H), 3.06 (sept, J=6.9 Hz, 1H), 2.19 (s, 6H), 1.11 (d, J=6.7 Hz, 6H).

LCMS; m/z 476 (M+H)⁺ (ES⁺); 474 (M−H)⁻ (ES⁻).

Example 44: ((1,2,3,5,6,7-Hexahydro-s-indacen-4-yl)carbamoyl)((1-methyl-5-((trimethylammonio)methyl)-1H-pyrazol-3-yl)sulfonyl)amide

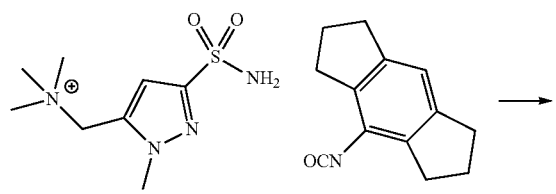

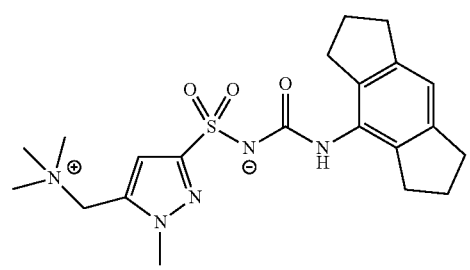

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from N,N,N-trimethyl-1-(1-methyl-3-sulfamoyl-1H-pyrazol-5-yl)methanaminium 2,2,2-trifluoroacetate (Intermediate P27) and 4-isocyanato-1,2,3,5,6,7-hexahydro-s-indacene (Intermediate A1) to afford the title compound (22 mg, 25%) as a white powder.

¹H NMR (DMSO-d₆) δ 7.45 (s, 1H), 6.78 (s, 1H), 6.76 (s, 1H), 4.66 (s, 2H), 3.90 (s, 3H), 3.05 (s, 9H), 2.75 (t, J=7.4 Hz, 4H), 2.65 (t, J=7.4 Hz, 4H), 1.90 (p, J=7.4 Hz, 4H).

LCMS; m/z 432.5 (M)+(ES⁺).

Example 45: N-((3'-Cyano-5-fluoro-3-isopropyl-[1,1'-biphenyl]-2-yl)carbamoyl)-5-((dimethylamino)methyl)-1-isopropyl-1H-pyrazole-3-sulfonamide

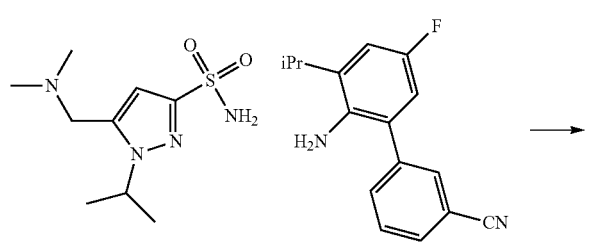

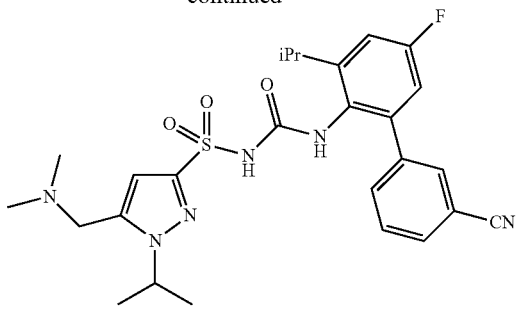

Prepared according to the general procedure of N-((5-bromo-2,3-dihydro-1H-inden-4-yl)carbamoyl)-5-((dimethylamino)methyl)-1-ethyl-1H-pyrazole-3-sulfonamide (Example 16) from 5-((dimethylamino)methyl)-1-isopropyl-H-pyrazole-3-sulfonamide (Intermediate P26) and 2'-amino-5'-fluoro-3'-isopropyl-[1,1'-biphenyl]-3-carbonitrile (Intermediate A5) to afford the title compound (28 mg, 24%) as a colourless powder.

¹H NMR (DMSO-d₆) δ 10.92 (s, 1H), 7.93 (s, 1H), 7.85-7.79 (m, 2H), 7.68-7.63 (m, 1H), 7.57-7.51 (m, 1H), 7.21 (dd, J=10.0, 3.0 Hz, 1H), 7.07 (dd, J=8.9, 3.0 Hz, 1H), 6.42 (s, 1H), 4.79 (sept, J=6.6 Hz, 1H), 3.48 (s, 2H), 3.00 (sept, J=6.9 Hz, 1H), 2.15 (s, 6H), 1.37 (d, J=6.6 Hz, 6H), 1.09 (s, 6H).

LCMS; m/z 527 (M+H)⁺ (ES⁺); 525 (M−H)⁻ (ES⁻).

Example 46: N-((3'-Cyano-5-fluoro-3-isopropyl-[1,1'-biphenyl]-2-yl)carbamoyl)-5-((dimethylamino)methyl)-1-methyl-1H-pyrazole-3-sulfonamide Prepared according to the general procedure of N-((5-bromo-2,3-dihydro-1H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 2'-amino-5'-fluoro-3'-isopropyl-[1,1'-biphenyl]-3-carbonitrile (Intermediate A5) to afford the title compound (37 mg, 34%) as a colourless powder.

¹H NMR (DMSO-d₆) δ 1.86 (s, 1H), 7.90 (s, 1H), 7.84-7.78 (m, 2H), 7.65-7.60 (m, 1H), 7.53 (t, J=7.7 Hz,

1H), 7.21 (dd, J=10.0, 3.0 Hz, 1H), 7.06 (dd, J=8.9, 3.0 Hz, 1H), 6.45 (s, 1H), 3.87 (s, 3H), 3.49 (s, 2H), 3.04 (sept, J=7.0 Hz, 1H), 2.17 (s, 6H), 1.10 (br s, 6H).
LCMS; m/z 499 (M+H)$^+$ (ES$^+$); 497 (M−H)$^-$ (ES$^-$).

Example 47: 5-((Dimethylamino)methyl)-N-((4-fluoro-2-isopropyl-6-(2-methoxypyridin-4-yl)phenyl)carbamoyl)-1-isopropyl-1H-pyrazole-3-sulfonamide

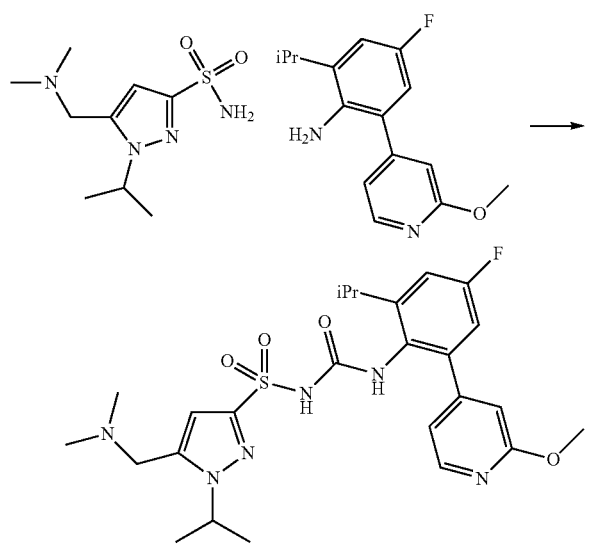

Prepare according to the general procedure of N-(5-bromo-2,3-dihydro-1H-inden-4-yl)carbamoyl)-5-((dimethylamino)methyl)-1-ethyl-1H-pyrazole-3-sulfonamide (Example 16) from 5-((dimethylamino)methyl)-1-isopropyl-1H-pyrazole-3-sulfonamide (Intermediate P26) and 4-fluoro-2-isopropyl-6-(2-methoxypyridin-4-yl)aniline (Intermediate A7) to afford the title compound (44 mg, 43%) as a colourless powder.

$^1$H NMR (DMSO-d$_6$) δ 10.92 (s, 1H), 8.09 (dd, J=5.3, 0.7 Hz, 1H), 7.87 (s, 1H), 7.22 (dd, J=10.0, 3.0 Hz, 1H), 7.04 (dd, J=8.9, 3.0 Hz, 1H), 6.92 (dd, J=5.2, 1.5 Hz, 1H), 6.79 (s, 1H), 6.48 (s, 1H), 4.81 (sept, J=6.6 Hz, 1H), 3.88 (s, 3H), 3.48 (s, 2H), 2.98 (sept, J=6.9 Hz, 1H), 2.15 (s, 6H), 1.37 (d, J=6.6 Hz, 6H), 1.08 (d, J=6.8 Hz, 6H).
LCMS; m/z 533 (M+H)$^+$ (ES$^+$); 531 (M−H)$^-$ (ES$^-$).

Example 48: 5-((Dimethylamino)methyl)-N-((4-fluoro-2-isopropyl-6-(2-methoxypyridin-4-yl)phenyl)carbamoyl)-1-methyl-1H-pyrazole-3-sulfonamide

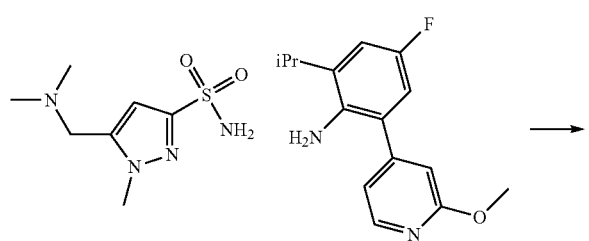

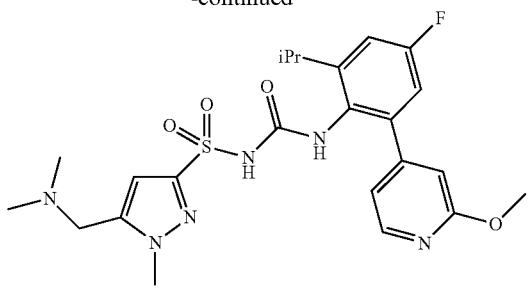

Prepared according to the general procedure of N-((5-bromo-2,3-dihydro-H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 4-fluoro-2-isopropyl-6-(2-methoxypyridin-4-yl)aniline (Intermediate A7) to afford the title compound (15 mg, 16%) as a colourless powder.

$^1$H NMR (DMSO-d$_6$) δ 10.87 (s, 1H), 8.09 (dd, J=5.3, 0.7 Hz, 1H), 7.85 (s, 1H), 7.22 (dd, J=10.0, 3.0 Hz, 1H), 7.04 (dd, J=8.8, 3.0 Hz, 1H), 6.89 (dd, J=5.3, 1.4 Hz, 1H), 6.77 (s, 1H), 6.51 (s, 1H), 3.88 (s, 6H), 3.49 (s, 2H), 3.02 (sept, J=7.2 Hz, 1H), 2.17 (s, 6H), 1.09 (d, J=6.8 Hz, 6H).
LCMS; m/z 505 (M+H)$^+$ (ES$^+$); 503 (M−H)$^-$ (ES$^-$).

Example 4A: 5-(Azetidin-1-ylmethyl)-1-ethyl-N-((1,2,3,5,6,7-hexahydro-s-indacen-4-yl)carbamoyl)-1H-pyrazole-3-sulfonamide

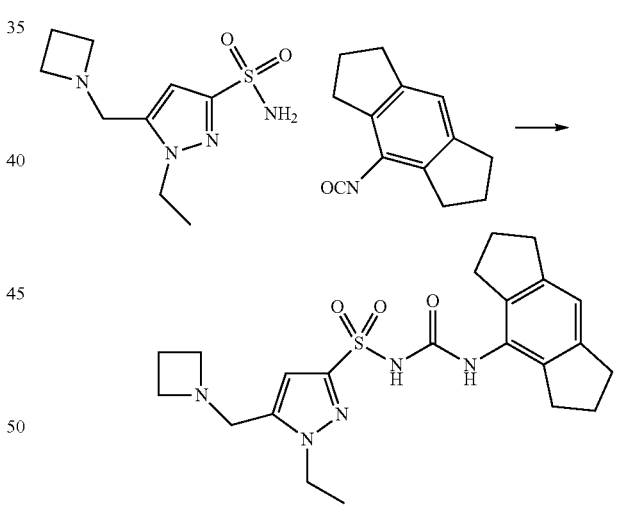

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(azetidin-1-ylmethyl)-1-ethyl-H-pyrazole-3-sulfonamide (Intermediate P28) and 4-isocyanato-1,2,3,5,6,7-hexahydro-s-indacene (Intermediate A1) to afford the title compound (52 mg, 40%) as a white solid.

$^1$H NMR (DMSO-d$_6$) δ 10.85 (br s, 1H), 7.99 (s, 1H), 6.92 (s, 1H), 6.61 (s, 1H), 4.18 (q, J=7.2 Hz, 2H), 3.68 (s, 2H), 3.22 (t, J=7.1 Hz, 4H), 2.79 (t, J=7.4 Hz, 4H), 2.59 (t, J=7.4 Hz, 4H), 2.01 (p, J=7.1 Hz, 2H), 1.94 (p, J=7.4 Hz, 4H), 1.35 (t, J=7.2 Hz, 3H).
LCMS; m/z 444.4 (M+H)$^+$ (ES$^+$).

Example 50: N-((1,2,3,5,6,7-Hexahydro-s-indacen-4-yl)carbamoyl)-1-isopropyl-5-((methylamino)methyl)-1H-pyrazole-3-sulfonamide

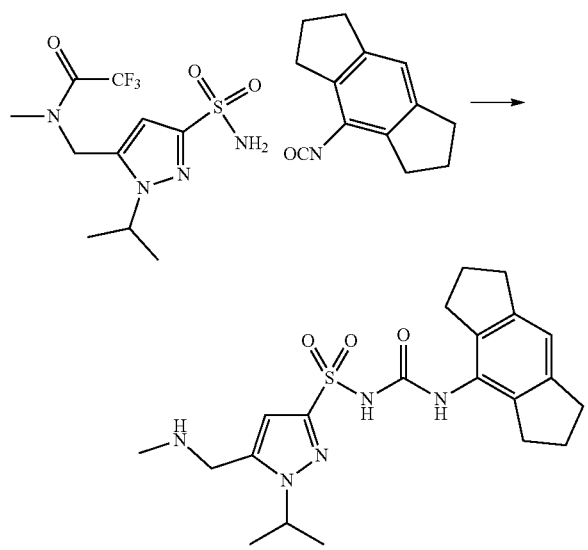

Sodium tert-butoxide (2 M in THF) (0.152 mL, 0.305 mmol) was added to a solution of 2,2,2-trifluoro-N-((1-isopropyl-3-sulfamoyl-1H-pyrazol-5-yl)methyl)-N—methylacetamide (Intermediate P29) (100 mg, 0.305 mmol) in THF (6 mL) and stirred at room temperature for 1 hour. Then 4-isocyanato-1,2,3,5,6,7-hexahydro-s-indacene (Intermediate A1) (67 mg, 0.336 mmol) was added and stirred at room temperature overnight. The volatiles were evaporated. MeOH (0.3 mL) and $K_2CO_3$ (44 mg, 0.318 mmol) were added and stirred for 16 hours. Another equivalent of $K_2CO_3$ (44 mg, 0.318 mmol) was added and stirred for further 16 hours. The volatiles were evaporated and the crude product was purified by reversed phase prep-HPLC (General Methods, basic prep) to afford the title compound (23 mg, 17%) as a white solid.

$^1$H NMR (DMSO-$d_6$) δ 7.83 (s, 1H), 6.86 (s, 1H), 6.59 (s, 1H), 4.70 (sept, J=6.4 Hz, 1H), 3.96 (s, 2H), 3.33 (bs, 1H), 2.77 (t, J=7.4 Hz, 4H), 2.63 (t, J=7.4 Hz, 4H), 2.42 (s, 3H), 1.92 (p, J=7.5 Hz, 4H), 1.35 (d, J=6.5 Hz, 6H). One exchangeable proton missing.

LCMS; m/z 432.5 (M+H)$^+$ (ES$^+$).

Example 51: 5-((Dimethylamino)methyl)-1-ethyl-N-((4-fluoro-2,6-diisopropylphenyl)carbamoyl)-1H-pyrazole-3-sulfonamide

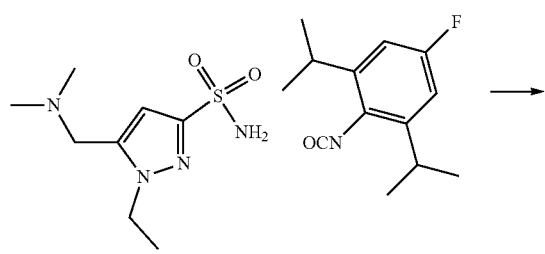

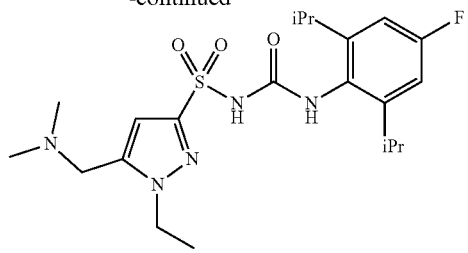

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 1-(2-(dimethylamino)ethyl)-5-((dimethylamino)methyl)-H-pyrazole-3-sulfonamide (Intermediate P7) and 5-fluoro-2-isocyanato-1,3-diisopropylbenzene (Intermediate A2) to afford the title compound (53 mg, 45%).

$^1$H NMR (DMSO-$d_6$) δ 10.96 (br s, 1H), 7.76 (s, 1H), 6.91 (d, J=9.9 Hz, 2H), 6.58 (s, 1H), 4.21 (q, J=7.2 Hz, 2H), 3.46 (s, 2H), 3.04-2.91 (m, 2H), 2.14 (s, 6H), 1.36 (t, J=7.2 Hz, 3H), 1.14-0.93 (m 12H).

LCMS; m/z 454.5 (M+H)$^+$ (ES$^+$).

Example 52: 5-((Dimethylamino)methyl)-1-ethyl-N-((1,2,3,5,6,7-hexahydro-s-indacen-4-yl)carbamoyl)-1H-pyrazole-3-sulfonamide

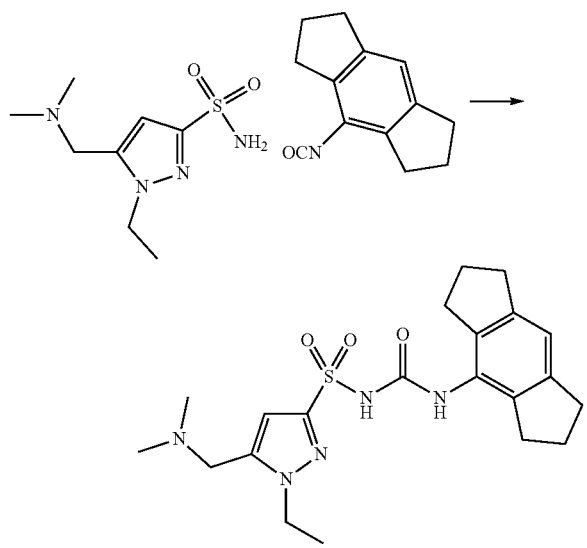

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 1-(2-(dimethylamino)ethyl)-5-((dimethylamino)methyl)-1H-pyrazole-3-sulfonamide (Intermediate P7) and 4-isocyanato-1,2,3,5,6,7-hexahydro-s-indacene (Intermediate A1) to afford the title compound (44 mg, 39%).

$^1$H NMR (DMSO-$d_6$) δ 10.79 (br s, 1H), 7.97 (s, 1H), 6.92 (s, 1H), 6.62 (s, 1H), 4.21 (q, J=7.2 Hz, 2H), 3.48 (s, 2H), 2.78 (t, J=7.4 Hz, 4H), 2.58 (t, J=7.4 Hz, 4H), 2.16 (s, 6H), 1.93 (p, J=7.4 Hz, 4H), 1.35 (t, J=7.2 Hz, 3H).

LCMS; m/z 432.4 (M+H)$^+$ (ES$^+$).

Example 53: 5-(Azetidin-1-ylmethyl)-N-((1,2,3,5,6,7-hexahydro-s-indacen-4-yl)carbamoyl)-1-isopropyl-1H-pyrazole-3-sulfonamide

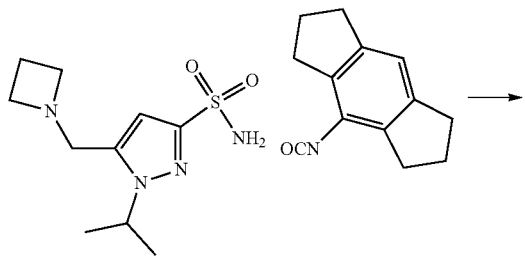

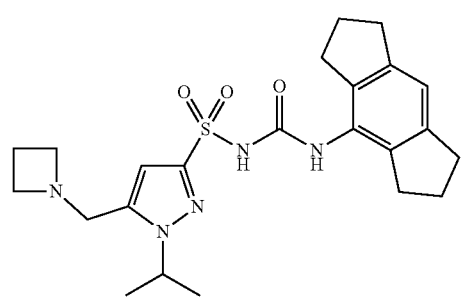

Prepared according to the general procedure of (((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-(azetidin-1-ylmethyl)-1-isopropyl-1H-pyrazole-3-sulfonamide (Intermediate P30) and 4-isocyanato-1,2,3,5,6,7-hexahydro-s-indacene (Intermediate A1) to afford the title compound (88 mg, 54%) as a white solid.

$^1$H NMR (DMSO-d$_6$) δ 10.78 (br s, 1H), 7.97 (s, 1H), 6.92 (s, 1H), 6.60 (s, 1H), 4.74 (sept, J=6.5 Hz, 1H), 3.66 (s, 2H), 3.18 (t, J=7.1 Hz, 4H), 2.79 (t, J=7.4 Hz, 4H), 2.58 (t, J=7.3 Hz, 4H), 2.03-1.97 (m, 2H), 1.96-1.90 (m, 4H), 1.38 (d, J=6.5 Hz, 6H).

LCMS; m/z 458.4 (M+H)$^+$ (ES$^+$).

Example 54: 5-((Dimethylamino)methyl)-N-((4-fluoro-2-isopropyl-6-(pyridin-3-yl)phenyl)carbamoyl)-1-isopropyl-1H-pyrazole-3-sulfonamide

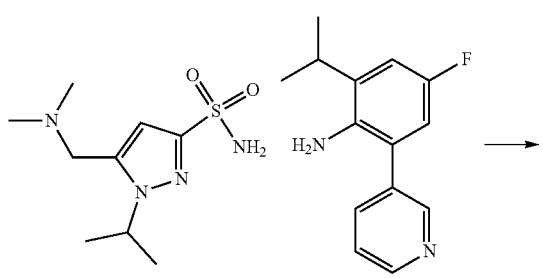

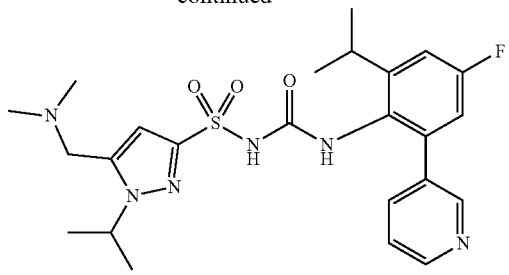

5-((Dimethylamino)methyl)-1-isopropyl-1H-pyrazole-3-sulfonamide (Intermediate P26; 0.020 g, 0.081 mmol) and N,N-dimethylaminopyridine (0.030 g, 0.244 mmol) were dissolved in dry MeCN (1 mL) at room temperature and stirred for 10 minutes, after which time the mixture had become homogeneous. Diphenyl carbonate (0.019 g, 0.089 mmol) was then added as a solid and the slightly turbid reaction mixture was stirred at room temperature overnight. This was repeated 4 times at different temperatures. The crude reaction mixtures were combined and added to 4-fluoro-2-isopropyl-6-(pyridin-3-yl)aniline (Intermediate A3) (36.4 mg, 0.158 mmol). The mixture was then heated to 70° C. for 2 hours, evaporated to dryness in vacuo and the brown residue obtained triturated with 1:4 EtOAc:DCM (4 mL). The filtrate was then purified by reversed phase prep-HPLC (General Methods, basic prep) to afford the title compound (26 mg, 30%) as a white solid.

$^1$H NMR (DMSO-d$_6$) δ 10.91 (br s, 1H), 8.60-8.39 (m, 2H), 7.86 (s, 1H), 7.73 (dt, 1H), 7.36 (ddd, 1H), 7.21 (dd, 1H), 7.07 (dd, 1H), 6.44 (s, 1H), 4.80 (sept, 1H), 3.48 (s, 2H), 3.04-2.93 (m, 1H), 2.15 (s, 6H), 1.38 (d, 6H) and 1.09 (d, 6H).

LCMS; m/z 503.6 (M+H)$^+$ (ES$^+$); 501.4 (M−H)$^-$ (ES$^-$).

Example 55: N-((4-Chloro-2,6-diisopropylphenyl)carbamoyl)-5-((dimethylamino)methyl)-1-isopropyl-1H-pyrazole-3-sulfonamide

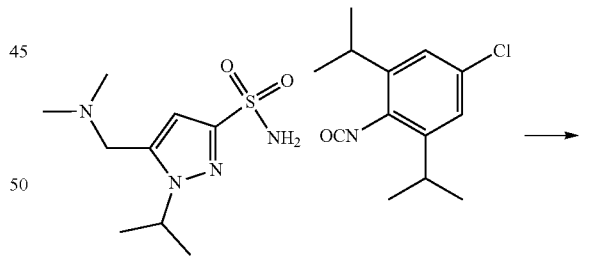

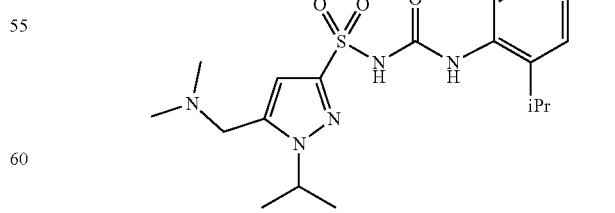

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(((dimethylamino)methyl)-1-isopropyl-H-pyrazole-3-sulfonamide (Intermediate P26) and 5-chloro-2-isocyanato-1,3-diisopropylbenzene (Intermediate A22) to afford the title compound (n mg, 11%) as a white solid.

$^1$H NMR (DMSO-d$_6$) δ 11.06 (s, 1H), 7.87 (s, 1H), 7.13 (s, 2H), 6.59 (s, 1H), 4.82 (sept, J=6.6 Hz, 1H), 3.48 (s, 2H), 2.95 (sept, J=6.9 Hz, 2H), 2.14 (s, 6H), 1.39 (d, J=6.6 Hz, 6H), 1.05 (br s, 12H).

LCMS; m/z 484/486 (M+H)$^+$ (ES$^+$); 482/484 (M−H)$^-$ (ES$^-$).

Example 56: 5-(((2,2-Difluoroethyl)(methyl)amino)methyl)-N-((1,2,3,5,6,7-hexahydro-s-indacen-4-yl)carbamoyl)-1-isopropyl-1H-pyrazole-3-sulfonamide, Sodium Salt

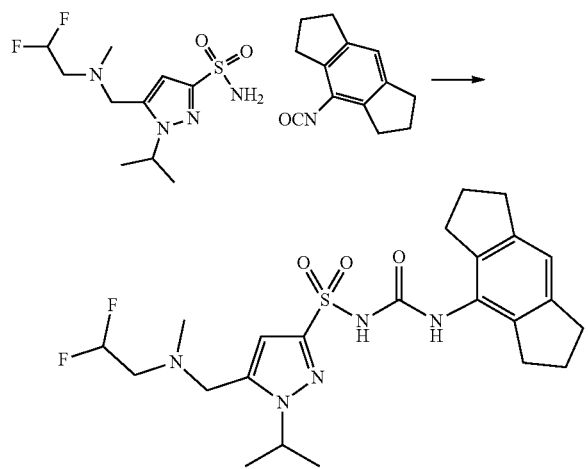

Prepare according to the general procedure of 5-(2-(dimethylamino)ethyl)-N-((1,2,3,5,6,7-hexahydro-s-indacen-4-yl)carbamoyl)-1-isopropyl-1H-pyrazole-3-sulfonamide, sodium salt (Example 33) from 5-(((2,2-difluoroethyl)(methyl)amino)methyl)-1-isopropyl-1H-pyrazole-3-sulfonamide (Intermediate P31) and 4-isocyanato-1,2,3,5,6,7-hexahydro-s-indacene (Intermediate A1) to afford the title compound (70 mg, 55%).

$^1$H NMR (DMSO-d$_6$) δ 7.55 (s, 1H), 6.76 (s, 1H), 6.32 (s, 1H), 6.12 (tt, J=55.7, 4.3 Hz, 1H), 4.67 (sept, J=6.7 Hz, 1H), 3.63 (s, 2H), 2.84-2.72 (m, 6H), 2.63 (t, J=7.3 Hz, 4H), 2.25 (s, 3H), 1.88 (p, J=7.4 Hz, 4H), 1.36 (d, J=6.6 Hz, 6H).

LCMS; m/z 496.5 (M+H)$^+$ (ES$^+$).

Example 57: 5-(((2-Fluoroethyl)(methyl)amino)methyl)-N-((1,2,3,5,6,7-hexahydro-s-indacen-4-yl)carbamoyl)-1-isopropyl-1H-pyrazole-3-sulfonamide, Sodium Salt

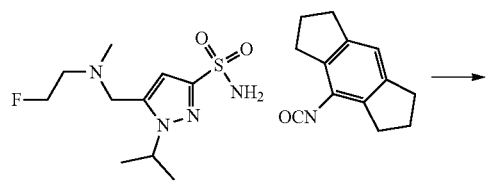

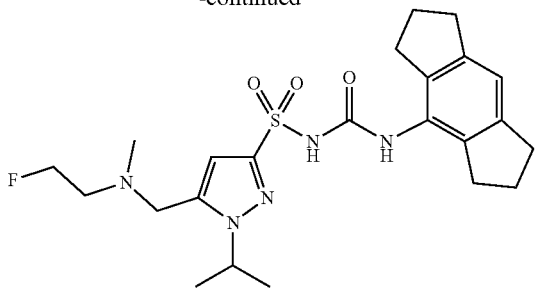

Prepared according to the general procedure of 5-(2-(dimethylamino)ethyl)-N-((1,2,3,5,6,7-hexahydro-s-indacen-4-yl)carbamoyl)-1-isopropyl-1H-pyrazole-3-sulfonamide, sodium salt (Example 33) from 5-(((2-fluoroethyl)(methyl)amino)methyl)-1-isopropyl-1H-pyrazole-3-sulfonamide (Intermediate P32) and 4-isocyanato-1,2,3,5,6,7-hexahydro-s-indacene (Intermediate A1) to afford the title compound (42 mg, 33%).

$^1$H NMR (DMSO-d$_6$) δ 7.57 (s, 1H), 6.77 (s, 1H), 6.31 (s, 1H), 4.74-4.65 (m, 1H), 4.52 (dt, J=47.8, 4.8 Hz, 2H), 3.55 (s, 2H), 2.75 (t, J=7.5 Hz, 4H), 2.71-2.60 (m, 6H), 2.19 (s, 3H), 1.89 (p, J=7.4 Hz, 4H), 1.35 (d, J=6.6 Hz, 6H).

LCMS; m/z 478.5 (M+H)$^+$ (ES$^+$).

Example 58: 5-(1-(Dimethylamino)cyclopropyl)-N-((1,2,3,5,6,7-hexahydro-s-indacen-4-yl)carbamoyl)-1-methyl-1H-pyrazole-3-sulfonamide, Sodium Salt

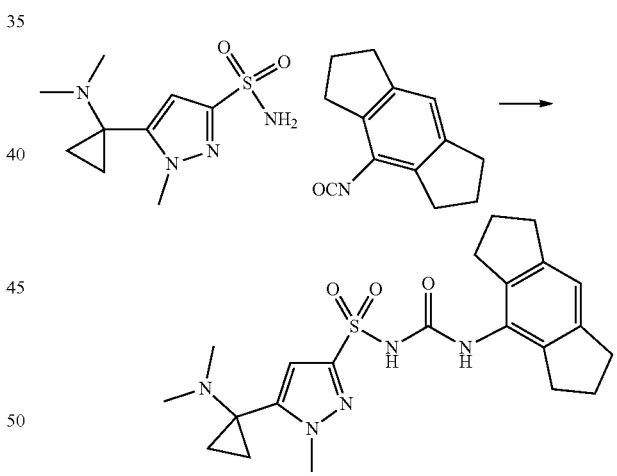

Prepared according to the general procedure of 5-(2-(dimethylamino)ethyl)-N-((1,2,3,5,6,7-hexahydro-s-indacen-4-yl)carbamoyl)-1-isopropyl-1H-pyrazole-3-sulfonamide, sodium salt (Example 33) from 5-(1-(dimethylamino)cyclopropyl)-1-methyl-1H-pyrazole-3-sulfonamide (Intermediate P33) and 4-isocyanato-1,2,3,5,6,7-hexahydro-s-indacene (Intermediate A1) to afford the title compound (64 mg, 65%) as a white solid.

$^1$H NMR (DMSO-d$_6$) δ 7.55 (s, 1H), 6.76 (s, 1H), 6.29 (s, 1H), 3.84 (s, 3H), 2.74 (t, J=7.5 Hz, 4H), 2.63 (t, J=7.4 Hz, 4H), 2.16 (s, 6H), 1.88 (p, J=7.4 Hz, 4H), 1.01-0.92 (m, 2H), 0.88-0.71 (m, 2H).

LCMS; m/z 444.5 (M+H)$^+$ (ES$^+$); 442.1 (M−H)$^-$ (ES$^-$).

Example 59: 5-(2-(Dimethylamino)ethyl)-N-((1,2,3,5,6,7-hexahydro-s-indacen-4-yl)carbamoyl)-1-methyl-1H-pyrazole-3-sulfonamide

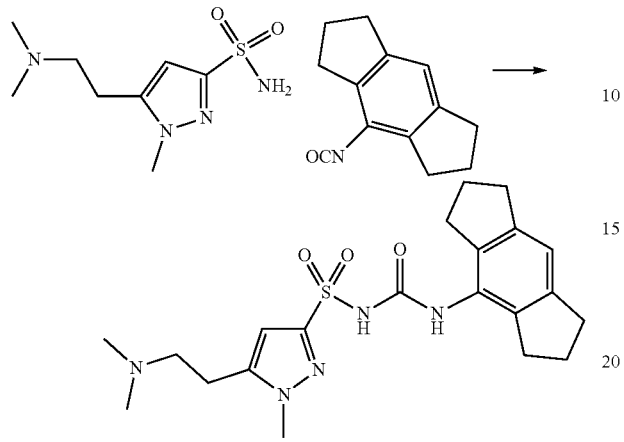

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(2-(dimethylamino)ethyl)-1-methyl-1H-pyrazole-3-sulfonamide (Intermediate P34) and 4-isocyanato-1,2,3,5,6,7-hexahydro-s-indacene (Intermediate A1) to afford the title compound (70 mg, 57%) as a clear glass, which gave a white solid after scratching.

$^1$H NMR (DMSO-$d_6$) δ 7.94 (s, 1H), 6.90 (s, 1H), 6.51 (s, 1H), 3.79 (s, 3H), 2.85 (t, J=7.5 Hz, 2H), 2.79 (t, J=7.4 Hz, 4H), 2.71 (t, J=7.5 Hz, 2H), 2.63 (t, J=7.4 Hz, 4H), 2.36 (s, 6H), 1.95 (p, J=7.4 Hz, 4H). NH not observed.

LCMS; m/z 432.5 (M+H)$^+$ (ES$^+$).

Example 60: 4-(Dimethylamino)-N-((1,2,3,5,6,7-hexahydro-s-indacen-4-yl)carbamoyl)-4,5,6,7-tetrahydropyrazolo[1,5-a]pyridine-2-sulfonamide

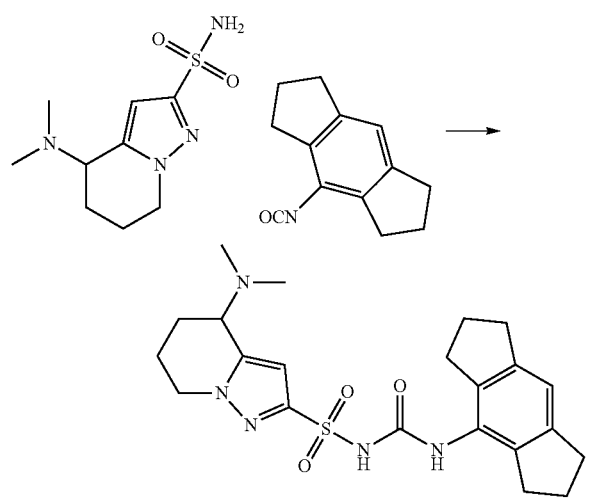

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 4-(dimethylamino)-4,5,6,7-tetrahydropyrazolo[1,5-a]pyridine-2-sulfonamide (Intermediate P35) and 4-isocyanato-1,2,3,5,6,7-hexahydro-s-indacene (Intermediate A1) to afford the title compound (57 mg, 64%) as a pale tan solid.

$^1$H NMR (DMSO-$d_6$) δ 10.75 (s, 1H), 8.03 (s, 1H), 6.93 (s, 1H), 6.60 (s, 1H), 4.20-4.12 (m, 1H), 4.08-3.98 (m, 1H), 3.93 (dd, J=9.9, 5.3 Hz, 1H), 2.79 (t, J=7.5 Hz, 4H), 2.59 (t, J=7.5, 4H), 2.24 (s, 6H), 2.20-2.11 (m, 1H), 2.02-1.82 (m, 6H), 1.74-1.61 (m, 1H).

LCMS; m/z 444.5 (M+H)$^+$ (ES$^+$).

Example 61: 5-((Dimethylamino)methyl)-N-((4-fluoro-2,6-diisopropylphenyl)carbamoyl)-1-isopropyl-1H-pyrazole-3-sulfonamide

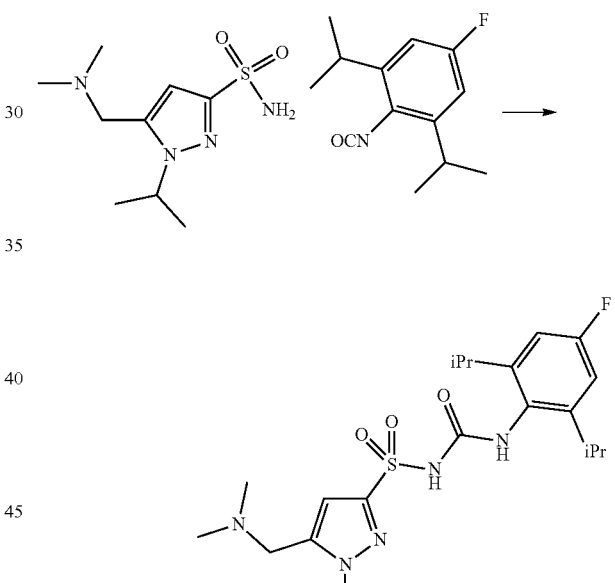

Prepared according to the general procedure of (((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-((dimethylamino)methyl)-1-isopropyl-1H-pyrazole-3-sulfonamide (Intermediate P26) and 5-fluoro-2-isocyanato-1,3-diisopropylbenzene (Intermediate A2) to afford the title compound (35 mg, 36%) as a colourless powder.

$^1$H NMR (DMSO-$d_6$) δ 11.01 (s, 1H), 7.79 (s, 1H), 6.92 (d, J=9.9 Hz, 2H), 6.60 (s, 1H), 4.83 (sept, J=6.5 Hz, 1H), 3.48 (s, 2H), 2.95 (sept, J=7.1 Hz, 2H), 2.14 (s, 6H), 1.39 (d, J=6.5 Hz, 6H), 1.05 (br s, 12H).

LCMS; m/z 468 (M+H)$^+$ (ES$^+$); 466 (M−H)$^−$ (ES$^−$).

Example 62: 5-(1-(Dimethylamino)propyl)-N-((4-fluoro-2,6-diisopropylphenyl)carbamoyl)-1-isopropyl-1H-pyrazole-3-sulfonamide

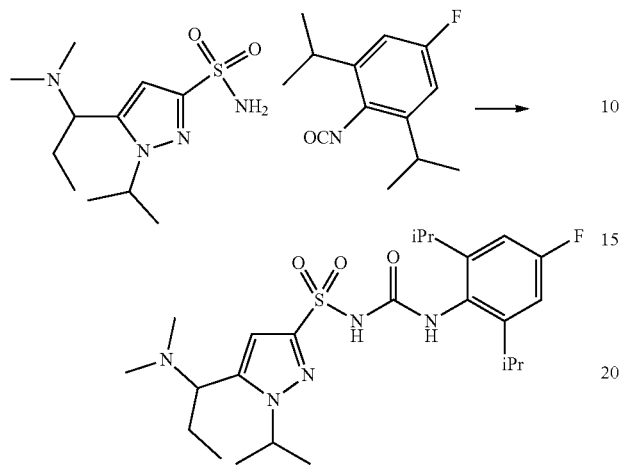

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)propyl)-1-isopropyl-1H-pyrazole-3-sulfonamide (Intermediate P36) and 5-fluoro-2-isocyanato-1,3-diisopropylbenzene (Intermediate A2) to afford the title compound (17 mg, 19%) as a clear colourless crystalline solid.

$^1$H NMR (DMSO-d$_6$) δ 11.00 (s, 1H), 7.77 (s, 1H), 6.91 (d, J=9.9 Hz, 2H), 6.57 (s, 1H), 4.91-4.80 (m, 1H), 3.68 (dd, J=10.0, 4.7 Hz, 1H), 3.03-2.91 (m, 2H), 2.11 (s, 6H), 1.86-1.77 (m, 1H), 1.68-1.59 (m, 1H), 1.41 (d, J=6.5 Hz, 3H), 1.35 (d, J=6.5 Hz, 3H), 1.04 (br s, 12H), 0.75 (t, J=7.3 Hz, 3H).
LCMS; m/z 496.6 (M+H)$^+$ (ES$^+$).

Example 63: 5-(1-(Dimethylamino)propyl)-N-((1,2,3,5,6,7-hexahydro-s-indacen-4-yl)carbamoyl)-1-isopropyl-1H-pyrazole-3-sulfonamide

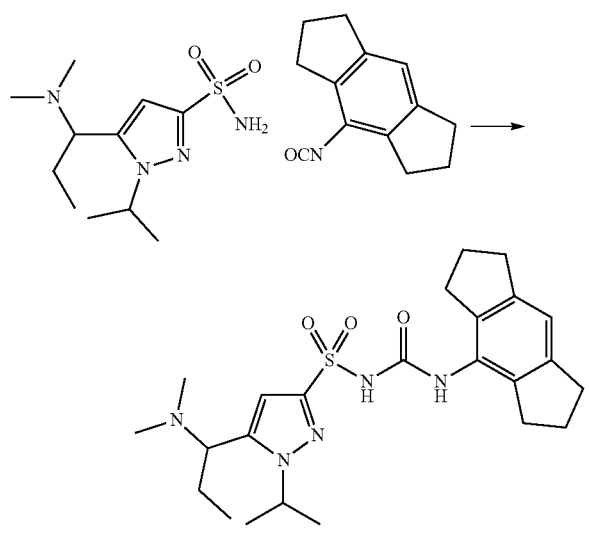

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)propyl)-1-isopropyl-H-pyrazole-3-sulfonamide (Intermediate P36) and 4-isocyanato-1,2,3,5,6,7-hexahydro-s-indacene (Intermediate A1) to afford the title compound (11 mg, 13%) as a clear colourless crystalline solid.

$^1$H NMR (DMSO-d$_6$) δ 10.84 (s, 1H), 7.86 (s, 1H), 6.86 (s, 1H), 6.49 (s, 1H), 4.87-4.76 (m, 1H), 3.64 (dd, J=9.8, 4.7 Hz, 1H), 2.76 (t, J=7.4 Hz, 4H), 2.57 (t, J=7.4 Hz, 4H), 2.11 (s, 6H), 1.94-1.78 (m, 5H), 1.71-1.56 (m, 1H), 1.39 (d, J=6.5 Hz, 3H), 1.33 (d, J=6.5 Hz, 3H), 0.77 (t, J=7.3 Hz, 3H).
LCMS; m/z 474.5 (M+H)$^+$ (ES$^+$).

Example 64: N-((4-Chloro-2,6-diisopropylphenyl)carbamoyl)-5-(1-(dimethylamino)propyl)-1-methyl-1H-pyrazole-3-sulfonamide

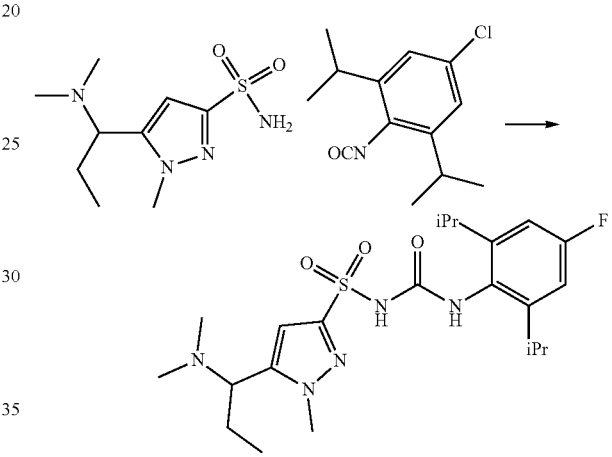

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)propyl)-1-methyl-H-pyrazole-3-sulfonamide (Intermediate P37) and 5-chloro-2-isocyanato-1,3-diisopropylbenzene (Intermediate A22) to afford the title compound (15 mg, 25%) as a colourless glass, which gave a white solid after scratching.

$^1$H NMR (DMSO-d$_6$) δ 10.99 (br s, 1H), 7.85 (s, 1H), 7.12 (s, 2H), 6.58 (s, 1H), 3.88 (s, 3H), 3.65 (dd, J=9.5, 5.1 Hz, 1H), 3.05-2.94 (m, 2H), 2.10 (s, 6H), 1.87-1.74 (m, 1H), 1.69-1.54 (m, 1H), 1.04 (d, J=6.6 Hz, 12H), 0.77 (t, J=7.3 Hz, 3H).
LCMS; m/z 484.5/486.5 (M+H)$^+$ (ES$^+$).

Example 65: 5-(1-(Dimethylamino)propyl)-N-((4-fluoro-2,6-diisopropylphenyl)carbamoyl)-1-methyl-1H-pyrazole-3-sulfonamide

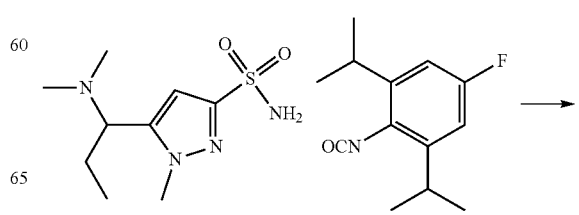

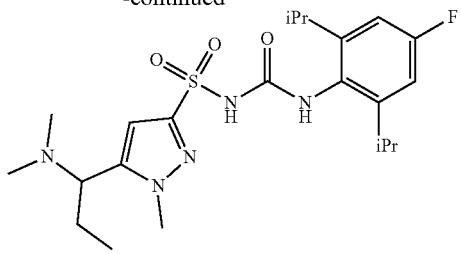

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)propyl)-1-methyl-H-pyrazole-3-sulfonamide (Intermediate P37) and 5-fluoro-2-isocyanato-1,3-diisopropylbenzene (Intermediate A2) to afford the title compound (18 mg, 32%) as a colourless glass, which gave a white solid after scratching.

$^1$H NMR (DMSO-d$_6$) δ 10-95 (br s, 1H), 7.80 (s, 1H), 6.91 (d, J=9.9 Hz, 2H), 6.59 (s, 1H), 3.89 (s, 3H), 3.65 (dd, J=9.5, 5.1 Hz, 1H), 3.03-2.94 (m, 2H), 2.10 (s, 6H), 1.87-1.75 (m, 1H), 1.69-1.56 (m, 1H), 1.04 (app. br s, 12H), 0.77 (t, J=7.3 Hz, 3H).

LCMS; m/z 468.5 (M+H)$^+$ (ES$^+$).

Example 66: 5-((Dimethylamino)methyl)-N-((5-fluoro-3-isopropyl-[1,1'-biphenyl]-2-yl)carbamoyl)-1-methyl-1H-pyrazole-3-sulfonamide

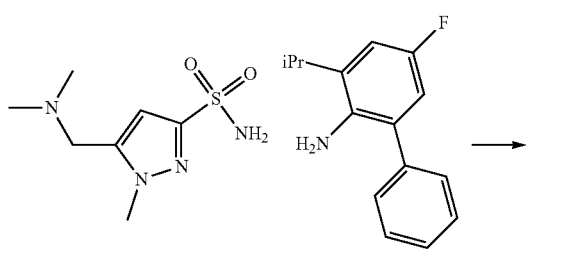

Prepared according to the general procedure of N-((5-bromo-2,3-dihydro-1H-inden-4-yl)carbamoyl)-5-((dimethylamino)methyl)-1-ethyl-1H-pyrazole-3-sulfonamide (Example 16) from 5-((dimethylamino)methyl)-1-methyl-H-pyrazole-3-sulfonamide (Intermediate P16) and 4-fluoro-2-isopropyl-6-(pyridin-3-yl)aniline (Intermediate A4) to afford the title compound (14 mg, 14%) as a colourless solid.

$^1$H NMR (DMSO-d$_6$) δ 10.73 (s, 1H), 7.68 (s, 1H), 7.42-7.30 (m, 3H), 7.31-7.24 (m, 2H), 7.16 (dd, J=10.0, 3.0 Hz, 1H), 6.96 (dd, J=9.0, 3.0 Hz, 1H), 6.54 (s, 1H), 3.90 (s, 3H), 3.50 (s, 2H), 2.99 (sept, J=7.6 Hz, 1H), 2.17 (s, 6H), 1.09 (d, J=6.8 Hz, 6H).

LCMS; m/z 474 (M+H)$^+$ (ES$^+$); 472 (M−H)$^−$ (ES$^−$).

Example 67: N-((1,2,3,5,6,7-Hexahydro-s-indacen-4-yl)carbamoyl)-1-methyl-5-((methylamino)methyl)-1H-pyrazole-3-sulfonamide

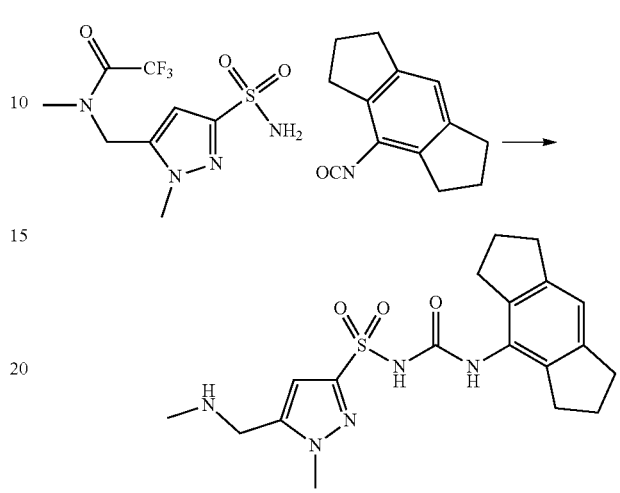

2 M sodium tert-butoxide in THF (47.2 μL, 0.094 mmol) was added to a solution of 2,2,2-trifluoro-N-methyl-N-((1-methyl-3-sulfamoyl-1H-pyrazol-5-yl)methyl)acetamide (Intermediate P38) (27 mg, 0.090 mmol) in THF (2 mL) and stirred at room temperature for 1 hour. Then 4-isocyanato-1,2,3,5,6,7-hexahydro-s-indacene (Intermediate A11 (20 mg, 0.100 mmol) was added and stirred at room temperature overnight. The volatiles were evaporated. MeOH (0.1 mL) and K$_2$CO$_3$ (13 mg, 0.094 mmol) were added and stirred for 16 hours. Volatiles were evaporated and the crude product was purified by chromatography on RP Flash C18 (12 g column, 5-50% MeCN/10 mM ammonium bicarbonate) to afford the title compound (15 mg, 39%) as a white solid.

$^1$H NMR (DMSO-d$_6$) δ 7.74 (s, 1H), 6.84 (s, 1H), 6.57 (s, 1H), 3.94 (s, 2H), 3.82 (s, 3H), 2.77 (t, J=7.2 Hz, 4H), 2.65 (t, J=7.4 Hz, 4H), 2.41 (s, 3H), 1.92 (p, J=7.3 Hz, 4H).

Two exchangeable protons not observed.

LCMS; m/z 404.5 (M+H)$^+$ (ES$^+$).

Example 68: 5-((Dimethylamino)methyl)-N-((1,2,3,5,6,7-hexahydro-s-indacen-4-yl)carbamoyl)-1-isopropyl-1H-pyrazole-3-sulfonamide

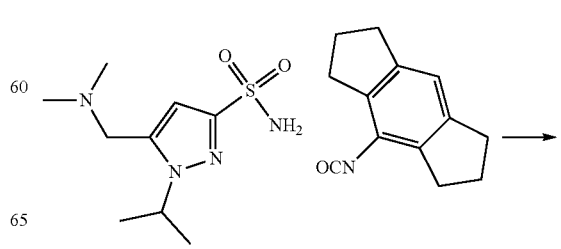

-continued

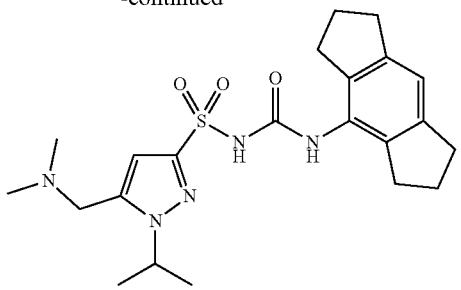

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-((dimethylamino)methyl)-1-isopropyl-1H-pyrazole-3-sulfonamide (Intermediate P26) and 4-isocyanato-1,2,3,5,6,7-hexahydro-s-indacene (Intermediate A1) to afford the title compound (5 mg, 7%) as a white solid.

$^1$H NMR (DMSO-d$_6$) δ 10.90 (s, 1H), 7.96 (s, 1H), 6.91 (s, 1H), 6.59 (s, 1H), 4.85-4.75 (m, 1H), 3.48 (s, 2H), 2.78 (t, J=7.4 Hz, 4H), 2.58 (t, J=7.4 Hz, 4H), 2.15 (s, 6H), 1.92 (p, J=7.5 Hz, 4H), 1.38 (d, J=6.5 Hz, 6H).

LCMS; m/z 446.4 (M+H)$^+$ (ES$^+$).

Example 6A: 5-(1-(Dimethylamino)ethyl)-N-((1,2,3,5,6,7-hexahydro-s-indacen-4-yl)carbamoyl)-1-methyl-1H-pyrazole-3-sulfonamide, Enantiomer 1

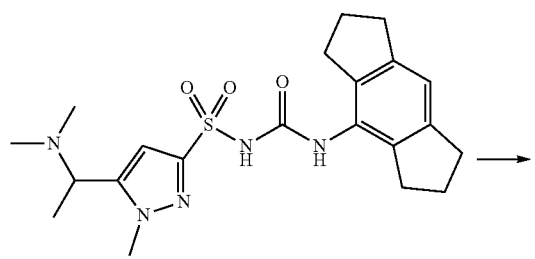

Enantiomer 1
Single enantiomer of unknown
absolute stereochemistry

Prepared by chiral separation of 5-(1-(dimethylamino)ethyl)-N-((1,2,3,5,6,7-hexahydro-s-indacen-4-yl)carbamoyl)-1-methyl-1H-pyrazole-3-sulfonamide (Example 77) (142.3 mg, 0.330 mmol) by SFC (AmyC (20 mm×250 mm, 5 μm) column, 40° C., 50 mL/min flow rate at 100 BarG isocratic 20:80 MeOH:CO$_2$ with 90.2 v/v NH$_3$, monitoring at 210 nm) to give the title compound (35 mg, 24%).

$^1$H NMR (DMSO-d$_6$) δ 10.77 (br s, 1H), 8.00 (s, 1H), 6.92 (s, 1H), 6.64 (s, 1H), 3.94 (q, J=6.8 Hz, 1H), 3.89 (s, 3H), 2.78 (t, J=7.4 Hz, 4H), 2.58 (t, J=7.4 Hz, 4H), 2.13 (s, 6H), 2.01-1.85 (m, 4H), 1.24 (d, J=6.8 Hz, 3H).

LCMS; m/z 432.5 (M+H)$^+$ (ES$^+$); 430.4 (M−H)$^−$ (ES$^−$).

Example 70: 5-(1-(Dimethylamino)ethyl)-N-((1,2,3,5,6,7-hexahydro-s-indacen-4-yl)carbamoyl)-1-methyl-1H-pyrazole-3-sulfonamide, Enantiomer 2

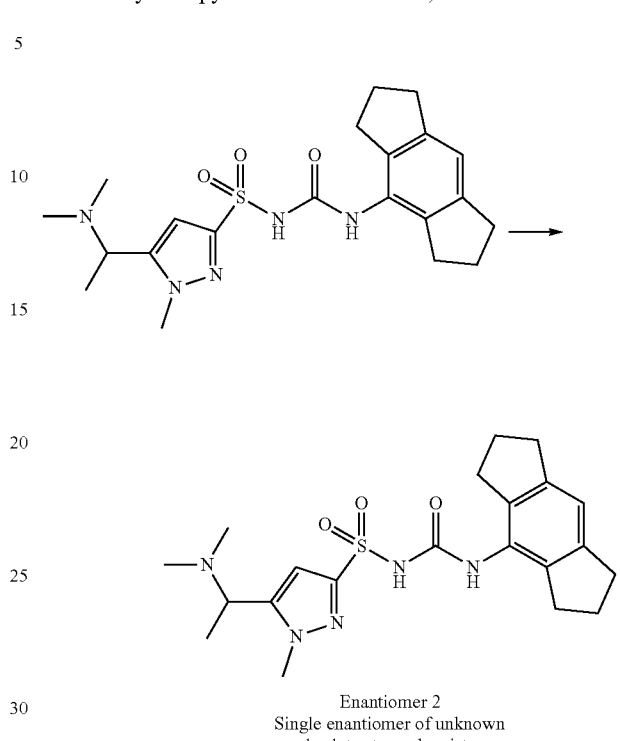

Enantiomer 2
Single enantiomer of unknown
absolute stereochemistry

Prepared by chiral separation of 5-(1-(dimethylamino)ethyl)-N-((1,2,3,5,6,7-hexahydro-s-indacen-4-yl)carbamoyl)-1-methyl-1H-pyrazole-3-sulfonamide (Example 77) (142.3 mg, 0.330 mmol) by SFC (AmyC (20 mm×250 mm, 5 μm) column, 40° C., 50 mL/min flow rate at 100 BarG isocratic 20:80 MeOH:CO$_2$ with 90.2 v/v NH$_3$, monitoring at 210 nm) to give the title compound (29 mg, 20%).

$^1$H NMR (DMSO-d$_6$) δ 10.73 (br s, 1H), 8.01 (s, 1H), 6.92 (s, 1H), 6.65 (s, 1H), 3.95 (q, J=6.8 Hz, 1H), 3.89 (s, 3H), 2.78 (t, J=7.4 Hz, 4H), 2.58 (t, J=7.4 Hz, 4H), 2.13 (s, 6H), 2.05-1.83 (m, 4H), 1.25 (d, J=6.8 Hz, 3H).

LCMS; m/z 432.4 (M+H)$^+$ (ES$^+$); 430.4 (M−H)$^−$ (ES$^−$).

Example 71: 5-(1-(Dimethylamino)propyl)-N-((1,2,3,5,6,7-hexahydro-s-indacen-4-yl)carbamoyl)-1-methyl-1H-pyrazole-3-sulfonamide, Enantiomer 1

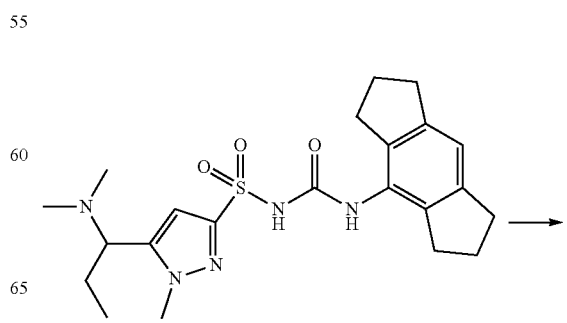

-continued

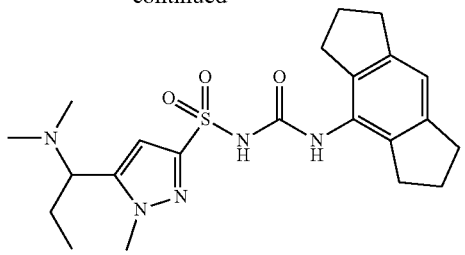

Enantiomer 1
Single enantiomer of unknown
absolute stereochemistry

Prepared by chiral separation of 5-(1-(dimethylamino)propyl)-N-((1,2,3,5,6,7-hexahydro-s-indacen-4-yl)carbamoyl)-1-methyl-1H-pyrazole-3-sulfonamide (Example 74) (68.8 mg, 0.330 mmol) by SFC (AmyC (20 mm×250 mm, 5 μm) column, 40° C., 50 mL/min flow rate at 100 BarG isocratic 20:80 MeOH:CO2 with 90.2 v/v NH$_3$, monitoring at 210 nm) to give the title compound (20 mg, 29%).

$^1$H NMR (DMSO-d$_6$) δ 10.73 (br s, 1H), 8.02 (s, 1H), 6.92 (s, 1H), 6.66 (s, 1H), 3.90 (s, 3H), 3.70 (dd, J=9.5, 5.1 Hz, 1H), 2.77 (t, J=7.4 Hz, 4H), 2.56 (t, J=7.4 Hz, 4H), 2.13 (s, 6H), 2.00-1.87 (m, 4H), 1.87-1.75 (m, 1H), 1.75-1.53 (m, 1H), 0.78 (t, J=7.3 Hz, 3H).

LCMS; m/z 446.4 (M+H)$^+$ (ES$^+$); 444.4 (M−H)$^−$ (ES$^−$).

Example 72: 5-(1-(Dimethylamino)propyl)-N-((1,2,3,5,6,7-hexahydro-s-indacen-4-yl)carbamoyl)-1-methyl-1H-pyrazole-3-sulfonamide, Enantiomer 2

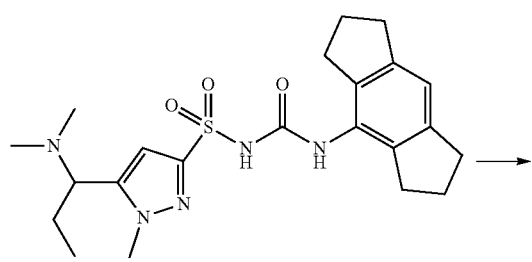

Enantiomer 2
Single enantiomer of unknown
absolute stereochemistry

Prepared by chiral separation of 5-(1-(dimethylamino)propyl)-N-((1,2,3,5,6,7-hexahydro-s-indacen-4-yl)carbamoyl)-1-methyl-1H-pyrazole-3-sulfonamide (Example 74) (68.8 mg, 0.330 mmol) by SFC (AmyC (20 mm×250 mm, 5 μm) column, 40° C., 50 mL/min flow rate at 100 BarG isocratic 20:80 MeOH:CO2 with 90.2 v/v NH$_3$, monitoring at 210 nm) to give the title compound (20 mg, 29%).

$^1$H NMR (DMSO-d$_6$) δ 10.73 (br s, 1H), 8.00 (s, 1H), 6.92 (s, 1H), 6.64 (s, 1H), 3.89 (s, 3H), 0.68 (dd, J=9.4, 5.1 Hz, 1H), 2.78 (t, J=7.4 Hz, 4H), 2.57 (t, J=7.4 Hz, 4H), 2.12 (s, 6H), 1.99-1.87 (m, 4H), 1.87-1.76 (m, 1H), 1.73-1.58 (m, 1H), 0.78 (t, J=7.3 Hz, 3H).

LCMS; m/z 446.4 (M+H)$^+$ (ES$^+$); 444.4 (M−H)$^−$ (ES$^−$).

Example 73: 5-(1-(Dimethylamino)ethyl)-N-((1,2,3,5,6,7-hexahydro-s-indacen-4-yl)carbamoyl)-1-isopropyl-1H-pyrazole-3-sulfonamide

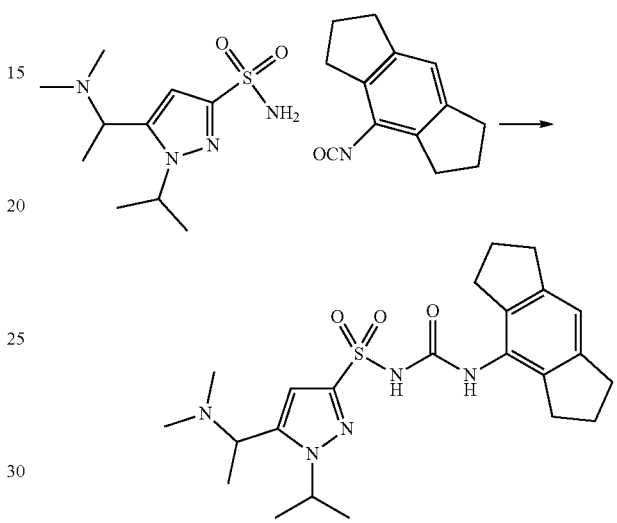

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)ethyl)-1-isopropyl-1H-pyrazole-3-sulfonamide (Intermediate P39) and 4-isocyanato-1,2,3,5,6,7-hexahydro-s-indacene (Intermediate A1) to afford the title compound (34 mg, 50%) as a colourless solid.

$^1$H NMR (DMSO-d$_6$) δ 10.79 (s, 1H), 8.01 (s, 1H), 6.93 (s, 1H), 6.62 (s, 1H), 4.97-4.82 (m, 1H), 3.99 (q, J=6.7 Hz, 1H), 2.79 (t, J=7.4 Hz, 4H), 2.57 (t, J=7.4 Hz, 4H), 2.14 (s, 6H), 1.98-1.85 (m, 4H), 1.43-1.33 (m, 6H), 1.26 (d, J=6.7 Hz, 3H).

LCMS; m/z 460.5 (M+H)$^+$ (ES$^+$).

Example 74: 5-(1-(Dimethylamino)propyl)-N-((1,2,3,5,6,7-hexahydro-s-indacen-4-yl)carbamoyl)-1-methyl-1H-pyrazole-3-sulfonamide

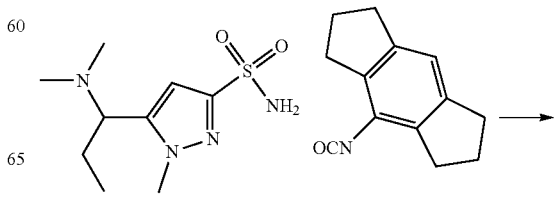

293
-continued

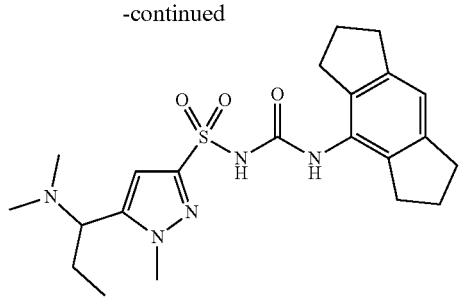

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)propyl)-1-methyl-H-pyrazole-3-sulfonamide (Intermediate P37) and 4-isocyanato-1,2,3,5,6,7-hexahydro-s-indacene (Intermediate A1) to afford the title compound (77 mg, 62%) as a white solid.

$^1$H NMR (DMSO-d$_6$) δ 10.73 (br s, 1H), 8.01 (s, 1H), 6.93 (s, 1H), 6.66 (s, 1H), 3.90 (s, 3H), 3.69 (dd, J=9.5, 5.1 Hz, 1H), 2.78 (t, J=7.4 Hz, 4H), 2.57 (t, J=7.4 Hz, 4H), 2.13 (s, 6H), 1.98-1.88 (m, 4H), 1.88-1.78 (m, 1H), 1.72-1.59 (m, 1H), 0.78 (t, J=7.3 Hz, 3H).

LCMS; m/z 446.5 (M+H)$^+$ (ES$^+$).

Example 75: N-((1,2,3,5,6,7-Hexahydro-s-indacen-4-yl)carbamoyl)-5-(3-hydroxy-1-methylazetidin-3-yl)-1-methyl-1H-pyrazole-3-sulfonamide

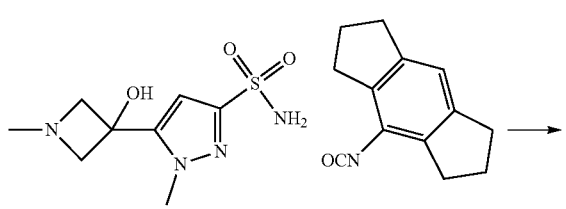

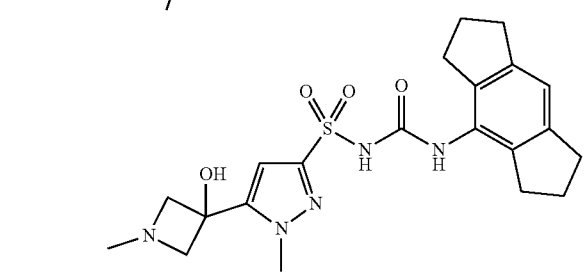

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(3-hydroxy-1-methylazetidin-3-yl)-1-methyl-H-pyrazole-3-sulfonamide (Intermediate P40) and 4-isocyanato-1,2,3,5,6,7-hexahydro-s-indacene (Intermediate A1) to afford the title compound (66 mg, 40%) as a white solid.

$^1$H NMR (DMSO-d$_6$) δ 10.75 (br s, 1H), 7.93 (s, 1H), 6.90 (s, 1H), 6.77 (s, 1H), 6.43 (s, 1H), 3.87 (d, J=8.1 Hz, 2H), 3.81 (s, 3H), 3.39 (d, J=8.1 Hz, 2H), 2.78 (t, J=7.4 Hz, 4H), 2.63 (t, J=7.3 Hz, 4H), 2.38 (s, 3H), 1.99-1.90 (m, 4H).

LCMS; m/z 446.4 (M+H)$^+$ (ES$^+$).

294
Example 76: 5-(1-(Azetidin-1-yl)ethyl)-N-((1,2,3,5,6,7-hexahydro-s-indacen-4-yl)carbamoyl)-1-methyl-1H-pyrazole-3-sulfonamide

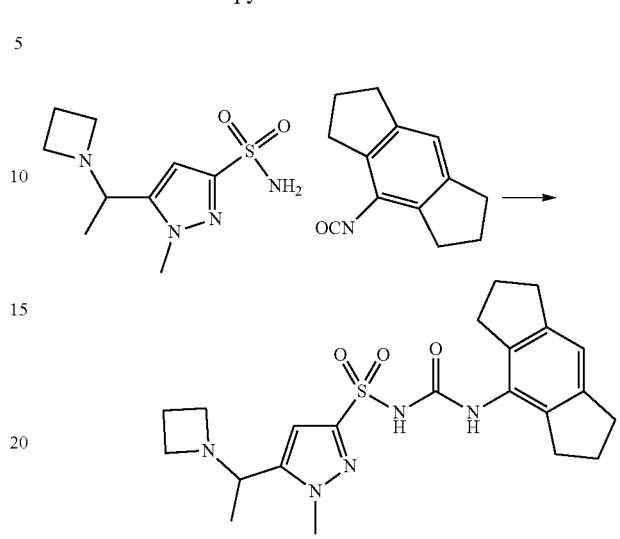

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(azetidin-1-yl)ethyl)-1-methyl-1H-pyrazole-3-sulfonamide (Intermediate P41) and 4-isocyanato-1,2,3,5,6,7-hexahydro-s-indacene (Intermediate A1) to afford the title compound (40 mg, 10%) as a white solid.

$^1$H NMR (DMSO-d$_6$) δ 10.76 (br s, 1H), 8.00 (s, 1H), 6.92 (s, 1H), 6.58 (s, 1H), 3.92 (s, 3H), 3.73-3.66 (m, 1H), 3.22-3.05 (m, 6H), 2.78 (t, J=7.5 Hz, 4H), 2.58 (t, J=7.4 Hz, 4H), 1.98-1.89 (m, 4H), 1.14 (d, J=6.5 Hz, 3H).

LCMS; m/z 444.5 (M+H)$^+$ (ES$^+$).

Example 77: 5-(1-(Dimethylamino)ethyl)-N-((1,2,3,5,6,7-hexahydro-s-indacen-4-yl)carbamoyl)-1-methyl-1H-pyrazole-3-sulfonamide

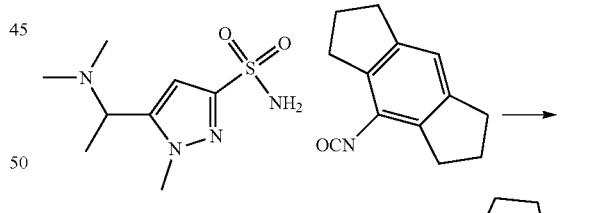

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(1-(dimethylamino)ethyl)-1-methyl-1H-pyrazole-3-sulfonamide (Intermediate P42) and 4-isocyanato-1,2,3,5,6,7-hexahydro-s-indacene (Intermediate A1) to afford the title compound (222 mg, 77%) as a white solid.

¹H NMR (DMSO-d₆) δ 10.73 (br s, 1H), 8.01 (s, 1H), 6.93 (s, 1H), 6.67 (s, 1H), 3.96 (q, J=6.7 Hz, 1H), 3.90 (s, 3H), 2.78 (t, J=7.4 Hz, 4H), 2.58 (t, J=7.4 Hz, 4H), 2.14 (s, 6H), 1.93 (p, J=7.4 Hz, 4H), 1.25 (d, J=6.8 Hz, 3H).

LCMS; m/z 432.5 (M+H)⁺ (ES⁺).

Example 78: N-((1,2,3,5,6,7-Hexahydro-s-indacen-4-yl)carbamoyl)-1-methyl-5-(pyrrolidin-1-ylmethyl)-1H-pyrazole-3-sulfonamide, Sodium Salt

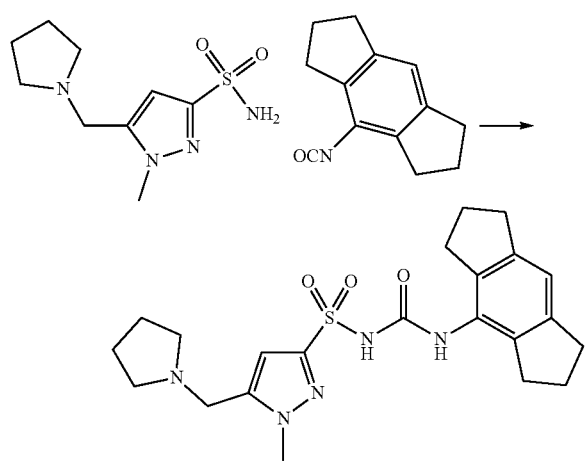

1-Methyl-5-(pyrrolidin-1-ylmethyl)-1H-pyrazole-3-sulfonamide (Intermediate P43) (35 mg, 0.143 mmol) was dissolved in 2-MeTHF (0.5 mL) and DMF (0.5 mL), and 2 M sodium tert-butoxide in THF (0.079 mL, 0.158 mmol) was added. After 1 hour, 4-isocyanato-1,2,3,5,6,7-hexahydro-s-indacene (Intermediate A1) (31.4 mg, 0.158 mmol) followed by 2-MeTHF (1 mL) was added and the mixture stirred at room temperature for 2 days. EtOAc (3 mL) was added and the mixture stirred for 1 hour. The solvent was removed under reduced pressure and the residue obtained was purified by chromatography on RP Flash C18 (13 g column, 5-50% MeCN/10 mM ammonium bicarbonate) to afford a white solid (30 mg). The white solid obtained was suspended in EtOAc (1 mL) and 1 molar equivalent of 2 M sodium tert-butoxide in THF was added. The solvent was removed under reduced pressure to give a pale yellow glass. A 1:1 mixture of MTBE: MeCN was added (2 mL) and the reaction mixture was left to settle for 2 hours. The soluble portion was decanted and concentrated to dryness to give the title compound (23 mg, 32%) as a white solid.

¹H NMR (DMSO-d₆) δ 7.50 (s, 1H), 6.75 (s, 1H), 6.27 (s, 1H), 3.75 (s, 3H), 3.57 (s, 2H), 2.74 (t, J=7.4 Hz, 4H), 2.64 (t, J=7.4 Hz, 4H), 2.44-2.37 (i, 4H), 2.02-1.76 (m, 4H), 1.76-1.58 (m, 4H).

LCMS; m/z 444.5 (M+H)⁺ (ES⁺); 442.3 (M−H)⁻ (ES⁻).

Example 79: N-((4-Fluoro-2,6-diisopropylphenyl)carbamoyl)-5-((3-fluoroazetidin-1-yl)methyl)-1-methyl-1H-pyrazole-3-sulfonamide

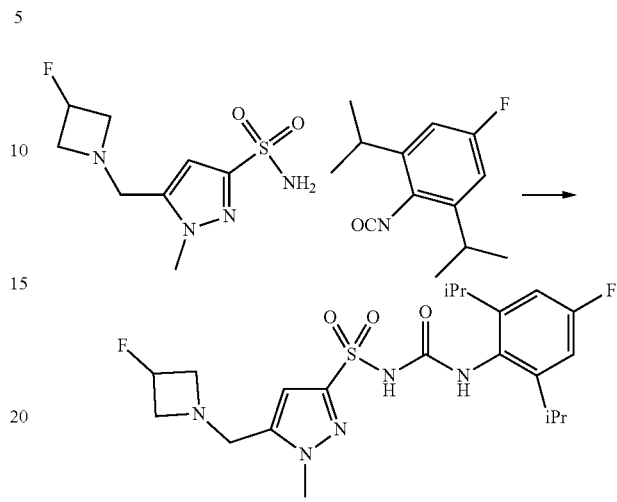

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-((3-fluoroazetidin-1-yl)methyl)-1-methyl-H-pyrazole-3-sulfonamide (Intermediate P44) and 5-fluoro-2-isocyanato-1,3-diisopropylbenzene (Intermediate A2) to afford the title compound (28 mg, 40%) as a white solid.

¹H NMR (DMSO-d₆) δ 10.96 (br s, 1H), 7.82 (s, 1H), 6.92 (d, J=9.9 Hz, 2H), 6.63 (s, 1H), 5.16 (dp, J=5.0, 57.6 Hz, 1H), 3.85 (s, 3H), 3.71 (s, 2H), 3.55 (m, 2H), 3.19 (m, 2H), 2.96 (m, 2H), 1.06 (d, J=12.0 Hz, 12H).

LCMS; m/z 470.5 (M+H)⁺ (ES⁺); 468.4 (M−H)⁻ (ES⁻).

Example 80: 5-((3-Fluoroazetidin-1-yl)methyl)-N-((1,2,3,5,6,7-hexahydro-s-indacen-4-yl)carbamoyl)-1-methyl-1H-pyrazole-3-sulfonamide

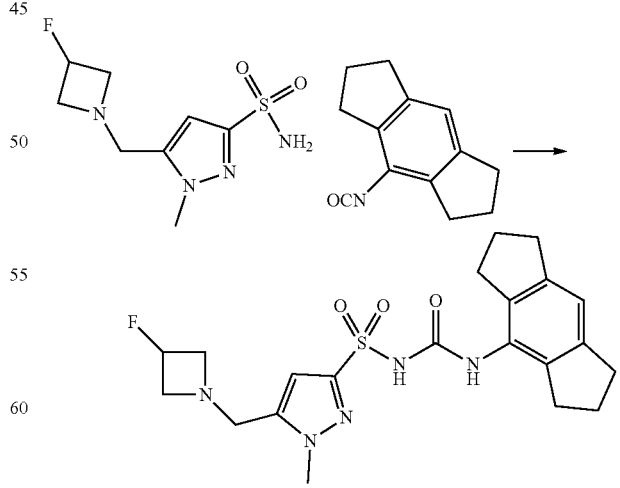

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-((3-fluoroazetidin-1-yl)methyl)-1-methyl-H-pyrazole-3-sulfonamide (Intermediate P44) and 4-isocyanato-1,2,3,5,6,7-hexahydro-s-indacene (Intermediate A1) to afford the title compound (25 mg, 38%) as a white solid.

$^1$H NMR (DMSO-d$_6$) δ 10.77 (br s, 1H), 8.02 (s, 1H), 6.94 (s, 1H), 6.66 (s, 1H), 5.17 (dp, J=5.0, 57.6 Hz, 1H), 3.85 (s, 3H), 3.72 (s, 2H), 3.55 (m, 2H), 3.20 (m, 2H), 2.79 (t, J=7.4 Hz, 4H), 2.60 (t, J=7.3 Hz, 4H), 1.95 (p, J=7.4 Hz, 4H).

LCMS; m/z 448.5 (M+H)$^+$ (ES$^+$); 446.3 (M–H)$^-$ (ES$^-$).

Example 81: N-((4-Fluoro-2,6-diisopropylphenyl)carbamoyl)-1-methyl-5-(pyrrolidin-1-ylmethyl)-1H-pyrazole-3-sulfonamide

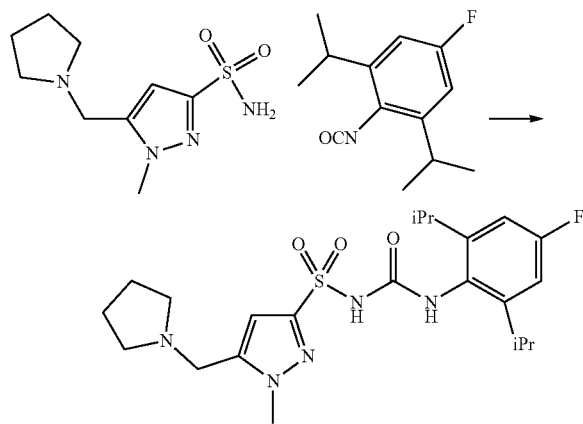

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 1-methyl-5-(pyrrolidin-1-ylmethyl)-1H-pyrazole-3-sulfonamide (Intermediate P43) and 5-fluoro-2-isocyanato-1,3-diisopropylbenzene (Intermediate A2) to afford the title compound (18 mg, 26%) as a white solid.

$^1$H NMR (DMSO-d$_6$) δ 10.93 (s, 1H), 7.78 (s, 1H), 6.91 (d, J=9.9 Hz, 2H), 6.60 (s, 1H), 3.87 (s, 3H), 3.66 (s, 2H), 3.00-2.92 (m, 2H), 2.44 (br s, 4H), 1.68 (br s, 4H), 1.04 (br s, 12H).

LCMS; m/z 466.5 (M+H)$^+$ (ES$^+$); 464.4 (M–H)$^-$ (ES$^-$).

Example 82: 5-((Diethylamino)methyl)-N-((1,2,3,5,6,7-hexahydro-s-indacen-4-yl)carbamoyl)-1-methyl-1H-pyrazole-3-sulfonamide, Sodium Salt

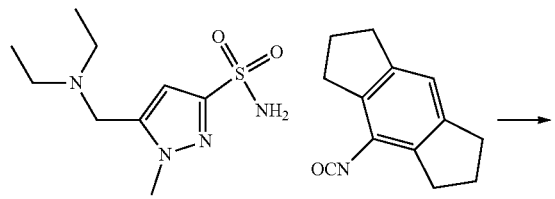

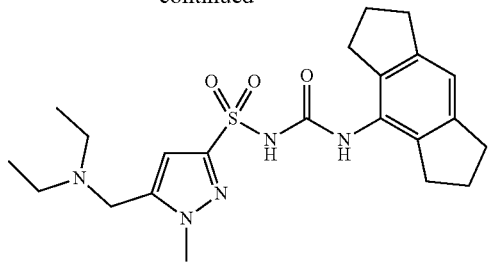

Sodium tert-butoxide, 2 M in THF (78 µL, 0.156 mmol) was added to a solution of 5-((diethylamino)methyl)-1-methyl-H-pyrazole-3-sulfonamide (Intermediate P45) (35 mg, 0.142 mmol) in 2-MeTHF (2 mL) and stirred for 30 minutes. Then 4-isocyanato-1,2,3,5,6,7-hexahydro-s-indacene (Intermediate A1) (31 mg, 0.156 mmol) was added and the reaction stirred for a further 2 days. The resulting solid was filtered off, washed with EtOAc and dried to afford the title compound (26 mg, 38%) as a white solid.

$^1$H NMR (DMSO-d$_6$) δ 7.52 (s, 1H), 6.77 (s, 1H), 6.29 (s, 1H), 3.77 (s, 3H), 3.52 (s, 2H), 2.75 (t, J=7.4 Hz, 4H), 2.64 (t, J=7.4 Hz, 4H), 2.45 (q, J=7.1 Hz, 4H), 1.89 (p, J=7.3 Hz, 4H), 0.97 (t, J=7.1 Hz, 6H).

LCMS; m/z 446.5 (M+H)$^+$ (ES$^+$); 444.4 (M–H)$^-$ (ES$^-$).

Example 83: 5-((Diethylamino)methyl)-N-((4-fluoro-2,6-diisopropylphenyl)carbamoyl)-1-methyl-1H-pyrazole-3-sulfonamide, sodium Salt

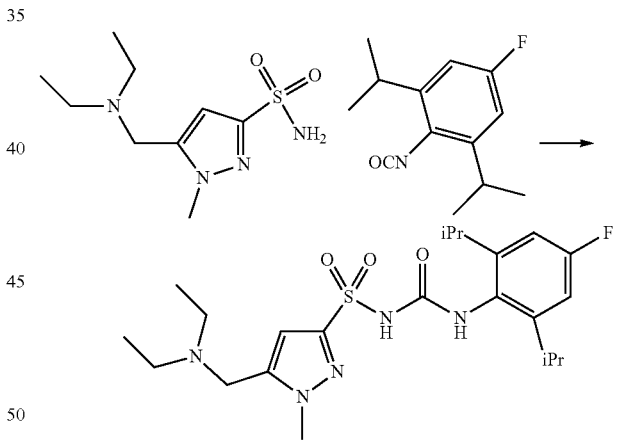

Prepared according to the general procedure of 5-((diethylamino)methyl)-N-((1,2,3,5,6,7-hexahydro-s-indacen-4-yl)carbamoyl)-1-methyl-1H-pyrazole-3-sulfonamide, sodium salt (Example 82) from 5-((diethylamino)methyl)-1-methyl-1H-pyrazole-3-sulfonamide (Intermediate P45) and 5-fluoro-2-isocyanato-1,3-diisopropylbenzene (Intermediate A2) to afford the title compound (53 mg, 75%) as a white solid.

$^1$H NMR (DMSO-d$_6$) δ 7.39 (s, 1H), 6.79 (d, J=10.1 Hz, 2H), 6.28 (s, 1H), 3.76 (s, 3H), 3.51 (s, 2H), 3.13 (m, 2H), 2.45 (q, J=7.1 Hz, 4H), 1.03 (d, J=6.8 Hz, 12H), 0.97 (t, J=7.1 Hz, 6H).

LCMS; m/z m/z 468.5 (M+H)$^+$ (ES$^+$); 466.3 (M–H)$^-$ (ES$^-$).

Example 84: 5-((Ethyl(methyl)amino)methyl)-N-((1,2,3,5,6,7-hexahydro-s-indacen-4-yl)carbamoyl)-1-methyl-1H-pyrazole-3-sulfonamide

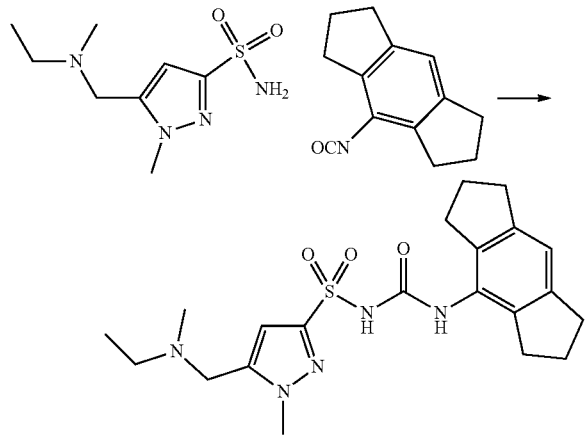

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-((ethyl(methyl)amino)methyl)-1-methyl-1H-pyrazole-3-sulfonamide (Intermediate P46) and 4-isocyanato-1,2,3,5,6,7-hexahydro-s-indacene (Intermediate A1) to afford the title compound (32 mg, 48%) as a white powder.

$^1$H NMR (DMSO-d$_6$) δ 10.75 (s, 1H), 8.01 (s, 1H), 6.94 (s, 1H), 6.66 (s, 1H), 3.88 (s, 3H), 3.56 (s, 2H), 2.79 (t, J=7.4 Hz, 4H), 2.59 (t, J=7.4 Hz, 4H), 2.42 (q, J=7.1 Hz, 2H), 2.13 (s, 3H), 1.94 (p, J=7.5 Hz, 4H), 1.02 (t, J=7.1 Hz, 3H).

LCMS; m/z 432.5 (M+H)$^+$ (ES$^+$); 430.4 (M−H)$^-$ (ES$^-$).

Example 8t: 5-((Cyclopropyl(methyl)amino)methyl)-N-((1,2,3,5,6,7-hexahydro-s-indacen-4-yl)carbamoyl)-1-methyl-1H-pyrazole-3-sulfonamide, Sodium Salt

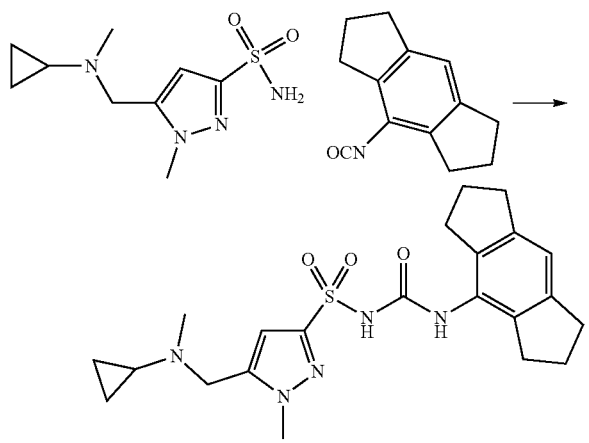

Sodium tert-butoxide, 2 M in THF (79 µL, 0.158 mmol) was added to a solution of 5-((cyclopropyl(methyl)amino) methyl)-1-methyl-1H-pyrazole-3-sulfonamide (Intermediate P47) (35 mg, 0.143 mmol) in THF (2 mL) and stirred for 30 minutes. Then 4-isocyanato-1,2,3,5,6,7-hexahydro-s-indacene (Intermediate A1) (32 mg, 0.161 mmol) was added and the reaction stirred for a further 2 days. The THF was evaporated in vacuo, the residue dissolved in a mixture of DMF/water/THF and purified by chromatography on RP Flash C18 (12 g column, 5-50% MeCN/10 mM ammonium bicarbonate) to afford a white solid. This solid (32 mg) was dissolved in THF (1 mL), treated with sodium tert-butoxide, 2 M in THF (38 µL, 0.076 mmol) and stirred for 1 hour. The resulting solid was filtered off, washed with EtOAc and dried to afford the title compound (17 mg, 25%) as a white solid.

$^1$H NMR (DMSO-d$_6$) δ 7.52 (s, 1H), 6.76 (s, 1H), 6.30 (s, 1H), 3.72 (s, 3H), 3.63 (s, 2H), 2.75 (t, J=7.4 Hz, 4H), 2.64 (t, J=7.4 Hz, 4H), 2.18 (s, 3H), 1.89 (p, J=7.5 Hz, 4H), 1.74-1.68 (m, 1H), 0.44 (m, 2H), 0.32 (m, 2H).

LCMS; m/z 444.4 (M+H)$^+$ (ES$^+$); 442.1 (M−H)$^-$ (ES$^-$).

Example 86: 5-(Azetidin-1-ylmethyl)-N-((1,2,3,5,6,7-hexahydro-s-indacen-4-yl)carbamoyl)-1-methyl-1H-pyrazole-3-sulfonamide, Sodium Salt

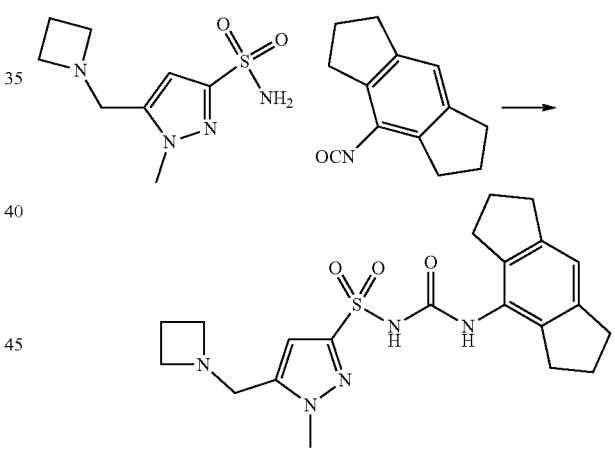

Prepared according to the general procedure of 5-((cyclopropyl(methyl)amino)methyl)-N-((1,2,3,5,6,7-hexahydro-s-indacen-4-yl)carbamoyl)-1-methyl-1H-pyrazole-3-sulfonamide, sodium salt (Example 85) from 5-(azetidin-1-ylmethyl)-1-methyl-1H-pyrazole-3-sulfonamide (Intermediate P48) and 4-isocyanato-1,2,3,5,6,7-hexahydro-s-indacene (Intermediate A1) to afford the title compound (15 mg, 21%) as a white powder.

$^1$H NMR (DMSO-d$_6$) δ 7.52 (s, 1H), 6.77 (s, 1H), 6.26 (s, 1H), 3.73 (s, 3H), 3.50 (s, 2H), 3.12 (t, J=7.0 Hz, 4H), 2.75 (t, J=7.3 Hz, 4H), 2.65 (t, J=7.4 Hz, 4H), 1.97 (m, 2H), 1.90 (p, J=7.4 Hz, 4H).

LCMS; m/z 430.5 (M+H)$^+$ (ES$^+$); 428.0 (M−H)$^-$ (ES$^-$).

Example 87: 5-((Cyclopropyl(methyl)amino) methyl)-N-((4-fluoro-2,6-diisopropylphenyl)carbamoyl)-1-methyl-1H-pyrazole-3-sulfonamide, sodium Salt

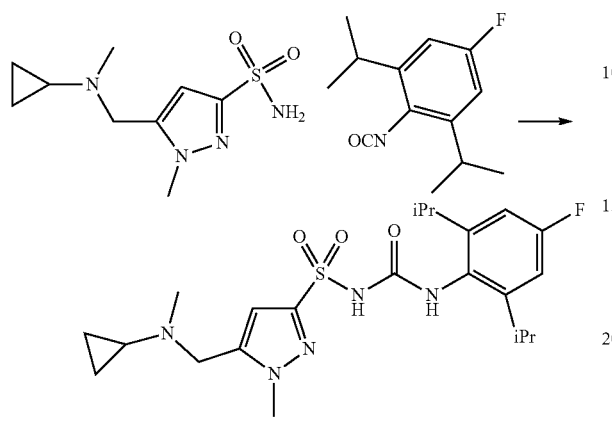

Sodium tert-butoxide, 2 M in THF (79 µL, 0.158 mmol) was added to a solution of 5-((cyclopropyl(methyl)amino) methyl)-1-methyl-1H-pyrazole-3-sulfonamide (Intermediate P47) (35 mg, 0.143 mmol) in THF (2 mL) and stirred for 30 minutes. Then 5-fluoro-2-isocyanato-1,3-diisopropylbenzene (Intermediate A2) (35 mg, 0.158 mmol) was added and the reaction stirred for a further 2 days. The resulting solid was filtered off, washed with EtOAc and dried to afford the title compound (47 mg, 67%) as a white solid.

$^1$H NMR (DMSO-d$_6$) δ 7.38 (s, 1H), 6.79 (d, J=10.1 Hz, 2H), 6.28 (s, 1H), 3.70 (s, 3H), 3.63 (s, 2H), 3.13 (m, 2H), 2.18 (s, 3H), 1.74-1.69 (m, 1H), 1.03 (d, J=6.8 Hz, 12H), 0.45 (m, 2H), 0.33 (m, 2H).

LCMS; m/z m/z 466.5 (M+H)$^+$ (ES$^+$); 464.4 (M-H)$^-$ (ES$^-$).

Example 88: 5-(Azetidin-1-ylmethyl)-N-((4-fluoro-2,6-diisopropylphenyl) carbamoyl)-1-methyl-1H-pyrazole-3-sulfonamide, Sodium Salt

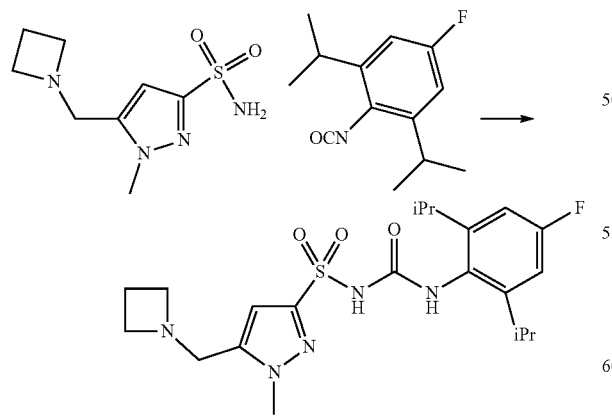

Prepared according to the general procedure of 5-((cyclopropyl(methyl)amino)methyl)-N-((4-fluoro-2,6-diisopropylphenyl)carbamoyl)-1-methyl-1H-pyrazole-3-sulfonamide, sodium salt (Example 87) from 5-(azetidin-1-ylmethyl)-1-methyl-H-pyrazole-3-sulfonamide (Intermediate P48) and 5-fluoro-2-isocyanato-1,3-diisopropylbenzene (Intermediate A2) to afford the title compound (46 mg, 63%) as a white solid.

$^1$H NMR (DMSO-d$_6$) δ 7.38 (s, 1H), 6.79 (d, J=10.2 Hz, 2H), 6.25 (s, 1H), 3.72 (s, 3H), 3.50 (s, 2H), 3.14 (m, 2H), 3.12 (t, J=7.0 Hz, 4H), 2.03-1.91 (m, 2H), 1.03 (d, J=6.8 Hz, 12H).

LCMS; m/z 452.5 (M+H)$^+$ (ES$^+$); 450.4 (M-H)$^-$ (ES$^-$).

Example 89: 5-((Ethyl(methyl)amino)methyl)-N-((4-fluoro-2,6-diisopropylphenyl)carbamoyl)-1-methyl-1H-pyrazole-3-sulfonamide, sodium Salt

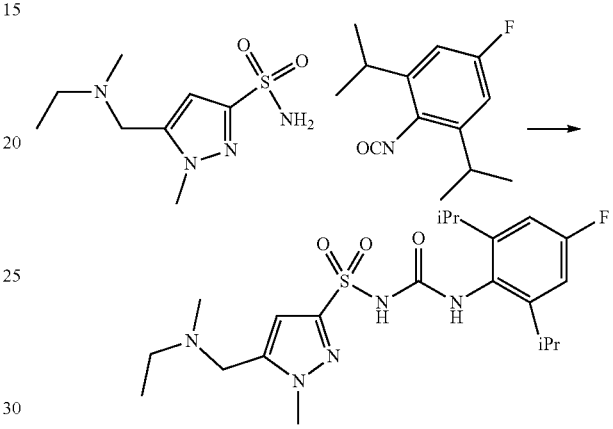

Prepare according to the general procedure of 5-((cyclopropyl(methyl)amino)methyl-N-((4-fluoro-2,6-diisopropylphenyl)carbamoyl)-1-methyl-1H-pyrazole-3-sulfonamide, sodium salt (Example 87) from 5-((ethyl(methyl)amino) methyl)-1-methyl-1H-pyrazole-3-sulfonamide (Intermediate P46) and 5-fluoro-2-isocyanato-1,3-diisopropylbenzene (Intermediate A2) to afford the title compound (39 mg, 54%) as a white solid.

$^1$H NMR (DMSO-d$_6$) δ 7.39 (s, 1H), 6.79 (d, J=10.1 Hz, 2H), 6.27 (s, 1H), 3.75 (s, 3H), 3.44 (s, 2H), 3.13 (m, 2H), 2.38 (q, J=7.2 Hz, 2H), 2.11 (s, 3H), 1.11-0.95 (m, 15H).

LCMS; m/z 454.5 (M+H)$^+$ (ES$^+$); 452.4 (M-H)$^-$ (ES$^-$).

Example 90: N-((4-Fluoro-2,6-diisopropylphenyl) carbamoyl)-5-((isopropyl(methyl)amino)methyl)-1-methyl-1H-pyrazole-3-sulfonamide, sodium Salt

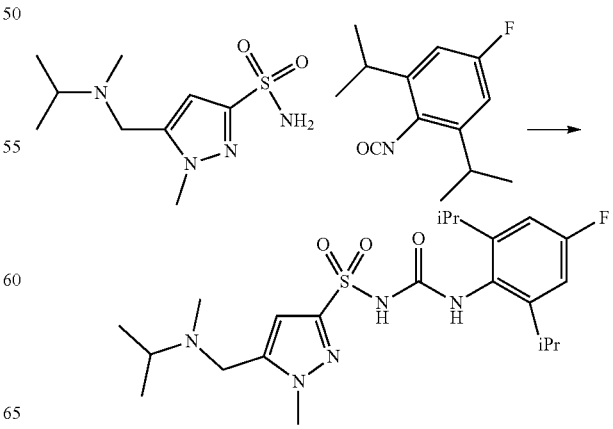

Prepared according to the general procedure of 5-((cyclopropyl(methyl)amino)methyl)-N-((4-fluoro-2,6-diisopropylphenyl)carbamoyl)-1-methyl-1H-pyrazole-3-sulfonamide, sodium salt (Example 87) from 5-((isopropyl(methyl)amino)methyl)-1-methyl-1H-pyrazole-3-sulfonamide (Intermediate P49) and 5-fluoro-2-isocyanato-1,3-diisopropylbenzene (Intermediate A2) to afford the title compound (45 mg, 64%) as a white solid.

$^1$H NMR (DMSO-d$_6$) δ 7.39 (s, 1H), 6.79 (d, J=10.1 Hz, 2H), 6.27 (s, 1H), 3.75 (s, 3H), 3.48 (s, 2H), 3.13 (m, 2H), 2.83 (sept, J=6.6 Hz, 1H), 2.05 (s, 3H), 1.03 (d, J=6.8 Hz, 12H), 1.00 (d, J=6.6 Hz, 6H).

LCMS; m/z 468.5 (M+H)$^+$ (ES$^+$); 466.4 (M−H)$^−$ (ES$^−$).

Example 1: N-((1,2,3,5,6,7-Hexahydro-s-indacen-4-yl)carbamoyl)-5-((isopropyl(methyl)amino)methyl)-1-methyl-1H-pyrazole-3-sulfonamide

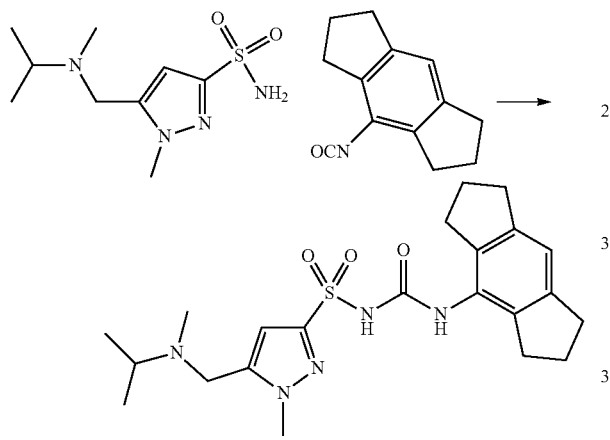

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from 5-((isopropyl(methyl)amino)methyl)-1-methyl-1H-pyrazole-3-sulfonamide (Intermediate P49) and 4-isocyanato-1,2,3,5,6,7-hexahydro-s-indacene (Intermediate A1) to afford the title compound (33 mg, 51%) as a white solid.

$^1$H NMR (DMSO-d$_6$) δ 10.65 (bs, 1H), 7.97 (s, 1H), 6.92 (s, 1H), 6.62 (s, 1H), 3.86 (s, 3H), 3.58 (s, 2H), 2.85 (m, 1H), 2.79 (t, J=7.4 Hz, 4H), 2.60 (t, J=7.4 Hz, 4H), 2.06 (s, 3H), 1.94 (p, J=7.5 Hz, 4H), 1.01 (d, J=6.6 Hz, 6H).

LCMS; m/z 446.5 (M+H)$^+$ (ES$^+$); 444.4 (M−H)$^−$ (ES$^−$).

Example 92: 5-((Dimethylamino)methyl)-N-((4-fluoro-2,6-diisopropyl-phenyl)carbamoyl)-1-methyl-1H-pyrazole-3-sulfonamide, Sodium Salt

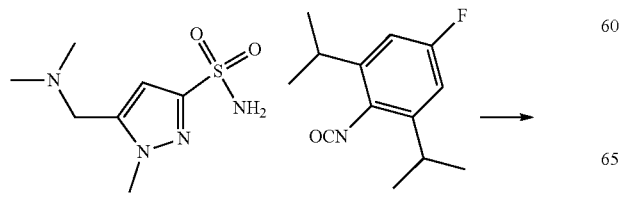

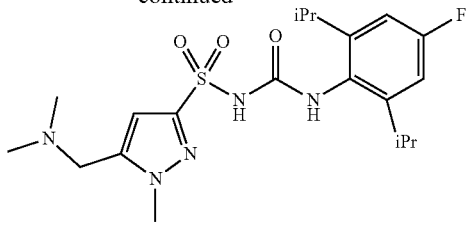

Prepared according to the general procedure of 5-((cyclopropyl(methyl)amino)methyl)-N-((4-fluoro-2,6-diisopropylphenyl)carbamoyl)-1-methyl-1H-pyrazole-3-sulfonamide, sodium salt (Example 87) from 5-((dimethylamino)methyl)-1-methyl-H-pyrazole-3-sulfonamide (Intermediate P16) and 5-fluoro-2-isocyanato-1,3-diisopropylbenzene (Intermediate A2) to afford the title compound (41 mg, 55%) as a white solid.

$^1$H NMR (DMSO-d$_6$) δ 7.37 (s, 1H), 6.78 (d, J=10.1 Hz, 2H), 6.26 (s, 1H), 3.74 (s, 3H), 3.37 (s, 2H), 3.12 (m, 2H), 2.13 (s, 6H), 1.01 (d, J=6.9 Hz, 12H).

LCMS; m/z 440.4 (M+H)$^+$ (ES$^+$); 438.4 (M−H)$^−$ (ES$^−$).

Example 93: N-((4-Chloro-2,6-diisopropylphenyl)carbamoyl)-5-((dimethylamino)methyl)-1-methyl-1H-pyrazole-3-sulfonamide, Sodium Salt

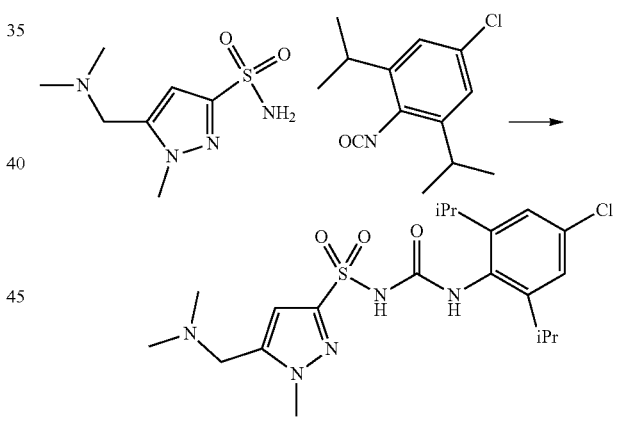

Prepared according to the general procedure of 5-((cyclopropyl(methyl)amino)methyl)-N-((4-fluoro-2,6-diisopropylphenyl)carbamoyl)-1-methyl-1H-pyrazole-3-sulfonamide, sodium salt (Example 87) from 5-((dimethylamino)methyl)-1-methyl-H-pyrazole-3-sulfonamide (Intermediate P16) and 5-chloro-2-isocyanato-1,3-diisopropylbenzene (Intermediate A22) to afford the title compound (43 mg, 64%) as a white solid.

$^1$H NMR (DMSO-d$_6$) δ 7.46 (s, 1H), 7.01 (s, 2H), 6.27 (s, 1H), 3.75 (s, 3H), 3.38 (s, 2H), 3.13 (m, 2H), 2.14 (s, 6H), 1.03 (d, J=6.8 Hz, 12H).

LCMS; m/z 456.4/458.4 (M+H)$^+$ (ES$^+$); 454.3/456.3 (M−H)$^−$ (ES$^−$).

Example 94: 5-((Dimethylamino)methyl)-N-((1,2,3,5,6,7-hexahydro-s-indacen-4-yl)carbamoyl)-1-methyl-1H-pyrazole-3-sulfonamide

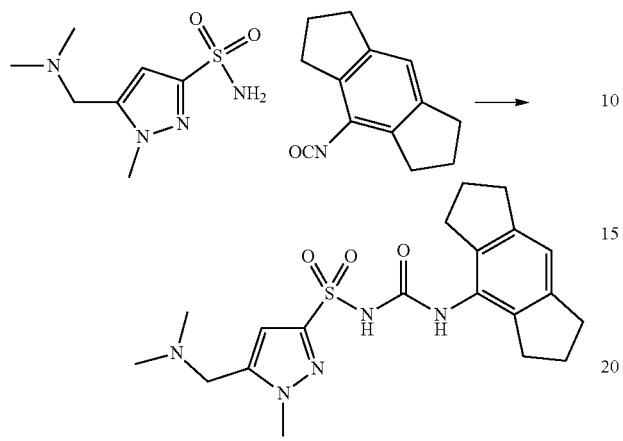

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-((dimethylamino)methyl)-1-methyl-H-pyrazole-3-sulfonamide (Intermediate P16) and 4-isocyanato-1,2,3,5,6,7-hexahydro-s-indacene (Intermediate A1) to afford the title compound (38 mg, 66%) as a white solid.

$^1$H NMR (DMSO-d$_6$) δ 10.74 (br s, 1H), 7.99 (s, 1H), 6.93 (s, 1H), 6.65 (s, 1H), 3.88 (s, 3H), 3.49 (s, 2H), 2.79 (t, J=7.4 Hz, 4H), 2.59 (t, J=7.4 Hz, 4H), 2.17 (s, 6H), 1.94 (quin, J=7.4 Hz, 4H).

LCMS; m/z 418.45 (M+H)$^+$ (ES$^+$); 416.36 (M−H)$^−$ (ES$^−$).

Example 95: 5-(~(Dimethylamino)-2,2,2-trifluoroethyl)-N-((1,2,3,5,6,7-hexahydro-s-indacen-4-yl)carbamoyl)-1-methyl-1H-pyrazole-3-sulfonamide

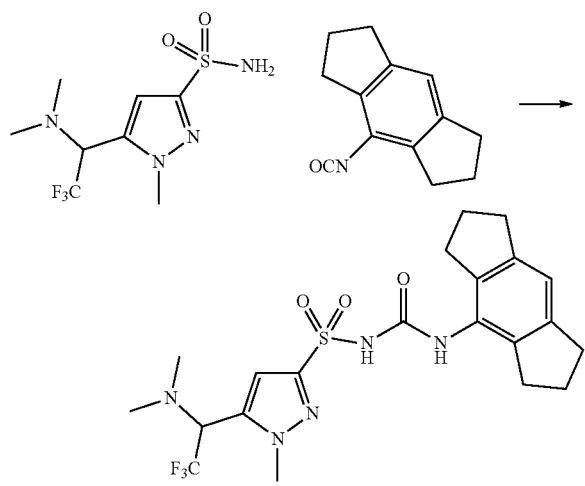

Sodium tert-butoxide, 2 M in THF (0.147 mL, 0.293 mmol) was added to a solution of 5-(1-(dimethylamino)-2,2,2-trifluoroethyl)-1-methyl-1H-pyrazole-3-sulfonamide (Intermediate P59) (80 mg, 0.279 mmol) in THF (1 mL) and stirred at room temperature for 1 hour. Then 4-isocyanato-1,2,3,5,6,7-hexahydro-s-indacene (Intermediate A1) (61.2 mg, 0.307 mmol) in THF (1 mL) was added and stirred at room temperature overnight. The reaction mixture was concentrated and the crude product was purified by chromatography on RP Flash C18 (12 g column, 5-50% MeCN/10 mM ammonium bicarbonate), followed by reversed phase prep-HPLC (General Methods, basic prep) to afford the title compound (9 mg, 7%) as a colourless solid.

$^1$H NMR (DMSO-d$_6$) δ 10.87 (s, 1H), 8.02 (s, 1H), 6.89 (s, 1H), 6.70 (s, 1H), 5.14 (q, J=8.4 Hz, 1H), 3.92 (s, 3H), 2.75 (t, J=7.4 Hz, 4H), 2.55 (t, J=7.4 Hz, 4H), 2.34 (s, 6H), 1.99-1.83 (m, 4H).

LCMS; m/z 486.3 (M+H)$^+$ (ES$^+$).

Example 96: N-((1,2,3,5,6,7-Hexahydro-s-indacen-4-yl)carbamoyl)-1-isopropyl-5-((methyl(2,2,2-trifluoroethyl)amino)methyl)-1H-pyrazole-3-sulfonamide

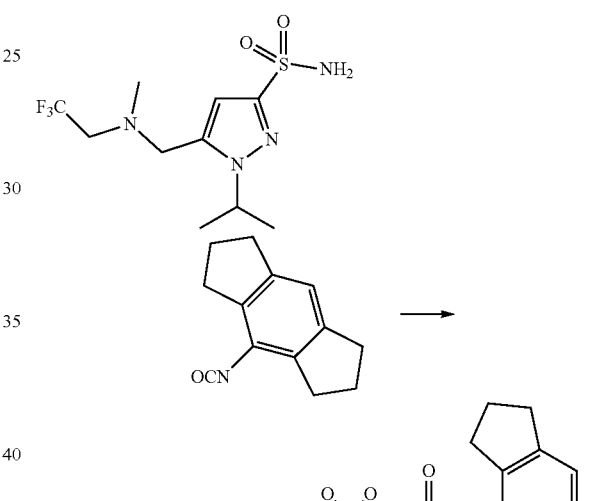

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 1-isopropyl-5-((methyl(2,2,2-trifluoroethyl)amino)methyl)-1H-pyrazole-3-sulfonamide (Intermediate P60) and 4-isocyanato-1,2,3,5,6,7-hexahydro-s-indacene (Intermediate A1) to afford the title compound (17 mg, 76%) as a white solid.

$^1$H NMR (DMSO-d$_6$) δ 1.86 (s, 1H), 8.00 (s, 1H), 6.93 (s, 1H), 6.70 (s, 1H), 4.81-4.75 (m, 1H), 3.82 (s, 2H), 3.31-3.26 (m, 2H), 2.78 (t, J=7.4 Hz, 4H), 2.57 (t, J=7.4 Hz, 4H), 2.30 (s, 3H), 1.92 (p, J=7.5 Hz, 4H), 1.39 (d, J=6.5 Hz, 6H).

LCMS; m/z 514.4 (M+H)$^+$ (ES$^+$).

Example 97: N-((1,2,3,5,6,7-Hexahydro-s-indacen-4-yl)carbamoyl)-1-methyl-5-((methyl(2,2,2-trifluoroethyl)amino)methyl)-1H-pyrazole-3-sulfonamide, Sodium Salt

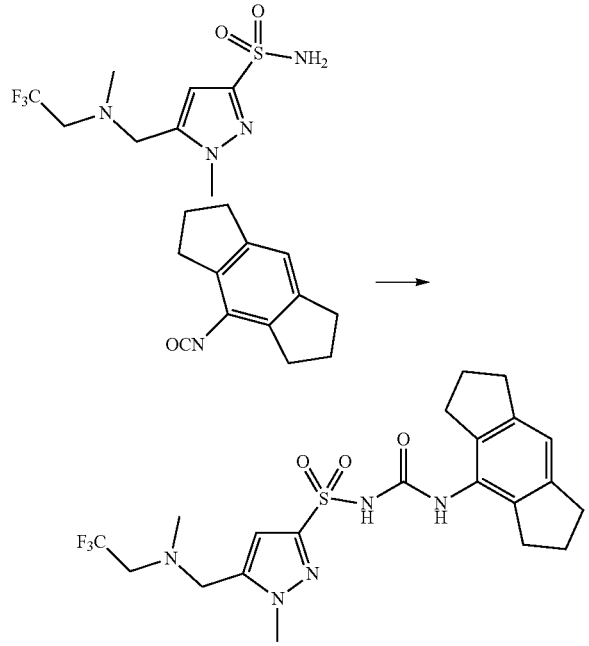

Sodium tert-butoxide, 2 M in THF (136 μL, 0.271 mmol) was added to a solution of 1-methyl-5-((methyl(2,2,2-trifluoroethyl)amino)methyl)-1H-pyrazole-3-sulfonamide (Intermediate P61) (74 mg, 0.258 mmol) in THF (5 mL) and stirred at room temperature for 1 hour. Then 4-isocyanato-1,2,3,5,6,7-hexahydro-s-indacene (Intermediate A1) (57 mg, 0.286 mmol) was added and stirred at room temperature overnight. The suspension was filtered and the collected solid washed with EtOAc (2 mL). The solid was dissolved in MeCN and then dried under vacuum to afford the title compound (110 mg, 83%).

$^1$H NMR (DMSO-$d_6$) δ 7.54 (s, 1H), 6.77 (s, 1H), 6.36 (s, 1H), 3.77 (s, 3H), 3.73 (s, 2H), 3.25 (q, J=10.1 Hz, 2H), 2.75 (t, J=7.3 Hz, 4H), 2.63 (t, J=7.3 Hz, 4H), 2.32 (s, 3H), 1.89 (p, J=7.4 Hz, 4H).

LCMS; m/z 486.5 (M+H)$^+$ (ES$^+$).

Example 98: 3-(N-((1,2,3,5,6,7-Hexahydro-s-indacen-4-yl)carbamoyl) sulfamoyl)-N,1-dimethyl-N-(2-(N-methylacetamido)ethyl)-1H-pyrazole-5-carboxamide, Partial ammonium Salt

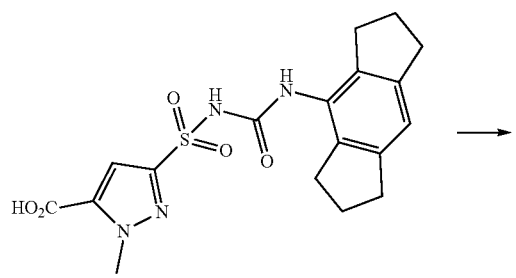

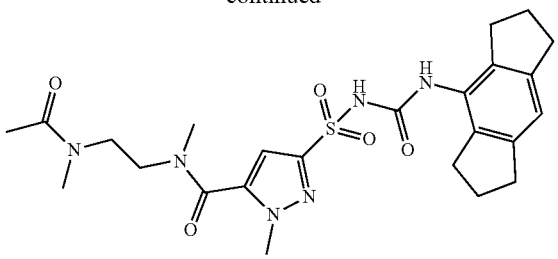

Prepared according to the general procedure of N-(3-(dimethylamino)propyl)-3-(N-((1,2,3,5,6,7-hexahydro-s-indacen-4-yl)carbamoyl)sulfamoyl)-N,1-dimethyl-1H-pyrazole-5-carboxamide (Example 10) from 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) and N-methyl-N-(2-(methylamino)ethyl)acetamide to afford the title compound (38 mg, 47%) as a white solid.

$^1$H NMR (DMSO-$d_6$), rotamers; δ 10.98 (br s, 1H), 7.90 (br s, 1H), 6.94-6.74 (m, 2H), 3.92-3.77 (m, 3H), 3.65-3.37 (m, 4H), 3.08-2.51 (m, 14H), 2.04-1.76 (m, 7H).

LCMS; m/z 517.4 (M+H)$^+$ (ES$^+$); 515.3 (M-H)$^-$ (ES$^-$).

Example 99: N-(2-Acetamidoethyl)-3-(N-((1,2,3,5,6,7-hexahydro-s-indacen-4-yl)carbamoyl)sulfamoyl)-N,1-dimethyl-1H-pyrazole-5-carboxamide, Partial ammonium Salt

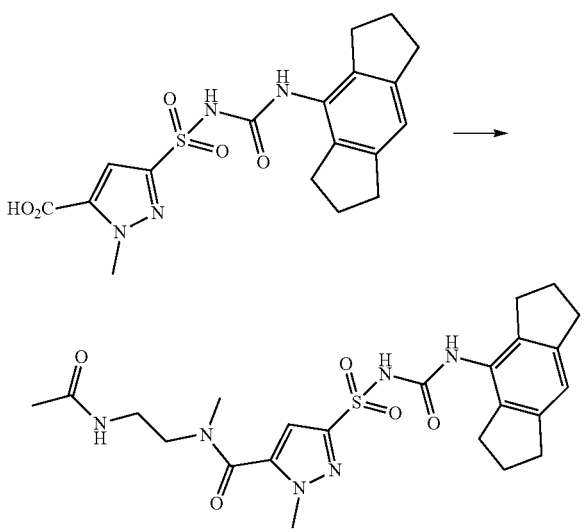

Prepared according to the general procedure of N-(3-(dimethylamino)propyl)-3-(N-((1,2,3,5,6,7-hexahydro-s-indacen-4-yl)carbamoyl)sulfamoyl)-N,1-dimethyl-1H-pyrazole-5-carboxamide (Example 10) from 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) and N-(2-(methylamino)ethyl)acetamide, HCl (34 mg, 0.223 mmol) to afford the title compound (26 mg, 33%) as a white solid.

$^1$H NMR (DMSO-$d_6$), rotamers; δ 10.94 (br s, 1H), 8.32-7.69 (m, 2H), 6.94-6.74 (m, 2H), 3.92-3.78 (m, 3H), 3.54-3.36 (m, 2H), 3.31-3.12 (m, 2H), 3.08-2.93 (m, 3H), 2.77 (t, J=7.4 Hz, 4H), 2.61 (t, J=7.4 Hz, 4H), 1.92 (p, J=7.5 Hz, 4H), 1.81-1.62 (m, 3H).

LCMS; m/z 503.5 (M+H)$^+$ (ES$^+$); 501.3 (M-H)$^-$ (ES$^-$).

Example 100: 3-(N-((1,2,3,5,6,7-Hexahydro-s-indacen-4-yl)carbamoyl) sulfamoyl)-N,1-dimethyl-N-(tetrahydro-2H-pyran-4-yl)-1H-pyrazole-5-carboxamide, sodium salt

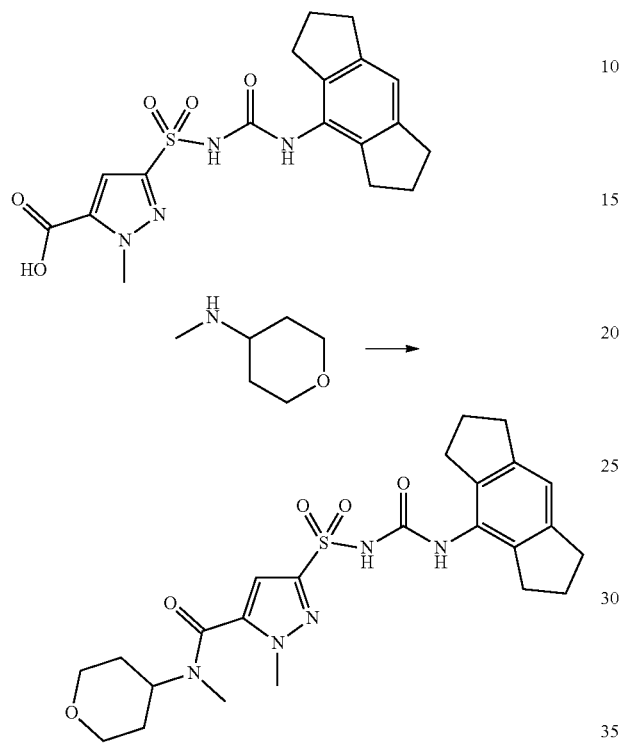

HATU (49.3 mg, 0.130 mmol) was added to a solution of 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) (67.3 mg, 0.150 mmol) and N-methyltetrahydro-2H-pyran-4-amine (14.93 mg, 0.130 mmol) in DMF (1 mL) and the reaction mixture was stirred at room temperature for 20 hours. Water (1 mL) was slowly added and the reaction mixture was stirred for 1 hour. The suspension was filtered and the collected solid triturated in water (3 mL) for 0.5 hour. The suspension was filtered and the collected solid was washed with water (0.5 mL) and TBME (1 mL). The solid was dried under reduced pressure for 6 hours to afford 3-(N-((1,2,3,5,6,7-hexahydro-s-indacen-4-yl)carbamoyl)sulfamoyl)-N,1-dimethyl-N-(tetrahydro-2H-pyran-4-yl)-1H-pyrazole-5-carboxamide. The solid was dissolved in THF (2 mL) and 2 M sodium tert-butoxide in THF (54.0 µL, 0.108 mmol) was added. The suspension was stirred at room temperature for 2 hours and filtered. The collected solid was washed with EtOAc (2 mL) and dried under reduced pressure for 6 hours to afford the title compound (46 mg, 80%) as a white solid.

$^1$H NMR (DMSO-d$_6$), rotamers; δ 7.47 (s, 1H), 6.77 (s, 1H), 6.58 (s, 1H), 4.53-4.49 (m, 0.6H), 3.94-3.90 (m, 2.4H), 3.80 (s, 3H), 3.43-3.41 (m, 1H), 3.16-3.12 (m, 1H), 2.89 (s, 3H), 2.75 (t, J=7.4 Hz, 4H), 2.66 (t, J=7.6 Hz, 4H), 1.93-1.80 (m, 6H), 1.59-1.55 (m, 2H).

LCMS; m/z 502 (M+H)$^+$ (ES$^+$).

Example 101: 3-(N-((1,2,3,5,6,7-Hexahydro-s-indacen-4-yl)carbamoyl) sulfamoyl)-N,N-bis(2-hydroxyethyl)-1-methyl-1H-pyrazole-5-carboxamide, Partial ammonium Salt

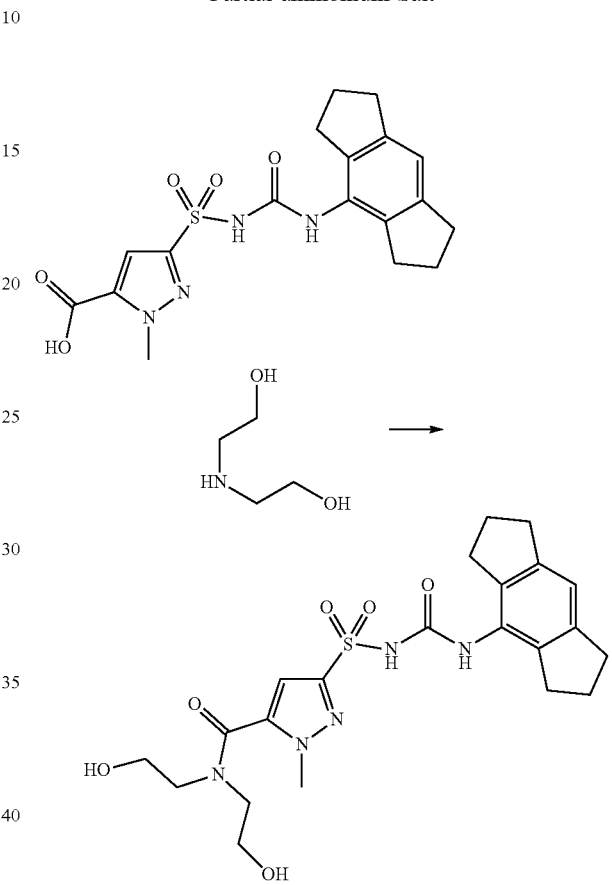

HATU (67.9 mg, 0.178 mmol) was added to a solution of 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) (66.7 mg, 0.149 mmol) and 2,2'-azanediylbis(ethan-1-ol) (17.11 µL, 0.178 mmol) in DMF (1 mL) and the reaction mixture was stirred at room temperature for 20 hours. Water (1 mL) was slowly added and the reaction mixture was stirred for 1 hour. The suspension was filtered and the collected solid triturated in water (3 mL) for 0.5 hour. The suspension was filtered and the collected solid was washed with water (0.5 mL) and TBME (1 mL). The solid was dried under reduced pressure for 6 hours to afford the title compound (32 mg, 42%) as a white solid.

$^1$H NMR (DMSO-d$_6$), rotamers; δ 7.60 (d, J=10.0 Hz, 1H), 7.24 (br s, 1H), 6.80 (s, 1H), 6.69 (s, 1H), 4.95-4.77 (m, 2H), 3.78 (s, 3H), 3.78-3.52 (m, 8H), 2.76 (t, J=7.4 Hz, 4H), 2.65 (t, J=7.6 Hz, 4H), 1.95-1.88 (m, 4H).

LCMS; m/z 492 (M+H)$^+$ (ES$^+$).

Example 102: 3-(N-((1,2,3,5,6,7-Hexahydro-s-indacen-4-yl)carbamoyl) sulfamoyl)-N-(2-hydroxyethyl)-N-(2-methoxyethyl)-1-methyl-1H-pyrazole-5-carboxamide, Partial ammonium Salt

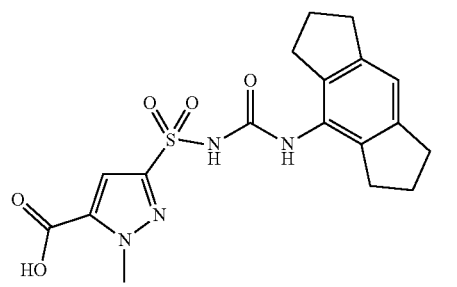

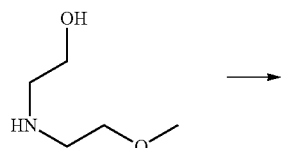

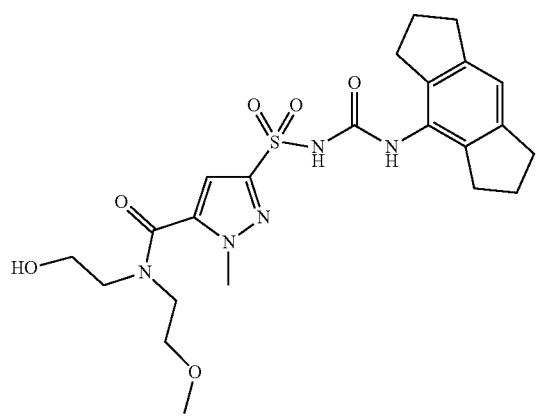

Prepared according to the general procedure of 3-(N-((1,2,3,5,6,7-hexahydro-s-indacen-4-yl)carbamoyl)sulfamoyl)-N,N-bis(2-hydroxyethyl)-1-methyl-1H-pyrazole-5-carboxamide, partial ammonium salt (Example 101) from 3-(N-((1,2,3,5,6,7-hexahydro-s-indacen-4-yl)carbamoyl)sulfamoyl)-1-methyl-1H-pyrazole-5-carboxylic acid disodium salt (Intermediate P53) and 2-((2-methoxyethyl)amino)ethan-1-ol to afford the title compound as a white solid (7 mg, 9%).

¹H NMR (DMSO-d₆), rotamers; δ 7.61 (s, 1H), 7.11 (br s, 1H), 6.81 (s, 1H), 6.60 (s, 1H), 4.89-4.82 (m, 1H), 3.78 (s, 3H), 3.67-3.36 (m, 8H), 3.28-3.15 (2×2s, 3H), 2.76 (t, J=7.4 Hz, 4H), 2.65 (t, J=7.4 Hz, 4H), 1.95-1.88 (m, 4H).

LCMS; m/z 506 (M+H)⁺ (ES⁺).

Example 103: 3-(N-((1,2,3,5,6,7-Hexahydro-s-indacen-4-yl)carbamoyl) sulfamoyl)-N,1-dimethyl-N-(oxetan-3-yl)-1H-pyrazole-5-carboxamide

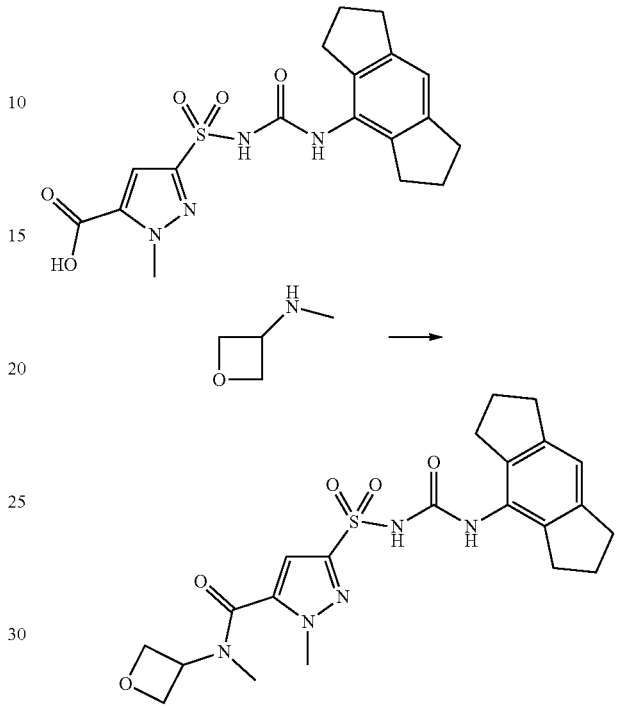

Prepared according to the general procedure of 3-(N-((1,2,3,5,6,7-hexahydro-s-indacen-4-yl)carbamoyl)sulfamoyl)-N,N-bis(2-hydroxyethyl)-1-methyl-1H-pyrazole-5-carboxamide, partial ammonium salt (Example 101) from 3-(N-((1,2,3,5,6,7-hexahydro-s-indacen-4-yl)carbamoyl) sulfamoyl)-1-methyl-1H-pyrazole-5-carboxylic acid disodium salt (Intermediate P53) and N-methyloxetan-3-amine to afford the title compound (27 mg, 36%) as a white solid.

¹H NMR (DMSO-d₆) rotamers: δ 10.95 (br s, 1H), 8.09 (s, 1H), 7.11 (s, 0.5H), 6.95 (s, 1H), 6.89 (s, 0.5H), 5.25-5.22 (m, 0.5H), 5.06-5.03 (m, 0.5H), 4.69-4.60 (m, 4H), 3.92 (s, 3H), 3.19-3.06 (m, 3H), 2.79 (t, J=7.4 Hz, 4H), 2.61 (t, J=7.5 Hz, 4H), 2.00-1.92 (m, 4H).

LCMS; m/z 474 (M+H)⁺ (ES⁺).

Example 104: 3-(N-((1,2,3,5,6,7-Hexahydro-s-indacen-4-yl)carbamoyl) sulfamoyl)-N-(3-hydroxypropyl)-N,1-dimethyl-1H-pyrazole-5-carboxamide, Partial ammonium Salt

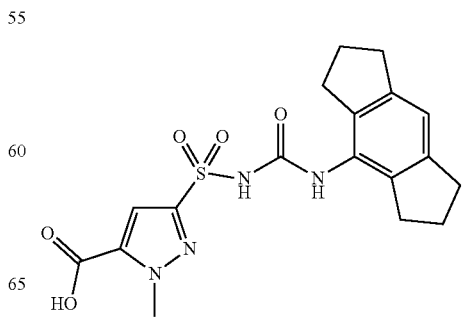

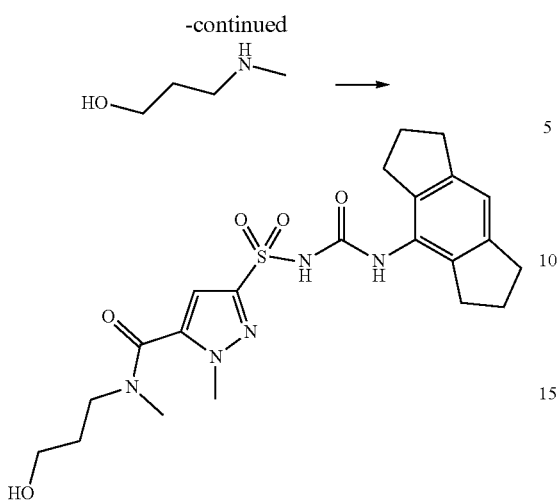

3-(Methylamino)propan-1-ol (19 µL, 0.195 mmol), NaHCO₃ (16 mg, 0.190 mmol) and HATU (72 mg, 0.189 mmol) were successively added to a suspension of 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) (70 mg, 0.156 mmol) in DMF (1 mL) and stirred for 2 days. The reaction was quenched with water (1 mL) and purified by reversed phase prep-HPLC (General Methods, basic prep) to afford the title compound (37 mg, 48%) as a white solid.

¹H NMR (DMSO-d₆), rotamers; δ 7.81 (s, 1H), 7.61-6.99 (br s, 1H), 6.85 (s, 1H), 6.82-6.71 (m, 1H), 4.48 (br s, 1H), 3.94-3.78 (m, 3H), 3.59-3.13 (m, 4H), 3.07-2.90 (m, 3H), 2.76 (t, J=7.4 Hz, 4H), 2.62 (t, J=7.4 Hz, 4H), 1.92 (p, J=7.4 Hz, 4H), 1.79-1.57 (m, 2H).

LCMS; m/z 476.4 (M+H)⁺ (ES⁺); 474.4 (M−H)⁻ (ES⁻).

Example 105: N-(2,3-Dihydroxypropyl)-3-(N-((1,2,3,5,6,7-hexahydro-s-indacen-4-yl)carbamoyl)sulfamoyl)-N,1-dimethyl-1H-pyrazole-5-carboxamide, Partial ammonium Salt

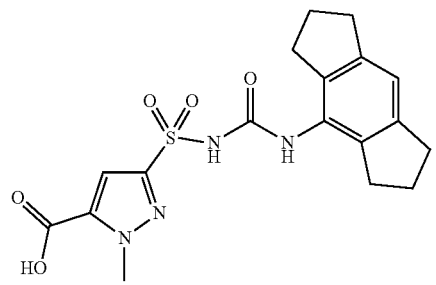

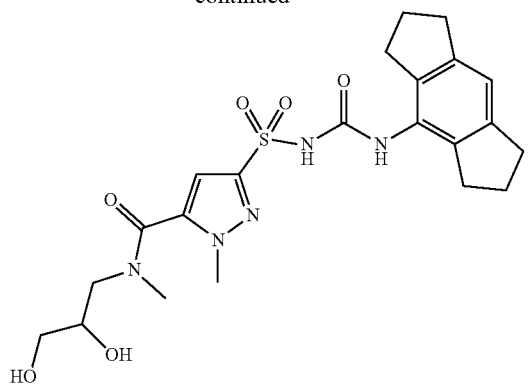

Prepared according to the general procedure of 3-(N-((1,2,3,5,6,7-hexahydro-s-indacen-4-yl)carbamoyl)sulfamoyl)-N-(3-hydroxypropyl)-N,1-dimethyl-1H-pyrazole-5-carboxamide, partial ammonium salt (Example 104) from 3-(N-((1,2,3,5,6,7-hexahydro-s-indacen-4-yl)carbamoyl)sulfamoyl)-1-methyl-1H-pyrazole-5-carboxylic acid disodium salt (Intermediate P53) and 3-(methylamino)propane-1,2-diol to afford the title compound (43 mg, 54%) as a white solid.

¹H NMR (DMSO-d₆), rotamers; δ 7.83-7.64 (m, 1H), 7.61-7.01 (m, 1H), 6.87-6.80 (m, 1H), 6.78-6.71 (m, 1H), 5.13-4.99 (m, 1H), 4.96-4.84 (m, 1H), 4.62 (s, 1H), 3.90-3.73 (m, 3H), 3.71-3.09 (m, 5H), 3.07 (s, 1H), 2.98 (s, 1H), 2.76 (t, J=7.4 Hz, 4H), 2.63 (t, J=7.4 Hz, 4H), 2.07-1.79 (m, 4H).

LCMS; m/z 492.4 (M+H)⁺ (ES⁺); 490.2 (M−H)⁻ (ES⁻).

Example 106: N-Ethyl-3-(N-((1,2,3,5,6,7-hexahydro-s-indacen-4-yl) carbamoyl)sulfamoyl)-N-(2-hydroxyethyl)-1-methyl-1H-pyrazole-5-carboxamide, Partial ammonium Salt

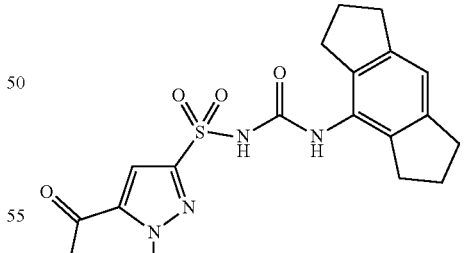

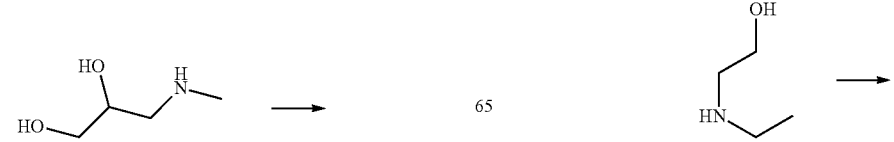

-continued

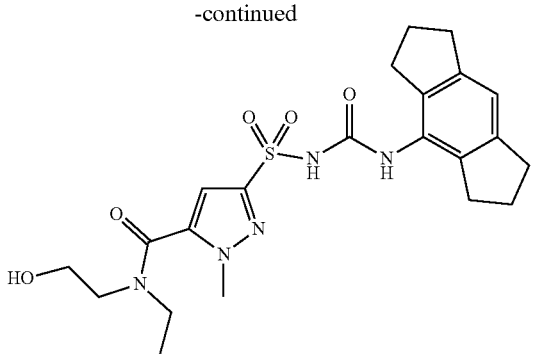

Prepared according to the general procedure of 3-(N-((1,2,3,5,6,7-hexahydro-s-indacen-4-yl)carbamoyl)sulfamoyl)-N-(3-hydroxypropyl)-N,1-dimethyl-1H-pyrazole-5-carboxamide, partial ammonium salt (Example 104) from 3-(N-((1,2,3,5,6,7-hexahydro-s-indacen-4-yl)carbamoyl)sulfamoyl)-1-methyl-1H-pyrazole-5-carboxylic acid disodium salt (Intermediate P53) and 2-(ethylamino)ethan-1-ol to afford the title compound (39 mg, 52%) as a white solid.

$^1$H NMR (DMSO-d$_6$), rotamers; δ 8.16-6.99 (br s, 1H), 7.82 & 7.80 (2×s, 1H), 6.86 (s, 1H), 6.79 & 6.74 (2×s, 1H), 4.93 & 4.82 (2×m, 1H), 3.82 (s, 3H), 3.65-3.33 (m, 6H), 2.77 (t, J=7.4 Hz, 4H), 2.63 (t, J=7.3 Hz, 4H), 1.93 (quin, J=7.4 Hz, 4H), 1.15 & 1.08 (2×t, J=7.1 Hz, 3H).

LCMS; m/z 476.5 (M+H)$^+$ (ES$^+$); 474.3 (M–H)$^-$ (ES$^-$).

Example 107: N-((2,6-Diisopropylphenyl)carbamoyl)-1-methyl-5-(morpholine-4-carbonyl)-1H-pyrazole-3-sulfonamide

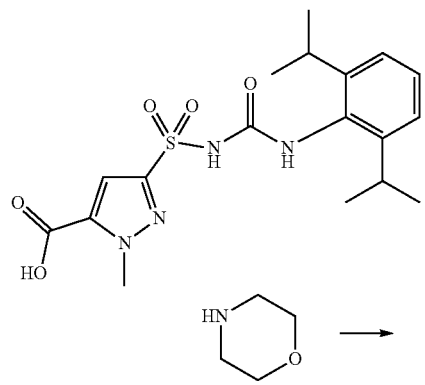

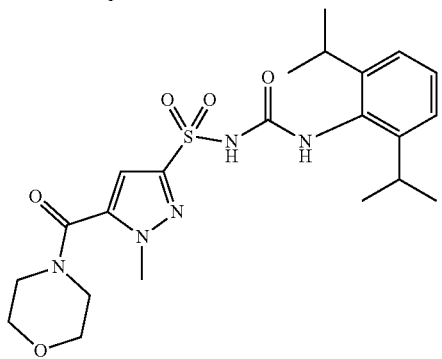

Morpholine (19 μL, 0.220 mmol) and HATU (82 mg, 0.217 mmol) were successively added to a solution of 3-(N-((2,6-diisopropylphenyl)carbamoyl)sulfamoyl)-1-methyl-1H-pyrazole-5-carboxylic acid, disodium salt (Intermediate P54) (70 mg, 0.155 mmol) in DMF (1 mL) and stirred for 20 hours. The reaction was quenched with water (0.1 mL) and purified by reversed phase prep-HPLC (General Methods, basic prep) to afford the title compound (41 mg, 53%) as a white solid.

$^1$H NMR (DMSO-d$_6$), rotamers; δ 11.11 (br s, 1H), 7.79 (s, 1H), 7.22 (t, J=7.7 Hz, 1H), 7.10 (d, J=7.7 Hz, 2H), 6.91 (s, 1H), 3.93 (s, 3H), 3.72-3.39 (m, 8H), 2.98 (sept, J=6.9 Hz, 2H), 1.05 (d, J=6.8 Hz, 12H).

LCMS; m/z 478.4 (M+H)$^+$ (ES$^+$); 476.4 (M–H)$^-$ (ES$^-$).

Example 108: 3-(N-((2,6-Diisopropylphenyl)carbamoyl)sulfamoyl)-N-(2-methoxyethyl)-N,1-dimethyl-1H-pyrazole-5-carboxamide

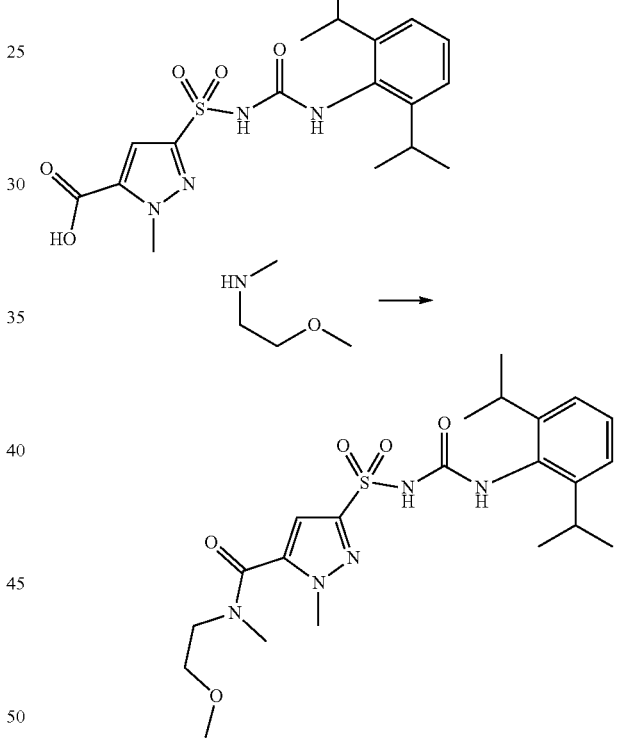

HATU (66.5 mg, 0.175 mmol) was added to a solution of 3-(N-((2,6-diisopropylphenyl)carbamoyl)sulfamoyl)-1-methyl-1H-pyrazole-5-carboxylic acid, disodium salt (Intermediate P54) (65.9 mg, 0.146 mmol) and 2-methoxy-N-methylethanamine (19.00 μL, 0.175 mmol) in DMF (1 mL) and the mixture stirred at room temperature for hours. Water (1 mL) was slowly added and the reaction mixture was stirred at room temperature for 1 hour. The suspension was filtered and the collected solid triturated in water (3 mL) for 0.5 hour. The suspension was filtered and the collected solid was washed with water (0.5 mL) and TBME (1 mL). The solid was dried under reduced pressure for 6 hours to afford the title compound (18 mg, 25%) as a white solid.

$^1$H NMR (DMSO-d$_6$), rotamers; δ 11.11 (s, 1H), 8.00-7.72 (m, 1H), 7.28-7.20 (m, 1H), 7.15-7.09 (m, 2H), 7.02-

6.86 (m, 1H), 3.93 (s, 1H), 3.86 (s, 2H), 3.66-3.57 (m, 1H), 3.57-3.45 (m, 2H), 3.44-3.37 (m, 1H), 3.27 (s, 1H), 3.16 (s, 2H), 3.03-2.87 (m, 4H), 1.17-0.77 (m, 12H).

LCMS; m/z 480 (M+H)⁺ (ES⁺).

Example 100: 3-(N-((2,6-Diisopropylphenyl)carbamoyl)sulfamoyl)-N,N— bis(2-methoxyethyl)-1-methyl-1H-pyrazole-5-carboxamide

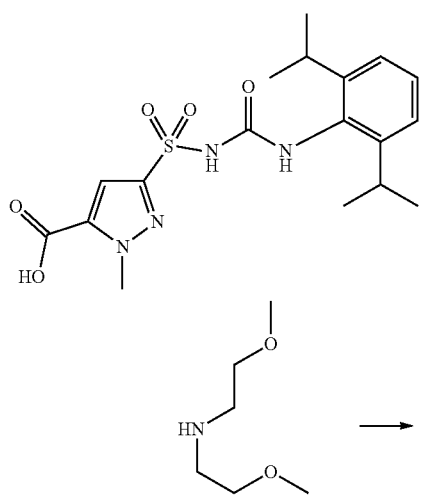

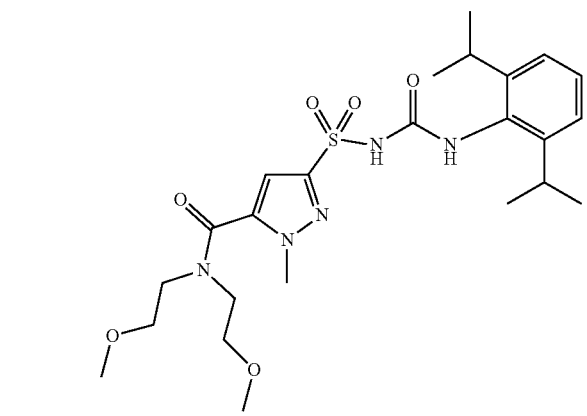

Prepared according to the general procedure of 3-(N-((2,6-diisopropylphenyl) carbamoyl)sulfamoyl)-N-(2-methoxyethyl)-N,1-dimethyl-1H-pyrazole-5-carboxamide (Example 108) from 3-(N-((2,6-diisopropylphenyl)carbamoyl)sulfamoyl)-1-methyl-1H-pyrazole-5-carboxylic acid, disodium salt (Intermediate P54) and bis(2-methoxyethyl)amine to afford the title compound (22 mg, 23%) as a white solid.

¹H NMR (DMSO-d₆), rotamers; δ 11.11 (s, 1H), 7.91 (s, 1H), 7.31-7.18 (m, 1H), 7.13 (s, 1H), 7.11 (s, 1H), 6.92 (s, 1H), 3.86 (s, 3H), 3.66-3.58 (m, 2H), 3.56-3.47 (m, 4H), 3.43-3.35 (m, 2H), 3.27 (s, 3H), 3.14 (s, 3H), 2.94 (sept, J=6.8 Hz, 2H), 1.18-0.87 (m, 12H).

LCMS; m/z 524 (M+H)⁺ (ES⁺).

Example 110: N-((1,2,3,5,6,7-Hexahydro-s-indacen-4-yl)carbamoyl)-5-(4-hydroxypiperidine-1-carbonyl)-1-methyl-1H-pyrazole-3-sulfonamide, Partial ammonium Salt

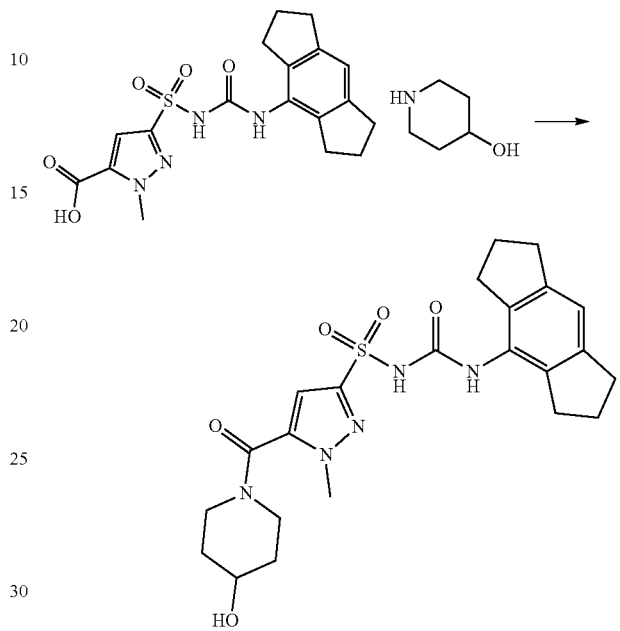

Prepared according to the general procedure of 3-(N-((1,2,3,5,6,7-hexahydro-s-indacen-4-yl)carbamoyl)sulfamoyl)-N-(3-hydroxypropyl)-N,1-dimethyl-1H-pyrazole-5-carboxamide, partial ammonium salt (Example 104) from 3-(N-((1,2,3,5,6,7-hexahydro-s-indacen-4-yl)carbamoyl)sulfamoyl)-1-methyl-1H-pyrazole-5-carboxylic acid disodium salt (Intermediate P53) and piperidin-4-ol to afford the title compound (44 mg, 57%) as a white solid.

¹H NMR (DMSO-d₆), rotamers; δ 7.88 (s, 1H), 7.48-6.92 (m, 1H), 6.88 (s, 1H), 6.78 (s, 1H), 4.83 (d, J=3.9 Hz, 1H), 3.96 (m, 1H), 3.87 (s, 3H), 3.77 (m, 1H), 3.63 (m, 1H), 3.32 (m, 2H), 2.78 (t, J=7.4 Hz, 4H), 2.61 (t, J=7.4 Hz, 4H), 1.94 (quin, J=7.5 Hz, 4H), 1.77 (m, 2H), 1.39 m, 2H).

LCMS; m/z 488.4 (M+H)⁺ (ES⁺); 486.3 (M–H)⁻ (ES⁻).

Example 11: N-((1,2,3,5,6,7-Hexahydro-s-indacen-4-yl)carbamoyl)-5-(3-methoxypyrrolidine-1-carbonyl)-1-methyl-1H-pyrazole-3-sulfonamide, Partial ammonium Salt

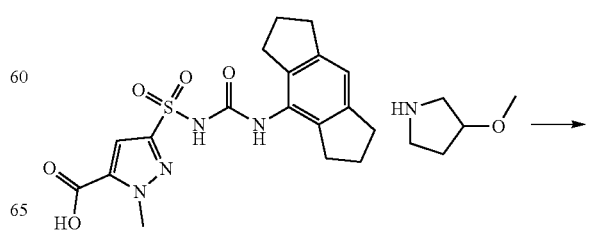

-continued

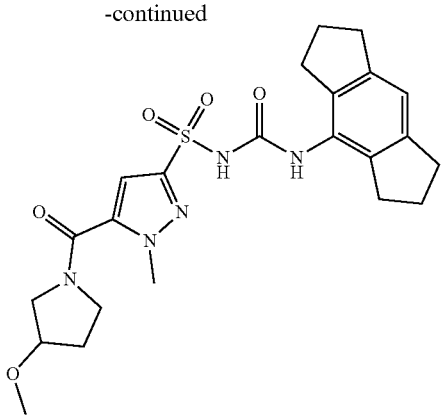

3-Methoxypyrrolidine (19 mg, 0.188 mmol) and HATU (72 mg, 0.189 mmol) were successively added to a suspension of 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) (70 mg, 0.156 mmol) in DMF (1 mL) and stirred for 20 hours. The solution was purified by chromatography on RP Flash C18 (12 g column, 5-50% MeCN/10 mM ammonium bicarbonate) to afford the title compound (25 mg, 32%) as a white solid.

$^1$H NMR (DMSO-$d_6$), rotamers; δ 7.82 (s, 1H), 7.08 (s, 1H), 6.96 (d, J=2.6 Hz, 1H), 6.86 (s, 1H), 4.07-3.90 (m, 4H), 3.75-3.67 (m, 1H), 3.64-3.39 (m, 4H), 3.26 (s, 1H), 3.19 (s, 1H), 2.76 (t, J=7.4 Hz, 4H), 2.61 (t, J=7.4 Hz, 4H), 2.06-1.84 (m, 6H).

LCMS; m/z 488.43 (M+H)$^+$ (ES$^+$); 48635 (M−H)$^−$ (ES$^−$).

Example 112: 3-(N-((1,2,3,5,6,7-Hexahydro-s-indacen-4-yl)carbamoyl) sulfamoyl)-N,N-bis(2-methoxyethyl)-1-methyl-1H-pyrazole-5-carboxamide, Partial ammonium Salt

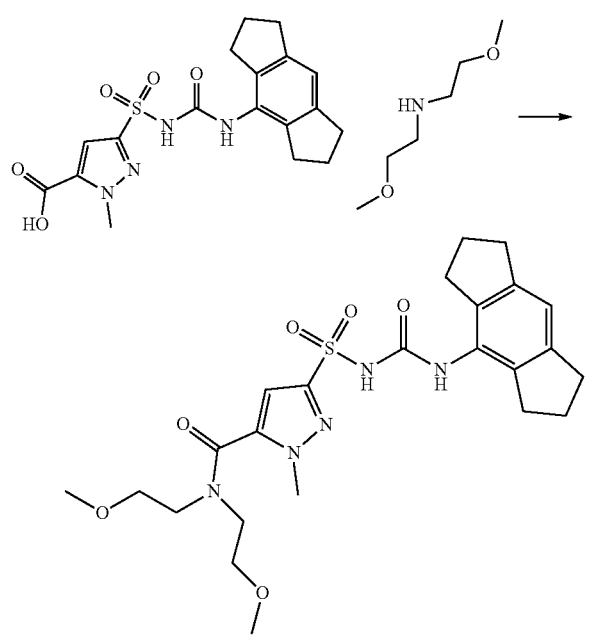

Prepared according to the general procedure of N-((1,2,3,5,6,7-hexahydro-s-indacen-4-yl)carbamoyl)-5-(3-methoxypyrrolidine-1-carbonyl)-1-methyl-1H-pyrazole-3-sulfonamide, partial ammonium salt (Example 111) from 3-(N-((1,2,3,5,6,7-hexahydro-s-indacen-4-yl)carbamoyl)sulfamoyl)-1-methyl-1H-pyrazole-5-carboxylic acid disodium salt (Intermediate P53) and bis(2-methoxyethyl)amine to afford the title compound (36 mg, 44%) as a white solid.

$^1$H NMR (DMSO-$d_6$), rotamers; δ 7.79 (s, 1H), 7.10 (br s, 1H), 6.85 (s, 1H), 6.73 (s, 1H), 3.80 (s, 3H), 3.63 (t, J=5.8 Hz, 2H), 3.58-3.49 (m, 4H), 3.39 (t, J=5.0 Hz, 2H), 3.28 (s, 3H), 3.14 (s, 3H), 2.77 (t, J=7.4 Hz, 4H), 2.63 (t, J=7.3 Hz, 4H), 1.92 (quin, J=7.5 Hz, 4H).

LCMS; m/z 520.44 (M+H)$^+$ (ES$^+$); 518.30 (M−H)$^−$ (ES$^−$).

Example 113: 3-(N-((1,2,3,5,6,7-Hexahydro-s-indacen-4-yl)carbamoyl) sulfamoyl)-N-(2-methoxyethyl)-N,1-dimethyl-1H-pyrazole-5-carboxamide, sodium Salt

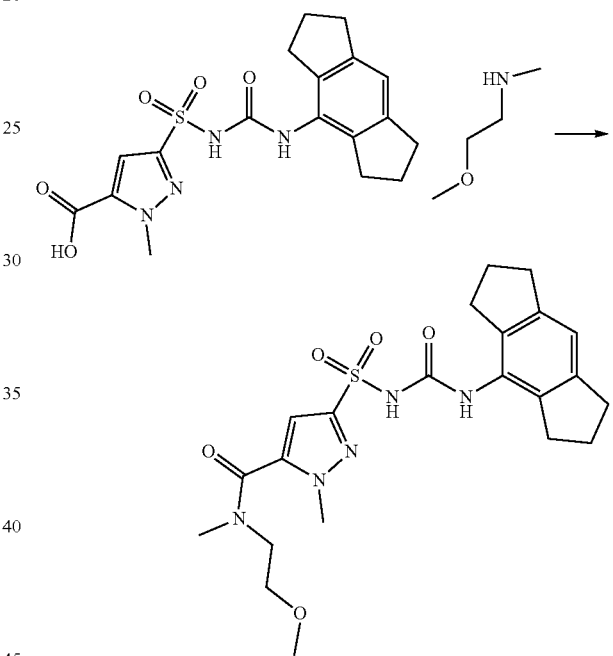

2-Methoxy-N-methylethanamine (19 μL, 0.173 mmol), HATU (71 mg, 0.187 mmol) and Hunig's base (65 μL, 0.372 mmol) were successively added to a solution of 3-(N-((1,2,3,5,6,7-hexahydro-s-indacen-4-yl)carbamoyl)sulfamoyl)-1-methyl-1H-pyrazole-5-carboxylic acid (Intermediate P51) (50 mg, 0.124 mmol) in DMF (1 mL) and stirred for 20 hours. The reaction was quenched with water (1 mL) and purified by chromatography on RP Flash C18 (12 g column, 5-50% MeCN/10 mM ammonium bicarbonate) to afford crude product. 18 mg of the crude product were partitioned between TBME (1 mL) and 0.1 M aqueous NaHCO$_3$ (340 μL, 0.034 mmol). The layers were separated and the aqueous layer washed with further TBME (2×1 mL). The aqueous layer was evaporated in vacuo and dried to afford the title compound (17 mg, 27%) as a white solid.

$^1$H NMR (DMSO-$d_6$), rotamers; δ 7.52 (s, 1H), 6.77 (s, 1H), 6.6 & 6.55 (2×s, 1H), 3.81 & 3.76 (2×s, 3H), 3.61 (m, 1H), 3.56 (m, 2H), 3.4 (m, 1H), 3.28 & 3.16 (2×s, 3H), 3.05 & 2.97 (2×s, 3H), 2.75 (t, J=7.4 Hz, 4H), 2.65 (t, J=7.5 Hz, 4H), 1.89 (quin, J=7.5 Hz, 4H).

LCMS; m/z 476.4 (M+H)$^+$ (ES$^+$); 474.3 (M−H)$^−$ (ES$^−$).

Example 14: N-((1,2,3,5,6,7-Hexahydro-s-indacen-4-yl)carbamoyl)-1-methyl-5-(morpholine-4-carbonyl)-1H-pyrazole-3-sulfonamide, Sodium Salt

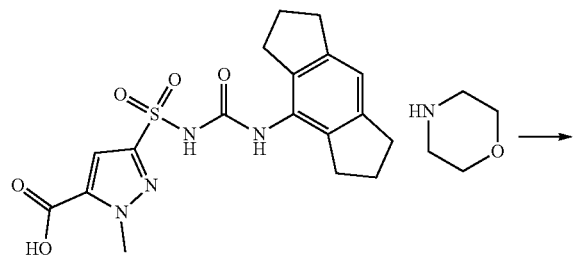

Prepared according to the general procedure of 3-(N-((1,2,3,5,6,7-hexahydro-s-indacen-4-yl)carbamoyl)sulfamoyl)-N-(2-methoxyethyl)-N,1-dimethyl-1H-pyrazole-5-carboxamide, sodium salt (Example 113) from 3-(N-((1,2,3,5,6,7-hexahydro-s-indacen-4-yl)carbamoyl)sulfamoyl)-1-methyl-1H-pyrazole-5-carboxylic acid disodium salt (Intermediate P53) and morpholine to afford the title compound (12 mg, 16%) as a white solid.

$^1$H NMR (DMSO-d$_6$), rotamers; δ 7.54 (s, 1H), 6.77 (s, 1H), 6.59 (s, 1H), 3.84 (s, 3H), 3.76-3.43 (m, 8H), 2.75 (t, J=7.4 Hz, 4H), 2.64 (t, J=7.3 Hz, 4H), 1.90 (quin, J=7.5 Hz, 4H).

LCMS; m/z 474.4 (M+H)$^+$ (ES$^+$); 472.3 (M–H)$^-$ (ES$^-$).

Example 115: 5-(3-(Dimethylamino)oxetan-3-yl)-N-((1,2,3,5,6,7-hexahydro-s-indacen-4-yl)carbamoyl)-1-methyl-1H-pyrazole-3-sulfonamide

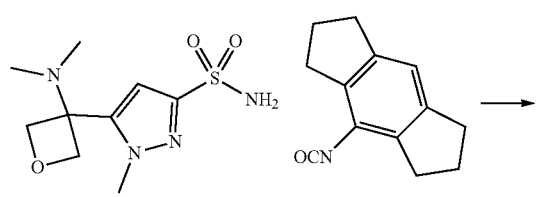

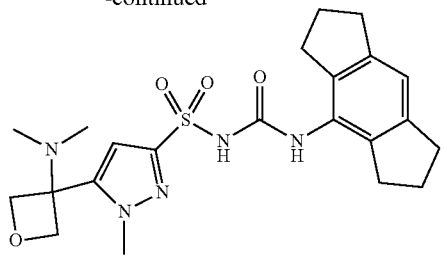

5-(3-(Dimethylamino)oxetan-3-yl)-1-methyl-1H-pyrazole-3-sulfonamide (Intermediate P62) (65 mg, 0.21 mmol) was dissolved in 4:1 THF:DMF (2.5 mL) and sodium tert-butoxide (2 M in THF; 0.117 mL, 0.233 mmol) was added. After 1 hour, 4-isocyanato-1,2,3,5,6,7-hexahydro-s-indacene (Intermediate A1) (46.5 mg, 0.233 mmol) was added and the mixture was stirred at room temperature for 18 hours. The reaction mixture was concentrated in vacuo and the crude product was purified by chromatography on reversed phase flash chromatography C18 (12 g column, 10-40% MeCN/10 mM ammonium bicarbonate) to afford the title compound (20 mg, 20%) as a white solid.

$^1$H NMR (DMSO-d$_6$) δ 1.82 (br s, 1H), 7.98 (s, 1H), 6.92 (s, 1H), 6.84 (s, 1H), 4.95 (d, J=7.2 Hz, 2H), 4.76 (d, J=7.2 Hz, 2H), 3.76 (s, 3H), 2.78 (t, J=7.4 Hz, 4H), 2.58 (t, J=7.4 Hz, 4H), 2.21 (s, 6H), 1.93 (p, J=7.4 Hz, 4H).

LCMS; m/z 460.3 (M+H)$^+$ (ES$^+$); 458.2 (M–H)$^-$ (ES$^-$).

Example 16: N-((4-Fluoro-2,6-diisopropylphenyl)carbamoyl)-5-(((2-hydroxyethyl)(methyl)amino)methyl)-1-methyl-1H-pyrazole-3-sulfonamide Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(((2-hydroxyethyl)(methyl)amino)methyl)-1-methyl-1H-pyrazole-3-sulfonamide (Intermediate P63) and 5-fluoro-2-isocyanato-1,3-diisopropylbenzene (Intermediate A2) to afford the title compound (28 mg, 32%) as a white solid.

$^1$H NMR (DMSO-d$_6$) δ 10.97 (br s, 1H), 7.82 (s, 1H), 6.93 (d, J=9.9 Hz, 2H), 6.64 (s, 1H), 4.48 (t, J=5.3 Hz, 1H), 3.90 (s, 3H), 3.59 (s, 2H), 3.52 (q, J=5.9 Hz, 2H), 2.97 (m, 2H), 2.46 (t, J=6.1 Hz, 2H), 2.15 (s, 3H), 1.06 (br s, 12H).

LCMS; m/z 470.5 (M+H)$^+$ (ES$^+$); 468.2 (M–H)$^-$ (ES$^-$).

Example 17: N-((1,2,3,5,6,7-Hexahydro-s-indacen-4-yl)carbamoyl)-5-(((2-hydroxyethyl)(methyl)amino)methyl)-1-methyl-1H-pyrazole-3-sulfonamide

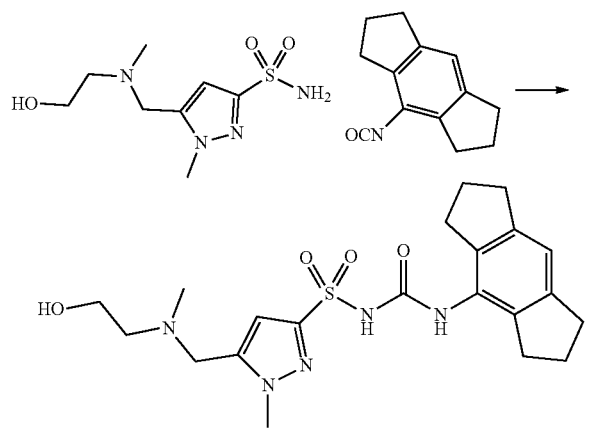

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(((2-hydroxyethyl)(methyl)amino)methyl)-1-methyl-1H-pyrazole-3-sulfonamide (Intermediate P63) and 4-isocyanato-1,2,3,5,6,7-hexahydro-s-indacene (Intermediate A1) to afford the title compound (22 mg, 27%) as a white solid.

$^1$H NMR (DMSO-$d_6$) δ 10.71 (br s, 1H), 7.94 (s, 1H), 6.91 (s, 1H), 6.61 (s, 1H), 4.47 (t, J=5.3 Hz, 1H), 3.88 (s, 3H), 3.59 (s, 2H), 3.52 (q, J=5.9 Hz, 2H), 2.79 (t, J=7.4 Hz, 4H), 2.61 (t, J=7.4 Hz, 4H), 2.46 (t, J=6.1 Hz, 2H), 2.15 (s, 3H), 1.94 (p, J=7.5 Hz, 4H).

LCMS; m/z 448.5 (M+H)$^+$ (ES$^+$); 446.1 (M–H)$^-$ (ES$^-$).

Example 118: N-((4-Fluoro-2,6-diisopropylphenyl)carbamoyl)-5-(((2-methoxyethyl)(methyl)amino)methyl)-1-methyl-1H-pyrazole-3-sulfonamide, Sodium Salt

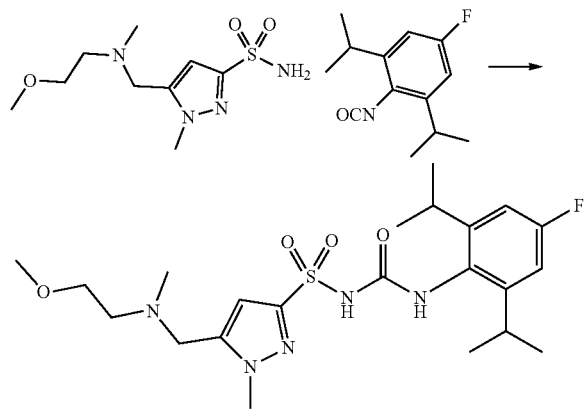

Prepared according to the general procedure of N-((1,2,3,5,6,7-hexahydro-s-indacen-4-yl)carbamoyl)-1-methyl-5-((methyl(2,2,2-trifluoroethyl)amino)methyl)-1H-pyrazole-3-sulfonamide, sodium salt (Example 97) from 5-(((2-methoxyethyl)(methyl)amino) methyl)-1-methyl-1H-pyrazole-3-sulfonamide (Intermediate P64) and 5-fluoro-2-isocyanato-1,3-diisopropylbenzene (Intermediate A2) to afford the title compound (22 mg, 39%) as a white solid.

$^1$H NMR (DMSO-$d_6$) δ 7.37 (s, 1H), 6.79 (d, J=10.0 Hz, 2H), 6.27 (s, 1H), 3.76 (s, 3H), 3.50 (s, 2H), 3.45 (t, J=5.8 Hz, 2H), 3.23 (s, 3H), 3.14 (m, 2H), 2.51 (t, J=5.8 Hz, 2H), 2.15 (s, 3H), 1.03 (d, J=6.8 Hz, 12H).

LCMS; m/z 484.5 (M+H)$^+$ (ES$^+$); 482.3 (M–H)$^-$ (ES$^-$).

Example 119: N-((1,2,3,5,6,7-Hexahydro-s-indacen-4-yl)carbamoyl)-5-(((2-methoxyethyl)(methyl)amino)methyl)-1-methyl-1H-pyrazole-3-sulfonamide, Sodium Salt

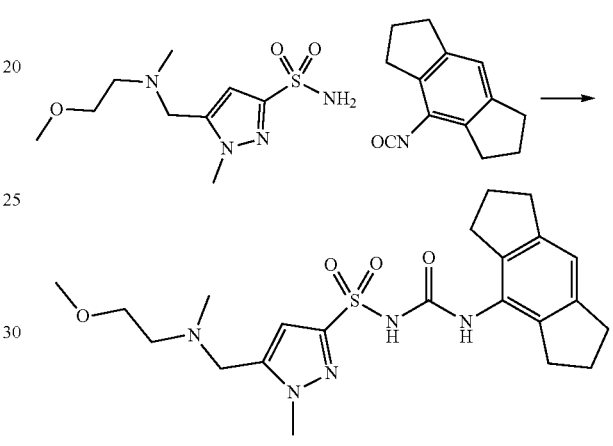

Prepared according to the general procedure of N-((1,2,3,5,6,7-hexahydro-s-indacen-4-yl)carbamoyl)-1-methyl-5-((methyl(2,2,2-trifluoroethyl)amino)methyl)-1H-pyrazole-3-sulfonamide, sodium salt (Example 97) from 5-(((2-methoxyethyl)(methyl)amino) methyl)-1-methyl-1H-pyrazole-3-sulfonamide (Intermediate P64) and 4-isocyanato-1,2,3,5,6,7-hexahydro-s-indacene (Intermediate A1) to afford the title compound (32 mg, 47%) as a white solid.

$^1$H NMR (DMSO-$d_6$) δ 7.59 (m, 1H), 6.79 (s, 1H), 6.34 (s, 1H), 3.79 (s, 3H), 3.52 (s, 2H), 3.44 (t, J=5.8 Hz, 2H), 3.23 (s, 3H), 2.75 (t, J=7.3 Hz, 4H), 2.64 (t, J=7.4 Hz, 4H), 2.51 (t, J=5.8 Hz, 2H), 2.16 (s, 3H), 1.90 (p, J=7.5 Hz, 4H).

LCMS; m/z 462.4 (M+H)$^+$ (ES$^+$); 460.4 (M–H)$^-$ (ES$^-$).

Example 120: N-((4-Chloro-2,6-diisopropylphenyl)carbamoyl)-1-methyl-5-(morpholinomethyl)-1H-pyrazole-3-sulfonamide, Sodium Salt

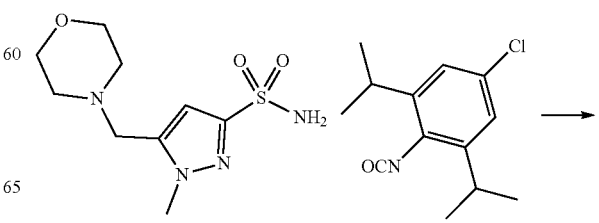

325
-continued

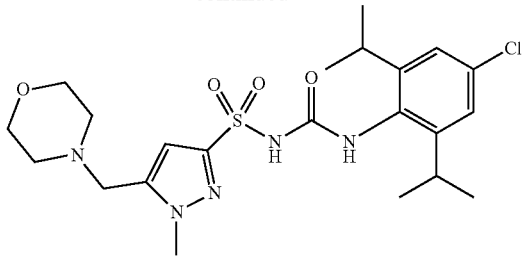

Prepared according to the general procedure of N-((1,2,3,5,6,7-hexahydro-s-indacen-4-yl)carbamoyl)-1-methyl-5-((methyl(2,2,2-trifluoroethyl)amino)methyl)-1H-pyrazole-3-sulfonamide, sodium salt (Example 97) from 1-methyl-5-(morpholinomethyl)-1H-pyrazole-3-sulfonamide (Intermediate P65) and 5-chloro-2-isocyanato-1,3-diisopropylbenzene (Intermediate A22) to afford the title compound (38 mg, 53%) as a white solid.

$^{1}$H NMR (DMSO-d$_6$) δ 7.45 (s, 1H), 7.01 (s, 2H), 6.28 (s, 1H), 3.77 (s, 3H), 3.56 (t, J=4.6 Hz, 4H), 3.48 (s, 2H), 3.13 (m, 2H), 2.36 (t, J=4.6 Hz, 4H), 1.03 (d, J=6.8 Hz, 12H).

LCMS; m/z 498.4/500.5 (M+H)$^+$ (ES$^+$); 496.3/498.4 (M−H)$^−$ (ES$^−$).

Example 121: N-((1,2,3,5,6,7-Hexahydro-s-indacen-4-yl)carbamoyl)-1-methyl-5-(morpholinomethyl)-1H-pyrazole-3-sulfonamide

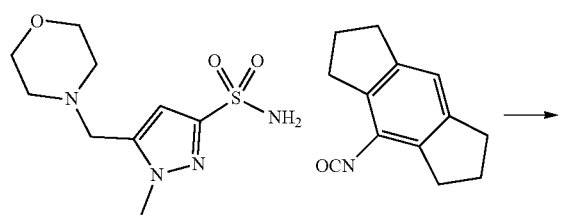

Prepared according to the general procedure of N-((1,2,3,5,6,7-hexahydro-s-indacen-4-yl)carbamoyl)-1-methyl-5-((methyl(2,2,2-trifluoroethyl)amino)methyl)-1H-pyrazole-3-sulfonamide, sodium salt (Example 97) from 1-methyl-5-(morpholinomethyl)-1H-pyrazole-3-sulfonamide (Intermediate P65) and 4-isocyanato-1,2,3,5,6,7-hexahydro-s-indacene (Intermediate A1) to afford the title compound (12 mg, 18%) as a white solid.

$^{1}$H NMR (DMSO-d$_6$) δ 10.81 (br s, 1H), 7.96 (s, 1H), 6.91 (s, 1H), 6.62 (s, 1H), 3.88 (s, 3H), 3.56 (s, 2H), 3.56 (m, 4H), 2.78 (t, J=7.4 Hz, 4H), 2.59 (t, J=7.4 Hz, 4H), 2.36 (m, 4H), 1.93 (p, J=7.5 Hz, 4H).

LCMS; m/z 460.4 (M+H)$^+$ (ES$^+$); 458.4 (M−H)$^−$ (ES$^−$).

326

Example 122: N-((3-(N-((1,2,3,5,6,7-Hexahydro-s-indacen-4-yl)carbamoyl)sulfamoyl)-1-isopropyl-1H-pyrazol-5-yl)methyl)-N-methylacetamide

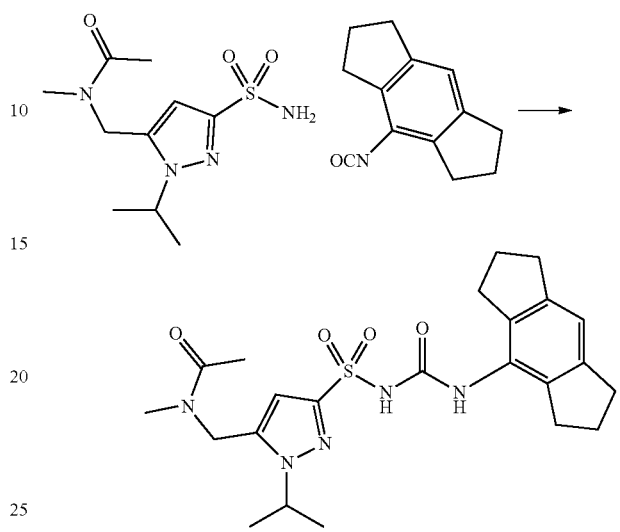

Prepared according to the general procedure of ((1,2,3,5,6,7-hexahydro-s-indacen-4-yl)carbamoyl)((1-isopropyl-5-(1-(trimethylammonio)ethyl)-1H-pyrazol-3-yl)sulfonyl)amide (Example 18) from N-((1-isopropyl-3-sulfamoyl-H-pyrazol-5-yl)methyl)-N-methylacetamide (Intermediate P68) and 4-isocyanato-1,2,3,5,6,7-hexahydro-s-indacene (Intermediate A1) to afford the title compound (20 mg, 38%) as a white solid.

$^{1}$H NMR (DMSO-d$_6$) δ 10.77 (br s, 1H), 7.93 (s, 1H), 6.88 (s, 1H), 6.62 (s, 1H), 4.75-4.61 (m, 1H), 4.59 (s, 2H), 2.90 (s, 3H), 2.75 (t, J=7.4 Hz, 4H), 2.56 (t, J=7.3 Hz, 4H), 2.02 (s, 3H), 1.90 (p, J=7.6 Hz, 4H), 1.31 (d, J=6.5 Hz, 6H).

LCMS; m/z 474.5 (M+H)$^+$ (ES$^+$)

Example 123: 5-(Azetidine-1-carbonyl)-N-((4-fluoro-2,6-diisopropylphenyl) carbamoyl)-1-isopropyl-1H-pyrazole-3-sulfonamide, Sodium Salt

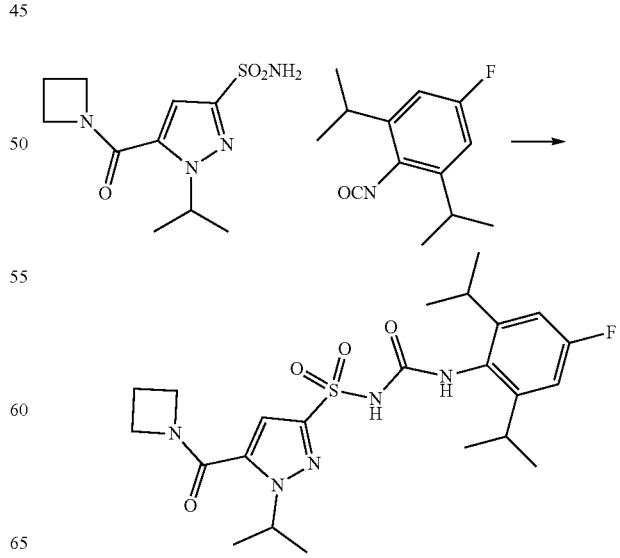

Prepared according to the general procedure of N-((1,2,3,5,6,7-hexahydro-s-indacen-4-yl)carbamoyl)-1-methyl-5-((methyl(2,2,2-trifluoroethyl)amino)methyl)-1H-pyrazole-3-sulfonamide, sodium salt (Example 97) from 5-(azetidine-1-carbonyl)-1-isopropyl-1H-pyrazole-3-sulfonamide (Intermediate P57) and 5-fluoro-2-isocyanato-1,3-diisopropylbenzene (Intermediate A2) to afford the title compound (46 mg, 48%) as a white solid.

¹H NMR (DMSO-d₆) δ 7.33 (s, 1H), 6.79 (d, J=10.1 Hz, 2H), 6.65 (s, 1H), 5.26 (sept, J=6.7 Hz, 1H), 4.25 (t, J=7.7 Hz, 2H), 4.02 (t, J=7.8 Hz, 2H), 3.22-2.93 (m, 2H), 2.26 (app. pent, J=7.7 Hz, 2H), 1.37 (d, J=6.6 Hz, 6H), 1.03 (d, J=6.8 Hz, 12H).

LCMS; m/z 494.4 (M+H)⁺ (ES⁺); 492.3 (M−H)⁻ (ES⁻)

Example 124: 5-(Azetidine-1-carbonyl)-N-((1,2,3,5,6,7-hexahydro-s-indacen-4-yl)carbamoyl)-1-isopropyl-1H-pyrazole-3-sulfonamide, Partial ammonium Salt

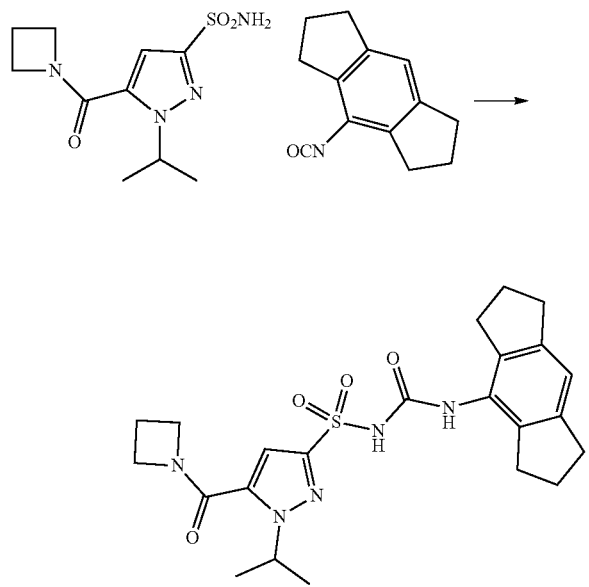

Prepared according to the general procedure of 5-(azetidin-1-ylmethyl)-1-cyclopropyl-N-((1,2,3,5,6,7-hexahydro-s-indacen-4-yl)carbamoyl)-1H-pyrazole-3-sulfonamide (Example 30) from 5-(azetidine-1-carbonyl)-1-isopropyl-H-pyrazole-3-sulfonamide (Intermediate P57) and 4-isocyanato-1,2,3,5,6,7-hexahydro-s-indacene (Intermediate A1) to afford the title compound (47 mg, 53%) as a white solid.

¹H NMR (DMSO-d₆) δ 7.77 (s, 1H), 6.92-6.68 (m, 2H), 5.28 (sept, J=6.5 Hz, 1H), 4.27 (t, J=7.7 Hz, 2H), 4.03 (t, J=7.7 Hz, 2H), 2.76 (t, J=7.4 Hz, 4H), 2.60 (t, J=7.3 Hz, 4H), 2.31-2.19 (m, 2H), 1.90 (p, J=7.4 Hz, 4H), 1.38 (d, J=6.6 Hz, 6H).

LCMS; m/z 472.5 (M+H)⁺ (ES⁺); 470.3 (M−H)⁻ (ES⁻).

Example 125: 3-(N-((4-Chloro-2,6-diisopropylphenyl)carbamoyl) sulfamoyl)-N,1-dimethyl-1H-pyrazole-5-carboxamide

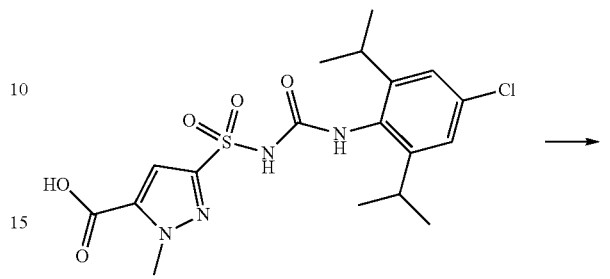

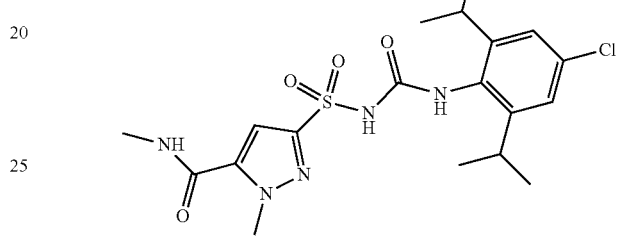

HATU (68.8 mg, 0.181 mmol) was added to a solution of 3-(N-((4-chloro-2,6-diisopropylphenyl)carbamoyl)sulfamoyl)-1-methyl-1H-pyrazole-5-carboxylic acid, disodium salt (Intermediate P56) (73.4 mg, 0.151 mmol) and methylamine (83 µL, 0.166 mmol) in DMF (1 mL). TEA (21 µL, 0.151 mmol) was added and the mixture stirred at room temperature for 20 hours. Water (1 mL) was slowly added and the mixture stirred for 1 hour, filtered, and the collected solid triturated in water (3 mL) for 0.5 hour. The suspension was filtered, the solid washed with water (0.5 mL) and MTBE (1 mL), and then purified by chromatography on RP Flash C18 (13 g column, 0-50% MeCN/10 mM ammonium bicarbonate). The product was triturated with MTBE (2 mL) for 1 hour, filtered and dried under vacuum for 15 hours to afford the title compound (7 mg, 10%) as a white solid.

¹H NMR (DMSO-d₆) δ 11.21 (s, 1H), 8.64 (s, 1H), 7.89 (s, 1H), 7.31 (s, 1H), 7.12 (s, 2H), 4.13 (s, 3H), 3.00-2.90 (m, 2H), 2.74 (d, J=4.5 Hz, 3H), 1.05-1.01 (m, 12H).

LCMS; m/z 456.4 and 458.4 (M+H)⁺ (ES⁺).

Example 126: 3-(N-((4-Fluoro-2-isopropyl-6-(tetrahydro-2H-pyran-4-yl)phenyl)carbamoyl)sulfamoyl)-N,N,1-trimethyl-1H-pyrazole-5-carboxamide, Sodium Salt

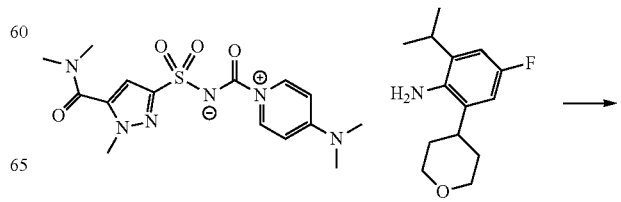

-continued

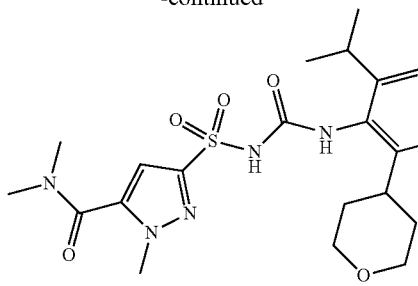

A mixture of (4-(dimethylamino)pyridin-1-ium-1-carbonyl)((5-(dimethylcarbamoyl)-1-methyl-1H-pyrazol-3-yl)sulfonyl)amide (Intermediate P58) (70 mg, 0.184 mmol) and 4-fluoro-2-isopropyl-6-(tetrahydro-2H-pyran-4-yl)aniline (Intermediate A15) (40 mg, 0.167 mmol) in MeCN (1 mL) was stirred at 50° C. for 1 hour. The crude product was purified by reversed phase prep-HPLC (General Methods, basic prep) to afford the desired carboxamide as a white solid (21 mg). To a solution of the carboxamide (21 mg) in THF (0.5 mL), a solution of 2.0 M NaO$^t$Bu in THF (1.0 eq) was added. The mixture was stirred for 1 hour, the solvent evaporated and the solid triturated with THF/MTBE. The precipitate was collected by filtration, washing with ether, and dried in vacuo to afford the title compound (5 mg, 6%) as a white solid.

$^1$H NMR (DMSO-d$_6$), rotamers; δ 7.39 (s, 1H), 6.81 (td, J=10.6, 2.9 Hz, 2H), 6.61 (s, 1H), 3.90-3.81 (m, 5H), 3.28-3.11 (m, 3H), 3.04-2.97 (m, 7H), 1.57-1.43 (m, 4H), 1.04 (d, J=6.8 Hz, 6H).

LCMS; m/z 496.5 (M+H)$^+$ (ES$^+$); 494.3 (M−H)$^−$ (ES$^−$).

Example 127: 3-(N-((2-Isopropyl-5-(pyrimidin-5-yl)phenyl)carbamoyl) sulfamoyl)-N,N,1-trimethyl-1H-pyrazole-5-carboxamide, Sodium Salt

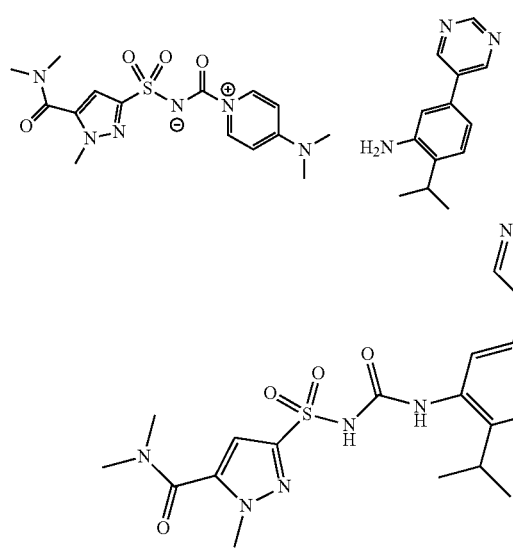

Prepare according to the general procedure or 3-(N-((4-fluoro-2-isopropyl-6-(tetrahydro-2H-pyran-4-yl)phenyl)carbamoyl)sulfamoyl)-N,N,1-trimethyl-1H-pyrazole-5-carboxamide, sodium salt (Example 126) from (4-(dimethylamino)pyridin-1-ium-1-carbonyl)((5-(dimethylcarbamoyl)-1-methyl-1H-pyrazol-3-yl)sulfonyl)amide (Intermediate P58) and 2-isopropyl-5-(pyrimidin-5-yl)aniline (Intermediate A17) to afford the title compound (27 mg, 23%) as a white solid.

$^1$H NMR (DMSO-d$_6$), rotamers; δ 9.15 (s, 1H), 9.01 (s, 2H), 8.14 (s, 1H), 7.77 (s, 1H), 7.31 (s, 2H), 6.63 (s, 1H), 3.82 (s, 3H), 3.19 (sept, J=6.8 Hz, 1H), 3.03 (s, 3H), 2.98 (s, 3H), 1.17 (d, J=6.8 Hz, 6H).

LCMS; m/z 472.4 (M+H)$^+$ (ES$^+$); 470.4 (M−H)$^−$ (ES$^−$).

Example 128: 3-(N-((4-Fluoro-2-isopropyl-6-(1-methyl-1H-pyrazol-4-yl)phenyl)carbamoyl)sulfamoyl)-N,N,1-trimethyl-1H-pyrazole-5-carboxamide, Sodium Salt

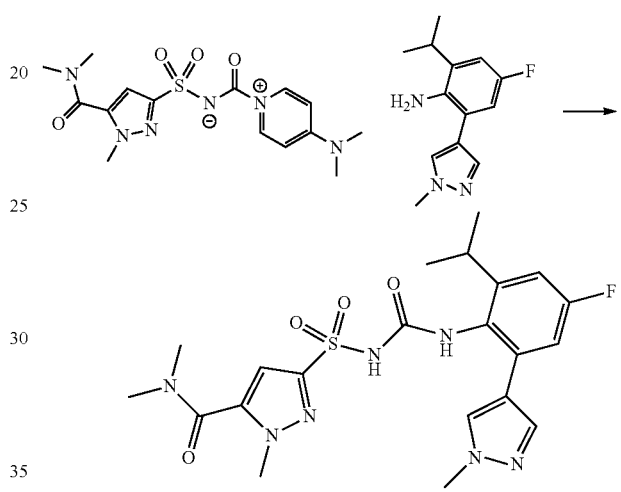

Prepared according to the general procedure for 3-(N-((4-fluoro-2-isopropyl-6-(tetrahydro-2H-pyran-4-yl)phenyl)carbamoyl)sulfamoyl)-N,N,1-trimethyl-1H-pyrazole-5-carboxamide, sodium salt (Example 126) from (4-(dimethylamino)pyridin-1-ium-1-carbonyl)((5-(dimethylcarbamoyl)-1-methyl-1H-pyrazol-3-yl)sulfonyl)amide (Intermediate P58) and 4-fluoro-2-isopropyl-6-(1-methyl-1H-pyrazol-4-yl)aniline (Intermediate A10) to afford the title compound (40 mg, 20%) as a white solid.

$^1$H NMR (DMSO-d$_6$), rotamers; δ 7.95 (s, 1H), 7.76 (s, 1H), 7.25 (s, 1H), 7.10 (dd, J=9.9, 3.0 Hz, 1H), 6.86 (dd, J=9.8, 2.9 Hz, 1H), 6.58 (s, 1H), 3.82 (s, 3H), 3.80 (s, 3H), 3.20 (m, 1H), 2.99 (s, 6H), 1.06 (d, J=6.8 Hz, 6H).

LCMS; m/z 492.4 (M+H)$^+$ (ES$^+$); 490.3 (M−H)$^−$ (ES$^−$).

Example 120: 3-(N-((2-Isopropyl-5-(1-methyl-1H-pyrazol-4-yl)phenyl)carbamoyl) sulfamoyl)-N,N,1-trimethyl-1H-pyrazole-5-carboxamide, Sodium Salt

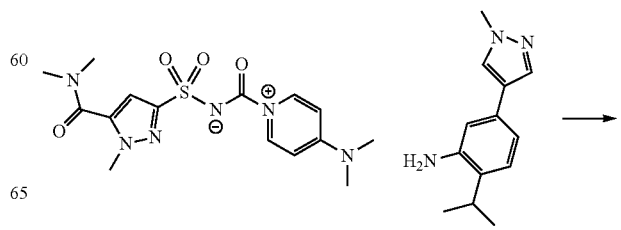

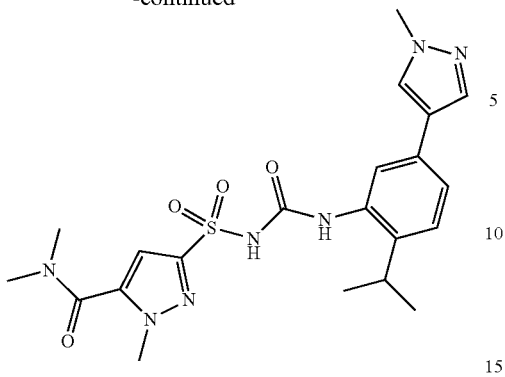

Prepared according to the general procedure for 3-(N-((4-fluoro-2-isopropyl-6-(tetrahydro-2H-pyran-4-yl)phenyl)carbamoyl)sulfamoyl)-N,N,1-trimethyl-1H-pyrazole-5-carboxamide, sodium salt (Example 126) from (4-(dimethylamino)pyridin-1-ium-1-carbonyl)((5-(dimethylcarbamoyl)-1-methyl-1H-pyrazol-3-yl)sulfonyl)amide (Intermediate P58) and 2-isopropyl-5-(1-methyl-1H-pyrazol-4-yl)aniline (Intermediate A16) to afford the title compound (6 mg, 5%) as a white solid.

$^1$H NMR (DMSO-d$_6$), rotamers; δ 7.94 (s, 1H), 7.89 (s, 1H), 7.65 (s, 1H), 7.57 (s, 1H), 7.11 (d, J=8.1 Hz, 1H), 7.10-7.05 (m, 1H), 6.61 (s, 1H), 3.85 (s, 3H), 3.82 (s, 3H), 3.09 (sept, J=6.8 Hz, 1H), 3.03 (s, 3H), 2.98 (s, 3H), 1.14 (d, J=6.8 Hz, 6H).

LCMS; m/z 474.5 (M+H)$^+$ (ES$^+$); 472.3 (M−H)$^−$ (ES$^−$).

Example 130: 3-(N-((4-Chloro-2,6-diisopropylphenyl)carbamoyl) sulfamoyl)-N-(cyanomethyl)-N,1-dimethyl-1H-pyrazole-5-carboxamide

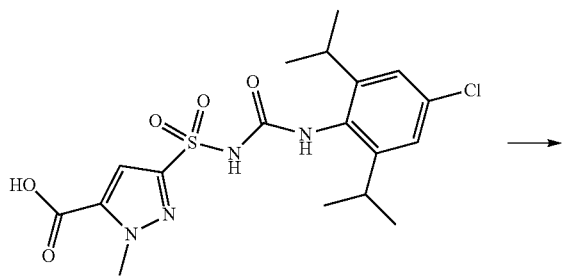

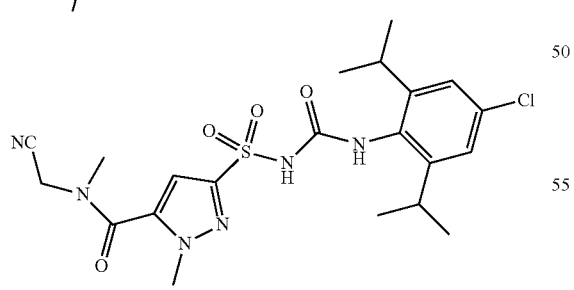

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((4-chloro-2,6-diisopropylphenyl)carbamoyl)sulfamoyl)-1-methyl-1H-pyrazole-5-carboxylic acid, disodium salt (Intermediate P56) and 2-(methylamino)acetonitrile, HCl to afford the title compound (26 mg, 42%).

$^1$H NMR (DMSO-d$_6$), rotamers; δ 11.25 (s, 1H), 7.99 (s, 1H), 7.14 (s, 3H), 4.58 (s, 2H), 3.97 (s, 3H), 3.12 (s, 3H), 2.98-2.85 (m, 2H), 1.05 (br s, 12H), LCMS; m/z 495.5 and 497.5 (M+H)$^+$ (ES$^+$).

Example 13: 3-(N-((2,6-Diisopropylphenyl)carbamoyl)sulfamoyl)-N— isopropyl-1-methyl-1H-pyrazole-5-carboxamide

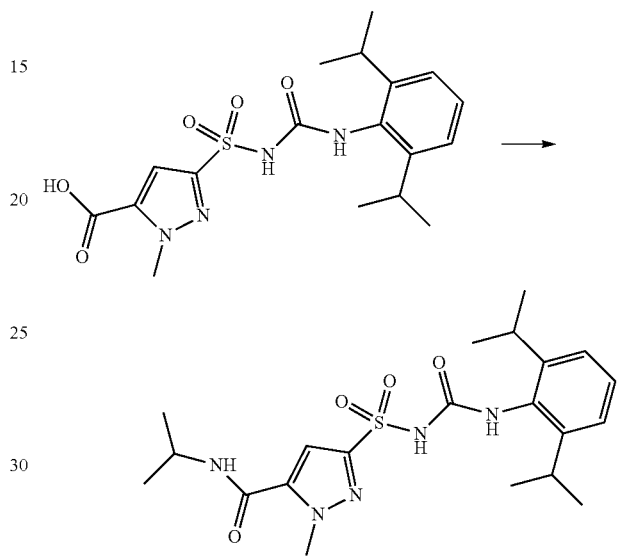

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((2,6-diisopropylphenyl)carbamoyl)sulfamoyl)-1-methyl-1H-pyrazole-5-carboxylic acid, disodium salt (Intermediate P54) and isopropylamine to afford the title compound (28 mg, 45%) as a white solid.

$^1$H NMR (DMSO-d$_6$) δ 11.06 (s, 1H), 8.49 (d, J=7.8 Hz, 1H), 7.85 (s, 1H), 7.47 (s, 1H), 7.27-7.20 (m, 1H), 7.11 (d, J=7.6 Hz, 2H), 4.15 (s, 3H), 4.09-3.99 (m, 1H), 2.90-2.86 (m, 2H), 1.13 (d, J=6.6 Hz, 6H), 1.05-1.03 (m, 12H).

LCMS; m/z 450 (M+H)$^+$ (ES$^+$).

Example 132: N-((2,6-Diisopropylphenyl)carbamoyl)-5-(3-fluoroazetidine-1-carbonyl)-1-methyl-1H-pyrazole-3-sulfonamide, Sodium Salt

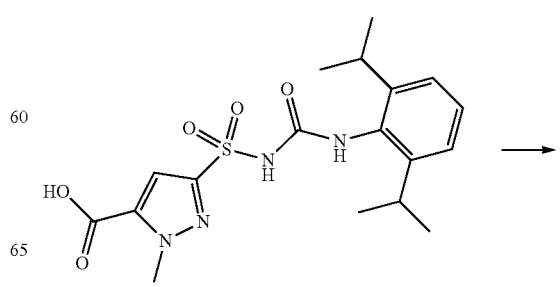

-continued

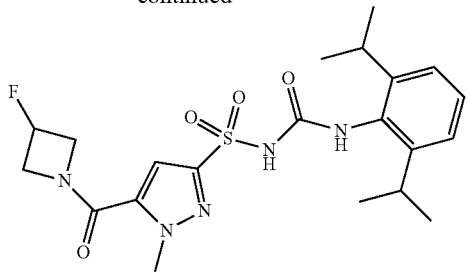

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((2,6-diisopropylphenyl)carbamoyl)sulfamoyl)-1-methyl-1H-pyrazole-5-carboxylic acid, disodium salt (Intermediate P54) and 3-fluoroazetidine, HCl. The sodium salt was generated by dissolving the free acid (19 mg, 0.041 mmol) in THF (1 mL) and adding 2 M solution of sodium tert-butoxide (20.50 µL, 0.041 mmol) in THF. The suspension was stirred for 2 hours and filtered. The collected solid was washed with EtOAc (2 mL) and dried under reduced pressure for 6 hours to afford the title compound (6 mg, 8%) as a white solid.

$^1$H NMR (DMSO-d$_6$), rotamers; δ 7.32 (s, 1H), 7.11-7.10 (m, 1H), 7.01 (d, J=7.3 Hz, 2H), 6.71 (s, 1H), 5.51-5.33 (m, 1H), 4.63-4.59 (m, 1H), 4.40-4.32 (m, 2H), 4.11-4.01 (m, 1H), 3.98 (s, 3H), 3.16-3.12 (m, 2H), 1.04 (d, J=6.8 Hz, 12H).

LCMS; m/z 466 (M+H)$^+$ (ES$^+$).

Example 133: N-(Cyanomethyl)-3-(N-((2,6-diisopropylphenyl)carbamoyl) sulfamoyl)-N,1-dimethyl-1H-pyrazole-5-carboxamide

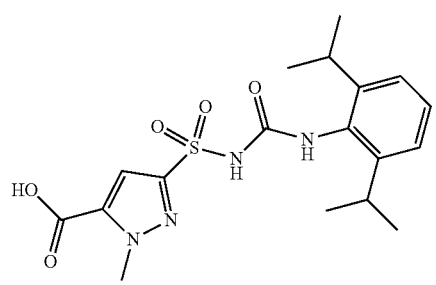

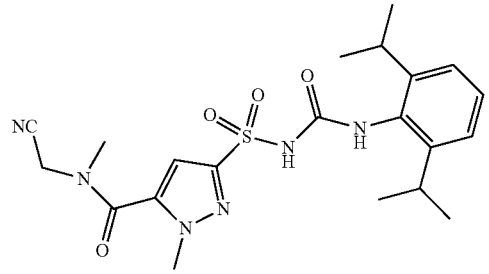

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((2,6-diisopropylphenyl)carbamoyl)sulfamoyl)-1-methyl-1H-pyrazole-5-carboxylic acid, disodium salt (Intermediate P54) and 2-(methylamino)acetonitrile, HCl to afford the title compound (25 mg, 33%) as a white solid.

$^1$H NMR (DMSO-d$_6$) δ 7.59 (s, 1H), 7.20-7.12 (m, 1H), 7.06 (d, J=7.6 Hz, 2H), 6.91 (s, 1H), 4.57 (s, 2H), 3.91 (s, 3H), 3.13 (s, 3H), 3.08-3.05 (m, 2H), 1.05 (d, J=6.9 Hz, 12H). Acidic NH not observed.

LCMS; m/z 461 (M+H)$^+$ (ES$^+$).

Example 134: 3-(N-((4-Fluoro-2-isopropyl-6-(pyridin-3-yl)phenyl) carbamoyl)sulfamoyl)-N,N,1-trimethyl-1H-pyrazole-5-carboxamide, sodium Salt

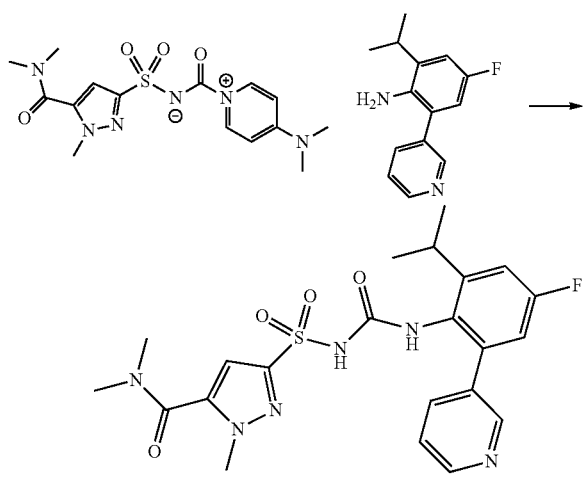

Prepared according to the general procedure for 3-(N-((4-fluoro-2-isopropyl-6-(tetrahydro-2H-pyran-4-yl)phenyl) carbamoyl)sulfamoyl)-N,N,1-trimethyl-1H-pyrazole-5-carboxamide, sodium salt (Example 126) from (4-(dimethylamino)pyridin-1-ium-1-carbonyl)((5-(dimethylcarbamoyl)-1-methyl-1H-pyrazol-3-yl)sulfonyl) amide (Intermediate P58) and 4-fluoro-2-isopropyl-6-(pyridin-3-yl)aniline (Intermediate A3) to afford the title compound (23 mg, 9%) as a white solid.

$^1$H NMR (DMSO-d$_6$, 70° C.) δ 8.55 (m, 1H), 8.45 (dd, J=4.8, 1.7 Hz, 1H), 7.77 (dt, J=7.8, 2.0 Hz, 1H), 7.25 (ddd, J=7.9, 4.8, 0.9 Hz, 1H), 7.06 (dd, J=10.2, 3.0 Hz, 1H), 6.91 (dd, J=9.1, 3.0 Hz, 1H), 6.44 (s, 1H), 3.84 (s, 3H), 3.26 (sept, J=6.9 Hz, 1H), 3.04 (s, 6H), 1.13 (d, J=6.9 Hz, 6H). NH not observed.

LCMS; m/z 489.4 (M+H)$^+$ (ES$^+$).

Example 135: 3-(N-((4-Fluoro-2-isopropyl-6-(pyrimidin-5-yl)phenyl) carbamoyl)sulfamoyl)-N,N,1-trimethyl-1H-pyrazole-5-carboxamide, sodium Salt

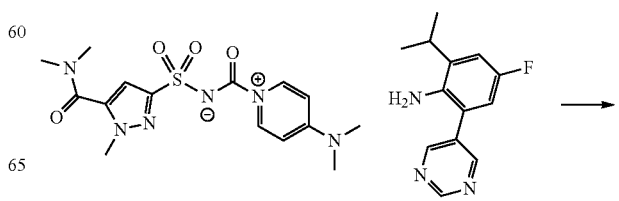

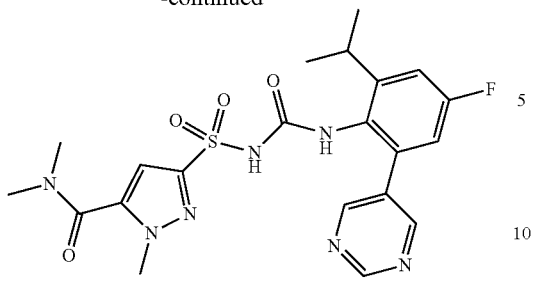

Prepared according to the general procedure for 3-(N-((4-fluoro-2-isopropyl-6-(tetrahydro-2H-pyran-4-yl)phenyl)carbamoyl)sulfamoyl)-N,N,1-trimethyl-1H-pyrazole-5-carboxamide, sodium salt (Example 126) from (4-(dimethylamino)pyridin-1-ium-1-carbonyl)((5-(dimethylcarbamoyl)-1-methyl-1H-pyrazol-3-yl)sulfonyl)amide (Intermediate P58) and 4-fluoro-2-isopropyl-6-(pyrimidin-5-yl)aniline (Intermediate A8) to afford the title compound (44 mg, 16%) as a white solid.

$^1$H NMR (DMSO-d$_6$, 70° C.) δ 9.03 (s, 1H), 8.76 (s, 2H), 7.30 (bs, 1H), 7.11 (dd, J=10.2, 3.0 Hz, 1H), 7.03 (dd, J=9.0, 3.0 Hz, 1H), 6.43 (s, 1H), 3.85 (s, 3H), 3.26 (sept, J=6.8 Hz, 1H), 3.04 (s, 6H), 1.14 (d, J=6.8 Hz, 6H).

LCMS; m/z 490.4 (M+H)$^+$ (ES$^+$).

Example 16: N-Cyclopropyl-3-(N-((2,6-diisopropylphenyl)carbamoyl) sulfamoyl)-N,1-dimethyl-1H-pyrazole-5-carboxamide

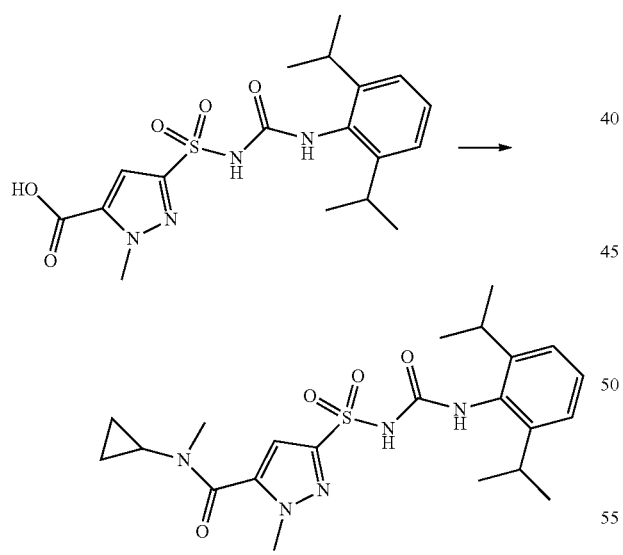

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((2,6-diisopropylphenyl)carbamoyl)sulfamoyl)-1-methyl-1H-pyrazole-5-carboxylic acid, disodium salt (Intermediate P54) and N—methylcyclopropanamine, HCl to afford the title compound (45 mg, 55%) as a white solid.

$^1$H NMR (DMSO-d$_6$), rotamers; 611.04 (s, 1H), 7.96-7.86 (2×s, 1H), 7.26-7.23 (m, 1H), 7.16-7.11 (m, 3H), 3.95 (s, 3H), 3.09-2.84 (m, 6H), 1.18-1.14 (m, 12H), 0.55-0.52 (m, 4H).

LCMS; m/z 462 (M+H)$^+$ (ES$^+$).

Example 137: 3-(N-((2,5-Diisopropylphenyl)carbamoyl)sulfamoyl)-N,N,1-trimethyl-1H-pyrazole-5-carboxamide, Sodium Salt

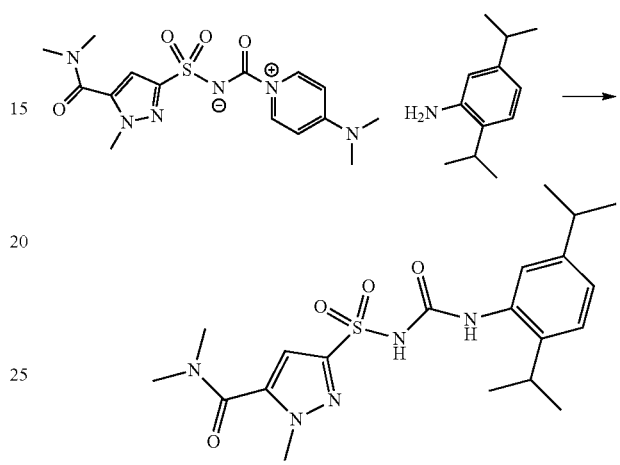

Prepared according to the general procedure for 3-(N-((4-fluoro-2-isopropyl-6-(tetrahydro-2H-pyran-4-yl)phenyl)carbamoyl)sulfamoyl)-N,N,1-trimethyl-1H-pyrazole-5-carboxamide, sodium salt (Example 126) from (4-(dimethylamino)pyridin-1-ium-1-carbonyl)((5-(dimethylcarbamoyl)-1-methyl-1H-pyrazol-3-yl)sulfonyl)amide (Intermediate P58) and 2,5-diisopropylaniline (Intermediate A18) to afford the title compound (8 mg, 7%) as a white solid.

$^1$H NMR (DMSO-d$_6$), rotamers; δ 7.51-7.47 (m, 2H), 7.05 (d, J=8.0 Hz, 1H), 6.80 (dd, J=8.0, 2.0 Hz, 1H), 6.62 (s, 1H), 3.83 (s, 3H), 3.04 (m, 4H), 2.99 (s, 3H), 2.75 (sept, J=6.9 Hz, 1H), 1.15 (d, J=6.9 Hz, 6H), 1.10 (d, J=6.8 Hz, 6H).

LCMS; m/z 436.5 (M+H)$^+$ (ES$^+$).

Example 138: 5-(Azetidine-1-carbonyl)-N-((4-fluoro-2,6-diisopropylphenyl) carbamoyl)-1-methyl-1H-pyrazole-3-sulfonamide, Sodium Salt

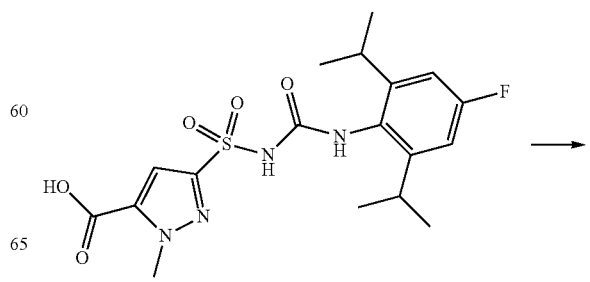

-continued

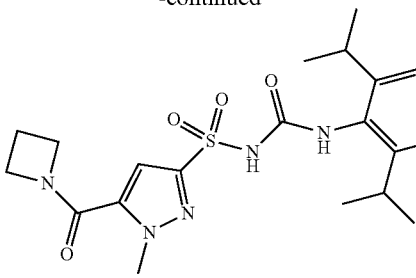

Azetidine hydrochloride (17 mg, 0.182 mmol), NaHCO₃ (30 mg, 0.357 mmol) and HATU (68 mg, 0.179 mmol) were successively added to a solution of 3-(N-((4-fluoro-2,6-diisopropylphenyl)carbamoyl)sulfamoyl)-1-methyl-1H-pyrazole-5-carboxylic acid, disodium salt (Intermediate P55) (70 mg, 0.149 mmol) in DMF (1 mL) and stirred for 20 hours. The reaction was quenched with water (1 mL) and purified by chromatography on RP Flash C18 (12 g column, 5-50% MeCN/10 mM ammonium bicarbonate) to afford the free acid (s mg, 84%) as a white solid. The sodium salt was generated by dissolving the free acid (55 mg, 0.12 mmol) in THF (3 mL) and adding a 2 M solution of sodium tert-butoxide (63 μL, 0.126 mmol) in THF. The suspension was stirred for 30 minutes and filtered. The collected solid was washed with EtOAc (2 mL), slurried in MeCN (3 mL), filtered and dried under vacuum to afford the title compound (29 mg, 40%) as a white solid.

$^1$H NMR (DMSO-d₆) δ 7.33 (s, 1H), 6.79 (d, J=10.1 Hz, 2H), 6.67 (s, 1H), 4.29 (t, J=7.7 Hz, 2H), 4.03 (t, J=7.7 Hz, 2H), 3.98 (s, 3H), 3.11 (m, 2H), 2.27 (p, J=7.7 Hz, 2H), 1.02 (d, J=7.7 Hz, 12H).

LCMS; m/z 466.4 (M+H)⁺ (ES⁺); 464.3 (M−H)⁻ (ES⁻).

Example 139: 3-(N-((1,2,3,5,6,7-Hexahydro-s-indacen-4-yl)carbamoyl) sulfamoyl)-N-isopropyl-1-methyl-1H-pyrazole-5-carboxamide

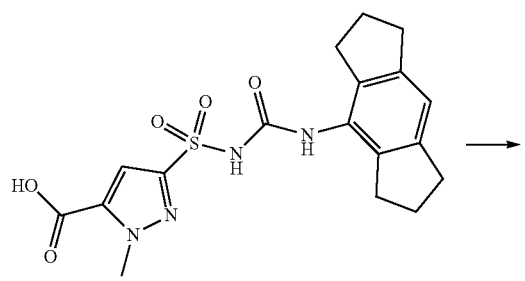

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((1,2,3,5,6,7-hexahydro-s-indacen-4-yl)carbamoyl) sulfamoyl)-1-methyl-H-pyrazole-5-carboxylic acid, disodium salt (Intermediate P53) and isopropylamine to afford the title compound (14 mg, 24%) as a white solid.

$^1$H NMR (DMSO-d₆) δ 10.94 (s, 1H), 8.50 (d, J=7.8 Hz, 1H), 8.02 (s, 1H), 7.46 (s, 1H), 6.94 (s, 1H), 4.13 (s, 3H), 4.09-3.98 (m, 1H), 2.79 (t, J=7.4 Hz, 4H), 2.60 (t, J=7.4 Hz, 4H), 1.98-1.91 (m, 4H), 1.14 (d, J=6.6 Hz, 6H).

LCMS; m/z 446 (M+H)⁺ (ES⁺).

Example 140: 3-(N-((4-Fluoro-2,6-diisopropylphenyl)carbamoyl) sulfamoyl)-N-isopropyl-N,1-dimethyl-1H-pyrazole-5-carboxamide

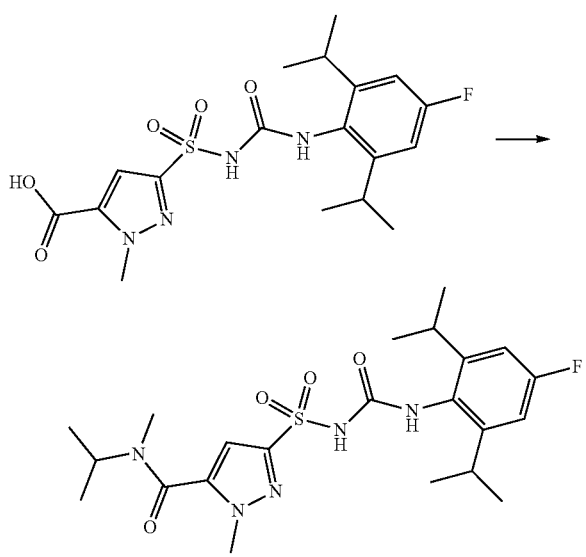

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((4-fluoro-2,6-diisopropylphenyl) carbamoyl)sulfamoyl)-1-methyl-1H-pyrazole-5-carboxylic acid, disodium salt (Intermediate P55) and N—methylpropan-2-amine to afford the title compound (33 mg, 45%) as a white solid.

$^1$H NMR (DMSO-d₆), rotamers; δ11.18 (bs, 1H), 7.82 (s, 1H), 6.92 & 6.80 (2×s, 1H), 6.90 (d, J=10.0 Hz, 2H), 4.67 & 3.96 (2×m, 1H), 3.89 & 3.87 (2×s, 3H), 2.99 (m, 2H), 2.85 & 2.82 (2×s, 3H), 1.14 (d, J=6.7 Hz, 6H), 1.04 (bs, 12H).

LCMS; m/z 482.4 (M+H)⁺ (ES⁺); 480.3 (M−H)⁻ (ES⁻).

Example 141: N,N-Diethyl-3-(N-((4-fluoro-2,6-diisopropylphenyl) carbamoyl)sulfamoyl)-1-methyl-1H-pyrazole-5-carboxamide, Sodium Salt

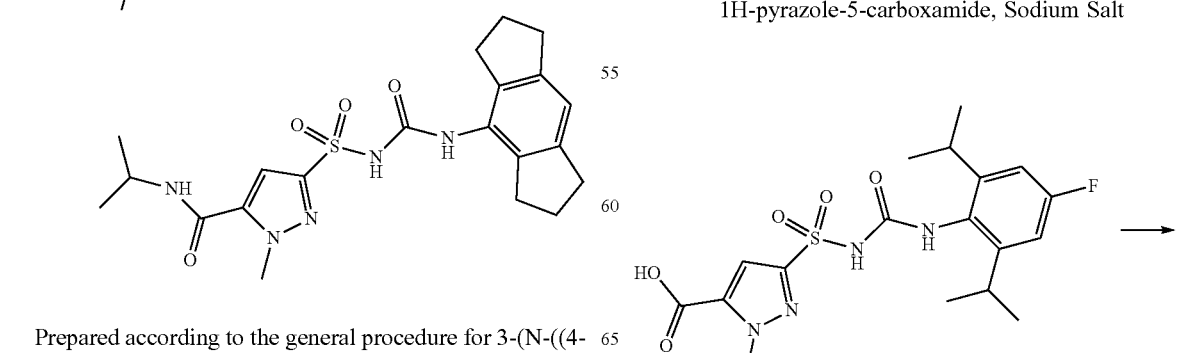

-continued

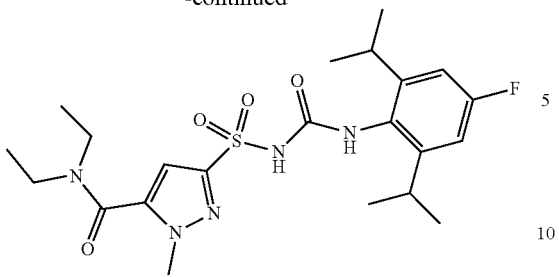

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((4-fluoro-2,6-diisopropylphenyl) carbamoyl)sulfamoyl)-1-methyl-1H-pyrazole-5-carboxylic acid, disodium salt (Intermediate P55) and diethylamine to afford the title compound (26 mg, 34%) as a white solid.

$^1$H NMR (DMSO-d$_6$), rotamers; δ 7.35 (s, 1H), 6.79 (d, J=10.0 Hz, 2H), 6.51 (s, 1H), 3.77 (s, 3H), 3.50-3.28 (m, 4H), 3.14 (m, 2H), 1.12 (bs, 6H), 1.03 (d, J=6.8 Hz, 12H).

LCMS; m/z 482.4 (M+H)$^+$ (ES$^+$); 480.4 (M−H)$^-$ (ES$^-$).

Example 142: N-Ethyl-3-(N-((4-fluoro-2,6-diisopropylphenyl)carbamoyl) sulfamoyl)-N,1-dimethyl-1H-pyrazole-5-carboxamide, Sodium Salt

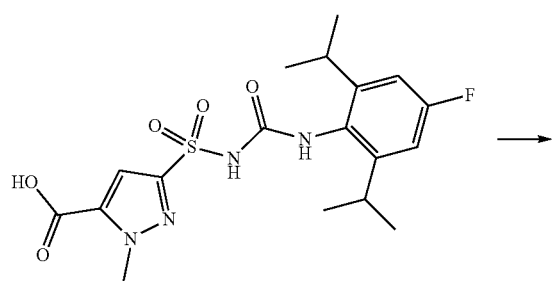

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((4-fluoro-2,6-diisopropylphenyl) carbamoyl)sulfamoyl)-1-methyl-1H-pyrazole-5-carboxylic acid, disodium salt (Intermediate P55) and N—methylethanamine to afford the title compound (24 mg, 33%) as a white solid.

$^1$H NMR (DMSO-d$_6$), rotamers; δ 7.34 (s, 1H), 6.79 (d, J=10.1 Hz, 2H), 6.58 & 6.52 (2×s, 1H), 3.80 (s, 3H), 3.52-3.35 (m, 2H), 3.14 (m, 2H), 3.0 & 2.96 (2×s, 3H), 1.12 (t, J=7.1 Hz, 3H), 1.03 (d, J=6.9 Hz, 12H).

LCMS; m/z 468.4 (M+H)$^+$ (ES$^+$); 466.3 (M−H)$^-$ (ES$^-$).

Example 14-: 3-(N-((4-Fluoro-2,6-diisopropylphenyl)carbamoyl) sulfamoyl)-N,1-dimethyl-1H-pyrazole-5-carboxamide

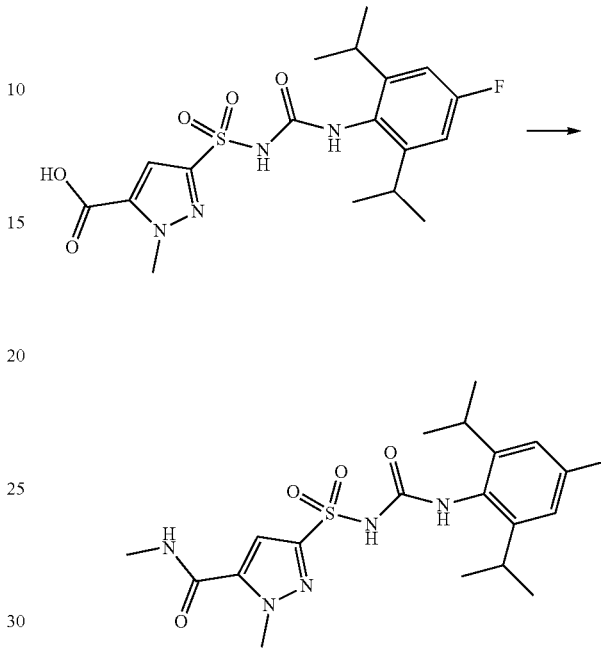

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((4-fluoro-2,6-diisopropylphenyl) carbamoyl)sulfamoyl)-1-methyl-1H-pyrazole-5-carboxylic acid, disodium salt (Intermediate P55) and methylamine to afford the title compound (26 mg, 39%) as a white solid.

$^1$H NMR (DMSO-d$_6$) δ 11.16 (bs, 1H), 8.62 (q, J=4.6 Hz, 1H), 7.76 (s, 1H), 7.28 (s, 1H), 6.89 (d, J=10.0 Hz, 2H), 4.12 (s, 3H), 2.95 (sept, J=6.4 Hz, 2H), 2.74 (d, J=4.6 Hz, 3H), 1.02 (bs, 12H).

LCMS; m/z 440.4 (M+H)$^+$ (ES$^+$); 438.4 (M−H)$^-$ (ES$^-$).

Example 144: 5-(Azetidine-1-carbonyl)-N-((2,6-diisopropylphenyl) carbamoyl)-1-methyl-1H-pyrazole-3-sulfonamide

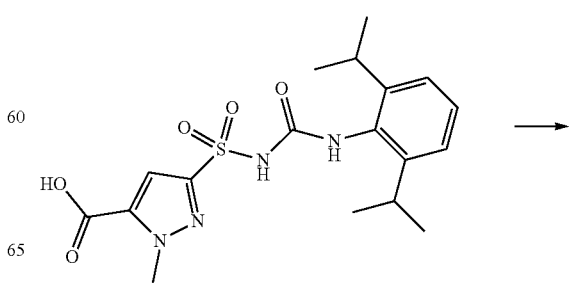

-continued

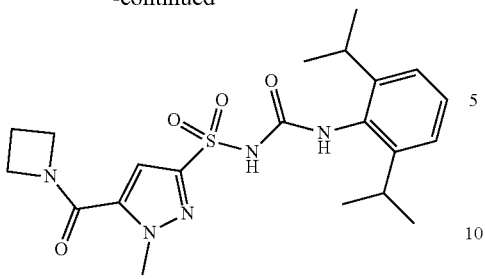

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((2,6-diisopropylphenyl)carbamoyl)sulfamoyl)-1-methyl-1H-pyrazole-5-carboxylic acid, disodium salt (Intermediate P54) and azetidine, HCl to afford the title compound (6 mg, 8%) as a white solid.

$^1$H NMR (DMSO-d$_6$) δ 7.38 (s, 1H), 7.11 (dd, J=8.4, 6.8 Hz, 1H), 7.06-6.99 (m, 2H), 6.71 (s, 1H), 4.29 (t, J=7.7 Hz, 2H), 4.07-3.97 (m, 5H), 3.12-3.08 (m, 2H), 2.31-2.22 (m, 2H), 1.04 (d, J=6.8 Hz, 12H). Acidic NH not observed.

LCMS; m/z 448 (M+H)$^+$ (ES$^+$).

Example 145: N-Cyclopropyl-3-(N-((1,2,3,5,6,7-hexahydro-s-indacen-4-yl)carbamoyl)sulfamoyl)-N,1-dimethyl-1H-pyrazole-5-carboxamide

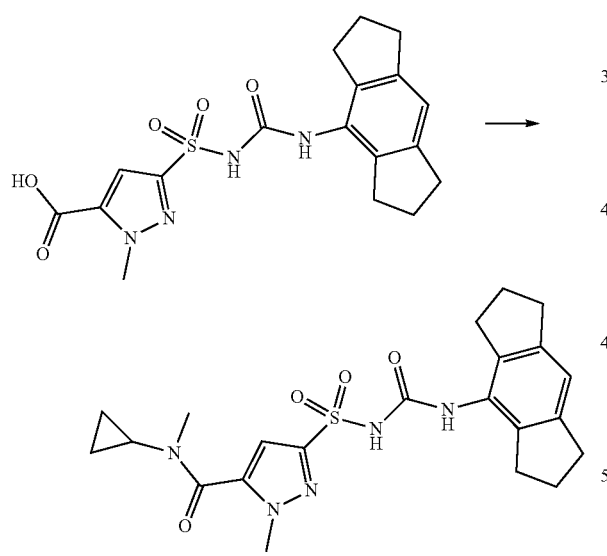

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and N-methylcyclopropanamine, HCl to afford the title compound (28 mg, 34%) as a white solid.

$^1$H NMR (DMSO-d$_6$) δ 10.90 (br s, 1H), 8.06 (s, 1H), 7.16 (br s, 1H), 6.95 (s, 1H), 3.94 (s, 3H), 2.99 (s, 3H), 2.79 (t, J=7.4 Hz, 4H), 2.59 (t, J=7.4 Hz, 4H), 1.99-1.91 (m, 4H), 0.60-0.50 (m, 4H). One exchangeable proton not observed.

LCMS; m/z 458 (M+H)$^+$ (ES$^+$).

Example 146: N-(Cyanomethyl)-3-(N-((1,2,3,5,6,7-hexahydro-s-indacen-4-yl)carbamoyl)sulfamoyl)-N,1-dimethyl-1H-pyrazole-5-carboxamide, Partial ammonium Salt

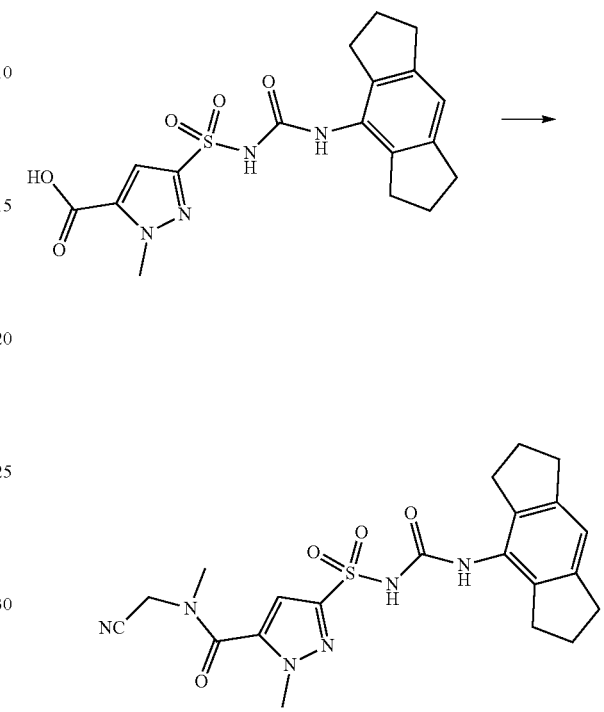

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and 2-(methylamino)acetonitrile, HCl to afford the title compound (33 mg, 46%) as a white solid.

$^1$H NMR (DMSO-d$_6$) δ 7.75 (s, 1H), 6.91 (s, 1H), 6.84 (s, 1H), 4.58 (s, 2H), 3.90 (s, 3H), 3.14 (s, 3H), 2.77 (t, J=7.4 Hz, 4H), 2.63 (t, J=7.4 Hz, 4H), 1.92 (quin, J=7.4 Hz, 4H).

LCMS; m/z 457.4 (M+H)$^+$ (ES$^+$); 455.3 (M−H)$^−$ (ES$^−$).

Example 147: 5-(Azetidine-1-carbonyl)-N-((1,2,3,5,6,7-hexahydro-s-indacen-4-yl)carbamoyl)-1-methyl-1H-pyrazole-3-sulfonamide

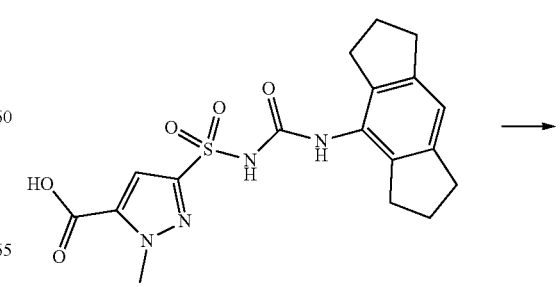

-continued

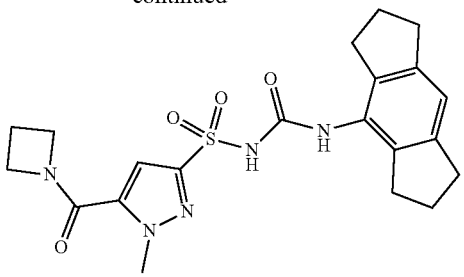

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and azetidine, HCl to afford the title compound (40 mg, 55%) as a white solid.

$^1$H NMR (DMSO-d$_6$) δ 10.93 (bs, 1H), 8.09 (s, 1H), 7.06 (s, 1H), 6.95 (s, 1H), 4.34 (t, J=7.7 Hz, 2H), 4.08 (s, 3H), 4.05 (t, J=7.7 Hz, 2H), 2.79 (t, J=7.4 Hz, 4H), 2.60 (t, J=7.3 Hz, 4H), 2.33-2.20 (m, 2H), 1.95 (quin, J=7.4 Hz, 4H).

LCMS; m/z 444.5 (M+H)$^+$ (ES$^+$); 442.3 (M–H)$^-$ (ES$^-$).

Example 148: 3-(N-((2,6-Diisopropylphenyl)carbamoyl)sulfamoyl)-N,1-dimethyl-1H-pyrazole-5-carboxamide

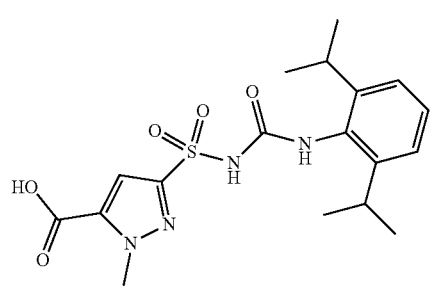

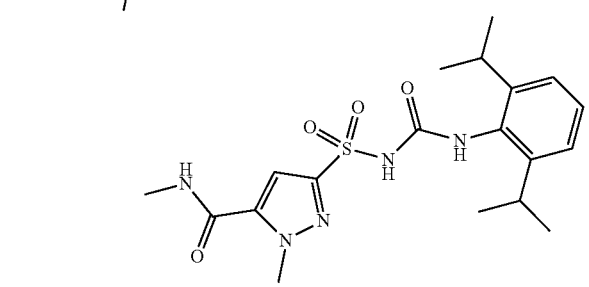

Methylamine in THF (108 μL, 0.217 mmol) and HATU (82 mg, 0.217 mmol) were successively added to a solution of 3-(N-((2,6-diisopropylphenyl)carbamoyl) sulfamoyl)-1-methyl-1H-pyrazole-5-carboxylic acid, disodium salt (Intermediate P54) (70 mg, 0.155 mmol) in DMF (1 mL) and stirred for 20 hours. The reaction was quenched with water (0.1 mL) and purified by reversed phase prep-HPLC (General Methods, basic prep) to afford the title compound (26 mg, 40%) as a white solid.

$^1$H NMR (DMSO-d$_6$) δ 11.07 (bs, 1H), 8.62 (d, J=5.1 Hz, 1H), 7.74 (s, 1H), 7.28 (s, 1H), 7.21 (t, J=7.7 Hz, 1H), 7.09 (d, J=7.7 Hz, 2H), 4.13 (s, 3H), 2.96 (m, 2H), 2.73 (d, J=4.5 Hz, 3H), 1.06-1.00 (m, 12H).

LCMS; m/z 422.4 (M+H)$^+$ (ES$^+$); 420.4 (M–H)$^-$ (ES$^-$).

Example 149: 3-(N-((2,6-Diisopropylphenyl)carbamoyl)sulfamoyl)-N-ethyl-N,1-dimethyl-1H-pyrazole-5-carboxamide

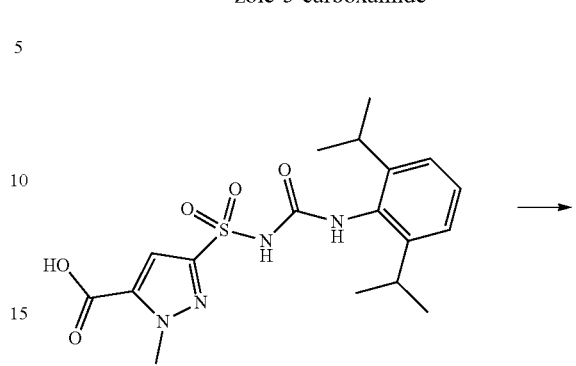

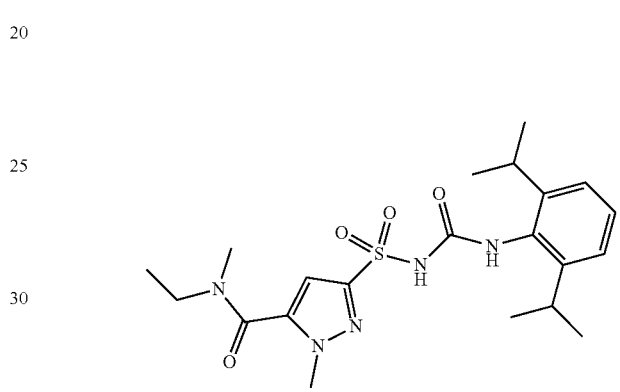

Prepared according to the general procedure for 3-(N-((2,6-diisopropylphenyl) carbamoyl) sulfamoyl)-N,1-dimethyl-1H-pyrazole-5-carboxamide (Example 148) from 3-(N-((2,6-diisopropylphenyl)carbamoyl)sulfamoyl)-1-methyl-1H-pyrazole-5-carboxylic acid, disodium salt (Intermediate P54) and N-methylethanamine to afford the title (10 mg, 14%) as a white solid.

$^1$H NMR (DMSO-d$_6$), rotamers; δ 11.09 (bs, 1H), 7.81 (s, 1H), 7.23 (t, J=7.7 Hz, 1H), 7.11 (d, J=7.6 Hz, 2H), 6.96 & 6.87 (2×s, 1H), 3.92 & 3.90 (2×s, 3H), 3.46 & 3.31 (2×q, J=7.1 Hz, 2H), 2.98 (brs, 5H), 1.16-1.0 (m, 15H).

LCMS; m/z 450.5 (M+H)$^+$ (ES$^+$); 448.4 (M–H)$^-$ (ES$^-$).

Example 150: 3-(N-((2,6-Diisopropylphenyl)carbamoyl)sulfamoyl)-N,N— diethyl-1-methyl-1H-pyrazole-5-carboxamide

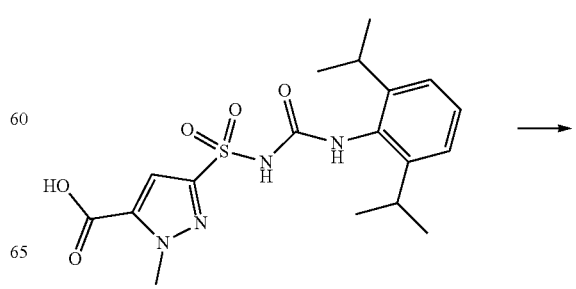

-continued

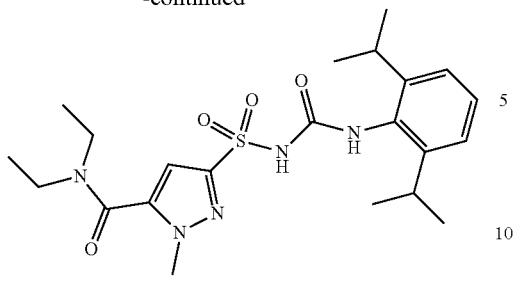

Prepared according to the general procedure for 3-(N-((2,6-diisopropylphenyl) carbamoyl)sulfamoyl)-N,1-dimethyl-1H-pyrazole-5-carboxamide (Example 148) from 3-(N-((2,6-diisopropylphenyl)carbamoyl)sulfamoyl)-1-methyl-1H-pyrazole-5-carboxylic acid, disodium salt (Intermediate P54) and diethylamine to afford the title compound (33 mg, 45%) as a white solid.

$^1$H NMR (DMSO-d$_6$), rotamers; δ 11.09 (bs, 1H), 7.83 (s, 1H), 7.23 (t, J=7.7 Hz, 1H), 7.11 (d, J=7.7 Hz, 2H), 6.87 (s, 1H), 3.88 (s, 3H), 3.45 (m, 2H), 3.31 (m, 2H), 2.98 (sept, J=6.8 Hz, 2H), 1.20-0.95 (m, 18H).

LCMS; m/z 464.5 (M+H)$^+$ (ES$^+$); 462.4 (M–H)$^-$ (ES$^-$).

Example 151: 3-(N-((2,6-Diisopropylphenyl)carbamoyl)sulfamoyl)-N—isopropyl-N,1-dimethyl-1H-pyrazole-5-carboxamide

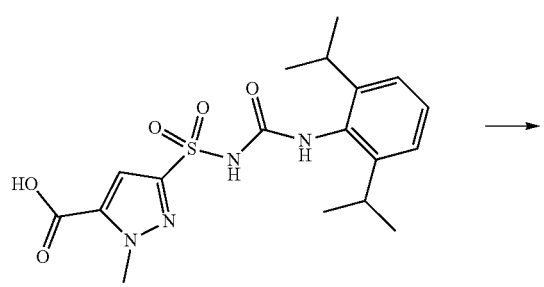

Prepared according to the general procedure for 3-(N-((2,6-diisopropylphenyl) carbamoyl)sulfamoyl)-N,1-dimethyl-1H-pyrazole-5-carboxamide (Example 148) from 3-(N-((2,6-diisopropylphenyl)carbamoyl)sulfamoyl)-1-methyl-1H-pyrazole-5-carboxylic acid, disodium salt (Intermediate P54) and N-methylpropan-2-amine to afford the title compound (47 mg, 58%) as a white solid.

$^1$H NMR (DMSO-d$_6$), rotamers; δ 11.13 (br s, 1H), 7.91 (s, 1H), 7.30-7.19 (m, 1H), 7.12 (d, J=7.7 Hz, 2H), 7.02 (s, o5H), 6.90 (s, o5H), 4.74-4.57 (m, 1H), 3.92-3.78 (m, 3H), 2.95-2.93 (m, 2H), 2.85-2.82 (m, 3H), 1.11-1.08 (m, 18H).

LCMS; m/z 464 (M+H)$^+$ (ES$^+$).

Example 152: N-((1,2,3,5,6,7-Hexahydro-s-indacen-4-yl)carbamoyl)-1-methyl-5-(pyrrolidine-1-carbonyl)-1H-pyrazole-3-sulfonamide

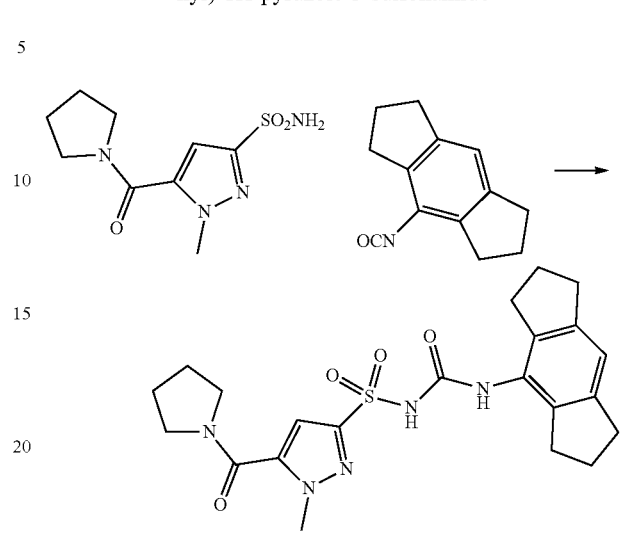

Prepared according to the general procedure for 5-(azetidine-1-carbonyl)-N-((4-fluoro-2,6-diisopropylphenyl) carbamoyl)-1-isopropyl-1H-pyrazole-3-sulfonamide (Example 123) from 1-methyl-5-(pyrrolidine-1-carbonyl)-1H-pyrazole-3-sulfonamide (Intermediate P52) and 4-isocyanato-1,2,3,5,6,7-hexahydro-s-indacene (Intermediate A1). The crude product was purified by chromatography on RP Flash C18 (13 g column, 0-50% MeCN/10 mM ammonium bicarbonate) to afford the title compound (25 mg, 28%) as a white solid.

$^1$H NMR (DMSO-d$_6$), rotamers; δ 10.9 (br s, 1H), 7.99 (s, 1H), 7.06 (s, 1H), 6.91 (s, 1H), 3.98 (s, 3H), 3.52 and 3.47 (2×t, J=6.2 Hz, 4H), 2.78 (t, J=7.4 Hz, 4H), 2.61 (t, J=7.4 Hz, 4H), 2.02-1.75 (m, 8H).

LCMS; m/z 458 (M+H)$^+$ (ES$^+$).

Example 153: 3-(N-((4-Fluoro-2,6-diisopropylphenyl)carbamoyl) sulfamoyl)-N,N,1-trimethyl-1H-pyrazole-5-carboxamide, Sodium Salt

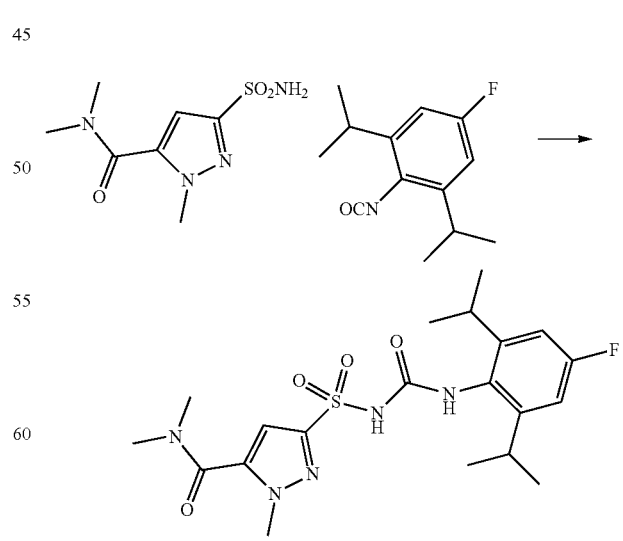

Prepared according to the general procedure for 5-(azetidine-1-carbonyl)-N-((4-fluoro-2,6-diisopropylphenyl) carbamoyl)-1-isopropyl-1H-pyrazole-3-sulfonamide (Example 123) from N,N,1-trimethyl-3-sulfamoyl-1H-pyrazole-5-carboxamide (Intermediate P50) and 5-fluoro-2-isocyanato-1,3-diisopropylbenzene (Intermediate A2) to afford the title compound (55 mg, 67%) as a white solid.

$^1$H NMR (DMSO-d$_6$), rotamers; δ 7.35 (s, 1H), 6.79 (d, J=10.1 Hz, 2H), 6.59 (s, 1H), 3.81 (s, 3H), 3.18-3.07 (m, 2H), 3.03 (s, 3H), 2.98 (s, 3H), 1.02 (d, J=6.9 Hz, 12H).

LCMS; m/z 454 (M+H)$^+$ (ES$^+$).

Example 154: 5-(3-Fluoroazetidine-1-carbonyl)-N-((1,2,3,5,6,7-hexahydro-s-indacen-4-yl)carbamoyl)-1-methyl-1H-pyrazole-3-sulfonamide, Partial ammonium Salt

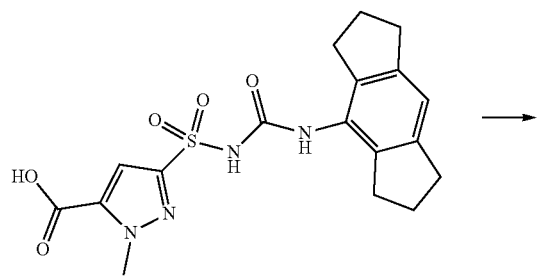

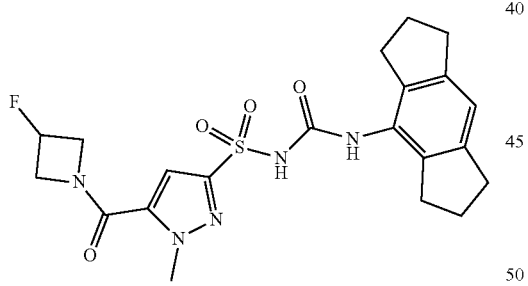

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and 3-fluoroazetidine, HCl to afford the title compound (36 mg, 50%) as a white solid.

$^1$H NMR (DMSO-d$_6$), rotamers; δ 7.74 (s, 1H), 6.87 (s, 1H), 6.78 (s, 1H), 5.45-5.26 (m, 1H), 4.61-4.47 (m, 1H), 4.44-4.22 (m, 2H), 4.08-3.95 (m, 1H), 3.95 (s, 3H), 2.70 (t, J=7.4 Hz, 4H), 2.55 (t, J=7.4 Hz, 4H), 1.85 (quin, J=7.5 Hz, 4H).

LCMS; m/z 462.4 (M+H)$^+$ (ES$^+$); 460.4 (M–H)$^-$ (ES$^-$).

Example 155: N-Ethyl-3-(N-((1,2,3,5,6,7-hexahydro-s-indacen-4-yl) carbamoyl)sulfamoyl)-N,1-dimethyl-1H-pyrazole-5-carboxamide

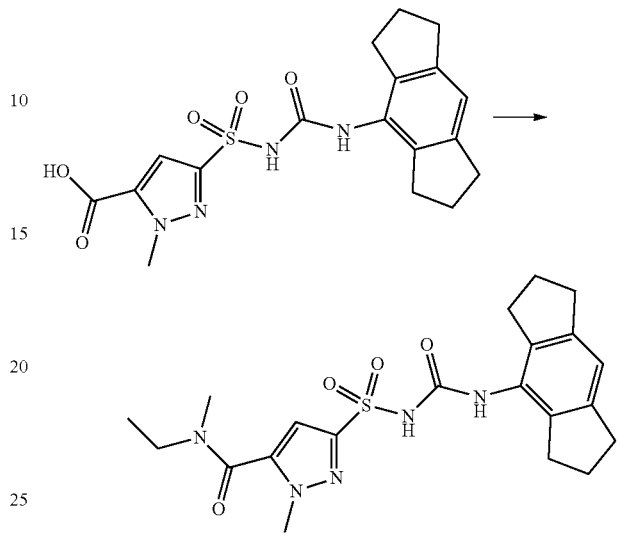

Prepared according to the general procedure for 5-(azetidine-1-carbonyl)-N-((4-fluoro-2,6-diisopropylphenyl) carbamoyl)-1-methyl-1H-pyrazole-3-sulfonamide, sodium salt (Example 138) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and N-methylethanamine to afford the title (31 mg, 44%) as a white solid.

$^1$H NMR (DMSO-d$_6$), rotamers; δ 10.98 (s, 1H), 8.00 (s, 1H), 6.96-6.87 (m, 2H), 3.90 & 3.88 (2×s, 3H), 3.47 and 3.33 (2×q, J=7.0 Hz, 2H), 3.00 and 2.97 (2×s, 3H), 2.78 (t, J=7.4 Hz, 4H), 2.60 (t, J=7.4 Hz, 4H), 1.94 (p, J=7.4 Hz, 4H), 1.15-1.08 (m, 3H).

LCMS; m/z 446.4 (M+H)$^+$ (ES$^+$); 444.4 (M–H)$^-$ (ES$^-$).

Example 156: N-((2,6-Diisopropylphenyl)carbamoyl)-1-methyl-5-(pyrrolidine-1-carbonyl)-1H-pyrazole-3-sulfonamide Prepared according to the general procedure for 5-(azetidine-1-carbonyl)-N-((4-fluoro-2,6-diisopropylphenyl)carbamoyl)-1-isopropyl-1H-pyrazole-3-sulfonamide (Example 123) from 1-methyl-5-(pyrrolidine-1-carbonyl)-1H-pyrazole-3-sulfonamide (Intermediate P52) and 2-isocyanato-1,3-diisopropylbenzene (Intermediate A19). The crude product was purified by chromatography on RP Flash C18 (12 g column, 5-50% MeCN/10 mM ammonium bicarbonate) to afford the title compound (40 mg, 43%) as a colourless solid.

$^1$H NMR (DMSO-d$_6$), rotamers; δ 11.11 (s, 1H), 7.89 (s, 1H), 7.30-7.18 (m, 1H), 7.16-7.07 (m, 3H), 4.01 (s, 3H), 3.57-3.40 (m, 4H), 3.03-2.85 (m, 2H), 1.91-1.78 (m, 4H), 1.04 (br s, 12H).

LCMS; m/z 462.5 (M+H)$^+$ (ES$^+$).

Example 157: 3-(N-((1,2,3,5,6,7-Hexahydro-s-indacen-4-yl)carbamoyl) sulfamoyl)-N-isopropyl-N,1-dimethyl-1H-pyrazole-5-carboxamide

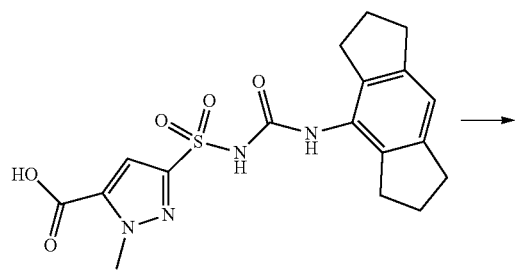

Prepared according to the general procedure for 3-(N-((4-chloro-2,6-diisopropylphenyl)carbamoyl)sulfamoyl)-N,1-dimethyl-1H-pyrazole-5-carboxamide (Example 125) from 3-(N-((1,2,3,5,6,7-hexahydro-s-indacen-4-yl)carbamoyl) sulfamoyl)-1-methyl-1H-pyrazole-5-carboxylic acid (Intermediate P51) and N— methylpropan-2-amine to afford the title compound (25 mg, 42%) as a white solid.

$^1$H NMR (DMSO-d$_6$), rotamers; δ 7.74 (s, 1H), 6.85 (s, 1H), 6.78 & 6.67 (2×s, 1H), 4.68 & 4.03 (s, 1H), 3.83 (s, 3H), 2.85 (s, 3H), 2.77 (t, J=7.4 Hz, 4H), 2.63 (t, J=7.4 Hz, 4H), 1.92 (quin, J=7.4 Hz, 4H), 1.15 (d, J=6.7 Hz, 6H). Acidic proton not observed.

LCMS; m/z 460.5 (M+H)$^+$ (ES$^+$); 458.3 (M–H)$^-$ (ES$^-$).

Example 158: N,N-diethyl-3-(N-((1,2,3,5,6,7-Hexahydro-s-indacen-4-yl) carbamoyl)sulfamoyl)-1-methyl-1H-pyrazole-5-carboxamide

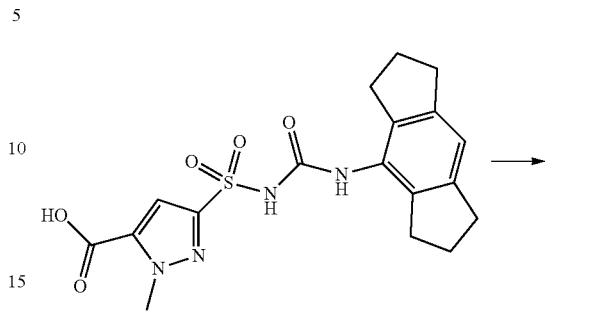

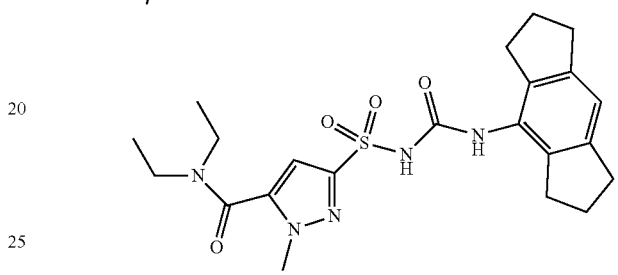

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((1,2,3,5,6,7-hexahydro-s-indacen-4-yl)carbamoyl) sulfamoyl)-1-methyl-H-pyrazole-5-carboxylic acid (Intermediate P51) and diethylamine to afford the title compound (35 mg, 8%) as a white solid.

$^1$H NMR (DMSO-d$_6$), rotamers; δ 10.96 (s, 1H), 7.92 (s, 1H), 6.90 (s, 1H), 6.83 (s, 1H), 3.86 (s, 3H), 3.45 & 3.30 (2×m, 4H), 2.78 (t, J=7.3 Hz, 4H), 2.61 (t, J=7.4 Hz, 4H), 1.94 (quin, J=7.4 Hz, 4H), 1.18-1.05 (m, 6H).

LCMS; m/z 460.5 (M+H)$^+$ (ES$^+$); 458.4 (M–H)$^-$ (ES$^-$).

Example 159: 3-(N-((1,2,3,5,6,7-Hexahydro-s-indacen-4-yl)carbamoyl) sulfamoyl)-N,1-dimethyl-1H-pyrazole-5-carboxamide

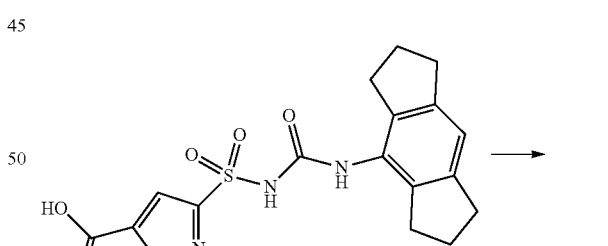

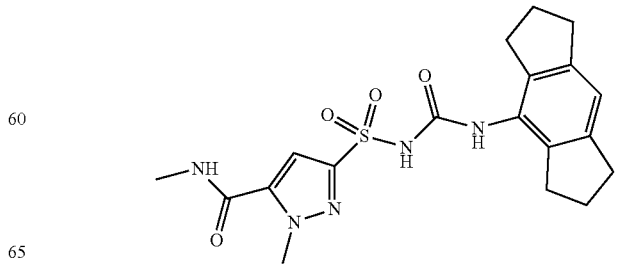

Prepared according to the general procedure for 3-(N-((4-chloro-2,6-diisopropylphenyl) carbamoyl)sulfamoyl)-N,1-dimethyl-1H-pyrazole-5-carboxamide (Example 125) from 3-(N-((1,2,3,5,6,7-hexahydro-s-indacen-4-yl)carbamoyl) sulfamoyl)-1-methyl-1H-pyrazole-5-carboxylic acid (Intermediate P51) and methylamine to afford the title compound (18 mg, 35%) as a white solid.

$^1$H NMR (DMSO-d$_6$) δ 10.88 (s, 1H), 8.61 (q, J=4.6 Hz, 1H), 7.97 (s, 1H), 7.28 (s, 1H), 6.87 (s, 1H), 4.07 (s, 3H), 2.71 (t, J=7.4 Hz, 4H), 2.67 (d, J=4.6 Hz, 3H), 2.52 (t, J=7.4 Hz, 4H), 1.87 (quin, J=7.5 Hz, 4H).

LCMS; m/z 418.4 (M+H)$^+$ (ES$^+$); 416.3 (M–H)$^−$ (ES$^−$).

Example 160: 3-(N-((2,6-Diisopropylphenyl)carbamoyl)sulfamoyl)-N,N,1-trimethyl-1H-pyrazole-5-carboxamide, Sodium Salt

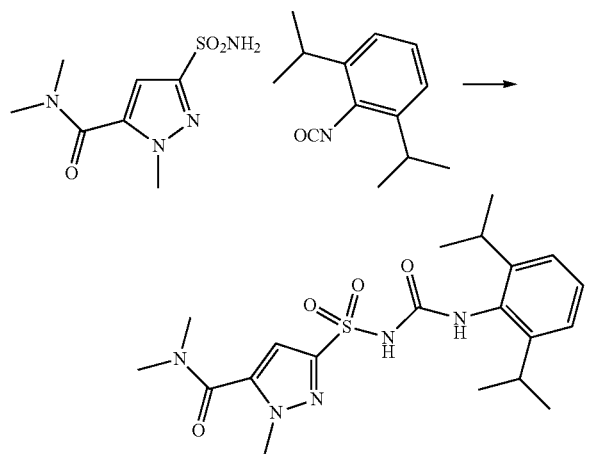

N,N,1-Trimethyl-3-sulfamoyl-1H-pyrazole-5-carboxamide (Intermediate P50) (105 mg, 0.452 mmol) was dissolved in THF (5 mL) and 2 M sodium tert-butoxide in THF (0.237 mL, 0.475 mmol) added. After 1 hour, 2-isocyanato-1,3-diisopropylbenzene (Intermediate A19) (92 mg, 0.452 mmol) was added and the mixture stirred at room temperature for 15 hours. The suspension was filtered and washed with THF (1 mL). The collected solid was triturated with EtOAc (5 mL) for 1 hour, filtered, and dried under vacuum to afford the title compound (137 mg, 64%) as a white solid.

$^1$H NMR (DMSO-d$_6$), rotamers; δ 7.37 (br s, 1H), 7.14-7.05 (m, 1H), 7.01 (d, J=7.5 Hz, 2H), 6.61 (s, 1H), 3.81 (s, 3H), 3.15-3.13 (m, 2H), 3.03 (s, 3H), 2.99 (s, 3H), 1.03 (d, J=6.8 Hz, 12H).

LCMS; m/z 436 (M+H)$^+$ (ES$^+$).

Example 161: 3-(N-((4-Chloro-2,6-diisopropylphenyl)carbamoyl) sulfamoyl)-N,N,1-trimethyl-1H-pyrazole-5-carboxamide

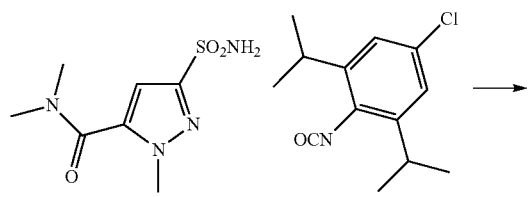

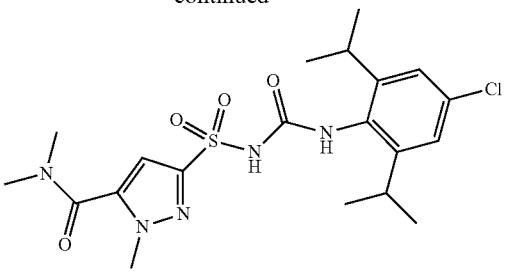

4-Chloro-2,6-diisopropylaniline, HCl (51.9 mg, 0.209 mmol) and triethylamine (0.064 ml, 0.460 mmol) were dissolved in dry THF (5 mL). Triphosgene (49.6 mg, 0.167 mmol) was added to the mixture at room temperature and stirred for 5 hours. The mixture was concentrated in vacuo and dried azeotropically with toluene (1 mL×3). Dry THF (2 mL) was added to the residue and N,N,1-trimethyl-3-sulfamoyl-1H-pyrazole-5-carboxamide (Intermediate P50) (48.6 mg, 0.209 mmol) added to the mixture. After 30 minutes, 60% sodium hydride (20.91 mg, 0.523 mmol) was added and the mixture heated at 60° C. for 15 hours. After cooling to room temperature, saturated aqueous ammonium chloride (10 mL) was added and the mixture extracted with EtOAc (10 mL×3). The combined organic phases were washed with brine (5 mL), dried over MgSO$_4$, concentrated in vacuo and the residue purified by chromatography on silica gel (25 g column, 5-100% EtOAc/isohexane) to afford the title compound (17 mg, 17%) as a white solid.

$^1$H NMR (DMSO-d$_6$), rotamers; δ 11.24 (s, 1H), 7.98 (s, 1H), 7.14 (s, 2H), 7.01 (s, 1H), 3.93 (s, 3H), 3.00 (s, 3H), 2.99 (s, 3H), 2.98-2.91 (m, 2H), 1.17-0.93 (br d, 12H).

LCMS; m/z 469 and 471 (M+H)$^+$ (ES$^+$).

Example 162: 3-(N-((1,2,3,5,6,7-Hexahydro-s-indacen-4-yl)carbamoyl) sulfamoyl)-N,N,1-trimethyl-1H-pyrazole-5-carboxamide, Sodium Salt

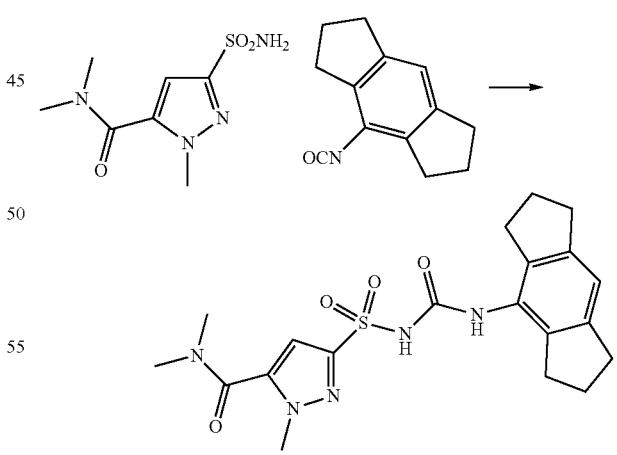

Prepared according to the general procedure for 3-(N-((2,6-diisopropylphenyl) carbamoyl)sulfamoyl)-N,N,1-trimethyl-1H-pyrazole-5-carboxamide, sodium salt (Example 160) from N,N,1-trimethyl-3-sulfamoyl-H-pyrazole-5-carboxamide (Intermediate P50) and 4-isocyanato-1,2,3,5,6,7-hexahydro-s-indacene (Intermediate A1) to afford the title compound (235 mg, 64%) as a white solid.

¹H NMR (DMSO-d₆), rotamers; δ 7.51 (s, 1H), 6.77 (s, 1H), 6.62 (s, 1H), 3.82 (s, 3H), 3.04 (s, 3H), 2.99 (s, 3H), 2.75 (t, J=7.4 Hz, 4H), 2.65 (t, J=7.4 Hz, 4H), 1.93-1.86 (m, 4H).

LCMS; m/z 432 (M+H)⁺ (ES⁺).

Example 163: 3-(N-((1,2,3,5,6,7-Hexahydro-s-indacen-4-yl)carbamoyl) sulfamoyl)-N,1-dimethyl-N-(thiazol-2-ylmethyl)-1H-pyrazole-5-carboxamide

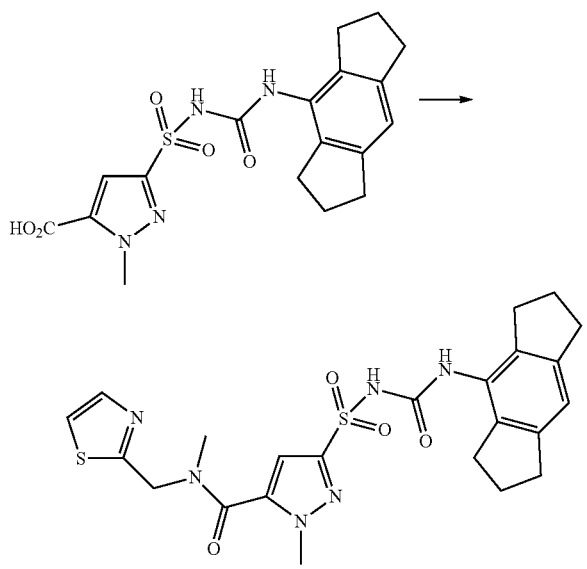

Prepared according to the general procedure of 3-(N-((2,6-diisopropylphenyl) carbamoyl)sulfamoyl)-N-(2-methoxyethyl)-N,1-dimethyl-1H-pyrazole-5-carboxamide (Example 108) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and N-methyl-1-(thiazol-2-yl)methanamine to afford the title compound (18 mg, 26%) as a white solid.

¹H NMR (DMSO-d₆), rotamers; 610.95 (br s, 1H), 8.09-8.07 (2×s, 1H), 7.89-7.65 (m, 2H), 7.11-7.08 (2×s, 1H), 6.94 (s, 1H), 4.97-4.92 (2×s, 2H), 3.97-3.95 (2×s, 3H), 3.12-3.01 (2×s, 3H), 2.78 (t, J=7.6 Hz, 4H), 2.64-2.53 (m, 4H), 1.94-1.92 (m, 4H).

LCMS; m/z 515 (M+H)⁺ (ES⁺).

Example 164: 3-(N-((1,2,3,5,6,7-Hexahydro-s-indacen-4-yl)carbamoyl) sulfamoyl)-N,1-dimethyl-N-((1-methyl-1H-imidazol-2-yl)methyl)-1H-pyrazole-5-carboxamide

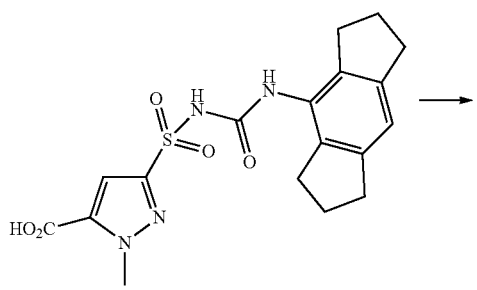

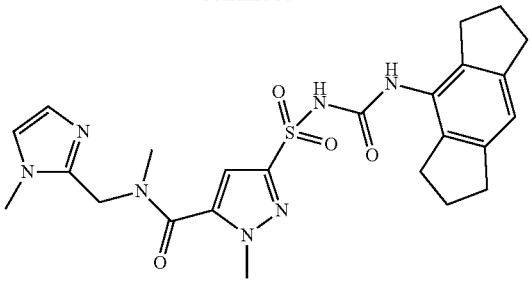

Prepared according to the general procedure of 3-(N-((2,6-diisopropylphenyl) carbamoyl)sulfamoyl)-N-(2-methoxyethyl)-N,1-dimethyl-1H-pyrazole-5-carboxamide (Example 108) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and N-methyl-1-(1-methyl-1H-imidazol-2-yl)methanamine to afford the title compound (11 mg, 14%) as a white solid.

¹H NMR (DMSO-d₆), rotamers; δ 7.71 (s, 1H), 7.20 (s, 0.4H), 7.14 (s, 0.6H), 7.05 (s, 0.6H), 6.93 (s, 0.4H), 6.85-6.83 (m, 2H), 4.73-4.17 (m, 2H), 3.89 (s, 3H), 3.64-3.45 (2×s, 3H), 2.98-2.94 (2×s, 3H), 2.76 (t, J=7.4 Hz, 4H), 2.63-2.59 (m, 4H), 1.94-1.87 (m, 4H). NH not observed.

LCMS; m/z 512 (M+H)⁺ (ES⁺).

Example 165: 3-(N-((1,2,3,5,6,7-Hexahydro-s-indacen-4-yl)carbamoyl) sulfamoyl)-N,1-dimethyl-N-(thiazol-2-yl)-1H-pyrazole-5-carboxamide

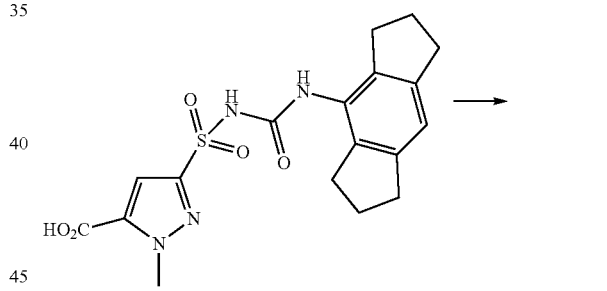

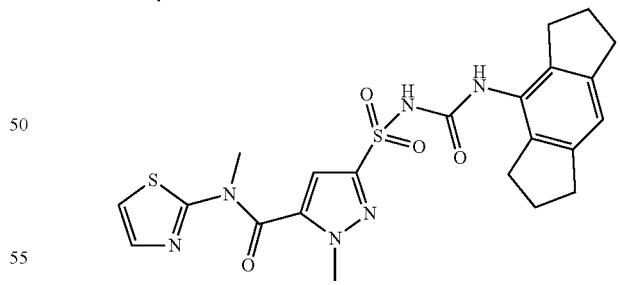

Prepared according to the general procedure of 3-(N-((2,6-diisopropylphenyl) carbamoyl)sulfamoyl)-N-(2-methoxyethyl)-N,1-dimethyl-1H-pyrazole-5-carboxamide (Example 108) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and N-methylthiazol-2-amine to afford the title compound (4 mg, 7%) as a white solid.

¹H NMR (DMSO-d₆) δ 11.03 (br s, 1H), 8.11 (br s, 1H), 7.66 (d, J=3.6 Hz, 1H), 7.45 (d, J=3.6 Hz, 1H), 7.38 (s, 1H), 6.95 (s, 1H), 4.05 (s, 3H), 3.72 (s, 3H), 2.79 (t, J=7.4 Hz, 4H), 2.61 (t, J=7.3 Hz, 4H), 1.99-1.92 (m, 4H).

LCMS; m/z 501 (M+H)+ (ES+).

Example 166: 3-(N-((1,2,3,5,6,7-Hexahydro-s-indacen-4-yl)carbamoyl) sulfamoyl)-N,1-dimethyl-N-((1-methyl-1H-pyrazol-5-yl)methyl)-1H-pyrazole-5-carboxamide, Partial ammonium Salt

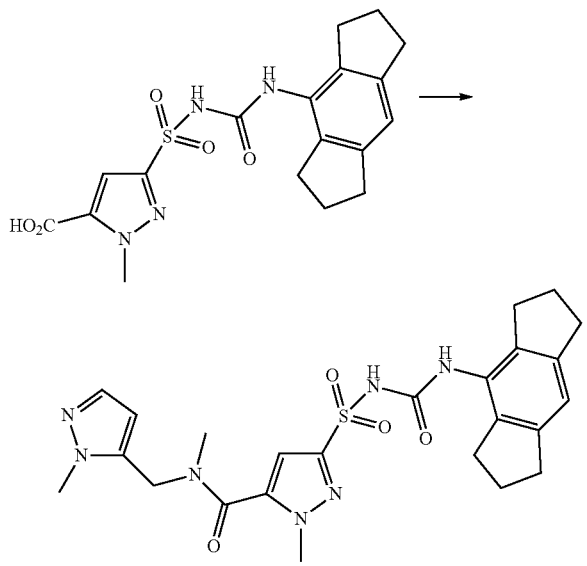

Prepared according to the general procedure of 3-(N-((1,2,3,5,6,7-hexahydro-s-indacen-4-yl)carbamoyl)sulfamoyl)-N-(3-hydroxypropyl)-N,1-dimethyl-1H-pyrazole-5-carboxamide, partial ammonium salt (Example 104) from 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) and N-methyl-1-(1-methyl-H-pyrazol-5-yl)methanamine to afford the title compound (14 mg, 17%) as a white solid.

$^1$H NMR (DMSO-$d_6$), rotamers; δ 7.65 & 7.58 (2×s, 1H), 7.50-7.00 (br s, 1H), 7.36 (d, J=1.9 Hz, 1H), 6.81 (s, 1H), 6.81 & 6.60 (2×s, 1H), 6.27 & 6.14 (2×s, 1H), 4.76 & 4.70 (2×s, 2H), 3.87 & 3.80 (2×s, 3H), 3.80 & 3.58 (2×s, 3H), 2.99 (s, 3H), 2.75 (t, J=7.4 Hz, 4H), 2.63 (t, J=7.5 Hz, 4H), 1.89 (p, J=7.5 Hz, 4H).

LCMS; m/z 512.4 (M+H)+ (ES+); 510.3 (M−H)− (ES−).

Example 167: 2-((Dimethylamino)methyl)-N-((1,2,3,5,6,7-hexahydro-s-indacen-4-yl)carbamoyl)-1-methyl-1H-imidazole-4-sulfonamide

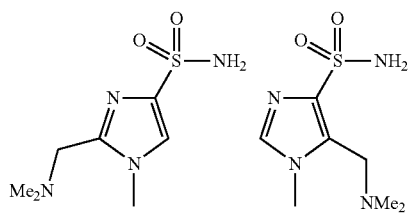

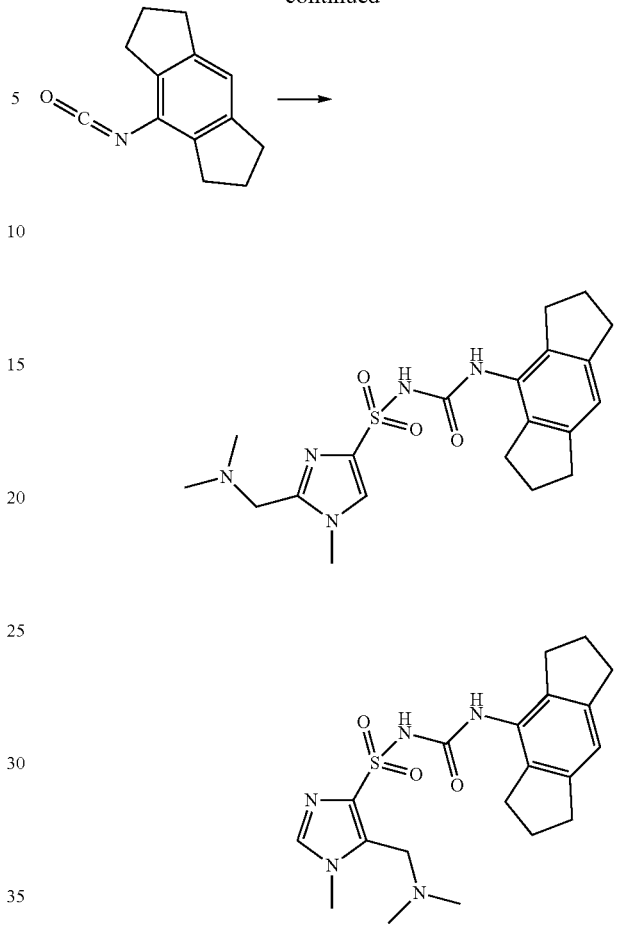

Sodium tert-butoxide, 2 M in THF (0.120 mL, 0.241 mmol) was added to a solution of a mixture of 2-((dimethylamino)methyl)-1-methyl-1H-imidazole-4-sulfonamide and 5-((dimethylamino)methyl)-1-methyl-1H-imidazole-4-sulfonamide (Intermediates P66 and P67) (50 mg, 0.229 mmol) in THF (1 mL) and stirred at room temperature for 1 hour. Then 4-isocyanato-1,2,3,5,6,7-hexahydro-s-indacene (Intermediate A1) (47.9 mg, 0.241 mmol) in THF (1 mL) was added and the reaction stirred at room temperature over the weekend. The reaction mixture was concentrated and the crude product was purified by chromatography (Companion apparatus, RP Flash C18, 12 g column, 5-50% MeCN/10 mM ammonium bicarbonate) to afford 2-((dimethylamino)methyl)-N-((1,2,3,5,6,7-hexahydro-s-indacen-4-yl)carbamoyl)-1-methyl-1H-imidazole-4-sulfonamide (Example 167) (44 mg, 46%) and 5-((dimethylamino)methyl)-N-((1,2,3,5,6,7-hexahydro-s-indacen-4-yl)carbamoyl)-1-methyl-1H-imidazole-4-sulfonamide (3 mg, 3%), both as colourless solids.

Example 167: $^1$H NMR (DMSO-$d_6$) δ 7.91 (s, 1H), 7.77 (s, 1H), 6.83 (s, 1H), 4.26 (s, 2H), 3.67 (s, 3H), 2.76 (t, J=7.4 Hz, 4H), 2.66-2.53 (m, 10H), 1.96-1.84 (m, 4H) (1 exchangeable NH not observed).

LCMS; m/z 418.3 (M+H)+ (ES+).

Example 168: 3-(N-((4-Chloro-2,6-diisopropylphenyl)carbamoyl) sulfamoyl)-N-(2-hydroxyethyl)-N,1-dimethyl-1H-pyrazole-5-carboxamide

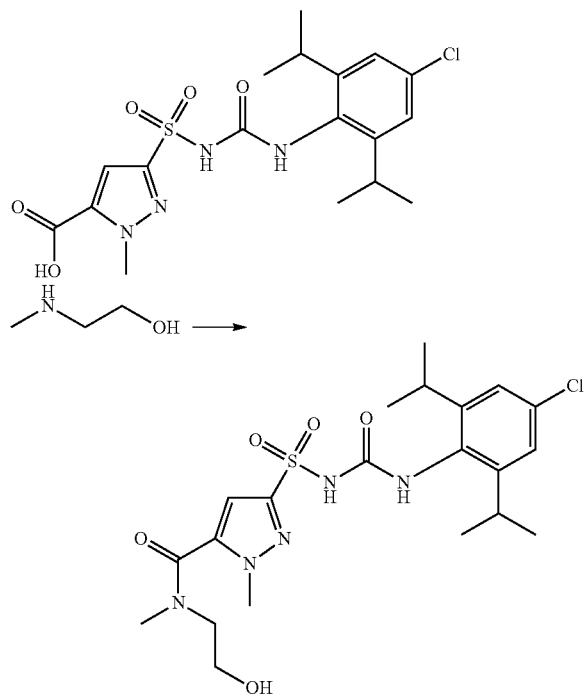

Prepared according to the general procedure for 3-(N-((4-chloro-2,6-diisopropylphenyl)carbamoyl)sulfamoyl)-N,1-dimethyl-1H-pyrazole-5-carboxamide (Example 125) from 3-(N-((4-chloro-2,6-diisopropylphenyl)carbamoyl)sulfamoyl)-1-methyl-1H-pyrazole-5-carboxylic acid, disodium salt (Intermediate P56) and 2-(methylamino)ethanol to afford the title compound (10 mg, 18%) as a white solid.

$^{1}$H NMR (DMSO-$d_6$), rotamers; δ 11.18 (s, 1H), 7.95 (s, 1H), 7.14 (s, 2H), 6.98 (s, 1H), 4.96-4.79 (m, 1H), 3.93-3.86 (m, 3H), 3.64-3.41 (m, 4H), 3.06-2.88 (m, 5H), 1.08 (br s, 12H).

LCMS; m/z 500.4/502.4 (M+H)$^+$ (ES$^+$).

Example 16A: 3-(N-((2,6-Diisopropylphenyl)carbamoyl)sulfamoyl)-N-(2-hydroxyethyl)-N,1-dimethyl-1H-pyrazole-5-carboxamide

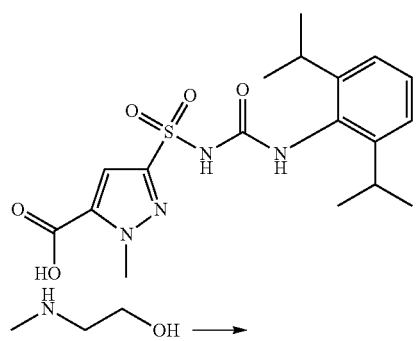

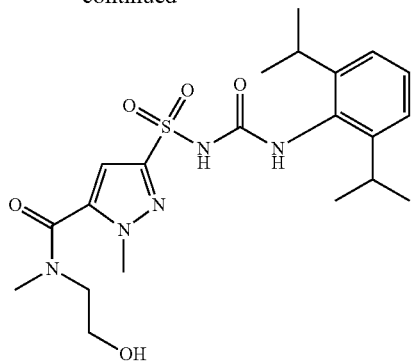

Prepared according to the general procedure for 3-(N-((2,6-diisopropylphenyl) carbamoyl)sulfamoyl)-N,1-dimethyl-1H-pyrazole-5-carboxamide (Example 148) from 3-(N-((2,6-diisopropylphenyl)carbamoyl)sulfamoyl)-1-methyl-1H-pyrazole-5-carboxylic acid, disodium salt (Intermediate P54) and 2-(methylamino)ethanol to afford the title compound (8 mg, 11%) as a white solid.

$^{1}$H NMR (DMSO-$d_6$), rotamers; 611.07 (s, 1H), 7.88 (s, 1H), 7.25 (t, J=7.7 Hz, 1H), 7.12 (d, J=7.7 Hz, 2H), 7.02 & 7.0 (2×s, 1H), 4.96 & 4.81 (t, J=5.0 & 5.7 Hz, 1H), 3.94 & 3.89 (2×s, 3H), 3.59 & 3.40 (2×t, J=5.6 & 5.1 Hz, 2H), 3.50 (2×t, J=5.6 & 5.2 Hz, 2H), 3.03 & 2.98 (2×s, 3H), 2.95 (m, 2H), 1.06 (br s, 12H).

LCMS; m/z 466.5 (M+H)$^+$ (ES$^+$); 464.4 (M–H)$^-$ (ES$^-$).

Example 170: 3-(N-((1,2,3,5,6,7-Hexahydro-s-indacen-4-yl)carbamoyl) sulfamoyl)-N-(2-hydroxyethyl)-1-methyl-1H-pyrazole-5-carboxamide, Partial ammonium Salt

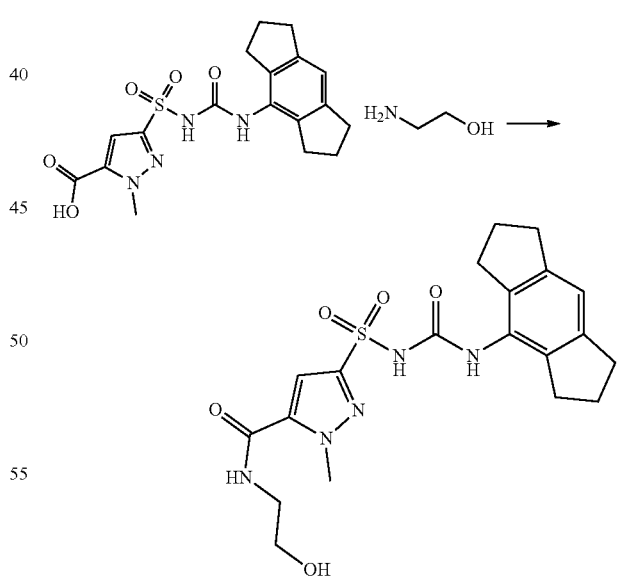

Prepared according to the general procedure for 3-(N-((2,6-diisopropylphenyl) carbamoyl)sulfamoyl)-N,1-dimethyl-1H-pyrazole-5-carboxamide (Example 148) from 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) and ethanolamine to afford the title compound (18 mg, 25%) as a white solid.

$^1$H NMR (DMSO-d$_6$) δ 8.61 (t, J=5.7 Hz, 1H), 7.84 (s, 1H), 7.32 (s, 1H), 6.88 (s, 1H), 4.73 (t, J=5.7 Hz, 1H), 4.10 (s, 3H), 3.48 (app q, J=6.0 Hz, 2H), 3.27 (app q, J=6.0 Hz, 2H), 2.78 (t, J=7.4 Hz, 4H), 2.60 (t, J=7.4 Hz, 4H), 1.93 (p, J=7.4 Hz, 4H). One exchangeable proton not seen.
LCMS; m/z 448.4 (M+H)$^+$ (ES$^+$); 446.4 (M–H)$^-$ (ES$^-$).

Example 171: 3-(N-((1,2,3,5,6,7-Hexahydro-s-indacen-4-yl)carbamoyl) sulfamoyl)-N-(2-methoxyethyl)-1-methyl-1H-pyrazole-5-carboxamide, Partial ammonium Salt

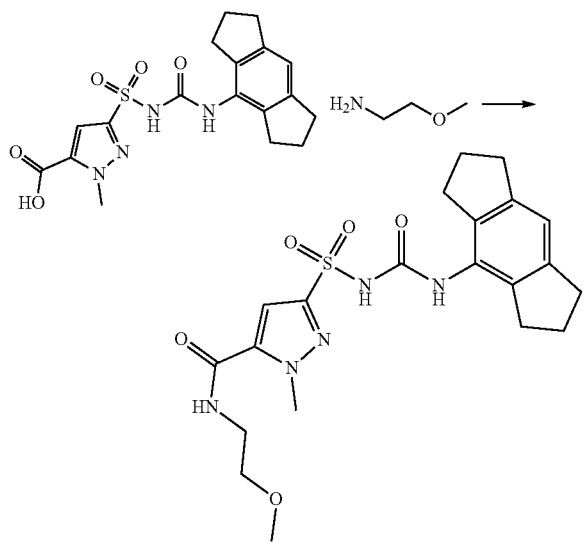

Prepared according to the general procedure for 3-(N-((2,6-diisopropylphenyl) carbamoyl)sulfamoyl)-N,1-dimethyl-1H-pyrazole-5-carboxamide (Example 148) from 3-(N-((1,2,3,5,6,7-hexahydro-s-indacen-4-yl)carbamoyl)sulfamoyl)-1-methyl-1H-pyrazole-5-carboxylic acid, disodium salt (Intermediate P53) and 2-methoxyethan-1-amine to afford the title compound (37 mg, 51%) as a colourless solid.

$^1$H NMR (DMSO-d$_6$) δ 10.93 (br s, 1H), 8.74 (t, J=5.5 Hz, 1H), 7.90 (s, 1H), 7.36 (s, 1H), 6.90 (s, 1H), 4.11 (s, 3H), 3.44 (t, J=5.5 Hz, 2H), 3.39 (t, J=5.5 Hz, 2H), 3.26 (s, 3H), 2.78 (t, J=7.4 Hz, 4H), 2.61 (t, J=7.3 Hz, 4H), 1.94 (p, J=7.5 Hz, 4H).
LCMS; m/z 462.4 (M+H)$^+$ (ES$^+$); 460.3 (M–H)$^-$ (ES$^-$).

Example 172: 3-(N-((1,2,3,5,6,7-Hexahydro-s-indacen-4-yl)carbamoyl) sulfamoyl)-N-(2-hydroxyethyl)-N,1-dimethyl-1H-pyrazole-5-carboxamide, Partial ammonium Salt

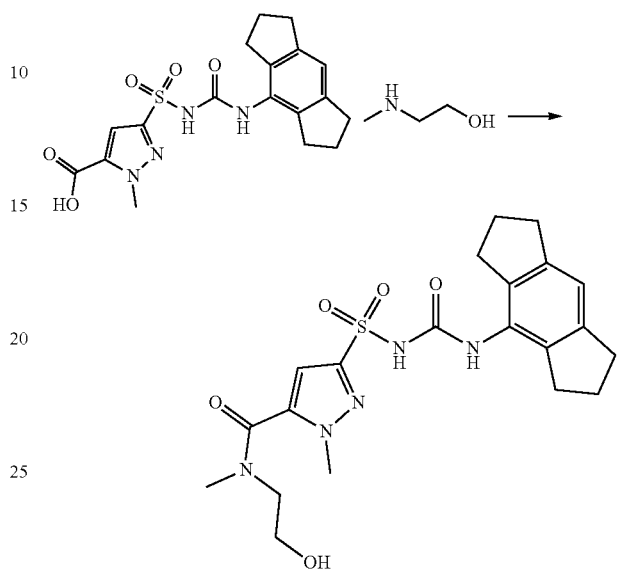

Prepared according to the general procedure for N-((2,6-diisopropylphenyl) carbamoyl)-1-methyl-5-(pyrrolidine-1-carbonyl)-1H-pyrazole-3-sulfonamide (Example 156) from 3-(N-((1,2,3,5,6,7-hexahydro-s-indacen-4-yl)carbamoyl) sulfamoyl)-1-methyl-1H-pyrazole-5-carboxylic acid, disodium salt (Intermediate P53) and 2-(methylamino)ethanol to afford the title compound (39 mg, 54%) as a white solid.

$^1$H NMR (DMSO-d$_6$), rotamers; δ 7.69 (s, 1H), 7.10 (s, 1H), 7.10 & 6.74 (2×s, 1H), 6.82 (s, 1H), 4.96 & 4.84 (2×t, J=5.5 Hz, 1H), 3.84 & 3.80 (2×s, 3H), 3.59 (m, 1H), 3.55-3.41 (m, 3H), 3.06 & 2.97 (2×s, 3H), 2.76 (t, J=7.4 Hz, 4H), 2.64 (t, J=7.5 Hz, 4H), 1.92 (p, J=7.5 Hz, 4H).
LCMS; m/z 462.42 (M+H)$^+$ (ES$^+$); 460.30 (M–H)$^-$ (ES$^-$).

The compound of example 173 was synthesised by methods analogous to those outlined above and below.

TABLE 1

| | $^1$H NMR and MS data | | | |
|---|---|---|---|---|
| Ex | Structure and Name | $^1$H NMR spectrum | MS | MW |
| 173 | N-((5-(3-Cyanophenyl)-2,3-dihydro-1H-inden-4-yl)carbamoyl)-5-((dimethylamino)methyl)-1-ethyl-1H-pyrazole-3-sulfonamide | $^1$H NMR (DMSO-d$_6$) δ 10.82 (s, 1H), 7.94 (s, 1H), 7.82-7.79 (m, 1H), 7.73-7.72 (m, 1H), 7.63-7.53 (m, 2H), 7.23 (d, J = 7.7 Hz, 1H), 7.13 (d, J = 7.7 Hz, 1H), 6.52 (s, 1H), 4.21 (q, J = 7.2 Hz, 2H), 3.49 (s, 2H), 2.92 (t, J = 7.4 Hz, 2H), 2.64 (t, J = 7.4 Hz, 2H), 2.17 (s, 6H), 1.98 (p, J = 7.5 Hz, 2H), 1.35 (t, J = 7.2 Hz, 3H). | m/z 493.0 (M + H)$^+$ (ES$^+$); 491.3 (M – H)$^-$ (ES$^-$). | 492.6 |

Example 174: 3-(N-((4-Fluoro-2-(2-isopropoxypyridin-4-yl)-6-isopropyl-phenyl)carbamoyl)sulfamoyl)-N,N-bis(2-methoxyethyl)-1-methyl-1H-pyrazole-5-carboxamide, sodium salt

Step A: 3-(N-((4-Fluoro-2-(2-isopropoxypyridin-4-yl)-6-isopropylphenyl)carbamoyl) sulfamoyl)-N,N-bis(2-methoxyethyl)-1-methyl-1H-pyrazole-5-carboxamide

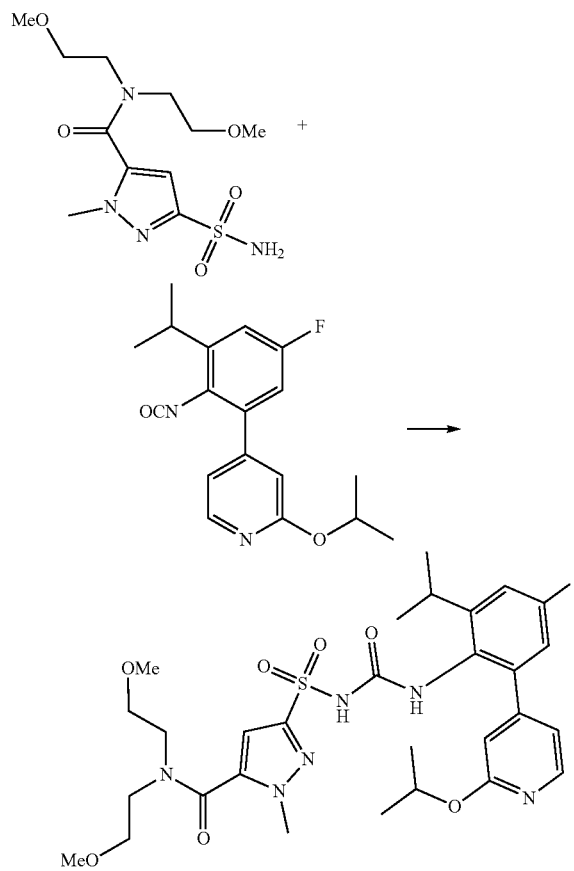

A solution of N,N-bis(2-methoxyethyl)-1-methyl-3-sulfamoyl-1H-pyrazole-5-carboxamide (Intermediate P70) (2.2 g, 6.87 mmol, 1 eq), 4-(5-fluoro-2-isocyanato-3-isopropylphenyl)-2-isopropoxypyridine (Intermediate A21) (2.16 g, 6.87 mmol, 1 eq) and t-BuONa (659 mg, 6.87 mmol, 1 eq) in THF (100 mL) was stirred at 25° C. for 30 minutes. The reaction mixture was concentrated in vacuo. The residue was purified by reversed phase flash chromatography (column: Welch Ultimate XB_C18, 41 mm*235 mm*20/40 μm, mobile phase: [A: water (10 mM NH$_4$HCO$_3$); B: MeCN]; B %: 0%-30%, 35 min) to give the title compound (2.5 g, 6% yield, 98% purity on LCMS) as a white solid.

$^1$H NMR (DMSO-d$_6$): δ 11.10 (br s, 1H), 8.06 (d, 1H), 7.79 (br s, 1H), 7.18 (d, 1H), 7.02 (d, 1H), 6.83-6.72 (m, 2H), 6.70 (s, 1H), 5.29-5.23 (m, 1H), 3.83 (s, 3H), 3.64-3.61 (m, 2H), 3.55-3.50 (m, 4H), 3.45-3.40 (m, 2H), 3.28 (s, 3H), 3.14 (s, 3H), 3.03-300 (m, 1H), 1.30 (d, 6H) and 1.09-1.05 (m, 6H).

LCMS: m/z 635.4 (M+H)$^+$ (ES$^+$).

Step B: 3-(N-((4-Fluoro-2-(2-isopropoxypyridin-4-yl)-6-isopropylphenyl)carbamoyl) sulfamoyl)-N,N-bis(2-methoxyethyl)-1-methyl-1H-pyrazole-5-carboxamide, Sodium Salt

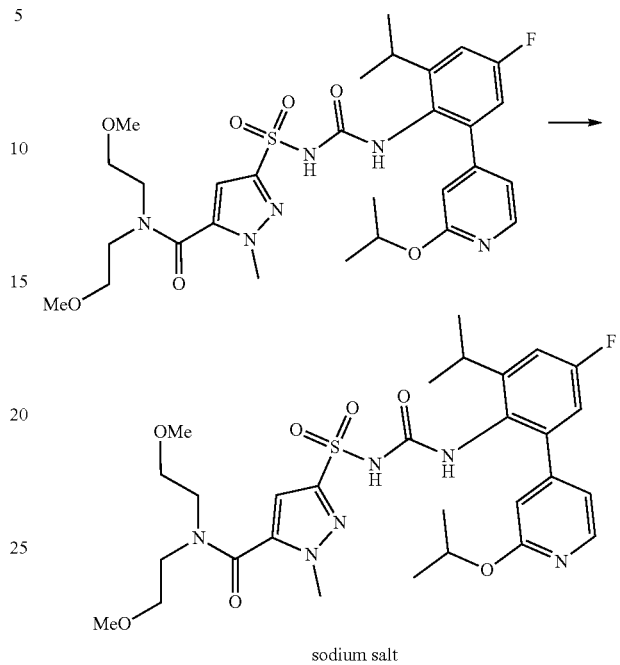

sodium salt

To a solution of 3-(N-((4-fluoro-2-(2-isopropoxypyridin-4-yl)-6-isopropylphenyl) carbamoyl)sulfamoyl)-N,N-bis(2-methoxyethyl)-1-methyl-1H-pyrazole-5-carboxamide (2.5 g, 3-94 mmol, 1 eq, free form) in THF (100 mL) was added with t-BuONa (378 mg, 3.94 mmol, 1 eq). The reaction mixture was stirred at 25° C. for 1 hour and then concentrated in vacuo. The residue was triturated with isopropyl ether (20 mL) to give the title compound (2.2 g, 85% yield, 99% purity on LCMS, sodium salt) as a white solid.

$^1$H NMR (DMSO-d$_6$): 7.99-7.88 (m, 1H), 7.53-7.40 (m, 1H), 7.15-7.08 (m, 1H), 6.94-6.82 (m, 2H), 6.68 (s, 1H), 6.51-6.44 (m, 1H), 5.28-5.22 (m, 1H), 3.75 (s, 3H), 3.74-3.56 (m, 6H), 3.45-3.38 (m, 2H), 3.29 (s, 3H), 3.17 (s, 3H), 3.12-307 (m, 1H), 1.29 (d, 6H) and 1.20-1.04 (m, 6H).

LCMS: m/z 635.1 (M+H)$^+$ (ES$^+$).

Example 175: N,N-Bis(2-methoxyethyl)-3-(N-((5-(2-methoxypyridin-4-yl)-2,3-dihydro-1H-inden-4-yl)carbamoyl)sulfamoyl)-1-methyl-1H-pyrazole-5-carboxamide, Sodium Salt

Step A: N,N-Bis(2-methoxyethyl)-3-(N-((5-(2-methoxypyridin-4-yl)-2,3-dihydro-1H-inden-4-yl)carbamoyl)sulfamoyl)-1-methyl-1H-pyrazole-5-carboxamide

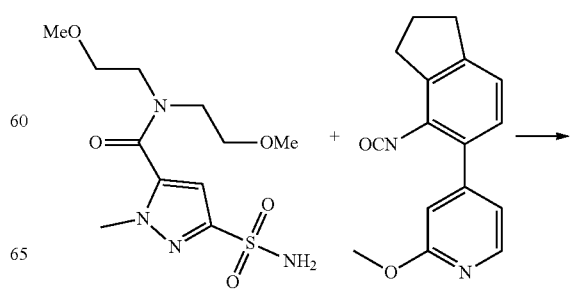

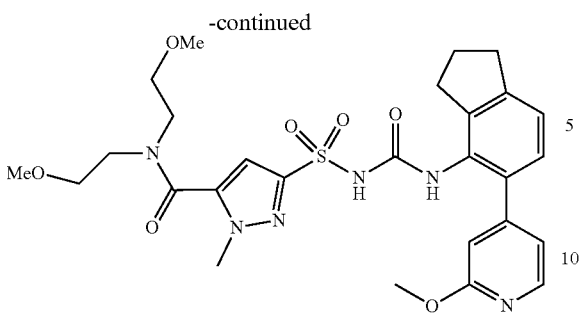

A solution of N,N-bis(2-methoxyethyl)-1-methyl-3-sulfamoyl-1H-pyrazole-5-carboxamide (Intermediate P70) (2.56 g, 7.99 mmol, 1 eq) and t-BuONa (768 mg, 7.99 mmol, 1 eq) in THF (200 mL) was stirred at 25° C. for 30 minutes. Then 4 (4-isocyanato-2,3-dihydro-1H-inden-5-yl)-2-methoxypyridine (Intermediate A20) (3.34 g, 8.79 mmol, 1.1 eq) was added. The reaction mixture was stirred at 70° C. for 2 hours and then concentrated in vacuo. The residue was purified by reversed phase flash chromatography (column: Welch Ultimate XB_C18, 41 mm*235 mm*20/40 μm, mobile phase: [A: water (0.05% ammonium hydroxide); B: MeCN]; B %: 0%-30%, 35 min) to give the title compound (1.35 g, 29% yield, 99% purity on LCMS) as a white solid.

$^1$H NMR (DMSO-d$_6$): δ 8.08 (d, 1H), 7.14-7.11 (m, 1H), 7.07-7.05 (m, 1H), 6.91 (d, 1H), 6.74 (s, 1H), 6.60 (s, 1H), 3.86 (s, 3H), 3.78 (s, 3H), 3.64-3.62 (m, 2H), 3.56-354 (m, 4H), 3.39-3.37 (m, 2H), 3.28 (s, 3H), 3.14 (s, 3H), 2.89 (t, 2H), 2.71 (t, 2H) and 1.99-1.94 (m, 2H).

LCMS: m/z 587.3 (M+H)$^+$ (ES$^+$).

Step B: N,N-Bis(2-methoxyethyl)-3-(N-((5-(2-methoxypyridin-4-yl)-2,3-dihydro-1H-inden-4-yl)carbamoyl)sulfamoyl)-1-methyl-1H-pyrazole-5-carboxamide, Sodium Salt

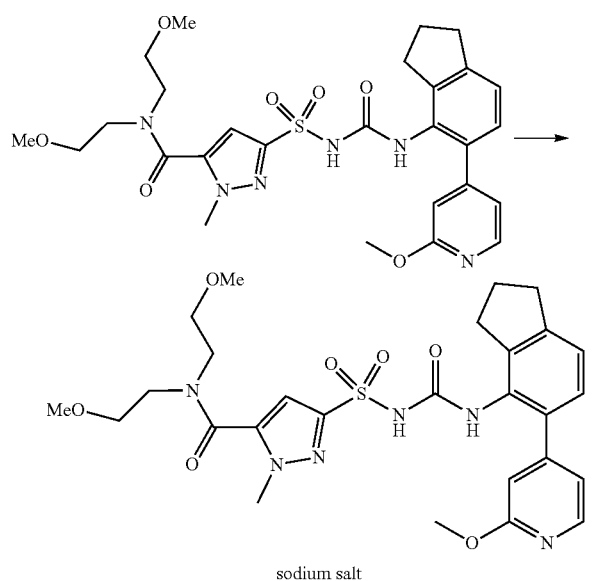

sodium salt

To a solution of N,N-bis(2-methoxyethyl)-3-(N-((5-(2-methoxypyridin-4-yl)-2,3-dihydro-1H-inden-4-yl)carbamoyl)sulfamoyl)-1-methyl-1H-pyrazole-5-carboxamide (1.35 g, 2.30 mmol, 1 eq, free form) in THF (20 mL) was added with t-BuONa (221 mg, 2.30 mmol, 1 eq). The reaction mixture was stirred at 25° C. for 1 hour and then concentrated in vacuo. The residue was triturated with isopropyl ether (20 mL) to give the title compound (1.2 g, 85% yield, 99% purity on HPLC) as a white solid.

$^1$H NMR (DMSO-d$_6$): δ 8.05 (d, 1H), 7.30 (br s, 1H), 7.04 (dd, 2H), 6.92 (d, 1H), 6.76 (s, 1H), 6.48 (d, 1H), 3.85 (s, 3H), 3.75 (s, 3H), 3.64-3.62 (m, 2H), 3.56-3.53 (m, 4H), 3.39-3.37 (m, 2H), 3.29 (s, 3H), 3.15 (s, 3H), 2.87 (t, 2H), 2.73-2.70 (m, 2H) and 1.98-1.91 (m, 2H).

LCMS: m/z 587.1 (M+H)$^+$ (ES$^+$).

Example 176: 3-(N-((4-Fluoro-2-(2-isopropoxypyridin-4-yl)-6-isopropyl-phenyl)carbamoyl)sulfamoyl)-N,N,1-trimethyl-1H-pyrazole-5-carboxamide, sodium salt Step A: 3-(N-((4-Fluoro-2-(2-isopropoxypyridin-4-yl)-6-isopropylphenyl)carbamoyl) sulfamoyl)-N,N,1-trimethyl-1H-pyrazole-5-carboxamide

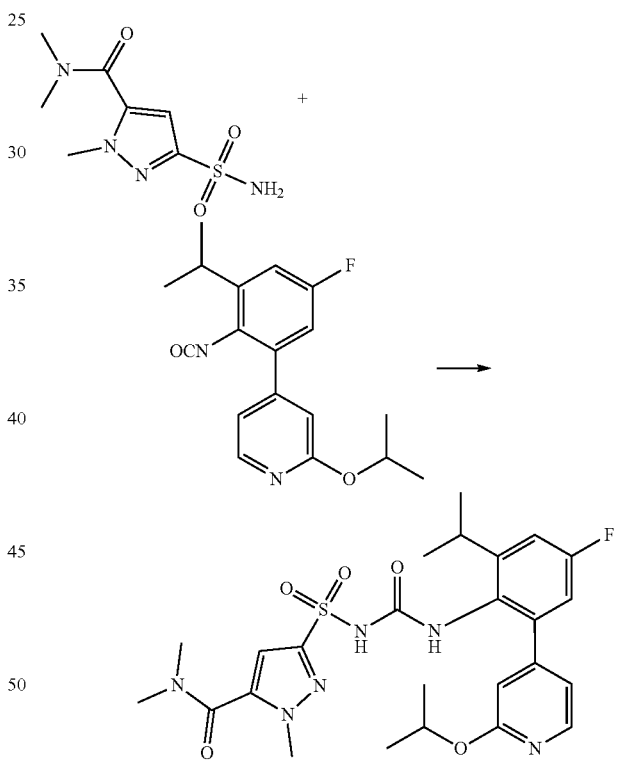

To a solution of N,N,1-trimethyl-3-sulfamoyl-H-pyrazole-5-carboxamide (Intermediate P50) (1.7 g, 7.32 mmol, 1 eq) in THF (20 mL) was added t-BuONa (703 mg, 7.32 mmol, 1 eq) at 25° C. and stirred for 0.5 hour. Then 4-(5-fluoro-2-isocyanato-3-isopropylphenyl)-2-isopropoxypyridine (Intermediate A21) (2.30 g, 7.32 mmol, 1 eq) was added and the resulting mixture was stirred for 0.5 hour. The mixture was concentrated in vacuo. The residue was purified by prep-HPLC (column: Welch Ultimate XB_C18, 41 mm*235 mm*20/40 μm; mobile phase: [water (10 mM NH$_4$HCO$_3$)-ACN]; B %: 0%-30%, 35 min) to give the title compound (2.34 g, 59% yield, 98% purity on HPLC) as a white solid.

¹H NMR (DMSO-d₆): δ 8.03 (d, 1H), 7.65 (br s, 1H), 7.16 (d, 1H), 6.98 (d, 1H), 6.85 (d, 1H), 6.74 (s, 1H), 6.70 (s, 1H), 5.30-5.21 (m, 1H), 3.89 (s, 3H), 3.09-3.03 (m, 1H), 3.00 (s, 6H), 1.30 (d, 6H) and 1.07 (d, 6H).

LCMS: m/z 547.4 (M+H)⁺ (ES⁺).

Step B: 3-(N-((4-Fluoro-2-(2-isopropoxypyridin-4-yl)-6-isopropylphenyl) carbamoyl)sulfamoyl)-N,N,1-trimethyl-1H-pyrazole-5-carboxamide, Sodium Salt

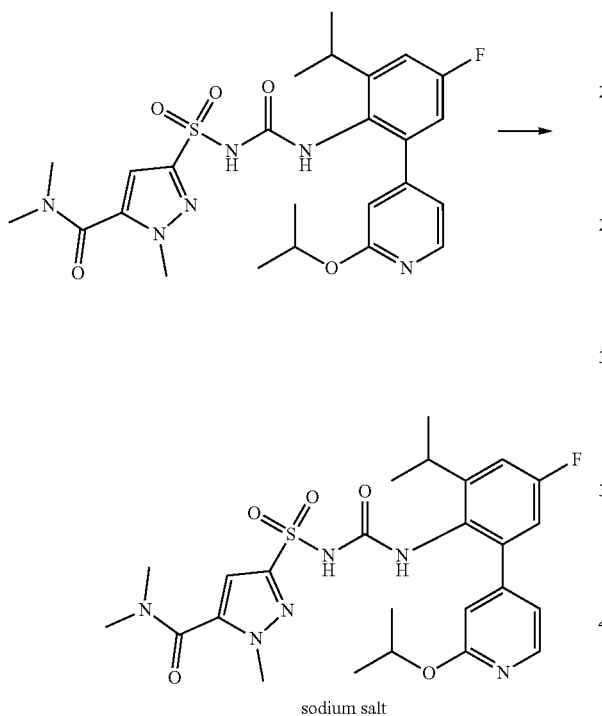

sodium salt

To a solution of 3-(N-((4-fluoro-2-(2-isopropoxypyridin-4-yl)-6-isopropylphenyl) carbamoyl)sulfamoyl)-N,N,1-trimethyl-1H-pyrazole-5-carboxamide (1.71 g, 3.13 mmol, 1 eq, free form) in THF (40 mL) was added t-BuONa (300 mg, 3.13 mmol, 1 eq) at 25° C. Then the mixture was stirred for 1 hour. The mixture was concentrated in vacuo. The residue was triturated with MTBE (100 mL). The solid was dissolved in water (100 mL) and then lyophilized to give the title compound (1.60 g, 90% yield, 99.9% purity on HPLC) as a white solid.

¹H NMR (DMSO-d₆): δ 7.95 (d, 1H), 7.37 (br s, 1H), 7.09 (d, 1H), 6.93-6.90 (m, 2H), 6.69 (s, 1H), 6.53 (s, 1H), 5.29-5.22 (m, 1H), 3.83 (s, 3H), 3.15-3.09 (m, 1H), 3.01 (d, 6H), 1.29 (d, 6H) and 1.05 (d, 6H).

LCMS: m/z 547.3 (M+H)⁺ (ES⁺).

Example 177: 3-(N-((5-(2-Methoxypyridin-4-yl)-2,3-dihydro-1H-inden-4-yl) carbamoyl)sulfamoyl)-N,N,1-trimethyl-1H-pyrazole-5-carboxamide, sodium Salt

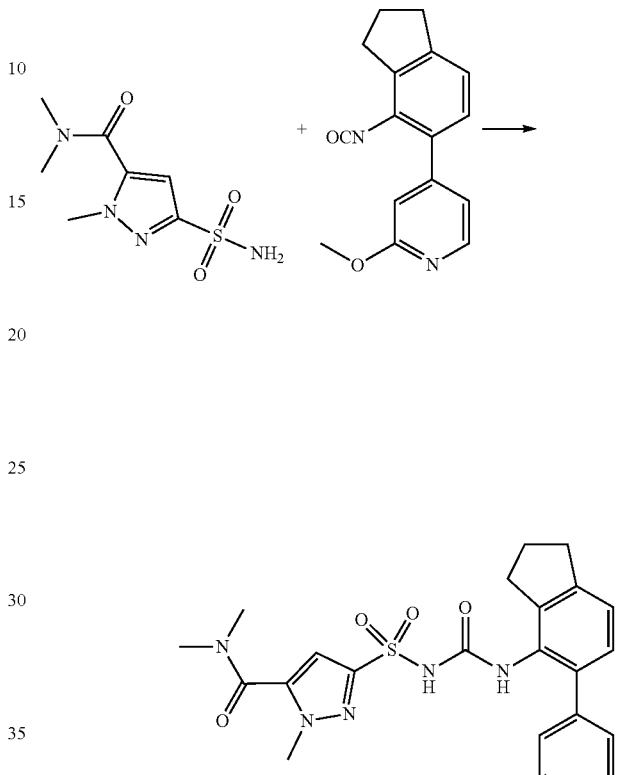

A solution of N,N,1-trimethyl-3-sulfamoyl-1H-pyrazole-5-carboxamide (Intermediate-P50) (6.59 g, 28.39 mmol, 0.9 eq) and t-BuONa (3.33 g, 34.70 mmol, 1.1 eq) in THF (200 mL) was stirred at 16° C. for 0.5 hour. Then 4-(4-isocyanato-2,3-dihydro-1H-inden-5-yl)-2-methoxypyridine (Intermediate A20) (8.4 g, 31-54 mmol, 1 eq) was added. The reaction mixture was stirred at 16° C. for 0.5 hour and then filtered. The filter cake was washed with MeCN (125 mL). Then the solid was dissolved in H₂O (100 mL) and filtered. The filtrate was lyophilized to give the title compound (8.02 g, 49% yield, 99.54% purity on LCMS, Na salt) as a white solid.

¹H NMR (DMSO-d₆): δ 8.02 (d, 1H), 7.42 (br s, 7.10-7.02 (m, 2H), 6.89 (dd, 1H), 6.74 (s, 1H), 6.59 (s, 1H), 3.84 (d, 6H), 3.02 (d, 6H), 2.87 (t, 2H), 2.72 (t, 2H) and 1.97-1.90 (m, 2H).

LCMS: m/z 499.3 (M+H)⁻ (ES⁺).

The compounds of examples 178-187 were synthesised by methods analogous to those outlined above.

TABLE 2

¹H NMR and MS data

| Ex | Structure and Name | ¹H NMR spectrum | MS | MW |
|---|---|---|---|---|
| 178 | 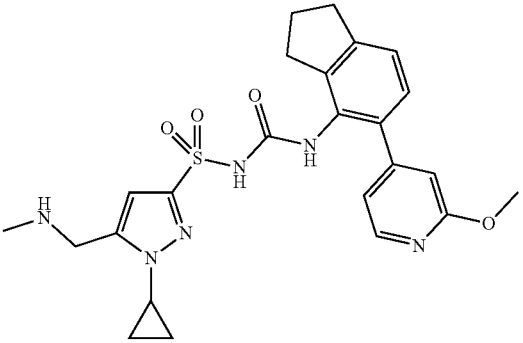<br>1-Cyclopropyl-N-((5-(2-methoxypyridin-4-yl)-2,3-dihydro-1H-inden-4-yl)carbamoyl)-5-((methylamino)methyl)-1H-pyrazole-3-sulfonamide, sodium salt | ¹H NMR (DMSO-$d_6$) δ 8.07-8.04 (m, 1H), 7.36 (s, 1H), 7.07 (d, J = 8.1 Hz, 1H), 7.04 (d, J = 7.6 Hz, 1H), 6.96-6.92 (m, 1H), 6.76 (s, 1H), 6.28-6.24 (m, 1H), 3.86 (s, 3H), 3.78-3.74 (m, 2H), 3.63-3.57 (m, 1H), 2.88 (t, J = 7.4 Hz, 2H), 2.72 (t, J = 7.4 Hz, 2H), 2.30 (d, J = 6.2 Hz, 3H), 2.08-1.99 (m, 1H), 1.94 (p, J = 7.5 Hz, 2H), 1.10-1.04 (m, 2H), 0.97-0.92 (m, 2H). | m/z 497.2 (M + H)⁺ (ES⁺); 495.0 (M − H)⁻ (ES⁻). | 496.6 |
| 179 | 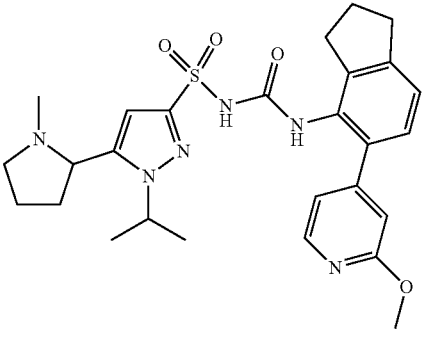<br>1-Isopropyl-N-((5-(2-methoxypyridin-4-yl)-2,3-dihydro-1H-inden-4-yl)carbamoyl)-5-(1-methylpyrrolidin-2-yl)-1H-pyrazole-3-sulfonamide, sodium salt | ¹H NMR (DMSO-$d_6$) δ 8.06 (d, J = 5.3 Hz, 1H), 7.45 (s, 1H), 7.08 (d, J = 7.7 Hz, 1H), 7.04 (d, J = 7.6 Hz, 1H), 6.95 (d, J = 5.3 Hz, 1H), 6.78 (s, 1H), 6.24 (s, 1H), 4.75 (sept, J = 6.7 Hz, 1H), 3.87 (s, 3H), 3.14-3.08 (m, 1H), 2.86 (t, J = 7.4 Hz, 2H), 2.63 (t, J = 7.5 Hz, 2H), 2.25-2.19 (m, 2H), 2.17 (s, 3H), 1.89 (p, J = 7.4 Hz, 2H), 1.85-1.58 (m, 4H), 1.38 (d, J = 6.6 Hz, 3H), 1.34 (d, J = 6.5 Hz, 3H). | m/z 539.3 (M + H)⁺ (ES⁺); 537.1 (M − H)⁻ (ES⁻). | 538.7 |
| 180 | 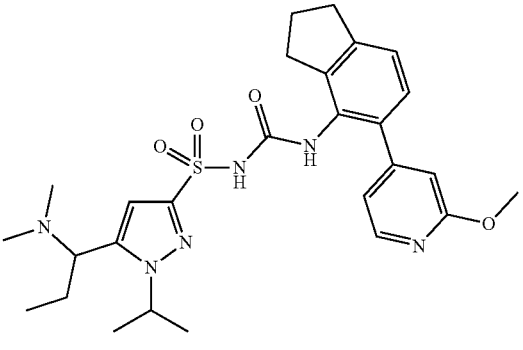<br>5-(1-(Dimethylamino)propyl)-1-isopropyl-N-((5-(2-methoxypyridin-4-yl)-2,3-dihydro-1H-inden-4-yl)carbamoyl)-1H-pyrazole-3-sulfonamide | ¹H NMR (DMSO-$d_6$) δ 10.84 (s, 1H), 8.15 (dd, J = 5.2, 0.6 Hz, 1H), 7.90 (s, 1H), 7.22 (d, J = 7.7 Hz, 1H), 7.12 (d, J = 7.6 Hz, 1H), 6.88 (dd, J = 5.3, 1.4 Hz, 1H), 6.72 (d, J = 1.4 Hz, 1H), 6.57 (s, 1H), 4.86 (sept, J = 6.6 Hz, 1H), 3.88 (s, 3H), 3.75-3.67 (m, 1H), 2.90 (t, J = 7.4 Hz, 2H), 2.56 (t, J = 7.7 Hz, 2H), 2.14 (s, 6H), 1.92 (p, J = 7.4 Hz, 2H), 1.89-1.80 (m, 1H), 1.71-1.60 (m, 1H), 1.41 (d, J = 6.5 Hz, 3H), 1.34 (d, J = 6.5 Hz, 3H), 0.77 (t, J = 7.3 Hz, 3H). | m/z 541.3 (M + H)⁺ (ES⁺); 539.3 (M − H)⁻ (ES⁻). | 540.7 |

TABLE 2-continued

¹H NMR and MS data

| Ex | Structure and Name | ¹H NMR spectrum | MS | MW |
|---|---|---|---|---|
| 181 | 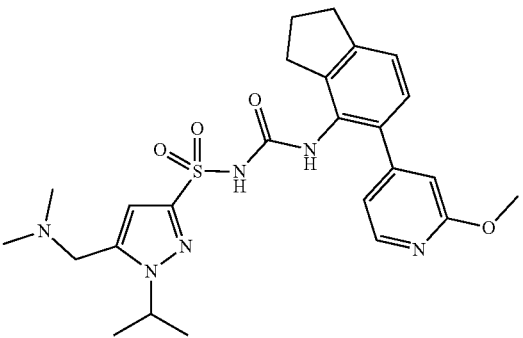<br>5-((Dimethylamino)methyl)-1-isopropyl-N-((5-(2-methoxypyridin-4-yl)-2,3-dihydro-1H-inden-4-yl)carbamoyl)-1H-pyrazole-3-sulfonamide | ¹H NMR (DMSO-$d_6$) δ 10.85 (s, 1H), 8.14 (d, J = 5.3 Hz, 1H), 7.91 (s, 1H), 7.22 (d, J = 7.6 Hz, 1H), 7.12 (d, J = 7.6 Hz, 1H), 6.88 (dd, J = 5.3, 1.5 Hz, 1H), 6.73-6.71 (m, 1H), 6.55 (s, 1H), 4.81 (sept, J = 6.6 Hz, 1H), 3.88 (s, 3H), 3.50 (s, 2H), 2.90 (t, J = 7.5 Hz, 2H), 2.59 (t, J = 7.4 Hz, 2H), 2.16 (s, 6H), 1.95 (p, J = 7.6 Hz, 2H), 1.38 (d, J = 6.6 Hz, 6H). | m/z 513.3 (M + H)⁺ (ES⁺); 511.3 (M − H)⁻ (ES⁻). | 512.6 |
| 182 | 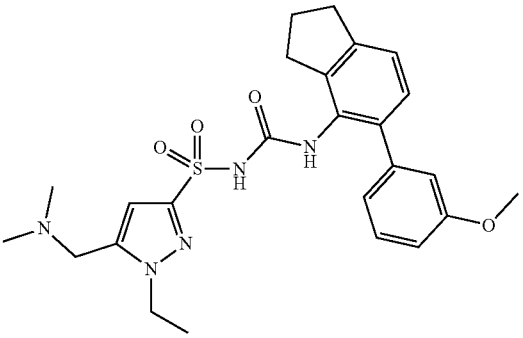<br>5-((Dimethylamino)methyl)-1-ethyl-N-((5-(3-methoxyphenyl)-2,3-dihydro-1H-inden-4-yl)carbamoyl)-1H-pyrazole-3-sulfonamide | ¹H NMR (DMSO-$d_6$) δ 10.74 (s, 1H), 7.79 (s, 1H), 7.33-7.28 (m, 1H), 7.19 (d, J = 7.7 Hz, 1H), 7.09 (d, J = 7.6 Hz, 1H), 6.95-6.91 (m, 1H), 6.87-6.79 (m, 2H), 6.61 (s, 1H), 4.23 (q, J = 7.2 Hz, 2H), 3.76 (s, 3H), 3.51 (s, 2H), 2.90 (t, J = 7.4 Hz, 2H), 2.58 (t, J = 7.4 Hz, 2H), 2.18 (s, 6H), 1.95 (p, J = 7.5 Hz, 2H), 1.36 (t, J = 7.2 Hz, 3H). | m/z 498.4 (M + H)⁺ (ES⁺); 496.1 (M − H)⁻ (ES⁻). | 497.6 |
| 183 | 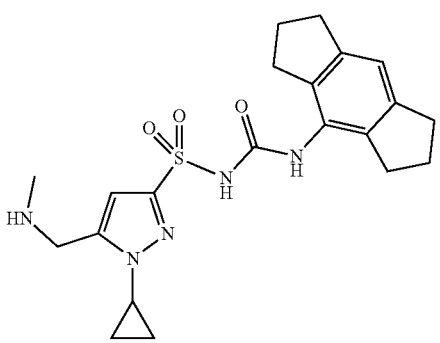<br>1-Cyclopropyl-N-((1,2,3,5,6,7-hexahydro-s-indacen-4-yl)carbamoyl)-5-((methylamino)methyl)-1H-pyrazole-3-sulfonamide | ¹H NMR (DMSO-$d_6$) δ 7.75 (s, 1H), 6.85 (s, 1H), 6.61 (s, 1H), 4.05 (s, 2H), 3.68 (s, 1H), 2.77 (t, J = 7.4 Hz, 4H), 2.63 (t, J = 7.3 Hz, 4H), 2.46 (s, 3H), 1.93 (p, J = 7.4 Hz, 4H), 1.09-0.96 (m, 4H). Amine NH and acidic NH are not resolved. | m/z 430.3 (M + H)⁺ (ES⁺); 428.4 (M − H)⁻ (ES⁻). | 429.5 |

TABLE 2-continued

¹H NMR and MS data

| Ex | Structure and Name | ¹H NMR spectrum | MS | MW |
|---|---|---|---|---|
| 184 | 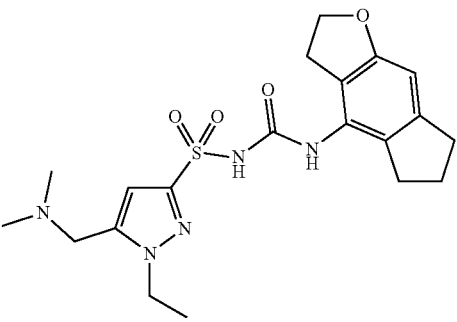<br>5-((Dimethylamino)methy)-1-ethyl-N-((3,5,6,7-tetrahydro-2H-indeno[5,6-b]furan-4-yl)carbamoyl)-1H-pyrazole-3-sulfonamide, sodium salt | ¹H NMR (DMSO-$d_6$) δ 7.68 (s, 1H), 6.31 (s, 1H), 6.29 (s, 1H), 4.37 (t, J = 8.6 Hz, 2H), 4.11 (q, J = 7.2 Hz, 2H), 3.39 (s, 2H), 2.95 (t, J = 8.6 Hz, 2H), 2.71 (t, J = 7.4 Hz, 2H), 2.60 (t, J = 7.3 Hz, 2H), 2.14 (s, 6H), 1.89 (p, J = 7.4 Hz, 2H), 1.31 (t, J = 7.2 Hz, 3H). | m/z 434.2 $(M + H)^+$ $(ES^+)$. | 433.5 |
| 185 | 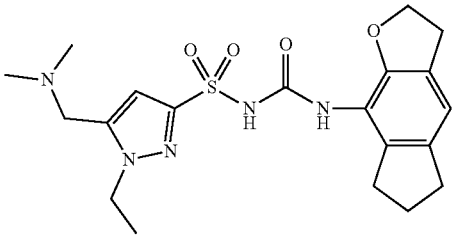<br>5-((Dimethylamino)methyl)-1-ethyl-N-((3,5,6,7-tetrahydro-2H-indeno[5,6-b]furan-8-yl)carbamoyl)-1H-pyrazole-3-sulfonamide, sodium salt | ¹H NMR (DMSO-$d_6$) δ 7.19 (s, 1H), 6.76 (s, 1H), 6.29 (s, 1H), 4.43 (t, J = 8.6 Hz, 2H), 4.11 (q, J = 7.2 Hz, 2H), 3.38 (s, 2H), 3.07 (t, J = 8.7 Hz, 2H), 2.71 (t, J = 7.3 Hz, 2H), 2.60 (t, J = 7.4 Hz, 2H), 2.14 (s, 6H), 1.86 (p, J = 7.4 Hz, 2H), 1.31 (t, J = 7.2 Hz, 3H). | m/z 434.4 $(M + H)^+$ $(ES^+)$. | 433.5 |
| 186 | 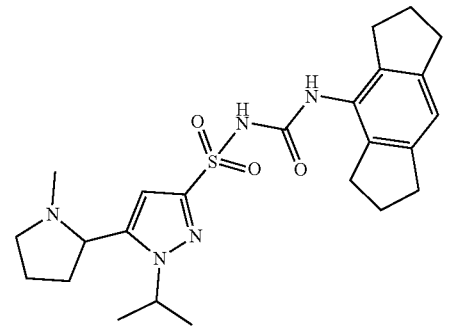<br>N-((1,2,3,5,6,7-Hexahydro-s-indacen-4-yl)carbamoyl)-1-isopropyl-5-(1-methylpyrrolidin-2-yl)-1H-pyrazole-3-sulfonamide, sodium salt | ¹H NMR(DMSO-$d_6$)δ 7.59 (s, 1H), 6.76 (s, 1H), 6.26 (s, 1H), 4.72 (pent., J = 6.5 Hz, 1H), 3.12-3.06 (m, 1H), 2.75 (t, J = 7.4 Hz, 4H), 2.62 (t, J = 7.3 Hz, 4H), 2.23-2.17 (m, 2H), 2.16 (s, 3H), 1.88 (p, J = 7.5 Hz, 4H), 1.84-1.72 (m, 2H), 1.66-1.57 (m, 1H), 1.37 (d, J = 6.6 Hz, 3H), 1.34 (d, J = 6.5 Hz, 3H). One NH not observed. | m/z 472.3 $(M + H)^+$ $(ES^+)$; 470.2 $(M - H)^-$ $(ES^-)$. | 471.6 |

TABLE 2-continued

¹H NMR and MS data

| Ex | Structure and Name | ¹H NMR spectrum | MS | MW |
|---|---|---|---|---|
| 187 | 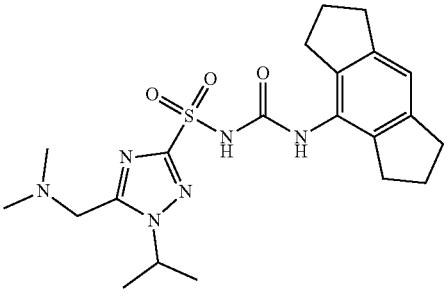<br><br>5-((Dimethylamino)methyl)-N-((1,2,3,5,6,7-hexahydro-s-indacen-4-yl)carbamoyl)-1-isopropyl-1H-1,2,4-triazole-3-sulfonamide | ¹H NMR (DMSO-d$_6$)δ 11.21 (s, 1H), 8.01 (s, 1H), 6.90 (s, 1H), 4.89 (sept, J = 6.6 Hz, 1H), 3.67 (s, 2H), 2.77 (t, J = 7.4 Hz, 4H), 2.61 (t,J = 7.2 Hz, 4H), 2.19 (s, 6H), 1.92 (p, J = 7.4 Hz, 4H), 1.39 (d, J = 6.6 Hz, 6H). | m/z 447.3 (M + H)$^+$ (ES$^+$); 445.2 (M − H)$^−$ (ES$^−$). | 446.6 |

Examples—Biological Studies

NLRP and Pyroptosis

It is well established that the activation of NLRP3 leads to cell pyroptosis and this feature plays an important part in the manifestation of clinical disease (Yan-gang Liu et al., Cell Death &Disease, 2017, 8(2), e2579; Alexander Wree et al., Hepatology, 2014, 59(3), 898-910; Alex Baldwin et al., Journal of Medicinal Chemistry, 2016, 59(5), 1691-171; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death &Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~10$^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 g/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C. in 5% CO$_2$
4. Add 5 μl nigericin (Sigma #N7143) (FAC 5 μM) to all wells
5. Incubate for 1 hr at 37° C. and 5% CO$_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% CO$_2$
8. Plates were read in an Envision reader at Ex 560 nm and Em 590 nm
9. IC$_{50}$ data is fitted to a non-linear regression equation (log inhibitor vs response-variable slope 4-parameters)

96-Well Plate Map

|   | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High MCC950 (10 uM)
Low Drug free control
Compound 8-point half-log dilution

The results of the pyroptosis assay performed are summarised in Table 3 below as THP IC$_{50}$.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with 10 μM top dose) or vehicle (DMSO 0.1% FAC) to the appropriate wells
3. Incubate for 3 hrs at 37° C., 5% $CO_2$
4. Add 10 μl Nigericin (Sigma #N7143) (10 μM FAC) to all wells
5. Incubate for 1 hr at 37° C., 5% $CO_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1β Kit AL220F-5000)
8. $IC_{50}$ data is fitted to a non-linear regression equation (log inhibitor vs response-variable slope 4-parameters)

The results of the human whole blood assay are summarised in Table 3 below as HWB $IC_{50}$.

TABLE 3

| Example No | THP $IC_{50}$ | HWB $IC_{50}$ |
| --- | --- | --- |
| 1 | + | ND |
| 2 | + | ND |
| 3 | +++++ | ***** |
| 4 | ++++ | **** |
| 5 | +++ | ** |
| 6 | +++ | *** |
| 7 | +++++ | **** |
| 8 | +++ | ND |
| 9 | + | ND |
| 10 | + | ND |
| 11 | +++ | * |
| 12 | ++ | ND |
| 13 | +++ | ND |
| 14 | ++ | ND |
| 15 | ++ | ND |
| 16 | ++ | ND |
| 17 | +++++ | ***** |
| 18 | ++ | ND |
| 19 | ++ | ND |
| 20 | +++++ | ***** |
| 21 | +++++ | ***** |
| 22 | +++++ | **** |
| 23 | +++++ | ***** |
| 24 | +++++ | ***** |
| 25 | +++++ | ***** |
| 26 | ++++ | ***** |
| 27 | ++++ | ***** |
| 28 | ++ | ND |
| 29 | ++++ | **** |
| 30 | ++++ | **** |
| 31 | ++++ | **** |
| 32 | ++++ | **** |
| 33 | +++ | **** |
| 34 | ++++ | **** |
| 35 | ++++ | ***** |
| 36 | ++++ | ***** |
| 37 | +++++ | * |
| 38 | ++++ | ** |
| 39 | ++ | ** |
| 40 | +++ | **** |
| 41 | ++++ | ***** |
| 42 | ++ | ND |
| 43 | ++ | ND |
| 44 | ++ | ***** |
| 45 | +++ | *** |
| 46 | ++++ | ***** |
| 47 | ++++ | ***** |
| 48 | +++++ | ***** |
| 49 | ++++ | ***** |
| 50 | ++++ | **** |
| 51 | +++ | ***** |
| 52 | +++++ | ***** |
| 53 | +++++ | **** |
| 54 | +++ | **** |
| 55 | ++++ | ** |
| 56 | ++++ | * |
| 57 | +++++ | ** |
| 58 | ++++ | *** |
| 59 | +++ | *** |
| 60 | +++++ | **** |
| 61 | +++ | ND |
| 62 | +++ | **** |
| 63 | +++++ | ***** |
| 64 | +++++ | *** |
| 65 | +++++ | ***** |
| 66 | +++ | **** |
| 67 | ++++ | **** |
| 68 | +++++ | **** |
| 69 | +++++ | ***** |
| 70 | +++++ | ***** |
| 71 | +++++ | ***** |
| 72 | +++++ | ***** |
| 73 | +++++ | ***** |
| 74 | +++++ | ***** |
| 75 | +++ | *** |
| 76 | ++++ | ***** |
| 77 | +++++ | ***** |
| 78 | ++++ | **** |
| 79 | ++ | *** |
| 80 | +++ | ** |
| 81 | +++ | ***** |
| 82 | ++++ | *** |
| 83 | ++ | **** |
| 84 | ++++ | **** |
| 85 | +++ | ND |
| 86 | +++ | *** |
| 87 | ++ | ND |
| 88 | +++ | ***** |
| 89 | +++ | ***** |
| 90 | +++ | ***** |
| 91 | +++ | **** |
| 92 | +++ | ***** |
| 93 | ++++ | *** |
| 94 | +++++ | ***** |
| 95 | +++++ | *** |
| 96 | ++++ | * |
| 97 | +++ | ND |
| 98 | + | ND |
| 99 | + | ND |
| 100 | + | ND |
| 101 | +++ | ***** |
| 102 | ++++ | **** |
| 103 | ++ | ND |
| 104 | +++ | ** |
| 105 | ++ | ND |
| 106 | +++ | *** |
| 107 | ++ | ND |
| 108 | + | ND |
| 109 | + | ND |
| 110 | + | ND |
| 111 | + | ND |
| 112 | ++++ | **** |
| 113 | ++++ | **** |
| 114 | ++ | ND |
| 115 | +++ | *** |
| 116 | +++ | ***** |
| 117 | ++++ | ***** |
| 118 | ++ | ND |

TABLE 3-continued

| Example No | THP IC$_{50}$ | HWB IC$_{50}$ |
|---|---|---|
| 119 | +++ | ** |
| 120 | ++ | ND |
| 121 | ++ | ND |
| 122 | ++++ | **** |
| 123 | +++ | ND |
| 124 | ++++ | *** |
| 125 | +++ | ** |
| 126 | ++ | **** |
| 127 | ++ | ND |
| 128 | ++ | ***** |
| 129 | ++ | ND |
| 130 | ++ | ND |
| 131 | + | ND |
| 132 | ++ | *** |
| 133 | + | ND |
| 134 | ++++ | ***** |
| 135 | +++ | ***** |
| 136 | ++++ | *** |
| 137 | +++ | * |
| 138 | ++++ | ***** |
| 139 | + | ND |
| 140 | ++++ | **** |
| 141 | +++ | ND |
| 142 | +++ | **** |
| 143 | +++ | ***** |
| 144 | +++ | ***** |
| 145 | ++++ | **** |
| 146 | +++ | *** |
| 147 | ++++ | ** |
| 148 | +++ | **** |
| 149 | ++ | ** |
| 150 | ++ | ND |
| 151 | +++ | **** |
| 152 | ++ | ND |
| 153 | +++ | ***** |
| 154 | ++ | ND |
| 155 | ++++ | **** |
| 156 | ++ | ND |
| 157 | ++++ | ** |
| 158 | ++++ | *** |
| 159 | ++ | ND |
| 160 | +++ | ***** |
| 161 | ++++ | ** |
| 162 | ++++ | ***** |
| 163 | +++ | ** |
| 164 | ++++ | *** |
| 165 | +++ | ND |
| 166 | ++ | ND |
| 167 | + | ND |
| 168 | ++++ | *** |
| 169 | ++ | ND |
| 170 | + | ND |
| 171 | + | ND |
| 172 | ++++ | ***** |
| 173 | ++++ | **** |
| 174 | + | * |
| 175 | +++ | ***** |
| 176 | +++ | ** |
| 177 | +++++ | ***** |
| 178 | ++++ | ***** |
| 179 | ++++ | *** |
| 180 | ++++ | ***** |
| 181 | +++++ | ***** |
| 182 | ++ | ND |
| 183 | ++++ | **** |
| 184 | +++++ | **** |
| 185 | +++ | ** |
| 186 | +++++ | **** |
| 187 | +++++ | *** |

NLRP3 inhibitory activity [THP IC$_{50}$ (≤0.04 μM = +++++, ≤0.16 μM = ++++, ≤0.64 μM = +++, ≤2.56 μM = ++, ≤10 μM = +, not determined = ND)] [HWB IC$_{50}$ (≤0.4 μM = ***, ≤0.8 μM = , ≤1.6 μM = *, ≤3.2 μM = **, ≤10 μM = *, not determined = ND)]

PK Protocol

Pharmacokinetic parameters were determined in male Sprague Dawley rats (Charles River, UK, 250-350 g; or Vital River Laboratory Animal Technology Co Ltd, Beijing, China, 7-9 weeks old). Animals were individually housed during the study and maintained under a 12 h light/dark cycle. Animals had free access to food and water except that some orally dosed animals were food deprived overnight prior to the study.

For intravenous administration, compounds were formulated as a solution in water or DMSO:PBS [1:90] in 2 mL/kg dosing volume and administered via tail vein. For oral administration, compounds were formulated as a solution in water or DMSO:water [10:90] in 5 mL/kg dosing volume and administered orally.

Serial blood samples (about 120-300 μL) were taken from each animal at each of 8 time-points post dose (0.083, 0.25, 0.5, 1, 2, 4, 8 and 24 h) or at each of 12 time-points post dose (0.03, 0.1, 0.17, 0.25, 0.5, 1, 2, 4, 6, 8, 12 and 24 h) or pre-dose and at each of 9 time-points post dose (0.25, 0.5, 1, 2, 4, 6, 8, 12 and 24 h). Samples were held on ice for no longer than 30 minutes before centrifugation (10,000 rpm (8,385 g) for 3 minutes; or 5,696 rpm (3,0009 for 15 minutes) for plasma generation. Plasma was frozen on dry ice prior to boanalysis. PK parameters were generated from LC-MS/MS data using Dotmatics or Phoenix WinNonlin 6.3 software.

TABLE 4

PK data (intravenous administration)

| Example No | Dose (mg/kg) | AUC (ng · hr/mL) | T$_{1/2}$ (hr) | V$_{dss}$ (L/kg) | Cl (mL/min/kg) |
|---|---|---|---|---|---|
| 3 | 2.5 | 1126.5 | 1.3 | 1.32 | 37.0 |
| 4 | 1 | 3777.3 | 1.6 | 0.12 | 4.4 |
| 7 | 1 | 3475.8 | 1.2 | 0.36 | 4.9 |
| 17 | 1.7 | 2710.4 | 3.8 | 1.23 | 10.5 |
| 24 | 1 | 1278.8 | 1.0 | 0.84 | 13.0 |
| 25 | 1.64 | 3457.0 | 1 | 0.58 | 10.0 |
| 27 | 1 | 3895.2 | 1.1 | 0.33 | 4.3 |
| 30 | 1 | 6210.6 | 2.8 | 0.53 | 2.7 |
| 40 | 1 | 259.1 | 0.5 | 0.98 | 65.6 |
| 41 | 1 | 259.0 | 0.5 | 0.75 | 64.9 |
| 44 | 1 | 3118.7 | 1.2 | 0.21 | 5.3 |
| 46 | 1 | 375.4 | 1.2 | 1.14 | 51.5 |
| 47 | 1 | 247.8 | 0.3 | 1.32 | 67.2 |
| 48 | 1 | 356.0 | 0.5 | 0.8 | 47.6 |
| 49 | 1 | 6626.6 | 2.2 | 0.34 | 2.7 |
| 50 | 1 | 11371 | 3.5 | 0.39 | 1.5 |
| 52 | 1.65 | 7969.2 | 1.5 | 0.39 | 3.5 |
| 63 | 1 | 4007.3 | 0.8 | 0.25 | 4.2 |
| 72 | 1.4 | 2777.5 | 2.4 | 0.51 | 8.5 |
| 73 | 1 | 4252.9 | 3.5 | 0.51 | 4.3 |
| 76 | 1.65 | 4896.0 | 3.2 | 0.66 | 5.8 |
| 77 | 1 | 4439.1 | 3.5 | 0.38 | 3.8 |
| 84 | 1 | 2492.6 | 1.0 | 0.47 | 6.7 |
| 86 | 1 | 4399.1 | 3.2 | 0.48 | 3.8 |
| 88 | 1 | 1496.3 | 4.3 | 1.64 | 11.2 |
| 89 | 1 | 1022.7 | 1.4 | 1.4 | 16.3 |
| 91 | 1 | 2619.9 | 4.3 | 1.03 | 6.9 |
| 92 | 1 | 1278.5 | 3.2 | 2.19 | 13.1 |
| 93 | 2.2 | 4229.8 | 3.3 | 1.71 | 10.8 |
| 94 | 1 | 4698.7 | 1.1 | 0.27 | 3.8 |
| 112 | 2.88 | 329.7 | 0.2 | 1.84 | 149.3 |
| 113 | 1 | 1162.1 | 2.9 | 2.24 | 14.4 |
| 117 | 1 | 2067.0 | 14.2 | 1.9 | 8.1 |
| 124 | 1 | 302.7 | 1.6 | 1.66 | 55.3 |
| 126 | 1 | 182.5 | 2.3 | 2.72 | 91.3 |
| 128 | 1 | 661.2 | 12.1 | 3.03 | 25.2 |
| 134 | 1 | 274.4 | 6.3 | 3.95 | 60.7 |
| 138 | 1 | 415.0 | 6.4 | 7.96 | 40.3 |
| 153 | 1 | 283.3 | 3.3 | 4.08 | 59.2 |
| 155 | 2.46 | 1723.1 | 0.1 | 0.24 | 25.0 |
| 160 | 0.83 | 333.7 | 0.5 | 0.99 | 48.7 |
| 161 | 3.34 | 353.3 | 1.3 | 10.55 | 160.9 |
| 162 | 5.05 | 3389.9 | 25.3 | 17.78 | 24.8 |
| 172 | 2.41 | 786.6 | 0.3 | 2.37 | 114.1 |

TABLE 5

| | | | PK data (oral administration) | | | | |
|---|---|---|---|---|---|---|---|
| Example No | Dose (mg/kg) | $C_{max}$ (ng/mL) | AUC (ng · hr/mL) | $T_{max}$ (hr) | $T_{1/2}$ (hr) | Cl/F (mL/min/kg) | Bioavailability |
| 7 | 3 | 6688.6 | 21246.8 | 1.0 | 2.2 | 2.4 | 203.8 |
| 50 | 2 | 2411 | 19053 | 1.3 | 3.3 | 1.8 | 84 |
| 69 | 4.2 | 7465.0 | 17003.1 | 0.38 | 1.2 | 4.2 | ND |
| 70 | 3.87 | 5665.0 | 11115.9 | 0.5 | 1.1 | 6.0 | ND |
| 76 | 4.17 | 2340.0 | 5646.9 | 0.5 | 2.9 | 12.3 | 45.6 |
| 93 | 5.5 | 1095.2 | 3309.1 | 0.36 | ND | 18.0 | 31.3 |
| 94 | 3 | 7178.7 | 12914.8 | 0.58 | 1.5 | 4.1 | 91.6 |
| 113 | 3 | 700.6 | 2415.2 | 0.08 | 4.9 | 21.5 | 67 |
| 153 | 5 | 494.7 | 769.7 | 0.17 | 9.7 | 109.8 | 54.3 |
| 162 | 3 | 599.6 | 1052.0 | 0.25 | 3.4 | 49.5 | 62.0 |

(ND = not determined)

As is evident from the results presented in Table 3, surprisingly in spite of the structural differences versus the prior art compounds, the compounds of the invention show high levels of NLRP3 inhibitory activity in the pyroptosis assay and in the human whole blood assay.

As is evident from the results presented in Tables 4 and 5, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

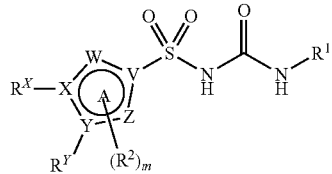

Formula (I)

or a pharmaceutically acceptable salt or solvate thereof, wherein:
Q is selected from O or S;
ring A is monocyclic;
V, X and Y are each independently selected from C and N, and W and Z are each independently selected from N, O, S, NH and CH, provided that at least one of V, W, X, Y and Z is N, O, S or NH;
$R^X$ and $R^Y$ are each independently any saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
$R^1$ is a cyclic group substituted at the α-position, wherein $R^1$ may optionally be further substituted;
m is 0, 1 or 2; and
each $R^2$ is independently a halo, —OH, —$NO_2$, —$NH_2$, —$N_3$, —SH, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

provided that at least one of $R^X$ and $R^Y$ comprises a nitrogen atom; and provided that the compound is not:

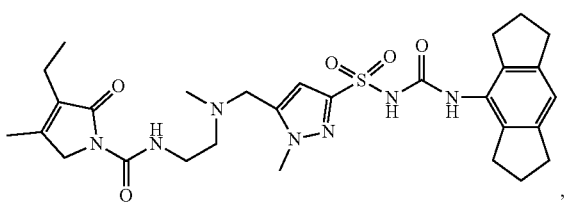

,

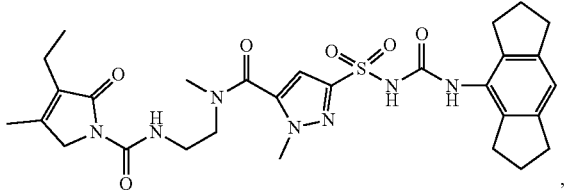

,

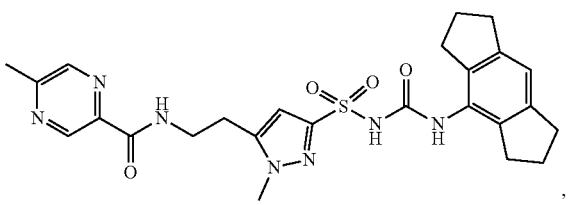

,

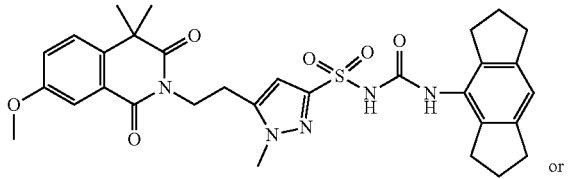

or

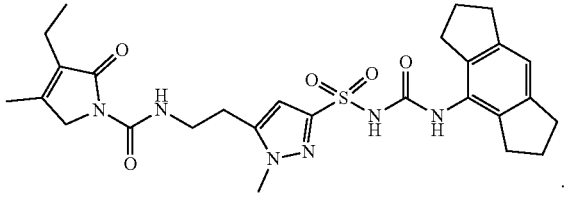

.

2. The compound or pharmaceutically acceptable salt or solvate thereof, as claimed in claim 1, wherein at least one of V, W, X, Y and Z is N or NH.

3. The compound or pharmaceutically acceptable salt or solvate thereof, as claimed in claim 1, wherein any monovalent $R^X$ or $R^Y$ contains from 1 to 7 carbon atoms.

4. The compound or a pharmaceutically acceptable salt or solvate or prodrug thereof, as claimed in claim 1, wherein:
(i) $R^X$ is a monovalent group having the formula:

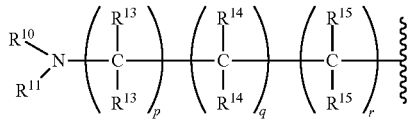

wherein:
p is 0 or 1;
q is 0 or 1;
r is 0 or 1;
$R^{10}$ is hydrogen or a $C_1$-$C_4$ alkyl or $C_3$-$C_4$ cycloalkyl group; and
$R^{11}$ is a $C_1$-$C_4$ alkyl or $C_3$-$C_4$ cycloalkyl group, or $R^{11}$ together with any one of $R^{13}$, $R^{14}$ or $R^{15}$ forms a $C_1$-$C_4$ alkylene group; or
$R^{10}$ and $R^{11}$ together form a $C_2$-$C_5$ alkylene group;
each $R^{13}$, $R^{14}$ and $R^{15}$ is independently selected from hydrogen or a halo, —CN, —OH, $C_1$-$C_4$ alkyl, $C_3$-$C_4$ cycloalkyl, —O—($C_1$-$C_4$ alkyl) or —O—($C_3$-$C_4$ cycloalkyl) group, and/or any two $R^{13}$, two $R^{14}$ or two $R^{15}$ may together with the carbon atom to which they are attached form a C=O group, and/or any two $R^{13}$, $R^{14}$ or $R^{15}$ may together form a $C_1$-$C_4$ alkylene group;
wherein any alkylene group may optionally include one or two heteroatoms independently selected from 0 and N in its carbon skeleton;
wherein any alkyl or alkylene group may optionally be substituted with one or more halo, —CN, —OH, —NH$_2$, oxo (=O), —OMe, —O-halomethyl, —NHMe, —NH(halomethyl), —NMe$_2$, —NMe(halomethyl) and/or —N(halomethyl)$_2$ groups; and
wherein any cycloalkyl group may optionally be substituted with one or more halo, —CN, —OH, —NH$_2$, oxo (=O), methyl, halomethyl, —OMe, —O-halomethyl, —NHMe, —NH(halomethyl), —NMe$_2$, —NMe(halomethyl) and/or —N(halomethyl)$_2$ groups; or
(ii) $R^X$ is a monovalent group having the formula:

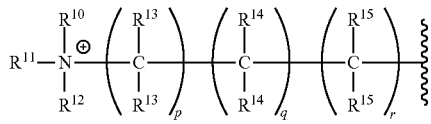

wherein:
p is 0 or 1;
q is 0 or 1;
r is 0 or 1;
$R^{10}$ is a $C_1$-$C_4$ alkyl or $C_3$-$C_4$ cycloalkyl group; and
$R^{11}$ is a $C_1$-$C_4$ alkyl or $C_3$-$C_4$ cycloalkyl group, or $R^{11}$ together with any one of $R^{13}$, $R^{14}$ or $R^{15}$ forms a $C_1$-$C_4$ alkylene group; or
$R^{10}$ and $R^{11}$ together form a $C_2$-$C_5$ alkylene group;
$R^{12}$ is a $C_1$-$C_4$ alkyl or $C_3$-$C_4$ cycloalkyl group;
each $R^{13}$, $R^{14}$ and $R^{15}$ is independently selected from hydrogen or a halo, —CN, —OH, $C_1$-$C_4$ alkyl, $C_3$-$C_4$ cycloalkyl, —O—($C_1$-$C_4$ alkyl) or —O—($C_3$-$C_4$ cycloalkyl) group, and/or any two $R^{13}$, two $R^{14}$ or two $R^{15}$ may together with the carbon atom to which they are attached form a C=O group, and/or any two $R^{13}$, $R^{14}$ or $R^{15}$ may together form a $C_1$-$C_4$ alkylene group;
wherein any alkylene group may optionally include one or two heteroatoms independently selected from 0 and N in its carbon skeleton;
wherein any alkyl or alkylene group may optionally be substituted with one or more halo, —CN, —OH, —NH$_2$, oxo (=O), —OMe, —O-halomethyl, —NHMe, —NH(halomethyl), —NMe$_2$, —NMe(halomethyl) and/or —N(halomethyl)$_2$ groups; and
wherein any cycloalkyl group may optionally be substituted with one or more halo, —CN, —OH, —NH$_2$, oxo (=O), methyl, halomethyl, —OMe, —O-halomethyl, —NHMe, —NH(halomethyl), —NMe$_2$, —NMe(halomethyl) and/or —N(halomethyl)$_2$ groups.

5. The compound or pharmaceutically acceptable salt or solvate thereof, as claimed in claim 1, wherein $R^X$ and $R^Y$ do not comprise an oxygen atom that is directly attached to a $sp^2$ hybridised atom.

6. The compound or pharmaceutically acceptable salt or solvate thereof, as claimed in claim 1, wherein the group:

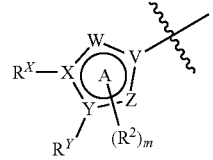

including any optional substituents, contains from 8 to 17 atoms other than hydrogen or halogen.

7. The compound or pharmaceutically acceptable salt or solvate thereof, as claimed in claim 1, wherein:
(i) Q is O; and/or
(ii) each $R^2$ is independently selected from
halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SORB; —SO$_2$H; —SO$_2$R$^\beta$; —SO$_2$NH$_2$; —SO$_2$NHR$^\beta$; SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; R$^\alpha$—SO$_2$NHR$^\beta$; —R$^\alpha$—SO$_2$N(R$^\beta$)$_2$; —NH$_2$; NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;
wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

8. The compound or pharmaceutically acceptable salt or solvate thereof, as claimed in claim 1, wherein R$^1$ is an aryl or a heteroaryl group, wherein the aryl or the heteroaryl group is substituted at the α-position, and wherein R$^1$ may optionally be further substituted, and optionally wherein:

(i) R$^1$ is an aryl or a heteroaryl group, wherein the aryl or the heteroaryl group is substituted at the α and α' positions, and wherein R$^1$ may optionally be further substituted; or (ii) R$^1$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein R$^1$ may optionally be further substituted.

9. The compound or pharmaceutically acceptable salt or solvate thereof, as claimed in claim 1, wherein the substituent at the α-position of the cyclic group of R$^1$ is a monovalent heterocyclic group or a monovalent aromatic group, wherein a ring atom of the heterocyclic or aromatic group is directly attached to the α-ring atom of the cyclic group, wherein the heterocyclic or aromatic group may optionally be substituted, and wherein the cyclic group may optionally be further substituted.

10. The compound or pharmaceutically acceptable salt or solvate thereof, as claimed in claim 1, wherein R$^1$ is a cyclic group substituted at the α and α' positions, wherein R$^1$ may optionally be further substituted, and wherein optionally each substituent at the α and α' positions comprises a carbon atom.

11. The compound or pharmaceutically acceptable salt or solvate thereof, as claimed in claim 1, which is (a) a compound selected from the group consisting of:

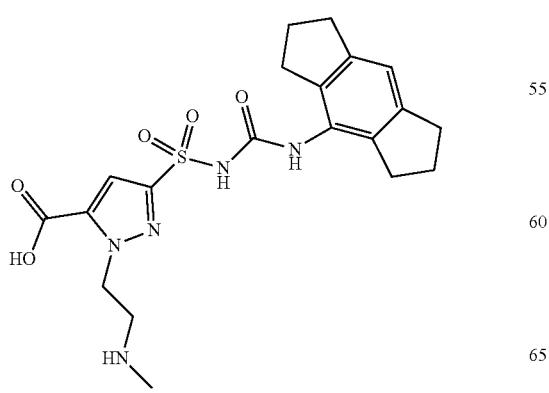

-continued

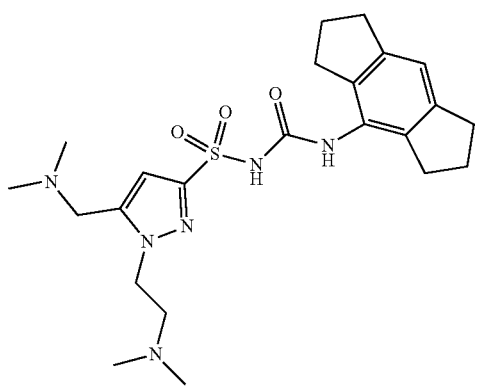

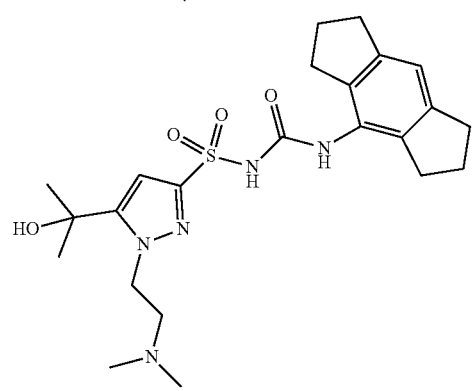

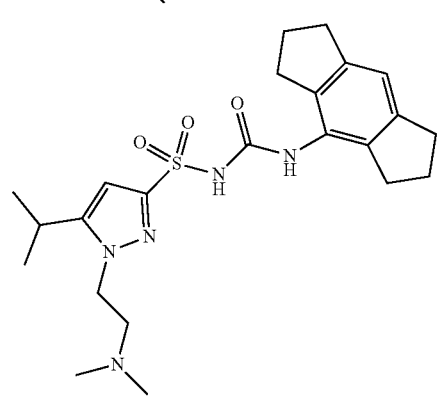

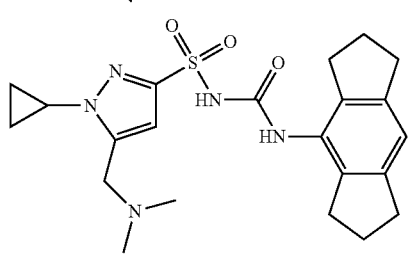

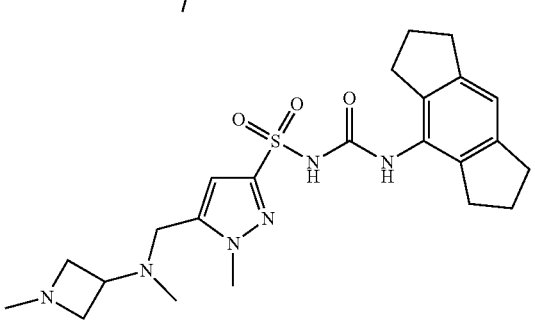

385
-continued
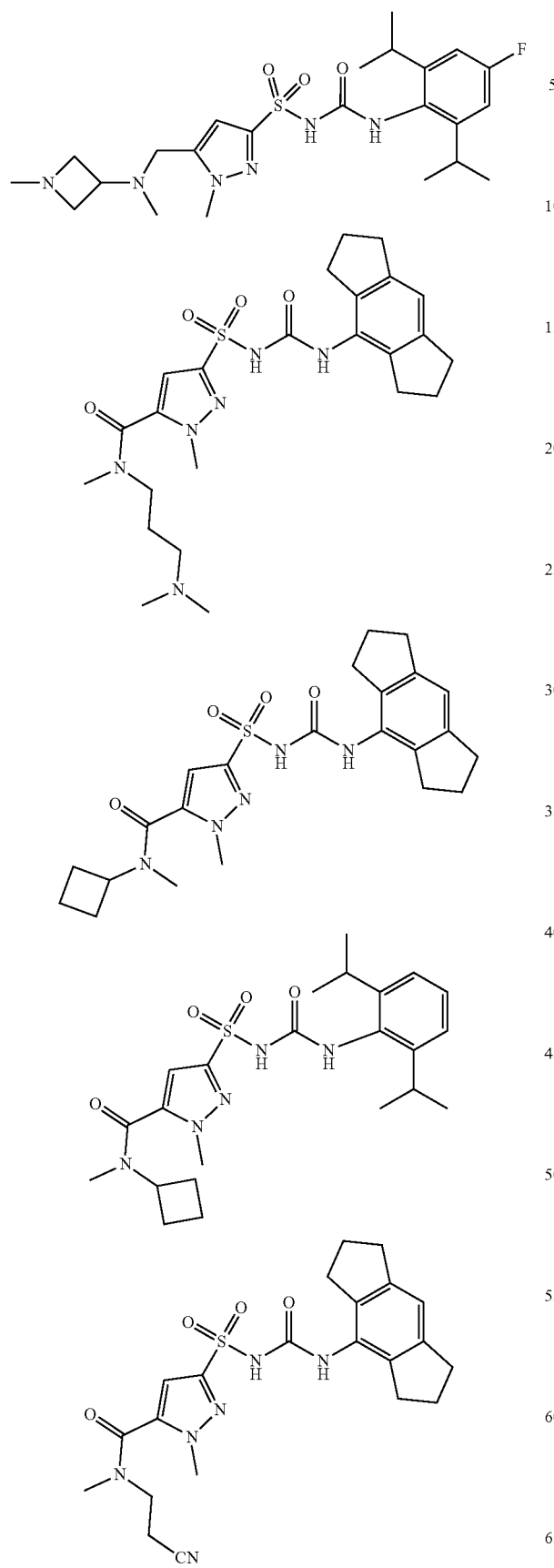
386
-continued
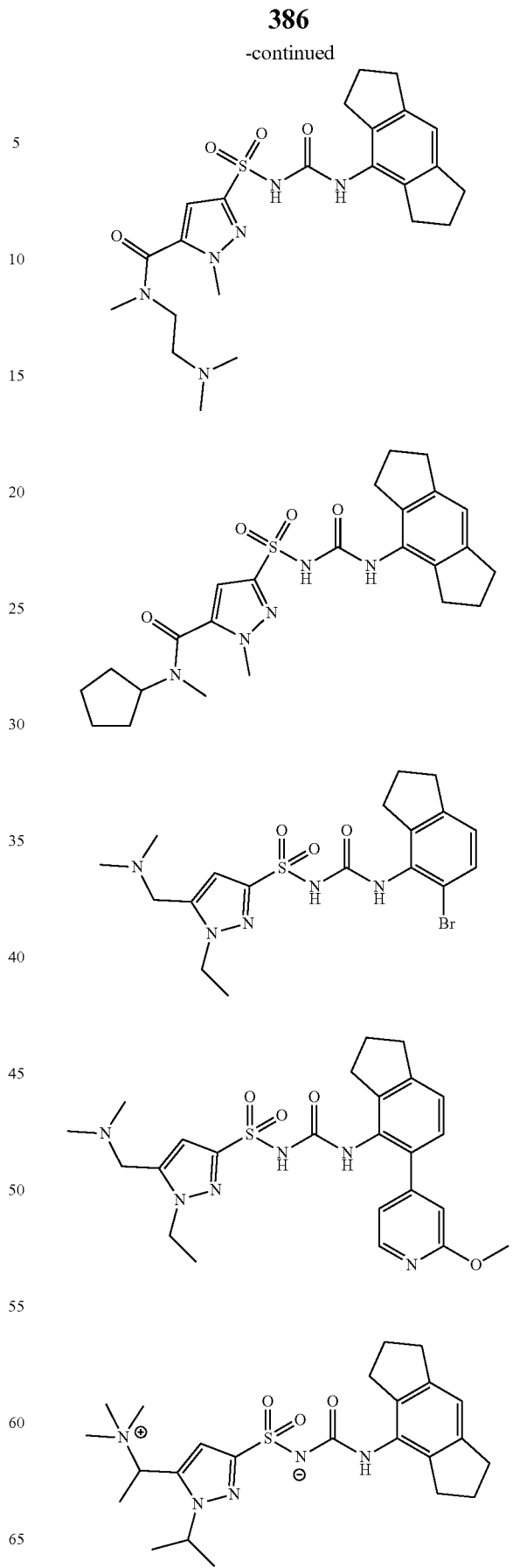

387
-continued
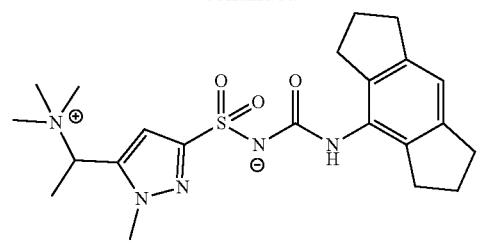
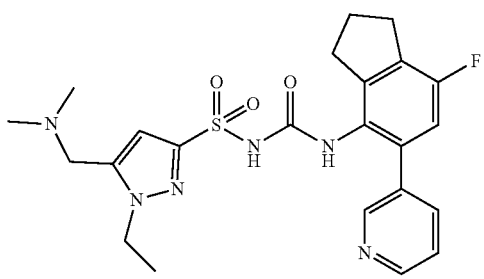
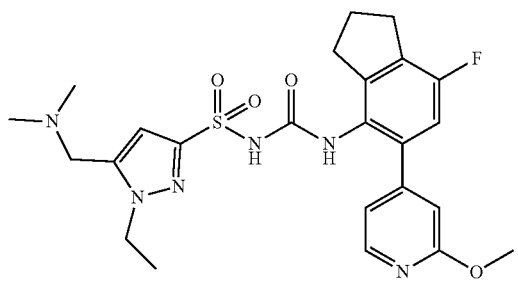
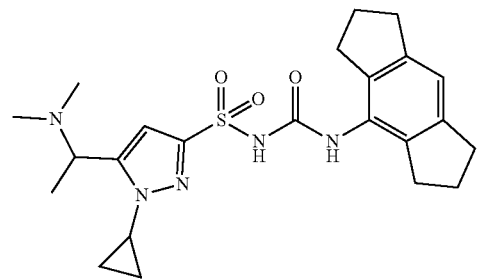
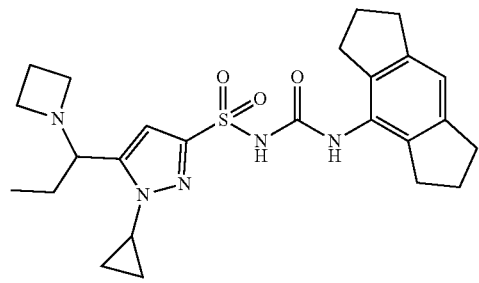
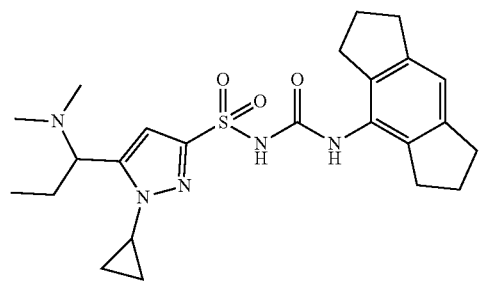
388
-continued
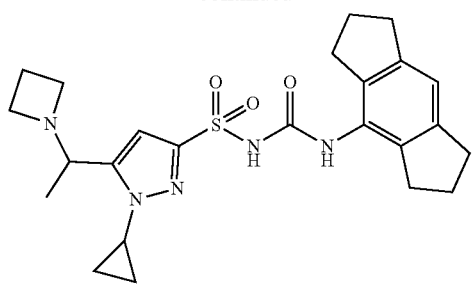
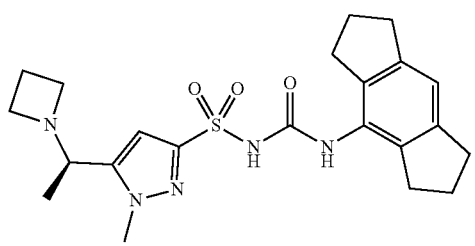
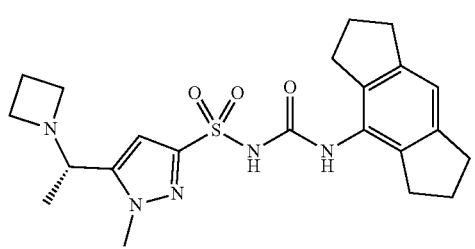
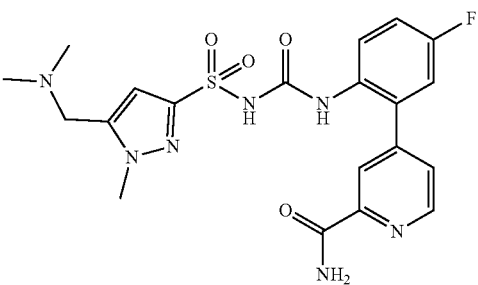
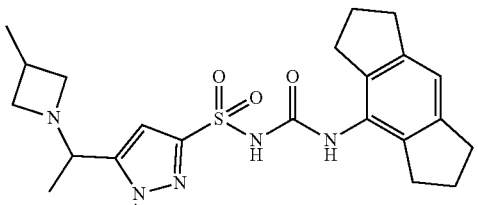
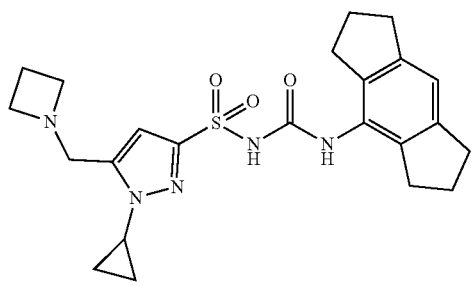

389
-continued
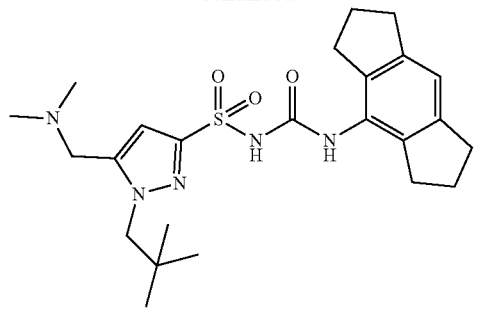
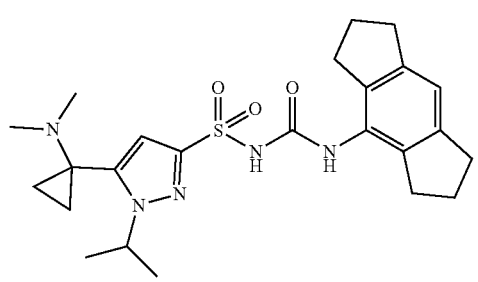
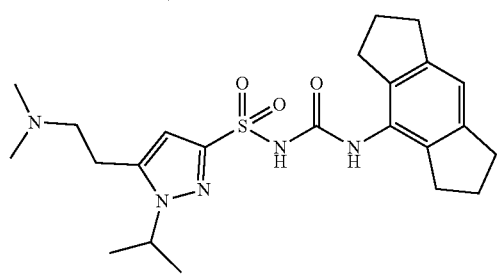
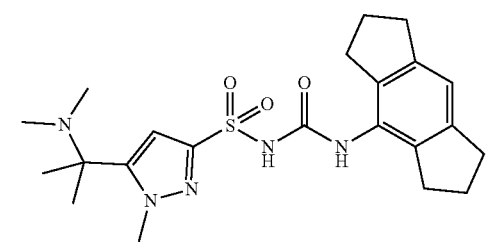
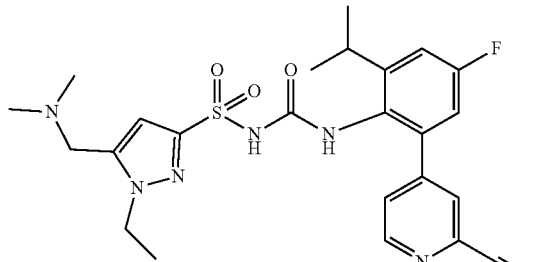
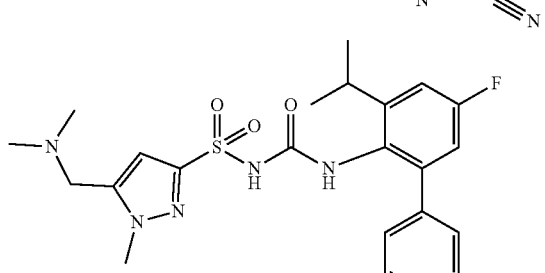
390
-continued
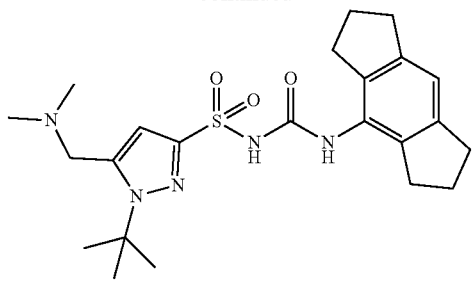
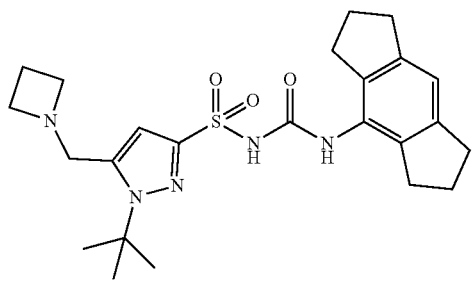
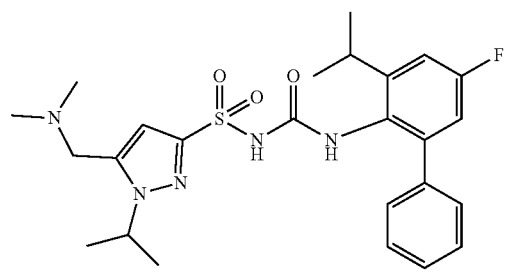
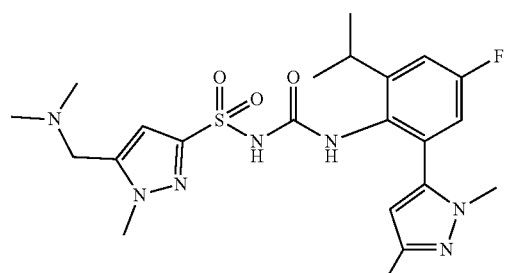
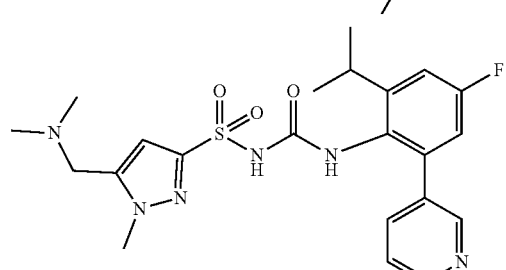
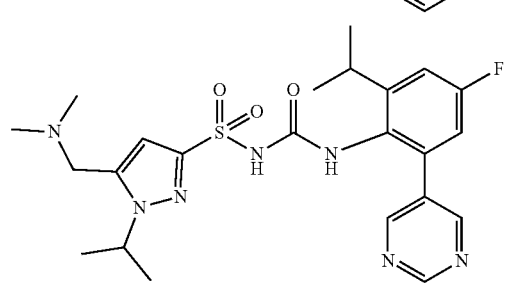

391
-continued
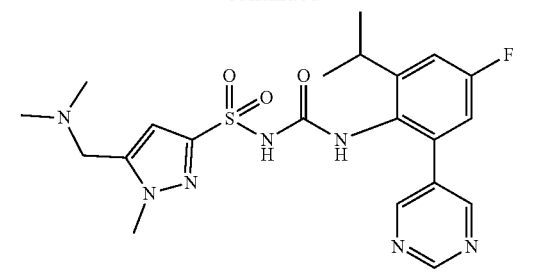
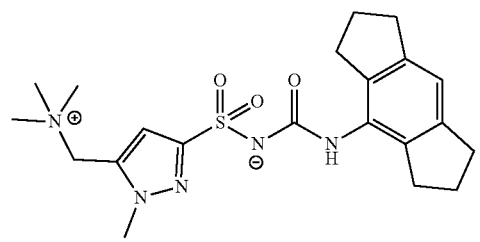
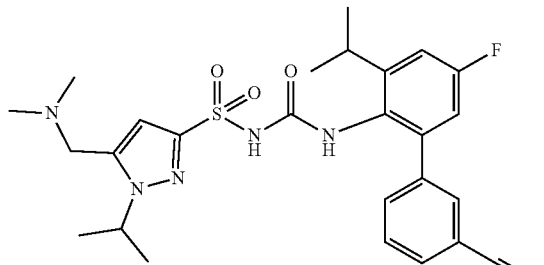
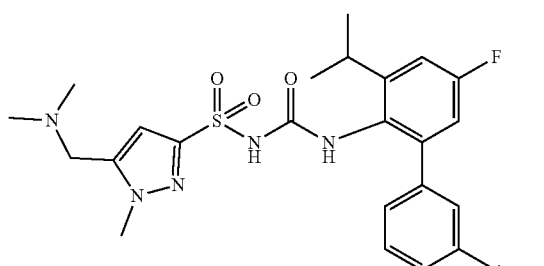
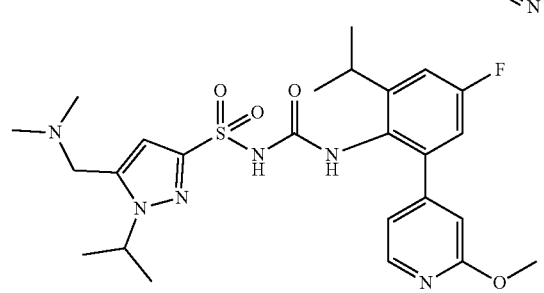
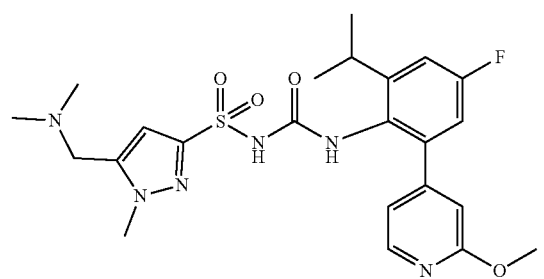
392
-continued
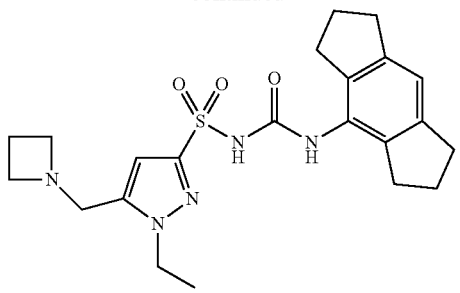
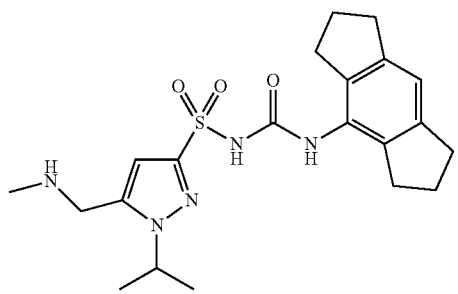
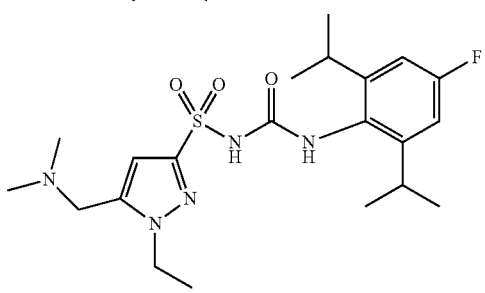
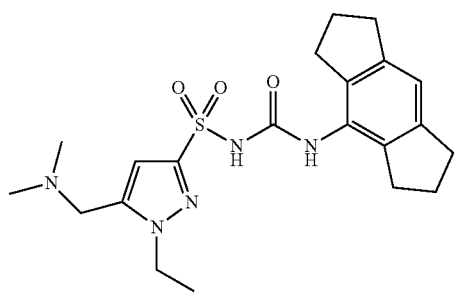
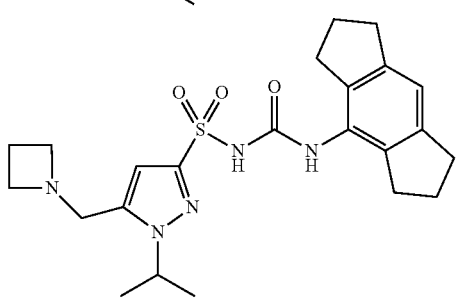
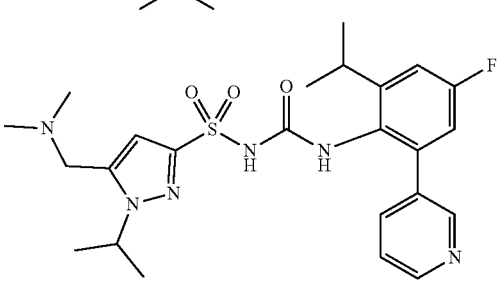

393 394
-continued -continued
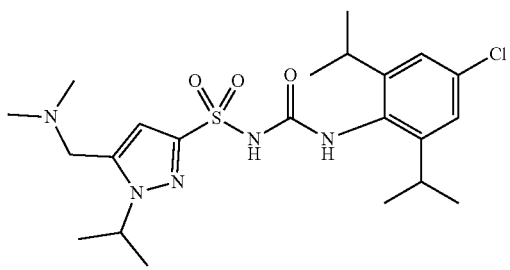
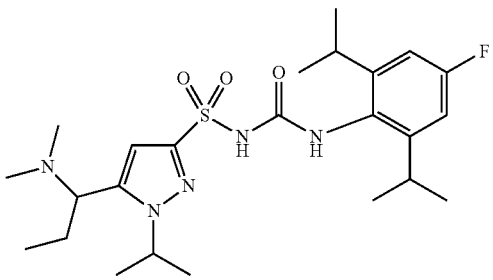

395
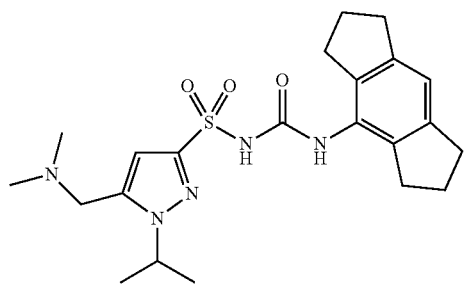
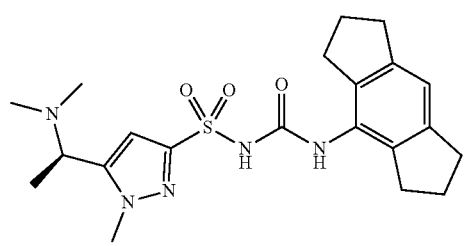
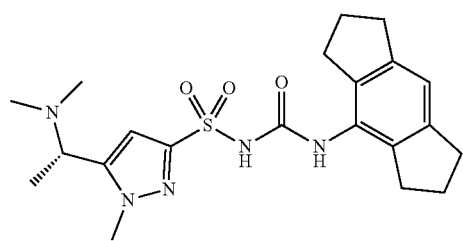
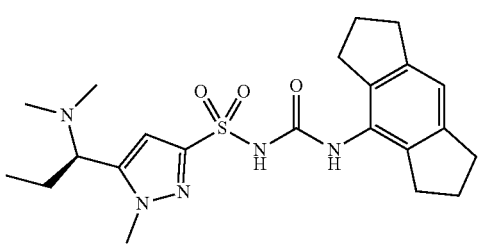
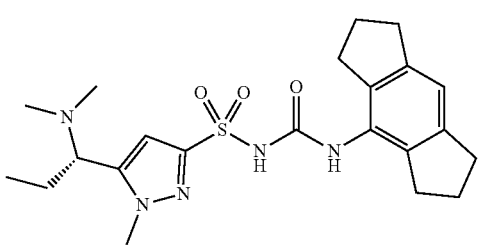
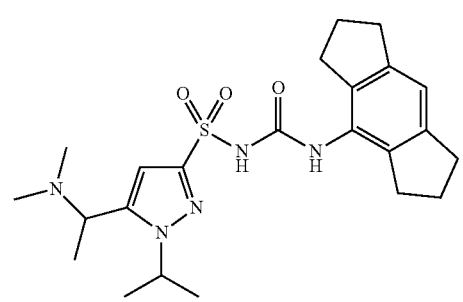
396
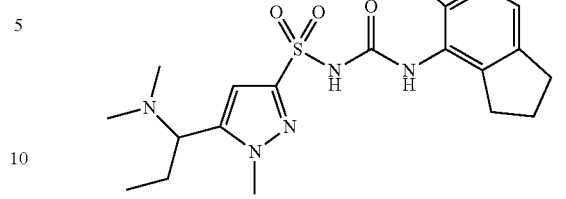
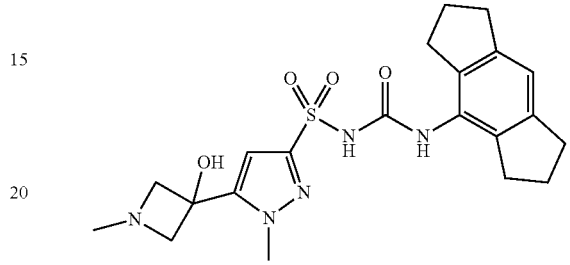
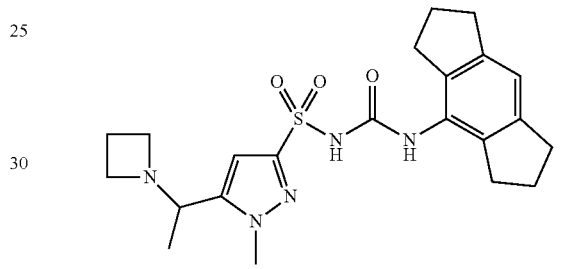
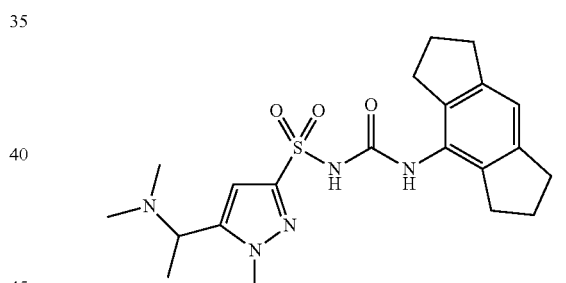
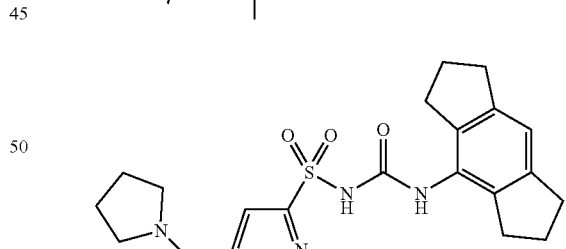
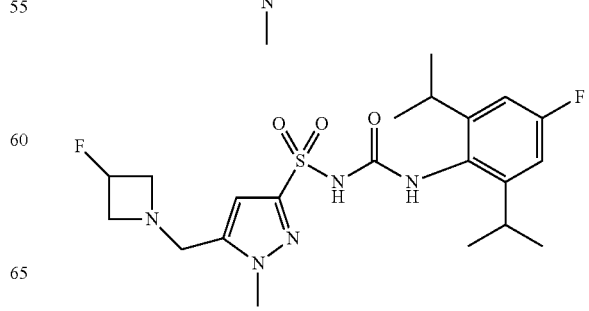

397
-continued
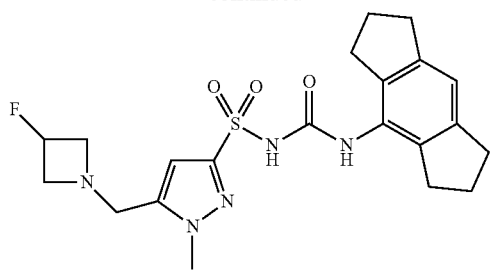
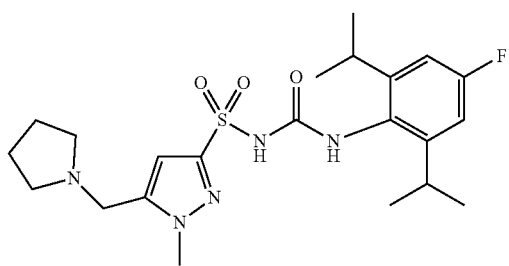
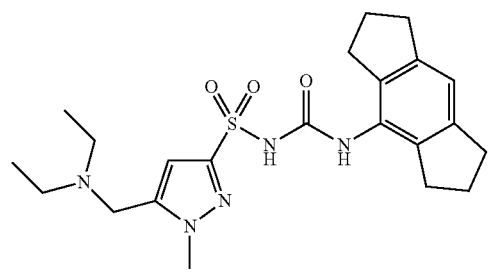
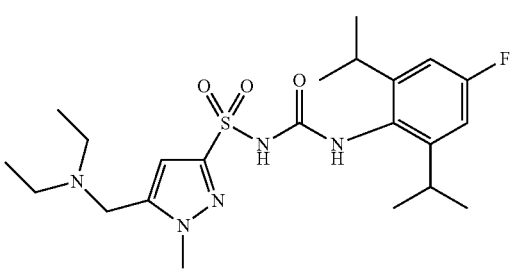
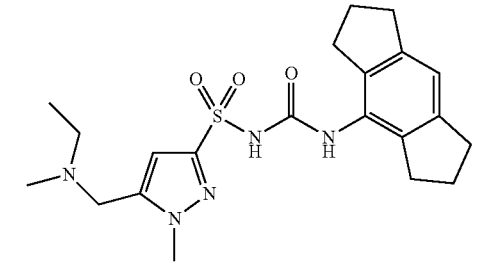
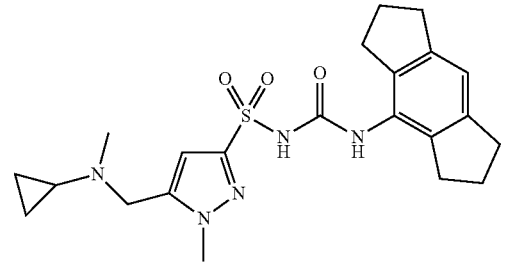
398
-continued
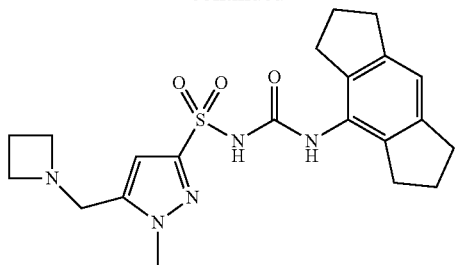
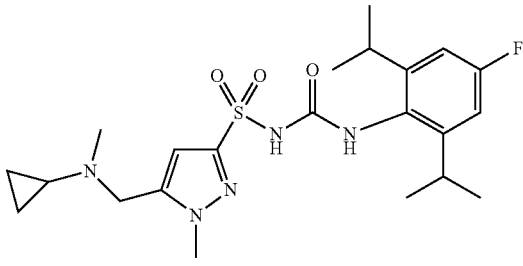
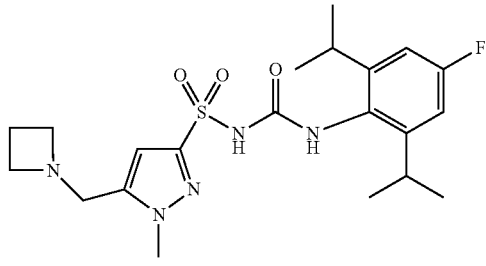
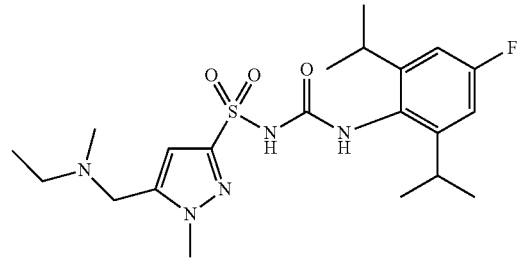
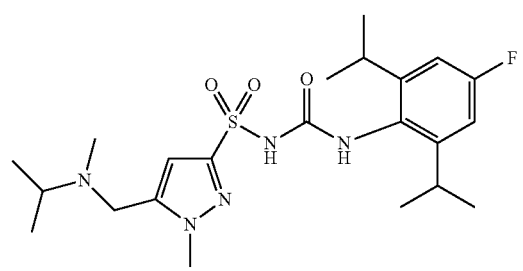
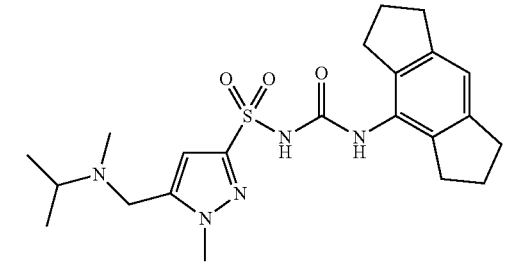

399
-continued
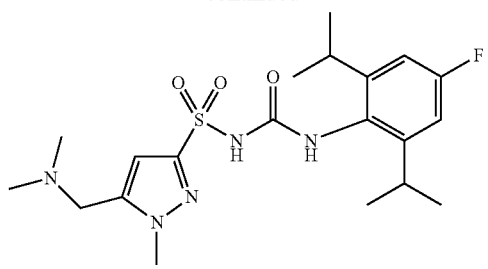
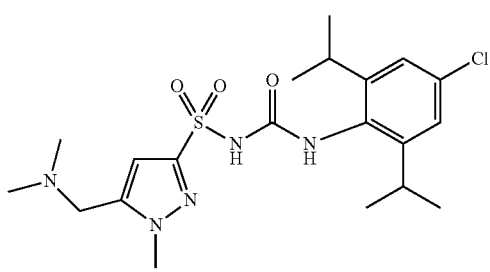
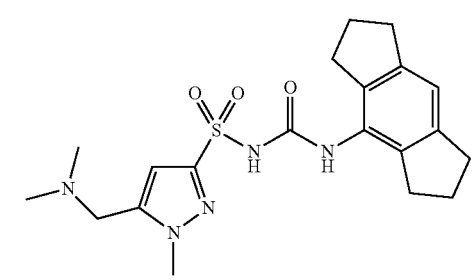
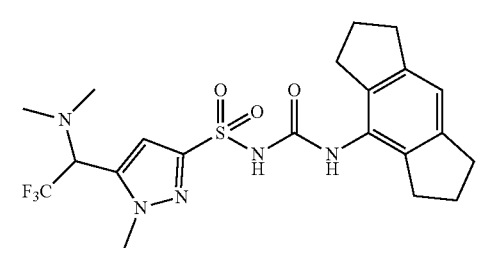
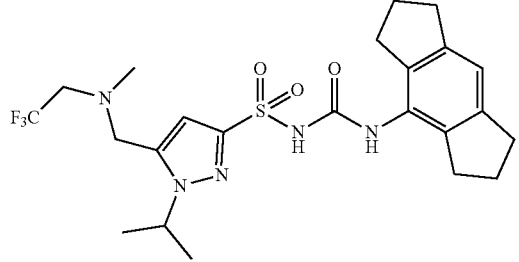
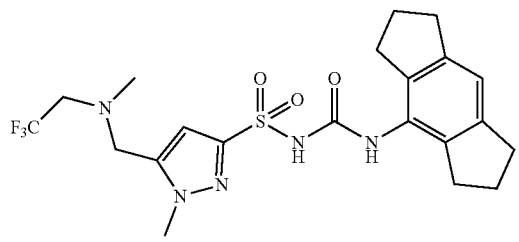
400
-continued
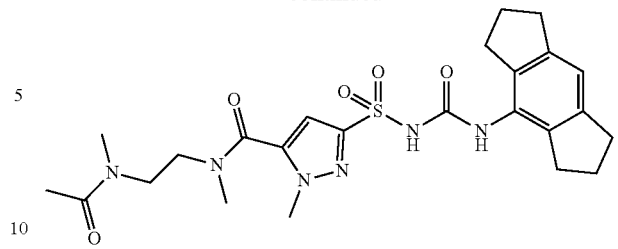
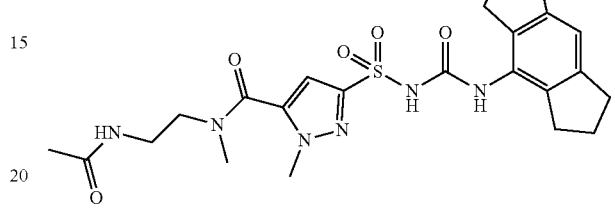
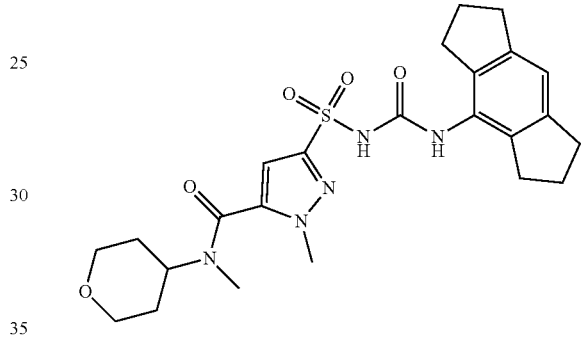
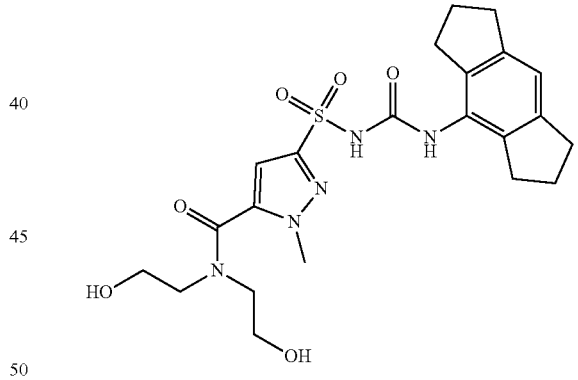
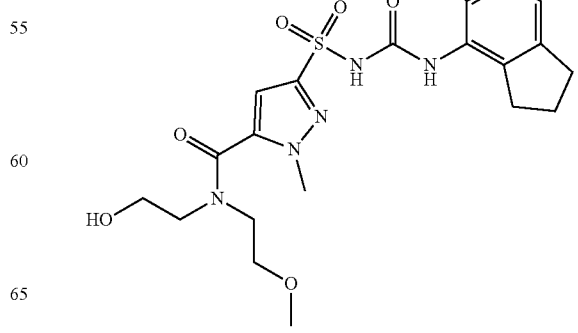

401
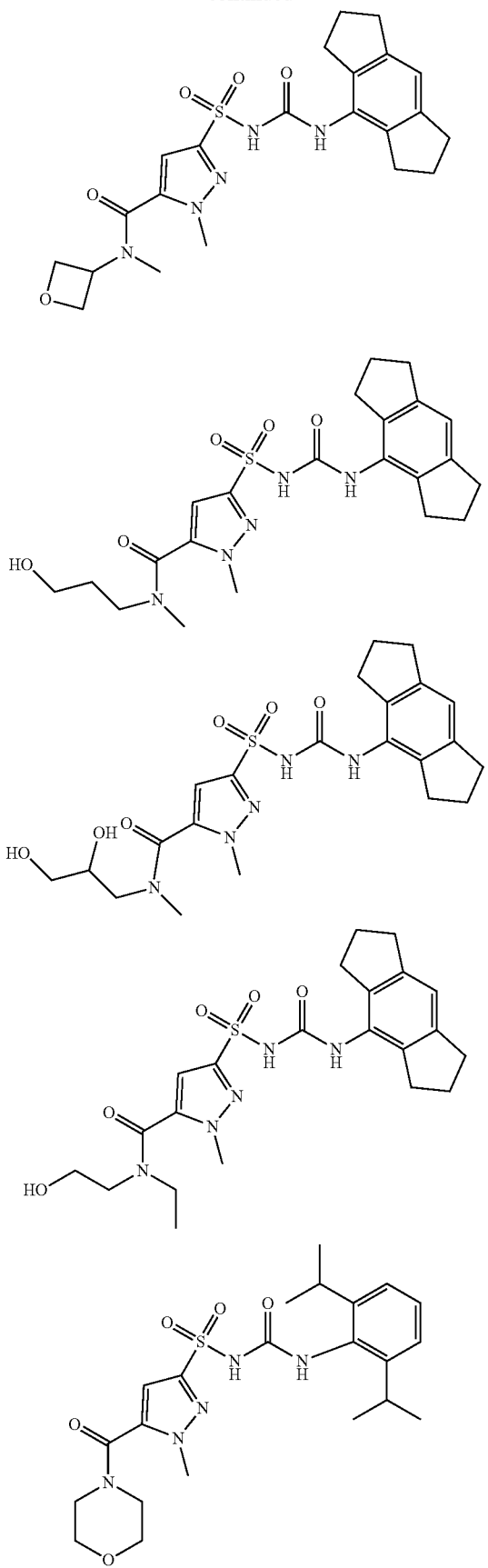
402
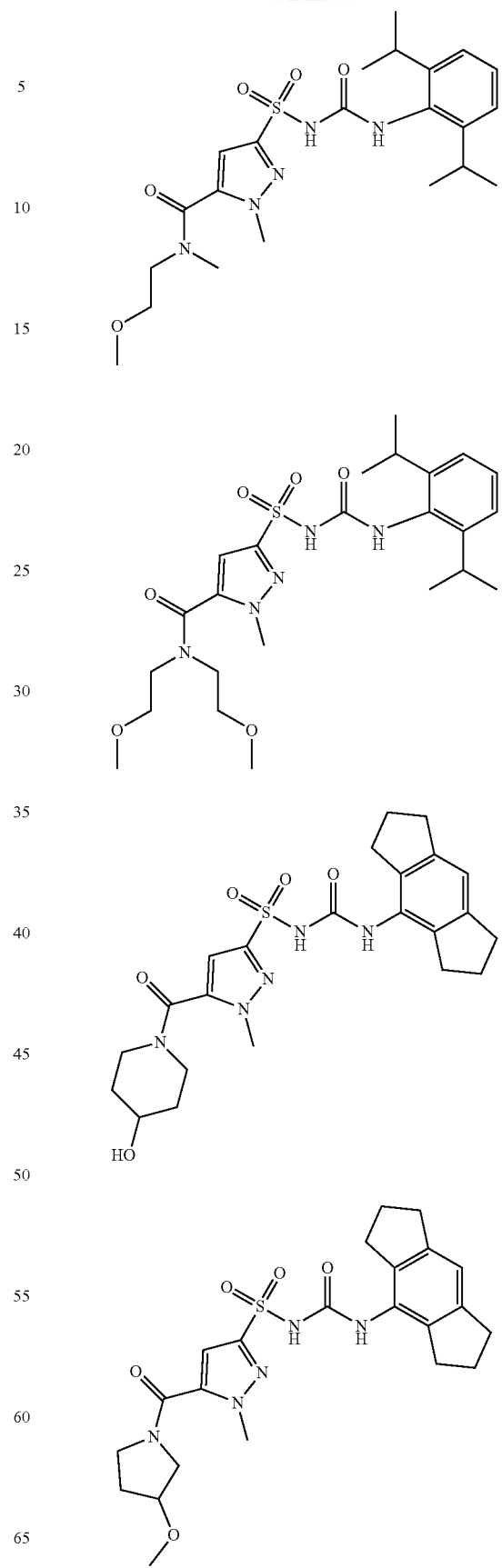

403
-continued
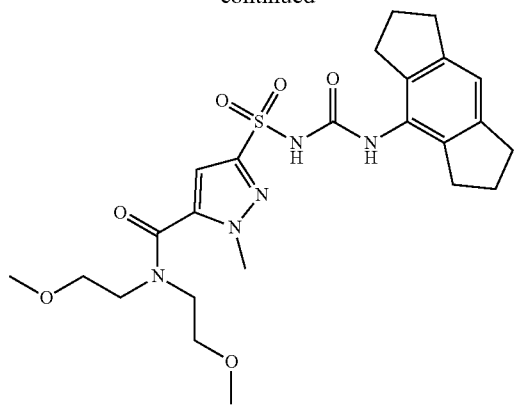
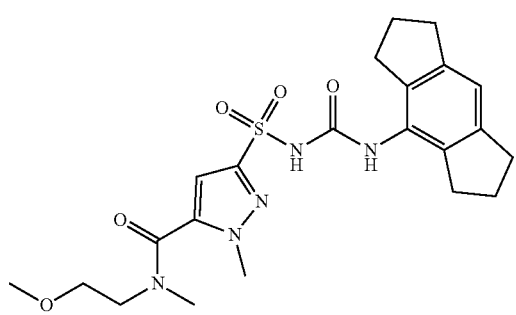
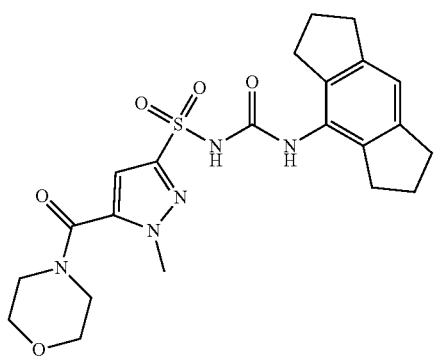
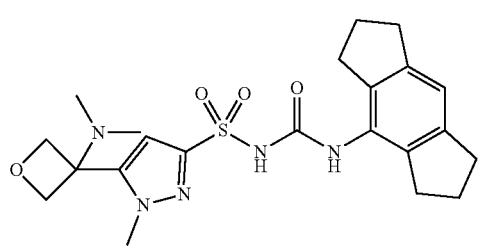
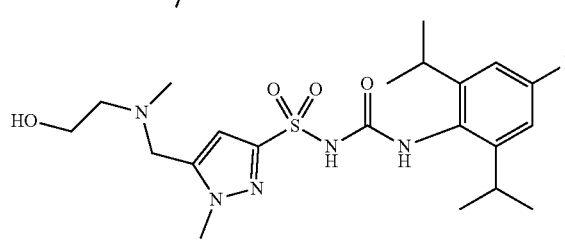
404
-continued
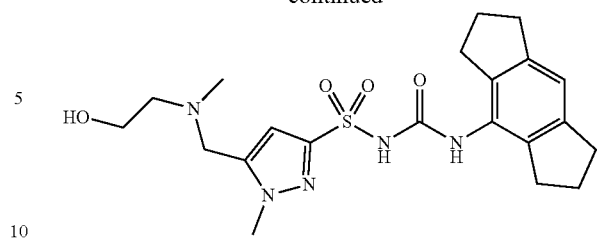
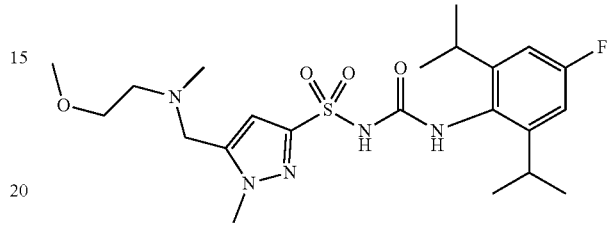
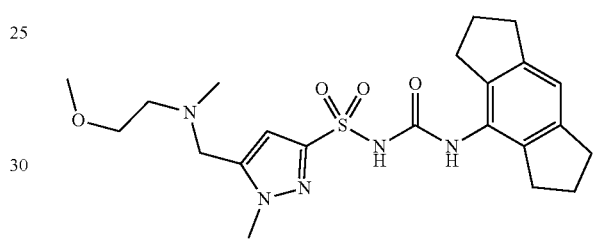
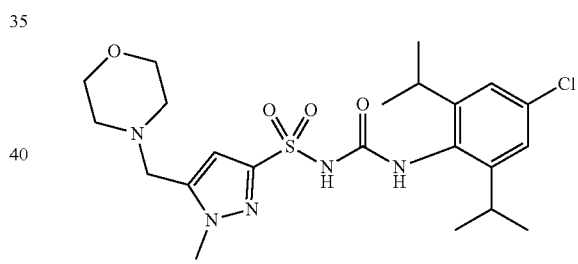
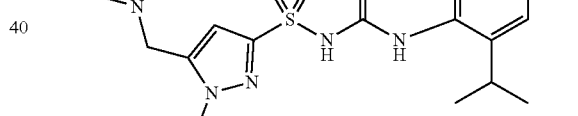
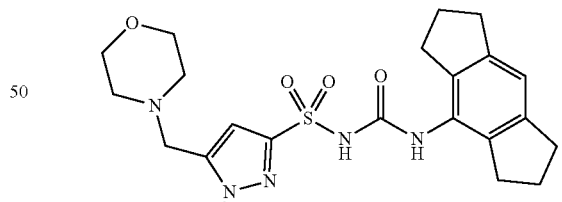
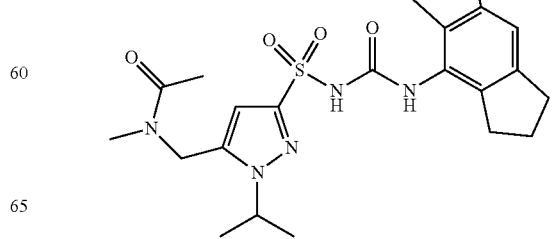

405
-continued
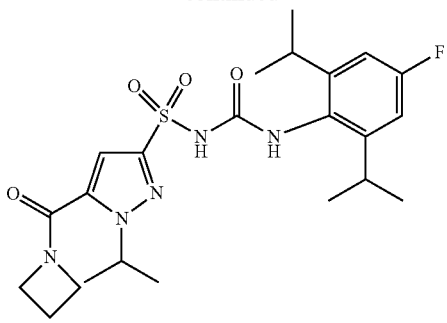
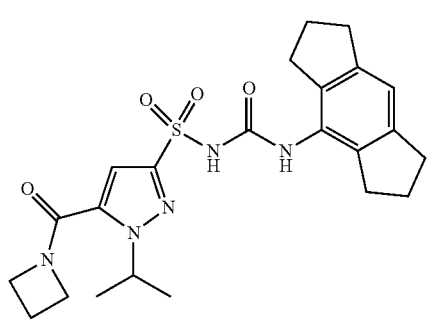
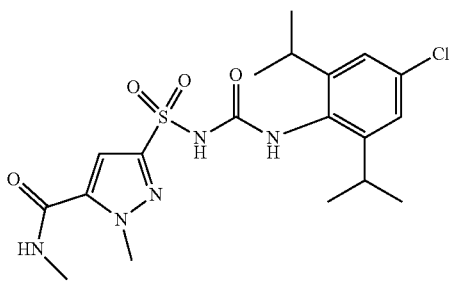
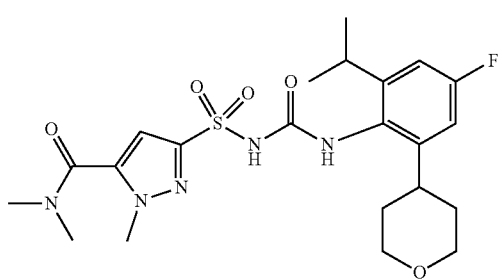
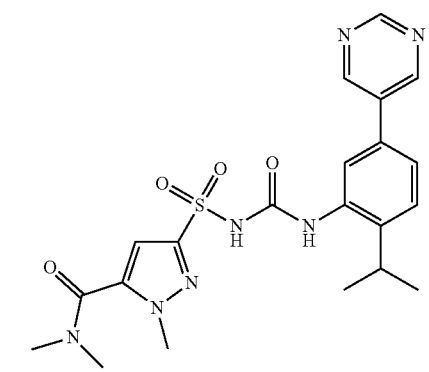
406
-continued
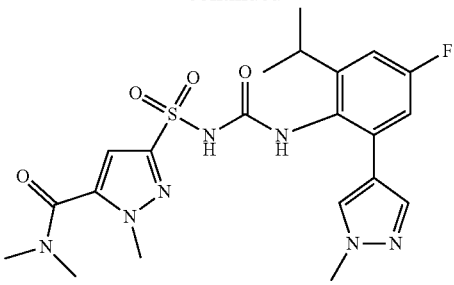
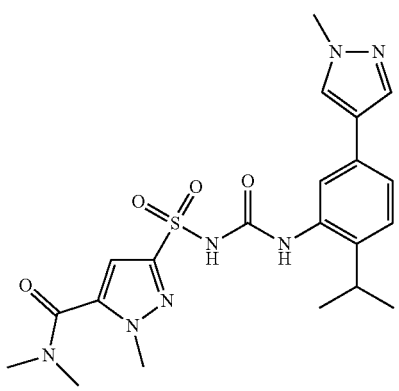
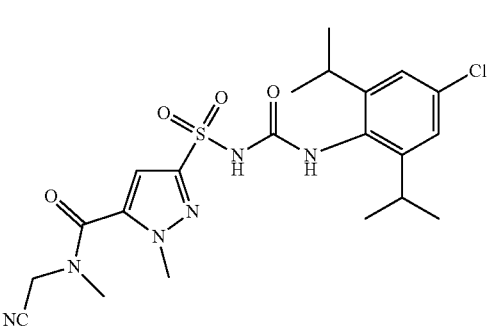
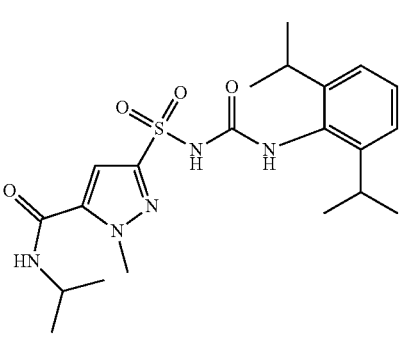
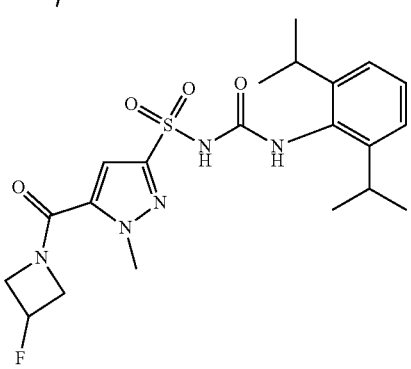

407
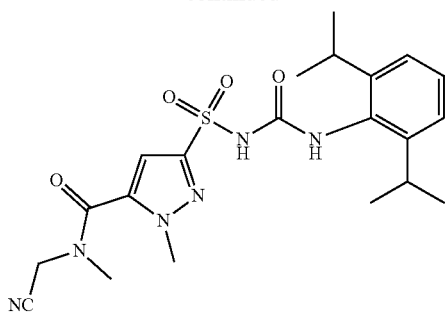
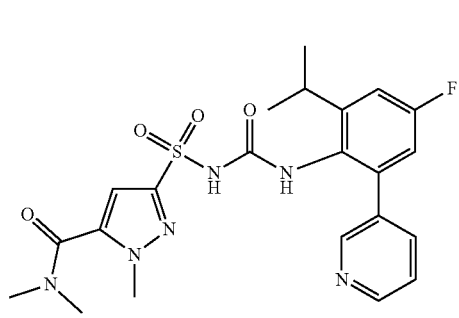
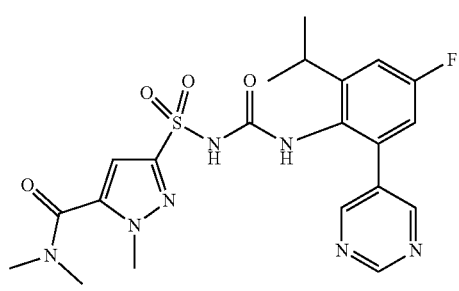
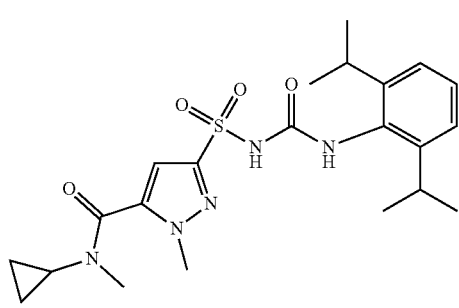
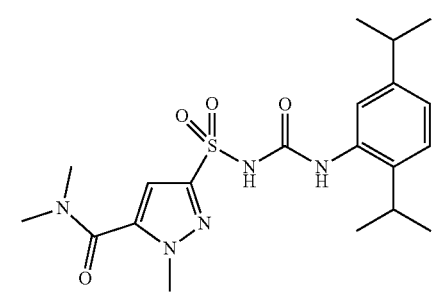
408
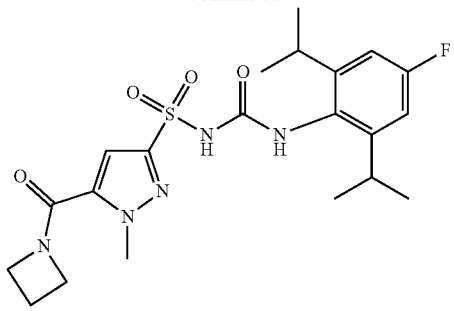
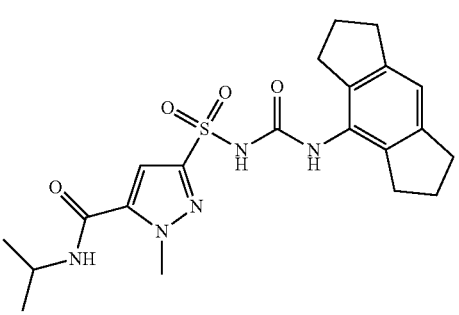
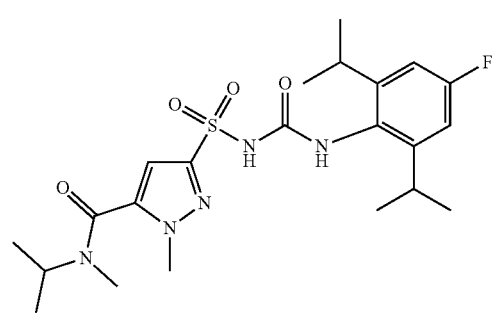
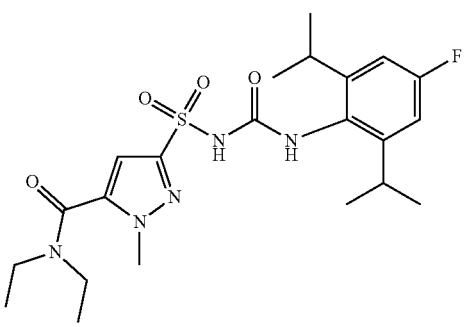
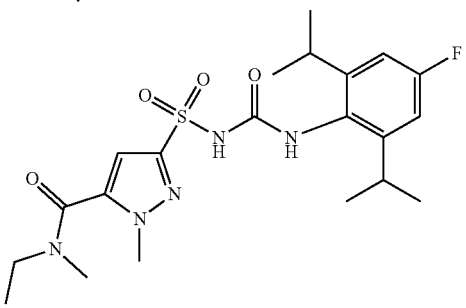

409
-continued
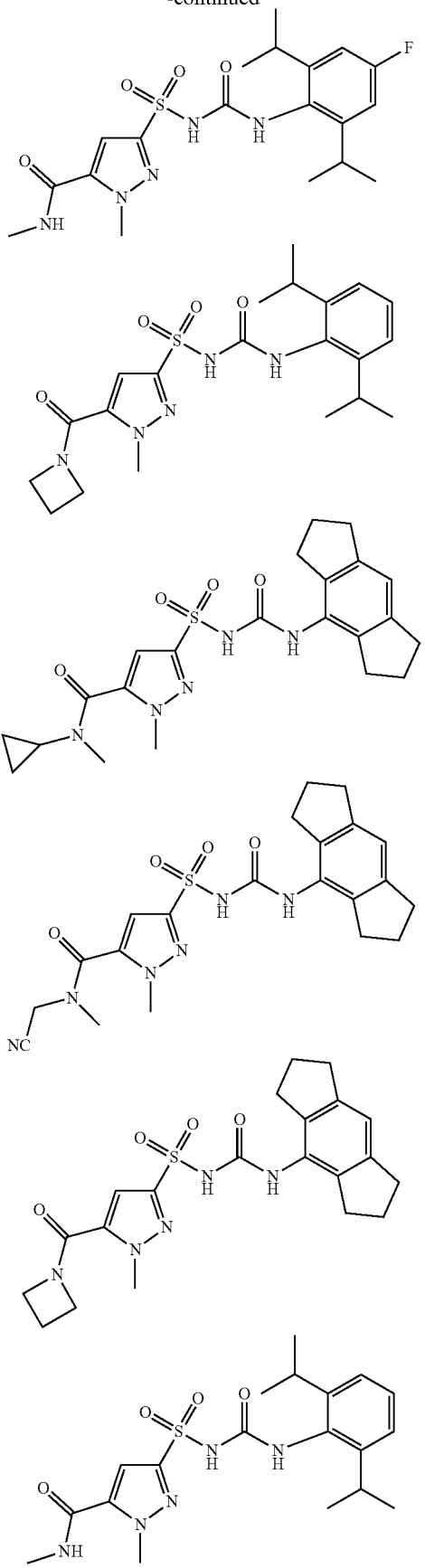
410
-continued
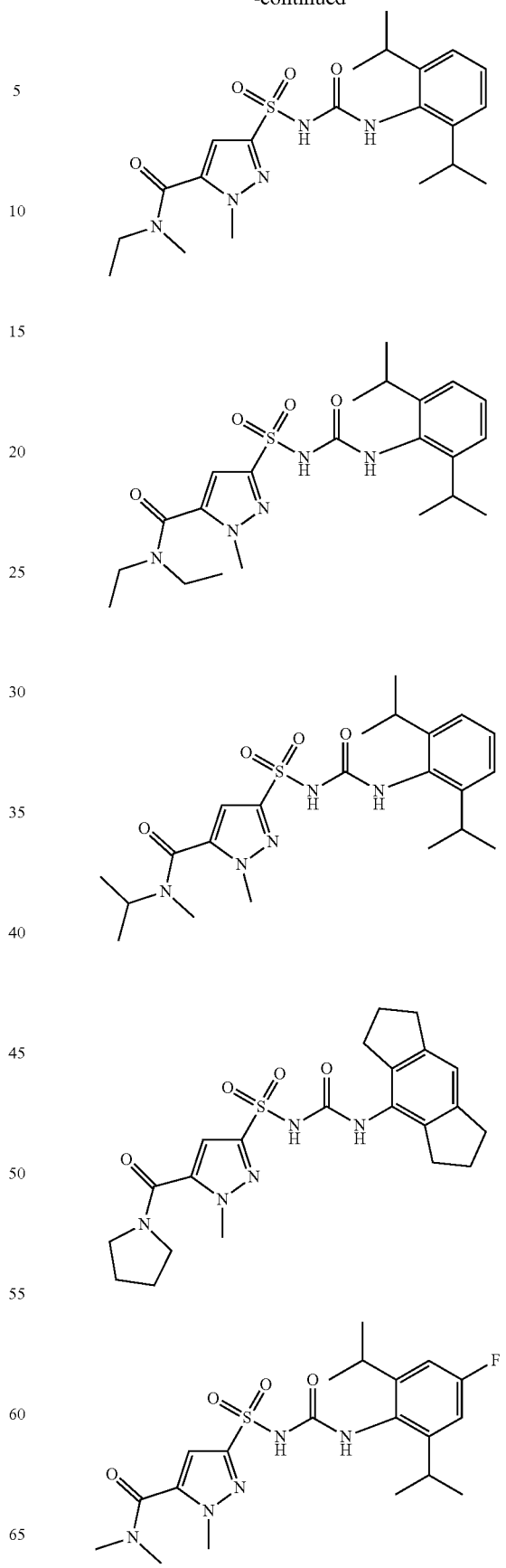

411
-continued
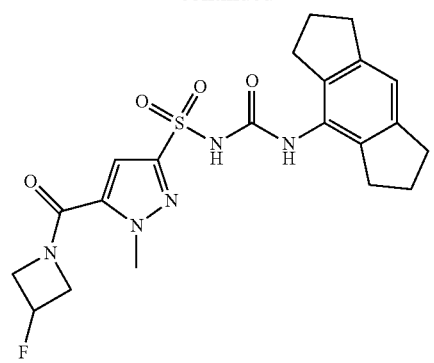
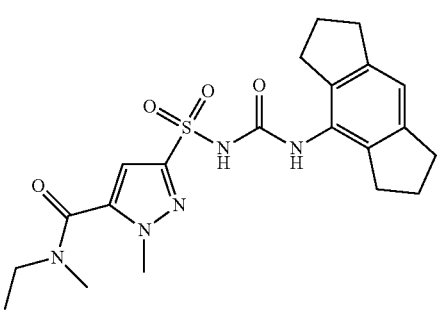
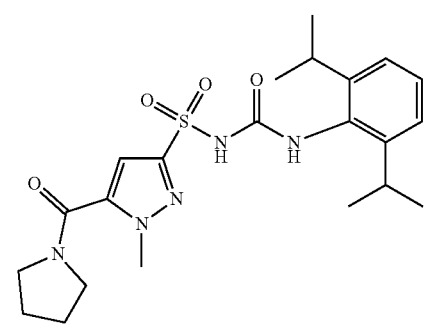
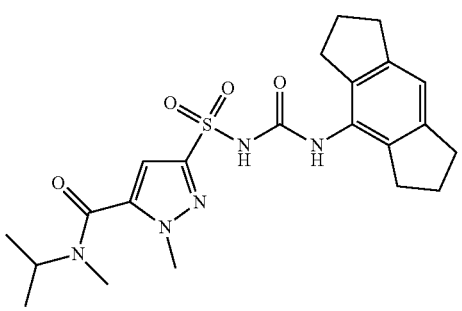
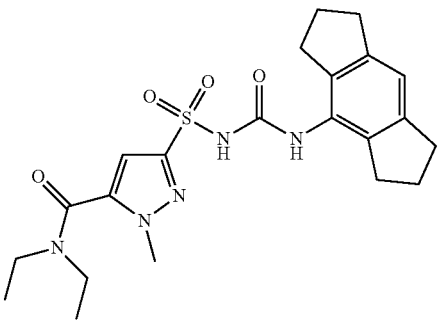
412
-continued
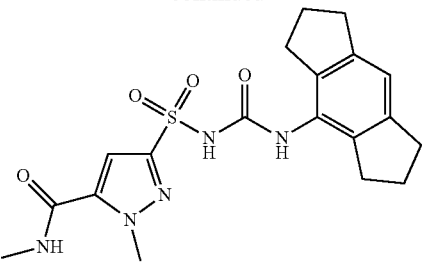
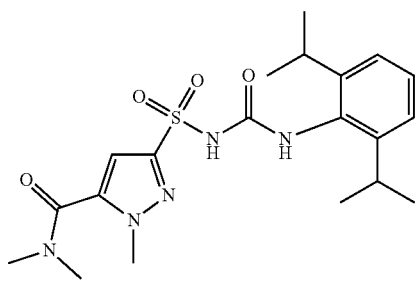
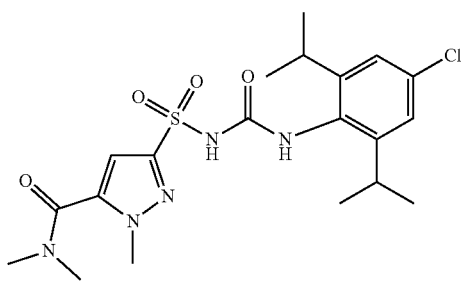
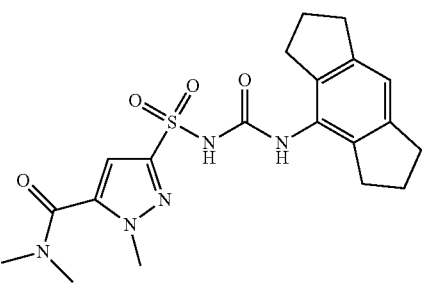
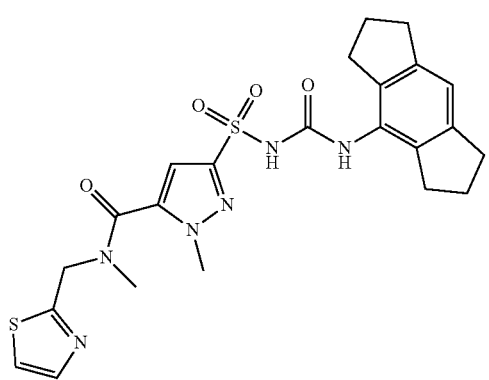

413
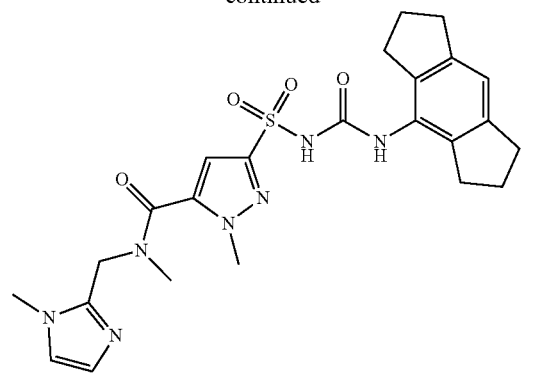
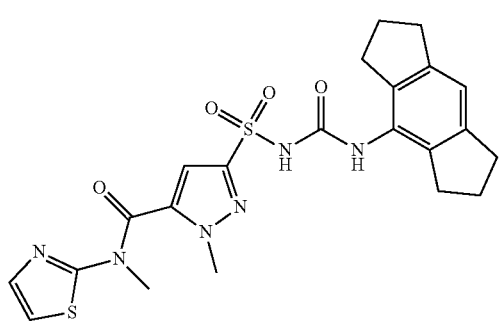
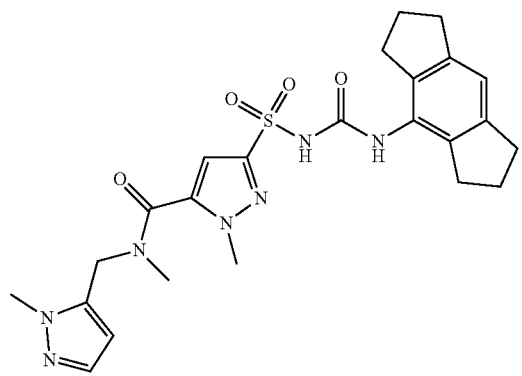
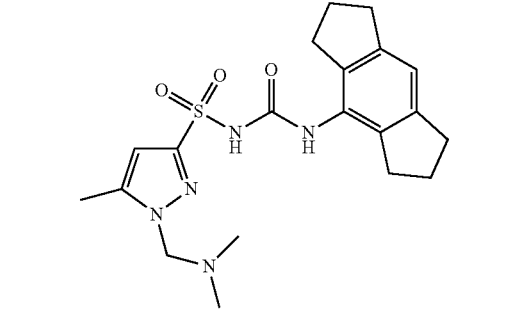
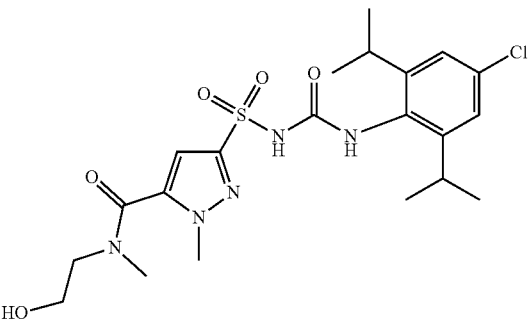
414
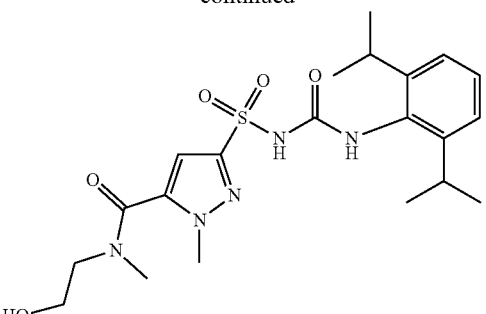
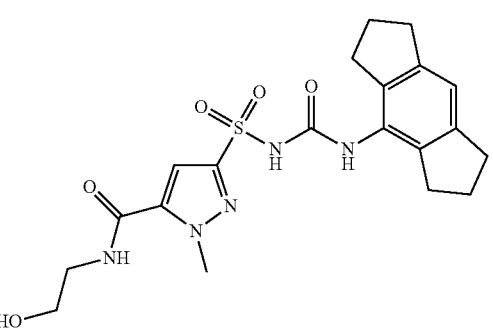
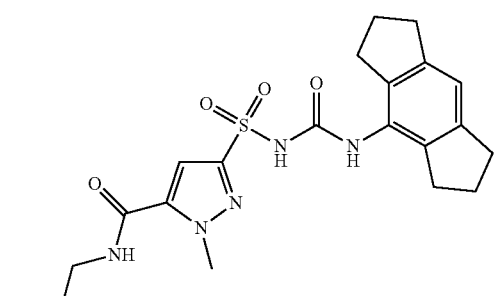
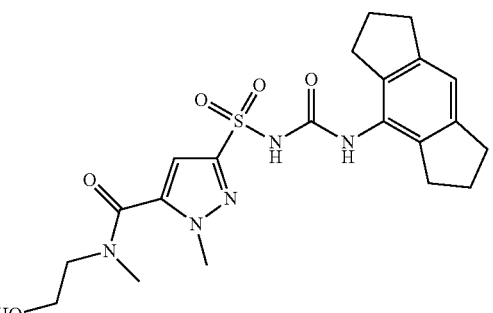
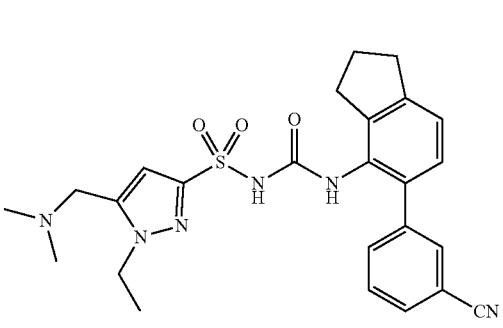

415
-continued
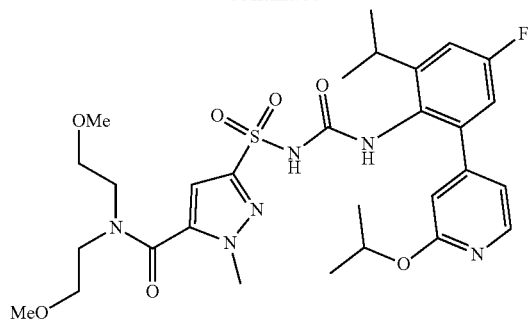
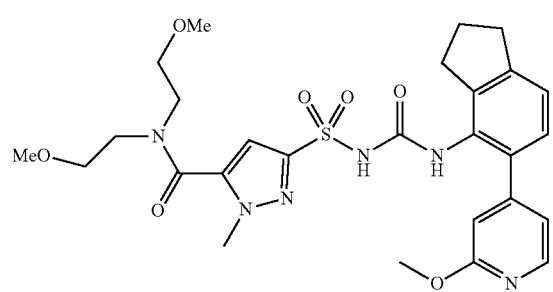
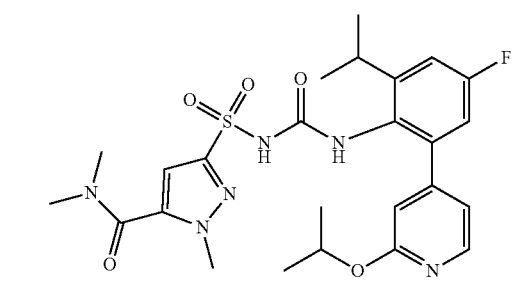
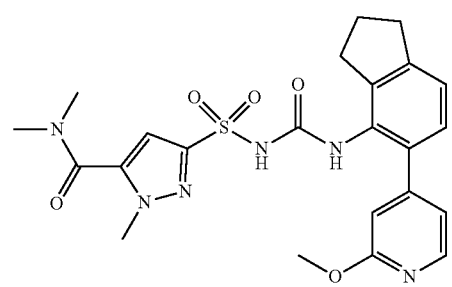
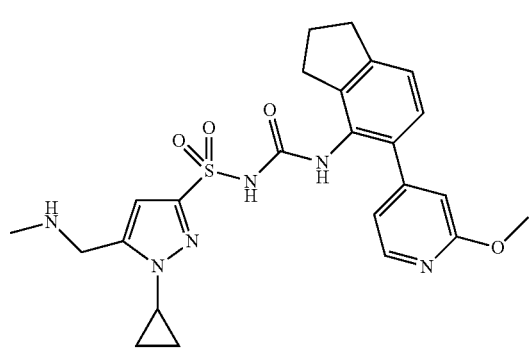
416
-continued
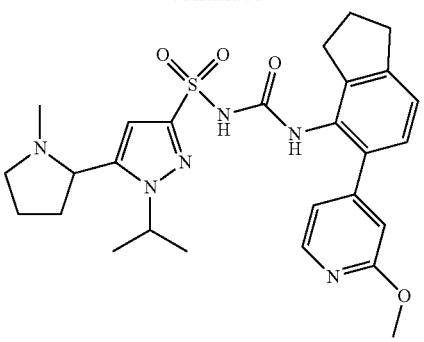
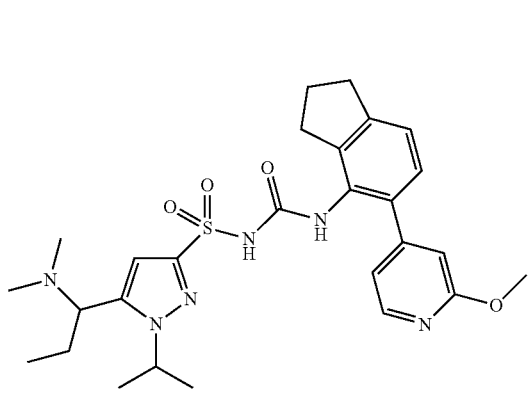
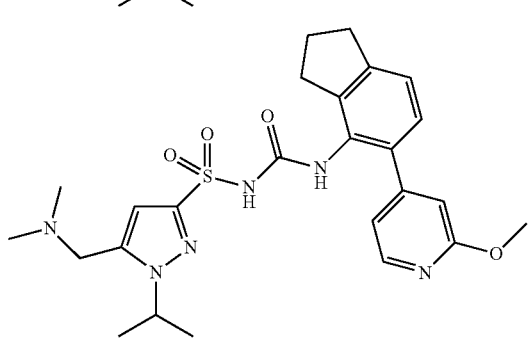
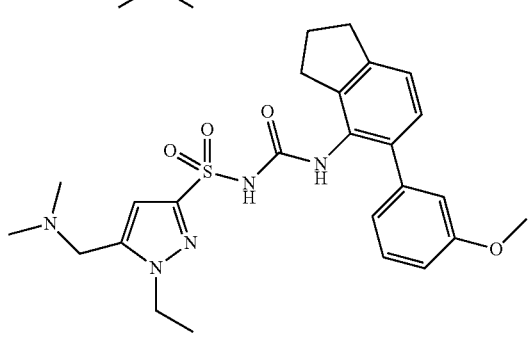
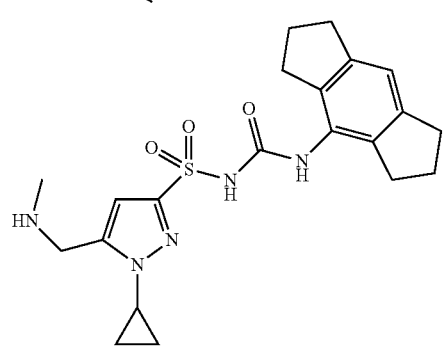

-continued

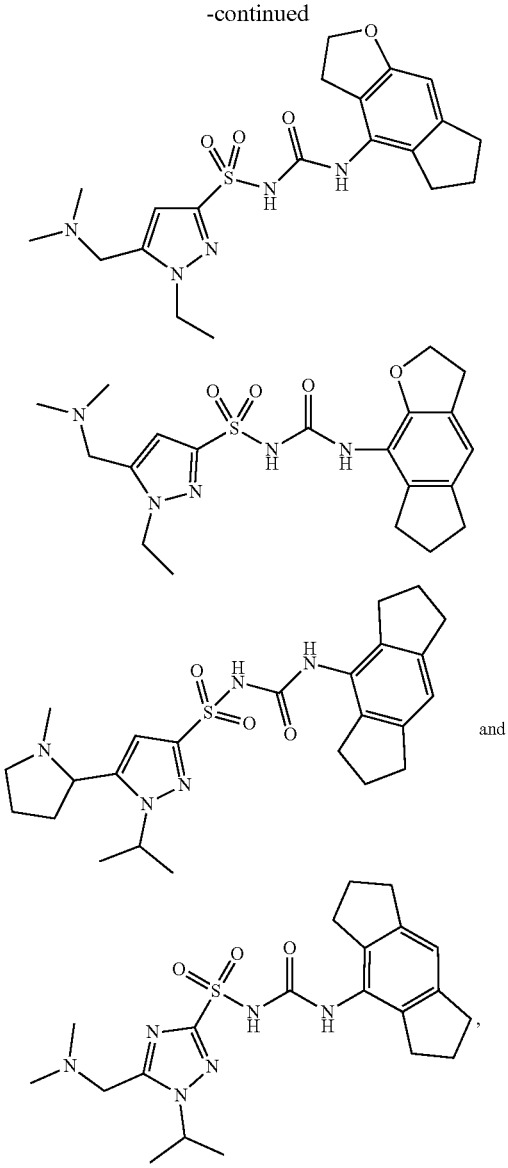

or (b) a pharmaceutically acceptable salt or solvate of the selected compound.

12. A pharmaceutical composition comprising the compound or the pharmaceutically acceptable salt or solvate thereof, as claimed in claim 1, and a pharmaceutically acceptable excipient.

13. A method of treating, or delaying onset or reducing risk of a disease, disorder or condition in a subject, the method comprising the step of administering an effective amount of the compound or the pharmaceutically acceptable salt or solvate thereof, as claimed in claim 1, to the subject, thereby treating or delaying onset or reducing risk of the disease, disorder or condition, wherein the disease, disorder or condition is responsive to NLRP3 inhibition.

14. The method as claimed in claim 13, wherein the disease, disorder or condition is selected from:
 (i) inflammation;
 (ii) an auto-immune disease;
 (iii) cancer;
 (iv) an infection;
 (v) a central nervous system disease;
 (vi) a metabolic disease;
 (vii) a cardiovascular disease;
 (viii) a respiratory disease;
 (ix) a liver disease;
 (x) a renal disease;
 (xi) an ocular disease;
 (xii) a skin disease;
 (xiii) a lymphatic condition;
 (xiv) a psychological disorder;
 (xv) graft versus host disease;
 (xvi) allodynia; and
 (xvii) any disease where an individual has been determined to carry a germline or somatic non-silent mutation in NLRP3.

15. The method as claimed in claim 13, wherein the disease, disorder or condition is selected from:
 (i) cryopyrin-associated periodic syndromes (CAPS);
 (ii) Muckle-Wells syndrome (MWS);
 (iii) familial cold autoinflammatory syndrome (FCAS);
 (iv) neonatal onset multisystem inflammatory disease (NOMID);
 (v) familial Mediterranean fever (FMF);
 (vi) pyogenic arthritis, pyoderma gangrenosum and acne syndrome (PAPA);
 (vii) hyperimmunoglobulinemia D and periodic fever syndrome (HIDS);
 (viii) Tumour Necrosis Factor (TNF) Receptor-Associated Periodic Syndrome (TRAPS);
 (ix) systemic juvenile idiopathic arthritis;
 (x) adult-onset Still's disease (AOSD);
 (xi) relapsing polychondritis;
 (xii) Schnitzler's syndrome;
 (xiii) Sweet's syndrome;
 (xiv) Behcet's disease;
 (xv) anti-synthetase syndrome;
 (xvi) deficiency of interleukin 1 receptor antagonist (DIRA); and
 (xvii) haploinsufficiency of A20 (HA20).

16. A method of inhibiting NLRP3 in a subject, the method comprising administering the compound or the pharmaceutically acceptable salt or solvate thereof, as claimed in claim 1, to the subject thereby inhibiting NLRP3.

17. A method of analysing inhibition of NLRP3 or an effect of inhibition of NLRP3 by a compound, comprising contacting a cell or non-human animal with the compound or the pharmaceutically acceptable salt or solvate thereof, as claimed in claim 1, and analysing inhibition of NLRP3 or an effect of inhibition of NLRP3 in the cell or non-human animal by the compound.

18. The method as claimed in claim 13, wherein the compound or the pharmaceutically acceptable salt or solvate thereof is administered as a pharmaceutical composition further comprising a pharmaceutically acceptable excipient.

19. The compound or the pharmaceutically acceptable salt or solvate thereof, as claimed in claim 1, wherein $R^X$ and $R^Y$ do not comprise a nitrogen atom that is directly attached to a $sp^2$ hybridised atom.

20. The compound or the pharmaceutically acceptable salt or solvate thereof, as claimed in claim 1, wherein $R^X$ and $R^Y$ contain only atoms selected from the group consisting of carbon, hydrogen, nitrogen and halogen atoms.

21. The compound or the pharmaceutically acceptable salt or solvate thereof, as claimed in claim 1, wherein:
 Q is O;
 V is C, X and Y are each independently selected from C and N, and W and Z are each independently selected from N, NH and CH, provided that at least one of W, X, Y and Z is C or CH, and at least two of W, X, Y and Z are N or NH;

$R^X$ is a saturated hydrocarbyl group, wherein the hydrocarbyl group is straight-chained or branched, or is or includes cyclic groups, wherein the hydrocarbyl group may optionally be substituted with one or more groups selected from halo, —CN, —OH, —NH$_2$ and oxo (=O), wherein the hydrocarbyl group includes at least one heteroatom N in its carbon skeleton, and wherein the hydrocarbyl group may optionally include one or two further heteroatoms independently selected from N and O in its carbon skeleton;

$R^Y$ is a saturated hydrocarbyl group, wherein the saturated hydrocarbyl group may be straight-chained or branched, or is or includes cyclic groups, wherein the saturated hydrocarbyl group may optionally be substituted with one or more groups selected from halo, —CN, —OH, —NH$_2$ and oxo (=O), and wherein the saturated hydrocarbyl group may optionally include one or two heteroatoms N or O in its carbon skeleton;

$R^X$ contains from 1 to 11 atoms other than hydrogen or halogen;

$R^Y$ contains from 1 to 11 atoms other than hydrogen or halogen;

m is 0; and $R^1$ is phenyl or a 5- or 6-membered heteroaryl group, wherein (i) the phenyl or 5- or 6-membered heteroaryl group is substituted at the α position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and the phenyl or 5- or 6-membered heteroaryl group is further substituted at the α' position with a substituent selected from —$R^{44}$, —$OR^{44}$ and —$COR^{44}$, wherein $R^{44}$ is selected from a $C_1$-$C_6$ alkyl, $C_2$-$C_6$ alkenyl, $C_2$-$C_6$ alkynyl or $C_2$-$C_6$ cyclic group and wherein $R^{44}$ is optionally substituted with one or more halo groups; and optionally the phenyl or 5- or 6-membered heteroaryl group is further substituted with one, two or three substituents independently selected from halo, —NO$_2$, —CN, —COOR$^{45}$, —CONH$_2$, —CONHR$^{45}$ or —CON(R$^{45}$)$_2$, wherein each —R$^{45}$ is independently selected from a $C_1$-$C_4$ alkyl or $C_1$-$C_4$ haloalkyl group; or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted with one or two substituents independently selected from halo, —NO$_2$, —CN, —COOR$^{45}$, —CONH$_2$, —CONHR$^{45}$ or —CON(R$^{45}$)$_2$, wherein each —R$^{45}$ is independently selected from a $C_1$-$C_4$ alkyl or $C_1$-$C_4$ haloalkyl group; or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted with a substituent selected from halo, —NO$_2$, —CN, —COOR$^{45}$, —CONH$_2$, —CONHR$^{45}$ or —CON(R$^{45}$)$_2$, wherein each —R$^{45}$ is independently selected from a $C_1$-$C_4$ alkyl or $C_1$-$C_4$ haloalkyl group; or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{42}$—$OR^{43}$, —$R^{42}$—N(R$^{43}$)$_2$, —$R^{42}$—CN or —$R^{42}$—C≡CR$^{43}$, and wherein a ring atom of the monovalent heterocyclic or aromatic group is directly attached to the α-ring atom of the parent phenyl or 5- or 6-membered heteroaryl group; wherein $R^{42}$ is independently selected from a bond or a $C_1$-$C_3$ alkylene group; and $R^{43}$ is independently selected from hydrogen or a $C_1$-$C_3$ alkyl or $C_1$-$C_3$ haloalkyl group; and the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted with one, two or three substituents independently selected from halo, —NO$_2$, —CN, —COOR$^{45}$, —CONH$_2$, —CONHR$^{45}$ or —CON(R$^{45}$)$_2$, wherein each —R$^{45}$ is independently selected from a $C_1$-$C_4$ alkyl or $C_1$-$C_4$ haloalkyl group; or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{42}$—$OR^{43}$, —$R^{42}$—N(R$^{43}$)$_2$, —$R^{42}$—CN or —$R^{42}$—C≡CR$^{43}$, and wherein a ring atom of the monovalent heterocyclic or aromatic group is directly attached to the α-ring atom of the parent phenyl or 5- or 6-membered heteroaryl group; wherein $R^{42}$ is independently selected from a bond or a $C_1$-$C_3$ alkylene group; and $R^{43}$ is independently selected from hydrogen or a $C_1$-$C_3$ alkyl or $C_1$-$C_3$ haloalkyl group; and the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted with one or two substituents independently selected from halo, —NO$_2$, —CN, —COOR$^{45}$, —CONH$_2$, —CONHR$^{45}$ or —CON(R$^{45}$)$_2$, wherein each —R$^{45}$ is independently selected from a C$_1$-C$_4$ alkyl or C$_1$-C$_4$ haloalkyl group.

22. The compound or the pharmaceutically acceptable salt or solvate thereof, as claimed in claim 21, wherein R$^X$ is a saturated hydrocarbyl group, wherein the hydrocarbyl group may be straight-chained or branched, or may be or include cyclic groups, wherein the saturated hydrocarbyl group may be unsubstituted or optionally substituted with one or more fluoro and/or chloro groups, wherein the saturated hydrocarbyl group includes at least one heteroatom N in its carbon skeleton, and wherein the saturated hydrocarbyl group may optionally include one or two further heteroatoms independently selected from N and O in its carbon skeleton; and R$^Y$ is a saturated hydrocarbyl group, wherein the hydrocarbyl group may be straight-chained or branched, or may be or include cyclic groups, wherein the saturated hydrocarbyl group may be unsubstituted or optionally substituted with one or more fluoro and/or chloro groups, and wherein the saturated hydrocarbyl group may optionally include one or two oxygen atoms in its carbon skeleton.

23. A prodrug of a compound of formula (I):

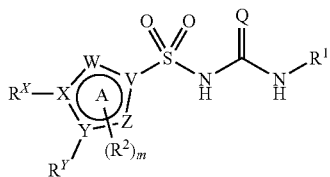

Formula (I)

or a pharmaceutically acceptable salt or solvate of the prodrug, wherein:

Q is selected from O or S;

ring A is monocyclic;

V, X and Y are each independently selected from C and N, and W and Z are each independently selected from N, O, S, NH and CH, provided that at least one of V, W, X, Y and Z is N, O, S or NH;

R$^X$ and R$^Y$ are each independently any saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

R$^1$ is a cyclic group substituted at the α-position, wherein R$^1$ may optionally be further substituted;

m is 0, 1 or 2; and each R$^2$ is independently a halo, —OH, —NO$_2$, —NH$_2$, —N$_3$, —SH, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

provided that at least one of R$^X$ and R$^Y$ comprises a nitrogen atom; and provided that the compound is not:

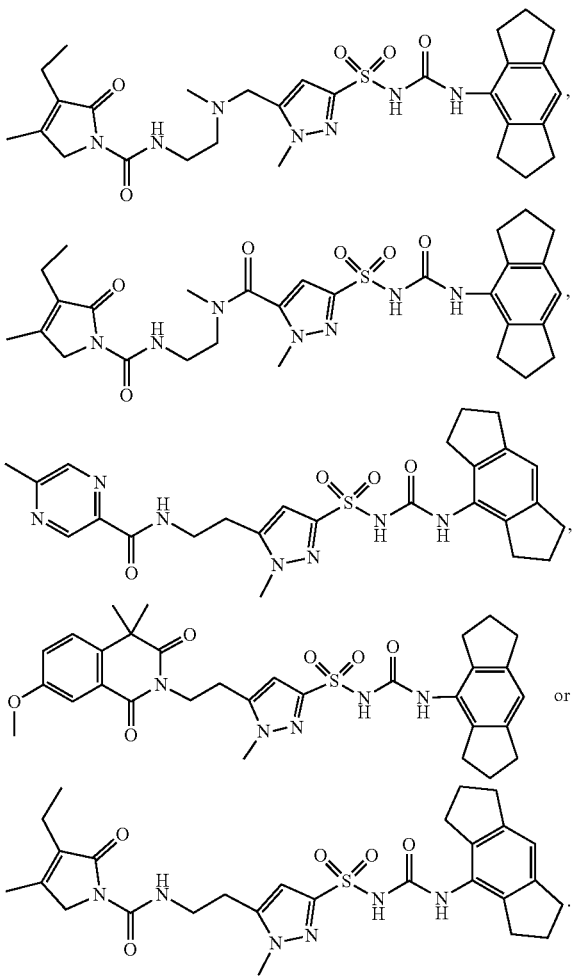

24. A method of treating, or delaying onset or reducing risk of a disease, disorder or condition in a subject, the method comprising the step of administering an effective amount of the prodrug or the pharmaceutically acceptable salt or solvate thereof, as claimed in claim 23, to the subject, thereby treating or delaying onset or reducing risk of the disease, disorder or condition, wherein the disease, disorder or condition is responsive to NLRP3 inhibition.

* * * * *